US008050871B2

(12) United States Patent
Bogoch et al.

(10) Patent No.: US 8,050,871 B2

(45) Date of Patent: Nov. 1, 2011

(54) METHOD OF PREDICTING INFLUENZA OUTBREAKS BY CORRELATING AN INCREASE IN REPLIKIN COUNT IN SHRIMP WHITE SPOT SYNDROME VIRUS AND/OR TAURA SYNDROME VIRUS

(76) Inventors: Samuel Bogoch, New York, NY (US); Elenore S. Bogoch, New York, NY (US); Samuel Winston Bogoch, Oakland, CA (US); Anne Elenore Borsanyi, Brookline, MA (US)

( * ) Notice: Subject to any disclaimer, the term of this patent is extended or adjusted under 35 U.S.C. 154(b) by 776 days.

(21) Appl. No.: 11/923,559

(22) Filed: Oct. 24, 2007

(65) Prior Publication Data

US 2008/0176217 A1 Jul. 24, 2008

Related U.S. Application Data

(63) Continuation-in-part of application No. 11/755,597, filed on May 30, 2007.

(60) Provisional application No. 60/935,816, filed on Aug. 31, 2007, provisional application No. 60/935,499, filed on Aug. 16, 2007, provisional application No. 60/954,743, filed on Aug. 8, 2007, provisional application No. 60/898,097, filed on Jan. 30, 2007, provisional application No. 60/880,966, filed on Jan. 18, 2007, provisional application No. 60/853,744, filed on Oct. 24, 2006.

(51) Int. Cl.

| | |
|---|---|
| ***G06F 19/00*** | (2011.01) |
| ***G06F 17/00*** | (2006.01) |
| ***G01N 33/48*** | (2006.01) |

(52) U.S. Cl. .............................................. 702/19; 703/2

(58) Field of Classification Search ........................ None
See application file for complete search history.

(56) References Cited

U.S. PATENT DOCUMENTS

| | | | |
|---|---|---|---|
| 5,104,854 | A | 4/1992 | Schlesinger |
| 5,231,167 | A | 7/1993 | Zanetti |
| 5,280,113 | A | 1/1994 | Rademacher |
| 5,679,352 | A | 10/1997 | Chong |
| 5,866,690 | A | 2/1999 | Bogoch |
| 6,023,659 | A | 2/2000 | Seilhamer |
| 6,070,126 | A | 5/2000 | Kokolus |
| 6,090,406 | A | 7/2000 | Popescu |
| 6,242,578 | B1 | 6/2001 | Bogoch |
| 6,256,647 | B1 | 7/2001 | Toh |
| 6,470,277 | B1 | 10/2002 | Chin |
| 6,484,166 | B1 | 11/2002 | Maynard |
| 6,638,505 | B2 | 10/2003 | Bogoch |
| 7,267,942 | B2 | 9/2007 | Peiris |
| 2002/0120106 | A1 | 8/2002 | Bogoch |
| 2002/0151677 | A1 | 10/2002 | Bogoch |
| 2003/0180328 | A1 | 9/2003 | Bogoch |
| 2003/0194414 | A1 | 10/2003 | Bogoch |
| 2005/0129715 | A1 | 6/2005 | Paterson et al. |
| 2005/0202415 | A1 | 9/2005 | Bogoch |
| 2005/0271676 | A1 | 12/2005 | Sette et al. |
| 2006/0024669 | A1 | 2/2006 | Bogoch |
| 2007/0026009 | A1 | 2/2007 | Bogoch |
| 2007/0128217 | A1 | 6/2007 | ter Meulen et al. |
| 2008/0241918 | A1 | 10/2008 | Sasisekharan et al. |
| 2008/0260764 | A1 | 10/2008 | Bogoch |
| 2009/0017052 | A1 | 1/2009 | Bogoch |
| 2009/0041795 | A1 | 2/2009 | Bogoch |

FOREIGN PATENT DOCUMENTS

| | | | |
|---|---|---|---|
| DE | 3628658 | A1 | 3/1988 |
| EP | 0 108 564 | A1 | 5/1984 |
| IT | 98MI0874 | | 10/1999 |
| JP | 3-503166 | T | 7/1991 |
| JP | 10-212300 | A | 8/1998 |
| JP | 11001493 | A | 1/1999 |
| JP | 2000-253876 | A | 9/2000 |
| WO | 8907112 | A1 | 10/1989 |
| WO | 96/32106 | | 10/1996 |
| WO | 0018351 | | 4/2000 |
| WO | 0104135 | A2 | 1/2001 |
| WO | 02085093 | A2 | 10/2002 |
| WO | 03005880 | A3 | 1/2003 |
| WO | 03083058 | A2 | 10/2003 |
| WO | 2005010032 | A2 | 2/2005 |
| WO | 2005004754 | A2 | 11/2005 |
| WO | 2006-088962 | A2 | 8/2006 |
| WO | 2006088962 | A2 | 8/2006 |
| WO | 2007022151 | A | 2/2007 |
| WO | 2007149715 | A | 12/2007 |
| WO | 2008060669 | A2 | 5/2008 |
| WO | 2008060702 | | 5/2008 |
| WO | 2008121329 | A2 | 10/2008 |
| WO | 2008140557 | | 11/2008 |
| WO | 2008143717 | | 11/2008 |
| WO | 2008156914 | | 12/2008 |

OTHER PUBLICATIONS

PCT International Search Report and Written Opinion PCT/US2009/041565, Jan. 25, 2010, EPO, International Searching Authority, Rijswijk, NL.
Witteveldt, et al., "Protection of Penaeus monodon against White Spot Syndrome Virus by oral Vaccination," Journal of Virology, Feb. 2004, p. 2057-2061 vol. 78, No. 4, entire document, esp. p. 2060, col. 1.
United States Patent and Trademark Office as International Searching Authority (ISA/RO'), International Search Report and Written Opinion of the International Searching Authority, mailed, Jan. 9, 2009.
Spackman et al., "Characterization of Low-Pathogenicity H5N1 Avian Influenza Viruses from North America," Journal of Virology, vol. 81, No. 21, Nov. 13, 2007, pp. 11612-11619.
PCT International Preliminary Report on Patentability, PCT/US2007/069978, May 1, 2009, USPTO, International Preliminary Examining Authority, Alexandria, VA, USA.
EP Office Action 04785929.3, Feb. 2, 2009, EPO, Netherlands.
NZ Office Action 560415, Mar. 6, 2009, IPO, New Zealand.
UnitProt/Swiss-Prot database entry O89746 1 Influenza A virus (strain A/Chicken/Hong Kong/220/1997 H5N1 genotype Gs/Gd) Nov. 1, 1998.

(Continued)

*Primary Examiner* — Jason Sims

(74) *Attorney, Agent, or Firm* — Kenyon & Kenyon LLP

(57) ABSTRACT

The present invention provides a method of predicting outbreaks in influenza virus comprising monitoring concentrations of small peptides having defined structure in influenza viruses, and in particular viral pathogens of shrimp.

21 Claims, 17 Drawing Sheets

OTHER PUBLICATIONS

Patil et al., "Identification of a Talin-binding Site in the Integrin β3 Subunit Distinct from the NPLY Regulatory Motif of a Post-ligand Binding Functions," The Journal of Biological Chemistry, vol. 274, No. 1, Oct. 1, 1999, p. 28575-28583.
Sharma et al., "Synthesis and Characterization of a Peptide Identified as a Functional element in αA-crystallin," The Journal of Biological Chemistry, vol. 275, No. 6, Feb. 11, 2000, p. 3767-3771.
Johansson et al., "Small, novel proteins from the mistletoe Pharadendron tementosum exhibit highly selective cytotoxity to human breast cancer cells," Cell Mol. Life Sci, Jan. 2003, 60: 165-175.
Kazazic et al., "Mutational analysis of the role of charged residues in target-cell binding, potency and specificity of the pediocin-like bacteriocin sakacin P," Microbiology, 148: 2019-27.
PepBank entry 42800, corresponding to UniProt database entry P15516, Apr. 1, 1990 (Homo sapiens salival protein histatin), available at http://pepbank.mgh.harvard.edu, accessed Oct. 6, 2008.
PCT International Preliminary Report on Patentability, PCT/US2006/05343, Jul. 22, 2008, USPTO, International Preliminary Examining Authority, Alexandria, VA, USA.
EP Office Action 04785929.3, Sep. 1, 2008, EPO, Netherlands.
NZ Office Action 553983, Jul. 16, 2008, IPO, New Zealand.
Bogoch et al. "In vitro production of the general transformation antibody related to survival in human cancer patients: antimalignin antibody," Cancer Detection and Prevention, Sep. 28, 1988, vol. 12, Nos. 1-6, pp. 313-320.
Seal et al., "Elevation of Serum Protein-Bound Carbohydrates and Haptoglobin in Schizophrenia," Clinical Chemistry; Oct. 1996, vol. 12, No. 10, pp. 709-716.
Schenk, S. et al., "Four recombinant isoforms of Cor a 1, the major allergen of hazel pollen, show different reactivities with allergen-specific T-lymphocyte clones," European Journal of Biochemistry, 1994, pp. 717-722, vol. 224, XP002371408, ISSN: 0014-2956.
Tanaka, T. et al., "Efficient Generation of Antibodies to Oncoproteins by using Synthetic Peptide Antigens." Proceedings of the National Academy of Sciences of USA, National Academy of Science, Washington, D.C., US, v. 82, No. 10, p. 3400-3404, tables 1, Peptide 21, XP000113798, ISSN: 0027-8424, May 1, 1985.
Weber, E. et al., "Fine Mapping of a Peptide Sequence Containing an Antigenic Site Conserved Among Arenaviruses," Virology, vol. 164, p. 30-38 (1988).
Yasuko, A-O, et al., "Intranasal administration of adjuvant-combined recombinant influenza virus HA vaccine protects mice from the lethal H5N1 virus infection." Microbes and Infection, vol. 8, Issues 12-13, pp. 2706-2714, Oct., 2006.
Zhao, Neutralizing monoclonal antibody against Anthrax lethal factor inhibits intoxication in a mouse model, Human Antibodies, vol. 12, pp. 129-135 (2003).
PCT International Search Report, PCT/US2002/09240, Jan. 14, 2004, USPTO, International Searching Authority, Washington DC.
PCT International Preliminary Examination Report, PCT/US2002/09240, Feb. 5, 2004, USPTO, International Preliminary Examination Authority, Alexandria, VA, USA.
PCT International Search Report, PCT/US2002/21494, May 30, 2003, USPTO, International Searching Authority, Washington DC.
PCT International Preliminary Examination Report, PCT/US2002/21494, Nov. 26, 2004, USPTO, International Searching Authority, Alexandria, VA, USA.
PCT International Search Report, PCT/US2003/08990, Dec. 7, 2005, International Searching Authority, USPTO, Alexandria, VA.
PCT Written Opinion of the International Searching Authority, PCT/US2004/017936, Apr. 7, 2005, EPO, International Searching Authority, Munich, DE.
PCT International Search Report, PCT/US2004/017936, Apr. 28, 2005, EPO, International Searching Authority, Rijswijk, NL.
PCT International Preliminary Report on Patentability, PCT/US2004/017936, Apr. 13, 2007, USPTO, International Preliminary Examining Authority, Alexandria, VA, USA.
PCT International Search Report, PCT/US2005/014443, Oct. 21, 2005, EPO, International Searching Authority, Rijswijk, NL.
PCT Written Opinion of the International Searching Authority, PCT/US2005/014443, Apr. 12, 2006, EPO, International Searching Authority, Munich, DE.
PCT International Preliminary Report on Patentability, PCT/US2005/014443, Nov. 1, 2006, WIPO, International Bureau of WIPO, Geneva, Switzerland.
PCT International Search Report, PCT/US2006/05343, Sep. 25, 2007, USPTO, International Searching Authority, Alexandria, VA, USA.
Supplementary Partial European Search Report 99944002, Apr. 20, 2004, EPO, Munich, DE.
Supplementary Partial European Search Report 02736514.7, Mar. 9, 2006.
Supplementary Partial European Search Report 02752202.8, Mar. 10, 2006.
Supplementary Partial European Search Report 03721445.9, Dec. 12, 2006, EPO, International Searching Authority, Munich, DE.
NCBI accession # gi 75059 Jul. 16, 1999.
NCBI Listing JQ0032, May 11, 2000.
NCBI Accession # AAK38298, Apr. 19, 2001.
Abrams M. B. et al., "Early Detection and Monitoring of cancer with the Anti-Malignin Antibody Test," Cancer detection and Prevention, XX, XX, vol. 18, No. 1, 1994, pp. 65-78, XP000673180, ISSN:0361-090X.
Atassi, M. Z. et al., "A novel approach for localization of the continuous protein antigenic sites by comprehensive synthetic surface scanning: Antibody and T cell activity to several influenza hemagglutinin synthetic sites," Immunological Communications, 1984, pp. 539-551, vol. 13, No. 6, Marcel Dekker, Inc., XP009062995, ISSN: 0090-0877.
Ben-Yedidia, T. et al., "Intranasal administration of peptide vaccine protects human/mouse radiation chimera from influenza infection," International Immunology, 1999, pp. 1043-1051, XP000914818, ISSN: 0953-8178.
Bogoch et al.: In vitro production of the general transformation antibody related to survival in human cancer patients; antimalignin antibody; Abstract, Cancer Detection and Prevention, 1988, vol. 12, Nos. 1-6, pp. 313-320. (Database Medline on STN National Library of Medicine (Bethesda, MD, USA) No. 89028479.
Bogoch, S. et al., "A Checklist for Suitability of Biomarkers as Surrogate Endpoints in Chemoprevention of Breast Cancer," Journal of Cellular Biochemistry, Supplement, Boston, US, vol. 19, pp. 173-185, XP009046492, ISSN: 0733-1959, 1994.
Bogoch et al., "Aglyco Pathology of Viral Receptors in Dementias," Annals of the New York Academy of Sciences, New York Academy of Sciences, New York Academy of Sciences, New York, NY, US, vol. 757, 1995, pp. 413-417, XP008003395, ISSN:0077-8923.
Bogoch et al., "Rapid replication and Replikintm structures: basis of the AMASRTest and CAVAXR," Cancer Detection and Prevention Online, Feb. 9, 2002, XP002350483.
Brown, L. R. et al., "Recognition of the influenza hemagglutinin by Class II MHC-restricted T lymphocytes and antibodies," Journal of Immunology, Oct. 14-15, 1991, pp. 2677-2684, vol. 147, No. 8, American Association of Immunologists, USA, XP002371257, ISSN: 0022-1767.
Brumeanu, T.M. et al., "Immunogenicity of a Contiguous T-B Synthetic Epitope of the A/PR/8/34 Influenza Virus," Journal of Virology, Jul. 1997, vol. 71, No. 7, pp. 5473-5480.
Bucher, D. et al., "M protein (M1) of influenza virus antigenic analysis and intracellular localization with monoclonal antibodies", J Virol. Sep. 1989; 63(9): pp. 3622-3633.
Carr C. M. et al., "A spring-loaded mechanism for the conformational change of influenza hemagglutinin," Cell, May 21, 1993, pp. 823-832, vol. 73, Cell Press, XP002059698, ISSN: 0092-8674.
Chambers, T.M. et al., "Antigenic and molecular characterization of subtype H13 hemagglutinin of influenza virus," Database NCBI on STN, Accession No. HMIVT2, Virology, pp. 180-188, abstract, 1989, 172(1).
Gao, Identification and characterization of T helper epitopes in the nucleoprotein of influenza a virus, J. Immunol. 1989, vol. 143, pp. 3007-3014.

Gelder, C.M. et al., "Human CD4+ T-cell repertoire of response to influnza A virus hemagglutinin after recent natural infection," Journal of Virology, Dec. 1995, vol. 69, No. 12, pp. 7497-7506A.
Keppeler et al., "Elongation of thr N-acyl side chain of sialic acid in MDCK II cells inhibits influenza a virus infection," abstract, Biochemical and Biophysical Research Communications, Dec. 18, 1998, vol. 253, No. 2. Database Medline on STN, National Library of Medicine, (Bethesda, MD, USA), No. 99097253.
Kornblith P. L. et al., "Growth-inhibitory effect of diphenylhydantoin on murine astrocytomas," Neurosurgery, vol. 5, No. 2, pp. 259-263 (Aug. 1979), MEDLINE, XP002199627.
Margalit et al., "Prediction of Immunodominant Helper T Cell Antigenic Sites From the Primary Sequence," Jour. Of Immunology, vol. 138, 2213-2229, Apr. 1, 1987.
Marra, M. et al., "The Genome Sequence of the Sars-Associated Coronavirus," Science, American Association for the Advancement of Science, US, v. 300, No. 5624, p. 1399-1404, XP002269483, ISSN: 0036-8075, May 30, 2003.
O'Donnell, F.T. et al., "Epidemiology and molecular characterization of co-circulating influenza A/H3N2 virus variants in children," Epidemiology and Infection, Jun. 2003, pp. 521-31, abstract, vol. 130, issue 3, The University of Texas-Houston School of Public Health, Houston, Texas. Database Medline U.S. National Library of Medicine (Bethesda, MD) Accession No. 2003:298060.
Orlando, C. et al., "A monoclonal antibody directed against the catalytic site of Bacillus anthracis adenylyl cyclase identifies a novel mammalian brain catalytic subunit," Biochemistry, 1992, pp. 3215-3222, vol. 31, American Chemical Society, XP002371438, ISSN: 0006-2960.
Pannifer, Crystal structure of the anthrax lethal factor, Nature, vol. 414, pp. 229-233 (Nov. 2001).
Qin, E. et al., "A Genome Sequence of Novel SARS-CoV Isolates: the Genotype, GD-Ins29, Leads to a Hypothesis of Viral Transmission in South China," Genomics Proteomics & Bioinformatics, vol. 1, No. 2, p. 101-107, XP001206098, ISSN: 1672-0229, May 2003.
Rodman, Toby C. et al., "Human Immunodeficiency Virus (HIV) Tat-reactive Antibodies Present in Normal HIV-negative Sera and Depleted in HIV-positive Sera. Identification of the Epitope," vol. 175, pp. 1247-1253, (May 1992).
Rota, P. et al., "Characterization of a Novel Coronavirus Associated with Severe Acute Respiratory Syndrome," Science, American Association for the Advancement of Science, US, v. 300, No. 5624, p. 1394-1399, XP002269482, ISSN: 0036-8075, May 30, 2003.
Tompkins, S.M. et al., "Matrix protein 2 vaccination and protection against influenza viruses, including subtype H5N1," Emerging Infectious Diseases, vol. 13, No. 3, p. 426-435, Mar. 2007, available at www.cdc.gov/eid.
PCT International Preliminary Report on Patentability, PCT/US2006/05343, Jul. 22, 2008, USPTO, International Preliminary Examining Authority, Alexandria, VA, USA.
PCT International Search Report and Written Opinion, PCT/US2007/069978, Jun. 3, 2008, EPO, International Searching Authority, Rijswijk, NL.
PCT International Search Report and Written Opinion, PCT/US2007/82436, Jan. 9, 2009, USPTO, International Searching Authority, Alexandria, VA, USA.
PCT International Search Report and Written Opinion, PCT/US2008/00645, Feb. 2, 2009, USPTO, International Searching Authority, Alexandria, VA, USA.
PCT International Search Report and Written Opinion, PCT/US2008/061336, Feb. 2, 2009, EPO, International Searching Authority, Rijswijk, NL.
EP Office Action 04785929.3, Sep. 1, 2008, EPO, Netherlands.
PepBank entry 42800, corresponding to UniProt database entry P15516, Apr. 1, 1990, available at http://pepbank.mgh.harvard.edu, accessed Oct. 6, 2008.
Bogoch et al., "Replikins: The Chemistry of Rapid Replication," Begell House, Inc. NY, NY (2005).
Kazazic et al., "Mutational analysis of the role of charged residues in target-cell binding, potency and specificity of the pediocin-like bacteriocin sakacin P," Microbiology, (2002) 148: 2019-27.
PCT Invitation to Pay Additional Fees and Communication Relating to the Results of the Partial International Search, PCT/US2009/061108, Mar. 8, 2010, EPO, Rijswijk, NL.
UnitProt A8DXX4, Journal of Virology, vol. 81, No. 21, Nov. 13, 2007, pp. 11612-11619.
US Office Action, U.S. Appl. No. 11/755,597, filed May 14, 2010.
AU Office Action, Application No. 2006214332, Jun. 10, 2010.
US Office Action, U.S. Appl. No. 12/010,027, filed Jul. 21, 2010.
SG Written Opinion, Application No. SG 200602419-4, Aug. 3, 2010.
US Office Action, U.S. Appl. No. 12/495,306, filed Sep. 1, 2010.
US Office Action, U.S. Appl. No. 11/755,597, filed Sep. 30, 2010.
PCT International Search Report and Written Opinion, PCT/US2009/061108, Jun. 11, 2010, EPO, Rijswik, NL.
NCBI Accession No. NP 740460 (2000).
NCBI Accession No. AAW59548 (Jan. 24, 2005).
NCBI Accession No. DQ100549 (Jul. 6, 2005).
Gen Bank Accession No. AAV74400.1 (Dec. 5, 2005).
NCBI Accession No. ABE97631 (Dec. 27, 2006).
NCBI Blast Searching, Gene Gateway—Exploring Genes and Genetic Disorders, "Sequence similarity searching using NCBI Blast" (http:www.ORNL.gov/sci/techresources/Human_Genome/chromosome/blast.shtml) (Apr. 27, 2005).
NCBI Query Tutorial "Introduction" (http://www.ncbi.nim.nih.gov/Education/BLASTinfo/query_tutorial.html) (Apr. 27, 2005).
NCBI Query Tutorial "Introduction to a BLAST Query" (http://www.ncbi.nim.nih.gov/Education/BLASTinfo/tut1.html) (Apr. 27, 2005).
NCBI Query Tutorial "Setting up a Blast Search" (http://www.ncbi.nim.nih.gov/Education/BLASTinfo/Blast_setup.html) (Apr. 27, 2005).
3MOTIF—Search Instructions, 3motif in three Dimensions, article titles "Submitting a protein sequence": http://brutlag.stanford.edu/3motif/search_instr.html) (screenshot Apr. 27, 2005 in U.S. Appl. No. 11/116,203).
Fern, J. "Promiscuous malaria peptide epitope stimulates CD45Ra T cells from peripheral blood of nonexposed donors," J. Immunology 1992, vol. 148, pp. 907-913.
Liu et al. Science, Aug. 19, 2005; 309 (5738); 1206. Epub Jul 6, 2005, "Highly pathogenic H5N1 influenza virus infection in migratory birds.".
Rodriguez et al., "*Plasmodium falciparum* EBA-175 kDa protein peptides which bind to human red blood cells." Parasitology (2000), vol. 120, pp. 225-235.
Shi, Immunogenicity and in vitro protective efficacy of a recombinant multistage *Plasmodium falciparum* candidate vaccine, PNAS vol. 96, No. 4, pp. 1615-1620 (Feb 1999).
U.S. Appl. No. 11/755,597, Response to Office Action, filed Nov. 30, 2011.
US Office Action, U.S. Appl. No. 12/108,458, filed Dec. 27, 2010.
US Office Action, U.S. Appl. No. 12/170,763, filed Feb. 15, 2011.
US Office Action, U.S. Appl. No. 12/252,028, filed Feb. 15, 2011.
US Office Action, U.S. Appl. No. 12/495,306, filed Feb. 15, 2011.
US Office Action, U.S. Appl. No. 12/010,027, filed Feb. 16, 2011.
Diggs et al., Experimental Parasitology, vol. 80, Issue 2, Mar. 1995, pp. 291-296.
Frankel, et al., PNAS 1989, vol. 86, pp. 7397-7401.
He, Z. et al., "Identification of epitopes in cucumber mosaic virus using a phage-displayed random peptide library," J Gen Virol 1998, vol. 79, pp. 3145-3153.
Patarroyo et al., Nature, vol. 328, No. 6131, pp. 629-632.
Wang et al., "ORF390 of white spot syndrome virus genome is identified as a novel anti-apoptosis gene," Biochemical and Biophysical Research Communications 325 (2004) 899-907.
Patarroyo et al., Nature, vol. 328, No. 6131, Aug. 13, 1987, pp. 629-632.
Japan Patent Office, Office Action in related Japanese Application No. 2009-024307, dated Sep. 8, 2009, Japan.
United States Patent and Trademark Office, US Office Action in related U.S. Appl. No. 11/615,578, dated Oct. 21, 2009, US.
NCBI Swiss-Prot Locus P33795, accessed Jul. 7, 2009.

Betakova et al., "The Vaccinia Virus A14.5L Gene Encodes a Hydrophobic 53-Amino-Acid Virion Membrane Protein That Enhances Virulence in Mice and Is Conserved among Vertebrate Poxviruses," Journal of Virology, vol. 74., No. 9, May 2000, p. 4085-4092.
Massung et al., "Potential virulence determinants in terminal regions of variola spallpox virus genome," Nature, vol. 366, Dec. 23/30, 1993, p. 748-751.
Replikins, Ltd. Press Release, "Replikins, Ltd. has discovered a group of virus peptides that predict whether a virus is rapidly replicating and whether it is likely to spread" (Apr. 21, 2006).
Replikins, Ltd. Press Release, "Virus Replication Discovery Helps Predict Epidemics" (Apr. 24, 2006).
Hendrickson, D., Mass High Tech, "Flu forecaster firm born" (Apr. 28, 2006).
Boggs, J, Diagnostics & Imaging Week, "Replikins: Predicting global epidemics replication data" (May 4, 2006).
Replikins, Ltd. Press Release, "Replikins' FluForecast® Software Pinpoints Change in Deadly Bird Flu Amino Acid Sequence In Humans" (Jun. 3, 2006).
Replikins, Ltd. Press Release, "Advance Warning of H5N1 Influenza Outbreaks May Be Found in Shrimp Virus Reservoirs" (Oct. 26, 2006).
Replikins, Ltd. Press Release, "Rising H5N1 'Bird Flu' High-Virulence Sequences Found by Replikins, Ltd." (Nov. 6, 2006).
Replikins, Ltd. Press Release, "Human H5N1 Virus Replikin Count Overtakes Levels in H5N1 'Bird Flu'" (Dec. 27, 2006).
Replikins, Ltd. Press Release, "Gene Segment Identified in Virulent Human H5N1 Viruses—Key Discovery May Enable Development of Vaccines, Therapeutics" (Jan. 25, 2007).
Replikins, Ltd. Press Release, "High Host Mortality Rate Quantitatively Related to High Virus Replikin Count" (Mar. 6, 2007).
Replikins, Ltd. Press Release, "FluForecast® Trial in 2006 Predicted High Human H5N1 Mortality in Indonesia" (May 9, 2007).
Replikins, Ltd. Press Release, "Indonesia Reports Experiencing Human H5N1 Mortality Increase, as Predicted Last Year by Replikins' FluForecast® Quantitative Virus Analysis" (Jun. 8, 2007).
Replikins, LLC Press Release, "Replikins, LLC Finds West Nile Virus Replikin Count™ Has Reached Its Highest Recorded Value" (Aug. 3, 2007).

White Spot Syndrome Virus Replikin Concentration and H5N1 Human Mortality and Replikin Concentration

- ◆ WSSV Replikin Concentration with Standard Deviation
- ■ H5N1 Human Mortality Percent
- ▲ H5N1 Peak Gene Replikin Concentration in Humans Taura Syndrome Virus Replikin Concentration and H5N1 Human Mortality and Replikin Concentration

- ▲ H5N1 Peak Gene Replikin Concentration in Humans
- ✶ TSV Replikin Concentration with Standard Deviation
- ◆ H5N1 Human Mortality per 10 infections Year 2003 2004 2005 2006 2007 1st Qtr
HUMAN H5N1
Light Gray = Whole virus Replikin Concentration (Number of Replikins per 100 amino acids)
Dark Gray = Replikin Peak Gene Replikin Count
Uncolored Bar = Standard Deviation
Black = % Human Mortality Rate (x 10)

Cumulative survival of *Litopenaeus vannamei per os* challenged with TSV isolates: A: Belize; B: Thailand; C: Hawaii; D: Venezuela.

2001 Epidemic
2007 Epidemic
Replikin Concentration
Foot and Mouth Disease Virus
Replikin Concentration Per Year
(all serotypes)
3.5
3
2.5
2
1.5
1
0.5
0
1996
1998
2000
2002
2004
2006
2008

Increase in Replikin Concentration of Replikin Peak Gene (RPG) in pB1 Genomic Area Only, Not in pA or pB2, One to Two Years in Advance of Equine Influenza Epidemics (E) 1977-2007

Series1 Means, RC in RPG, in pB1 area

Series2 SD of Means in pB1 area

Series3 RC-RPG Means, in pA area

Series4 RC-RPG in pB2 area

METHOD OF PREDICTING INFLUENZA OUTBREAKS BY CORRELATING AN INCREASE IN REPLIKIN COUNT IN SHRIMP WHITE SPOT SYNDROME VIRUS AND/OR TAURA SYNDROME VIRUS

This application claims priority to U.S. Provisional Appln. Ser. No. 60/935,816, filed Aug. 31, 2007, U.S. Provisional Appln. Ser. No. 60/935,499 filed Aug. 16, 2007, U.S. Provisional Appln. Ser. No. 60/954,743, filed Aug. 8, 2007, U.S. Provisional Appln. Ser. No. 60/898,097, filed Jan. 30, 2007, U.S. Provisional Appln. Ser. No. 60/880,966, filed Jan. 18, 2007, and U.S. Provisional Appln. Ser. No. 60/853,744, filed Oct. 24, 2006, each of which is incorporated herein by reference in its entirety. This application additionally incorporates herein by reference: U.S. application Ser. No. 11/355,120, filed Feb. 16, 2006, U.S. application Ser. No. 11/755,597, filed May 30, 2007, U.S. application Ser. No. 11/116,203, filed Apr. 28, 2005, U.S. application Ser. No. 10/860,050, filed Jun. 4, 2004, U.S. application Ser. No. 10/189,437, filed Jul. 8, 2002, U.S. application Ser. No. 10/105,232, filed Mar. 26, 2002, now U.S. Pat. No. 7,189,800, U.S. application Ser. No. 09/984,057, filed Oct. 26, 2001, and U.S. application Ser. No. 09/984,056, filed Oct. 26, 2001, now U.S. Pat. No. 7,176,275, each in its entirety.

TECHNICAL FIELD OF THE INVENTION

This invention relates generally to predicting influenza outbreaks through monitoring quantitative changes in the concentration of a class of peptide sequences known as Replikins in virus proteins, protein fragments, or genomes.

BACKGROUND OF THE INVENTION

Rapid replication is characteristic of virulence in, among other things, certain bacteria, viruses and malignancies. The inventors have described a quantitative chemistry common to rapid replication in different viruses and organisms. The chemistry of rapid replication described by the inventors is present in a family of conserved small protein sequences related to rapid replication, Replikins. An increase in the concentration of these Replikin sequences encoded in the genome of different strains of influenza virus has been correlated with an increase in the virulence of influenza. A correlation between increased concentrations of Replikin sequences and increased replication and virulence has likewise been observed in a range of viruses and organisms. Replikin sequences offer new targets for developing effective methods of predicting and treating influenza outbreaks. There continues to exist a particular need in the art for methods of predicting viral outbreaks.

Influenza is an acute respiratory illness of global importance. Despite international attempts to control influenza virus outbreaks through vaccination, influenza infections remain an important cause of morbidity and mortality. Worldwide influenza pandemics have occurred at irregular and previously unpredictable intervals throughout history and it is expected that influenza pandemics will continue to occur in the future. The impact of pandemic influenza is substantial in terms of morbidity, mortality and economic cost.

Influenza vaccines remain the most effective defense against influenza virus, but because of the ability of the virus to mutate, and the availability of non-human host reservoirs, it is expected that influenza will remain an emergent or re-emergent infection. Global influenza surveillance indicates that influenza viruses may vary within a country and between countries and continents during an influenza season. Virologic surveillance is of importance in monitoring antigenic shift and drift. Disease surveillance is also important in assessing the impact of epidemics. Both types of information have provided the basis of vaccine composition and use of antivirals. However, there has traditionally been only annual post hoc hematological classification of the increasing number of emerging influenza virus strains, and no specific chemical structure of the viruses was traditionally identified as an indicator of approaching influenza epidemic or pandemic. Until recently, the only basis for annual classification of influenza virus as active, inactive or prevalent in a given year was the activities of the virus hemagglutinin and neuraminidase proteins.

The small peptide structure called Replikins has now been identified within influenza virus proteins and correlated with an increase in virulence. A Replikin sequence is an amino acid sequence of 7 to about 50 amino acids comprising a Replikin motif. A Replikin motif comprises (1) at least one lysine residue located at a first terminus of the motif and at least one lysine residue or at least one histidine residue located at a second terminus of the motif, (2) a first lysine residue located six to ten residues from a second lysine residue; (3) at least one histidine residue; and (4) at least 6% lysine residues. A Replikin sequence may comprise a terminal lysine and may further comprise a terminal lysine or a terminal histidine. A Replikin peptide or Replikin protein is a peptide or protein consisting of a Replikin sequence.

Higher concentrations of Replikin sequences in the genomic code are associated with a variety of infectious agents including HIV, plant viruses, and a range of pathogenic animal and human viruses including flu viruses. Further, the correlation between the concentration of Replikin sequences in viral or organismal proteins and major outbreaks of disease is significant. Replikin sequences generally have been found to be conserved in both intrastrain and interstrain influenza viruses for as long as 89 years based on data going back to the 1917-18 flu pandemic. Concentration of Replikin sequences in viral genomes has been shown to increase prior to strain-specific flu outbreaks.

Within the last century there have been three influenza pandemics, each strain specific: H1N1 in 1918; H2N2 in 1957; and H3N2 in 1968. The inventors have established that prior to each pandemic there was a strain-specific increase in the concentration of Replikin sequences within the strain. The strain-specific increase in Replikin concentration was followed by a decrease in Replikin concentration and several years later a rebound increase in Replikin concentration associated with a strain-specific rebound epidemic. The Replikin algorithm provided the first chemistry that correlated with influenza epidemics and pandemics.

A similar correlation between the outbreaks of H5NI (Bird Flu) between 1997 and 2007 and the concentration of Replikin sequences in the viral proteins during each of those years has been demonstrated. Likewise, a correlation has been established between the global outbreak of SARS coronavirus in 2003 and an increase in the concentration of Replikin sequences in the proteins of coronavirus. In another study, Replikins in two strains of human HIV-1 virus demonstrated that the Replikin concentration in the rapidly replicating strain was six fold greater than that of a slowly replicating strain. No instances of rapid replication have been observed in all the viruses and organisms examined wherein the Replikin concentration did not significantly increase as compared to the Replikin concentration in the dormant state.

The highest concentration of Replikin sequences in an organism or virus that has to date been analyzed and reported is 111 Replikin sequences per 100 amino acids in the extraordinarily-rapidly-replicating parasitic protozoa *Plasmodium falciparum* (reportedly responsible for 90% of malarial deaths in humans) (herein sometimes referred to as malaria). *P. falciparum* has been observed to replicate 11,000 times in 48 hours during passage of the parasite from liver to blood in the host.

It has been believed that changes in the activity of different influenza strains are related to random sequence changes in influenza hemagglutinins, which in turn are the products of substitutions effected by one of two poorly understood processes: i) antigenic drift, thought to be due to the accumulation of a series of point mutations in the hemagglutinin molecule, or ii) antigenic shift, in which the changes are so great that genetic reassortment is postulated to occur between the viruses of human and non-human hosts. The data provided by the inventors suggests that change in activity in different influenza strains, rather than being related to non-specific random sequence changes, is based upon, or related to, an increase in concentration of strain-specific Replikins. Data were also examined for insight into which sequence changes were due to "drift" or "shift" and which were due to conservation, storage in "reservoirs," and reappearance. The data has shown that the epidemic-related increase in Replikin concentration is not due to the duplication of existing Replikins in the hemagglutinin of the emerging strain, but, instead is due to the reappearance of at least one Replikin composition from 1 to up to 59 years after its disappearance, plus (in the A strains only) the emergence of new strain-specific Replikin compositions. See U.S. Pat. No. 7,189,800 issued Mar. 13, 2007 (Tables 3-6).

In monitoring Replikin sequences in influenza virus, the inventors have additionally identified a sub-family of conserved Replikin sequences known as Replikin Scaffolds or Replikin Scaffold sequences. Replikin Scaffolds were initially identified in conserved structures in particularly virulent influenza viruses. Included among these strains were the viruses causing the pandemics of 1918, 1957, 1968 and virulent strains of the H5N1 "bird flu" strain of influenza virus. Analogues of Replikin Scaffold sequences have since been identified in the virulent and rapidly replicating SARS coronavirus. See U.S. Published Application No. 2007/0026009.

Scaffolding of Replikin sequences homologous but not identical to the algorithm of the identified Replikin Scaffold has also been identified in *P. falciparum*. Replikin scaffolding in general has been related to an increase in Replikin concentrations in pathogenic genomes where it has been identified. In *P. falciparum*, scaffolding contributes significantly to the very high Replikin concentration noted in the proteins of the protozoa.

There is a need in the art for methods of predicting increases in virulence of influenza prior to outbreaks. There is likewise a need in the art for methods of preventing and treating outbreaks caused by virulent strains of influenza. Because of the annual administration of influenza vaccines and the short period of time when a vaccine can be administered, strategies directed at improving vaccine coverage are of critical importance.

SUMMARY OF THE INVENTION

The present invention provides a method of determining an increased probability of an outbreak of influenza virus within about one to about three years following an increase in Replikin concentration in an isolate of White Spot Syndrome Virus or an isolate of Taura Syndrome Virus comprising identifying said increase in the concentration of Replikin sequences in at least one first isolate of White Spot Syndrome Virus or Taura Syndrome Virus as compared to at least one other isolate of White Spot Syndrome Virus or Taura Syndrome Virus wherein said at least one first isolate is isolated at least six months later than said at least one other isolate is isolated and wherein when said at least one first isolate is a White Spot Syndrome Virus isolate said at least one other isolate is a White Spot Syndrome Virus isolate and when said at least one first isolate is a Taura Syndrome Virus isolate said at least one other isolate is a Taura Syndrome Virus isolate, and wherein said increase in the concentration of Replikin sequences signifies the increased probability of the outbreak of influenza virus within about one to about three years following said increase in the concentration of Replikin sequences.

In an embodiment of the method of determining an increased probability of an outbreak of influenza virus, said identification of an increase in Replikin concentration in said at least one first isolate comprises (1) determining the concentration of Replikin sequences in (i) a plurality of isolates of White Spot Syndrome Virus wherein said at least one first isolate has been isolated about six months to about three years later than said at least one other of said isolates of White Spot Syndrome Virus, or (ii) a plurality of isolates of Taura Syndrome Virus wherein said at least one first isolate of Taura Syndrome Virus is isolated about six months to about three years later than at least one other isolate of Taura Syndrome Virus.

An embodiment of the present invention provides a method of determining an increased probability of an outbreak of influenza virus comprising:

(1) obtaining a plurality of isolates of White Spot Syndrome Virus or a plurality of isolates of Taura Syndrome Virus wherein at least one of said isolates of White Spot Syndrome Virus is isolated about six months to about 3 years later than at least one other of said isolates of White Spot Syndrome Virus or wherein at least one of said isolates of Taura Syndrome Virus is isolated about six months to about 3 years later than at least one other of said isolates of Taura Syndrome Virus;

(2) analyzing the amino acid sequence of at least one encoded protein or protein fragment or a combination of encoded proteins and/or protein fragments in each isolate of the plurality of isolates of White Spot Syndrome Virus or the plurality of isolates of Taura Syndrome Virus for the presence and concentration of encoded Replikin sequences;

(3) comparing the concentrations of encoded Replikin sequences in the at least one protein or protein fragment or in the combination of proteins or protein fragments in each isolate of the plurality of isolates of White Spot Syndrome Virus or in each isolate of the plurality of isolates of Taura Syndrome Virus;

(4) identifying an increase in the concentration of encoded Replikin sequences in said plurality of isolates of White Spot Syndrome Virus or in said plurality of isolates of Taura Syndrome Virus over at least one time period of about six months or greater; and (5) predicting an outbreak of influenza within about one to about three years following said identified increase in the concentration of Replikin sequences in said isolates of White Spot Syndrome Virus or in the concentration of Replikin sequences in said isolates of Taura Syndrome Virus.

In a further embodiment of the invention, the increase in concentration of encoded Replikin sequences in said plurality of isolates of White Spot Syndrome Virus or in said plurality of isolates of Taura Syndrome Virus over at least one time period of about six months or greater is an increase in the mean concentration of at least two isolates as compared to at least two other isolates isolated at a later time point of about six months or greater. In a further embodiment, the increase in concentration is an increase in the mean concentration of at least 10 isolates as compared to at least 10 other isolates. In a further embodiment, the increase in concentration is an increase in the mean concentration of all isolates available at a given time point as compared to all isolates available at another given time point, wherein said time points are separated by about six months or greater. In a further embodiment, the mean concentration of said plurality of isolates is increased over the at least one time period when the mean concentration of the isolates at a later time point is greater than the mean concentration plus one standard deviation of the earlier isolates. In a further embodiment, the mean concentration of said plurality of isolates is increased over the at least one time period when the mean concentration of the isolates at a later time point is greater than the mean concentration plus two standard deviations of the earlier isolates. In a further embodiment of the invention, analyzing the combination of encoded proteins and/or protein fragments preferably comprises all amino acid sequences available for White Spot Syndrome Virus or all amino acid sequences available for Taura Syndrome Virus at a given time point, such as, for example, all amino acid sequences available in a first year and all amino acid sequences available in some other year. In another embodiment, the combination comprises at least 100 amino acid sequences. In another embodiment, the combination comprsises at least 50 amino acid sequences. In another embodiment, the combination comprises at least 10 amino acid sequences. In another embodiment, the combination comprises at least 2 amino acid sequences.

In further embodiment of the invention, the method of predicting the outbreak of influenza virus may further comprise:

(1) identifying at least one Replikin Scaffold sequence present in at least one isolate of the plurality of isolates of White Spot Syndrome Virus identified as having an increase in the concentration of Replikin sequences as compared to at least one other isolate of the plurality of isolates of White Spot Syndrome Virus over a time period of about six months or greater or identifying at least one Replikin Scaffold sequence present in at least one isolate in the plurality of isolates of Taura Syndrome Virus identified as having an increase in the concentration of Replikin sequences as compared to at least one other isolate of the plurality of isolates of Taura Syndrome Virus over a time period of about six months or greater;

(2) identifying at least one Replikin Scaffold sequence present in at least one isolate of a strain of influenza virus, wherein said strain of influenza is isolated within the time period in which the increase in concentration of Replikin sequences is identified or wherein said strain of influenza is isolated within said time period of about one to about three years after said increase in concentration of Replikin sequences is identified; and (3) predicting the strain of influenza virus in which the at least one Replikin Scaffold sequence is identified as the strain of virus that will likely cause the predicted outbreak of influenza virus, wherein a Replikin Scaffold is a peptide having about 16 to about 34 amino acids comprising (a) a terminal lysine and optionally a lysine immediately adjacent to the terminal lysine; (b) a terminal histidine and optionally a histidine immediately adjacent to the terminal histidine, (c) a lysine within about 6 to about 10 amino acids of another lysine; and (d) at least 6% lysines. In an embodiment, the likelihood of an outbreak of influenza is preferably greater than 50%, more preferably greater than 60%, and even more preferably greater than 75%.

In a further embodiment of the invention, the Replikin Scaffold is a peptide having about 27 to about 33 amino acids. In an influenza virus, a Replikin Scaffold may refer to a Replikin peptide sequence comprising about 16 to about 34 amino acid residues, and in a preferred embodiment about 28 to about 30 amino acid residues. In a White Spot Syndrome Virus, a Replikin Scaffold may refer to a Replikin peptide sequence comprising about 16 to about 34 amino acid residues, and in a preferred embodiment about 29 to about 31 amino acid residues. In a Taura Syndrome Virus, a Replikin Scaffold may refer to a Replikin peptide sequence comprising about 16 to about 34 amino acid residues, and in a preferred embodiment about 29 to about 33 amino acid residues.

In an embodiment of the invention, the method of predicting an outbreak of influenza virus may comprise the prediction of an outbreak of any strain of influenza virus. In a further embodiment, the method of predicting an outbreak of influenza virus may comprise the prediction of an outbreak of influenza A. In a preferred embodiment, the outbreak of influenza A may be an outbreak of H5N1 ("bird flu") virus.

In a further embodiment of the invention, a plurality of isolates of White Spot Syndrome Virus may be obtained and analyzed for Replikin concentration or a plurality of isolates of Taura Syndrome Virus may be obtained and analyzed for Replikin concentration, or both in order to predict an outbreak of influenza virus.

In a further embodiment of the invention, the concentration of encoded Replikin sequences in said plurality of isolates of White Spot Syndrome Virus or said plurality of isolates of Taura Syndrome Virus over at least one time period of about six months or greater may increase by one or more Replikin sequences per 100 amino acids, may increase by five or more Replikin sequences per 100 amino acids, may increase by ten or more Replikin sequences per 100 amino acids, may increase by fifty or more Replikin sequences per 100 amino acids, may increase by 90 or more Replikin sequences per 100 amino acids, or may increase by 100 or more Replikin sequences per 100 amino acids.

The identified increase in concentration of encoded Replikin sequences in said plurality of isolates of White Spot Syndrome Virus or said plurality of isolates of Taura Syndrome Virus may occur over any time period including over one month or more, over six months or more, over one year or more, or over three years or more. In an embodiment of the invention, the identified increase in concentration of encoded Replikin sequences occurs over at least six months to about five years. In a further embodiment of the invention, the identified increase in concentration of encoded Replikin sequences preferably occurs over at least six months to about three years.

In a further embodiment of the invention, the method of predicting an outbreak of influenza may predict an outbreak within about one month to about five years or more following the identification of an increase in Replikin concentration in a plurality of isolates of White Spot Syndrome Virus or in a plurality of isolates of Taura Syndrome Virus. In a further embodiment of the invention, the method may predict an outbreak within several months to about three years.

In another embodiment, the method may predict an outbreak within about one year to about five years. In a further embodiment of the invention, the method may predict an outbreak within several months to about one year. In another embodiment, the method may predict an outbreak within about one year to about three years.

Another aspect of the invention provides a method of predicting an outbreak of influenza virus comprising analyzing Replikin concentration in reservoirs for influenza virus. A non-limiting embodiment of the invention provides a method of predicting an outbreak of influenza virus comprising:

(1) obtaining a plurality of isolates of a first virus from at least one reservoir of Replikin sequences shared by influenza virus wherein the reservoir of Replikin sequences shared by influenza is any source of Replikin sequences that may be shared with an influenza virus including any host of influenza virus, any food source of a host of the influenza virus, any vector of influenza virus, or any substance wherein the genetic information of the influenza virus may be shared, mingled, mixed, exchanged or come into the proximity of the Replikin sequences of the reservoir;

(2) analyzing the amino acid sequence of at least one encoded protein or protein fragment or a combination of encoded proteins and/or protein fragments in each isolate of the plurality of isolates of said first virus for the presence and concentration of encoded Replikin sequences;

(3) comparing the concentrations of encoded Replikin sequences in the at least one protein or protein fragment or in the combination of proteins or protein fragments in each isolate of the plurality of isolates of said first virus;

(4) identifying an increase in the concentration of encoded Replikin sequences in said plurality of isolates of said virus over at least one time period of about six months or greater; and (5) predicting an outbreak of influenza within about one to about three or more years following said identified increase in the concentration of Replikin sequences in said isolates of said first virus.

In a further non-limiting embodiment, the reservoir is shrimp. In another non-limiting embodiment, the reservoir is a bird. In another non-limiting embodiment, the reservoir is a migratory bird. In another non-limiting embodiment, the reservoir is a chicken, duck, goose, or other domestic bird.

In a further non-limiting embodiment, the method of predicting an outbreak of influenza virus further comprises:

(1) identifying at least one Replikin Scaffold sequence present in at least one isolate of the plurality of isolates of said first virus identified as having an increase in the concentration of Replikin sequences as compared to at least one other isolate of the plurality of isolates of said first virus over a time period of about six months;

(2) identifying at least one Replikin Scaffold sequence present in at least one isolate of a strain of influenza virus, wherein said strain of influenza is isolated within a time period in which the increase in concentration of Replikin sequences is identified or wherein said strain of influenza is isolated within a time period of about one year to about three years after said increase in concentration of Replikin sequences is identified; and (3) predicting the strain of influenza virus in which the at least one Replikin Scaffold sequence is identified as the strain of virus that will cause the predicted outbreak of influenza virus, wherein a Replikin Scaffold is a peptide consisting of about 16 to about 34 amino acids comprising (1) a terminal lysine and optionally a lysine immediately adjacent to the terminal lysine; (2) a terminal histidine and optionally a histidine immediately adjacent to the terminal histidine, (3) a lysine within about 6 to about 10 amino acids of another lysine; and (4) at least 6% lysines.

BRIEF DESCRIPTION OF THE DRAWINGS

FIG. 3 contains a graph comparing percent human mortality from H5N1 infections in years 2005 through the first quarter of 2007, mean concentration of Replikin sequences in the genome of H5N1 influenza strains isolated in 2003 through the first quarter of 2007 and mean concentration of Replikin sequences in the pB1 gene area of H5N1 influenza strains isolated in 2003 through the first quarter of 2007. Mean human mortality in deaths per 10 infections in a given year is represented by the black columns, mean Replikin concentration in the whole virus genome in a given year is represented by the light gray columns, mean Replikin concentration in the pB1 gene area in a given year is represented by the dark gray columns, and standard deviations are represented by the white columns.

FIG. 8 discloses a bar graph depicting the number (with standard deviation) of Replikins per 100 amino acids in the eight genes of H5N1 influenza virus identified annually in humans between 2003 and 2006. A significant increase is observed in the pB1 gene area as compared to the other seven genes of the H5N1 influenza virus strain.

FIG. 9 discloses a graph depicting the number (with standard deviation) of Replikins per 100 amino acids in the pB1 gene area (Replikin Peak Gene) of H5N1 influenza virus strains identified annually in duck and chicken in years 2001 through 2006, in goose in years 2001 and 2003 through 2006, and in human in years 2003 through 2006. The increase in Replikin concentration in these species over time correlates with an increase in virulence of the H5N1 virus strain over the same time period and correlates with an increase in mortality rate in humans during that time period. Changes in Replikin concentration in the Replikin Peak Gene of the H5N1 isolates in FIG. 9 allows for identification of those hosts in which the influenza virus strain is more virulent than other hosts.

FIG. 12 illustrates a remarkable constancy of low coronavirus Replikin concentration between 1995 and 2001 in the spike proteins, followed by a dramatic increase in 2002, one year before the SARS epidemic appeared in 2003.

FIG. 16 is a graph of the data disclosed in Table 10. The graph demonstrates that an increase in Replikin concentration is magnified in its correlation with human mortality when restricted from changes in Replikin concentration in the entire genome to changes in Replikin concentration in the polymerase gene and magnified even more when restricted solely to the Replikin Peak Gene identified using the methods described herein. In FIG. 16, a correlation was established between human mortality and (1) mean concentration of Replikin sequences in the whole genome, (2) mean concentration of Replikin sequences in the polymerase gene, and (3) mean concentration of Replikin sequences in the Replikin Peak Gene (pB1 gene area) of H5N1 influenza strains. As Replikin concentration increased by these three measures, human mortality was observed to increase. However, while all three measures provided a correlation with human mortality, changes in the Replikin concentration in the polymerase gene correlated more significantly with human mortality, and changes in the Replikin concentration in the Replikin Peak Gene (pB1 gene area) of the H5N1 genome correlated still more significantly with human mortality. FIG. 16 suggests, therefore, that identification of Replikin Peak Genes within viral genomes improves identification and prediction of virulence and mechanisms of virulence using Replikin concentration data.

FIG. 17 graphically compares percent human mortality from H5N1 infections in years 2005 through the first quarter of 2007 to mean concentration of Replikin sequences in (1) the pB1 gene area, (2) the pB2 gene area, and (3) the pA gene area, respectively, of H5N1 influenza strains isolated in 2003 through the first quarter of 2007. FIG. 17 illustrates a significant correlation between human mortality and the Replikin Peak Gene (pB1 gene area) of isolates of H5N1 influenza virus. No correlation is observed in neighboring gene areas of the pB1 gene area. In addition to the correlative aspect of the increase in Replikin concentration being related to percent mortality, FIG. 17 (graphically representing part of the data in Table 10) provides strong confirmation of the power and validity of the methodology of predicting changes in virulence and outbreaks of virus by monitoring changes in Replikin concentration.

DETAILED DESCRIPTION OF THE INVENTION

Definitions

Figure 1:
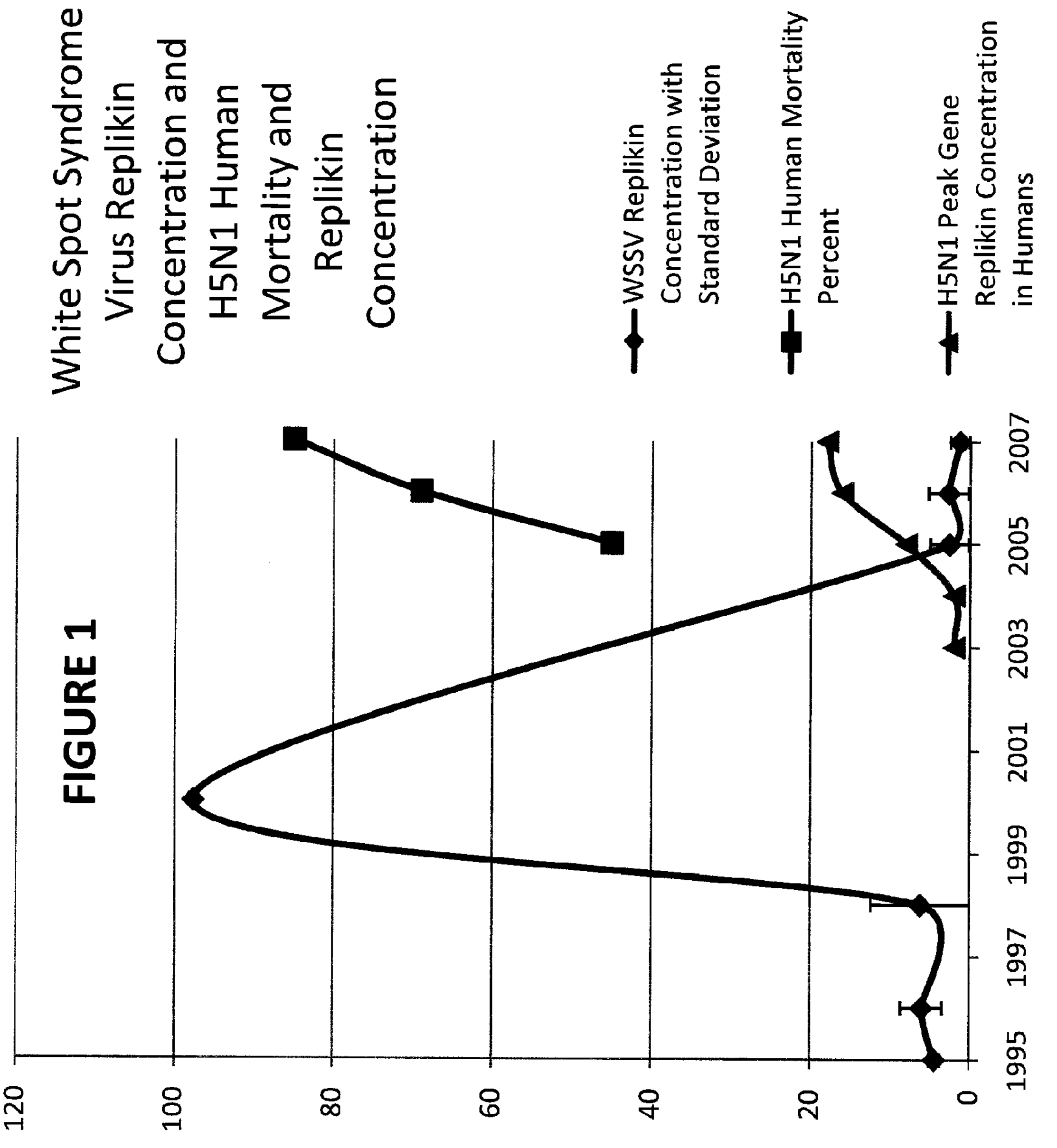
FIG. 1 illustrates a correlation between (1) the mean concentration and standard deviation of Replikin sequences observed in amino acid sequences of White Spot Syndrome Virus (WSSV) isolated between 1995 and 2007 that have publicly available accession numbers at www.pubmed.com, (2) the mean concentration of Replikin sequences in the pB1 gene area of H5N1 strains of influenza virus isolated in 2003, 2004, 2005, 2006, and 2007 that have publicly available accession numbers at www.pubmed.com, and (3) the mean mortality rate for humans infected with H5N1 influenza virus isolated in 2005, 2006 and 2007. The data demonstrate an exceptionally high Replikin sequence concentration in WSSV in 2000 followed within three years by an increase in Replikin sequence concentration in H5N1 isolates (from 2003 through 2007) and a concomitant outbreak of H5N1 influenza in humans with rising mortality.

As used herein, "animal" includes mammals, such as humans.

As used herein, the term "peptide" or "protein" refers to a compound of two or more amino acids in which the carboxyl group of one amino acid is attached to an amino group of another amino acid via a peptide bond. As used herein, "isolated" or "synthesized" peptide or biologically active portion thereof refers to a peptide that is, after purification, substantially free of cellular material or other contaminating proteins or peptides from the cell or tissue source from which the peptide is derived, or substantially free from chemical precursors or other chemicals when chemically synthesized by any method, or substantially free from contaminating peptides when synthesized by recombinant gene techniques. An "encoded" protein, protein sequence, protein fragment sequence, or peptide sequence is a sequence encoded by a nucleic acid sequence that encodes the amino acids of the protein or peptide sequence with any codon known to one of ordinary skill in the art now or hereafter. It should be noted that it is well-known in the art that, due to redundancy in the genetic code, individual nucleotides can be readily exchanged in a codon and still result in an identical amino acid sequence. As will be understood by one of skill in the art, a method of identifying a Replikin amino acid sequence also encompasses a method of identifying a nucleic acid sequence that encodes a Replikin amino acid sequence wherein the Replikin amino acid sequence is encoded by the identified nucleic acid sequence.

As used herein, a Replikin sequence is an amino acid sequence having about 7 to about 50 amino acids comprising:

(1) at least one lysine residue located six to ten amino acid residues from a second lysine residue;
(2) at least one histidine residue; and
(3) at least 6% lysine residues.

A Replikin sequence may comprise a terminal lysine and may further comprise a terminal lysine or a terminal histidine. A Replikin peptide or Replikin protein is a peptide or protein consisting of a Replikin sequence. A Replikin sequence may also be described as a Replikin sequence of about 7 to about 50 amino acids comprising or consisting of a Replikin motif wherein the Replikin motif comprises:

(1) at least one lysine residue located at a first terminus of said isolated influenza virus peptide and at least one lysine residue or at least one histidine residue located at a second terminus of said isolated influenza virus peptide;
(2) a first lysine residue located six to ten residues from a second lysine residue;
(3) at least one histidine residue; and
(4) at least 6% lysine residues.

For the purpose of determining Replikin concentration, a Replikin sequence must have a lysine residue at one terminus and a lysine or a histidine residue at the other terminus.

The term "Replikin sequence" can also refer to a nucleic acid sequence encoding an amino acid sequence having about 7 to about 50 amino acids comprising:

(1) at least one lysine residue located six to ten amino acid residues from a second lysine residue;
(2) at least one histidine residue; and
(3) at least 6% lysine residues, wherein the amino acid sequence may comprise a terminal lysine and may further comprise a terminal lysine or a terminal histidine.

As used herein, a Replikin Peak Gene (RPG) or a Replikin Peak Gene Area (RPGA) are used interchangeably to mean a segment of a genome, protein, segment of protein, or protein fragment in which an expressed gene or gene segment has a highest concentration of continuous, non-interrupted and overlapping Replikin sequences (number of Replikin sequences per 100 amino acids) when compared to other segments or named genes of the genome. Generally, the gene or gene segment associated with a whole protein or protein-expressing gene is known as the Replikin Peak Gene and the gene or gene segment associated with a protein fragment is known as a Replikin Peak Gene Area. More than one RPG or RPGA may be identified within a gene, gene segment, protein, or protein fragment. An RPG or RPGA may have a terminal lysine or a terminal histidine, two terminal lysines, or a terminal lysine and a terminal histidine. An RPG or RPGA may likewise have neither a terminal lysine or a terminal histidine as long as it contains a Replikin sequence or Replikin sequences defined by the definition of a Replikin sequence, namely, an amino acid sequence having about 7 to about 50 amino acids comprising:

(1) at least one lysine residue located six to ten amino acid residues from a second lysine residue;
(2) at least one histidine residue; and
(3) at least 6% lysine residues.

As used herein, "reservoir" is any source of Replikin sequences that may be shared with an influenza virus including any host of influenza virus, any food source of a host of the influenza virus, any vector of influenza virus, or any substance wherein the genetic information of the influenza virus may be shared, mingled, mixed, exchanged, or come into the proximity of the Replikin sequences of the reservoir.

As used herein, "different time periods" or "different time points" is any two time periods or points that may be differentiated one from another. For example, an isolate of virus isolated during the year 2004 is isolated in a different time period than an isolate of the same virus isolated during the year 2005. Likewise, an isolate of virus isolated in May 2004 is isolated in a different time period than an isolate of the same virus isolated in June 2004. When comparing Replikin concentrations of different isolates, it is preferred to use comparable time periods for comparison. For example, an isolate from 2004 is preferably compared to at least one other isolate from some other year such as 2002 or 2005. Likewise, an isolate from May 2004 is preferably compared to at least one isolate from some other month of some year, for example, an isolate from December 2003 or from June 2004. An isolate is any virus isolated from a natural source wherein a natural source includes, but is not limited to, a reservoir of a virus, a vector of a virus or a host of a virus. "Obtaining" an isolate is any action by which an amino acid or nucleic acid sequence within an isolate is obtained including, but not limited to, isolating an isolate and sequencing any portion of the genome or protein sequences of the isolate, obtaining any nucleic acid sequence or amino acid sequence of an isolate from any medium, including from a database such as PubMed, wherein the nucleic acid sequence or amino acid sequence may be analyzed for Replikin concentration, or any other means of obtaining the Replikin concentration of a virus isolated from a natural source at a time point.

As used herein, an "earlier-arising" virus or organism is a specimen of a virus or organism collected from a natural source of the virus or organism on a date prior to the date on which another specimen of the virus or organism was collected from a natural source. For viruses, a natural source includes, but is not limited to, a reservoir of a virus, a vector of a virus, or a host of the virus. A "later-arising" virus or organism is a specimen of a virus or organism collected from a natural source of the virus (including, but not limited to, a reservoir, a vector, or a host) or a natural source of the organism on a date subsequent to the date on which another specimen of the virus or organism was collected from a natural source.

As used herein, "emerging strain" refers to a strain of a virus identified as having an increased or increasing concentration of Replikin sequences in one or more of its protein sequences relative to the concentration of Replikins in other strains of such organism. The increased or increasing concentration of Replikins occurs over a period of preferably at least about six months, at least about one year or at least about three years, but may be a much shorter period of time for highly mutable viruses. An emerging strain of virus indicates an increase in virulence or replication.

As used herein, "bird" is any avian species including migratory and domestic birds, wherein said migratory and domestic birds includes, for example, chickens, ducks of all kinds, geese, pigeons, gulls, seabirds etc.

As used herein, "outbreak" is an increase in virulence, morbidity or mortality in a viral disease as compared to a baseline of an earlier occurring epidemiological pattern of infection in the same viral disease. One of ordinary skill in the art will know how to determine an epidemiological baseline.

As used herein, "morbidity," is the number of cases of a disease caused by the virus, either in excess of zero cases in the past or in excess of a baseline of endemic cases in the past. Therefore the baseline of endemic cases, in epidemiological terms, may, for example, relate to whether no or some cases were present in a geographic region in the immediate past. The past, in epidemiological terms, may mean more than one year and can mean several years or more as understood by one of ordinary skill in the art. The past may also mean less than one year as determined by one of ordinary skill in the art. In the case of annually-recurrent common influenza, for example, the baseline reflects an annual recurrence of common influenza.

As used herein, "mutation" refers to a change in the structure and properties of a virus or organism caused by substitution of amino acids. In contrast, the term "conservation" as used herein, refers to conservation of particular amino acids due to lack of substitution. A "point mutation" may refer to a change in a single amino acid residue or may refer to a change in a small number of amino acid residues.

As used herein, "replikin count" or "replikin concentration" refers to the number of Replikins per 100 amino acids in a protein, protein fragment, virus, or organism. A higher Replikin concentration in a first strain of a virus or organism has been found to correlate with more rapid replication of the first virus or organism as compared to a second, earlier-arising or later-arising strain of the virus or organism having a lower Replikin concentration.

As used herein a "Replikin Scaffold" refers to a series of conserved Replikin peptides wherein each of said Replikin peptide sequences comprises about 16 to about 34 amino acids, and preferably about 27 to about 33 amino acids and further comprises: (1) a terminal lysine and optionally a lysine immediately adjacent to the terminal lysine; (2) a terminal histidine and optionally a histidine immediately adjacent to the terminal histidine; (3) a lysine within 6 to 10 amino acid residues from another lysine; and (4) about 6% lysine. "Replikin Scaffold" also refers to an individual member or a plurality of members of a series of Replikin Scaffolds.

In an influenza virus, a Replikin Scaffold may refer to a Replikin peptide sequence comprising about 16 to about 34 amino acid residues, and in a preferred embodiment about 28 to about 30 amino acid residues. In a White Spot Syndrome Virus, a Replikin Scaffold may refer to a Replikin peptide sequence comprising about 16 to about 34 amino acid residues, and in a more preferred embodiment about 29 to about 31 amino acid residues. In a Taura Syndrome Virus, a Replikin Scaffold may refer to a Replikin peptide sequence comprising about 16 to about 34 amino acid residues, and in a more preferred embodiment about 29 to about 33 amino acid residues.

Predicting Virulence by Determining Replikin Concentration in Viral Reservoirs, Vectors and Hosts The inventors provide herein methods of predicting outbreaks of influenza by monitoring the presence and/or concentration of Replikin sequences both throughout the virus and in specific highest concentrations of Replikins in areas designated as Replikin Peak Genes, Replikin Peak Gene Areas and/or Replikin Scaffold sequences in WSSV and TSV in shrimp and influenza viruses.

Before identification of the Replikin structure in virus proteins there existed no quantitative measure of virus structure that correlated quantitatively with rapid replication or that gave advance warning of virus outbreaks or emerging virus disorders.

Since the identification of the Replikin structure, correlation between increased concentrations of Replikin sequences and increased replication and virulence has been observed in a range of viruses and organisms. These observations are made more accurate by the present isolation in silico of Replikin Peak Genes. A Replikin Peak Gene includes the area in a genome, protein, or protein fragment that has the highest concentration of Replikin sequences. While increased concentration of Replikin sequences in the genome of a virus offers both advance warning and new targets for developing effective methods of predicting and treating viral outbreaks, identification of an increase in concentration of Replikin sequences in a Replikin Peak Gene of a genome or protein heightens the predictive capacity of the change in Replikin concentration and the efficacy of new targets.

For example, more precise predictions of increased virulence are now available through identification of a Replikin Peak Gene in, among other viruses, the H5N1 strain of influenza (FIGS. 3 and 8-10), the H3N8 strain of influenza that causes equine influenza (FIG. 15), West Nile Virus (FIG. 13), Foot and Mouth Disease Virus (FIG. 14) and White Spot Syndrome Virus (Example 1). In these and other viruses, increased concentration of Replikin sequences in the whole genome, in a protein of the genome, or in a Replikin Peak Gene of the genome offer both advance warning and new targets for developing effective methods of predicting and treating viral outbreaks.

By monitoring changes in concentrations of Replikin sequences in viral genomes generally, emerging viral diseases can be identified in virus reservoirs and vectors in advance of their appearance in animal or human hosts. Identification of the emerging viruses and the Replikin sequences within the virus genome allows for appropriate, advance control efforts, including isolation and quarantine, and provides sufficient time for the synthesis and testing of vaccines specific to the sequences of the emerging virus.

Replikin sequences that had previously been shown to pass between several strains of the same virus, as in the H1N1, H2N2, H2N3 and H5N1 strains of influenza A virus, have now been found to pass between different viruses as well as different hosts, as though the Replikin structure is the key infectious and lethal unit of the disease and the virus is the carrier or vector of this infectious and lethal unit. Viewing the Replikin structure as an infectious unit of disease then allows the host organism or the virus itself to be viewed (at any given point in the infectious cycle) as a host, a reservoir, or a vector for Replikin units shared by viruses, host organisms, and vector organisms in the infectious pathway of the disease.

Identification of Replikin sequences as infectious units (and providing particular areas in the genome, i.e. Replikin Peak Genes, where those infectious units are correlated most significantly with virulence) has allowed the inventors to focus attention on the geographic area (see FIG. 10), the host (see FIG. 9), and the particular area of the genome of a virus (see FIG. 8) wherein virulence mechanisms are located and thereby increased virulence may be identified and predicted. Because the inventors have provided a method of focusing on particular units of a viral genome, the skilled artisan will understand the importance of looking for Replikin sequences in any portion of the life cycle or infectious pathway of a virus. For example, as described herein, the skilled artisan will understand that predictive and virulence-related Replikin sequences (or concentrations of Replikin sequences in Replikin Peak Genes) may be identified in reservoirs of influenza virus such as in WSSV and TSV. The skilled artisan will further understand that predictive and virulence-related Replikin sequences or Replikin Peak Genes may be identified in vectors of the influenza virus. The skilled artisan will additionally understand that predictive and virulence-related Replikin sequences or Replikin Peak Genes may be identified in hosts of the influenza virus or in any other place where viral genes may be located or wherein viral genetic information may encounter genetic information of other strains of virus, of other virus species, of vectors of the virus, of hosts of the virus, or of food sources of hosts of the virus. This method of locating relevant Replikin sequences finds support in the inventors' disclosure of data providing insight into what sequence changes in influenza since 1917 were due to "drift" or "shift" or, on the other hand, what sequence changes in influenza since 1917 were due to conservation, storage in "reservoirs," and reappearance in both intermediate vectors and eventual animal and human hosts. The data has shown that the epidemic-related increase in Replikin concentration is not due to the duplication of existing Replikins in the hemagglutinin of the emerging strain, but instead is due to the reappearance of at least one Replikin composition from 1 to up to 59 years after its disappearance, plus (in the A strains only) the emergence of new strain-specific Replikin compositions. See U.S. Pat. No. 7,189,800 issued Mar. 13, 2007 (Tables 3-6).

In another embodiment of the invention, an automated prediction of an outbreak of influenza virus is made by (1) measuring the Replikin concentration in a WSSV or TSV isolate structure, or other reservoir virus structure (2) comparing the measured concentration to the Replikin concentration determined at a previous time point in the same virus structure, and (3) observing an increase in Replikin concentration in that virus structure. If an increase has occurred, an outbreak within about one to about three years following the latest time point is predicted. In a further embodiment, the increase from one time point to another time point is statistically significant.

Figure 16:
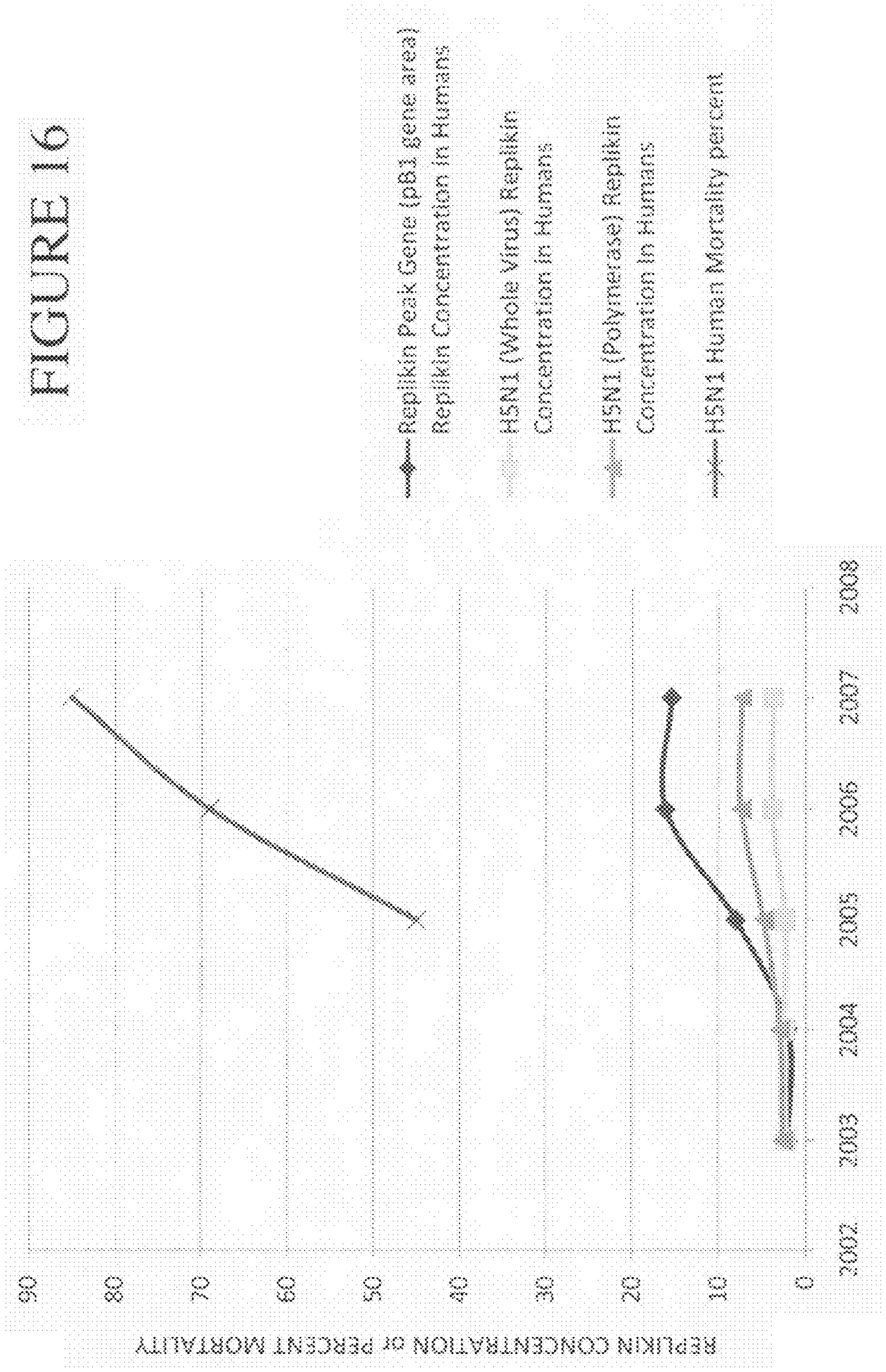
FIG. 16 illustrates a magnification of the effect of increases in Replikin concentration on human mortality from H5N1 infections when Replikin concentration is observed in the Replikin Peak Gene (pB1 gene area) as compared to the polymerase gene or compared to the entire genome of the H5N1 virus.
Figure 17:
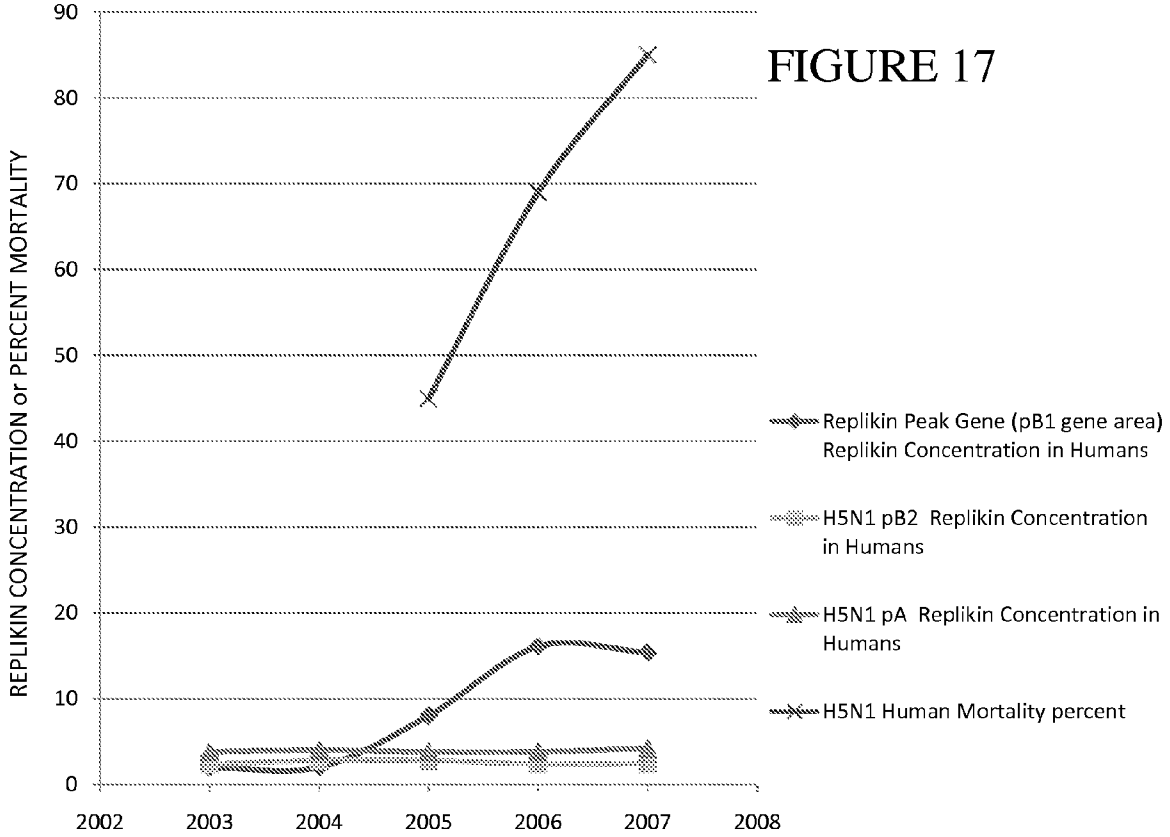
FIG. 17 illustrates a significant eight-fold increase in Replikin concentration in the pB1 gene area (Replikin Peak Gene) of isolates of H5N1 from 2003 through the first quarter of 2007 (that correlates with an increase in host mortality in humans), while no significant increase is observed in neighboring gene areas of the pB1 gene area, namely, the pA gene area and the pB2 gene area.

The magnitude of a Replikin increase in a virus may be a quantitative component of predicting an outbreak. For example, in H5N1 influenza virus, a two-fold (200%) increase in Replikin concentration predicted an outbreak of the virus in humans. See FIG. 16 and Example 9. Further, an eight-fold (800%) increase in the Replikin Peak Gene of the virus predicted the same outbreak, which included new morbidity and increased mortality in infections from the virus. See FIG. 17 and Example 9.

Replikin Concentration in WSSV and TSV Predicts Human Influenza Outbreaks

The present inventors have discovered that two viruses, White Spot Syndrome Virus (WSSV) (also known as white spot baculoform virus) and Taura Syndrome Virus (TSV), both global lethal pathogens for shrimp, are reservoirs for the peptide building blocks of influenza virus, including the H5N1 strain of influenza virus. The concentration of Replikins in WSSV, TSV, and in influenza has been shown to be related to rapid replication and epidemics in each of these viruses. An increase in the concentration of Replikin sequences has been correlated with the last three influenza pandemics of 1918, 1957 and 1968. See FIG. 11. Quantitative determination of the concentration of virus Replikins has made it possible to predict in advance recent influenza outbreaks including outbreaks of the H5N1 strain of influenza. Quantitative determination of the concentration of Replikins in viruses for which nucleic acid or protein sequences are available may now be automated using the proprietary FluForecast®, which is available from Replikins, LLC, Boston Mass.

The H5N1 virus recently has been responsible for huge poultry losses in many countries and for several hundred human cases with approximately 50% mortality. While migratory waterfowl are known to transport H5N1 influenza virus globally, no reservoirs for the virus had yet been identified. The inventors, however, have now identified shrimp as a reservoir for homologous Replikin sequences identified in White Spot Syndrome Virus (WSSV) and Taura Syndrome Virus (TSV). The homologous Replikin sequences have been identified in both shrimp and influenza virus and in particular in the H5N1 "bird flu" strain of influenza virus in both birds and humans.

Beginning with evidence of a sharing of homologous Replikin sequences among the three viruses, namely, WSSV, TSV, and strains of influenza virus including H5N1, the inventors identified a correlation between an increase in Replikin concentration in WSSV and/or TSV and an increase in virulence (and a concomitant increase in Replikin concentration) in the H5N1 strain of influenza virus. The inventors further identified homologous Replikin sequences shared within and between the virus strains including Replikin Scaffold sequences, the presence of which have been associated with high virulence, epidemics and pandemics.

Using these correlations and observations, the inventors have now devised a method of predicting an outbreak of influenza virus comprising:

(1) obtaining a plurality of isolates of White Spot Syndrome Virus or a plurality of isolates of Taura Syndrome Virus wherein at least one of said isolates of White Spot Syndrome Virus is isolated about six months to about 3 years later than at least one other of said isolates of White Spot Syndrome Virus, or wherein at least one of said isolates of Taura Syndrome Virus is isolated about six months to about 3 years later than at least one other of said isolates of Taura Syndrome Virus;

(2) analyzing the amino acid sequence of at least one encoded protein or protein fragment or a combination of encoded proteins and/or protein fragments in each isolate of the plurality of isolates of White Spot Syndrome Virus or the plurality of isolates of Taura Syndrome Virus for the presence and concentration of encoded Replikin sequences;

(3) comparing the concentrations of encoded Replikin sequences in the at least one protein or protein fragment or in the combination of proteins or protein fragments in each isolate of the plurality of isolates of White Spot Syndrome Virus or in each isolate of the plurality of isolates of Taura Syndrome Virus;

(4) identifying an increase in the concentration of encoded Replikin sequences in said plurality of isolates of White Spot Syndrome Virus or in said plurality of isolates of Taura Syndrome Virus over at least one time period of about six months or greater, at least about one year or greater, or at least about three year to five years; and (5) predicting an outbreak of influenza within about one to about three years following said identified increase in the concentration of Replikin sequences in said isolates of White Spot Syndrome Virus or in the concentration of Replikin sequences in said isolates of Taura Syndrome Virus.

Prediction of an outbreak of influenza may further comprise:

(1) identifying at least one Replikin Scaffold sequence present in at least one isolate of the plurality of isolates of White Spot Syndrome Virus identified as having an increase in the concentration of Replikin sequence as compared to at least one other isolate of the plurality of isolates of White Spot Syndrome Virus over a time period of about six months or greater, or identifying at least one Replikin Scaffold sequence present in at least one isolate in the plurality of isolates of Taura Syndrome Virus identified as having an increase in the concentration of Replikin sequences as compared to at least one other isolate of the plurality of isolates of Taura Syndrome Virus over a time period of about six months or greater;

(2) identifying at least one Replikin Scaffold sequence present in at least one isolate of a strain of influenza virus; and (3) predicting the strain of influenza virus in which the at least one Replikin Scaffold sequence is identified as the strain of virus that will likely cause the predicted outbreak of influenza virus wherein a Replikin Scaffold is a peptide having about 16 to about 34 amino acids comprising (a) a terminal lysine and optionally a lysine immediately adjacent to the terminal lysine; (b) a terminal histidine and optionally a histidine immediately adjacent to the terminal histidine, (c) a lysine within about 6 to about 10 amino acids of another lysine; and (d) at least 6% lysines.

In an influenza virus, a Replikin Scaffold may refer to a Replikin peptide sequence comprising about 16 to about 34 amino acid residues and in a preferred embodiment about 28 to about 30 amino acid residues. In a White Spot Syndrome Virus, a Replikin Scaffold may refer to a Replikin peptide sequence comprising about 16 to about 34 amino acid residues, and in a more preferred embodiment about 29 to about 31 amino acid residues. In a Taura Syndrome Virus, a Replikin Scaffold may refer to a Replikin peptide sequence comprising about 16 to about 34 amino acid residues, and in a more preferred embodiment about 29 to about 33 amino acid residues.

The shrimp industry understands that a first clue that virus infection from WSSV or TSV has occurred in shrimp ponds is observation of the death of migratory birds on the periphery of the pond. This observation suggested to the inventors that shrimp and birds shared some pathogenic mechanism related to shrimp infection with WSSV and/or TSV. By analyzing Replikin concentrations in publicly available amino acid sequences of WSSV, TSV and H5N1 isolates of virus using FluForecast® software available through Replikins, LLC, Boston, Mass., USA, the following findings were obtained, which demonstrated that the shrimp viruses WSSV and TSV serve as a reservoir of Replikin peptide building blocks for H5N1 and other influenza strains:

1) The shrimp viruses WSSV and TSV were found to contain Replikin peptide sequences and an increase in concentration in these sequences was correlated with specific outbreaks of the virus.

2) These shrimp virus sequences were found to be related in structure to Replikin peptide sequences in H5N1 and other strains of influenza virus that had been specifically associated with virulence, epidemics, pandemics and human mortality in influenza.

3) Shrimp WSSV Replikins increased markedly in concentration in the year 2000, just before an increase in Replikin concentration in H5N1 that directly preceded H5N1 outbreaks in chickens, other birds, and humans between 2001-2006. The increase in shrimp virus Replikin concentration was not trivial. In shrimp WSSV, which in dormant states was found to have well less than 10 Replikin sequences within 100 amino acids, Replikin concentration reached the remarkable height of 103.8 in an isolate in 2000 and a mean of 97.6 among all isolates with publicly available protein sequences. See Example 4. The remarkable Replikin concentration of 103.8 is comparable only to the highest Replikin concentration so far observed in any organism in nature, namely, *P. falciparum*, which has the highest Replikin concentration to date—111 Replikin sequences observed per 100 amino acid residues. *P. falciparum* is a cause of malaria and has been observed to replicate 11,000 times in 48 hours when passing in its life cycle from the liver to blood in its host.

4) Of the new shrimp Replikins that appeared in 2000, the percent that were short peptides was increased compared to dormant years. Short Replikins previously have been found to be related to high virulence and high mortality in the host, whether animal or man. See. e.g., U.S. application Ser. No. 10/860,050, filed Jun. 4, 2004.

5) These short shrimp virus Replikins share structures with short Replikins in both H5N1 and other influenza strains going back 89 years to the great pandemic of 1918.

6) Replikin Scaffold sequences were identified in proteins of WSSV and TSV that were highly homologous with Replikin Scaffold sequences in highly virulent strains of influenza virus including the H5N1 strain.

The occurrence of the major WSSV outbreak in the year 2000 places WSSV temporally in line with the influenza outbreaks that occurred successively in other hosts: (1) in ducks in 2004-2005; (2) in chickens in 2005-2006; and (3) in humans in 2006-2007. See FIG. 9. Each outbreak was preceded by major increases in the respective Replikin concentrations of the virus and in the Replikin concentrations of their Replikin Peak Genes. See, e.g., U.S. Appln. Ser. No. 60/898,097, filed Jan. 30, 2007, FIGS. 1-4. An outbreak of TSV in 2000 likewise was temporally in line with the influenza outbreaks of 2001-2007.

The mortality rate of shrimp for the WSSV shrimp virus is 80-100% and, as shown above, the Replikin concentration during outbreaks has exceeded 100 Replikin sequences per 100 amino acid residues. The Replikin concentrations and the mortality rates in H5N1 have not been as high in ducks and chickens. Replikin concentrations of twenty in the Replikin Peak Gene of H5N1 have been observed in humans in Indonesia along with mortality rates of approximately 80% in a small number of humans in 2006-2007. See U.S. application. Ser. No. 11/755,597, filed May 30, 2007, pages 36-39.

While Applicants do not wish to be constrained by theory, this evidence may reflect migration or vectoring of Replikin sequences between species, or may reflect successive independent stimulation of influenza strains in different hosts, or both, or even some other yet-to-be-determined mechanism. Data that supports migration of Replikin sequences between different strains of influenza virus rather than independent synthesis has been reported in previous patent applications by the Applicants (see, e.g., U.S. Pat. No. 7,189,800 and U.S. application Ser. No. 11/355,120, filed Feb. 16, 2006), but the present evidence of relation of shrimp viruses to influenza viruses is the first evidence of inter-virus species migration of Replikins. In effect, the "infectious unit" of a virus may not be the whole virus but, instead, a relatively small constituent of the virus structure, namely Replikin sequences.

Replikin Scaffold Sequences in WSSV, TSV, and Influenza

Replikin Scaffold sequences so far identified in WSSV begin with KK and end with H. The length of the Scaffold Sequence is about 27 to 31, which is similar to the about 28 to about 29 amino acid Replikin Scaffolds generally observed in the H5N1, H1N1, H2N2, H2N3, and H7N7 strains of influenza virus. The following Replikin Scaffold repeats were identified in Accession No. AAL89390, which discloses a 2000 isolate of WSSV.

(SEQ ID NO: 1)
$K^{66}$KNVKSAKQLPHLKV<u>H</u>LDV<u>K</u>SAKQLPHLKVH$^{96}$ (SEQ ID NO: 2)
$K^{160}$KNVKSAKQLPHLKV<u>H</u>LDV<u>K</u>GVKQLLH$^{186}$ (SEQ ID NO: 3)
$K^{239}$KNVKSAKQLPHLKV<u>L</u>LDV<u>R</u>GAKQLPH$^{265}$ (SEQ ID NO: 3)
$K^{303}$KNVKSAKQLPHLKV<u>L</u>LDV<u>R</u>GAKQLPH$^{329}$ (SEQ ID NO: 4)
$K^{397}$KNVKSAKQLPHLKV<u>L</u>LDV<u>R</u>GAKQLPHLKVH$^{427}$.

In the above-listed Replikin Scaffolds, the orderly substitution of H for L in positions 81 and 175 and K for R in positions 85 and 179 both result in an increase in the number of Replikins per 100 amino acids, i.e. in an increase in the Replikin concentration. The phenomenon of Replikin scaffolding also has been observed in *P. falciparum* (malaria). The substitution of lysines and histidines resulting in increased Replikin concentration and increased virulence also has been observed by the applicants in H5N1 in a Replikin Scaffold in China (See U.S. application Ser. No. 11/755,597, filed May 30, 2007, Table 1). The homologous structural properties in shrimp WSSV and TSV and influenza provide continuing support for the structural relationship between Replikin sequences in WSSV and TSV and influenza viruses.

Accordingly one aspect of the invention provides a method of predicting an influenza outbreak by correlating an increase in Replikin concentration in shrimp WSSV and/or TSV over Replikin concentration in previous isolates of WSSV and/or TSV with an increase in virulence and/or replication of influenza viruses.

Presence of Replikin Scaffold is Predictive of Epidemics

The inventors have established that the presence of Replikin Scaffolds in influenza strains is predictive of epidemics. As such, in addition to the total number of Replikins in a virus, the structure of each Replikin through time is informative. Table 1 shows a Replikin Scaffold first observed in a goose infected with influenza in 1917 (Goose Replikin). Constant length, constant lysines at the amino terminal and histidine residues at the carboxy terminal were conserved in different strains in a fixed scaffold for decades. Homologues of the Goose Replikin appeared from 1917 through 2006 in strains including each strain responsible for the three pandemics of 1918, 1957, and 19681, H1N1, H2N2 and H3N2, and with further substitutions between H1N2, H7N7, H5N2 and H5N1.

TABLE 1

Replikin Scaffold showing ordered substitution in the 89 year conservation of influenza virus Replikin peptides related to rapid replication, from a 1917 goose influenza Replikin and the 1918 human pandemic Replikin to 2006 H5N1 "Bird Flu" homologues. (SEQ ID NOS: 368-430, respectively, in order of appearance)

| \|<--------------29 Amino Acids------------→\| | Year | Strain |
|---|---|---|
| **kk**gtsyp**k**ls**k**sytnn**k**g**k**evlvlwgv**hh** | 1917 | H1N_Influenza Goose Replikin |
| **kk**g[redacted]syp**k**ls**k**sy[redacted]nn**k**g**k**evlvlwgv**hh** | 1918 | H1N1 Human Influenza Pandemic |
| **kk**[redacted]syp**k**ls**k**sy[redacted]nn**k**g**k**evlvlwgv**hh** | 1930 | H1N1 |
| **kk**g[redacted]syp**k**l[redacted]sy[redacted]nn**k**g**k**evlvlwgv**hh** | 1933 | H0N1 |
| **kk**gtsyp**k**ls**k**sytnn**k**g**k**evlvlwgv**hh** | 1976 | H1N1 |
| **kk**gtsyp**k**ls**k**sytnnkg**k**evlvlwgv**hh** | 1977 | H1N1 |

TABLE 1-continued

Replikin Scaffold showing ordered substitution in the 89 year conservation of influenza virus Replikin peptides related to rapid replication, from a 1917 goose influenza Replikin and the 1918 human pandemic Replikin to 2006 H5N1 "Bird Flu" homologues. (SEQ ID NOS: 368-430, respectively, in order of appearance)

| \|<--------------29 Amino Acids------------>\| | Year | Strain |
|---|---|---|
| kkg sypklsksytnnkgkevlv wgvhh | 1979 | H1N1 |
| kkg sypklsksytnnkgkevlv wgvhh | 1980 | H1N1 |
| kkgtsypklsksytnnkgkevlvlwgvhh | 1980 | H1N1 |
| kkg sypklsksytnnkgkevlv wgvhh | 1981 | H1N1 |
| kkgtsypklsksytnnkgkevlvlwgvhh | 1981 | H1N1 |
| kkgtsypklsksytnnkgkevlvlwgvhh | 1985 | H1N1 |
| kkg sypklsksytnnkgkevlv wgvhh | 1991 | H1N1 |
| kkg sypklsksytnnkgkevlv wgvhh | 1992 | H1N1 |
| kkg sypklsksytnnkgkevlv wgvhh | 1996 | H1N1 |
| kkg sypklsksytnnkgkevlv wgvhh | 1996 | H1N1 |
| kkg sypklsksy nnkgkevlvlwgvhh | 1997 | H1N1 |
| kkg sypklsksy nnkgkevlvlwgvhh | 1998 | H1N1 |
| kkg sypklsksytnnkgkevlv wgvhh | 1999 | H1N1 |
| kkg sypklsksytnnkgkevlv wgvhh | 2000 | H1N1 |
| kkg sypklsksytnnkgkevlv wgvhh | 2001 | H1N1 |
| kkg sypklsksytnnkgkevlv wgvhh | 2002 | H1N1 |
| kkg sypk sksy nnk kevlvlwg hh | 1999 | H1N2 Influenza |
| kkg sypklsksy nnk kevlv wg hh | 2000 | H1N2 |
| kkg sypklsksy nnkgk vlvlwg hh | 2001 | H1N2 |
| kkgtsypklsksytnnk kevlvlwgvhh | 2001 | H1N2 |
| -k yp lsksyannk kevlvlwgvhh | 2002 | H1N2 |
| -k yp lsksy nnk kevl lwgvhh | 2002 | H1N2 |
| kkg yp sy n g l wgvhh | 1957 | H2N2 Human Influenza Pandemic |
| kkg yp sy n g l wg hh | 1957 | H2N2 Human Influenza Pandemic |
| kk sypkl ks nk lv wg hh | 1968 | H3N2 Human Influenza Pandemic |
| ----------ksy n l wg hh | 1979-2003 | H7N7 Influenza |
| kk yp y n l lwg hh | 2002 | H5N2 Influenza |
| kk yp sy n lvlwg hh | 1959 | H5N1 Influenza (Scotland) |
| kk yp y n l lwg hh | 1975 | H5N1 (Wisconsin) |
| kk yp y n l lwg hh | 1981 | H5N1 (Minnesota) |
| kkg yp y n l lwg hh | 1983 | H5N1 (Pennsylvania) |
| kk yp sy n l lwg hh | 1988 | H5N1 (Scotland) |
| kk yp sy n lvlwg hh | 1996 | H5N1 (China) |
| kk yp sy n lvlwg hh | 1997 | H5N1 (China) |
| kk yp sy n lvlwg hh | 1998 | H5N1 (China) |
| kk yp sy n lvlwg hh | 1999 | H5N1 (China) |
| kk yp sy n lvlwg hh | 2000 | H5N1 (China) |
| kk yp sy n lvlwg hh | 2001 | H5N1 (China) |
| kk yp sy n lvlwg hh | 2001 | H5N1 (China) |
| kk yp sy n lvlwg hh | 2002 | H5N1 (China) |
| kk yp sy n lvlwg hh | 2002 | H5N1 (Thailand) |
| kk yp sy n lvlwgihh | 2002 | H5N1 (Vietnam) |
| kk yp sy n lvlwgihh | 2003 | H5N1 (Vietnam) |
| kk yp sy n lvlwgihh | 2003 | H5N1 (Thailand) |
| kk yp sy n lvlwgihh | 2003 | H5N1 (Sindong, China) |
| kk yp sy n lvlwgihh | 2003 | H5N1 (China) |
| kk yp sy n lvmwgihh | 2004 | H5N1 (Vietnam, highly pathogenic) |
| kk yp sy n lvlwgihh | 2004 | H5N1 (Vietnam, highly pathogenic, gull) |
| kk yp sy n lvlwgihh | 2004 | H5N1 (Vietnam highly pathogenic) |
| kk yp sy n lvlwgihh | 2004 | H5N1 (Thailand, highly pathogenic) |
| kk yp sy n lvlwgiqh | 2004 | H5N1 (Thailand, highly pathogenic) |
| kk yp sy n lvlwgihh | 2004 | H5N1 (China, highly pathogenic) |
| kk yp s lvlwgihh | 2004 | H5N1 (China, highly pathogenic, goose) |
| kk yp sy n lvlwgihh | 2004 | H5N1 (Japan) |
| kk yp sy n lvlwgihh | 2005 | HSN1 (Turkey) |
| kk yp ksy n lvlwgihh | 2006 | HSN1 (China, Anhui) |
| kk yp sy n lviwgihh | 2006 | HSN1 (Indonesia, highly pathogenic) |

* Residues identical to Goose Replikin amino acids are unshaded; amino acid substitutions are shaded lightly and darkly to show scaffold pattern across years and strains. Substitution at position 24 in 2004 and 2006 H5N1, 1957 H2N2, 1968 H3N2 and H7N7 are boxed.

Table 1 illustrates the history, by year or smaller time period, of the existence in the protein structure of the Goose Replikin and its homologues in other influenza Replikins. Table 1 further illustrates the history of amino acid substitutions in those homologues and the conservation of certain amino acids of the Replikin structure that are essential to the definition of a Replikin and the function of rapid replication supplied by Replikins.

A review of Table 1 illustrates that if random substitution of amino acids were to occur in virulent strains of influenza from 1917 through the present, certain framework amino acids of the Goose Replikin would not be conserved from year to year in strains in which epidemics occurred. However, contrary to what would result from random substitution, virulent strains of influenza from year to year consistently contain conserved amino acids at those positions that define a Replikin. That is, if a substitution were to occur in one of the amino acids that define a Replikin, e.g. lysine or a histidine, the definition of the Replikin would be lost. Nevertheless, the Replikin sequence is conserved over more than 89 years. Thus, since there is conservation of certain amino acids over decades, substitution cannot be said to be completely at random. The fact that substitutions do occur in amino acids that are not essential to the definition of a Replikin (i.e., amino acids other than lysines or histidines) demonstrates the importance of the Replikin and the Replikin Scaffold in the pathogenicity of the strain.

It may be further noted from Table 1 that when substitutions do occur, they are seen to occur at certain apparently preferred positions of the Replikin Scaffold. Table 1 illustrates recurring substitutions at positions 1, 3-24 and 26-27. Further, while substitutions occur throughout these positions, a lysine continues to exist at a position 6 to 10 amino acids from a second lysine (which has not been substituted in these virulent strains).

Even when there is a substitution of a lysine position within the 29 amino acid stretch, as is seen in 1957, when K at position 11 shifts to position 10, that new position is maintained until 2005. Additionally, YP (at positions 6-7), SY (at positions 12-13), N (at position 15), and LVLWG (SEQ ID NO: 5) (at positions 22-26) conserve the homologous structure of the Replikin Scaffold with few exceptions.

In the 1997H5N1 Hong Kong epidemic, the human mortality rate was approximately 27%. In 2004, of the fifty-two people reported to have been infected by H5N1 in Asia, approximately 70% died. Nine of the eleven people infected in Vietnam from Dec. 28, 2004 to Jan. 27, 2005 died. Although the virulence of the virus appears to have increased, any changes thought to be required for further spread from human to human, had been thought not yet to have occurred. However, the inventors observed substitutions in three H5N1 Replikin amino acid residues at position numbers 18, 24 and 28 of the Goose Replikin scaffold from isolates in Vietnam, Thailand and China in 2004 (see Table 1). Substitution at position number 24 has not occurred since the appearance of H5N1 in 1959 but was present in the last two influenza pandemics caused by other strains, H2N2 in 1957 and H3N2 in 1968, together responsible for over two million human deaths, and in a recent virulent epidemic caused by H7N7 (see Table 1). These data on substitution, combined with the rising Replikin concentration shown in FIG. 4, and the past correlation of such Replikin data with pandemics, predicted the small outbreak of H5N1 in humans in 2006 and 2007.

It is important to note that an extra K has also appeared in the Replikin Scaffold of a 2006 strain of H5N1 in China (Anhui). This presence of an extra K both produces and signals an increase in the Replikin count within the Replikin Scaffold. The 2006 China (Anhui) strain has a Replikin count of 6.6 (as discussed below). A Replikin count of 6.6 is the highest ever observed for an H5N1 strain and is comparable in the entire A strain of influenza only to the Replikin count of the influenza strain that caused the 1918 Pandemic.

Homologous Replikin Scaffold Sequences in Influenza, WSSV, and TSV

The inventors have further established a relationship between virulent influenza virus and WSSV and TSV in the Replikin Scaffold portions of the viruses as may be seen in Table 2 below. Although there is extensive substitution, several short Replikins of the Shrimp White Spot Syndrome Virus demonstrates significant homologies to the influenza virus Replikin sequences, especially with regard to length and key lysine (k) and histidine (h) residues. Similar, but less extensive, homologies are seen in Taura Syndrome Virus. These homologies suggest that the sequences are derived from a shared reservoir and/or that similar mechanisms of Replikin production are used in both virus groups.

TABLE 2

Shrimp White Spot and Taura Syndrome Scaffolding

| | | | |
|---|---|---|---|
| kkgtsypklsksytnnkgkevlvlwgvhh | (SEQ NO: 379) | 1971 | H1N_ Influenza goose peptide |
| kkgnsypklsksytnnkgkevlvlwgvhh | (SEQ NO: 380) | 2002 | H1N1 Swine Influenza |
| kknvksakqlphlkvlkkldvrgakqlph | (SEQ NO: 6) | 2000 | Shrimp White Spot Syndrome Virus |
| -kvhldvkgvkqllhlkvrldvrgakqlh | (SEQ NO: 7) | 2000 | Shrimp White Spot Syndrome Virus |
| kkensypklrksiiinkkevklviwgihh | (SEQ NO: 398) | 1968 | H3N2 Human Influenza Pandemic |
| ----------ksykntrkdpaliiwgihh | (SEQ NO: 399) | 1979-2003 | H7N7 Influenza |
| kkgpnypvakrsynntsgeqmliiwgvhh | (SEQ NO: 396) | 1957 | H2N2 Human Influenza Pandemic |
| kkgpnypvakrsynntsgeqmliiwgihh | (SEQ NO: 397) | 1957 | H2N2 Human Influenza Pandemic |
| kknnayptikrtynntnvedlliiwgihh | (SEQ NO: 400) | 2002 | H5N2 Influenza |
| kknnayptikrsysntnqedllvlwgihh | (SEQ NO: 401) | 1959 | H5N1 Influenza |
| kkvqanktrvfaasnqglalalrryylsfldh | (SEQ NO: 8) | 2000 | Taura Syndrome Virus |
| kkacrnagykeaclheldcksfllaqqgragah | (SEQ NO: 9) | 2005 | Taura Syndrome Virus |

Residues identical to original 1917 Goose Replikin residues are shown in medium grey.

Amino acid substitutions in light grey and dark grey

In addition, since many species, including but not limited to swine and birds, are known to provide animal "reservoirs" for human influenza infection, marine forms such as the shrimp virus can now be examined, with early warning diagnostic benefits for outbreaks such as swine flu and bird flu. While similarities of some influenza viruses were noted between species, and the transfer of these viruses interspecies was known, there was no previous quantitative method to gauge virus activity. The activity of Replikins in shrimp can now be monitored constantly for evidence of increased viral replication rate and thus emergence of epidemics that are likely to transfer to other species.

A related example of virus reservoir activity in which the Replikin concentration was increased prior to an outbreak was observed in corona viruses as a group. The Replikin concentration of the corona virus group increased markedly in 2002 before the outbreak of one of its members, SARS, in 2003. See FIG. 12.

With high mortality for its shrimp host, White Spot Syndrome Virus can now have its Replikins examined as earlier forms of virus Replikins, or as parallel morphological branches, that in either case may act as reservoirs for bird and animal Replikins such as those in influenza viruses. The diagnostic and preventive uses of these Replikin findings in shrimp follow as they do in influenza and for other organisms containing Replikins.

Advanced forecasts of influenza virus outbreaks are now conveniently achievable with Replikin concentration analysis using the proprietary software FluForecast® from Replikins, LLC, Boston, Mass. Such forecasts now may permit time for preventive public health measures to be mobilized and safer strain-specific vaccines to be synthesized, tested, and mass produced.

Replikin Repeats as a Mechanism for High Replikin Concentrations

The presence of repeat sequences of the Replikins of the nucleocapsid protein of shrimp White Spot Syndrome Virus (WSSV) accounts for the unusually high Replikin concentration of 103.8. This Replikin concentration is much higher than the Replikin concentration of for example, influenza viruses, which usually range from less than 1 up to 5 or 7 and comparable, as discussed above, with *P. falciparum*. Interestingly, while the shrimp White Spot Syndrome pathogen is a virus, and the *P. falciparum* is a trypanosome, both spend an essential part of their reproductive cycles in red blood cells, an unusual host cell whether in shrimp (White Spot Syndrome Virus) or man (malaria), both are fulminating, rapidly-replicating diseases with high mortality rates of their hosts, and both appear to use the same methods of increasing their high Replikin concentrations to such record highs, namely, Replikin repeats and Replikin overlap.

As illustrated in Table 3, examples of Replikin repeats and Replikin overlaps were found by the applicants in the above nucleocapsid protein of the shrimp White Spot Syndrome Virus. 497 Replikins were observed in the White Spot Syndrome Virus. Of those 497, the Replikins illustrated below in Table 3 were selected for their short sequences and high concentration of lysines which, as demonstrated throughout this application, is associated with high mortality. The chosen sequences are easier and less expensive to synthesize than the longer sequences that are not included in Table 3.

Table 3 illustrates intramolecular Replikin repeats and Replikin overlap in shrimp White Spot Syndrome Virus (WSSV) nucleocapsid protein (VP35) gene with a Replikin concentration (number of Replikins per 100 amino acids) of 103.8 (497 total Replikins per 479 amino acids). The nucleocapsid protein reportedly possesses thymidine kinase and thymidylate kinase activity.

TABLE 3

Intramolecular Replikin repeats and Replikin overlap in shrimp White Spot Syndrome Virus (WSSV) nucleocapsid protein (VP35) gene with Replikin concentration of 103.8
Individual Replikins at Different Positions in the same Molecule, in order of appearance in the sequence

| | | |
|---|---|---|
| 10) | $K^{24}Q^{25}L^{26}L^{27}H^{28}L^{29}K^{30}$ | (SEQ ID NO: 10) |
| 23) | $K^{30}V^{31}H^{32}L^{33}D^{34}V^{35}K^{36}$ | (SEQ ID NO: 11) |
| 25) | $K^{30}V^{31}H^{32}L^{33}D^{34}V^{35}K^{36}G^{37}V^{38}K^{39}Q^{40}L^{41}L^{42}H^{43}$ | (SEQ ID NO: 12) |
| 37) | $K^{39}Q^{40}L^{41}L^{43}H^{43}L^{44}K^{45}$ | (SEQ ID NO: 10) |
| 61) | $K^{66}K^{67}N^{68}V^{69}K^{70}S^{71}A^{72}K^{73}Q^{74}L^{75}P^{76}H^{77}$ | (SEQ ID NO: 13) |
| 72) | $K^{70}S^{71}A^{72}K^{73}Q^{74}L^{75}P^{76}H^{77}L^{78}K^{79}$ | (SEQ ID NO: 14) |
| 193) | $K^{160}K^{161}N^{162}V^{163}K^{164}S^{165}A^{166}K^{167}Q^{168}L^{169}P^{170}H^{171}$ | (SEQ ID NO: 13) |
| 307) | $K^{239}K^{240}N^{241}V^{242}K^{243}S^{244}A^{245}K^{246}Q^{247}L^{248}P^{249}H^{250}$ | (SEQ ID NO: 13) |
| 370) | $K^{303}K^{304}N^{305}V^{306}K^{307}S^{308}A^{309}K^{310}Q^{311}L^{312}P^{313}H^{314}$ | (SEQ ID NO: 13) |
| 462) | $K^{397}K^{398}N^{399}V^{400}K^{401}S^{402}A^{403}K^{404}Q^{405}L^{406}P^{407}H^{408}$ | (SEQ ID NO: 13) |

*Note in the shrimp virus the repeated use of identical whole Replikin sequences (underlined) and partial Replikin sequences (shaded) in different positions in the one molecule (each amino acid is numbered according to its order in the sequence).

Replikin concentration was determined for the ribonucleotide reductase gene in WSSV from Accession No. AAL89390. Accession No. AAL89390 discloses the amino acid sequence of ribonucleotide reductase translated from the total genome of a year 2000 isolate of White Spot Syndrome Virus made publicly available at Accession No. NC 003225.1. The Replikin concentration, as discussed above, was an unusually high at 103.8. Additionally, the Replikin concentration of the Replikin Peak Gene of the protein was even higher at 110.7. The Replikin concentration of the Replikin Peak Gene was determined by dividing the number of Replikin sequences identified in the segment of the protein containing the highest concentration of Replikin sequences, 497 Replikin sequences, by the total amino acid length of the Replikin Peak Gene, 449 amino acids, to arrive at 110.7 Replikin sequences per 100 amino acids. See Example 1.

The amino acid sequence of the protein publicly available at Accession No. AAL89390 is of particular interest because it demonstrates an overlapping of Replikin sequences that result in very high Replikin concentrations. The very large number of Replikin sequences present in the genome of the WSSV serves as a reservoir or vector for individual Replikins that are transferred or, via some other mechanism, otherwise appear in virulent strains of the influenza virus. This transfer or appearance of homologous Replikin sequences is seen in the Replikin Scaffold of the influenza virus and the Replikin Scaffold of the Shrimp White Spot Virus.

The amino acid sequence disclosed at Accession No. AAL89390 was further observed to contain significant Replikin Scaffold sequences. The presence of Replikin Scaffold sequences in Accession No. AAL89390 was not unexpected since Replikin Scaffolds are frequently present in viral genomes when the Replikin concentration is observed to move above 3 to 4 Replikin sequences per 100 amino acids. The presence of a Replikin Scaffold and a Replikin concentration above 3 or 4 correlates with viral outbreaks or epidemics and is another clear association with the rapid replication states of the isolated virus.

Replikin Concentration Correlates with $20^{th}$ Century Influenza Pandemics

As discussed above, Replikin concentration has been correlated with virulence in each influenza pandemic of the $20^{th}$ century. See FIG. 11. This shared correlation between Replikin concentration and outbreaks and mortality in WSSV and TSV and influenza provides evidence that the Replikin structure is transferable or repeatable between these viruses.

Figure 11:
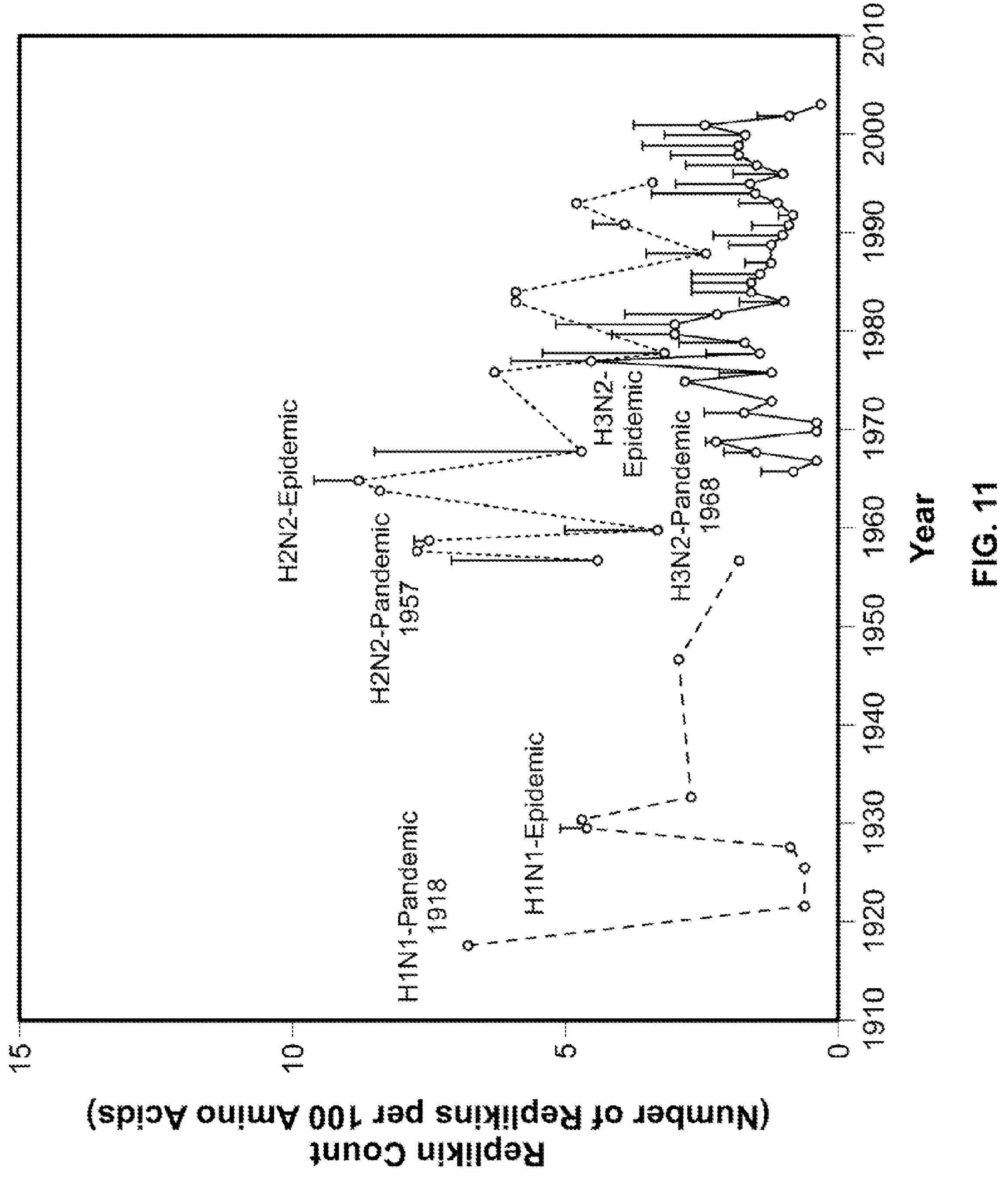
FIG. 11 is a graph correlating Replikin Count in each of three strains of influenza virus responsible for one of three pandemics during the $20^{th}$ century with virulence. Within the last century there have been three influenza pandemics, each pandemic being strain specific: H1N1 in 1918; H2N2 in 1957; and H3N2 in 1968. In the reported amino acid sequences of the strains responsible for each pandemic, there is a strain-specific increase in Replikin concentration correlated with the major pandemic within the strain, followed by a decrease in Replikin concentration and several years later a rebound increase associated in each case with a strain-specific rebound epidemic. The x-axis of FIG. 11 shows the year and the y-axis shows the Replikin concentration in Replikin sequences per 100 amino acids. Note that within FIG. 11 there is a separate graph for each strain responsible for each pandemic.

The correlation between Replikin concentration and influenza outbreaks is well established and unmistakable. Within the last century there have been three influenza pandemics, each strain specific: H1N1 in 1918; H2N2 in 1957; and H3N2 in 1968. In the reported amino acid sequences of the strains responsible for each pandemic, there is a strain-specific increase in the Replikin concentration correlated with the major pandemic within the strain, followed by a decrease in Replikin concentration and several years later a rebound increase associated in each case with a strain-specific rebound epidemic. The x-axis of FIG. 11 shows the year and the y-axis shows the Replikin concentration in Replikin sequences per 100 amino acids for each strain responsible for each pandemic. Note that within FIG. 11 there is a separate graph for each of the three strains.

FIG. 11 demonstrates that frequently a one to three year stepwise increase is observed before Replikin concentration reaches a peak. This stepwise increase precedes the occurrence of an epidemic, which occurs concurrently with the Replikin peak. Thus, the stepwise increase in concentration of a particular strain is a signal that a particular strain is the most likely candidate to cause an epidemic or pandemic.

H5N1 Influenza Replikin Concentration Correlates with Epidemics

Figure 4:
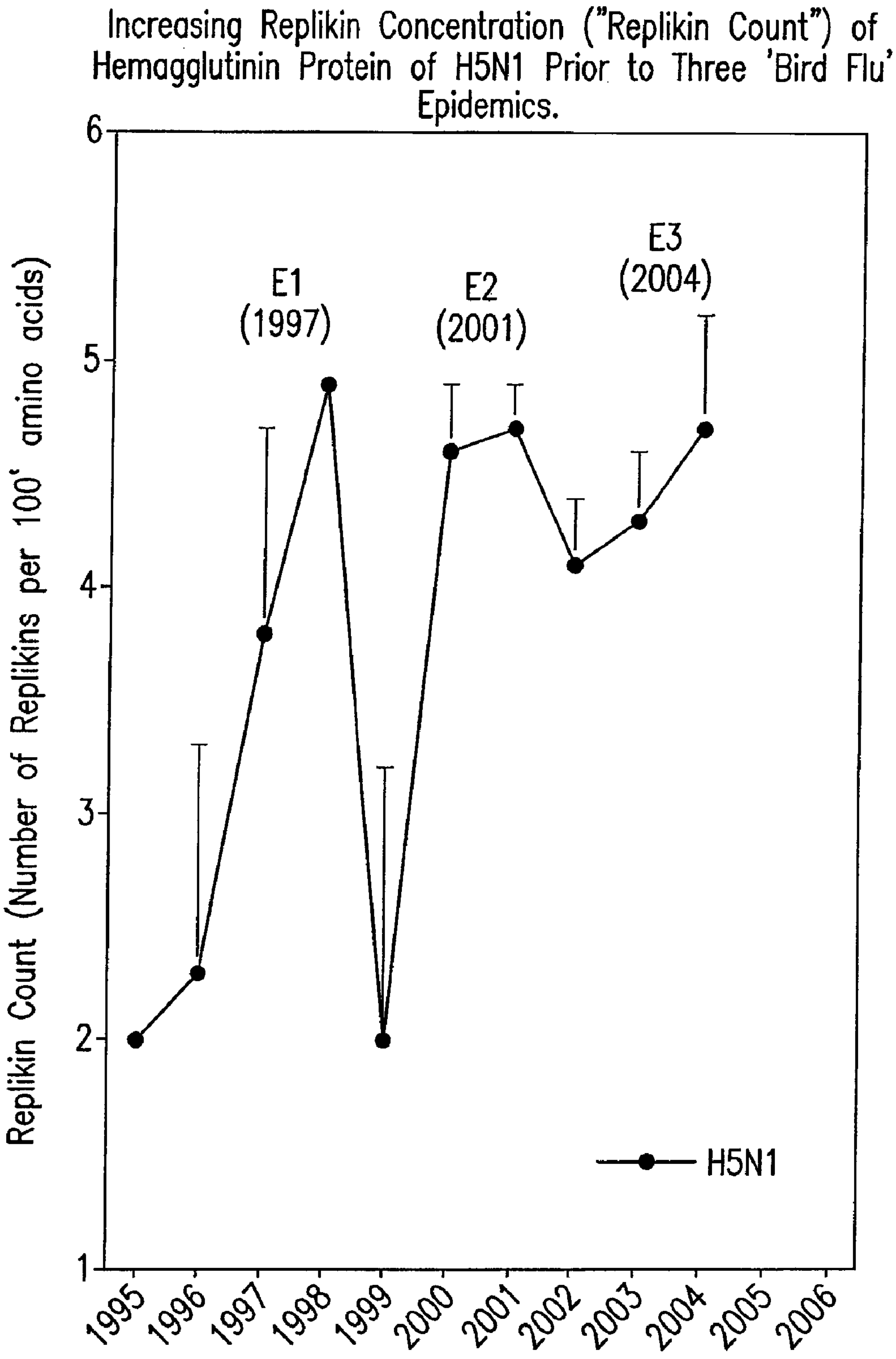
FIG. 4 illustrates that an increasing Replikin concentration of hemagglutinin protein in the H5N1 strain of influenza virus preceded three "Bird Flu" Epidemics. In H5N1 influenza, the increasing strain-specific Replikin concentration (Replikin Count, Means+/−SD) 1995 to 1997 preceded the Hong Kong H5N1 epidemic of 1997 (E1); the increase from 1999 to 2001 preceded the epidemic of 2001 (E2); and the increase from 2002 to 2004 preceded the epidemic in 2004 (E3). The decline in 1999 occurred with the massive culling of poultry in response to the E1 epidemic in Hong Kong.

Replikin concentration has also been correlated with virulence in each outbreak of H5N1 influenza ("Bird Flu") virus between the initial outbreak of 1997 and the present. FIG. 4, for example, illustrates a correlation between each outbreak of H5N1 between 1997 and 2004. The x-axis in FIG. 4 indicates the year and the y-axis indicates the Replikin concentration (number of Replikins per 100 amino acids). The time periods for each epidemic of H5N1 are denoted in FIG. 4 by E1, E2 and E3. In H5N1 influenza, an increasing strain-specific Replikin concentration (+/−SD) from 1995 to 1997 preceded the Hong Kong H5N1 epidemic of 1997 (E1); an increase from 1999 to 2001 preceded the epidemic of 2001 (E2); and an increase from 2002 to 2004 preceded the epidemic in 2004 (E3). A decline in 1999 occurred with the massive culling of poultry in response to the E1 epidemic in Hong Kong.

H5N1 Influenza Conservation of Replikin Scaffold in Highly Virulent Isolates

There is concern that current high mortality H5N1 "bird flu" in several countries may represent an early phase of an overdue influenza pandemic. Analysis of Replikin concentration changes in H5N1 have suggested that H5N1 virulence is continuing to increase. A 2006 report nevertheless suggested that in the first probable person-to-person transmission of H5N1, "sequencing of the viral genes identified no change in the receptor-binding site of hemagglutinin or other key features of the virus. The sequences of all eight viral gene segments clustered closely with other H5N1 sequences from recent avian isolates in Thailand." Phylogenetic analysis suggested that from the absence of evidence of "reassortment with human influenza viruses" that H5N1 is not a new variant. However, the inventors disclosed in 2006, three changes in a specific H5N1 protein sequence at sites which had not been changed in the last two H5N1 epidemics and in fact had been conserved since 1959. See U.S. Prov. Appln. Ser. No. 60/808,944, filed May 30, 2006.

The results set forth by the inventors in 2006 showed that 2005-2006 virus data indicated clearly that 1) the mortality rate of human H5N1 was increasing markedly, and that 2) the first country in which this would be clinically realized would be Indonesia. Bayu Krisnamurthi, the head of Indonesia's avian flu control commission, reported in June 2007 the clinical realization of both of these two predictions (Canadian Press, Jun. 6, 2007). In his comments to reporters, Dr. Krisnamurthi stated that recent changes in the H5N1 virus seem to be increasing its rate and ease of transmission from birds to humans. The World Health Organization (WHO), which has not yet implemented Replikin concentration analysis and tracking that had predicted the increase in rate and transmission in 2006, reported that they had no evidence of these changes.

Recent discovery of the Replikin Peak Gene have allowed prediction of the geographic location, as well as the gene location and the host animal species of each outbreak. See FIGS. 8, 9 and 10. The announcement by Dr. Krisnamurthi represents the first independent government confirmation of the success of these technological improvements. See, e.g., U.S. application Ser. No. 11/355,120, filed Feb. 16, 2006 and U.S. application Ser. No. 11/755,597, filed May 30, 2007.

Identification of Replikin Peak Gene for Targets and Prediction

The inventors have identified a Replikin Peak Gene in an isolate of the White Spot Syndrome Virus (WSSV). A Replikin Peak Gene may be identified, isolated or synthesized for diagnosis, prevention or treatment of, for example, an outbreak of WSSV or an outbreak of a virus for which WSSV is a reservoir, such as influenza virus, by the method comprising: (1) obtaining a plurality of isolates of WSSV; (2) analyzing the protein sequences or protein sequence fragments of each isolate of the plurality of isolates for the presence and concentration of Replikin sequences; (3) identifying the protein sequence or the protein sequence fragment having the highest concentration of Replikin sequences in each isolate; (4) comparing the protein or protein fragment having the highest concentration of Replikin sequences in each isolate to the protein or protein fragment having the highest concentration of Replikin sequences in each of the other isolates of the plurality of isolates; (5) selecting the protein or protein fragment having the highest concentration of Replikin sequences; (6) identifying the amino acid sequence of the selected protein or protein fragment as the Replikin Peak Gene of the plurality of isolates of WSSV; and (7) identifying, isolating or synthesizing the identified Replikin Peak Gene of at least one of the isolates of the plurality of isolates for diagnosis, prevention or treatment. The inventors have identified a Replikin Peak Gene in a ribonucleotide reductase gene of an isolate of WSSV. See Example 1.

Figure 2:
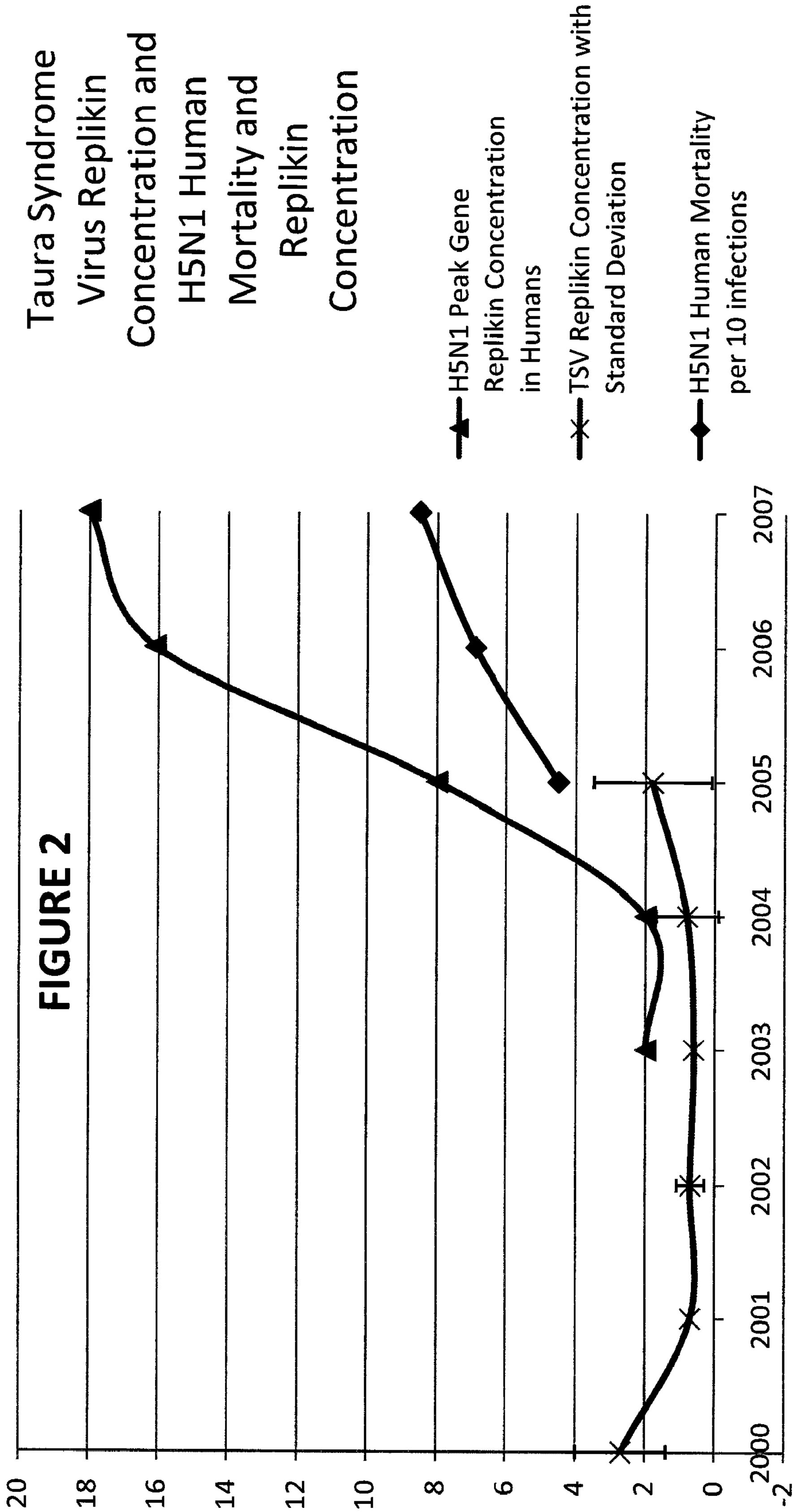
FIG. 2 illustrates a correlation between (1) the mean concentration and standard deviation of Replikin sequences observed in Taura Syndrome Virus (TSV) isolated between 2000 and 2005 that have publicly available accession numbers at www.pubmed.com, (2) the mean concentration of Replikin sequences in the pB1 gene area of H5N1 strains of influenza virus isolated in 2003, 2004, 2005, 2006, and 2007 that have publicly available accession numbers at www.pubmed.com, and (3) the mean mortality rate for humans infected with H5N1 influenza virus isolated in 2005, 2006, and 2007. The data demonstrate a higher Replikin sequence concentration in TSV in 2000 followed by a marked decrease in Replikin concentration in TSV in 2001 followed within three years by an increase in Replikin sequence concentration in H5N1 isolates (from 2003 through 2007) and a concomitant outbreak of H5N1 influenza in humans with increasing mortality.
Figure 3:
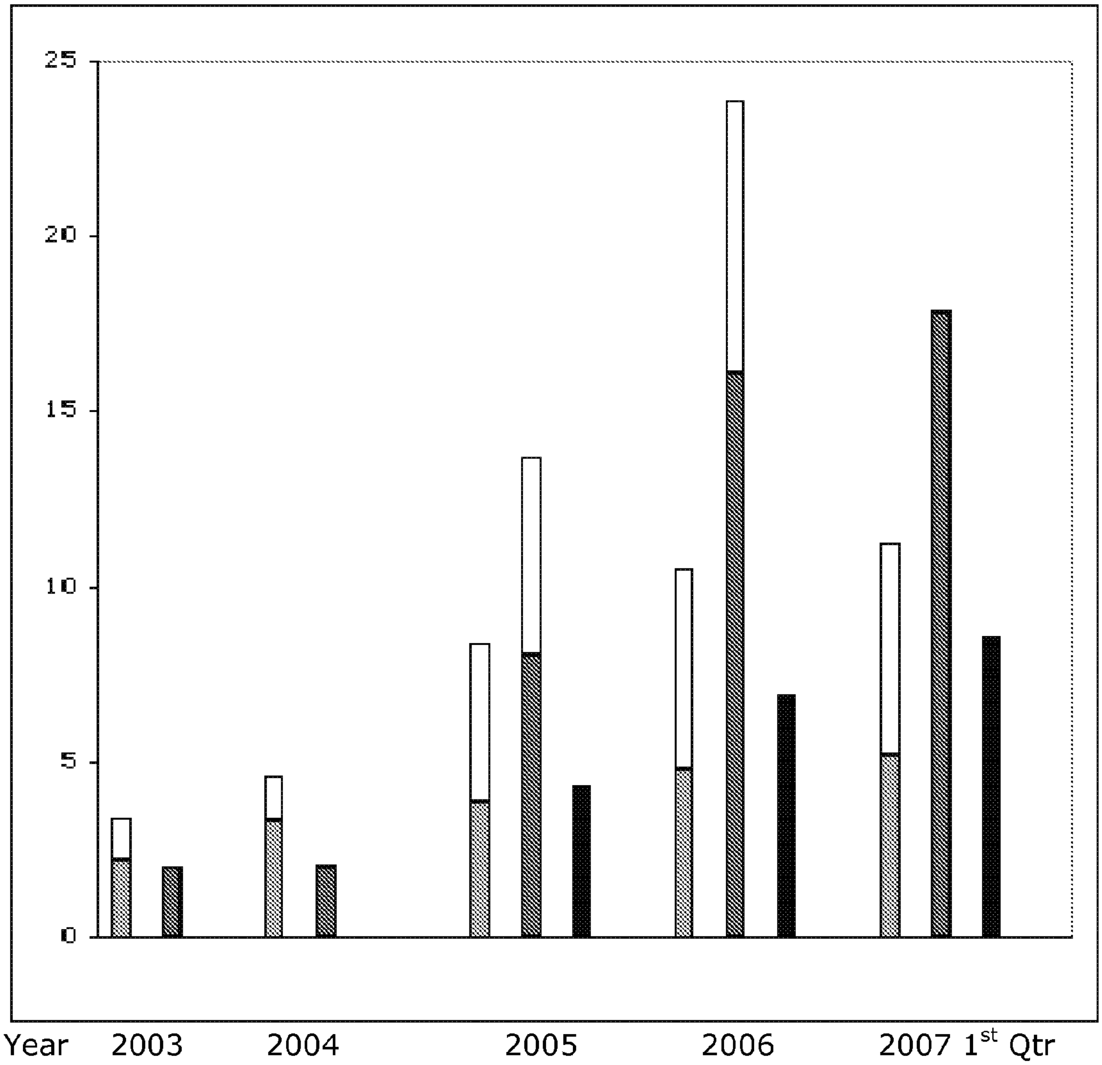
FIG. 3 illustrates a correlation between Replikin concentration in the H5N1 strain of influenza virus and human mortality from 2005 through the first quarter of 2007.

A Replikin Peak Gene is a segment of the genome or a protein or segment of a protein in which the expressed gene or expressed gene segment has the highest or a higher concentration of Replikins (number of Replikins per 100 amino acids) when compared to other segments or named genes of the genome. The gene or gene segment is known as the Replikin Peak Gene or Replikin Peak Gene Area. A Replikin Peak Gene has been identified in H5N1 influenza virus and an increase in concentration of Replikins in the Replikin Peak Gene of H5N1 has been correlated with epidemics, increased virulence, morbidity and human mortality. See FIGS. 11-13 and U.S. Provisional Appln. Ser. No. 60/898,097. Likewise, a Replikin Peak Gene has been identified in the VP1 protein of Foot and Mouth Disease Virus and has been correlated with outbreaks of the virus. See U.S. Provisional Appln. Ser. No. 60/954,743 (see FIG. 3 and Examples 1-4 therein). Further, a second Replikin Peak Gene has been identified in a fragment of the VP1 protein of Foot and Mouth Disease Virus and two particular Replikin sequences within the Replikin Peak Gene Area of the virus have been correlated with virulence of Foot and Mouth Disease Virus. See id. A Replikin Peak Gene has likewise been identified in West Nile Virus, Porcine Reproductive and Respiratory Syndrome Virus, Porcine Circovirus and Equine Influenza virus. See U.S. Provisional Appln. Ser. No. 60/853,744, filed Aug. 8, 2007 (FIG. 2 and Example 2 therein), and U.S. Provisional Appln. Ser. No. 60/935,816, filed Aug. 31, 2007 (FIGS. 1, 2 and 4).

Identification of Replikin sequences as infectious units has allowed the inventors to identify isolates having higher virulence relative to other isolates and to focus attention on the geographic area of an outbreak of virulent virus (see FIG. 10), the particular host of hosts of an outbreak of virulent virus (see FIG. 9) and the part of the genome of a virus (see FIG. 8) wherein virulence mechanisms are located and wherein increased virulence may be identified and predicted. Identification of Replikin Peak Genes within viral genomes has improved the focus that is available to make these identifications and predictions of both virulence and mechanisms of virulence.

Because the inventors have provided a method of focusing on particular units of a viral or organismal genome, the skilled artisan will understand the importance of looking for Replikin sequences in any portion of the life cycle or infectious pathway of a virus. For example, as described herein, the skilled artisan will understand that predictive and virulence-related Replikin sequences (or concentrations of Replikin sequence in Replikin Peak Genes) may be identified in reservoirs of influenza virus such as in WSSV and TSV. The skilled artisan will further understand that predictive and virulence-related Replikin sequences or Replikin Peak Genes may be identified in vectors of the influenza virus. The skilled artisan will additionally understand that predictive and virulence-related Replikin sequences or Replikin Peak Genes may be identified in hosts of the influenza virus or any other place where viral genes may be located or wherein viral genes may encounter genes of other strains of virus, other virus species, vectors or hosts.

SARS Replikin Count Correlates with Epidemics

Figure 12:
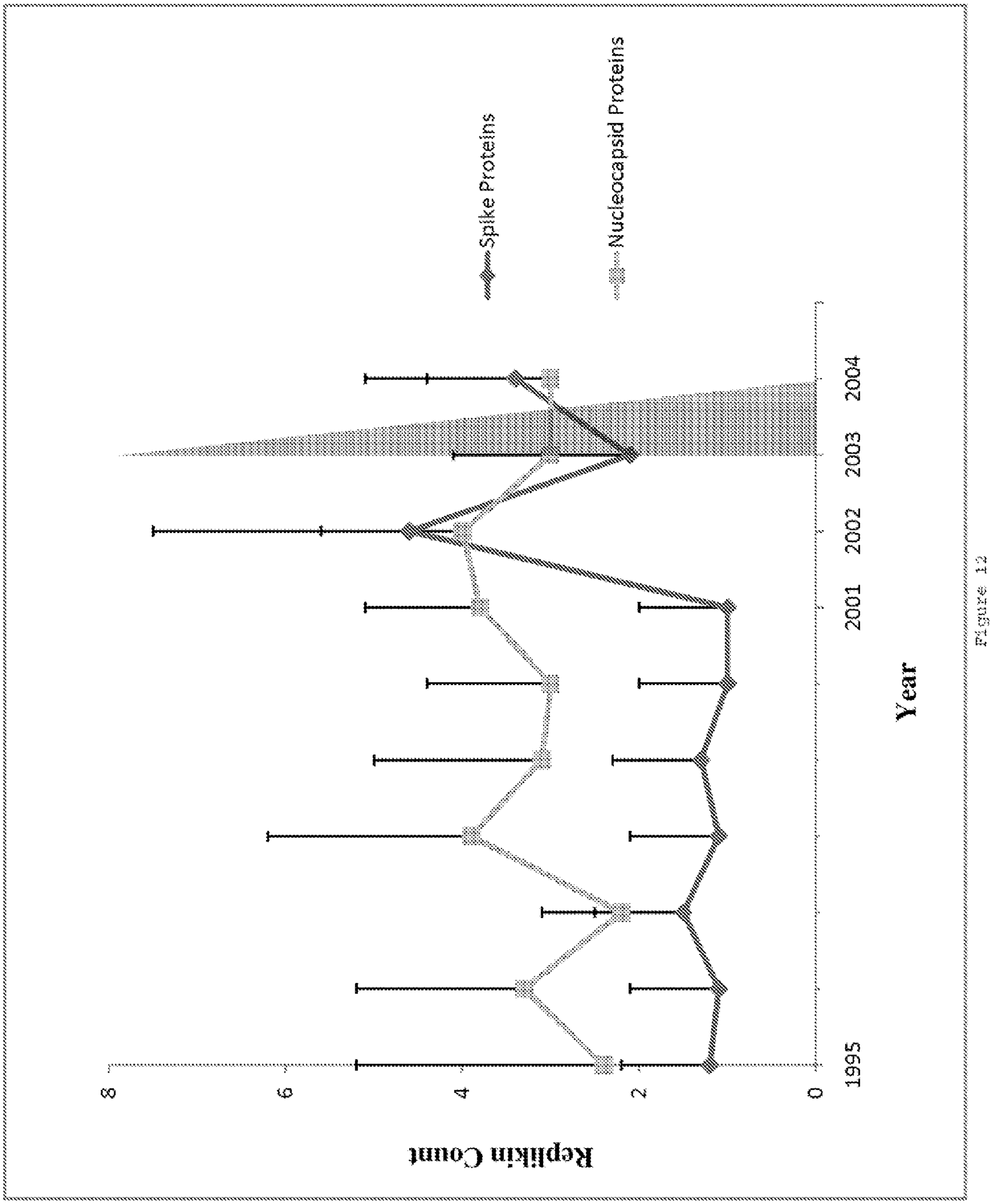
FIG. 12 is a graph illustrating an increase in Replikin concentration in spike and nucleocapsid coronavirus proteins preceding the SARS coronavirus epidemic of 2003. The x-axis indicates the year and the y-axis indicates the Replikin concentration. The appearance of the SARS outbreak and the eight countries involved in the outbreak is shown by the conical shaded area. The solid black symbols represent the mean Replikin concentration for spike coronavirus proteins and the vertical black bars represent the standard deviation of the mean.

An increase in Replikin concentration in coronaviruses also correlated with the SARS coronavirus epidemic of 2003. In particular, as may be seen in FIG. 12, Replikin concentration in Spike and Nucleocapsid Coronavirus Proteins preceded the SARS Coronavirus epidemic of 2003. In FIG. 12, the x-axis indicates the year and the y-axis indicates the Replikin concentration. The appearance of the SARS outbreak is shown by the shaded area in the graph between 2003 and 2004. The peak of the shaded area represents a total number of eight countries in which the SARS outbreak occurred in 2003. The solid black symbols represent the mean Replikin concentration for spike coronavirus proteins and the vertical black bars represent the standard deviation of the mean.

FIG. 12 shows a remarkable constancy of low coronavirus Replikin concentration between 1995 and 2001 in the spike proteins, followed by a dramatic increase in 2002, one year before the SARS epidemic appeared in 2003. Replikin concentration of the spike proteins in SARS then returned to their normal pre-2003 levels (correlated with the disappearance of SARS). The return to normal pre-2003 levels of Replikin concentration is thus a quantitative virus structural signal of the decline of the outbreak.

Replikin Concentration Correlates with Outbreaks in West Nile Virus, Foot and Mouth Disease and Equine Influenza In all viruses observed by the inventors, significant increases in Replikin concentration have been predictive of increases in viral virulence. For example, an increase in Replikin concentration has been correlated with outbreaks in West Nile Virus, Foot and Mouth Disease, and Equine Influenza, and is predictive of outbreaks in each of these diseases.

Figure 13:
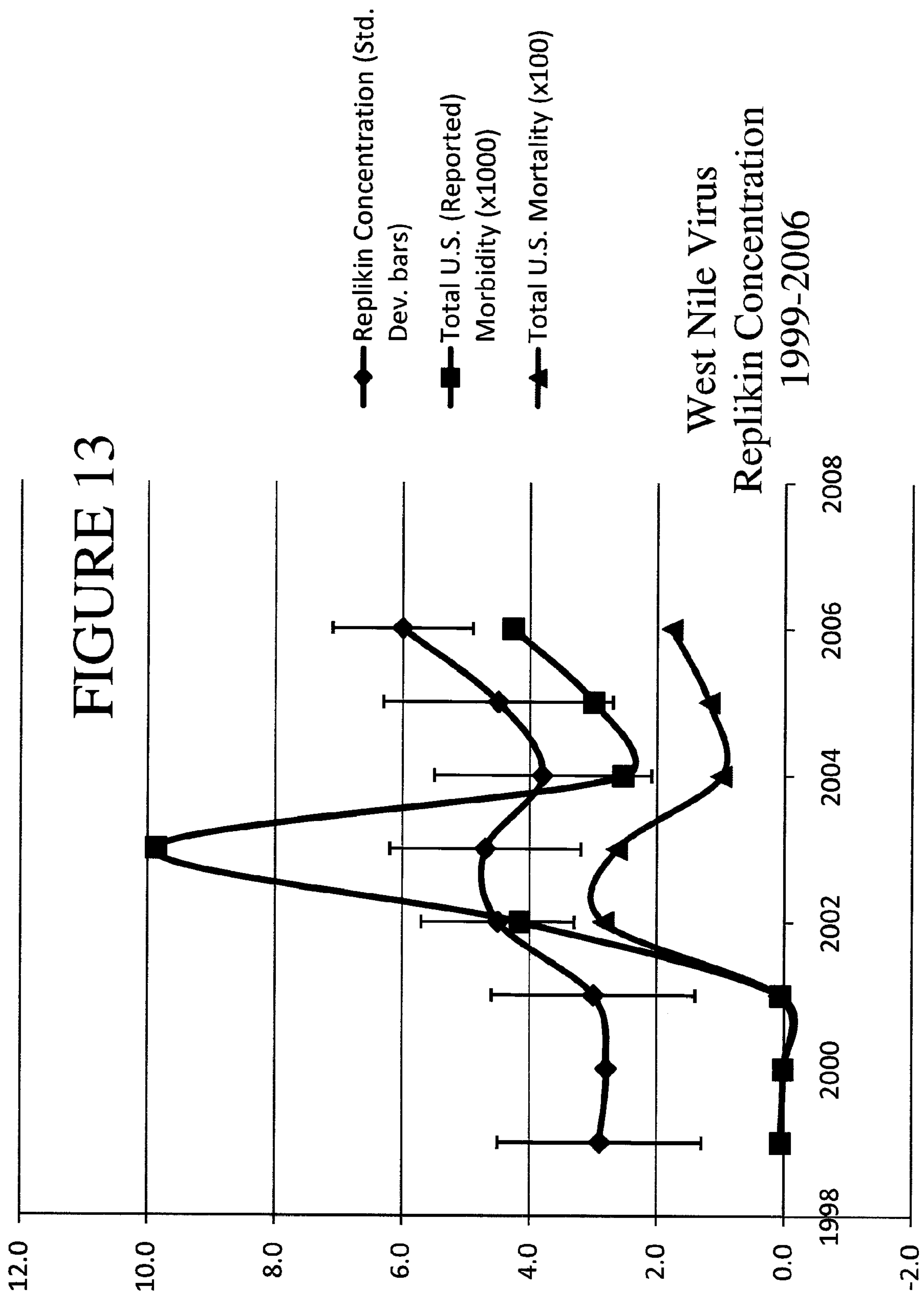
FIG. 13 is a graph comparing (1) the concentration of Replikin sequences observed in isolates of West Nile Virus having publicly available accession numbers on a year by year basis between 1999 and 2006 (with standard deviation bars for each Replikin concentration data point except 2000), (2) total morbidity reported in the United States on a year by year basis by the Center for Disease Control (total U.S. morbidity is the value denoted on the y-axis times 1000), and (3) total mortality resulting from WNV infection reported in the United States on a year by year basis by the Center for Disease Control (total U.S. mortality is the value denoted on the y-axis times 100). A correlation between Replikin concentration, morbidity and mortality is demonstrated.
Figure 14:
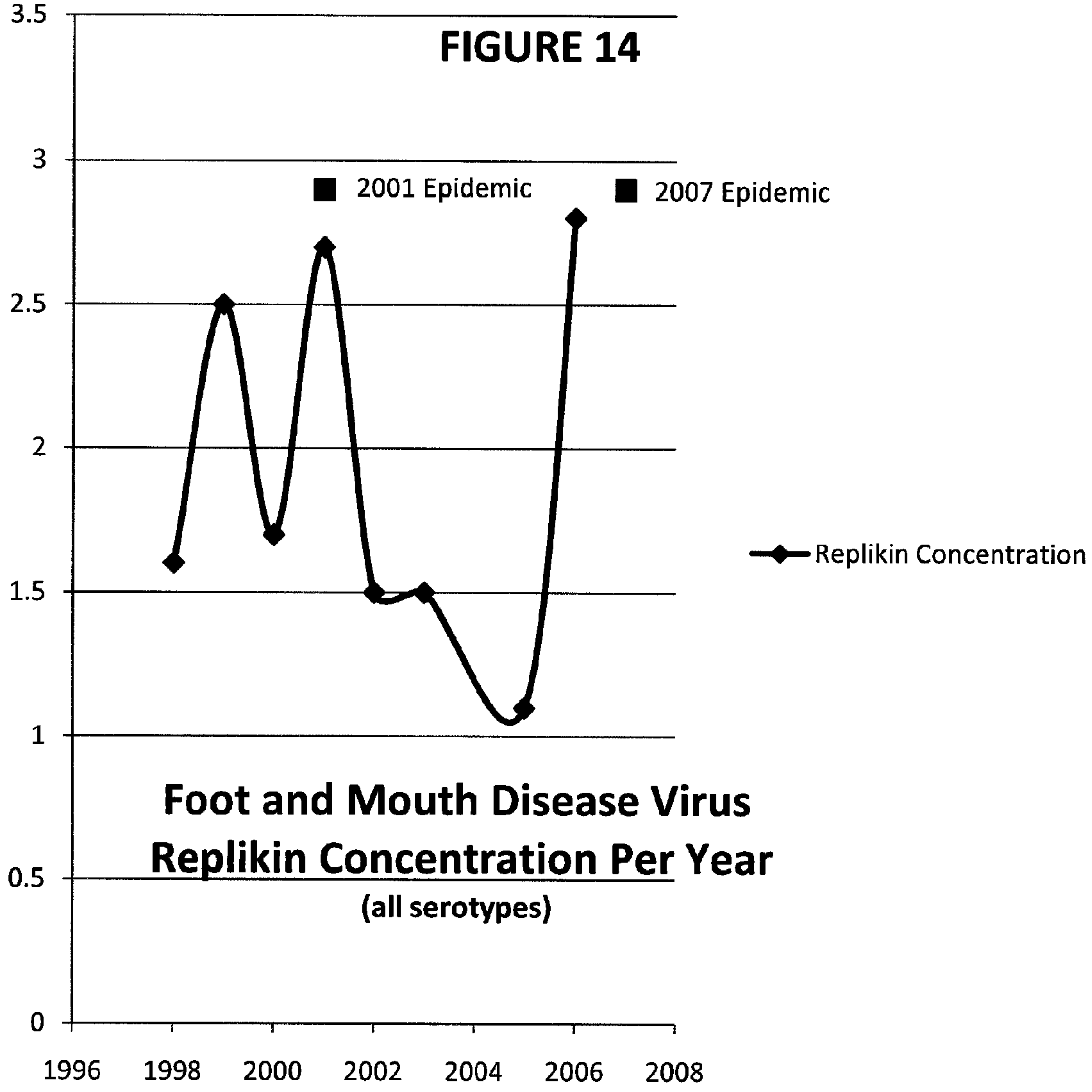
FIG. 14 is a graph illustrating the mean concentration of Replikins observed in the VP1 protein of isolates of Foot and Mouth Disease Virus having publicly available accession numbers on a year by year basis between 1998 and 2006. Observed outbreaks of Foot and Mouth Disease in the United Kingdom (UK) are noted in 2001 and 2007.

FIG. 13 is a graph illustrating a correlation between Replikin concentration and morbidity and mortality in U.S. populations for West Nile Virus. FIG. 14 is a graph illustrating a correlation between the concentration of Replikins observed in the VP1 protein of isolates of Foot and Mouth Disease Virus between 1998 and 2006 and epidemics in the United Kingdom in 2001 and 2007.

Figure 15:
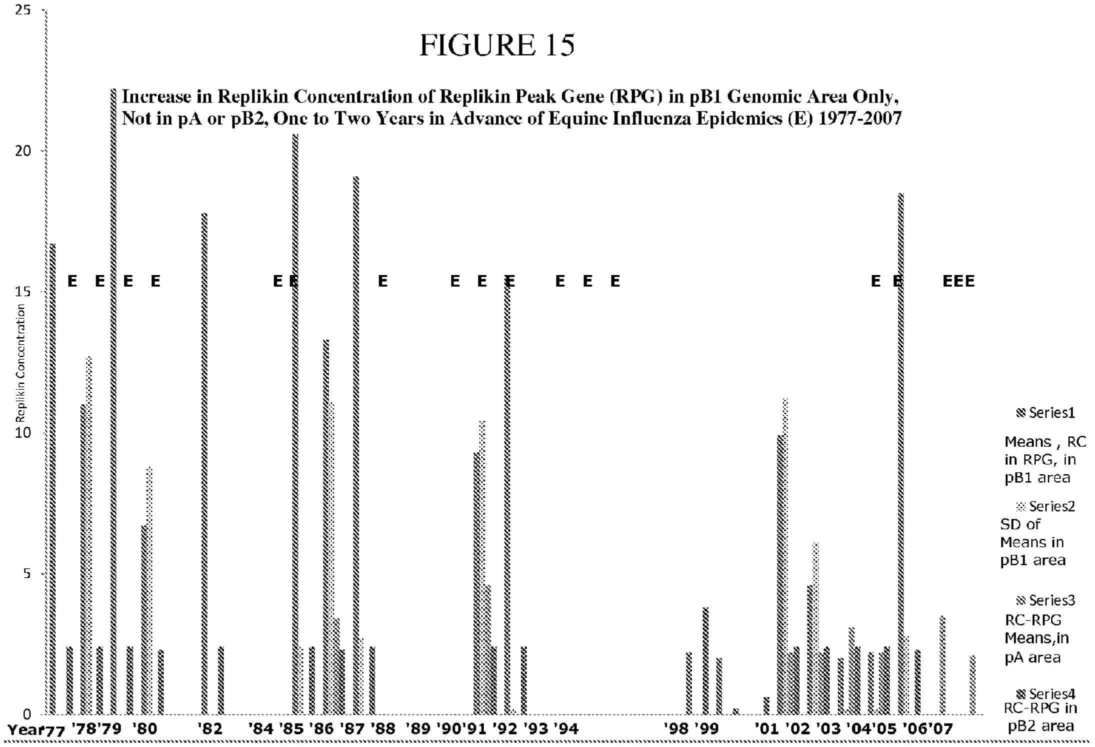
FIG. 15 illustrates an increase in Replikin concentration in a Replikin Peak Gene in the pB1 genomic area of Equine Influenza one to two years in advance of epidemics of Equine Influenza. The graph illustrates that no increase in Replikin concentration in pA or pB2 genes of the equine influenza virus correlates with the increase in the Replikin concentration of the Replikin Peak Gene or with outbreaks of the virus.

FIG. 15 is a graph illustrating a correlation between Replikin concentration in the Replikin Peak Gene of Equine Influenza virus and epidemics between 1977 and 2000. The Replikin Peak Gene in Equine Influenza is identified as the pB1 gene area. In years where the Replikin concentration increases in the pB1 gene area of the virus, no concomitant increase in the pA or pB2 virus is observed. These data demonstrate a significant effect on virulence by an observed increase in Replikin concentration particularly in a Replikin Peak Gene.

Vaccines, Treatments and Therapeutics

The observations of specific Replikins and their concentration in WSSV and TSV proteins and their correlation with outbreaks in influenza provides for early production and timely administration of vaccines tailored specifically to treat the prevalent emerging or re-emerging strain of influenza virus in a particular region of the world. By analyzing the protein sequences of isolates of a virus for the presence, concentration and/or conservation of Replikins, virus outbreaks and epidemics can be predicted and treatments developed. Furthermore, the severity of such outbreaks can be significantly lessened by administering a peptide vaccine based on the Replikin sequences identified using the methods provided herein or Replikin sequences found to be most abundant or shown to be on the rise in virus isolates over a given time period, such as about one to about three years. Vaccine products against SARS Replikin sequences and H5N1 influenza virus Replikin Scaffolds have been demonstrated by the inventors. See, e.g., U.S. application Ser. No. 11/355,120, filed Feb. 16, 2006 (Examples 6 and 7). Replikin sequences added to the feed source of shrimp have likewise imparted measurable resistance to challenges with Taura Syndrome Virus. See Example 7 below.

A peptide vaccine may include a single Replikin peptide sequence or may include a plurality of Replikin sequences observed in particular virus strains. Preferably, the peptide vaccine is based on Replikin sequence(s) shown to be increasing in concentration over a given time period and conserved for at least that period of time. However, a vaccine may include a conserved Replikin peptide(s) in combination with a new Replikin peptide(s) or may be based on new Replikin peptide sequences. Replikin peptides can be synthesized by any method, including chemical synthesis or recombinant gene technology, and may include non-Replikin sequences, although vaccines based on peptides containing only Replikin sequences are preferred. Preferably, vaccine compositions of the invention also contain a pharmaceutically acceptable carrier and/or adjuvant.

Vaccines can be administered alone or in combination with antiviral drugs, such as gancyclovir; interferon; interleukin; M2 inhibitors, such as, amantadine, rimantadine; neuraminidase inhibitors, such as zanamivir and oseltamivir; and the like, as well as with combinations of antiviral drugs.

Vaccines may be administered to any animal capable of producing antibodies in an immune response. For example, a vaccine may be administered to a rabbit, a chicken, a pig, or a human. Because of the universal nature of Replikin sequences, a vaccine of the invention may be directed at a variety of strains of virus or a particular strain of virus.

Passive Immunity

In another aspect of the invention, isolated Replikin peptides may be used to generate antibodies, which may be used, for example to provide passive immunity in an individual. Various procedures known in the art may be used for the production of antibodies to Replikin sequences. Such antibodies include but are not limited to polyclonal, monoclonal, chimeric, humanized, single chain, Fab fragments and fragments produced by a Fab expression library. Antibodies that are linked to a cytotoxic agent may also be generated. Antibodies may also be administered in combination with an antiviral agent. Furthermore, combinations of antibodies to different Replikins may be administered as an antibody cocktail.

Monoclonal antibodies to Replikins may be prepared by using any technique that provides for the production of antibody molecules. These include but are not limited to the hybridoma technique originally described by Kohler and Milstein, (Nature, 1975, 256:495-497), the human B-cell hybridoma technique (Kosbor et al., 1983, Immunology Today, 4:72), and the EBV hybridoma technique (Cole et al., Monoclonal Antibodies and Cancer Therapy, Alan R. Liss, Inc., pp. 77-96). In addition, techniques developed for the production of chimeric antibodies (Morrison et al., 1984, Proc. Nat. Acad. Sci USA, 81:6851-6855) or other techniques may be used. Alternatively, techniques described for the production of single chain antibodies (U.S. Pat. No. 4,946,778) can be adapted to produce Replikin-specific single chain antibodies.

Antibodies to any peptides observed to be present in an emerging or re-emerging strain of virus and combinations of such antibodies are useful in the treatment and/or prevention of viral infection.

Antibody fragments that contain binding sites for a Replikin may be generated by known techniques. For example, such fragments include but are not limited to F(ab')2 fragments which can be produced by pepsin digestion of the antibody molecules and the Fab fragments that can be generated by reducing the disulfide bridges of the F(ab')2 fragments. Alternatively, Fab expression libraries can be generated (Huse et al., 1989, Science, 246:1275-1281) to allow rapid and easy identification of monoclonal Fab fragments with the desired specificity.

In another aspect of the invention, immune serum containing antibodies to one or more Replikins obtained from an individual exposed to one or more Replikins may be used to induce passive immunity in another individual or animal. Immune serum may be administered via i.v. to a subject in need of treatment. Passive immunity also can be achieved by injecting a recipient with preformed antibodies to one or more Replikins. Passive immunization may be used to provide immediate protection to individuals who have been exposed to an infectious organism. Administration of immune serum or preformed antibodies is routine and the skilled practitioner can readily ascertain the amount of serum or antibodies needed to achieve the desired effect.

Replikin peptides, alone or in various combinations, may be administered to a subject, preferably by i.v. or intramuscular injection, in order to stimulate the immune system of the subject to produce antibodies to the peptide. Generally the dosage of peptides is in the range of from about 0.1 μg to about 10 mg. In another embodiment, the dosage of pepetides is about 10 μg to about 1 mg. In a preferred embodiment, the dosage of peptides is about 50 μg to about 500 μg. The skilled practitioner can readily determine the dosage and number of dosages needed to produce an effective immune response.

EXAMPLES

Example 1

Determination of Very High Replikin Concentration in Ribonucleotide Reductase from Accession No. AAL89390

Replikin concentration was determined for ribonucleotide reductase publicly available at Accession No. AAL89390. The amino acid sequence was translated from the total genome of a year 2000 isolate of White Spot Syndrome Virus made publicly available at Accession No. NC 003225.1. The Replikin concentration in the protein was an unusually high 103.8 and the Replikin concentration of the Replikin Peak Gene of the protein was a yet higher 110.7. The Replikin concentration of the protein was determined by dividing the number of Replikin sequences identified in the amino acid sequence of the protein, 497 Replikin sequences, by the total amino acid length of the protein, 479 amino acids, to arrive at 103.8 Replikin sequences per 100 amino acids. The Replikin concentration of the Replikin Peak Gene was determined by dividing the number of Replikin sequences identified in the segment of the protein containing the highest concentration of Replikin sequences, 497 Replikin sequences, by the total amino acid length of the Replikin Peak Gene, 449 amino acids, to arrive at 110.7 Replikin sequences per 100 amino acids.

The amino acid sequence of the protein publicly available at Accession No. AAL89390 is of particular interest because it demonstrates an overlapping of Replikin sequences that results in very high Replikin concentrations, comparable to *P. falciparum*. The high concentrations of Replikin sequences provide a reservoir for transfer to influenza viruses.

In Accession No. AAL89390, the inventors identified a Replikin Peak Gene. A Replikin Peak Gene is the segment of a protein having the highest concentration of continuous, uninterrupted, overlapping, Replikin sequences. In the sequence disclosed below, the Replikin Peak Gene is underlined. The Replikin Peak Gene is observed to occupy most of the disclosed protein. The expansiveness of the Replikin Peak Gene across most of the amino acid sequence of the protein is highly unusual and creates the remarkably high Replikin concentration. The amino acid sequence further contains significant Replikin Scaffold sequences. The following Replikin Scaffold repeats were identified in Accession No. AAL89390.

(SEQ ID NO: 1)
$K^{66}$KNVKSAKQLPHLKVHLDVKSAKQLPHLKVH$^{96}$ (SEQ ID NO: 2)
$K^{160}$KNVKSAKQLPHLKVHLDVKGVKQLLH$^{186}$ (SEQ ID NO: 3)
$K^{239}$KNVKSAKQLPHLKVLLDVRGAKQLPH$^{265}$ (SEQ ID NO: 3)
$K^{303}$KNVKSAKQLPHLKVLLDVRGAKQLPH$^{329}$ (SEQ ID NO: 4)
$K^{397}$KNVKSAKQLPHLKVLLDVRGAKQLPHLKVH$^{427}$

Replikin Analysis for AAL89390
PubMed Code: AAL89390
Description: Ribonucleotide reductase of shrimp white spot syndrome virus (WSSV):
Isolated Year: 2000
Source: Shrimp White Spot Syndrome Virus $M^{1}K^{2}I^{3}C^{4}Q^{5}I^{6}S^{7}S^{8}P^{9}T^{10}L^{11}T^{12}L^{13}S^{14}I^{15}P^{16}L^{17}E^{18}G^{19}V^{20}Y^{21}H^{22}V^{23}K^{24}Q^{25}L^{26}L^{27}H^{28}L^{29}K^{30}V^{31}H^{32}L^{33}D^{34}V^{35}K^{36}G^{37}$ $V^{38}K^{39}Q^{40}L^{41}L^{42}H^{43}L^{44}K^{45}V^{46}R^{47}L^{48}D^{49}V^{50}R^{51}G^{52}A^{53}K^{54}Q^{55}N^{56}P^{57}W^{58}R^{59}K^{60}N^{61}L^{62}C^{63}L^{64}L^{65}K^{66}K^{67}N^{68}V^{69}K^{70}S^{71}$ $A^{72}K^{73}Q^{74}L^{75}P^{76}H^{77}L^{78}K^{79}V^{80}H^{81}L^{82}D^{83}V^{84}K^{85}S^{86}A^{87}K^{88}Q^{89}L^{90}P^{91}H^{92}L^{93}K^{94}V^{95}H^{96}L^{97}D^{98}V^{99}R^{100}G^{101}A^{102}K^{103}$ $Q^{104}L^{105}P^{106}H^{107}L^{108}K^{109}V^{110}R^{111}L^{112}D^{113}V^{114}K^{115}S^{116}A^{117}K^{118}Q^{119}L^{120}P^{121}H^{122}L^{123}K^{124}V^{125}H^{126}L^{127}D^{128}$ $V^{129}R^{130}G^{131}A^{132}K^{133}Q^{134}L^{135}P^{136}H^{137}L^{138}K^{139}V^{140}R^{141}L^{142}D^{143}V^{144}R^{145}G^{146}A^{147}K^{148}Q^{149}N^{150}P^{151}W^{152}R^{153}$ $K^{154}N^{155}L^{156}C^{157}L^{158}L^{159}K^{160}K^{161}N^{162}V^{163}K^{164}S^{165}A^{166}K^{167}Q^{168}L^{169}P^{170}H^{171}L^{172}K^{173}V^{174}H^{175}L^{176}D^{177}V^{178}$ $K^{179}G^{180}V^{181}K^{182}Q^{183}L^{184}L^{185}H^{186}L^{187}K^{188}V^{189}R^{190}L^{191}D^{192}V^{193}R^{194}G^{195}A^{196}K^{197}Q^{198}L^{199}L^{200}H^{201}L^{202}K^{203}$ $V^{204}H^{205}L^{206}D^{207}V^{208}R^{209}G^{210}A^{211}K^{212}Q^{213}L^{214}P^{215}H^{216}L^{217}K^{218}V^{219}H^{220}L^{221}D^{222}V^{223}R^{224}G^{225}A^{226}K^{227}Q^{228}$ $N^{229}P^{230}W^{231}R^{232}K^{233}N^{234}L^{235}C^{236}L^{237}L^{238}K^{239}K^{240}N^{241}V^{242}K^{243}S^{244}A^{245}K^{246}Q^{247}L^{248}P^{249}H^{250}L^{251}K^{252}V^{253}$ $L^{254}L^{255}D^{256}V^{257}R^{258}G^{259}A^{260}K^{261}Q^{262}L^{263}P^{264}H^{265}L^{266}K^{267}V^{268}L^{269}L^{270}D^{271}V^{272}R^{273}G^{274}A^{275}K^{276}Q^{277}L^{278}$ $P^{279}H^{280}L^{281}K^{282}V^{283}H^{284}L^{285}D^{286}V^{287}R^{288}G^{289}A^{290}K^{291}Q^{292}N^{293}P^{294}W^{295}R^{296}K^{297}N^{298}L^{299}C^{300}L^{301}L^{302}K^{303}$ $K^{304}N^{305}V^{306}K^{307}S^{308}A^{309}K^{310}Q^{311}L^{312}P^{313}H^{314}L^{315}K^{316}V^{317}L^{318}L^{319}D^{320}V^{321}R^{322}G^{323}A^{324}K^{325}Q^{326}L^{327}P^{328}$ $H^{329}L^{330}K^{331}V^{332}L^{333}L^{334}D^{335}V^{336}R^{337}G^{338}A^{339}K^{340}Q^{341}L^{342}P^{343}H^{344}L^{345}K^{346}V^{347}H^{348}L^{349}D^{350}V^{351}R^{352}G^{353}$ $A^{354}K^{355}Q^{356}L^{357}P^{358}H^{359}L^{360}K^{361}V^{362}L^{363}L^{364}D^{365}V^{366}R^{367}G^{368}A^{369}K^{370}Q^{371}L^{372}P^{373}H^{374}L^{375}K^{376}V^{377}L^{378}$ $L^{379}D^{380}V^{381}R^{382}G^{383}A^{384}K^{385}Q^{386}N^{387}P^{388}W^{389}R^{390}K^{391}N^{392}L^{393}C^{394}L^{395}L^{396}K^{397}K^{398}N^{399}V^{400}K^{401}S^{402}A^{403}$ $K^{404}Q^{405}L^{406}P^{407}H^{408}L^{409}K^{410}V^{411}L^{412}L^{413}D^{414}V^{415}R^{416}G^{417}A^{418}K^{419}Q^{420}L^{421}P^{422}H^{423}L^{424}K^{425}V^{426}H^{427}L^{428}$ $D^{429}V^{430}R^{431}G^{432}A^{433}K^{434}Q^{435}Q^{436}Q^{437}Q^{438}L^{439}C^{440}L^{441}P^{442}L^{443}K^{444}T^{445}I^{446}S^{447}T^{448}S^{449}F^{450}T^{451}H^{452}L^{453}$ $L^{454}L^{455}C^{456}L^{457}Y^{458}M^{459}E^{460}Y^{461}G^{462}K^{463}H^{464}Q^{465}N^{466}L^{467}Q^{468}V^{469}K^{470}M^{471}W^{472}L^{473}N^{474}I^{475}T^{476}Y^{477}T^{478}$ $S^{479}$
(SEQ ID NO: 15)

Replikin Sequences in Amino-Terminal Portion of Peptide (1) $H^{22}V^{23}K^{24}Q^{25}L^{26}L^{27}H^{28}L^{29}K^{30}$
(SEQ ID NO: 16)

(2) $H^{22}V^{23}K^{24}Q^{25}L^{26}L^{27}H^{28}L^{29}K^{30}V^{31}H^{32}L^{33}D^{34}V^{35}K^{36}$
(SEQ ID NO: )

(3) $H^{22}V^{23}K^{24}Q^{25}L^{26}L^{27}H^{28}L^{29}K^{30}V^{31}H^{32}L^{33}D^{34}V^{35}K^{36}G^{37}V^{38}K^{39}$
(SEQ ID NO: 18)

(4) $H^{22}V^{23}K^{24}Q^{25}L^{26}L^{27}H^{28}L^{29}K^{30}V^{31}H^{32}L^{33}D^{34}V^{35}K^{36}G^{37}V^{38}K^{39}Q^{40}L^{41}L^{42}H^{43}L^{44}K^{45}$
(SEQ ID NO: 19)

(5) $H^{22}V^{23}K^{24}Q^{25}L^{26}L^{27}H^{28}L^{29}K^{30}V^{31}H^{32}L^{33}D^{34}V^{35}K^{36}G^{37}V^{38}K^{39}Q^{40}L^{41}L^{42}H^{43}L^{44}K^{45}V^{46}R^{47}L^{48}D^{49}V^{50}R^{51}G^{52}A^{53}$
$K^{54}$
(SEQ ID NO: 20)

(6) $H^{22}V^{23}K^{24}Q^{25}L^{26}L^{27}H^{28}L^{29}K^{30}V^{31}H^{32}L^{33}D^{34}V^{35}K^{36}G^{37}V^{38}K^{39}Q^{40}L^{41}L^{42}H^{43}L^{44}K^{45}V^{46}R^{47}L^{48}D^{49}V^{50}R^{51}G^{52}A^{53}$
$K^{54}Q^{55}N^{56}P^{57}W^{58}R^{59}K^{60}$
(SEQ ID NO: 21)

(7) $H^{22}V^{23}K^{24}Q^{25}L^{26}L^{27}H^{28}L^{29}K^{30}V^{31}H^{32}L^{33}D^{34}V^{35}K^{36}G^{37}V^{38}K^{39}Q^{40}L^{41}L^{42}H^{43}L^{44}K^{45}V^{46}R^{47}L^{48}D^{49}V^{50}R^{51}G^{52}A^{53}$
$K^{54}Q^{55}N^{56}P^{57}W^{58}R^{59}K^{60}N^{61}L^{62}C^{63}L^{64}L^{65}K^{66}$
(SEQ ID NO: 22)

(8) $H^{22}V^{23}K^{24}Q^{25}L^{26}L^{27}H^{28}L^{29}K^{30}V^{31}H^{32}L^{33}D^{34}V^{35}K^{36}G^{37}V^{38}K^{39}Q^{40}L^{41}L^{42}H^{43}L^{44}K^{45}V^{46}R^{47}L^{48}D^{49}V^{50}R^{51}G^{52}A^{53}$
$K^{54}Q^{55}N^{56}P^{57}W^{58}R^{59}K^{60}N^{61}L^{62}C^{63}L^{64}L^{65}K^{66}K^{67}$
(SEQ ID NO: 23)

(9) $H^{22}V^{23}K^{24}Q^{25}L^{26}L^{27}H^{28}L^{29}K^{30}V^{31}H^{32}L^{33}D^{34}V^{35}K^{36}G^{37}V^{38}K^{39}Q^{40}L^{41}L^{42}H^{43}L^{44}K^{45}V^{46}R^{47}L^{48}D^{49}V^{50}R^{51}G^{52}A^{53}$
$K^{54}Q^{55}N^{56}P^{57}W^{58}R^{59}K^{60}N^{61}L^{62}C^{63}L^{64}L^{65}K^{66}K^{67}N^{68}V^{69}K^{70}$
(SEQ ID NO: 24)

(10) $K^{24}Q^{25}L^{26}L^{27}H^{28}L^{29}K^{30}$
(SEQ ID NO: 10)

-continued

(11) $K^{24}Q^{25}L^{26}L^{27}H^{28}L^{29}K^{30}V^{31}H^{32}$
(SEQ ID NO: 25)

(12) $K^{24}Q^{25}L^{26}L^{27}H^{28}L^{29}K^{30}V^{31}H^{32}L^{33}D^{34}V^{35}K^{36}G^{37}V^{38}K^{39}Q^{40}L^{41}L^{42}H^{43}$
(SEQ ID NO: 26)

(13) $H^{28}L^{29}K^{30}V^{31}H^{32}L^{33}D^{34}V^{35}K^{36}$
(SEQ ID NO: 27)

(14) $H^{28}L^{29}K^{30}V^{31}H^{32}L^{33}D^{34}V^{35}K^{36}G^{37}V^{38}K^{39}$
(SEQ ID NO: 28)

(15) $H^{28}L^{29}K^{30}V^{31}H^{32}L^{33}D^{34}V^{35}K^{36}G^{37}V^{38}K^{39}Q^{40}L^{41}L^{42}H^{43}L^{44}K^{45}$
(SEQ ID NO: 29)

(16) $H^{28}L^{29}K^{30}V^{31}H^{32}L^{33}D^{34}V^{35}K^{36}G^{37}V^{38}K^{39}Q^{40}L^{41}L^{42}H^{43}L^{44}K^{45}V^{46}R^{47}L^{48}D^{49}V^{50}R^{51}G^{52}A^{53}K^{54}$
(SEQ ID NO: 30)

(17) $H^{28}L^{29}K^{30}V^{31}H^{32}L^{33}D^{34}V^{35}K^{36}G^{37}V^{38}K^{39}Q^{40}L^{41}L^{42}H^{43}L^{44}K^{45}V^{46}R^{47}L^{48}D^{49}V^{50}R^{51}G^{52}A^{53}K^{54}Q^{55}N^{56}P^{57}$
$W^{58}R^{59}K^{60}$
(SEQ ID NO: 31)

(18) $H^{28}L^{29}K^{30}V^{31}H^{32}L^{33}D^{34}V^{35}K^{36}G^{37}V^{38}K^{39}Q^{40}L^{41}L^{42}H^{43}L^{44}K^{45}V^{46}R^{47}L^{48}D^{49}V^{50}R^{51}G^{52}A^{53}K^{54}Q^{55}N^{56}P^{57}$
$W^{58}R^{59}K^{60}N^{61}L^{62}C^{63}L^{64}L^{65}K^{66}$
(SEQ ID NO: 32)

(19) $H^{28}L^{29}K^{30}V^{31}H^{32}L^{33}D^{34}V^{35}K^{36}G^{37}V^{38}K^{39}Q^{40}L^{41}L^{42}H^{43}L^{44}K^{45}V^{46}R^{47}L^{48}D^{49}V^{50}R^{51}G^{52}A^{53}K^{54}Q^{55}N^{56}P^{57}$
$W^{58}R^{59}K^{60}N^{61}L^{62}C^{63}L^{64}L^{65}K^{66}K^{67}$
(SEQ ID NO: 33)

(20) $H^{28}L^{29}K^{30}V^{31}H^{32}L^{33}D^{34}V^{35}K^{36}G^{37}V^{38}K^{39}Q^{40}L^{41}L^{42}H^{43}L^{44}K^{45}V^{46}R^{47}L^{48}D^{49}V^{50}R^{51}G^{52}A^{53}K^{54}Q^{55}N^{56}P^{57}$
$W^{58}R^{59}K^{60}N^{61}L^{62}C^{63}L^{64}L^{65}K^{66}K^{67}N^{68}V^{69}K^{70}$
(SEQ ID NO: 34)

(21) $H^{28}L^{29}K^{30}V^{31}H^{32}L^{33}D^{34}V^{35}K^{36}G^{37}V^{38}K^{39}Q^{40}L^{41}L^{42}H^{43}L^{44}K^{45}V^{46}R^{47}L^{48}D^{49}V^{50}R^{51}G^{52}A^{53}K^{54}Q^{55}N^{56}P^{57}$
$W^{58}R^{59}K^{60}N^{61}L^{62}C^{63}L^{64}L^{65}K^{66}K^{67}N^{68}V^{69}K^{70}S^{71}A^{72}K^{73}$
(SEQ ID NO: 35)

(22) $K^{30}V^{31}H^{32}L^{33}D^{34}V^{35}K^{36}G^{37}V^{38}K^{39}Q^{40}L^{41}L^{42}H^{43}L^{44}K^{45}V^{46}R^{47}L^{48}D^{49}V^{50}R^{51}G^{52}A^{53}K^{54}Q^{55}N^{56}P^{57}W^{58}R^{59}$
$K^{60}N^{61}L^{62}C^{63}L^{64}L^{65}K^{66}K^{67}N^{68}V^{69}K^{70}S^{71}A^{72}K^{73}Q^{74}L^{75}P^{76}H^{77}$
(SEQ ID NO: 36)

(23) $K^{30}V^{31}H^{32}L^{33}D^{34}V^{35}K^{36}$
(SEQ ID NO: 11)

(24) $K^{30}V^{31}H^{32}L^{33}D^{34}V^{35}K^{36}G^{37}V^{38}K^{39}$
(SEQ ID NO: 37)

(25) $K^{30}V^{31}H^{32}L^{33}D^{34}V^{35}K^{36}G^{37}V^{38}K^{39}Q^{40}L^{41}L^{42}H^{43}$
(SEQ ID NO: 12)

(26) $H^{32}L^{33}D^{34}V^{35}K^{36}G^{37}V^{38}K^{39}Q^{40}L^{41}L^{42}H^{43}L^{44}K^{45}$
(SEQ ID NO: 38)

(27) $H^{32}L^{33}D^{34}V^{35}K^{36}G^{37}V^{38}K^{39}Q^{40}L^{41}L^{42}H^{43}L^{44}K^{45}V^{46}R^{47}L^{48}D^{49}V^{50}R^{51}G^{52}A^{53}K^{54}$
(SEQ ID NO: 39)

(28) $H^{32}L^{33}D^{34}V^{35}K^{36}G^{37}V^{38}K^{39}Q^{40}L^{41}L^{42}H^{43}L^{44}K^{45}V^{46}R^{47}L^{48}D^{49}V^{50}R^{51}G^{52}A^{53}K^{54}Q^{55}N^{56}P^{57}W^{58}R^{59}K^{60}$
(SEQ ID NO: 40)

(29) $H^{32}L^{33}D^{34}V^{35}K^{36}G^{37}V^{38}K^{39}Q^{40}L^{41}L^{42}H^{43}L^{44}K^{45}V^{46}R^{47}L^{48}D^{49}V^{50}R^{51}G^{52}A^{53}K^{54}Q^{55}N^{56}P^{57}W^{58}R^{59}K^{60}N^{61}$
$L^{62}C^{63}L^{64}L^{65}K^{66}$
(SEQ ID NO: 41)

(30) $H^{32}L^{33}D^{34}V^{35}K^{36}G^{37}V^{38}K^{39}Q^{40}L^{41}L^{42}H^{43}L^{44}K^{45}V^{46}R^{47}L^{48}D^{49}V^{50}R^{51}G^{52}A^{53}K^{54}Q^{55}N^{56}P^{57}W^{58}R^{59}K^{60}N^{61}$
$L^{62}C^{63}L^{64}L^{65}K^{66}K^{67}$
(SEQ ID NO: 42)

(31) $H^{32}L^{33}D^{34}V^{35}K^{36}G^{37}V^{38}K^{39}Q^{40}L^{41}L^{42}H^{43}L^{44}K^{45}V^{46}R^{47}L^{48}D^{49}V^{50}R^{51}G^{52}A^{53}K^{54}Q^{55}N^{56}P^{57}W^{58}R^{59}K^{60}N^{61}$
$L^{62}C^{63}L^{64}L^{65}K^{66}K^{67}N^{68}V^{69}K^{70}$
(SEQ ID NO: 43)

(32) $H^{32}L^{33}D^{34}V^{35}K^{36}G^{37}V^{38}K^{39}Q^{40}L^{41}L^{42}H^{43}L^{44}K^{45}V^{46}R^{47}L^{48}D^{49}V^{50}R^{51}G^{52}A^{53}K^{54}Q^{55}N^{56}P^{57}W^{58}R^{59}K^{60}N^{61}$
$L^{62}C^{63}L^{64}L^{65}K^{66}K^{67}N^{68}V^{69}K^{70}S^{71}A^{72}K^{73}$
(SEQ ID NO: 44)

(33) $H^{32}L^{33}D^{34}V^{35}K^{36}G^{37}V^{38}K^{39}Q^{40}L^{41}L^{42}H^{43}L^{44}K^{45}V^{46}R^{47}L^{48}D^{49}V^{50}R^{51}G^{52}A^{53}K^{54}Q^{55}N^{56}P^{57}W^{58}R^{59}K^{60}N^{61}$
$L^{62}C^{63}L^{64}L^{65}K^{66}K^{67}N^{68}V^{69}K^{70}S^{71}A^{72}K^{73}Q^{74}L^{75}P^{76}H^{77}L^{78}K^{79}$
(SEQ ID NO: 45)

-continued

(34) $K^{36}G^{37}V^{38}K^{39}Q^{40}L^{41}L^{42}H^{43}L^{44}K^{45}$
(SEQ ID NO: 46)

(35) $K^{36}G^{37}V^{38}K^{39}Q^{40}L^{41}L^{42}H^{43}L^{44}K^{45}V^{46}R^{47}L^{48}D^{49}V^{50}R^{51}G^{52}A^{53}K^{54}Q^{55}N^{56}P^{57}W^{58}R^{59}K^{60}N^{61}L^{62}C^{63}L^{64}L^{65}$
$K^{66}K^{67}N^{68}V^{69}K^{70}S^{71}A^{72}K^{73}Q^{74}L^{75}P^{76}H^{77}$
(SEQ ID NO: 47)

(36) $K^{36}G^{37}V^{38}K^{39}Q^{40}L^{41}L^{42}H^{43}L^{44}K^{45}V^{46}R^{47}L^{48}D^{49}V^{50}R^{51}G^{52}A^{53}K^{54}Q^{55}N^{56}P^{57}W^{58}R^{59}K^{60}N^{61}L^{62}C^{63}L^{64}L^{65}$
$K^{66}K^{67}N^{68}V^{69}K^{70}S^{71}A^{72}K^{73}Q^{74}L^{75}P^{76}H^{77}L^{78}K^{79}V^{80}H^{81}$
(SEQ ID NO: 48)

(37) $K^{39}Q^{40}L^{41}L^{42}H^{43}L^{44}K^{45}$
(SEQ ID NO: 10)

(38) $K^{39}Q^{40}L^{41}L^{42}H^{43}L^{44}K^{45}V^{46}R^{47}L^{48}D^{49}V^{50}R^{51}G^{52}A^{53}K^{54}Q^{55}N^{56}P^{57}W^{58}R^{59}K^{60}N^{61}L^{62}C^{63}L^{64}L^{65}K^{66}K^{67}N^{68}$
$V^{69}K^{70}S^{71}A^{72}K^{73}Q^{74}L^{75}P^{76}H^{77}$
(SEQ ID NO: 49)

(39) $K^{39}Q^{40}L^{41}L^{42}H^{43}L^{44}K^{45}V^{46}R^{47}L^{48}D^{49}V^{50}R^{51}G^{52}A^{53}K^{54}Q^{55}N^{56}P^{57}W^{58}R^{59}K^{60}N^{61}L^{62}C^{63}L^{64}L^{65}K^{66}K^{67}N^{68}$
$V^{69}K^{70}S^{71}A^{72}K^{73}Q^{74}L^{75}P^{76}H^{77}L^{78}K^{79}V^{80}H^{81}$
(SEQ ID NO: 50)

(40) $H^{43}L^{44}K^{45}V^{46}R^{47}L^{48}D^{49}V^{50}R^{51}G^{52}A^{53}K^{54}$
(SEQ ID NO: 51)

(41) $H^{43}L^{44}K^{45}V^{46}R^{47}L^{48}D^{49}V^{50}R^{51}G^{52}A^{53}K^{54}Q^{55}N^{56}P^{57}W^{58}R^{59}K^{60}$
(SEQ ID NO: 52)

(42) $H^{43}L^{44}K^{45}V^{46}R^{47}L^{48}D^{49}V^{50}R^{51}G^{52}A^{53}K^{54}Q^{55}N^{56}P^{57}W^{58}R^{59}K^{60}N^{61}L^{62}C^{63}L^{64}L^{65}K^{66}$
(SEQ ID NO: 53)

(43) $H^{43}L^{44}K^{45}V^{46}R^{47}L^{48}D^{49}V^{50}R^{51}G^{52}A^{53}K^{54}Q^{55}N^{56}P^{57}W^{58}R^{59}K^{60}N^{61}L^{62}C^{63}L^{64}L^{65}K^{66}K^{67}$
(SEQ ID NO: 54)

(44) $H^{43}L^{44}K^{45}V^{46}R^{47}L^{48}D^{49}V^{50}R^{51}G^{52}A^{53}K^{54}Q^{55}N^{56}P^{57}W^{58}R^{59}K^{60}N^{61}L^{62}C^{63}L^{64}L^{65}K^{66}K^{67}N^{68}V^{69}K^{70}$
(SEQ ID NO: 55)

(45) $H^{43}L^{44}K^{45}V^{46}R^{47}L^{48}D^{49}V^{50}R^{51}G^{52}A^{53}K^{54}Q^{55}N^{56}P^{57}W^{58}R^{59}K^{60}N^{61}L^{62}C^{63}L^{64}L^{65}K^{66}K^{67}N^{68}V^{69}K^{70}S^{71}A^{72}$
$K^{73}$
(SEQ ID NO: 56)

(46) $H^{43}L^{44}K^{45}V^{46}R^{47}L^{48}D^{49}V^{50}R^{51}G^{52}A^{53}K^{54}Q^{55}N^{56}P^{57}W^{58}R^{59}K^{60}N^{61}L^{62}C^{63}L^{64}L^{65}K^{66}K^{67}N^{68}V^{69}K^{70}S^{71}A^{72}$
$K^{73}Q^{74}L^{75}P^{76}H^{77}L^{78}K^{79}$
(SEQ ID NO: 57)

(47) $H^{43}L^{44}K^{45}V^{46}R^{47}L^{48}D^{49}V^{50}R^{51}G^{52}A^{53}K^{54}Q^{55}N^{56}P^{57}W^{58}R^{59}K^{60}N^{61}L^{62}C^{63}L^{64}L^{65}K^{66}K^{67}N^{68}V^{69}K^{70}S^{71}A^{72}$
$K^{73}Q^{74}L^{75}P^{76}H^{77}L^{78}K^{79}V^{80}H^{81}L^{82}D^{83}V^{84}K^{85}$
(SEQ ID NO: 58)

(48) $H^{43}L^{44}K^{45}V^{46}R^{47}L^{48}D^{49}V^{50}R^{51}G^{52}A^{53}K^{54}Q^{55}N^{56}P^{57}W^{58}R^{59}K^{60}N^{61}L^{62}C^{63}L^{64}L^{65}K^{66}K^{67}N^{68}V^{69}K^{70}S^{71}A^{72}$
$K^{73}Q^{74}L^{75}P^{76}H^{77}L^{78}K^{79}V^{80}H^{81}L^{82}D^{83}V^{84}K^{85}S^{86}A^{87}K^{88}$
(SEQ ID NO: 59)

(49) $K^{45}V^{46}R^{47}L^{48}D^{49}V^{50}R^{51}G^{52}A^{53}K^{54}Q^{55}N^{56}P^{57}W^{58}R^{59}K^{60}N^{61}L^{62}C^{63}L^{64}L^{65}K^{66}K^{67}N^{68}V^{69}K^{70}S^{71}A^{72}K^{73}Q^{74}$
$L^{75}P^{76}H^{77}$
(SEQ ID NO: 60)

(50) $K^{45}V^{46}R^{47}L^{48}D^{49}V^{50}R^{51}G^{52}A^{53}K^{54}Q^{55}N^{56}P^{57}W^{58}R^{59}K^{60}N^{61}L^{62}C^{63}L^{64}L^{65}K^{66}K^{67}N^{68}V^{69}K^{70}S^{71}A^{72}K^{73}Q^{74}$
$L^{75}P^{76}H^{77}L^{78}K^{79}V^{80}H^{81}$
(SEQ ID NO: 61)

(51) $K^{45}V^{46}R^{47}L^{48}D^{49}V^{50}R^{51}G^{52}A^{53}K^{54}Q^{55}N^{56}P^{57}W^{58}R^{59}K^{60}N^{61}L^{62}C^{63}L^{64}L^{65}K^{66}K^{67}N^{68}V^{69}K^{70}S^{71}A^{72}K^{73}Q^{74}$
$L^{75}P^{76}H^{77}L^{78}K^{79}V^{80}H^{81}L^{82}D^{83}V^{84}K^{85}S^{86}A^{87}K^{88}Q^{89}L^{90}P^{91}H^{92}$
(SEQ ID NO: 62)

(52) $K^{54}Q^{55}N^{56}P^{57}W^{58}R^{59}K^{60}N^{61}L^{62}C^{63}L^{64}L^{65}K^{66}K^{67}N^{68}V^{69}K^{70}S^{71}A^{72}K^{73}Q^{74}L^{75}P^{76}H^{77}$
(SEQ ID NO: 63)

(53) $K^{54}Q^{55}N^{56}P^{57}W^{58}R^{59}K^{60}N^{61}L^{62}C^{63}L^{64}L^{65}K^{66}K^{67}N^{68}V^{69}K^{70}S^{71}A^{72}K^{73}Q^{74}L^{75}P^{76}H^{77}L^{78}K^{79}V^{80}H^{81}$
(SEQ ID NO: 64)

(54) $K^{54}Q^{55}N^{56}P^{57}W^{58}R^{59}K^{60}N^{61}L^{62}C^{63}L^{64}L^{65}K^{66}K^{67}N^{68}V^{69}K^{70}S^{71}A^{72}K^{73}Q^{74}L^{75}P^{76}H^{77}L^{78}K^{79}V^{80}H^{81}L^{82}D^{83}V^{84}K^{85}$
$S^{86}A^{87}K^{88}Q^{89}L^{90}P^{91}H^{92}$
(SEQ ID NO: 65)

(55) $K^{54}Q^{55}N^{56}P^{57}W^{58}R^{59}K^{60}N^{61}L^{62}C^{63}L^{64}L^{65}K^{66}K^{67}N^{68}V^{69}K^{70}S^{71}A^{72}K^{73}Q^{74}L^{75}P^{76}H^{77}L^{78}K^{79}V^{80}H^{81}L^{82}D^{83}V^{84}K^{85}$
$S^{86}A^{87}K^{88}Q^{89}L^{90}P^{91}H^{92}L^{93}K^{94}V^{95}H^{96}$
(SEQ ID NO: 66)

-continued

(56) $K^{60}N^{61}L^{62}C^{63}L^{64}L^{65}K^{66}K^{67}N^{68}V^{69}K^{70}S^{71}A^{72}K^{73}Q^{74}L^{75}P^{76}H^{77}L^{78}K^{79}V^{80}H^{81}L^{82}D^{83}V^{84}K^{85}S^{86}A^{87}K^{88}Q^{89}L^{90}P^{91}H^{92}L^{93}K^{94}V^{95}H^{96}L^{97}D^{98}V^{99}R^{100}G^{101}A^{102}K^{103}Q^{104}L^{105}P^{106}H^{107}$
(SEQ ID NO: 67)

(57) $K^{60}N^{61}L^{62}C^{63}L^{64}L^{65}K^{66}K^{67}N^{68}V^{69}K^{70}S^{71}A^{72}K^{73}Q^{74}L^{75}P^{76}H^{77}$
(SEQ ID NO: 68)

(58) $K^{60}N^{61}L^{62}C^{63}L^{64}L^{65}K^{66}K^{67}N^{68}V^{69}K^{70}S^{71}A^{72}K^{73}Q^{74}L^{75}P^{76}H^{77}L^{78}K^{79}V^{80}H^{81}$
(SEQ ID NO: 69)

(59) $K^{60}N^{61}L^{62}C^{63}L^{64}L^{65}K^{66}K^{67}N^{68}V^{69}K^{70}S^{71}A^{72}K^{73}Q^{74}L^{75}P^{76}H^{77}L^{78}K^{79}V^{80}H^{81}L^{82}D^{83}V^{84}K^{85}S^{86}A^{87}K^{88}Q^{89}L^{90}P^{91}H^{92}$
(SEQ ID NO: 70)

(60) $K^{60}N^{61}L^{62}C^{63}L^{64}L^{65}K^{66}K^{67}N^{68}V^{69}K^{70}S^{71}A^{72}K^{73}Q^{74}L^{75}P^{76}H^{77}L^{78}K^{79}V^{80}H^{81}L^{82}D^{83}V^{84}K^{85}S^{86}A^{87}K^{88}Q^{89}L^{90}P^{91}H^{92}L^{93}K^{94}V^{95}H^{96}$
(SEQ ID NO: 71)

(61) $K^{66}K^{67}N^{68}V^{69}K^{70}S^{71}A^{72}K^{73}Q^{74}L^{75}P^{76}H^{77}$
(SEQ ID NO: 13)

(62) $K^{66}K^{67}N^{68}V^{69}K^{70}S^{71}A^{72}K^{73}Q^{74}L^{75}P^{76}H^{77}L^{78}K^{79}V^{80}H^{81}$
(SEQ ID NO: 72)

(63) $K^{66}K^{67}N^{68}V^{69}K^{70}S^{71}A^{72}K^{73}Q^{74}L^{75}P^{76}H^{77}L^{78}K^{79}V^{80}H^{81}L^{82}D^{83}V^{84}K^{85}S^{86}A^{87}K^{88}Q^{89}L^{90}P^{91}H^{92}$
(SEQ ID NO: 73)

(64) $K^{66}K^{67}N^{68}V^{69}K^{70}S^{71}A^{72}K^{73}Q^{74}L^{75}P^{76}H^{77}L^{78}K^{79}V^{80}H^{81}L^{82}D^{83}V^{84}K^{85}S^{86}A^{87}K^{88}Q^{89}L^{90}P^{91}H^{92}L^{93}K^{94}V^{95}H^{96}$
(SEQ ID NO: 1)

(65) $K^{66}K^{67}N^{68}V^{69}K^{70}S^{71}A^{72}K^{73}Q^{74}L^{75}P^{76}H^{77}L^{78}K^{79}V^{80}H^{81}L^{82}D^{83}V^{84}K^{85}S^{86}A^{87}K^{88}Q^{89}L^{90}P^{91}H^{92}L^{93}K^{94}V^{95}H^{96}L^{97}D^{98}V^{99}R^{100}G^{101}A^{102}K^{103}Q^{104}L^{105}P^{106}H^{107}$
(SEQ ID NO: 74)

(66) $K^{67}N^{68}V^{69}K^{70}S^{71}A^{72}K^{73}Q^{74}L^{75}P^{76}H^{77}$
(SEQ ID NO: 75)

(67) $K^{67}N^{68}V^{69}K^{70}S^{71}A^{72}K^{73}Q^{74}L^{75}P^{76}H^{77}L^{78}K^{79}V^{80}H^{81}$
(SEQ ID NO: 76)

(68) $K^{67}N^{68}V^{69}K^{70}S^{71}A^{72}K^{73}Q^{74}L^{75}P^{76}H^{77}L^{78}K^{79}V^{80}H^{81}L^{82}D^{83}V^{84}K^{85}S^{86}A^{87}K^{88}Q^{89}L^{90}P^{91}H^{92}$
(SEQ ID NO: 77)

(69) $K^{67}N^{68}V^{69}K^{70}S^{71}A^{72}K^{73}Q^{74}L^{75}P^{76}H^{77}L^{78}K^{79}V^{80}H^{81}L^{82}D^{83}V^{84}K^{85}S^{86}A^{87}K^{88}Q^{89}L^{90}P^{91}H^{92}L^{93}K^{94}V^{95}H^{96}$
(SEQ ID NO: 78)

(70) $K^{67}N^{68}V^{69}K^{70}S^{71}A^{72}K^{73}Q^{74}L^{75}P^{76}H^{77}L^{78}K^{79}V^{80}H^{81}L^{82}D^{83}V^{84}K^{85}S^{86}A^{87}K^{88}Q^{89}L^{90}P^{91}H^{92}L^{93}K^{94}V^{95}H^{96}L^{97}D^{98}V^{99}R^{100}G^{101}A^{102}K^{103}Q^{104}L^{105}P^{106}H^{107}$
(SEQ ID NO: 79)

(71) $K^{70}S^{71}A^{72}K^{73}Q^{74}L^{75}P^{76}H^{77}L^{78}K^{79}V^{80}H^{81}L^{82}D^{83}V^{84}K^{85}S^{86}A^{87}K^{88}Q^{89}L^{90}P^{91}H^{92}L^{93}K^{94}V^{95}H^{96}L^{97}D^{98}V^{99}R^{100}G^{101}A^{102}K^{103}Q^{104}L^{105}P^{106}H^{107}$
(SEQ ID NO: 80)

(72) $K^{70}S^{71}A^{72}K^{73}Q^{74}L^{75}P^{76}H^{77}L^{78}K^{79}$
(SEQ ID NO: 14)

(73) $K^{70}S^{71}A^{72}K^{73}Q^{74}L^{75}P^{76}H^{77}L^{78}K^{79}V^{80}H^{81}$
(SEQ ID NO: 81)

(74) $K^{70}S^{71}A^{72}K^{73}Q^{74}L^{75}P^{76}H^{77}L^{78}K^{79}V^{80}H^{81}L^{82}D^{83}V^{84}K^{85}S^{86}A^{87}K^{88}Q^{89}L^{90}P^{91}H^{92}$
(SEQ ID NO: 82)

(75) $K^{70}S^{71}A^{72}K^{73}Q^{74}L^{75}P^{76}H^{77}L^{78}K^{79}V^{80}H^{81}L^{82}D^{83}V^{84}K^{85}S^{86}A^{87}K^{88}Q^{89}L^{90}P^{91}H^{92}L^{93}K^{94}V^{95}H^{96}$
(SEQ ID NO: 83)

(76) $K^{73}Q^{74}L^{75}P^{76}H^{77}L^{78}K^{79}$
(SEQ ID NO: 84)

(77) $K^{73}Q^{74}L^{75}P^{76}H^{77}L^{78}K^{79}V^{80}H^{81}$
(SEQ ID NO: 85)

(78) $K^{73}Q^{74}L^{75}P^{76}H^{77}L^{78}K^{79}V^{80}H^{81}L^{82}D^{83}V^{84}K^{85}S^{86}A^{87}K^{88}Q^{89}L^{90}P^{91}H^{92}L^{93}K^{94}V^{95}H^{96}L^{97}D^{98}V^{99}R^{100}G^{101}A^{102}K^{103}Q^{104}L^{105}P^{106}H^{107}$
(SEQ ID NO: 86)

(79) $K^{73}Q^{74}L^{75}P^{76}H^{77}L^{78}K^{79}V^{80}H^{81}L^{82}D^{83}V^{84}K^{85}S^{86}A^{87}K^{88}Q^{89}L^{90}P^{91}H^{92}$
(SEQ ID NO: 87)

(80) $K^{73}Q^{74}L^{75}P^{76}H^{77}L^{78}K^{79}V^{80}H^{81}L^{82}D^{83}V^{84}K^{85}S^{86}A^{87}K^{88}Q^{89}L^{90}P^{91}H^{92}L^{93}K^{94}V^{95}H^{96}$
(SEQ ID NO: 88)

-continued

(81) $K^{73}Q^{74}L^{75}P^{76}H^{77}L^{78}K^{79}V^{80}H^{81}L^{82}D^{83}V^{84}K^{85}S^{86}A^{87}K^{88}Q^{89}L^{90}P^{91}H^{92}L^{93}K^{94}V^{95}H^{96}L^{97}D^{98}V^{99}R^{100}G^{101}A^{102}$
$K^{103}Q^{104}L^{105}P^{106}H^{107}L^{108}K^{109}V^{110}R^{111}L^{112}D^{113}V^{114}K^{115}S^{116}A^{117}K^{118}Q^{119}L^{120}P^{121}H^{122}$
(SEQ ID NO: 89)

(82) $H^{77}L^{78}K^{79}V^{80}H^{81}L^{82}D^{83}V^{84}K^{85}$
(SEQ ID NO: 27)

(83) $H^{77}L^{78}K^{79}V^{80}H^{81}L^{82}D^{83}V^{84}K^{85}S^{86}A^{87}K^{88}$
(SEQ ID NO: 90)

(84) $H^{77}L^{78}K^{79}V^{80}H^{81}L^{82}D^{83}V^{84}K^{85}S^{86}A^{87}K^{88}Q^{89}L^{90}P^{91}H^{92}L^{93}K^{94}$
(SEQ ID NO: 91)

(85) $H^{77}L^{78}K^{79}V^{80}H^{81}L^{82}D^{83}V^{84}K^{85}S^{86}A^{87}K^{88}Q^{89}L^{90}P^{91}H^{92}L^{93}K^{94}V^{95}H^{96}L^{97}D^{98}V^{99}R^{100}G^{101}A^{102}K^{103}$
(SEQ ID NO: 92)

(86) $H^{77}L^{78}K^{79}V^{80}H^{81}L^{82}D^{83}V^{84}K^{85}S^{86}A^{87}K^{88}Q^{89}L^{90}P^{91}H^{92}L^{93}K^{94}V^{95}H^{96}L^{97}D^{98}V^{99}R^{100}G^{101}A^{102}K^{103}Q^{104}L^{105}$
$P^{106}H^{107}L^{108}K^{109}$
(SEQ ID NO: 93)

(87) $H^{77}L^{78}K^{79}V^{80}H^{81}L^{82}D^{83}V^{84}K^{85}S^{86}A^{87}K^{88}Q^{89}L^{90}P^{91}H^{92}L^{93}K^{94}V^{95}H^{96}L^{97}D^{98}V^{99}R^{100}G^{101}A^{102}K^{103}Q^{104}L^{105}$
$P^{106}H^{107}L^{108}K^{109}V^{110}R^{111}L^{112}D^{113}V^{114}K^{115}$
(SEQ ID NO: 94)

(88) $H^{77}L^{78}K^{79}V^{80}H^{81}L^{82}D^{83}V^{84}K^{85}S^{86}A^{87}K^{88}Q^{89}L^{90}P^{91}H^{92}L^{93}K^{94}V^{95}H^{96}L^{97}D^{98}V^{99}R^{100}G^{101}A^{102}K^{103}Q^{104}L^{105}$
$P^{106}H^{107}L^{108}K^{109}V^{110}R^{111}L^{112}D^{113}V^{114}K^{115}S^{116}A^{117}K^{118}$
(SEQ ID NO: 95)

(89) $H^{77}L^{78}K^{79}V^{80}H^{81}L^{82}D^{83}V^{84}K^{85}S^{86}A^{87}K^{88}Q^{89}L^{90}P^{91}H^{92}L^{93}K^{94}V^{95}H^{96}L^{97}D^{98}V^{99}R^{100}G^{101}A^{102}K^{103}Q^{104}L^{105}$
$P^{106}H^{107}L^{108}K^{109}V^{110}R^{111}L^{112}D^{113}V^{114}K^{115}S^{116}A^{117}K^{118}Q^{119}L^{120}P^{121}H^{122}L^{123}K^{124}$
(SEQ ID NO: 96)

(90) $K^{79}V^{80}H^{81}L^{82}D^{83}V^{84}K^{85}S^{86}A^{87}K^{88}Q^{89}L^{90}P^{91}H^{92}L^{93}K^{94}V^{95}H^{96}L^{97}D^{98}V^{99}R^{100}G^{101}A^{102}K^{103}Q^{104}L^{105}P^{106}H^{107}$
(SEQ ID NO: 97)

(91) $K^{79}V^{80}H^{81}L^{82}D^{83}V^{84}K^{85}S^{86}A^{87}K^{88}Q^{89}L^{90}P^{91}H^{92}L^{93}K^{94}V^{95}H^{96}L^{97}D^{98}V^{99}R^{100}G^{101}A^{102}K^{103}Q^{104}L^{105}P^{106}H^{107}$
$L^{108}K^{109}V^{110}R^{111}L^{112}D^{113}V^{114}K^{115}S^{116}A^{117}K^{118}Q^{119}L^{120}P^{121}H^{122}$
(SEQ ID NO: 98)

(92) $K^{79}V^{80}H^{81}L^{82}D^{83}V^{84}K^{85}S^{86}A^{87}K^{88}Q^{89}L^{90}P^{91}H^{92}L^{93}K^{94}V^{95}H^{96}L^{97}D^{98}V^{99}R^{100}G^{101}A^{102}K^{103}Q^{104}L^{105}P^{106}H^{107}$
$L^{108}K^{109}V^{110}R^{111}L^{112}D^{113}V^{114}K^{115}S^{116}A^{117}K^{118}Q^{119}L^{120}P^{121}H^{122}L^{123}K^{124}V^{125}H^{126}$
(SEQ ID NO: 99)

(93) $K^{79}V^{80}H^{81}L^{82}D^{83}V^{84}K^{85}$
(SEQ ID NO: 11)

(94) $K^{79}V^{80}H^{81}L^{82}D^{83}V^{84}K^{85}S^{86}A^{87}K^{88}$
(SEQ ID NO: 100)

(95) $K^{79}V^{80}H^{81}L^{82}D^{83}V^{84}K^{85}S^{86}A^{87}K^{88}Q^{89}L^{90}P^{91}H^{92}$
(SEQ ID NO: 101)

(96) $K^{79}V^{80}H^{81}L^{82}D^{83}V^{84}K^{85}S^{86}A^{87}K^{88}Q^{89}L^{90}P^{91}H^{92}L^{93}K^{94}V^{95}H^{96}$
(SEQ ID NO: 102)

(97) $H^{81}L^{82}D^{83}V^{84}K^{85}S^{86}A^{87}K^{88}Q^{89}L^{90}P^{91}H^{92}L^{93}K^{94}$
(SEQ ID NO: 103)

(98) $H^{81}L^{82}D^{83}V^{84}K^{85}S^{86}A^{87}K^{88}Q^{89}L^{90}P^{91}H^{92}L^{93}K^{94}V^{95}H^{96}L^{97}D^{98}V^{99}R^{100}G^{101}A^{102}K^{103}$
(SEQ ID NO: 104)

(99) $H^{81}L^{82}D^{83}V^{84}K^{85}S^{86}A^{87}K^{88}Q^{89}L^{90}P^{91}H^{92}L^{93}K^{94}V^{95}H^{96}L^{97}D^{98}V^{99}R^{100}G^{101}A^{102}K^{103}Q^{104}L^{105}P^{106}H^{107}L^{108}$
$K^{109}$
(SEQ ID NO: 105)

(100) $H^{81}L^{82}D^{83}V^{84}K^{85}S^{86}A^{87}K^{88}Q^{89}L^{90}P^{91}H^{92}L^{93}K^{94}V^{95}H^{96}L^{97}D^{98}V^{99}R^{100}G^{101}A^{102}K^{103}Q^{104}L^{105}P^{106}H^{107}L^{108}$
$K^{109}V^{110}R^{111}L^{112}D^{113}V^{114}K^{115}$
(SEQ ID NO: 106)

(101) $H^{81}L^{82}D^{83}V^{84}K^{85}S^{86}A^{87}K^{88}Q^{89}L^{90}P^{91}H^{92}L^{93}K^{94}V^{95}H^{96}L^{97}D^{98}V^{99}R^{100}G^{101}A^{102}K^{103}Q^{104}L^{105}P^{106}H^{107}L^{108}$
$K^{109}V^{110}R^{111}L^{112}D^{113}V^{114}K^{115}S^{116}A^{117}K^{118}$
(SEQ ID NO: 107)

(102) $H^{81}L^{82}D^{83}V^{84}K^{85}S^{86}A^{87}K^{88}Q^{89}L^{90}P^{91}H^{92}L^{93}K^{94}V^{95}H^{96}L^{97}D^{98}V^{99}R^{100}G^{101}A^{102}K^{103}Q^{104}L^{105}P^{106}H^{107}L^{108}$
$K^{109}V^{110}R^{111}L^{112}D^{113}V^{114}K^{115}S^{116}A^{117}K^{118}Q^{119}L^{120}P^{121}H^{122}L^{123}K^{124}$
(SEQ ID NO: 108)

(103) $K^{85}S^{86}A^{87}K^{88}Q^{89}L^{90}P^{91}H^{92}L^{93}K^{94}V^{95}H^{96}L^{97}D^{98}V^{99}R^{100}G^{101}A^{102}K^{103}Q^{104}L^{105}P^{106}H^{107}$
(SEQ ID NO: 109)

-continued (104) $K^{85}S^{86}A^{87}K^{88}Q^{89}L^{90}P^{91}H^{92}L^{93}K^{94}V^{95}H^{96}L^{97}D^{98}V^{99}R^{100}G^{101}A^{102}K^{103}Q^{104}L^{105}P^{106}H^{107}L^{108}K^{109}V^{110}R^{111}L^{112}D^{113}V^{114}K^{115}S^{116}A^{117}K^{118}Q^{119}L^{120}P^{121}H^{122}$
(SEQ ID NO: 110)

(105) $K^{85}S^{86}A^{87}K^{88}Q^{89}L^{90}P^{91}H^{92}L^{93}K^{94}V^{95}H^{96}L^{97}D^{98}V^{99}R^{100}G^{101}A^{102}K^{103}Q^{104}L^{105}P^{106}H^{107}L^{108}K^{109}V^{110}R^{111}L^{112}D^{113}V^{114}K^{115}S^{116}A^{117}K^{118}Q^{119}L^{120}P^{121}H^{122}L^{123}K^{124}V^{125}H^{126}$
(SEQ ID NO: 111)

(106) $K^{85}S^{86}A^{87}K^{88}Q^{89}L^{90}P^{91}H^{92}L^{93}K^{94}$
(SEQ ID NO: 14)

(107) $K^{85}S^{86}A^{87}K^{88}Q^{89}L^{90}P^{91}H^{92}L^{93}K^{94}V^{95}H^{96}$
(SEQ ID NO: 82)

(108) $K^{88}Q^{89}L^{90}P^{91}H^{92}L^{93}K^{94}V^{95}H^{96}L^{97}D^{98}V^{99}R^{100}G^{101}A^{102}K^{103}Q^{104}L^{105}P^{106}H^{107}$
(SEQ ID NO: 112)

(109) $K^{88}Q^{89}L^{90}P^{91}H^{92}L^{93}K^{94}V^{95}H^{96}L^{97}D^{98}V^{99}R^{100}G^{101}A^{102}K^{103}Q^{104}L^{105}P^{106}H^{107}L^{108}K^{109}V^{110}R^{111}L^{112}D^{113}V^{114}K^{115}S^{116}A^{117}K^{118}Q^{119}L^{120}P^{121}H^{122}$
(SEQ ID NO: 113)

(110) $K^{88}Q^{89}L^{90}P^{91}H^{92}L^{93}K^{94}V^{95}H^{96}L^{97}D^{98}V^{99}R^{100}G^{101}A^{102}K^{103}Q^{104}L^{105}P^{106}H^{107}L^{108}K^{109}V^{110}R^{111}L^{112}D^{113}V^{114}K^{115}S^{116}A^{117}K^{118}Q^{119}L^{120}P^{121}H^{122}L^{123}K^{124}V^{125}H^{126}$
(SEQ ID NO: 114)

(111) $K^{88}Q^{89}L^{90}P^{91}H^{92}L^{93}K^{94}$
(SEQ ID NO: 84)

(112) $K^{88}Q^{89}L^{90}P^{91}H^{92}L^{93}K^{94}V^{95}H^{96}$
(SEQ ID NO: 85)

(113) $K^{88}Q^{89}L^{90}P^{91}H^{92}L^{93}K^{94}V^{95}H^{96}L^{97}D^{98}V^{99}R^{100}G^{101}A^{102}K^{103}Q^{104}L^{105}P^{106}H^{107}L^{108}K^{109}V^{110}R^{111}L^{112}D^{113}V^{114}K^{115}S^{116}A^{117}K^{118}Q^{119}L^{120}P^{121}H^{122}L^{123}K^{124}V^{125}H^{126}L^{127}D^{128}V^{129}R^{130}G^{131}A^{132}K^{133}Q^{134}L^{135}P^{136}H^{137}$
(SEQ ID NO: 115)

(114) $H^{92}L^{93}K^{94}V^{95}H^{96}L^{97}D^{98}V^{99}R^{100}G^{101}A^{102}K^{103}Q^{104}L^{105}P^{106}H^{107}L^{108}K^{109}V^{110}R^{111}L^{112}D^{113}V^{114}K^{115}$
(SEQ ID NO: 116)

(115) $H^{92}L^{93}K^{94}V^{95}H^{96}L^{97}D^{98}V^{99}R^{100}G^{101}A^{102}K^{103}Q^{104}L^{105}P^{106}H^{107}L^{108}K^{109}V^{110}R^{111}L^{112}D^{113}V^{114}K^{115}S^{116}A^{117}K^{118}$
(SEQ ID NO: 117)

(116) $H^{92}L^{93}K^{94}V^{95}H^{96}L^{97}D^{98}V^{99}R^{100}G^{101}A^{102}K^{103}Q^{104}L^{105}P^{106}H^{107}L^{108}K^{109}V^{110}R^{111}L^{112}D^{113}V^{114}K^{115}S^{116}A^{117}K^{118}Q^{119}L^{120}P^{121}H^{122}L^{123}K^{124}$
(SEQ ID NO: 118)

(117) $H^{92}L^{93}K^{94}V^{95}H^{96}L^{97}D^{98}V^{99}R^{100}G^{101}A^{102}K^{103}Q^{104}L^{105}P^{106}H^{107}L^{108}K^{109}V^{110}R^{111}L^{112}D^{113}V^{114}K^{115}S^{116}A^{117}K^{118}Q^{119}L^{120}P^{121}H^{122}L^{123}K^{124}V^{125}H^{126}L^{127}D^{128}V^{129}R^{130}G^{131}A^{132}K^{133}$
(SEQ ID NO: 119)

(118) $H^{92}L^{93}K^{94}V^{95}H^{96}L^{97}D^{98}V^{99}R^{100}G^{101}A^{102}K^{103}Q^{104}L^{105}P^{106}H^{107}L^{108}K^{109}V^{110}R^{111}L^{112}D^{113}V^{114}K^{115}S^{116}A^{117}K^{118}Q^{119}L^{120}P^{121}H^{122}L^{123}K^{124}V^{125}H^{126}L^{127}D^{128}V^{129}R^{130}G^{131}A^{132}K^{133}Q^{134}L^{135}P^{136}H^{137}L^{138}K^{139}$
(SEQ ID NO: 120)

(119) $H^{92}L^{93}K^{94}V^{95}H^{96}L^{97}D^{98}V^{99}R^{100}G^{101}A^{102}K^{103}$
(SEQ ID NO: 121)

(120) $H^{92}L^{93}K^{94}V^{95}H^{96}L^{97}D^{98}V^{99}R^{100}G^{101}A^{102}K^{103}Q^{104}L^{105}P^{106}H^{107}L^{108}K^{109}$
(SEQ ID NO: 122)

(121) $K^{94}V^{95}H^{96}L^{97}D^{98}V^{99}R^{100}G^{101}A^{102}K^{103}$
(SEQ ID NO: 123)

(122) $K^{94}V^{95}H^{96}L^{97}D^{98}V^{99}R^{100}G^{101}A^{102}K^{103}Q^{104}L^{105}P^{106}H^{107}$
(SEQ ID NO: 124)

(123) $K^{94}V^{95}H^{96}L^{97}D^{98}V^{99}R^{100}G^{101}A^{102}K^{103}Q^{104}L^{105}P^{106}H^{107}L^{108}K^{109}V^{110}R^{111}L^{112}D^{113}V^{114}K^{115}S^{116}A^{117}K^{118}Q^{119}L^{120}P^{121}H^{122}$
(SEQ ID NO: 125)

(124) $K^{94}V^{95}H^{96}L^{97}D^{98}V^{99}R^{100}G^{101}A^{102}K^{103}Q^{104}L^{105}P^{106}H^{107}L^{108}K^{109}V^{110}R^{111}L^{112}D^{113}V^{114}K^{115}S^{116}A^{117}K^{118}Q^{119}L^{120}P^{121}H^{122}L^{123}K^{124}V^{125}H^{126}$
(SEQ ID NO: 126)

(125) $K^{94}V^{95}H^{96}L^{97}D^{98}V^{99}R^{100}G^{101}A^{102}K^{103}Q^{104}L^{105}P^{106}H^{107}L^{108}K^{109}V^{110}R^{111}L^{112}D^{113}V^{114}K^{115}S^{116}A^{117}K^{118}Q^{119}L^{120}P^{121}H^{122}L^{123}K^{124}V^{125}H^{126}L^{127}D^{128}V^{129}R^{130}G^{131}A^{132}K^{133}Q^{134}L^{135}P^{136}H^{137}$
(SEQ ID NO: 127)

(126) $H^{96}L^{97}D^{98}V^{99}R^{100}G^{101}A^{102}K^{103}Q^{104}L^{105}P^{106}H^{107}L^{108}K^{109}$
(SEQ ID NO: 128)

-continued (127) $H^{96}L^{97}D^{98}V^{99}R^{100}G^{101}A^{102}K^{103}Q^{104}L^{105}P^{106}H^{107}L^{108}K^{109}V^{110}R^{111}L^{112}D^{113}V^{114}K^{115}$
(SEQ ID NO: 129)

(128) $H^{96}L^{97}D^{98}V^{99}R^{100}G^{101}A^{102}K^{103}Q^{104}L^{105}P^{106}H^{107}L^{108}K^{109}V^{110}R^{111}L^{112}D^{113}V^{114}K^{115}S^{116}A^{117}K^{118}$
(SEQ ID NO: 130)

(129) $H^{96}L^{97}D^{98}V^{99}R^{100}G^{101}A^{102}K^{103}Q^{104}L^{105}P^{106}H^{107}L^{108}K^{109}V^{110}R^{111}L^{112}D^{113}V^{114}K^{115}S^{116}A^{117}K^{118}Q^{119}L^{120}$
$P^{121}H^{122}L^{123}K^{124}$
(SEQ ID NO: 131)

(130) $H^{96}L^{97}D^{98}V^{99}R^{100}G^{101}A^{102}K^{103}Q^{104}L^{105}P^{106}H^{107}L^{108}K^{109}V^{110}R^{111}L^{112}D^{113}V^{114}K^{115}S^{116}A^{117}K^{118}Q^{119}L^{120}$
$P^{121}H^{122}L^{123}K^{124}V^{125}H^{126}L^{127}D^{128}V^{129}R^{130}G^{131}A^{132}K^{133}$
(SEQ ID NO: 132)

(131) $H^{96}L^{97}D^{98}V^{99}R^{100}G^{101}A^{102}K^{103}Q^{104}L^{105}P^{106}H^{107}L^{108}K^{109}V^{110}R^{111}L^{112}D^{113}V^{114}K^{115}S^{116}A^{117}K^{118}Q^{119}L^{120}$
$P^{121}H^{122}L^{123}K^{124}V^{125}H^{126}L^{127}D^{128}V^{129}R^{130}G^{131}A^{132}K^{133}Q^{134}L^{135}P^{136}H^{137}L^{138}K^{139}$
(SEQ ID NO: 133)

(132) $K^{103}Q^{104}L^{105}P^{106}H^{107}L^{108}K^{109}$
(SEQ ID NO: 84)

(133) $K^{103}Q^{104}L^{105}P^{106}H^{107}L^{108}K^{109}V^{110}R^{111}L^{112}D^{113}V^{114}K^{115}S^{116}A^{117}K^{118}Q^{119}L^{120}P^{121}H^{122}$
(SEQ ID NO: 134)

(134) $K^{103}Q^{104}L^{105}P^{106}H^{107}L^{108}K^{109}V^{110}R^{111}L^{112}D^{113}V^{114}K^{115}S^{116}A^{117}K^{118}Q^{119}L^{120}P^{121}H^{122}L^{123}K^{124}V^{125}H^{126}$
(SEQ ID NO: 135)

(135) $K^{103}Q^{104}L^{105}P^{106}H^{107}L^{108}K^{109}V^{110}R^{111}L^{112}D^{113}V^{114}K^{115}S^{116}A^{117}K^{118}Q^{119}L^{120}P^{121}H^{122}L^{123}K^{124}V^{125}H^{126}$
$L^{127}D^{128}V^{129}R^{130}G^{131}A^{132}K^{133}Q^{134}L^{135}P^{136}H^{137}$
(SEQ ID NO: 136)

(136) $H^{107}L^{108}K^{109}V^{110}R^{111}L^{112}D^{113}V^{114}K^{115}$
(SEQ ID NO: 137)

(137) $H^{107}L^{108}K^{109}V^{110}R^{111}L^{112}D^{113}V^{114}K^{115}S^{116}A^{117}K^{118}$
(SEQ ID NO: 138)

(138) $H^{107}L^{108}K^{109}V^{110}R^{111}L^{112}D^{113}V^{114}K^{115}S^{116}A^{117}K^{118}Q^{119}L^{120}P^{121}H^{122}L^{123}K^{124}$
(SEQ ID NO: 139)

(139) $H^{107}L^{108}K^{109}V^{110}R^{111}L^{112}D^{113}V^{114}K^{115}S^{116}A^{117}K^{118}Q^{119}L^{120}P^{121}H^{122}L^{123}K^{124}V^{125}H^{126}L^{127}D^{128}V^{129}R^{130}$
$G^{131}A^{132}K^{133}$
(SEQ ID NO: 140)

(140) $H^{107}L^{108}K^{109}V^{110}R^{111}L^{112}D^{113}V^{114}K^{115}S^{116}A^{117}K^{118}Q^{119}L^{120}P^{121}H^{122}L^{123}K^{124}V^{125}H^{126}L^{127}D^{128}V^{129}R^{130}$
$G^{131}A^{132}K^{133}Q^{134}L^{135}P^{136}H^{137}L^{138}K^{139}$
(SEQ ID NO: 141)

(141) $H^{107}L^{108}K^{109}V^{110}R^{111}L^{112}D^{113}V^{114}K^{115}S^{116}A^{117}K^{118}Q^{119}L^{120}P^{121}H^{122}L^{123}K^{124}V^{125}H^{126}L^{127}D^{128}V^{129}R^{130}$
$G^{131}A^{132}K^{133}Q^{134}L^{135}P^{136}H^{137}L^{138}K^{139}V^{140}R^{141}L^{142}D^{143}V^{144}R^{145}G^{146}A^{147}K^{148}$
(SEQ ID NO: 142)

(142) $H^{107}L^{108}K^{109}V^{110}R^{111}L^{112}D^{113}V^{114}K^{115}S^{116}A^{117}K^{118}Q^{119}L^{120}P^{121}H^{122}L^{123}K^{124}V^{125}H^{126}L^{127}D^{128}V^{129}R^{130}$
$G^{131}A^{132}K^{133}Q^{134}L^{135}P^{136}H^{137}L^{138}K^{139}V^{140}R^{141}L^{142}D^{143}V^{144}R^{145}G^{146}A^{147}K^{148}Q^{149}N^{150}P^{151}W^{152}R^{153}K^{154}$
(SEQ ID NO: 143)

(143) $K^{109}V^{110}R^{111}L^{112}D^{113}V^{114}K^{115}S^{116}A^{117}K^{118}Q^{119}L^{120}P^{121}H^{122}$
(SEQ ID NO: 144)

(144) $K^{109}V^{110}R^{111}L^{112}D^{113}V^{114}K^{115}S^{116}A^{117}K^{118}Q^{119}L^{120}P^{121}H^{122}L^{123}K^{124}V^{125}H^{126}$
(SEQ ID NO: 145)

(145) $K^{109}V^{110}R^{111}L^{112}D^{113}V^{114}K^{115}S^{116}A^{117}K^{118}Q^{119}L^{120}P^{121}H^{122}L^{123}K^{124}V^{125}H^{126}L^{127}D^{128}V^{129}R^{130}G^{131}A^{132}$
$K^{133}Q^{134}L^{135}P^{136}H^{137}$
(SEQ ID NO: 146)

(146) $K^{115}S^{116}A^{117}K^{118}Q^{119}L^{120}P^{121}H^{122}L^{123}K^{124}$
(SEQ ID NO: 14)

(147) $K^{115}S^{116}A^{117}K^{118}Q^{119}L^{120}P^{121}H^{122}L^{123}K^{124}V^{125}H^{126}$
(SEQ ID NO: 81)

(148) $K^{115}S^{116}A^{117}K^{118}Q^{119}L^{120}P^{121}H^{122}L^{123}K^{124}V^{125}H^{126}L^{127}D^{128}V^{129}R^{130}G^{131}A^{132}K^{133}Q^{134}L^{135}P^{136}H^{137}$
(SEQ ID NO: 109)

(149) $K^{118}Q^{119}L^{120}P^{121}H^{122}L^{123}K^{124}$
(SEQ ID NO: 84)

(150) $K^{118}Q^{119}L^{120}P^{121}H^{122}L^{123}K^{124}V^{125}H^{126}$
(SEQ ID NO: 85)

-continued (151) $K^{118}Q^{119}L^{120}P^{121}H^{122}L^{123}K^{124}V^{125}H^{126}L^{127}D^{128}V^{129}R^{130}G^{131}A^{132}K^{133}Q^{134}L^{135}P^{136}H^{137}$
(SEQ ID NO: 112)

(152) $H^{122}L^{123}K^{124}V^{125}H^{126}L^{127}D^{128}V^{129}R^{130}G^{131}A^{132}K^{133}$
(SEQ ID NO: 121)

(153) $H^{122}L^{123}K^{124}V^{125}H^{126}L^{127}D^{128}V^{129}R^{130}G^{131}A^{132}K^{133}Q^{134}L^{135}P^{136}H^{137}L^{138}K^{139}$
(SEQ ID NO: 122)

(154) $H^{122}L^{123}K^{124}V^{125}H^{126}L^{127}D^{128}V^{129}R^{130}G^{131}A^{132}K^{133}Q^{134}L^{135}P^{136}H^{137}L^{138}K^{139}V^{140}R^{141}L^{142}D^{143}V^{144}R^{145}$
$G^{146}A^{147}K^{148}$
(SEQ ID NO: 147)

(155) $H^{122}L^{123}K^{124}V^{125}H^{126}L^{127}D^{128}V^{129}R^{130}G^{131}A^{132}K^{133}Q^{134}L^{135}P^{136}H^{137}L^{138}K^{139}V^{140}R^{141}L^{142}D^{143}V^{144}R^{145}$
$G^{146}A^{147}K^{148}Q^{149}N^{150}P^{151}W^{152}R^{153}K^{154}$
(SEQ ID NO: 148)

(156) $H^{122}L^{123}K^{124}V^{125}H^{126}L^{127}D^{128}V^{129}R^{130}G^{131}A^{132}K^{133}Q^{134}L^{135}P^{136}H^{137}L^{138}K^{139}V^{140}R^{141}L^{142}D^{143}V^{144}R^{145}$
$G^{146}A^{147}K^{148}Q^{149}N^{150}P^{151}W^{152}R^{153}K^{154}N^{155}L^{156}C^{157}L^{158}L^{159}K^{160}$
(SEQ ID NO: 149)

(157) $H^{122}L^{123}K^{124}V^{125}H^{126}L^{127}D^{128}V^{129}R^{130}G^{131}A^{132}K^{133}Q^{134}L^{135}P^{136}H^{137}L^{138}K^{139}V^{140}R^{141}L^{142}D^{143}V^{144}R^{145}$
$G^{146}A^{147}K^{148}Q^{149}N^{150}P^{151}W^{152}R^{153}K^{154}N^{155}L^{156}C^{157}L^{158}L^{159}K^{160}K^{161}$
(SEQ ID NO: 150)

(158) $H^{122}L^{123}K^{124}V^{125}H^{126}L^{127}D^{128}V^{129}R^{130}G^{131}A^{132}K^{133}Q^{134}L^{135}P^{136}H^{137}L^{138}K^{139}V^{140}R^{141}L^{142}D^{143}V^{144}R^{145}$
$G^{146}A^{147}K^{148}Q^{149}N^{150}P^{151}W^{152}R^{153}K^{154}N^{155}L^{156}C^{157}L^{158}L^{159}K^{160}K^{161}N^{162}V^{163}K^{164}$
(SEQ ID NO: 151)

(159) $H^{122}L^{123}K^{124}V^{125}H^{126}L^{127}D^{128}V^{129}R^{130}G^{131}A^{132}K^{133}Q^{134}L^{135}P^{136}H^{137}L^{138}K^{139}V^{140}R^{141}L^{142}D^{143}V^{144}R^{145}$
$G^{146}A^{147}K^{148}Q^{149}N^{150}P^{151}W^{152}R^{153}K^{154}N^{155}L^{156}C^{157}L^{158}L^{159}K^{160}K^{161}N^{162}V^{163}K^{164}S^{165}A^{166}K^{167}$
(SEQ ID NO: 152)

(160) $K^{124}V^{125}H^{126}L^{127}D^{128}V^{129}R^{130}G^{131}A^{132}K^{133}$
(SEQ ID NO: 123)

(161) $K^{124}V^{125}H^{126}L^{127}D^{128}V^{129}R^{130}G^{131}A^{132}K^{133}Q^{134}L^{135}P^{136}H^{137}$
(SEQ ID NO: 124)

(162) $K^{124}V^{125}H^{126}L^{127}D^{128}V^{129}R^{130}G^{131}A^{132}K^{133}Q^{134}L^{135}P^{136}H^{137}L^{138}K^{139}V^{140}R^{141}L^{142}D^{143}V^{144}R^{145}G^{146}A^{147}$
$K^{148}Q^{149}N^{150}P^{151}W^{152}R^{153}K^{154}N^{155}L^{156}C^{157}L^{158}L^{159}K^{160}K^{161}N^{162}V^{163}K^{164}S^{165}A^{166}K^{167}Q^{168}L^{169}P^{170}H^{171}$
(SEQ ID NO: 153)

(163) $H^{126}L^{127}D^{128}V^{129}R^{130}G^{131}A^{132}K^{133}Q^{134}L^{135}P^{136}H^{137}L^{138}K^{139}$
(SEQ ID NO: 128)

(164) $H^{126}L^{127}D^{128}V^{129}R^{130}G^{131}A^{132}K^{133}Q^{134}L^{135}P^{136}H^{137}L^{138}K^{139}V^{140}R^{141}L^{142}D^{143}V^{144}R^{145}G^{146}A^{147}K^{148}$
(SEQ ID NO: 154)

(165) $H^{126}L^{127}D^{128}V^{129}R^{130}G^{131}A^{132}K^{133}Q^{134}L^{135}P^{136}H^{137}L^{138}K^{139}V^{140}R^{141}L^{142}D^{143}V^{144}R^{145}G^{146}A^{147}K^{148}Q^{149}$
$N^{150}P^{151}W^{152}R^{153}K^{154}$
(SEQ ID NO: 155)

(166) $H^{126}L^{127}D^{128}V^{129}R^{130}G^{131}A^{132}K^{133}Q^{134}L^{135}P^{136}H^{137}L^{138}K^{139}V^{140}R^{141}L^{142}D^{143}V^{144}R^{145}G^{146}A^{147}K^{148}Q^{149}$
$N^{150}P^{151}W^{152}R^{153}K^{154}N^{155}L^{156}C^{157}L^{158}L^{159}K^{160}$
(SEQ ID NO: 156)

(167) $H^{126}L^{127}D^{128}V^{129}R^{130}G^{131}A^{132}K^{133}Q^{134}L^{135}P^{136}H^{137}L^{138}K^{139}V^{140}R^{141}L^{142}D^{143}V^{144}R^{145}G^{146}A^{147}K^{148}Q^{149}$
$N^{150}P^{151}W^{152}R^{153}K^{154}N^{155}L^{156}C^{157}L^{158}L^{159}K^{160}K^{161}$
(SEQ ID NO: 157)

(168) $H^{126}L^{127}D^{128}V^{129}R^{130}G^{131}A^{132}K^{133}Q^{134}L^{135}P^{136}H^{137}L^{138}K^{139}V^{140}R^{141}L^{142}D^{143}V^{144}R^{145}G^{146}A^{147}K^{148}Q^{149}$
$N^{150}P^{151}W^{152}R^{153}K^{154}N^{155}L^{156}C^{157}L^{158}L^{159}K^{160}K^{161}N^{162}V^{163}K^{164}$
(SEQ ID NO: 158)

(169) $H^{126}L^{127}D^{128}V^{129}R^{130}G^{131}A^{132}K^{133}Q^{134}L^{135}P^{136}H^{137}L^{138}K^{139}V^{140}R^{141}L^{142}D^{143}V^{144}R^{145}G^{146}A^{147}K^{148}Q^{149}$
$N^{150}P^{151}W^{152}R^{153}K^{154}N^{155}L^{156}C^{157}L^{158}L^{159}K^{160}K^{161}N^{162}V^{163}K^{164}S^{165}A^{166}K^{167}$
(SEQ ID NO: 159)

(170) $H^{126}L^{127}D^{128}V^{129}R^{130}G^{131}A^{132}K^{133}Q^{134}L^{135}P^{136}H^{137}L^{138}K^{139}V^{140}R^{141}L^{142}D^{143}V^{144}R^{145}G^{146}A^{147}K^{148}Q^{149}$
$N^{150}P^{151}W^{152}R^{153}K^{154}N^{155}L^{156}C^{157}L^{158}L^{159}K^{160}K^{161}N^{162}V^{163}K^{164}S^{165}A^{166}K^{167}Q^{168}L^{169}P^{170}H^{171}L^{172}K^{173}$
(SEQ ID NO: 160)

(171) $K^{133}Q^{134}L^{135}P^{136}H^{137}L^{138}K^{139}V^{140}R^{141}L^{142}D^{143}V^{144}R^{145}G^{146}A^{147}K^{148}Q^{149}N^{150}P^{151}W^{152}R^{153}K^{154}N^{155}L^{156}$
$C^{157}L^{158}L^{159}K^{160}K^{161}N^{162}V^{163}K^{164}S^{165}A^{166}K^{167}Q^{168}L^{169}P^{170}H^{171}L^{172}K^{173}V^{174}H^{175}$
(SEQ ID NO: 161)

(172) $K^{133}Q^{134}L^{135}P^{136}H^{137}L^{138}K^{139}$
(SEQ ID NO: 84)

-continued (173) $K^{133}Q^{134}L^{135}P^{136}H^{137}L^{138}K^{139}V^{140}R^{141}L^{142}D^{143}V^{144}R^{145}G^{146}A^{147}K^{148}Q^{149}N^{150}P^{151}W^{152}R^{153}K^{154}N^{155}L^{156}$
$C^{157}L^{158}L^{159}K^{160}K^{161}N^{162}V^{163}K^{164}S^{165}A^{166}K^{167}Q^{168}L^{169}P^{170}H^{171}$
(SEQ ID NO: 162)

(174) $H^{137}L^{138}K^{139}V^{140}R^{141}L^{142}D^{143}V^{144}R^{145}G^{146}A^{147}K^{148}$
(SEQ ID NO: 51)

(175) $H^{137}L^{138}K^{139}V^{140}R^{141}L^{142}D^{143}V^{144}R^{145}G^{146}A^{147}K^{148}Q^{149}N^{150}P^{151}W^{152}R^{153}K^{154}$
(SEQ ID NO: 52)

(176) $H^{137}L^{138}K^{139}V^{140}R^{141}L^{142}D^{143}V^{144}R^{145}G^{146}A^{147}K^{148}Q^{149}N^{150}P^{151}W^{152}R^{153}K^{154}N^{155}L^{156}C^{157}L^{158}L^{159}K^{160}$
(SEQ ID NO: 53)

(177) $H^{137}L^{138}K^{139}V^{140}R^{141}L^{142}D^{143}V^{144}R^{145}G^{146}A^{147}K^{148}Q^{149}N^{150}P^{151}W^{152}R^{153}K^{154}N^{155}L^{156}C^{157}L^{158}L^{159}K^{160}$
$K^{161}$
(SEQ ID NO: 54)

(178) $H^{137}L^{138}K^{139}V^{140}R^{141}L^{142}D^{143}V^{144}R^{145}G^{146}A^{147}K^{148}Q^{149}N^{150}P^{151}W^{152}R^{153}K^{154}N^{155}L^{156}C^{157}L^{158}L^{159}K^{160}$
$K^{161}N^{162}V^{163}K^{164}$
(SEQ ID NO: 55)

(179) $H^{137}L^{138}K^{139}V^{140}R^{141}L^{142}D^{143}V^{144}R^{145}G^{146}A^{147}K^{148}Q^{149}N^{150}P^{151}W^{152}R^{153}K^{154}N^{155}L^{156}C^{157}L^{158}L^{159}K^{160}$
$K^{161}N^{162}V^{163}K^{164}S^{165}A^{166}K^{167}$
(SEQ ID NO: 56)

(180) $H^{137}L^{138}K^{139}V^{140}R^{141}L^{142}D^{143}V^{144}R^{145}G^{146}A^{147}K^{148}Q^{149}N^{150}P^{151}W^{152}R^{153}K^{154}N^{155}L^{156}C^{157}L^{158}L^{159}K^{160}$
$K^{161}N^{162}V^{163}K^{164}S^{165}A^{166}K^{167}Q^{168}L^{169}P^{170}H^{171}L^{172}K^{173}$
(SEQ ID NO: 57)

(181) $H^{137}L^{138}K^{139}V^{140}R^{141}L^{142}D^{143}V^{144}R^{145}G^{146}A^{147}K^{148}Q^{149}N^{150}P^{151}W^{152}R^{153}K^{154}N^{155}L^{156}C^{157}L^{158}L^{159}K^{160}$
$K^{161}N^{162}V^{163}K^{164}S^{165}A^{166}K^{167}Q^{168}L^{169}P^{170}H^{171}L^{172}K^{173}V^{174}H^{175}L^{176}D^{177}V^{178}K^{179}$
(SEQ ID NO: 58)

(182) $H^{137}L^{138}K^{139}V^{140}R^{141}L^{142}D^{143}V^{144}R^{145}G^{146}A^{147}K^{148}Q^{149}N^{150}P^{151}W^{152}R^{153}K^{154}N^{155}L^{156}C^{157}L^{158}L^{159}K^{160}$
$K^{161}N^{162}V^{163}K^{164}S^{165}A^{166}K^{167}Q^{168}L^{169}P^{170}H^{171}L^{172}K^{173}V^{174}H^{175}L^{176}D^{177}V^{178}K^{179}G^{180}V^{181}K^{182}$
(SEQ ID NO: 163)

(183) $K^{139}V^{140}R^{141}L^{142}D^{143}V^{144}R^{145}G^{146}A^{147}K^{148}Q^{149}N^{150}P^{151}W^{152}R^{153}K^{154}N^{155}L^{156}C^{157}L^{158}L^{159}K^{160}K^{161}N^{162}$
$V^{163}K^{164}S^{165}A^{166}K^{167}Q^{168}L^{169}P^{170}H^{171}$
(SEQ ID NO: 60)

(184) $K^{139}V^{140}R^{141}L^{142}D^{143}V^{144}R^{145}G^{146}A^{147}K^{148}Q^{149}N^{150}P^{151}W^{152}R^{153}K^{154}N^{155}L^{156}C^{157}L^{158}L^{159}K^{160}K^{161}N^{162}$
$V^{163}K^{164}S^{165}A^{166}K^{167}Q^{168}L^{169}P^{170}H^{171}L^{172}K^{173}V^{174}H^{175}$
(SEQ ID NO: 61)

(185) $K^{139}V^{140}R^{141}L^{142}D^{143}V^{144}R^{145}G^{146}A^{147}K^{148}Q^{149}N^{150}P^{151}W^{152}R^{153}K^{154}N^{155}L^{156}C^{157}L^{158}L^{159}K^{160}K^{161}N^{162}$
$V^{163}K^{164}S^{165}A^{166}K^{167}Q^{168}L^{169}P^{170}H^{171}L^{172}K^{173}V^{174}H^{175}L^{176}D^{177}V^{178}K^{179}G^{180}V^{181}K^{182}Q^{183}L^{184}L^{185}H^{186}$
(SEQ ID NO: 164)

(186) $K^{148}Q^{149}N^{150}P^{151}W^{152}R^{153}K^{154}N^{155}L^{156}C^{157}L^{158}L^{159}K^{160}K^{161}N^{162}V^{163}K^{164}S^{165}A^{166}K^{167}Q^{168}L^{169}P^{170}H^{171}$
(SEQ ID NO: 63)

(187) $K^{148}Q^{149}N^{150}P^{151}W^{152}R^{153}K^{154}N^{155}L^{156}C^{157}L^{158}L^{159}K^{160}K^{161}N^{162}V^{163}K^{164}S^{165}A^{166}K^{167}Q^{168}L^{169}P^{170}H^{171}$
$L^{172}K^{173}V^{174}H^{175}$
(SEQ ID NO: 64)

(188) $K^{148}Q^{149}N^{150}P^{151}W^{152}R^{153}K^{154}N^{155}L^{156}C^{157}L^{158}L^{159}K^{160}K^{161}N^{162}V^{163}K^{164}S^{165}A^{166}K^{167}Q^{168}L^{169}P^{170}H^{171}$
$L^{172}K^{173}V^{174}H^{175}L^{176}D^{177}V^{178}K^{179}G^{180}V^{181}K^{182}Q^{183}L^{184}L^{185}H^{186}$
(SEQ ID NO: 165)

(189) $K^{154}N^{155}L^{156}C^{157}L^{158}L^{159}K^{160}K^{161}N^{162}V^{163}K^{164}S^{165}A^{166}K^{167}Q^{168}L^{169}P^{170}H^{171}L^{172}K^{173}V^{174}H^{175}L^{176}D^{177}$
$V^{178}K^{179}G^{180}V^{181}K^{182}Q^{183}L^{184}L^{185}H^{186}L^{187}K^{188}V^{189}R^{190}L^{191}D^{192}V^{193}R^{194}G^{195}A^{196}K^{197}Q^{198}L^{199}L^{200}H^{201}$
(SEQ ID NO: 166)

(190) $K^{154}N^{155}L^{156}C^{157}L^{158}L^{159}K^{160}K^{161}N^{162}V^{163}K^{164}S^{165}A^{166}K^{167}Q^{168}L^{169}P^{170}H^{171}$
(SEQ ID NO: 68)

(191) $K^{154}N^{155}L^{156}C^{157}L^{158}L^{159}K^{160}K^{161}N^{162}V^{163}K^{164}S^{165}A^{166}K^{167}Q^{168}L^{169}P^{170}H^{171}L^{172}K^{173}V^{174}H^{175}$
(SEQ ID NO: 69)

(192) $K^{154}N^{155}L^{156}C^{157}L^{158}L^{159}K^{160}K^{161}N^{162}V^{163}K^{164}S^{165}A^{166}K^{167}Q^{168}L^{169}P^{170}H^{171}L^{172}K^{173}V^{174}H^{175}L^{176}D^{177}$
$V^{178}K^{179}G^{180}V^{181}K^{182}Q^{183}L^{184}L^{185}H^{186}$
(SEQ ID NO: 167)

(193) $K^{160}K^{161}N^{162}V^{163}K^{164}S^{165}A^{166}K^{167}Q^{168}L^{169}P^{170}H^{171}$
(SEQ ID NO: 13)

(194) $K^{160}K^{161}N^{162}V^{163}K^{164}S^{165}A^{166}K^{167}Q^{168}L^{169}P^{170}H^{171}L^{172}K^{173}V^{174}H^{175}$
(SEQ ID NO: 72)

-continued (195) $K^{160}K^{161}N^{162}V^{163}K^{164}S^{165}A^{166}K^{167}Q^{168}L^{169}P^{170}H^{171}L^{172}K^{173}V^{174}H^{175}L^{176}D^{177}V^{178}K^{179}G^{180}V^{181}K^{182}Q^{183}$
$L^{184}L^{185}H^{186}$
(SEQ ID NO: 2)

(196) $K^{160}K^{161}N^{162}V^{163}K^{164}S^{165}A^{166}K^{167}Q^{168}L^{169}P^{170}H^{171}L^{172}K^{173}V^{174}H^{175}L^{176}D^{177}V^{178}K^{179}G^{180}V^{181}K^{182}Q^{183}$
$L^{184}L^{185}H^{186}L^{187}K^{188}V^{189}R^{190}L^{191}D^{192}V^{193}R^{194}G^{195}A^{196}K^{197}Q^{198}L^{199}L^{200}H^{201}$
(SEQ ID NO: 168)

(197) $K^{160}K^{161}N^{162}V^{163}K^{164}S^{165}A^{166}K^{167}Q^{168}L^{169}P^{170}H^{171}L^{172}K^{173}V^{174}H^{175}L^{176}D^{177}V^{178}K^{179}G^{180}V^{181}K^{182}Q^{183}$
$L^{184}L^{185}H^{186}L^{187}K^{188}V^{189}R^{190}L^{191}D^{192}V^{193}R^{194}G^{195}A^{196}K^{197}Q^{198}L^{199}L^{200}H^{201}L^{202}K^{203}V^{204}H^{205}$
(SEQ ID NO: 169)

Replikin Sequences in Mid-molecule Portion of Peptide (198) $K^{161}N^{162}V^{163}K^{164}S^{165}A^{166}K^{167}Q^{168}L^{169}P^{170}H^{171}$
(SEQ ID NO: 75)

(199) $K^{161}N^{162}V^{163}K^{164}S^{165}A^{166}K^{167}Q^{168}L^{169}P^{170}H^{171}L^{172}K^{173}V^{174}H^{175}$
(SEQ ID NO: 76)

(200) $K^{161}N^{162}V^{163}K^{164}S^{165}A^{166}K^{167}Q^{168}L^{169}P^{170}H^{171}L^{172}K^{173}V^{174}H^{175}L^{176}D^{177}V^{178}K^{179}G^{180}V^{181}K^{182}Q^{183}L^{184}$
$L^{185}H^{186}$
(SEQ ID NO: 170)

(201) $K^{161}N^{162}V^{163}K^{164}S^{165}A^{166}K^{167}Q^{168}L^{169}P^{170}H^{171}L^{172}K^{173}V^{174}H^{175}L^{176}D^{177}V^{178}K^{179}G^{180}V^{181}K^{182}Q^{183}L^{184}$
$L^{185}H^{186}L^{187}K^{188}V^{189}R^{190}L^{191}D^{192}V^{193}R^{194}G^{195}A^{196}K^{197}Q^{198}L^{199}L^{200}H^{201}$
(SEQ ID NO: 171)

(202) $K^{161}N^{162}V^{163}K^{164}S^{165}A^{166}K^{167}Q^{168}L^{169}P^{170}H^{171}L^{172}K^{173}V^{174}H^{175}L^{176}D^{177}V^{178}K^{179}G^{180}V^{181}K^{182}Q^{183}L^{184}$
$L^{185}H^{186}L^{187}K^{188}V^{189}R^{190}L^{191}D^{192}V^{193}R^{194}G^{195}A^{196}K^{197}Q^{198}L^{199}L^{200}H^{201}L^{202}K^{203}V^{204}H^{205}$
(SEQ ID NO: 172)

(203) $K^{164}S^{165}A^{166}K^{167}Q^{168}L^{169}P^{170}H^{171}L^{172}K^{173}$
(SEQ ID NO: 14)

(204) $K^{164}S^{165}A^{166}K^{167}Q^{168}L^{169}P^{170}H^{171}L^{172}K^{173}V^{174}H^{175}$
(SEQ ID NO: 81)

(205) $K^{164}S^{165}A^{166}K^{167}Q^{168}L^{169}P^{170}H^{171}L^{172}K^{173}V^{174}H^{175}L^{176}D^{177}V^{178}K^{179}G^{180}V^{181}K^{182}Q^{183}L^{184}L^{185}H^{186}$
(SEQ ID NO: 173)

(206) $K^{164}S^{165}A^{166}K^{167}Q^{168}L^{169}P^{170}H^{171}L^{172}K^{173}V^{174}H^{175}L^{176}D^{177}V^{178}K^{179}G^{180}V^{181}K^{182}Q^{183}L^{184}L^{185}H^{186}L^{187}$
$K^{188}V^{189}R^{190}L^{191}D^{192}V^{193}R^{194}G^{195}A^{196}K^{197}Q^{198}L^{199}L^{200}H^{201}$
(SEQ ID NO: 174)

(207) $K^{164}S^{165}A^{166}K^{167}Q^{168}L^{169}P^{170}H^{171}L^{172}K^{173}V^{174}H^{175}L^{176}D^{177}V^{178}K^{179}G^{180}V^{181}K^{182}Q^{183}L^{184}L^{185}H^{186}L^{187}$
$K^{188}V^{189}R^{190}L^{191}D^{192}V^{193}R^{194}G^{195}A^{196}K^{197}Q^{198}L^{199}L^{200}H^{201}L^{202}K^{203}V^{204}H^{205}$
(SEQ ID NO: 175)

(208) $K^{167}Q^{168}L^{169}P^{170}H^{171}L^{172}K^{173}$
(SEQ ID NO: 84)

(209) $K^{167}Q^{168}L^{169}P^{170}H^{171}L^{172}K^{173}V^{174}H^{175}$
(SEQ ID NO: 85)

(210) $K^{167}Q^{168}L^{169}P^{170}H^{171}L^{172}K^{173}V^{174}H^{175}L^{176}D^{177}V^{178}K^{179}G^{180}V^{181}K^{182}Q^{183}L^{184}L^{185}H^{186}$
(SEQ ID NO: 176)

(211) $K^{167}Q^{168}L^{169}P^{170}H^{171}L^{172}K^{173}V^{174}H^{175}L^{176}D^{177}V^{178}K^{179}G^{180}V^{181}K^{182}Q^{183}L^{184}L^{185}H^{186}L^{187}K^{188}V^{189}R^{190}$
$L^{191}D^{192}V^{193}R^{194}G^{195}A^{196}K^{197}Q^{198}L^{199}L^{200}H^{201}$
(SEQ ID NO: 177)

(212) $K^{167}Q^{168}L^{169}P^{170}H^{171}L^{172}K^{173}V^{174}H^{175}L^{176}D^{177}V^{178}K^{179}G^{180}V^{181}K^{182}Q^{183}L^{184}L^{185}H^{186}L^{187}K^{188}V^{189}R^{190}$
$L^{191}D^{192}V^{193}R^{194}G^{195}A^{196}K^{197}Q^{198}L^{199}L^{200}H^{201}L^{202}K^{203}V^{204}H^{205}$
(SEQ ID NO: 178)

(213) $K^{167}Q^{168}L^{169}P^{170}H^{171}L^{172}K^{173}V^{174}H^{175}L^{176}D^{177}V^{178}K^{179}G^{180}V^{181}K^{182}Q^{183}L^{184}L^{185}H^{186}L^{187}K^{188}V^{189}R^{190}$
$L^{191}D^{192}V^{193}R^{194}G^{195}A^{196}K^{197}Q^{198}L^{199}L^{200}H^{201}L^{202}K^{203}V^{204}H^{205}L^{206}D^{207}V^{208}R^{209}G^{210}A^{211}K^{212}Q^{213}L^{214}$
$P^{215}H^{216}$
(SEQ ID NO: 179)

(214) $H^{171}L^{172}K^{173}V^{174}H^{175}L^{176}D^{177}V^{178}K^{179}$
(SEQ ID NO: 27)

(215) $H^{171}L^{172}K^{173}V^{174}H^{175}L^{176}D^{177}V^{178}K^{179}G^{180}V^{181}K^{182}$
(SEQ ID NO: 28)

(216) $H^{171}L^{172}K^{173}V^{174}H^{175}L^{176}D^{177}V^{178}K^{179}G^{180}V^{181}K^{182}Q^{183}L^{184}L^{185}H^{186}L^{187}K^{188}$
(SEQ ID NO: 29)

-continued (217) $H^{171}L^{172}K^{173}V^{174}H^{175}L^{176}D^{177}V^{178}K^{179}G^{180}V^{181}K^{182}Q^{183}L^{184}L^{185}H^{186}L^{187}K^{188}V^{189}R^{190}L^{191}D^{192}V^{193}R^{194}$
$G^{195}A^{196}K^{197}Q^{198}L^{199}L^{200}H^{201}L^{202}K^{203}$
(SEQ ID NO: 180)

(218) $H^{171}L^{172}K^{173}V^{174}H^{175}L^{176}D^{177}V^{178}K^{179}G^{180}V^{181}K^{182}Q^{183}L^{184}L^{185}H^{186}L^{187}K^{188}V^{189}R^{190}L^{191}D^{192}V^{193}R^{194}$
$G^{195}A^{196}K^{197}$
(SEQ ID NO: 30)

(219) $H^{171}L^{172}K^{173}V^{174}H^{175}L^{176}D^{177}V^{178}K^{179}G^{180}V^{181}K^{182}Q^{183}L^{184}L^{185}H^{186}L^{187}K^{188}V^{189}R^{190}L^{191}D^{192}V^{193}R^{194}$
$G^{195}A^{196}K^{197}Q^{198}L^{199}L^{200}H^{201}L^{202}K^{203}V^{204}H^{205}L^{206}D^{207}V^{208}R^{209}G^{210}A^{211}K^{212}$
(SEQ ID NO: 181)

(220) $H^{171}L^{172}K^{173}V^{174}H^{175}L^{176}D^{177}V^{178}K^{179}G^{180}V^{181}K^{182}Q^{183}L^{184}L^{185}H^{186}L^{187}K^{188}V^{189}R^{190}L^{191}D^{192}V^{193}R^{194}$
$G^{195}A^{196}K^{197}Q^{198}L^{199}L^{200}H^{201}L^{202}K^{203}V^{204}H^{205}L^{206}D^{207}V^{208}R^{209}G^{210}A^{211}K^{212}Q^{213}L^{214}P^{215}H^{216}L^{217}K^{218}$
(SEQ ID NO: 182)

(221) $K^{173}V^{174}H^{175}L^{176}D^{177}V^{178}K^{179}$
(SEQ ID NO: 11)

(222) $K^{173}V^{174}H^{175}L^{176}D^{177}V^{178}K^{179}G^{180}V^{181}K^{182}$
(SEQ ID NO: 37)

(223) $K^{173}V^{174}H^{175}L^{176}D^{177}V^{178}K^{179}G^{180}V^{181}K^{182}Q^{183}L^{184}L^{185}H^{186}$
(SEQ ID NO: 12)

(224) $K^{173}V^{174}H^{175}L^{176}D^{177}V^{178}K^{179}G^{180}V^{181}K^{182}Q^{183}L^{184}L^{185}H^{186}L^{187}K^{188}V^{189}R^{190}L^{191}D^{192}V^{193}R^{194}G^{195}A^{196}$
$K^{197}Q^{198}L^{199}L^{200}H^{201}$
(SEQ ID NO: 183)

(225) $K^{173}V^{174}H^{175}L^{176}D^{177}V^{178}K^{179}G^{180}V^{181}K^{182}Q^{183}L^{184}L^{185}H^{186}L^{187}K^{188}V^{189}R^{190}L^{191}D^{192}V^{193}R^{194}G^{195}A^{196}$
$K^{197}Q^{198}L^{199}L^{200}H^{201}L^{202}K^{203}V^{204}H^{205}$
(SEQ ID NO: 184)

(226) $K^{173}V^{174}H^{175}L^{176}D^{177}V^{178}K^{179}G^{180}V^{181}K^{182}Q^{183}L^{184}L^{185}H^{186}L^{187}K^{188}V^{189}R^{190}L^{191}D^{192}V^{193}R^{194}G^{195}A^{196}$
$K^{197}Q^{198}L^{199}L^{200}H^{201}L^{202}K^{203}V^{204}H^{205}L^{206}D^{207}V^{208}R^{209}G^{210}A^{211}K^{212}Q^{213}L^{214}P^{215}H^{216}$
(SEQ ID NO: 185)

(227) $K^{173}V^{174}H^{175}L^{176}D^{177}V^{178}K^{179}G^{180}V^{181}K^{182}Q^{183}L^{184}L^{185}H^{186}L^{187}K^{188}V^{189}R^{190}L^{191}D^{192}V^{193}R^{194}G^{195}A^{196}$
$K^{197}Q^{198}L^{199}L^{200}H^{201}L^{202}K^{203}V^{204}H^{205}L^{206}D^{207}V^{208}R^{209}G^{210}A^{211}K^{212}Q^{213}L^{214}P^{215}H^{216}L^{217}K^{218}V^{219}H^{220}$
(SEQ ID NO: 186)

(228) $H^{175}L^{176}D^{177}V^{178}K^{179}G^{180}V^{181}K^{182}Q^{183}L^{184}L^{185}H^{186}L^{187}K^{188}V^{189}R^{190}L^{191}D^{192}V^{193}R^{194}G^{195}A^{196}K^{197}Q^{198}$
$L^{199}L^{200}H^{201}L^{202}K^{203}V^{204}H^{205}L^{206}D^{207}V^{208}R^{209}G^{210}A^{211}K^{212}$
(SEQ ID NO: 187)

(229) $H^{175}L^{176}D^{177}V^{178}K^{179}G^{180}V^{181}K^{182}Q^{183}L^{184}L^{185}H^{186}L^{187}K^{188}V^{189}R^{190}L^{191}D^{192}V^{193}R^{194}G^{195}A^{196}K^{197}Q^{198}$
$L^{199}L^{200}H^{201}L^{202}K^{203}V^{204}H^{205}L^{206}D^{207}V^{208}R^{209}G^{210}A^{211}K^{212}Q^{213}L^{214}P^{215}H^{216}L^{217}K^{218}$
(SEQ ID NO: 188)

(230) $H^{175}L^{176}D^{177}V^{178}K^{179}G^{180}V^{181}K^{182}Q^{183}L^{184}L^{185}H^{186}L^{187}K^{188}$
(SEQ ID NO: 38)

(231) $H^{175}L^{176}D^{177}V^{178}K^{179}G^{180}V^{181}K^{182}Q^{183}L^{184}L^{185}H^{186}L^{187}K^{188}V^{189}R^{190}L^{191}D^{192}V^{193}R^{194}G^{195}A^{196}K^{197}Q^{198}$
$L^{199}L^{200}H^{201}L^{202}K^{203}$
(SEQ ID NO: 189)

(232) $H^{175}L^{176}D^{177}V^{178}K^{179}G^{180}V^{181}K^{182}Q^{183}L^{184}L^{185}H^{186}L^{187}K^{188}V^{189}R^{190}L^{191}D^{192}V^{193}R^{194}G^{195}A^{196}K^{197}$
(SEQ ID NO: 39)

(233) $K^{179}G^{180}V^{181}K^{182}Q^{183}L^{184}L^{185}H^{186}L^{187}K^{188}$
(SEQ ID NO: 46)

(234) $K^{179}G^{180}V^{181}K^{182}Q^{183}L^{184}L^{185}H^{186}L^{187}K^{188}V^{189}R^{190}L^{191}D^{192}V^{193}R^{194}G^{195}A^{196}K^{197}Q^{198}L^{199}L^{200}H^{201}$
(SEQ ID NO: 190)

(235) $K^{179}G^{180}V^{181}K^{182}Q^{183}L^{184}L^{185}H^{186}L^{187}K^{188}V^{189}R^{190}L^{191}D^{192}V^{193}R^{194}G^{195}A^{196}K^{197}Q^{198}L^{199}L^{200}H^{201}L^{202}$
$K^{203}V^{204}H^{205}$
(SEQ ID NO: 191)

(236) $K^{179}G^{180}V^{181}K^{182}Q^{183}L^{184}L^{185}H^{186}L^{187}K^{188}V^{189}R^{190}L^{191}D^{192}V^{193}R^{194}G^{195}A^{196}K^{197}Q^{198}L^{199}L^{200}H^{201}L^{202}$
$K^{203}V^{204}H^{205}L^{206}D^{207}V^{208}R^{209}G^{210}A^{211}K^{212}Q^{213}L^{214}P^{215}H^{216}$
(SEQ ID NO: 192)

(237) $K^{179}G^{180}V^{181}K^{182}Q^{183}L^{184}L^{185}H^{186}L^{187}K^{188}V^{189}R^{190}L^{191}D^{192}V^{193}R^{194}G^{195}A^{196}K^{197}Q^{198}L^{199}L^{200}H^{201}L^{202}$
$K^{203}V^{204}H^{205}L^{206}D^{207}V^{208}R^{209}G^{210}A^{211}K^{212}Q^{213}L^{214}P^{215}H^{216}L^{217}K^{218}V^{219}H^{220}$
(SEQ ID NO: 193)

(238) $K^{182}Q^{183}L^{184}L^{185}H^{186}L^{187}K^{188}$
(SEQ ID NO: 10)

-continued (239) $K^{182}Q^{183}L^{184}L^{185}H^{186}L^{187}K^{188}V^{189}R^{190}L^{191}D^{192}V^{193}R^{194}G^{195}A^{196}K^{197}Q^{198}L^{199}L^{200}H^{201}$
(SEQ ID NO: 194)

(240) $K^{182}Q^{183}L^{184}L^{185}H^{186}L^{187}K^{188}V^{189}R^{190}L^{191}D^{192}V^{193}R^{194}G^{195}A^{196}K^{197}Q^{198}L^{199}L^{200}H^{201}L^{202}K^{203}V^{204}H^{205}$
(SEQ ID NO: 195)

(241) $K^{182}Q^{183}L^{184}L^{185}H^{186}L^{187}K^{188}V^{189}R^{190}L^{191}D^{192}V^{193}R^{194}G^{195}A^{196}K^{197}Q^{198}L^{199}L^{200}H^{201}L^{202}K^{203}V^{204}H^{205}$
$L^{206}D^{207}V^{208}R^{209}G^{210}A^{211}K^{212}Q^{213}L^{214}P^{215}H^{216}$
(SEQ ID NO: 196)

(242) $K^{182}Q^{183}L^{184}L^{185}H^{186}L^{187}K^{188}V^{189}R^{190}L^{191}D^{192}V^{193}R^{194}G^{195}A^{196}K^{197}Q^{198}L^{199}L^{200}H^{201}L^{202}K^{203}V^{204}H^{205}$
$L^{206}D^{207}V^{208}R^{209}G^{210}A^{211}K^{212}Q^{213}L^{214}P^{215}H^{216}L^{217}K^{218}V^{219}H^{220}$
(SEQ ID NO: 197)

(243) $H^{186}L^{187}K^{188}V^{189}R^{190}L^{191}D^{192}V^{193}R^{194}G^{195}A^{196}K^{197}Q^{198}L^{199}L^{200}H^{201}L^{202}K^{203}$
(SEQ ID NO: 198)

(244) $H^{186}L^{187}K^{188}V^{189}R^{190}L^{191}D^{192}V^{193}R^{194}G^{195}A^{196}K^{197}$
(SEQ ID NO: 51)

(245) $H^{186}L^{187}K^{188}V^{189}R^{190}L^{191}D^{192}V^{193}R^{194}G^{195}A^{196}K^{197}Q^{198}L^{199}L^{200}H^{201}L^{202}K^{203}V^{204}H^{205}L^{206}D^{207}V^{208}R^{209}$
$G^{210}A^{211}K^{212}$
(SEQ ID NO: 199)

(246) $H^{186}L^{187}K^{188}V^{189}R^{190}L^{191}D^{192}V^{193}R^{194}G^{195}A^{196}K^{197}Q^{198}L^{199}L^{200}H^{201}L^{202}K^{203}V^{204}H^{205}L^{206}D^{207}V^{208}R^{209}$
$G^{210}A^{211}K^{212}Q^{213}L^{214}P^{215}H^{216}L^{217}K^{218}$
(SEQ ID NO: 200)

(247) $H^{186}L^{187}K^{188}V^{189}R^{190}L^{191}D^{192}V^{193}R^{194}G^{195}A^{196}K^{197}Q^{198}L^{199}L^{200}H^{201}L^{202}K^{203}V^{204}H^{205}L^{206}D^{207}V^{208}R^{209}$
$G^{210}A^{211}K^{212}Q^{213}L^{214}P^{215}H^{216}L^{217}K^{218}V^{219}H^{220}L^{221}D^{222}V^{223}R^{224}G^{225}A^{226}K^{227}$
(SEQ ID NO: 201)

(248) $H^{186}L^{187}K^{188}V^{189}R^{190}L^{191}D^{192}V^{193}R^{194}G^{195}A^{196}K^{197}Q^{198}L^{199}L^{200}H^{201}L^{202}K^{203}V^{204}H^{205}L^{206}D^{207}V^{208}R^{209}$
$G^{210}A^{211}K^{212}Q^{213}L^{214}P^{215}H^{216}L^{217}K^{218}V^{219}H^{220}L^{221}D^{222}V^{223}R^{224}G^{225}A^{226}K^{227}Q^{228}N^{229}P^{230}W^{231}R^{232}K^{233}$
(SEQ ID NO: 202)

(249) $K^{188}V^{189}R^{190}L^{191}D^{192}V^{193}R^{194}G^{195}A^{196}K^{197}Q^{198}L^{199}L^{200}H^{201}$
(SEQ ID NO: 203)

(250) $K^{188}V^{189}R^{190}L^{191}D^{192}V^{193}R^{194}G^{195}A^{196}K^{197}Q^{198}L^{199}L^{200}H^{201}L^{202}K^{203}V^{204}H^{205}$
(SEQ ID NO: 204)

(251) $K^{188}V^{189}R^{190}L^{191}D^{192}V^{193}R^{194}G^{195}A^{196}K^{197}Q^{198}L^{199}L^{200}H^{201}L^{202}K^{203}V^{204}H^{205}L^{206}D^{207}V^{208}R^{209}G^{210}A^{211}$
$K^{212}Q^{213}L^{214}P^{215}H^{216}$
(SEQ ID NO: 205)

(252) $K^{188}V^{189}R^{190}L^{191}D^{192}V^{193}R^{194}G^{195}A^{196}K^{197}Q^{198}L^{199}L^{200}H^{201}L^{202}K^{203}V^{204}H^{205}L^{206}D^{207}V^{208}R^{209}G^{210}A^{211}$
$K^{212}Q^{213}L^{214}P^{215}H^{216}L^{217}K^{218}V^{219}H^{220}$
(SEQ ID NO: 206)

(253) $K^{197}Q^{198}L^{199}L^{200}H^{201}L^{202}K^{203}$
(SEQ ID NO: 10)

(254) $K^{197}Q^{198}L^{199}L^{200}H^{201}L^{202}K^{203}V^{204}H^{205}$
(SEQ ID NO: 25)

(255) $K^{197}Q^{198}L^{199}L^{200}H^{201}L^{202}K^{203}V^{204}H^{205}L^{206}D^{207}V^{208}R^{209}G^{210}A^{211}K^{212}Q^{213}L^{214}P^{215}H^{216}$
(SEQ ID NO: 207)

(256) $K^{197}Q^{198}L^{199}L^{200}H^{201}L^{202}K^{203}V^{204}H^{205}L^{206}D^{207}V^{208}R^{209}G^{210}A^{211}K^{212}Q^{213}L^{214}P^{215}H^{216}L^{217}K^{218}V^{219}H^{220}$
(SEQ ID NO: 208)

(257) $H^{201}L^{202}K^{203}V^{204}H^{205}L^{206}D^{207}V^{208}R^{209}G^{210}A^{211}1K^{212}$
(SEQ ID NO: 121)

(258) $H^{201}L^{202}K^{203}V^{204}H^{205}L^{206}D^{207}V^{208}R^{209}G^{210}A^{211}K^{212}Q^{213}L^{214}P^{215}H^{216}L^{217}K^{218}$
(SEQ ID NO: 122)

(259) $H^{201}L^{202}K^{203}V^{204}H^{205}L^{206}D^{207}V^{208}R^{209}G^{210}A^{211}K^{212}Q^{213}L^{214}P^{215}H^{216}L^{217}K^{218}V^{219}H^{220}L^{221}D^{222}V^{223}R^{224}$
$G^{225}A^{226}K^{227}$
(SEQ ID NO: 209)

(260) $H^{201}L^{202}K^{203}V^{204}H^{205}L^{206}D^{207}V^{208}R^{209}G^{210}A^{211}K^{212}Q^{213}L^{214}P^{215}H^{216}L^{217}K^{218}V^{219}H^{220}L^{221}D^{222}V^{223}R^{224}$
$G^{225}A^{226}K^{227}Q^{228}N^{229}P^{230}W^{231}R^{232}K^{233}$
(SEQ ID NO: 210)

(261) $H^{201}L^{202}K^{203}V^{204}H^{205}L^{206}D^{207}V^{208}R^{209}G^{210}A^{211}K^{212}Q^{213}L^{214}P^{215}H^{216}L^{217}K^{218}V^{219}H^{220}L^{221}D^{222}V^{223}R^{224}$
$G^{225}A^{226}K^{227}Q^{228}N^{229}P^{230}W^{231}R^{232}K^{233}N^{234}L^{235}C^{236}L^{237}L^{238}K^{239}$
(SEQ ID NO: 211)

-continued (262) $H^{201}L^{202}K^{203}V^{204}H^{205}L^{206}D^{207}V^{208}R^{209}G^{210}A^{211}K^{212}Q^{213}L^{214}P^{215}H^{216}L^{217}K^{218}V^{219}H^{220}L^{221}D^{222}V^{223}R^{224}$
$G^{225}A^{226}K^{227}Q^{228}N^{229}P^{230}W^{231}R^{232}K^{233}N^{234}L^{235}C^{236}L^{237}L^{238}K^{239}K^{240}$
(SEQ ID NO: 212)

(263) $H^{201}L^{202}K^{203}V^{204}H^{205}L^{206}D^{207}V^{208}R^{209}G^{210}A^{211}K^{212}Q^{213}L^{214}P^{215}H^{216}L^{217}K^{218}V^{219}H^{220}L^{221}D^{222}V^{223}R^{224}$
$G^{225}A^{226}K^{227}Q^{228}N^{229}P^{230}W^{231}R^{232}K^{233}N^{234}L^{235}C^{236}L^{237}L^{238}K^{239}K^{240}N^{241}V^{242}K^{243}$
(SEQ ID NO: 213)

(264) $H^{201}L^{202}K^{203}V^{204}H^{205}L^{206}D^{207}V^{208}R^{209}G^{210}A^{211}K^{212}Q^{213}L^{214}P^{215}H^{216}L^{217}K^{218}V^{219}H^{220}L^{221}D^{222}V^{223}R^{224}$
$G^{225}A^{226}K^{227}Q^{228}N^{229}P^{230}W^{231}R^{232}K^{233}N^{234}L^{235}C^{236}L^{237}L^{238}K^{239}K^{240}N^{241}V^{242}K^{243}S^{244}A^{245}K^{246}$
(SEQ ID NO: 214)

(265) $K^{203}V^{204}H^{205}L^{206}D^{207}V^{208}R^{209}G^{210}A^{211}K^{212}$
(SEQ ID NO: 123)

(266) $K^{203}V^{204}H^{205}L^{206}D^{207}V^{208}R^{209}G^{210}A^{211}K^{212}Q^{213}L^{214}P^{215}H^{216}$
(SEQ ID NO: 124)

(267) $K^{203}V^{204}H^{205}L^{206}D^{207}V^{208}R^{209}G^{210}A^{211}K^{212}Q^{213}L^{214}P^{215}H^{216}L^{217}K^{218}V^{219}H^{220}$
(SEQ ID NO: 215)

(268) $K^{203}V^{204}H^{205}L^{206}D^{207}V^{208}R^{209}G^{210}A^{211}K^{212}Q^{213}L^{214}P^{215}H^{216}L^{217}K^{218}V^{219}H^{220}L^{221}D^{222}V^{223}R^{224}G^{225}A^{226}$
$K^{227}Q^{228}N^{229}P^{230}W^{231}R^{232}K^{233}N^{234}L^{235}C^{236}L^{237}L^{238}K^{239}K^{240}N^{241}V^{242}K^{243}S^{244}A^{245}K^{246}Q^{247}L^{248}P^{249}H^{250}$
(SEQ ID NO: 216)

(269) $H^{205}L^{206}D^{207}V^{208}R^{209}G^{210}A^{211}K^{212}Q^{213}L^{214}P^{215}H^{216}L^{217}K^{218}$
(SEQ ID NO: 128)

(270) $H^{205}L^{206}D^{207}V^{208}R^{209}G^{210}A^{211}K^{212}Q^{213}L^{214}P^{215}H^{216}L^{217}K^{218}V^{219}H^{220}L^{221}D^{222}V^{223}R^{224}G^{225}A^{226}K^{227}$
(SEQ ID NO: 217)

(271) $H^{205}L^{206}D^{207}V^{208}R^{209}G^{210}A^{211}K^{212}Q^{213}L^{214}P^{215}H^{216}L^{217}K^{218}V^{219}H^{220}L^{221}D^{222}V^{223}R^{224}G^{225}A^{226}K^{227}Q^{228}$
$N^{229}P^{230}W^{231}R^{232}K^{233}$
(SEQ ID NO: 218)

(272) $H^{205}L^{206}D^{207}V^{208}R^{209}G^{210}A^{211}K^{212}Q^{213}L^{214}P^{215}H^{216}L^{217}K^{218}V^{219}H^{220}L^{221}D^{222}V^{223}R^{224}G^{225}A^{226}K^{227}Q^{228}$
$N^{229}P^{230}W^{231}R^{232}K^{233}N^{234}L^{235}C^{236}L^{237}L^{238}K^{239}$
(SEQ ID NO: 219)

(273) $H^{205}L^{206}D^{207}V^{208}R^{209}G^{210}A^{211}K^{212}Q^{213}L^{214}P^{215}H^{216}L^{217}K^{218}V^{219}H^{220}L^{221}D^{222}V^{223}R^{224}G^{225}A^{226}K^{227}Q^{228}$
$N^{229}P^{230}W^{231}R^{232}K^{233}N^{234}L^{235}C^{236}L^{237}L^{238}K^{239}K^{240}$
(SEQ ID NO: 220)

(274) $H^{205}L^{206}D^{207}V^{208}R^{209}G^{210}A^{211}K^{212}Q^{213}L^{214}P^{215}H^{216}L^{217}K^{218}V^{219}H^{220}L^{221}D^{222}V^{223}R^{224}G^{225}A^{226}K^{227}Q^{228}$
$N^{229}P^{230}W^{231}R^{232}K^{233}N^{234}L^{235}C^{236}L^{237}L^{238}K^{239}K^{240}N^{241}V^{242}K^{243}$
(SEQ ID NO: 221)

(275) $H^{205}L^{206}D^{207}V^{208}R^{209}G^{210}A^{211}K^{212}Q^{213}L^{214}P^{215}H^{216}L^{217}K^{218}V^{219}H^{220}L^{221}D^{222}V^{223}R^{224}G^{225}A^{226}K^{227}Q^{228}$
$N^{229}P^{230}W^{231}R^{232}K^{233}N^{234}L^{235}C^{236}L^{237}L^{238}K^{239}K^{240}N^{241}V^{242}K^{243}S^{244}A^{245}K^{246}$
(SEQ ID NO: 222)

(276) $H^{205}L^{206}D^{207}V^{208}R^{209}G^{210}A^{211}K^{212}Q^{213}L^{214}P^{215}H^{216}L^{217}K^{218}V^{219}H^{220}L^{221}D^{222}V^{223}R^{224}G^{225}A^{226}K^{227}Q^{228}$
$N^{229}P^{230}W^{231}R^{232}K^{233}N^{234}L^{235}C^{236}L^{237}L^{238}K^{239}K^{240}N^{241}V^{242}K^{243}S^{244}A^{245}K^{246}Q^{247}L^{248}P^{249}H^{250}L^{251}K^{252}$
(SEQ ID NO: 223)

(277) $K^{212}Q^{213}L^{214}P^{215}H^{216}L^{217}K^{218}$
(SEQ ID NO: 84)

(278) $K^{212}Q^{213}L^{214}P^{215}H^{216}L^{217}K^{218}V^{219}H^{220}$
(SEQ ID NO: 85)

(279) $K^{212}Q^{213}L^{214}P^{215}H^{216}L^{217}K^{218}V^{219}H^{220}L^{221}D^{222}V^{223}R^{224}G^{225}A^{226}K^{227}Q^{228}N^{229}P^{230}W^{231}R^{232}K^{233}N^{234}L^{235}$
$C^{236}L^{237}L^{238}K^{239}K^{240}N^{241}V^{242}K^{243}S^{244}A^{245}K^{246}Q^{247}L^{248}P^{249}H^{250}$
(SEQ ID NO: 224)

(280) $H^{216}L^{217}K^{218}V^{219}H^{220}L^{221}D^{222}V^{223}R^{224}G^{225}A^{226}K^{227}$
(SEQ ID NO: 121)

(281) $H^{216}L^{217}K^{218}V^{219}H^{220}L^{221}D^{222}V^{223}R^{224}G^{225}A^{226}K^{227}Q^{228}N^{229}P^{230}W^{231}R^{232}K^{233}$
(SEQ ID NO: 225)

(282) $H^{216}L^{217}K^{218}V^{219}H^{220}L^{221}D^{222}V^{223}R^{224}G^{225}A^{226}K^{227}Q^{228}N^{229}P^{230}W^{231}R^{232}K^{233}N^{234}L^{235}C^{236}L^{237}L^{238}K^{239}$
(SEQ ID NO: 226)

(283) $H^{216}L^{217}K^{218}V^{219}H^{220}L^{221}D^{222}V^{223}R^{224}G^{225}A^{226}K^{227}Q^{228}N^{229}P^{230}W^{231}R^{232}K^{233}N^{234}L^{235}C^{236}L^{237}L^{238}K^{239}$
$K^{240}$
(SEQ ID NO: 227)

(284) $H^{216}L^{217}K^{218}V^{219}H^{220}L^{221}D^{222}V^{223}R^{224}G^{225}A^{226}K^{227}Q^{228}N^{229}P^{230}W^{231}R^{232}K^{233}N^{234}L^{235}C^{236}L^{237}L^{238}K^{239}$
$K^{240}N^{241}V^{242}K^{243}$
(SEQ ID NO: 228)

-continued (285) $H^{216}L^{217}K^{218}V^{219}H^{220}L^{221}D^{222}V^{223}R^{224}G^{225}A^{226}K^{227}Q^{228}N^{229}P^{230}W^{231}R^{232}K^{233}N^{234}L^{235}C^{236}L^{237}L^{238}K^{239}$
$K^{240}N^{241}V^{242}K^{243}S^{244}A^{245}K^{246}$
(SEQ ID NO: 229)

(286) $H^{216}L^{217}K^{218}V^{219}H^{220}L^{221}D^{222}V^{223}R^{224}G^{225}A^{226}K^{227}Q^{228}N^{229}P^{230}W^{231}R^{232}K^{233}N^{234}L^{235}C^{236}L^{237}L^{238}K^{239}$
$K^{240}N^{241}V^{242}K^{243}S^{244}A^{245}K^{246}Q^{247}L^{248}P^{249}H^{250}L^{251}K^{252}$
(SEQ ID NO: 230)

(287) $H^{216}L^{217}K^{218}V^{219}H^{220}L^{221}D^{222}V^{223}R^{224}G^{225}A^{226}K^{227}Q^{228}N^{229}P^{230}W^{231}R^{232}K^{233}N^{234}L^{235}C^{236}L^{237}L^{238}K^{239}$
$K^{240}N^{241}V^{242}K^{243}S^{244}A^{245}K^{246}Q^{247}L^{248}P^{249}H^{250}L^{251}K^{252}V^{253}L^{254}L^{255}D^{256}V^{257}R^{258}G^{259}A^{260}K^{261}$
(SEQ ID NO: 231)

(288) $K^{218}V^{219}H^{220}L^{221}D^{222}V^{223}R^{224}G^{225}A^{226}K^{227}Q^{228}N^{229}P^{230}W^{231}R^{232}K^{233}N^{234}L^{235}C^{236}L^{237}L^{238}K^{239}K^{240}N^{241}$
$V^{242}K^{243}S^{244}A^{245}K^{246}Q^{247}L^{248}P^{249}H^{250}$
(SEQ ID NO: 232)

(289) $K^{218}V^{219}H^{220}L^{221}D^{222}V^{223}R^{224}G^{225}A^{226}K^{227}Q^{228}N^{229}P^{230}W^{231}R^{232}K^{233}N^{234}L^{235}C^{236}L^{237}L^{238}K^{239}K^{240}N^{241}$
$V^{242}K^{243}S^{244}A^{245}K^{246}Q^{247}L^{248}P^{249}H^{250}L^{251}K^{252}V^{253}L^{254}L^{255}D^{256}V^{257}R^{258}G^{259}A^{260}K^{261}Q^{262}L^{263}P^{264}H^{265}$
(SEQ ID NO: 233)

(290) $K^{218}V^{219}H^{220}L^{221}D^{222}V^{223}R^{224}G^{225}A^{226}K^{227}$
(SEQ ID NO: 123)

(291) $H^{220}L^{221}D^{222}V^{223}R^{224}G^{225}A^{226}K^{227}Q^{228}N^{229}P^{230}W^{231}R^{232}K^{233}$
(SEQ ID NO: 234)

(292) $H^{220}L^{221}D^{222}V^{223}R^{224}G^{225}A^{226}K^{227}Q^{228}N^{229}P^{230}W^{231}R^{232}K^{233}N^{234}L^{235}C^{236}L^{237}L^{238}K^{239}$
(SEQ ID NO: 235)

(293) $H^{220}L^{221}D^{222}V^{223}R^{224}G^{225}A^{226}K^{227}Q^{228}N^{229}P^{230}W^{231}R^{232}K^{233}N^{234}L^{235}C^{236}L^{237}L^{238}K^{239}K^{240}$
(SEQ ID NO: 236)

(294) $H^{220}L^{221}D^{222}V^{223}R^{224}G^{225}A^{226}K^{227}Q^{228}N^{229}P^{230}W^{231}R^{232}K^{233}N^{234}L^{235}C^{236}L^{237}L^{238}K^{239}K^{240}N^{241}V^{242}K^{243}$
(SEQ ID NO: 237)

(295) $H^{220}L^{221}D^{222}V^{223}R^{224}G^{225}A^{226}K^{227}Q^{228}N^{229}P^{230}W^{231}R^{232}K^{233}N^{234}L^{235}C^{236}L^{237}L^{238}K^{239}K^{240}N^{241}V^{242}K^{243}$
$S^{244}A^{245}K^{246}$
(SEQ ID NO: 238)

(296) $H^{220}L^{221}D^{222}V^{223}R^{224}G^{225}A^{226}K^{227}Q^{228}N^{229}P^{230}W^{231}R^{232}K^{233}N^{234}L^{235}C^{236}L^{237}L^{238}K^{239}K^{240}N^{241}V^{242}K^{243}$
$S^{244}A^{245}K^{246}Q^{247}L^{248}P^{249}H^{250}L^{251}K^{252}$
(SEQ ID NO: 239)

(297) $H^{220}L^{221}D^{222}V^{223}R^{224}G^{225}A^{226}K^{227}Q^{228}N^{229}P^{230}W^{231}R^{232}K^{233}N^{234}L^{235}C^{236}L^{237}L^{238}K^{239}K^{240}N^{241}V^{242}K^{243}$
$S^{244}A^{245}K^{246}Q^{247}L^{248}P^{249}H^{250}L^{251}K^{252}V^{253}L^{254}L^{255}D^{256}V^{257}R^{258}G^{259}A^{260}K^{261}$
(SEQ ID NO: 240)

(298) $H^{220}L^{221}D^{222}V^{223}R^{224}G^{225}A^{226}K^{227}Q^{228}N^{229}P^{230}W^{231}R^{232}K^{233}N^{234}L^{235}C^{236}L^{237}L^{238}K^{239}K^{240}N^{241}V^{242}K^{243}$
$S^{244}A^{245}K^{246}Q^{247}L^{248}P^{249}H^{250}L^{251}K^{252}V^{253}L^{254}L^{255}D^{256}V^{257}R^{258}G^{259}A^{260}K^{261}Q^{262}L^{263}P^{264}H^{265}L^{266}K^{267}$
(SEQ ID NO: 241)

(299) $K^{227}Q^{228}N^{229}P^{230}W^{231}R^{232}K^{233}N^{234}L^{235}C^{236}L^{237}L^{238}K^{239}K^{240}N^{241}V^{242}K^{243}S^{244}A^{245}K^{246}Q^{247}L^{248}P^{249}H^{250}$
(SEQ ID NO: 63)

(300) $K^{227}Q^{228}N^{229}P^{230}W^{231}R^{232}K^{233}N^{234}L^{235}C^{236}L^{237}L^{238}K^{239}K^{240}N^{241}V^{242}K^{243}S^{244}A^{245}K^{246}Q^{247}L^{248}P^{249}H^{250}$
$L^{251}K^{252}V^{253}L^{254}L^{255}D^{256}V^{257}R^{258}G^{259}A^{260}K^{261}Q^{262}L^{263}P^{264}H^{265}$
(SEQ ID NO: 242)

(301) $K^{233}N^{234}L^{235}C^{236}L^{237}L^{238}K^{239}K^{240}N^{241}V^{242}K^{243}S^{244}A^{245}K^{246}Q^{247}L^{248}P^{249}H^{250}$
(SEQ ID NO: 68)

(302) $K^{233}N^{234}L^{235}C^{236}L^{237}L^{238}K^{239}K^{240}N^{241}V^{242}K^{243}S^{244}A^{245}K^{246}Q^{247}L^{248}P^{249}H^{250}L^{251}K^{252}V^{253}L^{254}L^{255}D^{256}$
$V^{257}R^{258}G^{259}A^{260}K^{261}Q^{262}L^{263}P^{264}H^{265}$
(SEQ ID NO: 243)

(303) $K^{233}N^{234}L^{235}C^{236}L^{237}L^{238}K^{239}K^{240}N^{241}V^{242}K^{243}S^{244}A^{245}K^{246}Q^{247}L^{248}P^{249}H^{250}L^{251}K^{252}V^{253}L^{254}L^{255}D^{256}$
$V^{257}R^{258}G^{259}A^{260}K^{261}Q^{262}L^{263}P^{264}H^{265}L^{266}K^{267}V^{268}L^{269}L^{270}D^{271}V^{272}R^{273}G^{274}A^{275}K^{276}Q^{277}L^{278}P^{279}H^{280}$
(SEQ ID NO: 244)

(304) $K^{239}K^{240}N^{241}V^{242}K^{243}S^{244}A^{245}K^{246}Q^{247}L^{248}P^{249}H^{250}L^{251}K^{252}V^{253}L^{254}L^{255}D^{256}V^{257}R^{258}G^{259}A^{260}K^{261}Q^{262}$
$L^{263}P^{264}H^{265}$
(SEQ ID NO: 3)

(305) $K^{239}K^{240}N^{241}V^{242}K^{243}S^{244}A^{245}K^{246}Q^{247}L^{248}P^{249}H^{250}L^{251}K^{252}V^{253}L^{254}L^{255}D^{256}V^{257}R^{258}G^{259}A^{260}K^{261}Q^{262}$
$L^{263}P^{264}H^{265}L^{266}K^{267}V^{268}L^{269}L^{270}D^{271}V^{272}R^{273}G^{274}A^{275}K^{276}Q^{277}L^{278}P^{279}H^{280}$
(SEQ ID NO: 245)

(306) $K^{239}K^{240}N^{241}V^{242}K^{243}S^{244}A^{245}K^{246}Q^{247}L^{248}P^{249}H^{250}L^{251}K^{252}V^{253}L^{254}L^{255}D^{256}V^{257}R^{258}G^{259}A^{260}K^{261}Q^{262}$
$L^{263}P^{264}H^{265}L^{266}K^{267}V^{268}L^{269}L^{270}D^{271}V^{272}R^{273}G^{274}A^{275}K^{276}Q^{277}L^{278}P^{279}H^{280}L^{281}K^{282}V^{283}H^{284}$
(SEQ ID NO: 246)

-continued (307) $K^{239}K^{240}N^{241}V^{242}K^{243}S^{244}A^{245}K^{246}Q^{247}L^{248}P^{249}H^{250}$
(SEQ ID NO: 13)

(308) $K^{240}N^{241}V^{242}K^{243}S^{244}A^{245}K^{246}Q^{247}L^{248}P^{249}H^{250}$
(SEQ ID NO: 75)

(309) $K^{240}N^{241}V^{242}K^{243}S^{244}A^{245}K^{246}Q^{247}L^{248}P^{249}H^{250}L^{251}K^{252}V^{253}L^{254}L^{255}D^{256}V^{257}R^{258}G^{259}A^{260}K^{261}Q^{262}L^{263}$
$P^{264}H^{265}$
(SEQ ID NO: 247)

(310) $K^{240}N^{241}V^{242}K^{243}S^{244}A^{245}K^{246}Q^{247}L^{248}P^{249}H^{250}L^{251}K^{252}V^{253}L^{254}L^{255}D^{256}V^{257}R^{258}G^{259}A^{260}K^{261}Q^{262}L^{263}$
$P^{264}H^{265}L^{266}K^{267}V^{268}L^{269}L^{270}D^{271}V^{272}R^{273}G^{274}A^{275}K^{276}Q^{277}L^{278}P^{279}H^{280}$
(SEQ ID NO: 248)

(311) $K^{240}N^{241}V^{242}K^{243}S^{244}A^{245}K^{246}Q^{247}L^{248}P^{249}H^{250}L^{251}K^{252}V^{253}L^{254}L^{255}D^{256}V^{257}R^{258}G^{259}A^{260}K^{261}Q^{262}L^{263}$
$P^{264}H^{265}L^{266}K^{267}V^{268}L^{269}L^{270}D^{271}V^{272}R^{273}G^{274}A^{275}K^{276}Q^{277}L^{278}P^{279}H^{280}L^{281}K^{282}V^{283}H^{284}$
(SEQ ID NO: 249)

(312) $K^{243}S^{244}A^{245}K^{246}Q^{247}L^{248}P^{249}H^{250}L^{251}K^{252}$
(SEQ ID NO: 14)

(313) $K^{243}S^{244}A^{245}K^{246}Q^{247}L^{248}P^{249}H^{250}L^{251}K^{252}V^{253}L^{254}L^{255}D^{256}V^{257}R^{258}G^{259}A^{260}K^{261}Q^{262}L^{263}P^{264}H^{265}$
(SEQ ID NO: 250)

(314) $K^{243}S^{244}A^{245}K^{246}Q^{247}L^{248}P^{249}H^{250}L^{251}K^{252}V^{253}L^{254}L^{255}D^{256}V^{257}R^{258}G^{259}A^{260}K^{261}Q^{262}L^{263}P^{264}H^{265}L^{266}$
$K^{267}V^{268}L^{269}L^{270}D^{271}V^{272}R^{273}G^{274}A^{275}K^{276}Q^{277}L^{278}P^{279}H^{280}$
(SEQ ID NO: 251)

(315) $K^{243}S^{244}A^{245}K^{246}Q^{247}L^{248}P^{249}H^{250}L^{251}K^{252}V^{253}L^{254}L^{255}D^{256}V^{257}R^{258}G^{259}A^{260}K^{261}Q^{262}L^{263}P^{264}H^{265}L^{266}$
$K^{267}V^{268}L^{269}L^{270}D^{271}V^{272}R^{273}G^{274}A^{275}K^{276}Q^{277}L^{278}P^{279}H^{280}L^{281}K^{282}V^{283}H^{284}$
(SEQ ID NO: 252)

(316) $K^{246}Q^{247}L^{248}P^{249}H^{250}L^{251}K^{252}$
(SEQ ID NO: 84)

(317) $K^{246}Q^{247}L^{248}P^{249}H^{250}L^{251}K^{252}V^{253}L^{254}L^{255}D^{256}V^{257}R^{258}G^{259}A^{260}K^{261}Q^{262}L^{263}P^{264}H^{265}$
(SEQ ID NO: 253)

(318) $K^{246}Q^{247}L^{248}P^{249}H^{250}L^{251}K^{252}V^{253}L^{254}L^{255}D^{256}V^{257}R^{258}G^{259}A^{260}K^{261}Q^{262}L^{263}P^{264}H^{265}L^{266}K^{267}V^{268}L^{269}$
$L^{270}D^{271}V^{272}R^{273}G^{274}A^{275}K^{276}Q^{277}L^{278}P^{279}H^{280}$
(SEQ ID NO: 254)

(319) $K^{246}Q^{247}L^{248}P^{249}H^{250}L^{251}K^{252}V^{253}L^{254}L^{255}D^{256}V^{257}R^{258}G^{259}A^{260}K^{261}Q^{262}L^{263}P^{264}H^{265}L^{266}K^{267}V^{268}L^{269}$
$L^{270}D^{271}V^{272}R^{273}G^{274}A^{275}K^{276}Q^{277}L^{278}P^{279}H^{280}L^{281}K^{282}V^{283}H^{284}$
(SEQ ID NO: 255)

(320) $H^{250}L^{251}K^{252}V^{253}L^{254}L^{255}D^{256}V^{257}R^{258}G^{259}A^{260}K^{261}$
(SEQ ID NO: 256)

(321) $H^{250}L^{251}K^{252}V^{253}L^{254}L^{255}D^{256}V^{257}R^{258}G^{259}A^{260}K^{261}Q^{262}L^{263}P^{264}H^{265}L^{266}K^{267}$
(SEQ ID NO: 257)

(322) $H^{250}L^{251}K^{252}V^{253}L^{254}L^{255}D^{256}V^{257}R^{258}G^{259}A^{260}K^{261}Q^{262}L^{263}P^{264}H^{265}L^{266}K^{267}V^{268}L^{269}L^{270}D^{271}V^{272}R^{273}$
$G^{274}A^{275}K^{276}$
(SEQ ID NO: 258)

(323) $H^{250}L^{251}K^{252}V^{253}L^{254}L^{255}D^{256}V^{257}R^{258}G^{259}A^{260}K^{261}Q^{262}L^{263}P^{264}H^{265}L^{266}K^{267}V^{268}L^{269}L^{270}D^{271}V^{272}R^{273}$
$G^{274}A^{275}K^{276}Q^{277}L^{278}P^{279}H^{280}L^{281}K^{282}$
(SEQ ID NO: 259)

(324) $H^{250}L^{251}K^{252}V^{253}L^{254}L^{255}D^{256}V^{257}R^{258}G^{259}A^{260}K^{261}Q^{262}L^{263}P^{264}H^{265}L^{266}K^{267}V^{268}L^{269}L^{270}D^{271}V^{272}R^{273}$
$G^{274}A^{275}K^{276}Q^{277}L^{278}P^{279}H^{280}L^{281}K^{282}V^{283}H^{284}L^{285}D^{286}V^{287}R^{288}G^{289}A^{290}K^{291}$
(SEQ ID NO: 260)

(325) $H^{250}L^{251}K^{252}V^{253}L^{254}L^{255}D^{256}V^{257}R^{258}G^{259}A^{260}K^{261}Q^{262}L^{263}P^{264}H^{265}L^{266}K^{267}V^{268}L^{269}L^{270}D^{271}V^{272}R^{273}$
$G^{274}A^{275}K^{276}Q^{277}L^{278}P^{279}H^{280}L^{281}K^{282}V^{283}H^{284}L^{285}D^{286}V^{287}R^{288}G^{289}A^{290}K^{291}Q^{292}N^{293}P^{294}W^{295}R^{296}K^{297}$
(SEQ ID NO: 261)

(326) $K^{252}V^{253}L^{254}L^{255}D^{256}V^{257}R^{258}G^{259}A^{260}K^{261}Q^{262}L^{263}P^{264}H^{265}$
(SEQ ID NO: 262)

(327) $K^{252}V^{253}L^{254}L^{255}D^{256}V^{257}R^{258}G^{259}A^{260}K^{261}Q^{262}L^{263}P^{264}H^{265}L^{266}K^{267}V^{268}L^{269}L^{270}D^{271}V^{272}R^{273}G^{274}A^{275}$
$K^{276}Q^{277}L^{278}P^{279}H^{280}$
(SEQ ID NO: 263)

(328) $K^{252}V^{253}L^{254}L^{255}D^{256}V^{257}R^{258}G^{259}A^{260}K^{261}Q^{262}L^{263}P^{264}H^{265}L^{266}K^{267}V^{268}L^{269}L^{270}D^{271}V^{272}R^{273}G^{274}A^{275}$
$K^{276}Q^{277}L^{278}P^{279}H^{280}L^{281}K^{282}V^{283}H^{284}$
(SEQ ID NO: 264)

(329) $K^{261}Q^{262}L^{263}P^{264}H^{265}L^{266}K^{267}V^{268}L^{269}L^{270}D^{271}V^{272}R^{273}G^{274}A^{275}K^{276}Q^{277}L^{278}P^{279}H^{280}$
(SEQ ID NO: 253)

-continued (330) $K^{261}Q^{262}L^{263}P^{264}H^{265}L^{266}K^{267}V^{268}L^{269}L^{270}D^{271}V^{272}R^{273}G^{274}A^{275}K^{276}Q^{277}L^{278}P^{279}H^{280}L^{281}K^{282}V^{283}H^{284}$
(SEQ ID NO: 265)

(331) $K^{261}Q^{262}L^{263}P^{264}H^{265}L^{266}K^{267}$
(SEQ ID NO: 84)

(332) $H^{265}L^{266}K^{267}V^{268}L^{269}L^{270}D^{271}V^{272}R^{273}G^{274}A^{275}K^{276}$
(SEQ ID NO: 256)

(333) $H^{265}L^{266}K^{267}V^{268}L^{269}L^{270}D^{271}V^{272}R^{273}G^{274}A^{275}K^{276}Q^{277}L^{278}P^{279}H^{280}L^{281}K^{282}$
(SEQ ID NO: 257)

(334) $H^{265}L^{266}K^{267}V^{268}L^{269}L^{270}D^{271}V^{272}R^{273}G^{274}A^{275}K^{276}Q^{277}L^{278}P^{279}H^{280}L^{281}K^{282}V^{283}H^{284}L^{285}D^{286}V^{287}R^{288}$
$G^{289}A^{290}K^{291}$
(SEQ ID NO: 266)

(335) $H^{265}L^{266}K^{267}V^{268}L^{269}L^{270}D^{271}V^{272}R^{273}G^{274}A^{275}K^{276}Q^{277}L^{278}P^{279}H^{280}L^{281}K^{282}V^{283}H^{284}L^{285}D^{286}V^{287}R^{288}$
$G^{289}A^{290}K^{291}Q^{292}N^{293}P^{294}W^{295}R^{296}K^{297}N^{298}L^{299}C^{300}L^{301}L^{302}K^{303}$
(SEQ ID NO: 267)

(336) $H^{265}L^{266}K^{267}V^{268}L^{269}L^{270}D^{271}V^{272}R^{273}G^{274}A^{275}K^{276}Q^{277}L^{278}P^{279}H^{280}L^{281}K^{282}V^{283}H^{284}L^{285}D^{286}V^{287}R^{288}$
$G^{289}A^{290}K^{291}Q^{292}N^{293}P^{294}W^{295}R^{296}K^{297}N^{298}L^{299}C^{300}L^{301}L^{302}K^{303}K^{304}$
(SEQ ID NO: 268)

(337) $H^{265}L^{266}K^{267}V^{268}L^{269}L^{270}D^{271}V^{272}R^{273}G^{274}A^{275}K^{276}Q^{277}L^{278}P^{279}H^{280}L^{281}K^{282}V^{283}H^{284}L^{285}D^{286}V^{287}R^{288}$
$G^{289}A^{290}K^{291}Q^{292}N^{293}P^{294}W^{295}R^{296}K^{297}N^{298}L^{299}C^{300}L^{301}L^{302}K^{303}K^{304}N^{305}V^{306}K^{307}$
(SEQ ID NO: 269)

(338) $H^{265}L^{266}K^{267}V^{268}L^{269}L^{270}D^{271}V^{272}R^{273}G^{274}A^{275}K^{276}Q^{277}L^{278}P^{279}H^{280}L^{281}K^{282}V^{283}H^{284}L^{285}D^{286}V^{287}R^{288}$
$G^{289}A^{290}K^{291}Q^{292}N^{293}P^{294}W^{295}R^{296}K^{297}$
(SEQ ID NO: 270)

(339) $H^{265}L^{266}K^{267}V^{268}L^{269}L^{270}D^{271}V^{272}R^{273}G^{274}A^{275}K^{276}Q^{277}L^{278}P^{279}H^{280}L^{281}K^{282}V^{283}H^{284}L^{285}D^{286}V^{287}R^{288}$
$K^{291}Q^{292}N^{293}P^{294}W^{295}R^{296}K^{297}N^{298}L^{299}C^{300}L^{301}L^{302}K^{303}K^{304}N^{305}V^{306}K^{307}S^{308}A^{309}K^{310}$
(SEQ ID NO: 271)

(340) $K^{267}V^{268}L^{269}L^{270}D^{271}V^{272}R^{273}G^{274}A^{275}K^{276}Q^{277}L^{278}P^{279}H^{280}$
(SEQ ID NO: 264)

(341) $K^{267}V^{268}L^{269}L^{270}D^{271}V^{272}R^{273}G^{274}A^{275}K^{276}Q^{277}L^{278}P^{279}H^{280}L^{281}K^{282}V^{283}H^{284}$
(SEQ ID NO: 272)

(342) $K^{267}V^{268}L^{269}L^{270}D^{271}V^{272}R^{273}G^{274}A^{275}K^{276}Q^{277}L^{278}P^{279}H^{280}L^{281}K^{282}V^{283}H^{284}L^{285}D^{286}V^{287}R^{288}G^{289}A^{290}$
$K^{291}Q^{292}N^{293}P^{294}W^{295}R^{296}K^{297}N^{298}L^{299}C^{300}L^{301}L^{302}K^{303}K^{304}N^{305}V^{306}K^{307}S^{308}A^{309}K^{310}Q^{311}L^{312}P^{313}H^{314}$
(SEQ ID NO: 273)

(343) $K^{276}Q^{277}L^{278}P^{279}H^{280}L^{281}K^{282}$
(SEQ ID NO: 84)

(344) $K^{276}Q^{277}L^{278}P^{279}H^{280}L^{281}K^{282}V^{283}H^{284}$
(SEQ ID NO: 85)

(345) $K^{276}Q^{277}L^{278}P^{279}H^{280}L^{281}K^{282}V^{283}H^{284}L^{285}D^{286}V^{287}R^{288}G^{289}A^{290}K^{291}Q^{292}N^{293}P^{294}W^{295}R^{296}K^{297}N^{298}L^{299}$
$C^{300}L^{301}L^{302}K^{303}K^{304}N^{305}V^{306}K^{307}S^{308}A^{309}K^{310}Q^{311}L^{312}P^{313}H^{314}$
(SEQ ID NO: 224)

(346) $H^{280}L^{281}K^{282}V^{283}H^{284}L^{285}D^{286}V^{287}R^{288}G^{289}A^{290}K^{291}$
(SEQ ID NO: 121)

(347) $H^{280}L^{281}K^{282}V^{283}H^{284}L^{285}D^{286}V^{287}R^{288}G^{289}A^{290}K^{291}Q^{292}N^{293}P^{294}W^{295}R^{296}K^{297}N^{298}L^{299}C^{300}L^{301}L^{302}K^{303}$
(SEQ ID NO: 226)

(348) $H^{280}L^{281}K^{282}V^{283}H^{284}L^{285}D^{286}V^{287}R^{288}G^{289}A^{290}K^{291}Q^{292}N^{293}P^{294}W^{295}R^{296}K^{297}N^{298}L^{299}C^{300}L^{301}L^{302}K^{303}$
$K^{304}$
(SEQ ID NO: 227)

(349) $H^{280}L^{281}K^{282}V^{283}H^{284}L^{285}D^{286}V^{287}R^{288}G^{289}A^{290}K^{291}Q^{292}N^{293}P^{294}W^{295}R^{296}K^{297}N^{298}L^{299}C^{300}L^{301}L^{302}K^{303}$
$K^{304}N^{305}V^{306}K^{307}$
(SEQ ID NO: 228)

(350) $H^{280}L^{281}K^{282}V^{283}H^{284}L^{285}D^{286}V^{287}R^{288}G^{289}A^{290}K^{291}Q^{292}N^{293}P^{294}W^{295}R^{296}K^{297}$
(SEQ ID NO: 225)

(351) $H^{280}L^{281}K^{282}V^{283}H^{284}L^{285}D^{286}V^{287}R^{288}G^{289}A^{290}K^{291}Q^{292}N^{293}P^{294}W^{295}R^{296}K^{297}N^{298}L^{299}C^{300}L^{301}L^{302}K^{303}$
$K^{304}N^{305}V^{306}K^{307}S^{308}A^{309}K^{310}$
(SEQ ID NO: 229)

(352) $H^{280}L^{281}K^{282}V^{283}H^{284}L^{285}D^{286}V^{287}R^{288}G^{289}A^{290}K^{291}Q^{292}N^{293}P^{294}W^{295}R^{296}K^{297}N^{298}L^{299}C^{300}L^{301}L^{302}K^{303}$
$K^{304}N^{305}V^{306}K^{307}S^{308}A^{309}K^{310}Q^{311}L^{312}P^{313}H^{314}L^{315}K^{316}$
(SEQ ID NO: 230)

-continued (353) $H^{280}L^{281}K^{282}V^{283}H^{284}L^{285}D^{286}V^{287}R^{288}G^{289}A^{290}K^{291}Q^{292}N^{293}P^{294}W^{295}R^{296}K^{297}N^{298}L^{299}C^{300}L^{301}L^{302}K^{303}$
$K^{304}N^{305}V^{306}K^{307}S^{308}A^{309}K^{310}Q^{311}L^{312}P^{313}H^{314}L^{315}K^{316}V^{317}L^{318}L^{319}D^{320}V^{321}R^{322}G^{323}A^{324}K^{325}$
(SEQ ID NO: 231)

(354) $K^{282}V^{283}H^{284}L^{285}D^{286}V^{287}R^{288}G^{289}A^{290}K^{291}Q^{292}N^{293}P^{294}W^{295}R^{296}K^{297}N^{298}L^{299}C^{300}L^{301}L^{302}K^{303}K^{304}N^{305}$
$V^{306}K^{307}S^{308}A^{309}K^{310}Q^{311}L^{312}P^{313}H^{314}$
(SEQ ID NO: 232)

(355) $K^{282}V^{283}H^{284}L^{285}D^{286}V^{287}R^{288}G^{289}A^{290}K^{291}Q^{292}N^{293}P^{294}W^{295}R^{296}K^{297}N^{298}L^{299}C^{300}L^{301}L^{302}K^{303}K^{304}N^{305}$
$V^{306}K^{307}S^{308}A^{309}K^{310}Q^{311}L^{312}P^{313}H^{314}L^{315}K^{316}V^{317}L^{318}L^{319}D^{320}V^{321}R^{322}G^{323}A^{324}K^{325}Q^{326}L^{327}P^{328}H^{329}$
(SEQ ID NO: 233)

(356) $K^{282}V^{283}H^{284}L^{285}D^{286}V^{287}R^{288}G^{289}A^{290}K^{291}$
(SEQ ID NO: 123)

(357) $H^{284}L^{285}D^{286}V^{287}R^{288}G^{289}A^{290}K^{291}Q^{292}N^{293}P^{294}W^{295}R^{296}K^{297}N^{298}L^{299}C^{300}L^{301}L^{302}K^{303}$
(SEQ ID NO: 235)

(358) $H^{284}L^{285}D^{286}V^{287}R^{288}G^{289}A^{290}K^{291}Q^{292}N^{293}P^{294}W^{295}R^{296}K^{297}N^{298}L^{299}C^{300}L^{301}L^{302}K^{303}K^{304}$
(SEQ ID NO: 236)

(359) $H^{284}L^{285}D^{286}V^{287}R^{288}G^{289}A^{290}K^{291}Q^{292}N^{293}P^{294}W^{295}R^{296}K^{297}N^{298}L^{299}C^{300}L^{301}L^{302}K^{303}K^{304}N^{305}V^{306}K^{307}$
(SEQ ID NO: 237)

(360) $H^{284}L^{285}D^{286}V^{287}R^{288}G^{289}A^{290}K^{291}Q^{292}N^{293}P^{294}W^{295}R^{296}K^{297}$
(SEQ ID NO: 234)

(361) $H^{284}L^{285}D^{286}V^{287}R^{288}G^{289}A^{290}K^{291}Q^{292}N^{293}P^{294}W^{295}R^{296}K^{297}N^{298}L^{299}C^{300}L^{301}L^{302}K^{303}K^{304}N^{305}V^{306}K^{307}$
$S^{308}A^{309}K^{310}$
(SEQ ID NO: 238)

(362) $H^{284}L^{285}D^{286}V^{287}R^{288}G^{289}A^{290}K^{291}Q^{292}N^{293}P^{294}W^{295}R^{296}K^{297}N^{298}L^{299}C^{300}L^{301}L^{302}K^{303}K^{304}N^{305}V^{306}K^{307}$
$S^{308}A^{309}K^{310}Q^{311}L^{312}P^{313}H^{314}L^{315}K^{316}$
(SEQ ID NO: 239)

(363) $H^{284}L^{285}D^{286}V^{287}R^{288}G^{289}A^{290}K^{291}Q^{292}N^{293}P^{294}W^{295}R^{296}K^{297}N^{298}L^{299}C^{300}L^{301}L^{302}K^{303}K^{304}N^{305}V^{306}K^{307}$
$S^{308}A^{309}K^{310}Q^{311}L^{312}P^{313}H^{314}L^{315}K^{316}V^{317}L^{318}L^{319}D^{320}V^{321}R^{322}G^{323}A^{324}K^{325}$
(SEQ ID NO: 240)

(364) $H^{284}L^{285}D^{286}V^{287}R^{288}G^{289}A^{290}K^{291}Q^{292}N^{293}P^{294}W^{295}R^{296}K^{297}N^{298}L^{299}C^{300}L^{301}L^{302}K^{303}K^{304}N^{305}V^{306}K^{307}$
$S^{308}A^{309}K^{310}Q^{311}L^{312}P^{313}H^{314}L^{315}K^{316}V^{317}L^{318}L^{319}D^{320}V^{321}R^{322}G^{323}A^{324}K^{325}Q^{326}L^{327}P^{328}H^{329}L^{330}K^{331}$
(SEQ ID NO: 241)

(365) $K^{291}Q^{292}N^{293}P^{294}W^{295}R^{296}K^{297}N^{298}L^{299}C^{300}L^{301}L^{302}K^{303}K^{304}N^{305}V^{306}K^{307}S^{308}A^{309}K^{310}Q^{311}L^{312}P^{313}H^{314}$
(SEQ ID NO: 63)

(366) $K^{291}Q^{292}N^{293}P^{294}W^{295}R^{296}K^{297}N^{298}L^{299}C^{300}L^{301}L^{302}K^{303}K^{304}N^{305}V^{306}K^{307}S^{308}A^{309}K^{310}Q^{311}L^{312}P^{313}H^{314}$
$L^{315}K^{316}V^{317}L^{318}L^{319}D^{320}V^{321}R^{322}G^{323}A^{324}K^{325}Q^{326}L^{327}P^{328}H^{329}$
(SEQ ID NO: 242)

(367) $K^{297}N^{298}L^{299}C^{300}L^{301}L^{302}K^{303}K^{304}N^{305}V^{306}K^{307}S^{308}A^{309}K^{310}Q^{311}L^{312}P^{313}H^{314}$
(SEQ ID NO: 68)

(368) $K^{297}N^{298}L^{299}C^{300}L^{301}L^{302}K^{303}K^{304}N^{305}V^{306}K^{307}S^{308}A^{309}K^{310}Q^{311}L^{312}P^{313}H^{314}L^{315}K^{316}V^{317}L^{318}L^{319}D^{320}$
$V^{321}R^{322}G^{323}A^{324}K^{325}Q^{326}L^{327}P^{328}H^{329}$
(SEQ ID NO: 243)

(369) $K^{297}N^{298}L^{299}C^{300}L^{301}L^{302}K^{303}K^{304}N^{305}V^{306}K^{307}S^{308}A^{309}K^{310}Q^{311}L^{312}P^{313}H^{314}L^{315}K^{316}V^{317}L^{318}L^{319}D^{320}$
$V^{321}R^{322}G^{323}A^{324}K^{325}Q^{326}L^{327}P^{328}H^{329}L^{330}K^{331}V^{332}L^{333}L^{334}D^{335}V^{336}R^{337}G^{338}A^{339}K^{340}Q^{341}L^{342}P^{343}H^{344}$
(SEQ ID NO: 244)

(370) $K^{303}K^{304}N^{305}V^{306}K^{307}S^{308}A^{309}K^{310}Q^{311}L^{312}P^{313}H^{314}$
(SEQ ID NO: 13)

(371) $K^{303}K^{304}N^{305}V^{306}K^{307}S^{308}A^{309}K^{310}Q^{311}L^{312}P^{313}H^{314}L^{315}K^{316}V^{317}L^{318}L^{319}D^{320}V^{321}R^{322}G^{323}A^{324}K^{325}Q^{326}$
$L^{327}P^{328}H^{329}$
(SEQ ID NO: 3)

(372) $K^{303}K^{304}N^{305}V^{306}K^{307}S^{308}A^{309}K^{310}Q^{311}L^{312}P^{313}H^{314}L^{315}K^{316}V^{317}L^{318}L^{319}D^{320}V^{321}R^{322}G^{323}A^{324}K^{325}Q^{326}$
$L^{327}P^{328}H^{329}L^{330}K^{331}V^{332}L^{333}L^{334}D^{335}V^{336}R^{337}G^{338}A^{339}K^{340}Q^{341}L^{342}P^{343}H^{344}$
(SEQ ID NO: 245)

(373) $K^{303}K^{304}N^{305}V^{306}K^{307}S^{308}A^{309}K^{310}Q^{311}L^{312}P^{313}H^{314}L^{315}K^{316}V^{317}L^{318}L^{319}D^{320}V^{321}R^{322}G^{323}A^{324}K^{325}Q^{326}$
$L^{327}P^{328}H^{329}L^{330}K^{331}V^{332}L^{333}L^{334}D^{335}V^{336}R^{337}G^{338}A^{339}K^{340}Q^{341}L^{342}P^{343}H^{344}L^{345}K^{346}V^{347}H^{348}$
(SEQ ID NO: 276)

(374) $K^{304}N^{305}V^{306}K^{307}S^{308}A^{309}K^{310}Q^{311}L^{312}P^{313}H^{314}L^{315}K^{316}V^{317}L^{318}L^{319}D^{320}V^{321}R^{322}G^{323}A^{324}K^{325}Q^{326}L^{327}$
$P^{328}H^{329}$
(SEQ ID NO: 247)

-continued (375) $K^{304}N^{305}V^{306}K^{307}S^{308}A^{309}K^{310}Q^{311}L^{312}P^{313}H^{314}L^{315}K^{316}V^{317}L^{318}L^{319}D^{320}V^{321}R^{322}G^{323}A^{324}K^{325}Q^{326}L^{327}$
$P^{328}H^{329}L^{330}K^{331}V^{332}L^{333}L^{334}D^{335}V^{336}R^{337}G^{338}A^{339}K^{340}Q^{341}L^{342}P^{343}H^{344}$
(SEQ ID NO: 248)

(376) $K^{304}N^{305}V^{306}K^{307}S^{308}A^{309}K^{310}Q^{311}L^{312}P^{313}H^{314}L^{315}K^{316}V^{317}L^{318}L^{319}D^{320}V^{321}R^{322}G^{323}A^{324}K^{325}Q^{326}L^{327}$
$P^{328}H^{329}L^{330}K^{331}V^{332}L^{333}L^{334}D^{335}V^{336}R^{337}G^{338}A^{339}K^{340}Q^{341}L^{342}P^{343}H^{344}L^{345}K^{346}V^{347}H^{348}$
(SEQ ID NO: 249)

(377) $K^{304}N^{305}V^{306}K^{307}S^{308}A^{309}K^{310}Q^{311}L^{312}P^{313}H^{314}$
(SEQ ID NO: 75)

(378) $K^{307}S^{308}A^{309}K^{310}Q^{311}L^{312}P^{313}H^{314}L^{315}K^{316}$
(SEQ ID NO: 14)

(379) $K^{307}S^{308}A^{309}K^{310}Q^{311}L^{312}P^{313}H^{314}L^{315}K^{316}V^{317}L^{318}L^{319}D^{320}V^{321}R^{322}G^{323}A^{324}K^{325}Q^{326}L^{327}P^{328}H^{329}$
(SEQ ID NO: 250)

(380) $K^{307}S^{308}A^{309}K^{310}Q^{311}L^{312}P^{313}H^{314}L^{315}K^{316}V^{317}L^{318}L^{319}D^{320}V^{321}R^{322}G^{323}A^{324}K^{325}Q^{326}L^{327}P^{328}H^{329}L^{330}$
$K^{331}V^{332}L^{333}L^{334}D^{335}V^{336}R^{337}G^{338}A^{339}K^{340}Q^{341}L^{342}P^{343}H^{344}$
(SEQ ID NO: 251)

(381) $K^{307}S^{308}A^{309}K^{310}Q^{311}L^{312}P^{313}H^{314}L^{315}K^{316}V^{317}L^{318}L^{319}D^{320}V^{321}R^{322}G^{323}A^{324}K^{325}Q^{326}L^{327}P^{328}H^{329}L^{330}$
$K^{331}V^{332}L^{333}L^{334}D^{335}V^{336}R^{337}G^{338}A^{339}K^{340}Q^{341}L^{342}P^{343}H^{344}L^{345}K^{346}V^{347}H^{348}$
(SEQ ID NO: 252)

(382) $K^{310}Q^{311}L^{312}P^{313}H^{314}L^{315}K^{316}$
(SEQ ID NO: 84)

(383) $K^{310}Q^{311}L^{312}P^{313}H^{314}L^{315}K^{316}V^{317}L^{318}L^{319}D^{320}V^{321}R^{322}G^{323}A^{324}K^{325}Q^{326}L^{327}P^{328}H^{329}$
(SEQ ID NO: 253)

(384) $K^{310}Q^{311}L^{312}P^{313}H^{314}L^{315}K^{316}V^{317}L^{318}L^{319}D^{320}V^{321}R^{322}G^{323}A^{324}K^{325}Q^{326}L^{327}P^{328}H^{329}L^{330}K^{331}V^{332}L^{333}$
$L^{334}D^{335}V^{336}R^{337}G^{338}A^{339}K^{340}Q^{341}L^{342}P^{343}H^{344}$
(SEQ ID NO: 254)

(385) $K^{310}Q^{311}L^{312}P^{313}H^{314}L^{315}K^{316}V^{317}L^{318}L^{319}D^{320}V^{321}R^{322}G^{323}A^{324}K^{325}Q^{326}L^{327}P^{328}H^{329}L^{330}K^{331}V^{332}L^{333}$
$L^{334}D^{335}V^{336}R^{337}G^{338}A^{339}K^{340}Q^{341}L^{342}P^{343}H^{344}L^{345}K^{346}V^{347}H^{348}$
(SEQ ID NO: 255)

(386) $K^{310}Q^{311}L^{312}P^{313}H^{314}L^{315}K^{316}V^{317}L^{318}L^{319}D^{320}V^{321}R^{322}G^{323}A^{324}K^{325}Q^{326}L^{327}P^{328}H^{329}L^{330}K^{331}V^{332}L^{333}$
$L^{334}D^{335}V^{336}R^{337}G^{338}A^{339}K^{340}Q^{341}L^{342}P^{343}H^{344}L^{345}K^{346}V^{347}H^{348}L^{349}D^{350}V^{351}R^{352}G^{353}A^{354}K^{355}Q^{356}L^{357}$
$P^{358}H^{359}$
(SEQ ID NO: 277)

(387) $H^{314}L^{315}K^{316}V^{317}L^{318}L^{319}D^{320}V^{321}R^{322}G^{323}A^{324}K^{325}$
(SEQ ID NO: 256)

(388) $H^{314}L^{315}K^{316}V^{317}L^{318}L^{319}D^{320}V^{321}R^{322}G^{323}A^{324}K^{325}Q^{326}L^{327}P^{328}H^{329}L^{330}K^{331}$
(SEQ ID NO: 257)

(389) $H^{314}L^{315}K^{316}V^{317}L^{318}L^{319}D^{320}V^{321}R^{322}G^{323}A^{324}K^{325}Q^{326}L^{327}P^{328}H^{329}L^{330}K^{331}V^{332}L^{333}L^{334}D^{335}V^{336}R^{337}$
$G^{338}A^{339}K^{340}$
(SEQ ID NO: 258)

(390) $H^{314}L^{315}K^{316}V^{317}L^{318}L^{319}D^{320}V^{321}R^{322}G^{323}A^{324}K^{325}Q^{326}L^{327}P^{328}H^{329}L^{330}K^{331}V^{332}L^{333}L^{334}D^{335}V^{336}R^{337}$
$G^{338}A^{339}K^{340}Q^{341}L^{342}P^{343}H^{344}L^{345}K^{346}$
(SEQ ID NO: 259)

(391) $H^{314}L^{315}K^{316}V^{317}L^{318}L^{319}D^{320}V^{321}R^{322}G^{323}A^{324}K^{325}Q^{326}L^{327}P^{328}H^{329}L^{330}K^{331}V^{332}L^{333}L^{334}D^{335}V^{336}R^{337}$
$G^{338}A^{339}K^{340}Q^{341}L^{342}P^{343}H^{344}L^{345}K^{346}V^{347}H^{348}L^{349}D^{350}V^{351}R^{352}G^{353}A^{354}K^{355}$
(SEQ ID NO: 260)

(392) $H^{314}L^{315}K^{316}V^{317}L^{318}L^{319}D^{320}V^{321}R^{322}G^{323}A^{324}K^{325}Q^{326}L^{327}P^{328}H^{329}L^{330}K^{331}V^{332}L^{333}L^{334}D^{335}V^{336}R^{337}$
$G^{338}A^{339}K^{340}Q^{341}L^{342}P^{343}H^{344}L^{345}K^{346}V^{347}H^{348}L^{349}D^{350}V^{351}R^{352}G^{353}A^{354}K^{355}Q^{356}L^{357}P^{358}H^{359}L^{360}K^{361}$
(SEQ ID NO: 278)

(393) $K^{316}V^{317}L^{318}L^{319}D^{320}V^{321}R^{322}G^{323}A^{324}K^{325}Q^{326}L^{327}P^{328}H^{329}L^{330}K^{331}V^{332}L^{333}L^{334}D^{335}V^{336}R^{337}G^{338}A^{339}$
$K^{340}Q^{341}L^{342}P^{343}H^{344}L^{345}K^{346}V^{347}H^{348}L^{349}D^{350}V^{351}R^{352}G^{353}A^{354}K^{355}Q^{356}L^{357}P^{358}H^{359}$
(SEQ ID NO: 279)

(394) $K^{316}V^{317}L^{318}L^{319}D^{320}V^{321}R^{322}G^{323}A^{324}K^{325}Q^{326}L^{327}P^{328}H^{329}$
(SEQ ID NO: 262)

(395) $K^{316}V^{317}L^{318}L^{319}D^{320}V^{321}R^{322}G^{323}A^{324}K^{325}Q^{326}L^{327}P^{328}H^{329}L^{330}K^{331}V^{332}L^{333}L^{334}D^{335}V^{336}R^{337}G^{338}A^{339}$
$K^{340}Q^{341}L^{342}P^{343}H^{344}$
(SEQ ID NO: 263)

(396) $K^{316}V^{317}L^{318}L^{319}D^{320}V^{321}R^{322}G^{323}A^{324}K^{325}Q^{326}L^{327}P^{328}H^{329}L^{330}K^{331}V^{332}L^{333}L^{334}D^{335}V^{336}R^{337}G^{338}A^{339}$
$K^{340}Q^{341}L^{342}P^{343}H^{344}L^{345}K^{346}V^{347}H^{348}$
(SEQ ID NO: 264)

-continued

Replikin Sequences in Carboxy-Terminal Portion of Peptide (397) $K^{325}Q^{326}L^{327}P^{328}H^{329}L^{330}K^{331}V^{332}L^{333}L^{334}D^{335}V^{336}R^{337}G^{338}A^{339}K^{340}Q^{341}L^{342}P^{343}H^{344}$
(SEQ ID NO: 253)

(398) $K^{325}Q^{326}L^{327}P^{328}H^{329}L^{330}K^{331}V^{332}L^{333}L^{334}D^{335}V^{336}R^{337}G^{338}A^{339}K^{340}Q^{341}L^{342}P^{343}H^{344}L^{345}K^{346}V^{347}H^{348}$
(SEQ ID NO: 265)

(399) $K^{325}Q^{326}L^{327}P^{328}H^{329}L^{330}K^{331}V^{332}L^{333}L^{334}D^{335}V^{336}R^{337}G^{338}A^{339}K^{340}Q^{341}L^{342}P^{343}H^{344}L^{345}K^{346}V^{347}H^{348}$
$L^{349}D^{350}V^{351}R^{352}G^{353}A^{354}K^{355}Q^{356}L^{357}P^{358}H^{359}$
(SEQ ID NO: 280)

(400) $K^{325}Q^{326}L^{327}P^{328}H^{329}L^{330}K^{331}V^{332}L^{333}L^{334}D^{335}V^{336}R^{337}G^{338}A^{339}K^{340}Q^{341}L^{342}P^{343}H^{344}L^{345}K^{346}V^{347}H^{348}$
$L^{349}D^{350}V^{351}R^{352}G^{353}A^{354}K^{355}Q^{356}L^{357}P^{358}H^{359}L^{360}K^{361}V^{362}L^{363}L^{364}D^{365}V^{366}R^{367}G^{368}A^{369}K^{370}Q^{371}L^{372}$
$P^{373}H^{374}$
(SEQ ID NO: 281)

(401) $K^{325}Q^{326}L^{327}P^{328}H^{329}L^{330}K^{331}$
(SEQ ID NO: 84)

(402) $H^{329}L^{330}K^{331}V^{332}L^{333}L^{334}D^{335}V^{336}R^{337}G^{338}A^{339}K^{340}$
(SEQ ID NO: 256)

(403) $H^{329}L^{330}K^{331}V^{332}L^{333}L^{334}D^{335}V^{336}R^{337}G^{338}A^{339}K^{340}Q^{341}L^{342}P^{343}H^{344}L^{345}K^{346}$
(SEQ ID NO: 257)

(404) $H^{329}L^{330}K^{331}V^{332}L^{333}L^{334}D^{335}V^{336}R^{337}G^{338}A^{339}K^{340}Q^{341}L^{342}P^{343}H^{344}L^{345}K^{346}V^{347}H^{348}L^{349}D^{350}V^{351}R^{352}$
$G^{353}A^{354}K^{355}$
(SEQ ID NO: 266)

(405) $H^{329}L^{330}K^{331}V^{332}L^{333}L^{334}D^{335}V^{336}R^{337}G^{338}A^{339}K^{340}Q^{341}L^{342}P^{343}H^{344}L^{345}K^{346}V^{347}H^{348}L^{349}D^{350}V^{351}R^{352}$
$G^{353}A^{354}K^{355}Q^{356}L^{357}P^{358}H^{359}L^{360}K^{361}$
(SEQ ID NO: 282)

(406) $H^{329}L^{330}K^{331}V^{332}L^{333}L^{334}D^{335}V^{336}R^{337}G^{338}A^{339}K^{340}Q^{341}L^{342}P^{343}H^{344}L^{345}K^{346}V^{347}H^{348}L^{349}D^{350}V^{351}R^{352}$
$G^{353}A^{354}K^{355}Q^{356}L^{357}P^{358}H^{359}L^{360}K^{361}V^{362}L^{363}L^{364}D^{365}V^{366}R^{367}G^{368}A^{369}K^{370}$
(SEQ ID NO: 283)

(407) $H^{329}L^{330}K^{331}V^{332}L^{333}L^{334}D^{335}V^{336}R^{337}G^{338}A^{339}K^{340}Q^{341}L^{342}P^{343}H^{344}L^{345}K^{346}V^{347}H^{348}L^{349}D^{350}V^{351}R^{352}$
$G^{353}A^{354}K^{355}Q^{356}L^{357}P^{358}H^{359}L^{360}K^{361}V^{362}L^{363}L^{364}D^{365}V^{366}R^{367}G^{368}A^{369}K^{370}Q^{371}L^{372}P^{373}H^{374}L^{375}K^{376}$
(SEQ ID NO: 284)

(408) $K^{331}V^{332}L^{333}L^{334}D^{335}V^{336}R^{337}G^{338}A^{339}K^{340}Q^{341}L^{342}P^{343}H^{344}$
(SEQ ID NO: 262)

(409) $K^{331}V^{332}L^{333}L^{334}D^{335}V^{336}R^{337}G^{338}A^{339}K^{340}Q^{341}L^{342}P^{343}H^{344}L^{345}K^{346}V^{347}H^{348}$
(SEQ ID NO: 272)

(410) $K^{331}V^{332}L^{333}L^{334}D^{335}V^{336}R^{337}G^{338}A^{339}K^{340}Q^{341}L^{342}P^{343}H^{344}L^{345}K^{346}V^{347}H^{348}L^{349}D^{350}V^{351}R^{352}G^{353}A^{354}$
$K^{355}Q^{356}L^{357}P^{358}H^{359}$
(SEQ ID NO: 285)

(411) $K^{331}V^{332}L^{333}L^{334}D^{335}V^{336}R^{337}G^{338}A^{339}K^{340}Q^{341}L^{342}P^{343}H^{344}L^{345}K^{346}V^{347}H^{348}L^{349}D^{350}V^{351}R^{352}G^{353}A^{354}$
$K^{355}Q^{356}L^{357}P^{358}H^{359}L^{360}K^{361}V^{362}L^{363}L^{364}D^{365}V^{366}R^{367}G^{368}A^{369}K^{370}Q^{371}L^{372}P^{373}H^{374}$
(SEQ ID NO: 286)

(412) $K^{340}Q^{341}L^{342}P^{343}H^{344}L^{345}K^{346}$
(SEQ ID NO: 84)

(413) $K^{340}Q^{341}L^{342}P^{343}H^{344}L^{345}K^{346}V^{347}H^{348}$
(SEQ ID NO: 85)

(414) $K^{340}Q^{341}L^{342}P^{343}H^{344}L^{345}K^{346}V^{347}H^{348}L^{349}D^{350}V^{351}R^{352}G^{353}A^{354}K^{355}Q^{356}L^{357}P^{358}H^{359}$
(SEQ ID NO: 112)

(415) $K^{340}Q^{341}L^{342}P^{343}H^{344}L^{345}K^{346}V^{347}H^{348}L^{349}D^{350}V^{351}R^{352}G^{353}A^{354}K^{355}Q^{356}L^{357}P^{358}H^{359}L^{360}K^{361}V^{362}L^{363}$
$L^{364}D^{365}V^{366}R^{367}G^{368}A^{369}K^{370}Q^{371}L^{372}P^{373}H^{374}$
(SEQ ID NO: 287)

(416) $H^{344}L^{345}K^{346}V^{347}H^{348}L^{349}D^{350}V^{351}R^{352}G^{353}A^{354}K^{355}$
(SEQ ID NO: 121)

(417) $H^{344}L^{345}K^{346}V^{347}H^{348}L^{349}D^{350}V^{351}R^{352}G^{353}A^{354}K^{355}Q^{356}L^{357}P^{358}H^{359}L^{360}K^{361}$
(SEQ ID NO: 122)

(418) $H^{344}L^{345}K^{346}V^{347}H^{348}L^{349}D^{350}V^{351}R^{352}G^{353}A^{354}K^{355}Q^{356}L^{357}P^{358}H^{359}L^{360}K^{361}V^{362}L^{363}L^{364}D^{365}V^{366}R^{367}$
$G^{368}A^{369}K^{370}$
(SEQ ID NO: 288)

(419) $H^{344}L^{345}K^{346}V^{347}H^{348}L^{349}D^{350}V^{351}R^{352}G^{353}A^{354}K^{355}Q^{356}L^{357}P^{358}H^{359}L^{360}K^{361}V^{362}L^{363}L^{364}D^{365}V^{366}R^{367}$
$G^{368}A^{369}K^{370}Q^{371}L^{372}P^{373}H^{374}L^{375}K^{376}$
(SEQ ID NO: 289)

-continued (420) $H^{344}L^{345}K^{346}V^{347}H^{348}L^{349}D^{350}V^{351}R^{352}G^{353}A^{354}K^{355}Q^{356}L^{357}P^{358}H^{359}L^{360}K^{361}V^{362}L^{363}L^{364}D^{365}V^{366}R^{367}$
$G^{368}A^{369}K^{370}Q^{371}L^{372}P^{373}H^{374}L^{375}K^{376}V^{377}L^{378}L^{379}D^{380}V^{381}R^{382}G^{383}A^{384}K^{385}$
(SEQ ID NO: 290)

(421) $H^{344}L^{345}K^{346}V^{347}H^{348}L^{349}D^{350}V^{351}R^{352}G^{353}A^{354}K^{355}Q^{356}L^{357}P^{358}H^{359}L^{360}K^{361}V^{362}L^{363}L^{364}D^{365}V^{366}R^{367}$
$G^{368}A^{369}K^{370}Q^{371}L^{372}P^{373}H^{374}L^{375}K^{376}V^{377}L^{378}L^{379}D^{380}V^{381}R^{382}G^{383}A^{384}K^{385}Q^{386}N^{387}P^{388}W^{389}R^{390}K^{391}$
(SEQ ID NO: 291)

(422) $K^{346}V^{347}H^{348}L^{349}D^{350}V^{351}R^{352}G^{353}A^{354}K^{355}$
(SEQ ID NO: 123)

(423) $K^{346}V^{347}H^{348}L^{349}D^{350}V^{351}R^{352}G^{353}A^{354}K^{355}Q^{356}L^{357}P^{358}H^{359}$
(SEQ ID NO: 124)

(424) $K^{346}V^{347}H^{348}L^{349}D^{350}V^{351}R^{352}G^{353}A^{354}K^{355}Q^{356}L^{357}P^{358}H^{359}L^{360}K^{361}V^{362}L^{363}L^{364}D^{365}V^{366}R^{367}G^{368}A^{369}$
$K^{370}Q^{371}L^{372}P^{373}H^{374}$
(SEQ ID NO: 292)

(425) $H^{348}L^{349}D^{350}V^{351}R^{352}G^{353}A^{354}K^{355}Q^{356}L^{357}P^{358}H^{359}L^{360}K^{361}$
(SEQ ID NO: 128)

(426) $H^{348}L^{349}D^{350}V^{351}R^{352}G^{353}A^{354}K^{355}Q^{356}L^{357}P^{358}H^{359}L^{360}K^{361}V^{362}L^{363}L^{364}D^{365}V^{366}R^{367}G^{368}A^{369}K^{370}$
(SEQ ID NO: 293)

(427) $H^{348}L^{349}D^{350}V^{351}R^{352}G^{353}A^{354}K^{355}Q^{356}L^{357}P^{358}H^{359}L^{360}K^{361}V^{362}L^{363}L^{364}D^{365}V^{366}R^{367}G^{368}A^{369}K^{370}Q^{371}$
$L^{372}P^{373}H^{374}L^{375}K^{376}$
(SEQ ID NO: 294)

(428) $H^{348}L^{349}D^{350}V^{351}R^{352}G^{353}A^{354}K^{355}Q^{356}L^{357}P^{358}H^{359}L^{360}K^{361}V^{362}L^{363}L^{364}D^{365}V^{366}R^{367}G^{368}A^{369}K^{370}Q^{371}$
$L^{372}P^{373}H^{374}L^{375}K^{376}V^{377}L^{378}L^{379}D^{380}V^{381}R^{382}G^{383}A^{384}K^{385}$
(SEQ ID NO: 295)

(429) $H^{348}L^{349}D^{350}V^{351}R^{352}G^{353}A^{354}K^{355}Q^{356}L^{357}P^{358}H^{359}L^{360}K^{361}V^{362}L^{363}L^{364}D^{365}V^{366}R^{367}G^{368}A^{369}K^{370}Q^{371}$
$L^{372}P^{373}H^{374}L^{375}K^{376}V^{377}L^{378}L^{379}D^{380}V^{381}R^{382}G^{383}A^{384}K^{385}Q^{386}N^{387}P^{388}W^{389}R^{390}K^{391}$
(SEQ ID NO: 296)

(430) $H^{348}L^{349}D^{350}V^{351}R^{352}G^{353}A^{354}K^{355}Q^{356}L^{357}P^{358}H^{359}L^{360}K^{361}V^{362}L^{363}L^{364}D^{365}V^{366}R^{367}G^{368}A^{369}K^{370}Q^{371}$
$L^{372}P^{373}H^{374}L^{375}K^{376}V^{377}L^{378}L^{379}D^{380}V^{381}R^{382}G^{383}A^{384}K^{385}Q^{386}N^{387}P^{388}W^{389}R^{390}K^{391}N^{392}L^{393}C^{394}L^{395}$
$L^{396}K^{397}$
(SEQ ID NO: 297)

(431) $H^{348}L^{349}D^{350}V^{351}R^{352}G^{353}A^{354}K^{355}Q^{356}L^{357}P^{358}H^{359}L^{360}K^{361}V^{362}L^{363}L^{364}D^{365}V^{366}R^{367}G^{368}A^{369}K^{370}Q^{371}$
$L^{372}P^{373}H^{374}L^{375}K^{376}V^{377}L^{378}L^{379}D^{380}V^{381}R^{382}G^{383}A^{384}K^{385}Q^{386}N^{387}P^{388}W^{389}R^{390}K^{391}N^{392}L^{393}C^{394}L^{395}$
$L^{396}K^{397}K^{398}$
(SEQ ID NO: 298)

(432) $K^{355}Q^{356}L^{357}P^{358}H^{359}L^{360}K^{361}$
(SEQ ID NO: 84)

(433) $K^{355}Q^{356}L^{357}P^{358}H^{359}L^{360}K^{361}V^{362}L^{363}L^{364}D^{365}V^{366}R^{367}G^{368}A^{369}K^{370}Q^{371}L^{372}P^{373}H^{374}$
(SEQ ID NO: 253)

(434) $H^{359}L^{360}K^{361}V^{362}L^{363}L^{364}D^{365}V^{366}R^{367}G^{368}A^{369}K^{370}$
(SEQ ID NO: 256)

(435) $H^{359}L^{360}K^{361}V^{362}L^{363}L^{364}D^{365}V^{366}R^{367}G^{368}A^{369}K^{370}Q^{371}L^{372}P^{373}H^{374}L^{375}K^{376}$
(SEQ ID NO: 257)

(436) $H^{359}L^{360}K^{361}V^{362}L^{363}L^{364}D^{365}V^{366}R^{367}G^{368}A^{369}K^{370}Q^{371}L^{372}P^{373}H^{374}L^{375}K^{376}V^{377}L^{378}L^{379}D^{380}V^{381}R^{382}$
$G^{383}A^{384}K^{385}$
(SEQ ID NO: 258)

(437) $H^{359}L^{360}K^{361}V^{362}L^{363}L^{364}D^{365}V^{366}R^{367}G^{368}A^{369}K^{370}Q^{371}L^{372}P^{373}H^{374}L^{375}K^{376}V^{377}L^{378}L^{379}D^{380}V^{381}R^{382}$
$G^{383}A^{384}K^{385}Q^{386}N^{387}P^{388}W^{389}R^{390}K^{391}N^{392}L^{393}C^{394}L^{395}L^{396}K^{397}K^{398}N^{399}V^{400}K^{401}$
(SEQ ID NO: 299)

(438) $H^{359}L^{360}K^{361}V^{362}L^{363}L^{364}D^{365}V^{366}R^{367}G^{368}A^{369}K^{370}Q^{371}L^{372}P^{373}H^{374}L^{375}K^{376}V^{377}L^{378}L^{379}D^{380}V^{381}R^{382}$
$G^{383}A^{384}K^{385}Q^{386}N^{387}P^{388}W^{389}R^{390}K^{391}$
(SEQ ID NO: 300)

(439) $H^{359}L^{360}K^{361}V^{362}L^{363}L^{364}D^{365}V^{366}R^{367}G^{368}A^{369}K^{370}Q^{371}L^{372}P^{373}H^{374}L^{375}K^{376}V^{377}L^{378}L^{379}D^{380}V^{381}R^{382}$
$G^{383}A^{384}K^{385}Q^{386}N^{387}P^{388}W^{389}R^{390}K^{391}N^{392}L^{393}C^{394}L^{395}L^{396}K^{397}K^{398}N^{399}V^{400}K^{401}S^{402}A^{403}K^{404}$
(SEQ ID NO: 301)

(440) $H^{359}L^{360}K^{361}V^{362}L^{363}L^{364}D^{365}V^{366}R^{367}G^{368}A^{369}K^{370}Q^{371}L^{372}P^{373}H^{374}L^{375}K^{376}V^{377}L^{378}L^{379}D^{380}V^{381}R^{382}$
$G^{383}A^{384}K^{385}Q^{386}N^{387}P^{388}W^{389}R^{390}K^{391}N^{392}L^{393}C^{394}L^{395}L^{396}K^{397}$
(SEQ ID NO: 302)

(441) $H^{359}L^{360}K^{361}V^{362}L^{363}L^{364}D^{365}V^{366}R^{367}G^{368}A^{369}K^{370}Q^{371}L^{372}P^{373}H^{374}L^{375}K^{376}V^{377}L^{378}L^{379}D^{380}V^{381}R^{382}$
$G^{383}A^{384}K^{385}Q^{386}N^{387}P^{388}W^{389}R^{390}K^{391}N^{392}L^{393}C^{394}L^{395}L^{396}K^{397}K^{398}$
(SEQ ID NO: 303)

-continued (442) $K^{361}V^{362}L^{363}L^{364}D^{365}V^{366}R^{367}G^{368}A^{369}K^{370}Q^{371}L^{372}P^{373}H^{374}$
(SEQ ID NO: 262)

(443) $K^{361}V^{362}L^{363}L^{364}D^{365}V^{366}R^{367}G^{368}A^{369}K^{370}Q^{371}L^{372}P^{373}H^{374}L^{375}K^{376}V^{377}L^{378}L^{379}D^{380}V^{381}R^{382}G^{383}A^{384}$
$K^{385}Q^{386}N^{387}P^{388}W^{389}R^{390}K^{391}N^{392}L^{393}C^{394}L^{395}L^{396}K^{397}K^{398}N^{399}V^{400}K^{401}S^{402}A^{403}K^{404}Q^{405}L^{406}P^{407}H^{408}$
(SEQ ID NO: 304)

(444) $K^{370}Q^{371}L^{372}P^{373}H^{374}L^{375}K^{376}$
(SEQ ID NO: 84)

(445) $K^{370}Q^{371}L^{372}P^{373}H^{374}L^{375}K^{376}V^{377}L^{378}L^{379}D^{380}V^{381}R^{382}G^{383}A^{384}K^{385}Q^{386}N^{387}P^{388}W^{389}R^{390}K^{391}N^{392}L^{393}$
$C^{394}L^{395}L^{396}K^{397}K^{398}N^{399}V^{400}K^{401}S^{402}A^{403}K^{404}Q^{405}L^{406}P^{407}H^{408}$
(SEQ ID NO: 305)

(446) $H^{374}L^{375}K^{376}V^{377}L^{378}L^{379}D^{380}V^{381}R^{382}G^{383}A^{384}K^{385}$
(SEQ ID NO: 256)

(447) $H^{374}L^{375}K^{376}V^{377}L^{378}L^{379}D^{380}V^{381}R^{382}G^{383}A^{384}K^{385}Q^{386}N^{387}P^{388}W^{389}R^{390}K^{391}N^{392}L^{393}C^{394}L^{395}L^{396}K^{397}$
$K^{398}N^{399}V^{400}K^{401}$
(SEQ ID NO: 306)

(448) $H^{374}L^{375}K^{376}V^{377}L^{378}L^{379}D^{380}V^{381}R^{382}G^{383}A^{384}K^{385}Q^{386}N^{387}P^{388}W^{389}R^{390}K^{391}$
(SEQ ID NO: 307)

(449) $H^{374}L^{375}K^{376}V^{377}L^{378}L^{379}D^{380}V^{381}R^{382}G^{383}A^{384}K^{385}Q^{386}N^{387}P^{388}W^{389}R^{390}K^{391}N^{392}L^{393}C^{394}L^{395}L^{396}K^{397}$
$K^{398}N^{399}V^{400}K^{401}S^{402}A^{403}K^{404}$
(SEQ ID NO: 308)

(450) $H^{374}L^{375}K^{376}V^{377}L^{378}L^{379}D^{380}V^{381}R^{382}G^{383}A^{384}K^{385}Q^{386}N^{387}P^{388}W^{389}R^{390}K^{391}N^{392}L^{393}C^{394}L^{395}L^{396}K^{397}$
(SEQ ID NO: 309)

(451) $H^{374}L^{375}K^{376}V^{377}L^{378}L^{379}D^{380}V^{381}R^{382}G^{383}A^{384}K^{385}Q^{386}N^{387}P^{388}W^{389}R^{390}K^{391}N^{392}L^{393}C^{394}L^{395}L^{396}K^{397}$
$K^{398}$
(SEQ ID NO: 310)

(452) $H^{374}L^{375}K^{376}V^{377}L^{378}L^{379}D^{380}V^{381}R^{382}G^{383}A^{384}K^{385}Q^{386}N^{387}P^{388}W^{389}R^{390}K^{391}N^{392}L^{393}C^{394}L^{395}L^{396}K^{397}$
$K^{398}N^{399}V^{400}K^{401}S^{402}A^{403}K^{404}Q^{405}L^{406}P^{407}H^{408}L^{409}K^{410}$
(SEQ ID NO: 311)

(453) $H^{374}L^{375}K^{376}V^{377}L^{378}L^{379}D^{380}V^{381}R^{382}G^{383}A^{384}K^{385}Q^{386}N^{387}P^{388}W^{389}R^{390}K^{391}N^{392}L^{393}C^{394}L^{395}L^{396}K^{397}$
$K^{398}N^{399}V^{400}K^{401}S^{402}A^{403}K^{404}Q^{405}L^{406}P^{407}H^{408}L^{409}K^{410}V^{411}L^{412}L^{413}D^{414}V^{415}R^{416}G^{417}A^{418}K^{419}$
(SEQ ID NO: 312)

(454) $K^{376}V^{377}L^{378}L^{379}D^{380}V^{381}R^{382}G^{383}A^{384}K^{385}Q^{386}N^{387}P^{388}W^{389}R^{390}K^{391}N^{392}L^{393}C^{394}L^{395}L^{396}K^{397}K^{398}N^{399}$
$V^{400}K^{401}S^{402}A^{403}K^{404}Q^{405}L^{406}P^{407}H^{408}$
(SEQ ID NO: 313)

(455) $K^{376}V^{377}L^{378}L^{379}D^{380}V^{381}R^{382}G^{383}A^{384}K^{385}Q^{386}N^{387}P^{388}W^{389}R^{390}K^{391}N^{392}L^{393}C^{394}L^{395}L^{396}K^{397}K^{398}N^{399}$
$V^{400}K^{401}S^{402}A^{403}K^{404}Q^{405}L^{406}P^{407}H^{408}L^{409}K^{410}V^{411}L^{412}L^{413}D^{414}V^{415}R^{416}G^{417}A^{418}K^{419}Q^{420}L^{421}P^{422}H^{423}$
(SEQ ID NO: 314)

(456) $K^{385}Q^{386}N^{387}P^{388}W^{389}R^{390}K^{391}N^{392}L^{393}C^{394}L^{395}L^{396}K^{397}K^{398}N^{399}V^{400}K^{401}S^{402}A^{403}K^{404}Q^{405}L^{406}P^{407}H^{408}$
(SEQ ID NO: 63)

(457) $K^{385}Q^{386}N^{387}P^{388}W^{389}R^{390}K^{391}N^{392}L^{393}C^{394}L^{395}L^{396}K^{397}K^{398}N^{399}V^{400}K^{401}S^{402}A^{403}K^{404}Q^{405}L^{406}P^{407}H^{408}$
$L^{409}K^{410}V^{411}L^{412}L^{413}D^{414}V^{415}R^{416}G^{417}A^{418}K^{419}Q^{420}L^{421}P^{422}H^{423}$
(SEQ ID NO: 242)

(458) $K^{385}Q^{386}N^{387}P^{388}W^{389}R^{390}K^{391}N^{392}L^{393}C^{394}L^{395}L^{396}K^{397}K^{398}N^{399}V^{400}K^{401}S^{402}A^{403}K^{404}Q^{405}L^{406}P^{407}H^{408}$
$L^{409}K^{410}V^{411}L^{412}L^{413}D^{414}V^{415}R^{416}G^{417}A^{418}K^{419}Q^{420}L^{421}P^{422}H^{423}L^{424}K^{425}V^{426}H^{427}$
(SEQ ID NO: 315)

(459) $K^{391}N^{392}L^{393}C^{394}L^{395}L^{396}K^{397}K^{398}N^{399}V^{400}K^{401}S^{402}A^{403}K^{404}Q^{405}L^{406}P^{407}H^{408}$
(SEQ ID NO: 68)

(460) $K^{391}N^{392}L^{393}C^{394}L^{395}L^{396}K^{397}K^{398}N^{399}V^{400}K^{401}S^{402}A^{403}K^{404}Q^{405}L^{406}P^{407}H^{408}L^{409}K^{410}V^{411}L^{412}L^{413}D^{414}$
$V^{415}R^{416}G^{417}A^{418}K^{419}Q^{420}L^{421}P^{422}H^{423}$
(SEQ ID NO: 243)

(461) $K^{391}N^{392}L^{393}C^{394}L^{395}L^{396}K^{397}K^{398}N^{399}V^{400}K^{401}S^{402}A^{403}K^{404}Q^{405}L^{406}P^{407}H^{408}L^{409}K^{410}V^{411}L^{412}L^{413}D^{414}$
$V^{415}R^{416}G^{417}A^{418}K^{419}Q^{420}L^{421}P^{422}H^{423}L^{424}K^{425}V^{426}H^{427}$
(SEQ ID NO: 316)

(462) $K^{397}K^{398}N^{399}V^{400}K^{401}S^{402}A^{403}K^{404}Q^{405}L^{406}P^{407}H^{408}$
(SEQ ID NO: 13)

(463) $K^{397}K^{398}N^{399}V^{400}K^{401}S^{402}A^{403}K^{404}Q^{405}L^{406}P^{407}H^{408}L^{409}K^{410}V^{411}L^{412}L^{413}D^{414}V^{415}R^{416}G^{417}A^{418}K^{419}Q^{420}$
$L^{421}P^{422}H^{423}$
(SEQ ID NO: 3)

-continued (464) $K^{397}K^{398}N^{399}V^{400}K^{401}S^{402}A^{403}K^{404}Q^{405}L^{406}P^{407}H^{408}L^{409}K^{410}V^{411}L^{412}L^{413}D^{414}V^{415}R^{416}G^{417}A^{418}K^{419}Q^{420}$
$L^{421}P^{422}H^{423}L^{424}K^{425}V^{426}H^{427}$
(SEQ ID NO: 4)

(465) $K^{398}N^{399}V^{400}K^{401}S^{402}A^{403}K^{404}Q^{405}L^{406}P^{407}H^{408}$
(SEQ ID NO: 75)

(466) $K^{398}N^{399}V^{400}K^{401}S^{402}A^{403}K^{404}Q^{405}L^{406}P^{407}H^{408}L^{409}K^{410}V^{411}L^{412}L^{413}D^{414}V^{415}R^{416}G^{417}A^{418}K^{419}Q^{420}L^{421}$
$P^{422}H^{423}$
(SEQ ID NO: 247)

(467) $K^{398}N^{399}V^{400}K^{401}S^{402}A^{403}K^{404}Q^{405}L^{406}P^{407}H^{408}L^{409}K^{410}V^{411}L^{412}L^{413}D^{414}V^{415}R^{416}G^{417}A^{418}K^{419}Q^{420}L^{421}$
$P^{422}H^{423}L^{424}K^{425}V^{426}H^{427}$
(SEQ ID NO: 318)

(468) $K^{401}S^{402}A^{403}K^{404}Q^{405}L^{406}P^{407}H^{408}L^{409}K^{410}$
(SEQ ID NO: 14)

(469) $K^{401}S^{402}A^{403}K^{404}Q^{405}L^{406}P^{407}H^{408}L^{409}K^{410}V^{411}L^{412}L^{413}D^{414}V^{415}R^{416}G^{417}A^{418}K^{419}Q^{420}L^{421}P^{422}H^{423}$
(SEQ ID NO: 250)

(470) $K^{401}S^{402}A^{403}K^{404}Q^{405}L^{406}P^{407}H^{408}L^{409}K^{410}V^{411}L^{412}L^{413}D^{414}V^{415}R^{416}G^{417}A^{418}K^{419}Q^{420}L^{421}P^{422}H^{423}L^{424}$
$K^{425}V^{426}H^{427}$
(SEQ ID NO: 319)

(471) $K^{404}Q^{405}L^{406}P^{407}H^{408}L^{409}K^{410}$
(SEQ ID NO: 84)

(472) $K^{404}Q^{405}L^{406}P^{407}H^{408}L^{409}K^{410}V^{411}L^{412}L^{413}D^{414}V^{415}R^{416}G^{417}A^{418}K^{419}Q^{420}L^{421}P^{422}H^{423}$
(SEQ ID NO: 253)

(473) $K^{404}Q^{405}L^{406}P^{407}H^{408}L^{409}K^{410}V^{411}L^{412}L^{413}D^{414}V^{415}R^{416}G^{417}A^{418}K^{419}Q^{420}L^{421}P^{422}H^{423}L^{424}K^{425}V^{426}H^{427}$
(SEQ ID NO: 265)

(474) $K^{404}Q^{405}L^{406}P^{407}H^{408}L^{409}K^{410}V^{411}L^{412}L^{413}D^{414}V^{415}R^{416}G^{417}A^{418}K^{419}Q^{420}L^{421}P^{422}H^{423}L^{424}K^{425}V^{426}H^{427}$
$L^{428}D^{429}V^{430}R^{431}G^{432}A^{433}K^{434}Q^{435}Q^{436}Q^{437}Q^{438}L^{439}C^{440}L^{441}P^{442}L^{443}K^{444}T^{445}I^{446}S^{447}T^{448}S^{449}F^{450}T^{451}$
$H^{452}$
(SEQ ID NO: 320)

(475) $H^{408}L^{409}K^{410}V^{411}L^{412}L^{413}D^{414}V^{415}R^{416}G^{417}A^{418}K^{419}$
(SEQ ID NO: 256)

(476) $H^{408}L^{409}K^{410}V^{411}L^{412}L^{413}D^{414}V^{415}R^{416}G^{417}A^{418}K^{419}Q^{420}L^{421}P^{422}H^{423}L^{424}K^{425}$
(SEQ ID NO: 257)

(477) $H^{408}L^{409}K^{410}V^{411}L^{412}L^{413}D^{414}V^{415}R^{416}G^{417}A^{418}K^{419}Q^{420}L^{421}P^{422}H^{423}L^{424}K^{425}V^{426}H^{427}L^{428}D^{429}V^{430}R^{431}$
$G^{432}A^{433}K^{434}$
(SEQ ID NO: 266)

(478) $H^{408}L^{409}K^{410}V^{411}L^{412}L^{413}D^{414}V^{415}R^{416}G^{417}A^{418}K^{419}Q^{420}L^{421}P^{422}H^{423}L^{424}K^{425}V^{426}H^{427}L^{428}D^{429}V^{430}R^{431}$
$G^{432}A^{433}K^{434}Q^{435}Q^{436}Q^{437}Q^{438}L^{439}C^{440}L^{441}P^{442}L^{443}K^{444}$
(SEQ ID NO: 321)

(479) $K^{410}V^{411}L^{412}L^{413}D^{414}V^{415}R^{416}G^{417}A^{418}K^{419}Q^{420}L^{421}P^{422}H^{423}$
(SEQ ID NO: 262)

(480) $K^{410}V^{411}L^{412}L^{413}D^{414}V^{415}R^{416}G^{417}A^{418}K^{419}Q^{420}L^{421}P^{422}H^{423}L^{424}K^{425}V^{426}H^{427}$
(SEQ ID NO: 272)

(481) $K^{410}V^{411}L^{412}L^{413}D^{414}V^{415}R^{416}G^{417}A^{418}K^{419}Q^{420}L^{421}P^{422}H^{423}L^{424}K^{425}V^{426}H^{427}L^{428}D^{429}V^{430}R^{431}G^{432}A^{433}$
$K^{434}Q^{435}Q^{436}Q^{437}Q^{438}L^{439}C^{440}L^{441}P^{442}L^{443}K^{444}T^{445}I^{446}S^{447}T^{448}S^{449}F^{450}T^{451}H^{452}$
(SEQ ID NO: 322)

(482) $K^{419}Q^{420}L^{421}P^{422}H^{423}L^{424}K^{425}$
(SEQ ID NO: 84)

(483) $K^{419}Q^{420}L^{421}P^{422}H^{423}L^{424}K^{425}V^{426}H^{427}$
(SEQ ID NO: 85)

(484) $K^{419}Q^{420}L^{421}P^{422}H^{423}L^{424}K^{425}V^{426}H^{427}L^{428}D^{429}V^{430}R^{431}G^{432}A^{433}K^{434}Q^{435}Q^{436}Q^{437}Q^{438}L^{439}C^{440}L^{441}P^{442}$
$L^{443}K^{444}T^{445}I^{446}S^{447}T^{448}S^{449}F^{450}T^{451}H^{452}$
(SEQ ID NO: 323)

(485) $K^{419}Q^{420}L^{421}P^{422}H^{423}L^{424}K^{425}V^{426}H^{427}L^{428}D^{429}V^{430}R^{431}G^{432}A^{433}K^{434}Q^{435}Q^{436}Q^{437}Q^{438}L^{439}C^{440}L^{441}P^{442}$
$L^{443}K^{444}T^{445}I^{446}S^{447}T^{448}S^{449}F^{450}T^{451}H^{452}L^{453}L^{454}L^{455}C^{456}L^{457}Y^{458}M^{459}E^{460}Y^{461}G^{462}K^{463}H^{464}$
(SEQ ID NO: 324)

(486) $H^{423}L^{424}K^{425}V^{426}H^{427}L^{428}D^{429}V^{430}R^{431}G^{432}A^{433}K^{434}Q^{435}Q^{436}Q^{437}Q^{438}L^{439}C^{440}L^{441}P^{442}L^{443}K^{444}$
(SEQ ID NO: 325)

-continued (487) $H^{423}L^{424}K^{425}V^{426}H^{427}L^{428}D^{429}V^{430}R^{431}G^{432}A^{433}K^{434}Q^{435}Q^{436}Q^{437}Q^{438}L^{439}C^{440}L^{441}P^{442}L^{443}K^{444}T^{445}I^{446}$
$S^{447}T^{448}S^{449}F^{450}T^{451}H^{452}L^{453}L^{454}L^{455}C^{456}L^{457}Y^{458}M^{459}E^{460}Y^{461}G^{462}K^{463}H^{464}Q^{465}N^{466}L^{467}Q^{468}V^{469}K^{470}$
(SEQ ID NO: 326)

(488) $H^{423}L^{424}K^{425}V^{426}H^{427}L^{428}D^{429}V^{430}R^{431}G^{432}A^{433}K^{434}$
(SEQ ID NO: 121)

(489) $K^{425}V^{426}H^{427}L^{428}D^{429}V^{430}R^{431}G^{432}A^{433}K^{434}$
(SEQ ID NO: 123)

(490) $K^{425}V^{426}H^{427}L^{428}D^{429}V^{430}R^{431}G^{432}A^{433}K^{434}Q^{435}Q^{436}Q^{437}Q^{438}L^{439}C^{440}L^{441}P^{442}L^{443}K^{444}T^{445}I^{446}S^{447}T^{448}$
$S^{449}F^{450}T^{451}H^{452}$
(SEQ ID NO: 327)

(491) $K^{425}V^{426}H^{427}L^{428}D^{429}V^{430}R^{431}G^{432}A^{433}K^{434}Q^{435}Q^{436}Q^{437}Q^{438}L^{439}C^{440}L^{441}P^{442}L^{443}K^{444}T^{445}I^{446}S^{447}T^{448}$
$S^{449}F^{450}I^{451}H^{452}L^{453}L^{454}L^{455}C^{456}L^{457}Y^{458}M^{459}E^{460}Y^{461}G^{462}K^{463}H^{464}$
(SEQ ID NO: 328)

(492) $H^{427}L^{428}D^{429}V^{430}R^{431}G^{432}A^{433}K^{434}Q^{435}Q^{436}Q^{437}Q^{438}L^{439}C^{440}L^{441}P^{442}L^{443}K^{444}$
(SEQ ID NO: 329)

(493) $H^{427}L^{428}D^{429}V^{430}R^{431}G^{432}A^{433}K^{434}Q^{435}Q^{436}Q^{437}Q^{438}L^{439}C^{440}L^{441}P^{442}L^{443}K^{444}T^{445}I^{446}S^{447}T^{448}S^{449}F^{450}$
$T^{451}H^{452}L^{453}L^{454}L^{455}C^{456}L^{457}Y^{458}M^{459}E^{460}Y^{461}G^{462}K^{463}H^{464}Q^{465}N^{466}L^{467}Q^{468}V^{469}K^{470}$
(SEQ ID NO: 330)

(494) $K^{434}Q^{435}Q^{436}Q^{437}Q^{438}L^{439}C^{440}L^{441}P^{442}L^{443}K^{444}T^{445}I^{446}S^{447}T^{448}S^{449}F^{450}T^{451}H^{452}$
(SEQ ID NO: 331)

(495) $K^{434}Q^{435}Q^{436}Q^{437}Q^{438}L^{439}C^{440}L^{441}P^{442}L^{443}K^{444}T^{445}I^{446}S^{447}T^{448}S^{449}F^{450}T^{451}H^{452}L^{453}L^{454}L^{455}C^{456}L^{457}$
$Y^{458}M^{459}E^{460}Y^{461}G^{462}K^{463}H^{464}$
(SEQ ID NO: 332)

(496) $H^{452}L^{453}L^{454}L^{455}C^{456}L^{457}Y^{458}M^{459}E^{460}Y^{461}G^{462}K^{463}H^{464}Q^{465}N^{466}L^{467}Q^{468}V^{469}K^{470}$
(SEQ ID NO: 333)

(497) $K^{463}H^{464}Q^{465}N^{466}L^{467}Q^{468}V^{469}K^{470}$
(SEQ ID NO: 334)

Example 2

Determination of Very High Replikin Concentration at Accession No. NP 478030.

Replikin concentration was determined for a functionally undefined protein in the genome of an isolate of White Spot Syndrome Virus from 2000 made publicly available at NP 478030. The Replikin Concentration in the protein was again an unusually high 97.6 Replikin sequences per 100 amino acids. The Replikin concentration was determined by dividing the number of Replikin sequences identified in the amino acid sequence of the protein, 361 Replikin sequences, by the total amino acid length of the protein, 370 amino acids.

The amino acid sequence of NP 478030 is of interest because, like the protien in Example 1, it demonstrates an overlapping of Replikin sequences that results in very high Replikin concentration comparable to the highly-replicating *P. falciparum* of malaria. These high concentrations of Replikin sequences again provide a reservoir of Replikins for transfer to influenza viruses.

PubMed Accession Number NP 478030
Description: Protein of unknown function translated from complete genome sequence of the shrimp white spot baculoform virus (WSSV) publicly available at PubMed Accession No. NC003225.1.
Isolated Year: 2000
Source: Shrimp White Spot Syndrome Virus (Shrimp White Spot Baculoform Virus)
$M^{1}K^{2}I^{3}C^{4}Q^{5}I^{6}S^{7}S^{8}P^{9}T^{10}L^{11}T^{12}L^{13}S^{14}I^{15}P^{16}L^{17}E^{18}G^{19}V^{20}Y^{21}H^{22}V^{23}K^{24}Q^{25}L^{26}L^{27}H^{28}L^{29}K^{30}V^{31}H^{32}L^{33}D^{34}V^{35}K^{36}G^{37}$ $V^{38}K^{39}Q^{40}L^{41}L^{42}H^{43}L^{44}K^{45}V^{46}R^{47}L^{48}D^{49}V^{50}R^{51}G^{52}A^{53}K^{54}Q^{55}N^{56}P^{57}W^{58}R^{59}K^{60}N^{61}L^{62}C^{63}L^{64}L^{65}K^{66}K^{67}N^{68}V^{69}K^{70}$ $S^{71}A^{72}K^{73}Q^{74}L^{75}P^{76}H^{77}L^{78}K^{79}V^{80}H^{81}L^{82}D^{83}V^{84}K^{85}S^{86}A^{87}K^{88}Q^{89}L^{90}P^{91}H^{92}L^{93}K^{94}V^{95}H^{96}L^{97}D^{98}V^{99}R^{100}G^{101}A^{102}$ $K^{103}Q^{104}L^{105}P^{106}H^{107}L^{108}K^{109}V^{110}R^{111}L^{112}D^{113}V^{114}K^{115}S^{116}A^{117}K^{118}Q^{119}L^{120}P^{121}H^{122}L^{123}K^{124}V^{125}H^{126}L^{127}$ $D^{128}V^{129}R^{130}G^{131}A^{132}K^{133}Q^{134}L^{135}P^{136}H^{137}L^{138}K^{139}V^{140}R^{141}L^{142}D^{143}V^{144}R^{145}G^{146}A^{147}K^{148}Q^{149}N^{150}P^{151}W^{152}$ $R^{153}K^{154}N^{155}L^{156}C^{157}L^{158}L^{159}K^{160}K^{161}N^{162}V^{163}K^{164}S^{165}A^{166}K^{167}Q^{168}L^{169}P^{170}H^{171}L^{172}K^{173}V^{174}H^{175}L^{176}D^{177}$ $V^{178}K^{179}G^{180}V^{181}K^{182}Q^{183}L^{184}L^{185}H^{186}L^{187}K^{188}V^{189}R^{190}L^{191}D^{192}V^{193}R^{194}G^{195}A^{196}K^{197}Q^{198}L^{199}P^{200}H^{201}L^{202}$ $K^{203}V^{204}H^{205}L^{206}D^{207}V^{208}R^{209}G^{210}A^{211}K^{212}Q^{213}N^{214}P^{215}W^{216}R^{217}K^{218}N^{219}L^{220}C^{221}L^{222}L^{223}K^{224}K^{225}N^{226}V^{227}$ $K^{228}S^{229}A^{230}K^{231}Q^{232}L^{233}P^{234}H^{235}L^{236}K^{237}V^{238}L^{239}L^{240}D^{241}V^{242}R^{243}G^{244}A^{245}K^{246}Q^{247}L^{248}P^{249}H^{250}L^{251}K^{252}$ $V^{253}L^{254}L^{255}D^{256}V^{257}R^{258}G^{259}A^{260}K^{261}Q^{262}L^{263}P^{264}H^{265}L^{266}K^{267}V^{268}L^{269}L^{270}D^{271}V^{272}R^{273}G^{274}A^{275}K^{276}Q^{277}$ -continued $N^{278}P^{279}W^{280}R^{281}K^{282}N^{283}L^{284}C^{285}L^{286}L^{287}K^{288}K^{289}N^{290}V^{291}K^{292}S^{293}A^{294}K^{295}Q^{296}L^{297}P^{298}H^{299}L^{300}K^{301}V^{302}$ $L^{303}L^{304}D^{305}V^{306}R^{307}G^{308}A^{309}K^{310}Q^{311}L^{312}P^{313}H^{314}L^{315}K^{316}V^{317}H^{318}L^{319}D^{320}V^{321}R^{322}G^{323}A^{324}K^{325}Q^{326}Q^{327}$ $Q^{328}Q^{329}L^{330}C^{331}L^{332}P^{333}L^{334}K^{335}T^{336}I^{337}S^{338}T^{339}S^{340}F^{341}T^{342}H^{343}L^{344}L^{345}L^{346}C^{347}L^{348}Y^{349}M^{350}E^{351}Y^{352}$ $G^{353}K^{354}H^{355}Q^{356}N^{357}L^{358}Q^{359}V^{360}K^{361}M^{362}W^{363}L^{364}N^{365}I^{366}T^{367}Y^{368}T^{369}S^{370}$
(SEQ ID NO: 335)

Replikin Sequences Identified in Accession No. ABS00973
Replikin Sequences Located in Amino-Terminal of Peptide (1) $H^{22}V^{23}K^{24}Q^{25}L^{26}L^{27}H^{28}L^{29}K^{30}$
(SEQ ID NO: 16)

(2) $H^{22}V^{23}K^{24}Q^{25}L^{26}L^{27}H^{28}L^{29}K^{30}V^{31}H^{32}L^{33}D^{34}V^{35}K^{36}$
(SEQ ID NO: 17)

(3) $H^{22}V^{23}K^{24}Q^{25}L^{26}L^{27}H^{28}L^{29}K^{30}V^{31}H^{32}L^{33}D^{34}V^{35}K^{36}G^{37}V^{38}K^{39}$
(SEQ ID NO: 18)

(4) $H^{22}V^{23}K^{24}Q^{25}L^{26}L^{27}H^{28}L^{29}K^{30}V^{31}H^{32}L^{33}D^{34}V^{35}K^{36}G^{37}V^{38}K^{39}Q^{40}L^{41}L^{42}H^{43}L^{44}K^{45}$
(SEQ ID NO: 19)

(5) $H^{22}V^{23}K^{24}Q^{25}L^{26}L^{27}H^{28}L^{29}K^{30}V^{31}H^{32}L^{33}D^{34}V^{35}K^{36}G^{37}V^{38}K^{39}Q^{40}L^{41}L^{42}H^{43}L^{44}K^{45}V^{46}R^{47}L^{48}D^{49}V^{50}R^{51}G^{52}A^{53}$
$K^{54}$
(SEQ ID NO: 20)

(6) $H^{22}V^{23}K^{24}Q^{25}L^{26}L^{27}H^{28}L^{29}K^{30}V^{31}H^{32}L^{33}D^{34}V^{35}K^{36}G^{37}V^{38}K^{39}Q^{40}L^{41}L^{42}H^{43}L^{44}K^{45}V^{46}R^{47}L^{48}D^{49}V^{50}R^{51}G^{52}A^{53}$
$K^{54}Q^{55}N^{56}P^{57}W^{58}R^{59}K^{60}$
(SEQ ID NO: 21)

(7) $H^{22}V^{23}K^{24}Q^{25}L^{26}L^{27}H^{28}L^{29}K^{30}V^{31}H^{32}L^{33}D^{34}V^{35}K^{36}G^{37}V^{38}K^{39}Q^{40}L^{41}L^{42}H^{43}L^{44}K^{45}V^{46}R^{47}L^{48}D^{49}V^{50}R^{51}G^{52}A^{53}$
$K^{54}Q^{55}N^{56}P^{57}W^{58}R^{59}K^{60}N^{61}L^{62}C^{63}L^{64}L^{65}K^{66}$
(SEQ ID NO: 22)

(8) $H^{22}V^{23}K^{24}Q^{25}L^{26}L^{27}H^{28}L^{29}K^{30}V^{31}H^{32}L^{33}D^{34}V^{35}K^{36}G^{37}V^{38}K^{39}Q^{40}L^{41}L^{42}H^{43}L^{44}K^{45}V^{46}R^{47}L^{48}D^{49}V^{50}R^{51}G^{52}A^{53}$
$K^{54}Q^{55}N^{56}P^{57}W^{58}R^{59}K^{60}N^{61}L^{62}C^{63}L^{64}L^{65}K^{66}K^{67}$
(SEQ ID NO: 23)

(9) $H^{22}V^{23}K^{24}Q^{25}L^{26}L^{27}H^{28}L^{29}K^{30}V^{31}H^{32}L^{33}D^{34}V^{35}K^{36}G^{37}V^{38}K^{39}Q^{40}L^{41}L^{42}H^{43}L^{44}K^{45}V^{46}R^{47}L^{48}D^{49}V^{50}R^{51}G^{52}A^{53}$
$K^{54}Q^{55}N^{56}P^{57}W^{58}R^{59}K^{60}N^{61}L^{62}C^{63}L^{64}L^{65}K^{66}K^{67}N^{68}V^{69}K^{70}$
(SEQ ID NO: 24)

(10) $K^{24}Q^{25}L^{26}L^{27}H^{28}L^{29}K^{30}$
(SEQ ID NO: 10)

(11) $K^{24}Q^{25}L^{26}L^{27}H^{28}L^{29}K^{30}V^{31}H^{32}$
(SEQ ID NO: 25)

(12) $K^{24}Q^{25}L^{26}L^{27}H^{28}L^{29}K^{30}V^{31}H^{32}L^{33}D^{34}V^{35}K^{36}G^{37}V^{38}K^{39}Q^{40}L^{41}L^{42}H^{43}$
(SEQ ID NO: 26)

(13) $H^{28}L^{29}K^{30}V^{31}H^{32}L^{33}D^{34}V^{35}K^{36}$
(SEQ ID NO: 27)

(14) $H^{28}L^{29}K^{30}V^{31}H^{32}L^{33}D^{34}V^{35}K^{36}G^{37}V^{38}K^{39}$
(SEQ ID NO: 28)

(15) $H^{28}L^{29}K^{30}V^{31}H^{32}L^{33}D^{34}V^{35}K^{36}G^{37}V^{38}K^{39}Q^{40}L^{41}L^{42}H^{43}L^{44}K^{45}$
(SEQ ID NO: 29)

(16) $H^{28}L^{29}K^{30}V^{31}H^{32}L^{33}D^{34}V^{35}K^{36}G^{37}V^{38}K^{39}Q^{40}L^{41}L^{42}H^{43}L^{44}K^{45}V^{46}R^{47}L^{48}D^{49}V^{50}R^{51}G^{52}A^{53}K^{54}$
(SEQ ID NO: 30)

(17) $H^{28}L^{29}K^{30}V^{31}H^{32}L^{33}D^{34}V^{35}K^{36}G^{37}V^{38}K^{39}Q^{40}L^{41}L^{42}H^{43}L^{44}K^{45}V^{46}R^{47}L^{48}D^{49}V^{50}R^{51}G^{52}A^{53}K^{54}Q^{55}N^{56}P^{57}$
$W^{58}R^{59}K^{60}$
(SEQ ID NO: 31)

(18) $H^{28}L^{29}K^{30}V^{31}H^{32}L^{33}D^{34}V^{35}K^{36}G^{37}V^{38}K^{39}Q^{40}L^{41}L^{42}H^{43}L^{44}K^{45}V^{46}R^{47}L^{48}D^{49}V^{50}R^{51}G^{52}A^{53}K^{54}Q^{55}N^{56}P^{57}$
$W^{58}R^{59}K^{60}N^{61}L^{62}C^{63}L^{64}L^{65}K^{66}$
(SEQ ID NO: 32)

(19) $H^{28}L^{29}K^{30}V^{31}H^{32}L^{33}D^{34}V^{35}K^{36}G^{37}V^{38}K^{39}Q^{40}L^{41}L^{42}H^{43}L^{44}K^{45}V^{46}R^{47}L^{48}D^{49}V^{50}R^{51}G^{52}A^{53}K^{54}Q^{55}N^{56}P^{57}$
$W^{58}R^{59}K^{60}N^{61}L^{62}C^{63}L^{64}L^{65}K^{66}K^{67}$
(SEQ ID NO: 33)

(20) $H^{28}L^{29}K^{30}V^{31}H^{32}L^{33}D^{34}V^{35}K^{36}G^{37}V^{38}K^{39}Q^{40}L^{41}L^{42}H^{43}L^{44}K^{45}V^{46}R^{47}L^{48}D^{49}V^{50}R^{51}G^{52}A^{53}K^{54}Q^{55}N^{56}P^{57}$
$W^{58}R^{59}K^{60}N^{61}L^{62}C^{63}L^{64}L^{65}K^{66}K^{67}N^{68}V^{69}K^{70}$
(SEQ ID NO: 34)

-continued

(21) $H^{28}L^{29}K^{30}V^{31}H^{32}L^{33}D^{34}V^{35}K^{36}G^{37}V^{38}K^{39}Q^{40}L^{41}L^{42}H^{43}L^{44}K^{45}V^{46}R^{47}L^{48}D^{49}V^{50}R^{51}G^{52}A^{53}K^{54}Q^{55}N^{56}P^{57}$
$W^{58}R^{59}K^{60}N^{61}L^{62}C^{63}L^{64}L^{65}K^{66}K^{67}N^{68}V^{69}K^{70}S^{71}A^{72}K^{73}$
(SEQ ID NO: 35)

(22) $K^{30}V^{31}H^{32}L^{33}D^{34}V^{35}K^{36}G^{37}V^{38}K^{39}Q^{40}L^{41}L^{42}H^{43}L^{44}K^{45}V^{46}R^{47}L^{48}D^{49}V^{50}R^{51}G^{52}A^{53}K^{54}Q^{55}N^{56}P^{57}W^{58}R^{59}$
$K^{60}N^{61}L^{62}C^{63}L^{64}L^{65}K^{66}K^{67}N^{68}V^{69}K^{70}S^{71}A^{72}K^{73}Q^{74}L^{75}P^{76}H^{77}$
(SEQ ID NO: 36)

(23) $K^{30}V^{31}H^{32}L^{33}D^{34}V^{35}K^{36}$
(SEQ ID NO: 11)

(24) $K^{30}V^{31}H^{32}L^{33}D^{34}V^{35}K^{36}G^{37}V^{38}K^{39}$
(SEQ ID NO: 37)

(25) $K^{30}V^{31}H^{32}L^{33}D^{34}V^{35}K^{36}G^{37}V^{38}K^{39}Q^{40}L^{41}L^{42}H^{43}$
(SEQ ID NO: 12)

(26) $H^{32}L^{33}D^{34}V^{35}K^{36}G^{37}V^{38}K^{39}Q^{40}L^{41}L^{42}H^{43}L^{44}K^{45}$
(SEQ ID NO: 38)

(27) $H^{32}L^{33}D^{34}V^{35}K^{36}G^{37}V^{38}K^{39}Q^{40}L^{41}L^{42}H^{43}L^{44}K^{45}V^{46}R^{47}L^{48}D^{49}V^{50}R^{51}G^{52}A^{53}K^{54}$
(SEQ ID NO: 39)

(28) $H^{32}L^{33}D^{34}V^{35}K^{36}G^{37}V^{38}K^{39}Q^{40}L^{41}L^{42}H^{43}L^{44}K^{45}V^{46}R^{47}L^{48}D^{49}V^{50}R^{51}G^{52}A^{53}K^{54}Q^{55}N^{56}P^{57}W^{58}R^{59}K^{60}$
(SEQ ID NO: 40)

(29) $H^{32}L^{33}D^{34}V^{35}K^{36}G^{37}V^{38}K^{39}Q^{40}L^{41}L^{42}H^{43}L^{44}K^{45}V^{46}R^{47}L^{48}D^{49}V^{50}R^{51}G^{52}A^{53}K^{54}Q^{55}N^{56}P^{57}W^{58}R^{59}K^{60}N^{61}$
$L^{62}C^{63}L^{64}L^{65}K^{66}$
(SEQ ID NO: 41)

(30) $H^{32}L^{33}D^{34}V^{35}K^{36}G^{37}V^{38}K^{39}Q^{40}L^{41}L^{42}H^{43}L^{44}K^{45}V^{46}R^{47}L^{48}D^{49}V^{50}R^{51}G^{52}A^{53}K^{54}Q^{55}N^{56}P^{57}W^{58}R^{59}K^{60}N^{61}$
$L^{62}C^{63}L^{64}L^{65}K^{66}K^{67}$
(SEQ ID NO: 42)

(31) $H^{32}L^{33}D^{34}V^{35}K^{36}G^{37}V^{38}K^{39}Q^{40}L^{41}L^{42}H^{43}L^{44}K^{45}V^{46}R^{47}L^{48}D^{49}V^{50}R^{51}G^{52}A^{53}K^{54}Q^{55}N^{56}P^{57}W^{58}R^{59}K^{60}N^{61}$
$L^{62}C^{63}L^{64}L^{65}K^{66}K^{67}N^{68}V^{69}K^{70}$
(SEQ ID NO: 43)

(32) $H^{32}L^{33}D^{34}V^{35}K^{36}G^{37}V^{38}K^{39}Q^{40}L^{41}L^{42}H^{43}L^{44}K^{45}V^{46}R^{47}L^{48}D^{49}V^{50}R^{51}G^{52}A^{53}K^{54}Q^{55}N^{56}P^{57}W^{58}R^{59}K^{60}N^{61}$
$L^{62}C^{63}L^{64}L^{65}K^{66}K^{67}N^{68}V^{69}K^{70}S^{71}A^{72}K^{73}$
(SEQ ID NO: 44)

(33) $H^{32}L^{33}D^{34}V^{35}K^{36}G^{37}V^{38}K^{39}Q^{40}L^{41}L^{42}H^{43}L^{44}K^{45}V^{46}R^{47}L^{48}D^{49}V^{50}R^{51}G^{52}A^{53}K^{54}Q^{55}N^{56}P^{57}W^{58}R^{59}K^{60}N^{61}$
$L^{62}C^{63}L^{64}L^{65}K^{66}K^{67}N^{68}V^{69}K^{70}S^{71}A^{72}K^{73}Q^{74}L^{75}P^{76}H^{77}L^{78}K^{79}$
(SEQ ID NO: 45)

(34) $K^{36}G^{37}V^{38}K^{39}Q^{40}L^{41}L^{42}H^{43}L^{44}K^{45}$
(SEQ ID NO: 46)

(35) $K^{36}G^{37}V^{38}K^{39}Q^{40}L^{41}L^{42}H^{43}L^{44}K^{45}V^{46}R^{47}L^{48}D^{49}V^{50}R^{51}G^{52}A^{53}K^{54}Q^{55}N^{56}P^{57}W^{58}R^{59}K^{60}N^{61}L^{62}C^{63}L^{64}L^{65}$
$K^{66}K^{67}N^{68}V^{69}K^{70}S^{71}A^{72}K^{73}Q^{74}L^{75}P^{76}H^{77}$
(SEQ ID NO: 47)

(36) $K^{36}G^{37}V^{38}K^{39}Q^{40}L^{41}L^{42}H^{43}L^{44}K^{45}V^{46}R^{47}L^{48}D^{49}V^{50}R^{51}G^{52}A^{53}K^{54}Q^{55}N^{56}P^{57}W^{58}R^{59}K^{60}N^{61}L^{62}C^{63}L^{64}L^{65}$
$K^{66}K^{67}N^{68}V^{69}K^{70}S^{71}A^{72}K^{73}Q^{74}L^{75}P^{76}H^{77}L^{78}K^{79}V^{80}H^{81}$
(SEQ ID NO: 48)

(37) $K^{39}Q^{40}L^{41}L^{42}H^{43}L^{44}K^{45}$
(SEQ ID NO: 10)

(38) $K^{39}Q^{40}L^{41}L^{42}H^{43}L^{44}K^{45}V^{46}R^{47}L^{48}D^{49}V^{50}R^{51}G^{52}A^{53}K^{54}Q^{55}N^{56}P^{57}W^{58}R^{59}K^{60}N^{61}L^{62}C^{63}L^{64}L^{65}K^{66}K^{67}N^{68}$
$V^{69}K^{70}S^{71}A^{72}K^{73}Q^{74}L^{75}P^{76}H^{77}$
(SEQ ID NO: 49)

(39) $K^{39}Q^{40}L^{41}L^{42}H^{43}L^{44}K^{45}V^{46}R^{47}L^{48}D^{49}V^{50}R^{51}G^{52}A^{53}K^{54}Q^{55}N^{56}P^{57}W^{58}R^{59}K^{60}N^{61}L^{62}C^{63}L^{64}L^{65}K^{66}K^{67}N^{68}$
$V^{69}K^{70}S^{71}A^{72}K^{73}Q^{74}L^{75}P^{76}H^{77}L^{78}K^{79}V^{80}H^{81}$
(SEQ ID NO: 50)

(40) $H^{43}L^{44}K^{45}V^{46}R^{47}L^{48}D^{49}V^{50}R^{51}G^{52}A^{53}K^{54}$
(SEQ ID NO: 51)

(41) $H^{43}L^{44}K^{45}V^{46}R^{47}L^{48}D^{49}V^{50}R^{51}G^{52}A^{53}K^{54}Q^{55}N^{56}P^{57}W^{58}R^{59}K^{60}$
(SEQ ID NO: 52)

(42) $H^{43}L^{44}K^{45}V^{46}R^{47}L^{48}D^{49}V^{50}R^{51}G^{52}A^{53}K^{54}Q^{55}N^{56}P^{57}W^{58}R^{59}K^{60}N^{61}L^{62}C^{63}L^{64}L^{65}K^{66}$
(SEQ ID NO: 53)

(43) $H^{43}L^{44}K^{45}V^{46}R^{47}L^{48}D^{49}V^{50}R^{51}G^{52}A^{53}K^{54}Q^{55}N^{56}P^{57}W^{58}R^{59}K^{60}N^{61}L^{62}C^{63}L^{64}L^{65}K^{66}K^{67}$
(SEQ ID NO: 54)

-continued

(44) $H^{43}L^{44}K^{45}V^{46}R^{47}L^{48}D^{49}V^{50}R^{51}G^{52}A^{53}K^{54}Q^{55}N^{56}P^{57}W^{58}R^{59}K^{60}N^{61}L^{62}C^{63}L^{64}L^{65}K^{66}K^{67}N^{68}V^{69}K^{70}$
(SEQ ID NO: 55)

(45) $H^{43}L^{44}K^{45}V^{46}R^{47}L^{48}D^{49}V^{50}R^{51}G^{52}A^{53}K^{54}Q^{55}N^{56}P^{57}W^{58}R^{59}K^{60}N^{61}L^{62}C^{63}L^{64}L^{65}K^{66}K^{67}N^{68}V^{69}K^{70}S^{71}A^{72}K^{73}$
(SEQ ID NO: 56)

(46) $H^{43}L^{44}K^{45}V^{46}R^{47}L^{48}D^{49}V^{50}R^{51}G^{52}A^{53}K^{54}Q^{55}N^{56}P^{57}W^{58}R^{59}K^{60}N^{61}L^{62}C^{63}L^{64}L^{65}K^{66}K^{67}N^{68}V^{69}K^{70}S^{71}A^{72}$
$K^{73}Q^{74}L^{75}P^{76}H^{77}L^{78}K^{79}$
(SEQ ID NO: 57)

(47) $H^{43}L^{44}K^{45}V^{46}R^{47}L^{48}D^{49}V^{50}R^{51}G^{52}A^{53}K^{54}Q^{55}N^{56}P^{57}W^{58}R^{59}K^{60}N^{61}L^{62}C^{63}L^{64}L^{65}K^{66}K^{67}N^{68}V^{69}K^{70}S^{71}A^{72}$
$K^{73}Q^{74}L^{75}P^{76}H^{77}L^{78}K^{79}V^{80}H^{81}L^{82}D^{83}V^{84}K^{85}$
(SEQ ID NO: 58)

(48) $H^{43}L^{44}K^{45}V^{46}R^{47}L^{48}D^{49}V^{50}R^{51}G^{52}A^{53}K^{54}Q^{55}N^{56}P^{57}W^{58}R^{59}K^{60}N^{61}L^{62}C^{63}L^{64}L^{65}K^{66}K^{67}N^{68}V^{69}K^{70}S^{71}A^{72}$
$K^{73}Q^{74}L^{75}P^{76}H^{77}L^{78}K^{79}V^{80}H^{81}L^{82}D^{83}V^{84}K^{85}S^{86}A^{87}K^{88}$
(SEQ ID NO: 59)

(49) $K^{45}V^{46}R^{47}L^{48}D^{49}V^{50}R^{51}G^{52}A^{53}K^{54}Q^{55}N^{56}P^{57}W^{58}R^{59}K^{60}N^{61}L^{62}C^{63}L^{64}L^{65}K^{66}K^{67}N^{68}V^{69}K^{70}S^{71}A^{72}K^{73}Q^{74}$
$L^{75}P^{76}H^{77}$
(SEQ ID NO: 60)

(50) $K^{45}V^{46}R^{47}L^{48}D^{49}V^{50}R^{51}G^{52}A^{53}K^{54}Q^{55}N^{56}P^{57}W^{58}R^{59}K^{60}N^{61}L^{62}C^{63}L^{64}L^{65}K^{66}K^{67}N^{68}V^{69}K^{70}S^{71}A^{72}K^{73}$
$Q^{74}L^{75}P^{76}H^{77}L^{78}K^{79}V^{80}H^{81}$
(SEQ ID NO: 61)

(51) $K^{45}V^{46}R^{47}L^{48}D^{49}V^{50}R^{51}G^{52}A^{53}K^{54}Q^{55}N^{56}P^{57}W^{58}R^{59}K^{60}N^{61}L^{62}C^{63}L^{64}L^{65}K^{66}K^{67}N^{68}V^{69}K^{70}S^{71}A^{72}K^{73}Q^{74}$
$L^{75}P^{76}H^{77}L^{78}K^{79}V^{80}H^{81}L^{82}D^{83}V^{84}K^{85}S^{86}A^{87}K^{88}Q^{89}L^{90}P^{91}H^{92}$
(SEQ ID NO: 62)

(52) $K^{54}Q^{55}N^{56}P^{57}W^{58}R^{59}K^{60}N^{61}L^{62}C^{63}L^{64}L^{65}K^{66}K^{67}N^{68}V^{69}K^{70}S^{71}A^{72}K^{73}Q^{74}L^{75}P^{76}H^{77}$
(SEQ ID NO: 63)

(53) $K^{54}Q^{55}N^{56}P^{57}W^{58}R^{59}K^{60}N^{61}L^{62}C^{63}L^{64}L^{65}K^{66}K^{67}N^{68}V^{69}K^{70}S^{71}A^{72}K^{73}Q^{74}L^{75}P^{76}H^{77}L^{78}K^{79}V^{80}H^{81}$
(SEQ ID NO: 64)

(54) $K^{54}Q^{55}N^{56}P^{57}W^{58}R^{59}K^{60}N^{61}L^{62}C^{63}L^{64}L^{65}K^{66}K^{67}N^{68}V^{69}K^{70}S^{71}A^{72}K^{73}Q^{74}L^{75}P^{76}H^{77}L^{78}K^{79}V^{80}H^{81}L^{82}D^{83}V^{84}K^{85}$
$S^{86}A^{87}K^{88}Q^{89}L^{90}P^{91}H^{92}$
(SEQ ID NO: 65)

(55) $K^{54}Q^{55}N^{56}P^{57}W^{58}R^{59}K^{60}N^{61}L^{62}C^{63}L^{64}L^{65}K^{66}K^{67}N^{68}V^{69}K^{70}S^{71}A^{72}K^{73}Q^{74}L^{75}P^{76}H^{77}L^{78}K^{79}V^{80}H^{81}L^{82}D^{83}V^{84}K^{85}$
$S^{86}A^{87}K^{88}Q^{89}L^{90}P^{91}H^{92}L^{93}K^{94}V^{95}H^{96}$
(SEQ ID NO: 66)

(56) $K^{60}N^{61}L^{62}C^{63}L^{64}L^{65}K^{66}K^{67}N^{68}V^{69}K^{70}S^{71}A^{72}K^{73}Q^{74}L^{75}P^{76}H^{77}L^{78}K^{79}V^{80}H^{81}L^{82}D^{83}V^{84}K^{85}S^{86}A^{87}K^{88}Q^{89}L^{90}P^{91}$
$H^{92}L^{93}K^{94}V^{95}H^{96}L^{97}D^{98}V^{99}R^{100}G^{101}A^{102}K^{103}Q^{104}L^{105}P^{106}H^{107}$
(SEQ ID NO: 67)

(57) $K^{60}N^{61}L^{62}C^{63}L^{64}L^{65}K^{66}K^{67}N^{68}V^{69}K^{70}S^{71}A^{72}K^{73}Q^{74}L^{75}P^{76}H^{77}$
(SEQ ID NO: 68)

(58) $K^{60}N^{61}L^{62}C^{63}L^{64}L^{65}K^{66}K^{67}N^{68}V^{69}K^{70}S^{71}A^{72}K^{73}Q^{74}L^{75}P^{76}H^{77}L^{78}K^{79}V^{80}H^{81}$
(SEQ ID NO: 69)

(59) $K^{60}N^{61}L^{62}C^{63}L^{64}L^{65}K^{66}K^{67}N^{68}V^{69}K^{70}S^{71}A^{72}K^{73}Q^{74}L^{75}P^{76}H^{77}L^{78}K^{79}V^{80}H^{81}L^{82}D^{83}V^{84}K^{85}S^{86}A^{87}K^{88}Q^{89}L^{90}P^{91}$
$H^{92}$
(SEQ ID NO: 70)

(60) $K^{60}N^{61}L^{62}C^{63}L^{64}L^{65}K^{66}K^{67}N^{68}V^{69}K^{70}S^{71}A^{72}K^{73}Q^{74}L^{75}P^{76}H^{77}L^{78}K^{79}V^{80}H^{81}L^{82}D^{83}V^{84}K^{85}S^{86}A^{87}K^{88}Q^{89}L^{90}P^{91}$
$H^{92}L^{93}K^{94}V^{95}H^{96}$
(SEQ ID NO: 71)

(61) $K^{66}K^{67}N^{68}V^{69}K^{70}S^{71}A^{72}K^{73}Q^{74}L^{75}P^{76}H^{77}$
(SEQ ID NO: 13)

(62) $K^{66}K^{67}N^{68}V^{69}K^{70}S^{71}A^{72}K^{73}Q^{74}L^{75}P^{76}H^{77}L^{78}K^{79}V^{80}H^{81}$
(SEQ ID NO: 72)

(63) $K^{66}K^{67}N^{68}V^{69}K^{70}S^{71}A^{72}K^{73}Q^{74}L^{75}P^{76}H^{77}L^{78}K^{79}V^{80}H^{81}L^{82}D^{83}V^{84}K^{85}S^{86}A^{87}K^{88}Q^{89}L^{90}P^{91}H^{92}$
(SEQ ID NO: 73)

(64) $K^{66}K^{67}N^{68}V^{69}K^{70}S^{71}A^{72}K^{73}Q^{74}L^{75}P^{76}H^{77}L^{78}K^{79}V^{80}H^{81}L^{82}D^{83}V^{84}K^{85}S^{86}A^{87}K^{88}Q^{89}L^{90}P^{91}H^{92}L^{93}K^{94}V^{95}H^{96}$
(SEQ ID NO: 1)

(65) $K^{66}K^{67}N^{68}V^{69}K^{70}S^{71}A^{72}K^{73}Q^{74}L^{75}P^{76}H^{77}L^{78}K^{79}V^{80}H^{81}L^{82}D^{83}V^{84}K^{85}S^{86}A^{87}K^{88}Q^{89}L^{90}P^{91}H^{92}L^{93}K^{94}V^{95}H^{96}L^{97}$
$D^{98}V^{99}R^{100}G^{101}A^{102}K^{103}Q^{104}L^{105}P^{106}H^{107}$
(SEQ ID NO: 74)

(66) $K^{67}N^{68}V^{69}K^{70}S^{71}A^{72}K^{73}Q^{74}L^{75}P^{76}H^{77}$
(SEQ ID NO: 75)

-continued

(67) $K^{67}N^{68}V^{69}K^{70}S^{71}A^{72}K^{73}Q^{74}L^{75}P^{76}H^{77}L^{78}K^{79}V^{80}H^{81}$
(SEQ ID NO: 76)

(68) $K^{67}N^{68}V^{69}K^{70}S^{71}A^{72}K^{73}Q^{74}L^{75}P^{76}H^{77}L^{78}K^{79}V^{80}H^{81}L^{82}D^{83}V^{84}K^{85}S^{86}A^{87}K^{88}Q^{89}L^{90}P^{91}H^{92}$
(SEQ ID NO: 77)

(69) $K^{67}N^{68}V^{69}K^{70}S^{71}A^{72}K^{73}Q^{74}L^{75}P^{76}H^{77}L^{78}K^{79}V^{80}H^{81}L^{82}D^{83}V^{84}K^{85}S^{86}A^{87}K^{88}Q^{89}L^{90}P^{91}H^{92}L^{93}K^{94}V^{95}H^{96}$
(SEQ ID NO: 78)

(70) $K^{67}N^{68}V^{69}K^{70}S^{71}A^{72}K^{73}Q^{74}L^{75}P^{76}H^{77}L^{78}K^{79}V^{80}H^{81}L^{82}D^{83}V^{84}K^{85}S^{86}A^{87}K^{88}Q^{89}L^{90}P^{91}H^{92}L^{93}K^{94}V^{95}H^{96}L^{97}D^{98}$
$V^{99}R^{100}G^{101}A^{102}K^{103}Q^{104}L^{105}P^{106}H^{107}$
(SEQ ID NO: 79)

(71) $K^{70}S^{71}A^{72}K^{73}Q^{74}L^{75}P^{76}H^{77}L^{78}K^{79}V^{80}H^{81}L^{82}D^{83}V^{84}K^{85}S^{86}A^{87}K^{88}Q^{89}L^{90}P^{91}H^{92}L^{93}K^{94}V^{95}H^{96}L^{97}D^{98}V^{99}R^{100}$
$G^{101}A^{102}K^{103}Q^{104}L^{105}P^{106}H^{107}$
(SEQ ID NO: 80)

(72) $K^{70}S^{71}A^{72}K^{73}Q^{74}L^{75}P^{76}H^{77}L^{78}K^{79}$
(SEQ ID NO: 14)

(73) $K^{70}S^{71}A^{72}K^{73}Q^{74}L^{75}P^{76}H^{77}L^{78}K^{79}V^{80}H^{81}$
(SEQ ID NO: 81)

(74) $K^{70}S^{71}A^{72}K^{73}Q^{74}L^{75}P^{76}H^{77}L^{78}K^{79}V^{80}H^{81}L^{82}D^{83}V^{84}K^{85}S^{86}A^{87}K^{88}Q^{89}L^{90}P^{91}H^{92}$
(SEQ ID NO: 82)

(75) $K^{70}S^{71}A^{72}K^{73}Q^{74}L^{75}P^{76}H^{77}L^{78}K^{79}V^{80}H^{81}L^{82}D^{83}V^{84}K^{85}S^{86}A^{87}K^{88}Q^{89}L^{90}P^{91}H^{92}L^{93}K^{94}V^{95}H^{96}$
(SEQ ID NO: 83)

(76) $K^{73}Q^{74}L^{75}P^{76}H^{77}L^{78}K^{79}$
(SEQ ID NO: 84)

(77) $K^{73}Q^{74}L^{75}P^{76}H^{77}L^{78}K^{79}V^{80}H^{81}$
(SEQ ID NO: 85)

(78) $K^{73}Q^{74}L^{75}P^{76}H^{77}L^{78}K^{79}V^{80}H^{81}L^{82}D^{83}V^{84}K^{85}S^{86}A^{87}K^{88}Q^{89}L^{90}P^{91}H^{92}L^{93}K^{94}V^{95}H^{96}L^{97}D^{98}V^{99}R^{100}G^{101}A^{102}$
$K^{103}Q^{104}L^{105}P^{106}H^{107}$
(SEQ ID NO: 86)

(79) $K^{73}Q^{74}L^{75}P^{76}H^{77}L^{78}K^{79}V^{80}H^{81}L^{82}D^{83}V^{84}K^{85}S^{86}A^{87}K^{88}Q^{89}L^{90}P^{91}H^{92}$
(SEQ ID NO: 87)

(80) $K^{73}Q^{74}L^{75}P^{76}H^{77}L^{78}K^{79}V^{80}H^{81}L^{82}D^{83}V^{84}K^{85}S^{86}A^{87}K^{88}Q^{89}L^{90}P^{91}H^{92}L^{93}K^{94}V^{95}H^{96}$
(SEQ ID NO: 88)

(81) $K^{73}Q^{74}L^{75}P^{76}H^{77}L^{78}K^{79}V^{80}H^{81}L^{82}D^{83}V^{84}K^{85}S^{86}A^{87}K^{88}Q^{89}L^{90}P^{91}H^{92}L^{93}K^{94}V^{95}H^{96}L^{97}D^{98}V^{99}R^{100}G^{101}A^{102}$
$K^{103}Q^{104}L^{105}P^{106}H^{107}L^{108}K^{109}V^{110}R^{111}L^{112}D^{113}V^{114}K^{115}S^{116}A^{117}K^{118}Q^{119}L^{120}P^{121}H^{122}$
(SEQ ID NO: 89)

(82) $H^{77}L^{78}K^{79}V^{80}H^{81}L^{82}D^{83}V^{84}K^{85}$
(SEQ ID NO: 27)

(83) $H^{77}L^{78}K^{79}V^{80}H^{81}L^{82}D^{83}V^{84}K^{85}S^{86}A^{87}K^{88}$
(SEQ ID NO: 90)

(84) $H^{77}L^{78}K^{79}V^{80}H^{81}L^{82}D^{83}V^{84}K^{85}S^{86}A^{87}K^{88}Q^{89}L^{90}P^{91}H^{92}L^{93}K^{94}$
(SEQ ID NO: 91)

(85) $H^{77}L^{78}K^{79}V^{80}H^{81}L^{82}D^{83}V^{84}K^{85}S^{86}A^{87}K^{88}Q^{89}L^{90}P^{91}H^{92}L^{93}K^{94}V^{95}H^{96}L^{97}D^{98}V^{99}R^{100}G^{101}A^{102}K^{103}$
(SEQ ID NO: 92)

(86) $H^{77}L^{78}K^{79}V^{80}H^{81}L^{82}D^{83}V^{84}K^{85}S^{86}A^{87}K^{88}Q^{89}L^{90}P^{91}H^{92}L^{93}K^{94}V^{95}H^{96}L^{97}D^{98}V^{99}R^{100}G^{101}A^{102}K^{103}Q^{104}L^{105}$
$P^{106}H^{107}L^{108}K^{109}$
(SEQ ID NO: 93)

(87) $H^{77}L^{78}K^{79}V^{80}H^{81}L^{82}D^{83}V^{84}K^{85}S^{86}A^{87}K^{88}Q^{89}L^{90}P^{91}H^{92}L^{93}K^{94}V^{95}H^{96}L^{97}D^{98}V^{99}R^{100}G^{101}A^{102}K^{103}Q^{104}L^{105}$
$P^{106}H^{107}L^{108}K^{109}V^{110}R^{111}L^{112}D^{113}V^{114}K^{115}$
(SEQ ID NO: 94)

(88) $H^{77}L^{78}K^{79}V^{80}H^{81}L^{82}D^{83}V^{84}K^{85}S^{86}A^{87}K^{88}Q^{89}L^{90}P^{91}H^{92}L^{93}K^{94}V^{95}H^{96}L^{97}D^{98}V^{99}R^{100}G^{101}A^{102}K^{103}Q^{104}L^{105}$
$P^{106}H^{107}L^{108}K^{109}V^{110}R^{111}L^{112}D^{113}V^{114}K^{115}S^{116}A^{117}K^{118}$
(SEQ ID NO: 95)

(89) $H^{77}L^{78}K^{79}V^{80}H^{81}L^{82}D^{83}V^{84}K^{85}S^{86}A^{87}K^{88}Q^{89}L^{90}P^{91}H^{92}L^{93}K^{94}V^{95}H^{96}L^{97}D^{98}V^{99}R^{100}G^{101}A^{102}K^{103}Q^{104}L^{105}$
$P^{106}H^{107}L^{108}K^{109}V^{110}R^{111}L^{112}D^{113}V^{114}K^{115}S^{116}A^{117}K^{118}Q^{119}L^{120}P^{121}H^{122}L^{123}K^{124}$
(SEQ ID NO: 96)

(90) $K^{79}V^{80}H^{81}L^{82}D^{83}V^{84}K^{85}S^{86}A^{87}K^{88}Q^{89}L^{90}P^{91}H^{92}L^{93}K^{94}V^{95}H^{96}L^{97}D^{98}V^{99}R^{100}G^{101}A^{102}K^{103}Q^{104}L^{105}P^{106}H^{107}$
(SEQ ID NO: 97)

-continued

(91) $K^{79}V^{80}H^{81}L^{82}D^{83}V^{84}K^{85}S^{86}A^{87}K^{88}Q^{89}L^{90}P^{91}H^{92}L^{93}K^{94}V^{95}H^{96}L^{97}D^{98}V^{99}R^{100}G^{101}A^{102}K^{103}Q^{104}L^{105}P^{106}H^{107}$
$L^{108}K^{109}V^{110}R^{111}L^{112}D^{113}V^{114}K^{115}S^{116}A^{117}K^{118}Q^{119}L^{120}P^{121}H^{122}$
(SEQ ID NO: 98)

(92) $K^{79}V^{80}H^{81}L^{82}D^{83}V^{84}K^{85}S^{86}A^{87}K^{88}Q^{89}L^{90}P^{91}H^{92}L^{93}K^{94}V^{95}H^{96}L^{97}D^{98}V^{99}R^{100}G^{101}A^{102}K^{103}Q^{104}L^{105}P^{106}H^{107}$
$L^{108}K^{109}V^{110}R^{111}L^{112}D^{113}V^{114}K^{115}S^{116}A^{117}K^{118}Q^{119}L^{120}P^{121}H^{122}L^{123}K^{124}V^{125}H^{126}$
(SEQ ID NO: 99)

(93) $K^{79}V^{80}H^{81}L^{82}D^{83}V^{84}K^{85}$
(SEQ ID NO: 11)

(94) $K^{79}V^{80}H^{81}L^{82}D^{83}V^{84}K^{85}S^{86}A^{87}K^{88}$
(SEQ ID NO: 100)

(95) $K^{79}V^{80}H^{81}L^{82}D^{83}V^{84}K^{85}S^{86}A^{87}K^{88}Q^{89}L^{90}P^{91}H^{92}$
(SEQ ID NO: 101)

(96) $K^{79}V^{80}H^{81}L^{82}D^{83}V^{84}K^{85}S^{86}A^{87}K^{88}Q^{89}L^{90}P^{91}H^{92}L^{93}K^{94}V^{95}H^{96}$
(SEQ ID NO: 102)

(97) $H^{81}L^{82}D^{83}V^{84}K^{85}S^{86}A^{87}K^{88}Q^{89}L^{90}P^{91}H^{92}L^{93}K^{94}$
(SEQ ID NO: 103)

(98) $H^{81}L^{82}D^{83}V^{84}K^{85}S^{86}A^{87}K^{88}Q^{89}L^{90}P^{91}H^{92}L^{93}K^{94}V^{95}H^{96}L^{97}D^{98}V^{99}R^{100}G^{101}A^{102}K^{103}$
(SEQ ID NO: 104)

(99) $H^{81}L^{82}D^{83}V^{84}K^{85}S^{86}A^{87}K^{88}Q^{89}L^{90}P^{91}H^{92}L^{93}K^{94}V^{95}H^{96}L^{97}D^{98}V^{99}R^{100}G^{101}A^{102}K^{103}Q^{104}L^{105}P^{106}H^{107}L^{108}$
$K^{109}$
(SEQ ID NO: 105)

(100) $H^{81}L^{82}D^{83}V^{84}K^{85}S^{86}A^{87}K^{88}Q^{89}L^{90}P^{91}H^{92}L^{93}K^{94}V^{95}H^{96}L^{97}D^{98}V^{99}R^{100}G^{101}A^{102}K^{103}Q^{104}L^{105}P^{106}H^{107}L^{108}$
$K^{109}V^{110}R^{111}L^{112}D^{113}V^{114}K^{115}$
(SEQ ID NO: 106)

(101) $H^{81}L^{82}D^{83}V^{84}K^{85}S^{86}A^{87}K^{88}Q^{89}L^{90}P^{91}H^{92}L^{93}K^{94}V^{95}H^{96}L^{97}D^{98}V^{99}R^{100}G^{101}A^{102}K^{103}Q^{104}L^{105}P^{106}H^{107}L^{108}$
$K^{109}V^{110}R^{111}L^{112}D^{113}V^{114}K^{115}S^{116}A^{117}K^{118}$
(SEQ ID NO: 107)

(102) $H^{81}L^{82}D^{83}V^{84}K^{85}S^{86}A^{87}K^{88}Q^{89}L^{90}P^{91}H^{92}L^{93}K^{94}V^{95}H^{96}L^{97}D^{98}V^{99}R^{100}G^{101}A^{102}K^{103}Q^{104}L^{105}P^{106}H^{107}L^{108}$
$K^{109}V^{110}R^{111}L^{112}D^{113}V^{114}K^{115}S^{116}A^{117}K^{118}Q^{119}L^{120}P^{121}H^{122}L^{123}K^{124}$
(SEQ ID NO: 108)

(103) $K^{85}S^{86}A^{87}K^{88}Q^{89}L^{90}P^{91}H^{92}L^{93}K^{94}V^{95}H^{96}L^{97}D^{98}V^{99}R^{100}G^{101}A^{102}K^{103}Q^{104}L^{105}P^{106}H^{107}$
(SEQ ID NO: 109)

(104) $K^{85}S^{86}A^{87}K^{88}Q^{89}L^{90}P^{91}H^{92}L^{93}K^{94}V^{95}H^{96}L^{97}D^{98}V^{99}R^{100}G^{101}A^{102}K^{103}Q^{104}L^{105}P^{106}H^{107}L^{108}K^{109}V^{110}R^{111}$
$L^{112}D^{113}V^{114}K^{115}S^{116}A^{117}K^{118}Q^{119}L^{120}P^{121}H^{122}$
(SEQ ID NO: 110)

(105) $K^{85}S^{86}A^{87}K^{88}Q^{89}L^{90}P^{91}H^{92}L^{93}K^{94}V^{95}H^{96}L^{97}D^{98}V^{99}R^{100}G^{101}A^{102}K^{103}Q^{104}L^{105}P^{106}H^{107}L^{108}K^{109}V^{110}R^{111}$
$L^{112}D^{113}V^{114}K^{115}S^{116}A^{117}K^{118}Q^{119}L^{120}P^{121}H^{122}L^{123}K^{124}V^{125}H^{126}$
(SEQ ID NO: 111)

(106) $K^{85}S^{86}A^{87}K^{88}Q^{89}L^{90}P^{91}H^{92}L^{93}K^{94}$
(SEQ ID NO: 14)

(107) $K^{85}S^{86}A^{87}K^{88}Q^{89}L^{90}P^{91}H^{92}L^{93}K^{94}V^{95}H^{96}$
(SEQ ID NO: 81)

(108) $K^{88}Q^{89}L^{90}P^{91}H^{92}L^{93}K^{94}V^{95}H^{96}L^{97}D^{98}V^{99}R^{100}G^{101}A^{102}K^{103}Q^{104}L^{105}P^{106}H^{107}$
(SEQ ID NO: 112)

(109) $K^{88}Q^{89}L^{90}P^{91}H^{92}L^{93}K^{94}V^{95}H^{96}L^{97}D^{98}V^{99}R^{100}G^{101}A^{102}K^{103}Q^{104}L^{105}P^{106}H^{107}L^{108}K^{109}V^{110}R^{111}L^{112}D^{113}V^{114}$
$K^{115}S^{116}A^{117}K^{118}Q^{119}L^{120}P^{121}H^{122}$
(SEQ ID NO: 113)

(110) $K^{88}Q^{89}L^{90}P^{91}H^{92}L^{93}K^{94}V^{95}H^{96}L^{97}D^{98}V^{99}R^{100}G^{101}A^{102}K^{103}Q^{104}L^{105}P^{106}H^{107}L^{108}K^{109}V^{110}R^{111}L^{112}D^{113}V^{114}$
$K^{115}S^{116}A^{117}K^{118}Q^{119}L^{120}P^{121}H^{122}L^{123}K^{124}V^{125}H^{126}$
(SEQ ID NO: 114)

(111) $K^{88}Q^{89}L^{90}P^{91}H^{92}L^{93}K^{94}$
(SEQ ID NO: 84)

(112) $K^{88}Q^{89}L^{90}P^{91}H^{92}L^{93}K^{94}V^{95}H^{96}$
(SEQ ID NO: 85)

(113) $K^{88}Q^{89}L^{90}P^{91}H^{92}L^{93}K^{94}V^{95}H^{96}L^{97}D^{98}V^{99}R^{100}G^{101}A^{102}K^{103}Q^{104}L^{105}P^{106}H^{107}L^{108}K^{109}V^{110}R^{111}L^{112}D^{113}V^{114}$
$K^{115}S^{116}A^{117}K^{118}Q^{119}L^{120}P^{121}H^{122}L^{123}K^{124}V^{125}H^{126}L^{127}D^{128}V^{129}R^{130}G^{131}A^{132}K^{133}Q^{134}L^{135}P^{136}H^{137}$
(SEQ ID NO: 115)

-continued (114) $H^{92}L^{93}K^{94}V^{95}H^{96}L^{97}D^{98}V^{99}R^{100}G^{101}A^{102}K^{103}Q^{104}L^{105}P^{106}H^{107}L^{108}K^{109}V^{110}R^{111}L^{112}D^{113}V^{114}K^{115}$ (SEQ ID NO: 116)

(115) $H^{92}L^{93}K^{94}V^{95}H^{96}L^{97}D^{98}V^{99}R^{100}G^{101}A^{102}K^{103}Q^{104}L^{105}P^{106}H^{107}L^{108}K^{109}V^{110}R^{111}L^{112}D^{113}V^{114}K^{115}S^{116}A^{117}K^{118}$ (SEQ ID NO: 117)

(116) $H^{92}L^{93}K^{94}V^{95}H^{96}L^{97}D^{98}V^{99}R^{100}G^{101}A^{102}K^{103}Q^{104}L^{105}P^{106}H^{107}L^{108}K^{109}V^{110}R^{111}L^{112}D^{113}V^{114}K^{115}S^{116}A^{117}K^{118}Q^{119}L^{120}P^{121}H^{122}L^{123}K^{124}$ (SEQ ID NO: 118)

(117) $H^{92}L^{93}K^{94}V^{95}H^{96}L^{97}D^{98}V^{99}R^{100}G^{101}A^{102}K^{103}Q^{104}L^{105}P^{106}H^{107}L^{108}K^{109}V^{110}R^{111}L^{112}D^{113}V^{114}K^{115}S^{116}A^{117}K^{118}Q^{119}L^{120}P^{121}H^{122}L^{123}K^{124}V^{125}H^{126}L^{127}D^{128}V^{129}R^{130}G^{131}A^{132}K^{133}$ (SEQ ID NO: 119)

(118) $H^{92}L^{93}K^{94}V^{95}H^{96}L^{97}D^{98}V^{99}R^{100}G^{101}A^{102}K^{103}Q^{104}L^{105}P^{106}H^{107}L^{108}K^{109}V^{110}R^{111}L^{112}D^{113}V^{114}K^{115}S^{116}A^{117}K^{118}Q^{119}L^{120}P^{121}H^{122}L^{123}K^{124}V^{125}H^{126}L^{127}D^{128}V^{129}R^{130}G^{131}A^{132}K^{133}Q^{134}L^{135}P^{136}H^{137}L^{138}K^{139}$ (SEQ ID NO: 120)

(119) $H^{92}L^{93}K^{94}V^{95}H^{96}L^{97}D^{98}V^{99}R^{100}G^{101}A^{102}K^{103}$ (SEQ ID NO: 121)

(120) $H^{92}L^{93}K^{94}V^{95}H^{96}L^{97}D^{98}V^{99}R^{100}G^{101}A^{102}K^{103}Q^{104}L^{105}P^{106}H^{107}L^{108}K^{109}$ (SEQ ID NO: 122)

(121) $K^{94}V^{95}H^{96}L^{97}D^{98}V^{99}R^{100}G^{101}A^{102}K^{103}$ (SEQ ID NO: 123)

(122) $K^{94}V^{95}H^{96}L^{97}D^{98}V^{99}R^{100}G^{101}A^{102}K^{103}Q^{104}L^{105}P^{106}H^{107}$ (SEQ ID NO: 124)

(123) $K^{94}V^{95}H^{96}L^{97}D^{98}V^{99}R^{100}G^{101}A^{102}K^{103}Q^{104}L^{105}P^{106}H^{107}L^{108}K^{109}V^{110}R^{111}L^{112}D^{113}V^{114}K^{115}S^{116}A^{117}K^{118}Q^{119}L^{120}P^{121}H^{122}$ (SEQ ID NO: 125)

(124) $K^{94}V^{95}H^{96}L^{97}D^{98}V^{99}R^{100}G^{101}A^{102}K^{103}Q^{104}L^{105}P^{106}H^{107}L^{108}K^{109}V^{110}R^{111}L^{112}D^{113}V^{114}K^{115}S^{116}A^{117}K^{118}Q^{119}L^{120}P^{121}H^{122}L^{123}K^{124}V^{125}H^{126}$ (SEQ ID NO: 126)

(125) $K^{94}V^{95}H^{96}L^{97}D^{98}V^{99}R^{100}G^{101}A^{102}K^{103}Q^{104}L^{105}P^{106}H^{107}L^{108}K^{109}V^{110}R^{111}L^{112}D^{113}V^{114}K^{115}S^{116}A^{117}K^{118}Q^{119}L^{120}P^{121}H^{122}L^{123}K^{124}V^{125}H^{126}L^{127}D^{128}V^{129}R^{130}G^{131}A^{132}K^{133}Q^{134}L^{135}P^{136}H^{137}$ (SEQ ID NO: 127)

(126) $H^{96}L^{97}D^{98}V^{99}R^{100}G^{101}A^{102}K^{103}Q^{104}L^{105}P^{106}H^{107}L^{108}K^{109}$ (SEQ ID NO: 128)

(127) $H^{96}L^{97}D^{98}V^{99}R^{100}G^{101}A^{102}K^{103}Q^{104}L^{105}P^{106}H^{107}L^{108}K^{109}V^{110}R^{111}L^{112}D^{113}V^{114}K^{115}$ (SEQ ID NO: 129)

(128) $H^{96}L^{97}D^{98}V^{99}R^{100}G^{101}A^{102}K^{103}Q^{104}L^{105}P^{106}H^{107}L^{108}K^{109}V^{110}R^{111}L^{112}D^{113}V^{114}K^{115}S^{116}A^{117}K^{118}$ (SEQ ID NO: 130)

(129) $H^{96}L^{97}D^{98}V^{99}R^{100}G^{101}A^{102}K^{103}Q^{104}L^{105}P^{106}H^{107}L^{108}K^{109}V^{110}R^{111}L^{112}D^{113}V^{114}K^{115}S^{116}A^{117}K^{118}Q^{119}L^{120}P^{121}H^{122}L^{123}K^{124}$ (SEQ ID NO: 131)

(130) $H^{96}L^{97}D^{98}V^{99}R^{100}G^{101}A^{102}K^{103}Q^{104}L^{105}P^{106}H^{107}L^{108}K^{109}V^{110}R^{111}L^{112}D^{113}V^{114}K^{115}S^{116}A^{117}K^{118}Q^{119}L^{120}P^{121}H^{122}L^{123}K^{124}V^{125}H^{126}L^{127}D^{128}V^{129}R^{130}G^{131}A^{132}K^{133}$ (SEQ ID NO: 132)

(131) $H^{96}L^{97}D^{98}V^{99}R^{100}G^{101}A^{102}K^{103}Q^{104}L^{105}P^{106}H^{107}L^{108}K^{109}V^{110}R^{111}L^{112}D^{113}V^{114}K^{115}S^{116}A^{117}K^{118}Q^{119}L^{120}P^{121}H^{122}L^{123}K^{124}V^{125}H^{126}L^{127}D^{128}V^{129}R^{130}G^{131}A^{132}K^{133}Q^{134}L^{135}P^{136}H^{137}L^{138}K^{139}$ (SEQ ID NO: 133)

(132) $K^{103}Q^{104}L^{105}P^{106}H^{107}L^{108}K^{109}$ (SEQ ID NO: 84)

(133) $K^{103}Q^{104}L^{105}P^{106}H^{107}L^{108}K^{109}V^{110}R^{111}L^{112}D^{113}V^{114}K^{115}S^{116}A^{117}K^{118}Q^{119}L^{120}P^{121}H^{122}$ (SEQ ID NO: 134)

(134) $K^{103}Q^{104}L^{105}P^{106}H^{107}L^{108}K^{109}V^{110}R^{111}L^{112}D^{113}V^{114}K^{115}S^{116}A^{117}K^{118}Q^{119}L^{120}P^{121}H^{122}L^{123}K^{124}V^{125}H^{126}$ (SEQ ID NO: 135)

(135) $K^{103}Q^{104}L^{105}P^{106}H^{107}L^{108}K^{109}V^{110}R^{111}L^{112}D^{113}V^{114}K^{115}S^{116}A^{117}K^{118}Q^{119}L^{120}P^{121}H^{122}L^{123}K^{124}V^{125}H^{126}L^{127}D^{128}V^{129}R^{130}G^{131}A^{132}K^{133}Q^{134}L^{135}P^{136}H^{137}$ (SEQ ID NO: 136)

(136) $H^{107}L^{108}K^{109}V^{110}R^{111}L^{112}D^{113}V^{114}K^{115}$ (SEQ ID NO: 137)

-continued (137) $H^{107}L^{108}K^{109}V^{110}R^{111}L^{112}D^{113}V^{114}K^{115}S^{116}A^{117}K^{118}$
(SEQ ID NO: 138)

(138) $H^{107}L^{108}K^{109}V^{110}R^{111}L^{112}D^{113}V^{114}K^{115}S^{116}A^{117}K^{118}Q^{119}L^{120}P^{121}H^{122}L^{123}K^{124}$
(SEQ ID NO: 139)

(139) $H^{107}L^{108}K^{109}V^{110}R^{111}L^{112}D^{113}V^{114}K^{115}S^{116}A^{117}K^{118}Q^{119}L^{120}P^{121}H^{122}L^{123}K^{124}V^{125}H^{126}L^{127}D^{128}V^{129}R^{130}$
$G^{131}A^{132}K^{133}$
(SEQ ID NO: 140)

(140) $H^{107}L^{108}K^{109}V^{110}R^{111}L^{112}D^{113}V^{114}K^{115}S^{116}A^{117}K^{118}Q^{119}L^{120}P^{121}H^{122}L^{123}K^{124}V^{125}H^{126}L^{127}D^{128}V^{129}R^{130}$
$G^{131}A^{132}K^{133}Q^{134}L^{135}P^{136}H^{137}L^{138}K^{139}$
(SEQ ID NO: 141)

(141) $H^{107}L^{108}K^{109}V^{110}R^{111}L^{112}D^{113}V^{114}K^{115}S^{116}A^{117}K^{118}Q^{119}L^{120}P^{121}H^{122}L^{123}K^{124}V^{125}H^{126}L^{127}D^{128}V^{129}R^{130}$
$G^{131}A^{132}K^{133}Q^{134}L^{135}P^{136}H^{137}L^{138}K^{139}V^{140}R^{141}L^{142}D^{143}V^{144}R^{145}G^{146}A^{147}K^{148}$
(SEQ ID NO: 142)

(142) $H^{107}L^{108}K^{109}V^{110}R^{111}L^{112}D^{113}V^{114}K^{115}S^{116}A^{117}K^{118}Q^{119}L^{120}P^{121}H^{122}L^{123}K^{124}V^{125}H^{126}L^{127}D^{128}V^{129}R^{130}$
$G^{131}A^{132}K^{133}Q^{134}L^{135}P^{136}H^{137}L^{138}K^{139}V^{140}R^{141}L^{142}D^{143}V^{144}R^{145}G^{146}A^{147}K^{148}Q^{149}N^{150}P^{151}W^{152}R^{153}K^{154}$
(SEQ ID NO: 143)

(143) $K^{109}V^{110}R^{111}L^{112}D^{113}V^{114}K^{115}S^{116}A^{117}K^{118}Q^{119}L^{120}P^{121}H^{122}$
(SEQ ID NO: 144)

(144) $K^{109}V^{110}R^{111}L^{112}D^{113}V^{114}K^{115}S^{116}A^{117}K^{118}Q^{119}L^{120}P^{121}H^{122}L^{123}K^{124}V^{125}H^{126}$
(SEQ ID NO: 145)

(145) $K^{109}V^{110}R^{111}L^{112}D^{113}V^{114}K^{115}S^{116}A^{117}K^{118}Q^{119}L^{120}P^{121}H^{122}L^{123}K^{124}V^{125}H^{126}L^{127}D^{128}V^{129}R^{130}G^{131}A^{132}$
$K^{133}Q^{134}L^{135}P^{136}H^{137}$
(SEQ ID NO: 146)

(146) $K^{115}S^{116}A^{117}K^{118}Q^{119}L^{120}P^{121}H^{122}L^{123}K^{124}$
(SEQ ID NO: 14)

(147) $K^{115}S^{116}A^{117}K^{118}Q^{119}L^{120}P^{121}H^{122}L^{123}K^{124}V^{125}H^{126}$
(SEQ ID NO: 81)

(148) $K^{115}S^{116}A^{117}K^{118}Q^{119}L^{120}P^{121}H^{122}L^{123}K^{124}V^{125}H^{126}L^{127}D^{128}V^{129}R^{130}G^{131}A^{132}K^{133}Q^{134}L^{135}P^{136}H^{137}$
(SEQ ID NO: 109)

(149) $K^{118}Q^{119}L^{120}P^{121}H^{122}L^{123}K^{124}$
(SEQ ID NO: 84)

(150) $K^{118}Q^{119}L^{120}P^{121}H^{122}L^{123}K^{124}V^{125}H^{126}$
(SEQ ID NO: 85)

(151) $K^{118}Q^{119}L^{120}P^{121}H^{122}L^{123}K^{124}V^{125}H^{126}L^{127}D^{128}V^{129}R^{130}G^{131}A^{132}K^{133}Q^{134}L^{135}P^{136}H^{137}$
(SEQ ID NO: 112)

(152) $H^{122}L^{123}K^{124}V^{125}H^{126}L^{127}D^{128}V^{129}R^{130}G^{131}A^{132}K^{133}$
(SEQ ID NO: 121)

(153) $H^{122}L^{123}K^{124}V^{125}H^{126}L^{127}D^{128}V^{129}R^{130}G^{131}A^{132}K^{133}Q^{134}L^{135}P^{136}H^{137}L^{138}K^{139}$
(SEQ ID NO: 122)

(154) $H^{122}L^{123}K^{124}V^{125}H^{126}L^{127}D^{128}V^{129}R^{130}G^{131}A^{132}K^{133}Q^{134}L^{135}P^{136}H^{137}L^{138}K^{139}V^{140}R^{141}L^{142}D^{143}V^{144}R^{145}$
$G^{146}A^{147}K^{148}$
(SEQ ID NO: 147)

(155) $H^{122}L^{123}K^{124}V^{125}H^{126}L^{127}D^{128}V^{129}R^{130}G^{131}A^{132}K^{133}Q^{134}L^{135}P^{136}H^{137}L^{138}K^{139}V^{140}R^{141}L^{142}D^{143}V^{144}R^{145}$
$G^{146}A^{147}K^{148}Q^{149}N^{150}P^{151}W^{152}R^{153}K^{154}$
(SEQ ID NO: 148)

(156) $H^{122}L^{123}K^{124}V^{125}H^{126}L^{127}D^{128}V^{129}R^{130}G^{131}A^{132}K^{133}Q^{134}L^{135}P^{136}H^{137}L^{138}K^{139}V^{140}R^{141}L^{142}D^{143}V^{144}R^{145}$
$G^{146}A^{147}K^{148}Q^{149}N^{150}P^{151}W^{152}R^{153}K^{154}N^{155}L^{156}C^{157}L^{158}L^{159}K^{160}$
(SEQ ID NO: 149)

(157) $H^{122}L^{123}K^{124}V^{125}H^{126}L^{127}D^{128}V^{129}R^{130}G^{131}A^{132}K^{133}Q^{134}L^{135}P^{136}H^{137}L^{138}K^{139}V^{140}R^{141}L^{142}D^{143}V^{144}R^{145}$
$G^{146}A^{147}K^{148}Q^{149}N^{150}P^{151}W^{152}R^{153}K^{154}N^{155}L^{156}C^{157}L^{158}L^{159}K^{160}K^{161}$
(SEQ ID NO: 150)

(158) $H^{122}L^{123}K^{124}V^{125}H^{126}L^{127}D^{128}V^{129}R^{130}G^{131}A^{132}K^{133}Q^{134}L^{135}P^{136}H^{137}L^{138}K^{139}V^{140}R^{141}L^{142}D^{143}V^{144}R^{145}$
$G^{146}A^{147}K^{148}Q^{149}N^{150}P^{151}W^{152}R^{153}K^{154}N^{155}L^{156}C^{157}L^{158}L^{159}K^{160}K^{161}N^{162}V^{163}K^{164}$
(SEQ ID NO: 151)

(159) $H^{122}L^{123}K^{124}V^{125}H^{126}L^{127}D^{128}V^{129}R^{130}G^{131}A^{132}K^{133}Q^{134}L^{135}P^{136}H^{137}L^{138}K^{139}V^{140}R^{141}L^{142}D^{143}V^{144}R^{145}$
$G^{146}A^{147}K^{148}Q^{149}N^{150}P^{151}W^{152}R^{153}K^{154}N^{155}L^{156}C^{157}L^{158}L^{159}K^{160}K^{161}N^{162}V^{163}K^{164}S^{165}A^{166}K^{167}$
(SEQ ID NO: 152)

-continued (160) $K^{124}V^{125}H^{126}L^{127}D^{128}V^{129}R^{130}G^{131}A^{132}K^{133}$
(SEQ ID NO: 123)

(161) $K^{124}V^{125}H^{126}L^{127}D^{128}V^{129}R^{130}G^{131}A^{132}K^{133}Q^{134}L^{135}P^{136}H^{137}$
(SEQ ID NO: 124)

(162) $K^{124}V^{125}H^{126}L^{127}D^{128}V^{129}R^{130}G^{131}A^{132}K^{133}Q^{134}L^{135}P^{136}H^{137}L^{138}K^{139}V^{140}R^{141}L^{142}D^{143}V^{144}R^{145}G^{146}A^{147}$
$K^{148}Q^{149}N^{150}P^{151}W^{152}R^{153}K^{154}N^{155}L^{156}C^{157}L^{158}L^{159}K^{160}K^{161}N^{162}V^{163}K^{164}S^{165}A^{166}K^{167}Q^{168}L^{169}P^{170}H^{171}$
(SEQ ID NO: 153)

Replikin Sequences Located in Mid-Molecule Portion of Peptide (163) $H^{126}L^{127}D^{128}V^{129}R^{130}G^{131}A^{132}K^{133}Q^{134}L^{135}P^{136}H^{137}L^{138}K^{139}$
(SEQ ID NO: 128)

(164) $H^{126}L^{127}D^{128}V^{129}R^{130}G^{131}A^{132}K^{133}Q^{134}L^{135}P^{136}H^{137}L^{138}K^{139}V^{140}R^{141}L^{142}D^{143}V^{144}R^{145}G^{146}A^{147}K^{148}$
(SEQ ID NO: 154)

(165) $H^{126}L^{127}D^{128}V^{129}R^{130}G^{131}A^{132}K^{133}Q^{134}L^{135}P^{136}H^{137}L^{138}K^{139}V^{140}R^{141}L^{142}D^{143}V^{144}R^{145}G^{146}A^{147}K^{148}Q^{149}$
$N^{150}P^{151}W^{152}R^{153}K^{154}$
(SEQ ID NO: 155)

(166) $H^{126}L^{127}D^{128}V^{129}R^{130}G^{131}A^{132}K^{133}Q^{134}L^{135}P^{136}H^{137}L^{138}K^{139}V^{140}R^{141}L^{142}D^{143}V^{144}R^{145}G^{146}A^{147}K^{148}Q^{149}$
$N^{150}P^{151}W^{152}R^{153}K^{154}N^{155}L^{156}C^{157}L^{158}L^{159}K^{160}$
(SEQ ID NO: 156)

(167) $H^{126}L^{127}D^{128}V^{129}R^{130}G^{131}A^{132}K^{133}Q^{134}L^{135}P^{136}H^{137}L^{138}K^{139}V^{140}R^{141}L^{142}D^{143}V^{144}R^{145}G^{146}A^{147}K^{148}Q^{149}$
$N^{150}P^{151}W^{152}R^{153}K^{154}N^{155}L^{156}C^{157}L^{158}L^{159}K^{160}K^{161}$
(SEQ ID NO: 157)

(168) $H^{126}L^{127}D^{128}V^{129}R^{130}G^{131}A^{132}K^{133}Q^{134}L^{135}P^{136}H^{137}L^{138}K^{139}V^{140}R^{141}L^{142}D^{143}V^{144}R^{145}G^{146}A^{147}K^{148}Q^{149}$
$N^{150}P^{151}W^{152}R^{153}K^{154}N^{155}L^{156}C^{157}L^{158}L^{159}K^{160}K^{161}N^{162}V^{163}K^{164}$
(SEQ ID NO: 158)

(169) $H^{126}L^{127}D^{128}V^{129}R^{130}G^{131}A^{132}K^{133}Q^{134}L^{135}P^{136}H^{137}L^{138}K^{139}V^{140}R^{141}L^{142}D^{143}V^{144}R^{145}G^{146}A^{147}K^{148}Q^{149}$
$N^{150}P^{151}W^{152}R^{153}K^{154}N^{155}L^{156}C^{157}L^{158}L^{159}K^{160}K^{161}N^{162}V^{163}K^{164}S^{165}A^{166}K^{167}$
(SEQ ID NO: 159)

(170) $H^{126}L^{127}D^{128}V^{129}R^{130}G^{131}A^{132}K^{133}Q^{134}L^{135}P^{136}H^{137}L^{138}K^{139}V^{140}R^{141}L^{142}D^{143}V^{144}R^{145}G^{146}A^{147}K^{148}Q^{149}$
$N^{150}P^{151}W^{152}R^{153}K^{154}N^{155}L^{156}C^{157}L^{158}L^{159}K^{160}K^{161}N^{162}V^{163}K^{164}S^{165}A^{166}K^{167}Q^{168}L^{169}P^{170}H^{171}L^{172}K^{173}$
(SEQ ID NO: 160)

(171) $K^{133}Q^{134}L^{135}P^{136}H^{137}L^{138}K^{139}V^{140}R^{141}L^{142}D^{143}V^{144}R^{145}G^{146}A^{147}K^{148}Q^{149}N^{150}P^{151}W^{152}R^{153}K^{154}N^{155}L^{156}$
$C^{157}L^{158}L^{159}K^{160}K^{161}N^{162}V^{163}K^{164}S^{165}A^{166}K^{167}Q^{168}L^{169}P^{170}H^{171}L^{172}K^{173}V^{174}H^{175}$
(SEQ ID NO: 161)

(172) $K^{133}Q^{134}L^{135}P^{136}H^{137}L^{138}K^{139}$
(SEQ ID NO: 84)

(173) $K^{133}Q^{134}L^{135}P^{136}H^{137}L^{138}K^{139}V^{140}R^{141}L^{142}D^{143}V^{144}R^{145}G^{146}A^{147}K^{148}Q^{149}N^{150}P^{151}W^{152}R^{153}K^{154}N^{155}L^{156}$
$C^{157}L^{158}L^{159}K^{160}K^{161}N^{162}V^{163}K^{164}S^{165}A^{166}K^{167}Q^{168}L^{169}P^{170}H^{171}$
(SEQ ID NO: 162)

(174) $H^{137}L^{138}K^{139}V^{140}R^{141}L^{142}D^{143}V^{144}R^{145}G^{146}A^{147}K^{148}$
(SEQ ID NO: 51)

(175) $H^{137}L^{138}K^{139}V^{140}R^{141}L^{142}D^{143}V^{144}R^{145}G^{146}A^{147}K^{148}Q^{149}N^{150}P^{151}W^{152}R^{153}K^{154}$
(SEQ ID NO: 52)

(176) $H^{137}L^{138}K^{139}V^{140}R^{141}L^{142}D^{143}V^{144}R^{145}G^{146}A^{147}K^{148}Q^{149}N^{150}P^{151}W^{152}R^{153}K^{154}N^{155}L^{156}C^{157}L^{158}L^{159}K^{160}$
(SEQ ID NO: 53)

(177) $H^{137}L^{138}K^{139}V^{140}R^{141}L^{142}D^{143}V^{144}R^{145}G^{146}A^{147}K^{148}Q^{149}N^{150}P^{151}W^{152}R^{153}K^{154}N^{155}L^{156}C^{157}L^{158}L^{159}K^{160}$
$K^{161}$
(SEQ ID NO: 54)

(178) $H^{137}L^{138}K^{139}V^{140}R^{141}L^{142}D^{143}V^{144}R^{145}G^{146}A^{147}K^{148}Q^{149}N^{150}P^{151}W^{152}R^{153}K^{154}N^{155}L^{156}C^{157}L^{158}L^{159}K^{160}$
$K^{161}N^{162}V^{163}K^{164}$
(SEQ ID NO: 55)

(179) $H^{137}L^{138}K^{139}V^{140}R^{141}L^{142}D^{143}V^{144}R^{145}G^{146}A^{147}K^{148}Q^{149}N^{150}P^{151}W^{152}R^{153}K^{154}N^{155}L^{156}C^{157}L^{158}L^{159}K^{160}$
$K^{161}N^{162}V^{163}K^{164}S^{165}A^{166}K^{167}$
(SEQ ID NO: 56)

(180) $H^{137}L^{138}K^{139}V^{140}R^{141}L^{142}D^{143}V^{144}R^{145}G^{146}A^{147}K^{148}Q^{149}N^{150}P^{151}W^{152}R^{153}K^{154}N^{155}L^{156}C^{157}L^{158}L^{159}K^{160}$
$K^{161}N^{162}V^{163}K^{164}S^{165}A^{166}K^{167}Q^{168}L^{169}P^{170}H^{171}L^{172}K^{173}$
(SEQ ID NO: 57)

(181) $H^{137}L^{138}K^{139}V^{140}R^{141}L^{142}D^{143}V^{144}R^{145}G^{146}A^{147}K^{148}Q^{149}N^{150}P^{151}W^{152}R^{153}K^{154}N^{155}L^{156}C^{157}L^{158}L^{159}K^{160}$
$K^{161}N^{162}V^{163}K^{164}S^{165}A^{166}K^{167}Q^{168}L^{169}P^{170}H^{171}L^{172}K^{173}V^{174}H^{175}L^{176}D^{177}V^{178}K^{179}$
(SEQ ID NO: 58)

-continued (182) $H^{137}L^{138}K^{139}V^{140}R^{141}L^{142}D^{143}V^{144}R^{145}G^{146}A^{147}K^{148}Q^{149}N^{150}P^{151}W^{152}R^{153}K^{154}N^{155}L^{156}C^{157}L^{158}L^{159}K^{160}$
$K^{161}N^{162}V^{163}K^{164}S^{165}A^{166}K^{167}Q^{168}L^{169}P^{170}H^{171}L^{172}K^{173}V^{174}H^{175}L^{176}D^{177}V^{178}K^{179}G^{180}V^{181}K^{182}$
(SEQ ID NO: 163)

(183) $K^{139}V^{140}R^{141}L^{142}D^{143}V^{144}R^{145}G^{146}A^{147}K^{148}Q^{149}N^{150}P^{151}W^{152}R^{153}K^{154}N^{155}L^{156}C^{157}L^{158}L^{159}K^{160}K^{161}N^{162}$
$V^{163}K^{164}S^{165}A^{166}K^{167}Q^{168}L^{169}P^{170}H^{171}$
(SEQ ID NO: 60)

(184) $K^{139}V^{140}R^{141}L^{142}D^{143}V^{144}R^{145}G^{146}A^{147}K^{148}Q^{149}N^{150}P^{151}W^{152}R^{153}K^{154}N^{155}L^{156}C^{157}L^{158}L^{159}K^{160}K^{161}N^{162}$
$V^{163}K^{164}S^{165}A^{166}K^{167}Q^{168}L^{169}P^{170}H^{171}L^{172}K^{173}V^{174}H^{175}$
(SEQ ID NO: 61)

(185) $K^{139}V^{140}R^{141}L^{142}D^{143}V^{144}R^{145}G^{146}A^{147}K^{148}Q^{149}N^{150}P^{151}W^{152}R^{153}K^{154}N^{155}L^{156}C^{157}L^{158}L^{159}K^{160}K^{161}N^{162}$
$V^{163}K^{164}S^{165}A^{166}K^{167}Q^{168}L^{169}P^{170}H^{171}L^{172}K^{173}V^{174}H^{175}L^{176}D^{177}V^{178}K^{179}G^{180}V^{181}K^{182}Q^{183}L^{184}L^{185}H^{186}$
(SEQ ID NO: 164)

(186) $K^{148}Q^{149}N^{150}P^{151}W^{152}R^{153}K^{154}N^{155}L^{156}C^{157}L^{158}L^{159}K^{160}K^{161}N^{162}V^{163}K^{164}S^{165}A^{166}K^{167}Q^{168}L^{169}P^{170}H^{171}$
(SEQ ID NO: 63)

(187) $K^{148}Q^{149}N^{150}P^{151}W^{152}R^{153}K^{154}N^{155}L^{156}C^{157}L^{158}L^{159}K^{160}K^{161}N^{162}V^{163}K^{164}S^{165}A^{166}K^{167}Q^{168}L^{169}P^{170}H^{171}$
$L^{172}K^{173}V^{174}H^{175}$
(SEQ ID NO: 64)

(188) $K^{148}Q^{149}N^{150}P^{151}W^{152}R^{153}K^{154}N^{155}L^{156}C^{157}L^{158}L^{159}K^{160}K^{161}N^{162}V^{163}K^{164}S^{165}A^{166}K^{167}Q^{168}L^{169}P^{170}H^{171}$
$L^{172}K^{173}V^{174}H^{175}L^{176}D^{177}V^{178}K^{179}G^{180}V^{181}K^{182}Q^{183}L^{184}L^{185}H^{186}$
(SEQ ID NO: 165)

(189) $K^{154}N^{155}L^{156}C^{157}L^{158}L^{159}K^{160}K^{161}N^{162}V^{163}K^{164}S^{165}A^{166}K^{167}Q^{168}L^{169}P^{170}H^{171}L^{172}K^{173}V^{174}H^{175}L^{176}D^{177}$
$V^{178}K^{179}G^{180}V^{181}K^{182}Q^{183}L^{184}L^{185}H^{186}L^{187}K^{188}V^{189}R^{190}L^{191}D^{192}V^{193}R^{194}G^{195}A^{196}K^{197}Q^{198}L^{199}P^{200}H^{201}$
(SEQ ID NO: 336)

(190) $K^{154}N^{155}L^{156}C^{157}L^{158}L^{159}K^{160}K^{161}N^{162}V^{163}K^{164}S^{165}A^{166}K^{167}Q^{168}L^{169}P^{170}H^{171}$
(SEQ ID NO: 68)

(191) $K^{154}N^{155}L^{156}C^{157}L^{158}L^{159}K^{160}K^{161}N^{162}V^{163}K^{164}S^{165}A^{166}K^{167}Q^{168}L^{169}P^{170}H^{171}L^{172}K^{173}V^{174}H^{175}$
(SEQ ID NO: 69)

(192) $K^{154}N^{155}L^{156}C^{157}L^{158}L^{159}K^{160}K^{161}N^{162}V^{163}K^{164}S^{165}A^{166}K^{167}Q^{168}L^{169}P^{170}H^{171}L^{172}K^{173}V^{174}H^{175}L^{176}D^{177}$
$V^{178}K^{179}G^{180}V^{181}K^{182}Q^{183}L^{184}L^{185}H^{186}$
(SEQ ID NO: 167)

(193) $K^{160}K^{161}N^{162}V^{163}K^{164}S^{165}A^{166}K^{167}Q^{168}L^{169}P^{170}H^{171}$
(SEQ ID NO: 13)

(194) $K^{160}K^{161}N^{162}V^{163}K^{164}S^{165}A^{166}K^{167}Q^{168}L^{169}P^{170}H^{171}L^{172}K^{173}V^{174}H^{175}$
(SEQ ID NO: 72)

(195) $K^{160}K^{161}N^{162}V^{163}K^{164}S^{165}A^{166}K^{167}Q^{168}L^{169}P^{170}H^{171}L^{172}K^{173}V^{174}H^{175}L^{176}D^{177}V^{178}K^{179}G^{180}V^{181}K^{182}Q^{183}$
$L^{184}L^{185}H^{186}$
(SEQ ID NO: 2)

(196) $K^{160}K^{161}N^{162}V^{163}K^{164}S^{165}A^{166}K^{167}Q^{168}L^{169}P^{170}H^{171}L^{172}K^{173}V^{174}H^{175}L^{176}D^{177}V^{178}K^{179}G^{180}V^{181}K^{182}Q^{183}$
$L^{184}L^{185}H^{186}L^{187}K^{188}V^{189}R^{190}L^{191}D^{192}V^{193}R^{194}G^{195}A^{196}K^{197}Q^{198}L^{199}P^{200}H^{201}$
(SEQ ID NO: 337)

(197) $K^{160}K^{161}N^{162}V^{163}K^{164}S^{165}A^{166}K^{167}Q^{168}L^{169}P^{170}H^{171}L^{172}K^{173}V^{174}H^{175}L^{176}D^{177}V^{178}K^{179}G^{180}V^{181}K^{182}Q^{183}$
$L^{184}L^{185}H^{186}L^{187}K^{188}V^{189}R^{190}L^{191}D^{192}V^{193}R^{194}G^{195}A^{196}K^{197}Q^{198}L^{199}P^{200}H^{201}L^{202}K^{203}V^{204}H^{205}$
(SEQ ID NO: 338)

(198) $K^{161}N^{162}V^{163}K^{164}S^{165}A^{166}K^{167}Q^{168}L^{169}P^{170}H^{171}$
(SEQ ID NO: 75)

(199) $K^{161}N^{162}V^{163}K^{164}S^{165}A^{166}K^{167}Q^{168}L^{169}P^{170}H^{171}L^{172}K^{173}V^{174}H^{175}$
(SEQ ID NO: 76)

(200) $K^{161}N^{162}V^{163}K^{164}S^{165}A^{166}K^{167}Q^{168}L^{169}P^{170}H^{171}L^{172}K^{173}V^{174}H^{175}L^{176}D^{177}V^{178}K^{179}G^{180}V^{181}K^{182}Q^{183}L^{184}$
$L^{185}H^{186}$
(SEQ ID NO: 170)

(201) $K^{161}N^{162}V^{163}K^{164}S^{165}A^{166}K^{167}Q^{168}L^{169}P^{170}H^{171}L^{172}K^{173}V^{174}H^{175}L^{176}D^{177}V^{178}K^{179}G^{180}V^{181}K^{182}Q^{183}L^{184}$
$L^{185}H^{186}L^{187}K^{188}V^{189}R^{190}L^{191}D^{192}V^{193}R^{194}G^{195}A^{196}K^{197}Q^{198}L^{199}P^{200}H^{201}$
(SEQ ID NO: 339)

(202) $K^{161}N^{162}V^{163}K^{164}S^{165}A^{166}K^{167}Q^{168}L^{169}P^{170}H^{171}L^{172}K^{173}V^{174}H^{175}L^{176}D^{177}V^{178}K^{179}G^{180}V^{181}K^{182}Q^{183}L^{184}$
$L^{185}H^{186}L^{187}K^{188}V^{189}R^{190}L^{191}D^{192}V^{193}R^{194}G^{195}A^{196}K^{197}Q^{198}L^{199}P^{200}H^{201}L^{202}K^{203}V^{204}H^{205}$
(SEQ ID NO: 340)

(203) $K^{164}S^{165}A^{166}K^{167}Q^{168}L^{169}P^{170}H^{171}L^{172}K^{173}$
(SEQ ID NO: 14)

-continued (204) $K^{164}S^{165}A^{166}K^{167}Q^{168}L^{169}P^{170}H^{171}L^{172}K^{173}V^{174}H^{175}$
(SEQ ID NO: 81)

(205) $K^{164}S^{165}A^{166}K^{167}Q^{168}L^{169}P^{170}H^{171}L^{172}K^{173}V^{174}H^{175}L^{176}D^{177}V^{178}K^{179}G^{180}V^{181}K^{182}Q^{183}L^{184}L^{185}H^{186}$
(SEQ ID NO: 173)

(206) $K^{164}S^{165}A^{166}K^{167}Q^{168}L^{169}P^{170}H^{171}L^{172}K^{173}V^{174}H^{175}L^{176}D^{177}V^{178}K^{179}G^{180}V^{181}K^{182}Q^{183}L^{184}L^{185}H^{186}L^{187}$
$K^{188}V^{189}R^{190}L^{191}D^{192}V^{193}R^{194}G^{195}A^{196}K^{197}Q^{198}L^{199}P^{200}H^{201}$
(SEQ ID NO: 341)

(207) $K^{164}S^{165}A^{166}K^{167}Q^{168}L^{169}P^{170}H^{171}L^{172}K^{173}V^{174}H^{175}L^{176}D^{177}V^{178}K^{179}G^{180}V^{181}K^{182}Q^{183}L^{184}L^{185}H^{186}L^{187}$
$K^{188}V^{189}R^{190}L^{191}D^{192}V^{193}R^{194}G^{195}A^{196}K^{197}Q^{198}L^{199}P^{200}H^{201}L^{202}K^{203}V^{204}H^{205}$
(SEQ ID NO: 342)

(208) $K^{167}Q^{168}L^{169}P^{170}H^{171}L^{172}K^{173}$
(SEQ ID NO: 84)

(209) $K^{167}Q^{168}L^{169}P^{170}H^{171}L^{172}K^{173}V^{174}H^{175}$
(SEQ ID NO: 85)

(210) $K^{167}Q^{168}L^{169}P^{170}H^{171}L^{172}K^{173}V^{174}H^{175}L^{176}D^{177}V^{178}K^{179}G^{180}V^{181}K^{182}Q^{183}L^{184}L^{185}H^{186}$
(SEQ ID NO: 176)

(211) $K^{167}Q^{168}L^{169}P^{170}H^{171}L^{172}K^{173}V^{174}H^{175}L^{176}D^{177}V^{178}K^{179}G^{180}V^{181}K^{182}Q^{183}L^{184}L^{185}H^{186}L^{187}K^{188}V^{189}R^{190}$
$L^{191}D^{192}V^{193}R^{194}G^{195}A^{196}K^{197}Q^{198}L^{199}P^{200}H^{201}$
(SEQ ID NO: 343)

(212) $K^{167}Q^{168}L^{169}P^{170}H^{171}L^{172}K^{173}V^{174}H^{175}L^{176}D^{177}V^{178}K^{179}G^{180}V^{181}K^{182}Q^{183}L^{184}L^{185}H^{186}L^{187}K^{188}V^{189}R^{190}$
$L^{191}D^{192}V^{193}R^{194}G^{195}A^{196}K^{197}Q^{198}L^{199}P^{200}H^{201}L^{202}K^{203}V^{204}H^{205}$
(SEQ ID NO: 344)

(213) $H^{171}L^{172}K^{173}V^{174}H^{175}L^{176}D^{177}V^{178}K^{179}$
(SEQ ID NO: 27)

(214) $H^{171}L^{172}K^{173}V^{174}H^{175}L^{176}D^{177}V^{178}K^{179}G^{180}V^{181}K^{182}$
(SEQ ID NO: 28)

(215) $H^{171}L^{172}K^{173}V^{174}H^{175}L^{176}D^{177}V^{178}K^{179}G^{180}V^{181}K^{182}Q^{183}L^{184}L^{185}H^{186}L^{187}K^{188}$
(SEQ ID NO: 29)

(216) $H^{171}L^{172}K^{173}V^{174}H^{175}L^{176}D^{177}V^{178}K^{179}G^{180}V^{181}K^{182}Q^{183}L^{184}L^{185}H^{186}L^{187}K^{188}V^{189}R^{190}L^{191}D^{192}V^{193}R^{194}$
$G^{195}A^{196}K^{197}Q^{198}L^{199}P^{200}H^{201}L^{202}K^{203}$
(SEQ ID NO: 345)

(217) $H^{171}L^{172}K^{173}V^{174}H^{175}L^{176}D^{177}V^{178}K^{179}G^{180}V^{181}K^{182}Q^{183}L^{184}L^{185}H^{186}L^{187}K^{188}V^{189}R^{190}L^{191}D^{192}V^{193}R^{194}$
$G^{195}A^{196}K^{197}$
(SEQ ID NO: 30)

(218) $H^{171}L^{172}K^{173}V^{174}H^{175}L^{176}D^{177}V^{178}K^{179}G^{180}V^{181}K^{182}Q^{183}L^{184}L^{185}H^{186}L^{187}K^{188}V^{189}R^{190}L^{191}D^{192}V^{193}R^{194}$
$G^{195}A^{196}K^{197}Q^{198}L^{199}P^{200}H^{201}L^{202}K^{203}V^{204}H^{205}L^{206}D^{207}V^{208}R^{209}G^{210}A^{211}K^{212}$
(SEQ ID NO: 346)

(219) $H^{171}L^{172}K^{173}V^{174}H^{175}L^{176}D^{177}V^{178}K^{179}G^{180}V^{181}K^{182}Q^{183}L^{184}L^{185}H^{186}L^{187}K^{188}V^{189}R^{190}L^{191}D^{192}V^{193}R^{194}$
$G^{195}A^{196}K^{197}Q^{198}L^{199}P^{200}H^{201}L^{202}K^{203}V^{204}H^{205}L^{206}D^{207}V^{208}R^{209}G^{210}A^{211}K^{212}Q^{213}N^{214}P^{215}W^{216}R^{217}K^{218}$
(SEQ ID NO: 347)

(220) $K^{173}V^{174}H^{175}L^{176}D^{177}V^{178}K^{179}$
(SEQ ID NO: 11)

(221) $K^{173}V^{174}H^{175}L^{176}D^{177}V^{178}K^{179}G^{180}V^{181}K^{182}$
(SEQ ID NO: 37)

(222) $K^{173}V^{174}H^{175}L^{176}D^{177}V^{178}K^{179}G^{180}V^{181}K^{182}Q^{183}L^{184}L^{185}H^{186}$
(SEQ ID NO: 12)

(223) $K^{173}V^{174}H^{175}L^{176}D^{177}V^{178}K^{179}G^{180}V^{181}K^{182}Q^{183}L^{184}L^{185}H^{186}L^{187}K^{188}V^{189}R^{190}L^{191}D^{192}V^{193}R^{194}G^{195}A^{196}$
$K^{197}Q^{198}L^{199}P^{200}H^{201}$
(SEQ ID NO: 348)

(224) $K^{173}V^{174}H^{175}L^{176}D^{177}V^{178}K^{179}G^{180}V^{181}K^{182}Q^{183}L^{184}L^{185}H^{186}L^{187}K^{188}V^{189}R^{190}L^{191}D^{192}V^{193}R^{194}G^{195}A^{196}$
$K^{197}Q^{198}L^{199}P^{200}H^{201}L^{202}K^{203}V^{204}H^{205}$
(SEQ ID NO: 349)

(225) $H^{175}L^{176}D^{177}V^{178}K^{179}G^{180}V^{181}K^{182}Q^{183}L^{184}L^{185}H^{186}L^{187}K^{188}V^{189}R^{190}L^{191}D^{192}V^{193}R^{194}G^{195}A^{196}K^{197}Q^{198}$
$L^{199}P^{200}H^{201}L^{202}K^{203}V^{204}H^{205}L^{206}D^{207}V^{208}R^{209}G^{210}A^{211}K^{212}$
(SEQ ID NO: 350)

(226) $H^{175}L^{176}D^{177}V^{178}K^{179}G^{180}V^{181}K^{182}Q^{183}L^{184}L^{185}H^{186}L^{187}K^{188}V^{189}R^{190}L^{191}D^{192}V^{193}R^{194}G^{195}A^{196}K^{197}Q^{198}$
$L^{199}P^{200}H^{201}L^{202}K^{203}V^{204}H^{205}L^{206}D^{207}V^{208}R^{209}G^{210}A^{211}K^{212}Q^{213}N^{214}P^{215}W^{216}R^{217}K^{218}$
(SEQ ID NO: 351)

-continued (227) $H^{175}L^{176}D^{177}V^{178}K^{179}G^{180}V^{181}K^{182}Q^{183}L^{184}L^{185}H^{186}L^{187}K^{188}V^{189}R^{190}L^{191}D^{192}V^{193}R^{194}G^{195}A^{196}K^{197}Q^{198}L^{199}P^{200}H^{201}L^{202}K^{203}V^{204}H^{205}L^{206}D^{207}V^{208}R^{209}G^{210}A^{211}K^{212}Q^{213}N^{214}P^{215}W^{216}R^{217}K^{218}N^{219}L^{220}C^{221}L^{222}L^{223}K^{224}$
(SEQ ID NO: 352)

(228) $H^{175}L^{176}D^{177}V^{178}K^{179}G^{180}V^{181}K^{182}Q^{183}L^{184}L^{185}H^{186}L^{187}K^{188}V^{189}R^{190}L^{191}D^{192}V^{193}R^{194}G^{195}A^{196}K^{197}Q^{198}L^{199}P^{200}H^{201}L^{202}K^{203}V^{204}H^{205}L^{206}D^{207}V^{208}R^{209}G^{210}A^{211}K^{212}Q^{213}N^{214}P^{215}W^{216}R^{217}K^{218}N^{219}L^{220}C^{221}L^{222}L^{223}K^{224}K^{225}$
(SEQ ID NO: 353)

(229) $H^{175}L^{176}D^{177}V^{178}K^{179}G^{180}V^{181}K^{182}Q^{183}L^{184}L^{185}H^{186}L^{187}K^{188}$
(SEQ ID NO: 38)

(230) $H^{175}L^{176}D^{177}V^{178}K^{179}G^{180}V^{181}K^{182}Q^{183}L^{184}L^{185}H^{186}L^{187}K^{188}V^{189}R^{190}L^{191}D^{192}V^{193}R^{194}G^{195}A^{196}K^{197}Q^{198}L^{199}P^{200}H^{201}L^{202}K^{203}$
(SEQ ID NO: 354)

(231) $H^{175}L^{176}D^{177}V^{178}K^{179}G^{180}V^{181}K^{182}Q^{183}L^{184}L^{185}H^{186}L^{187}K^{188}V^{189}R^{190}L^{191}D^{192}V^{193}R^{194}G^{195}A^{196}K^{197}$
(SEQ ID NO: 39)

(232) $K^{179}G^{180}V^{181}K^{182}Q^{183}L^{184}L^{185}H^{186}L^{187}K^{188}$
(SEQ ID NO: 46)

(233) $K^{179}G^{180}V^{181}K^{182}Q^{183}L^{184}L^{185}H^{186}L^{187}K^{188}V^{189}R^{190}L^{191}D^{192}V^{193}R^{194}G^{195}A^{196}K^{197}Q^{198}L^{199}P^{200}H^{201}$
(SEQ ID NO: 355)

(234) $K^{179}G^{180}V^{181}K^{182}Q^{183}L^{184}L^{185}H^{186}L^{187}K^{188}V^{189}R^{190}L^{191}D^{192}V^{193}R^{194}G^{195}A^{196}K^{197}Q^{198}L^{199}P^{200}H^{201}L^{202}K^{203}V^{204}H^{205}$
(SEQ ID NO: 356)

(235) $K^{182}Q^{183}L^{184}L^{185}H^{186}L^{187}K^{188}$
(SEQ ID NO: 10)

(236) $K^{182}Q^{183}L^{184}L^{185}H^{186}L^{187}K^{188}V^{189}R^{190}L^{191}D^{192}V^{193}R^{194}G^{195}A^{196}K^{197}Q^{198}L^{199}P^{200}H^{201}$
(SEQ ID NO: 357)

(237) $K^{182}Q^{183}L^{184}L^{185}H^{186}L^{187}K^{188}V^{189}R^{190}L^{191}D^{192}V^{193}R^{194}G^{195}A^{196}K^{197}Q^{198}L^{199}P^{200}H^{201}L^{202}K^{203}V^{204}H^{205}$
(SEQ ID NO: 358)

(238) $H^{186}L^{187}K^{188}V^{189}R^{190}L^{191}D^{192}V^{193}R^{194}G^{195}A^{196}K^{197}Q^{198}L^{199}P^{200}H^{201}L^{202}K^{203}$
(SEQ ID NO: 359)

(239) $H^{186}L^{187}K^{188}V^{189}R^{190}L^{191}D^{192}V^{193}R^{194}G^{195}A^{196}K^{197}$
(SEQ ID NO: 51)

(240) $H^{186}L^{187}K^{188}V^{189}R^{190}L^{191}D^{192}V^{193}R^{194}G^{195}A^{196}K^{197}Q^{198}L^{199}P^{200}H^{201}L^{202}K^{203}V^{204}H^{205}L^{206}D^{207}V^{208}R^{209}G^{210}A^{211}K^{212}$
(SEQ ID NO: 360)

(241) $H^{186}L^{187}K^{188}V^{189}R^{190}L^{191}D^{192}V^{193}R^{194}G^{195}A^{196}K^{197}Q^{198}L^{199}P^{200}H^{201}L^{202}K^{203}V^{204}H^{205}L^{206}D^{207}V^{208}R^{209}G^{210}A^{211}K^{212}Q^{213}N^{214}P^{215}W^{216}R^{217}K^{218}$
(SEQ ID NO: 361)

(242) $H^{186}L^{187}K^{188}V^{189}R^{190}L^{191}D^{192}V^{193}R^{194}G^{195}A^{196}K^{197}Q^{198}L^{199}P^{200}H^{201}L^{202}K^{203}V^{204}H^{205}L^{206}D^{207}V^{208}R^{209}G^{210}A^{211}K^{212}Q^{213}N^{214}P^{215}W^{216}R^{217}K^{218}N^{219}L^{220}C^{221}L^{222}L^{223}K^{224}$
(SEQ ID NO: 362)

(243) $H^{186}L^{187}K^{188}V^{189}R^{190}L^{191}D^{192}V^{193}R^{194}G^{195}A^{196}K^{197}Q^{198}L^{199}P^{200}H^{201}L^{202}K^{203}V^{204}H^{205}L^{206}D^{207}V^{208}R^{209}G^{210}A^{211}K^{212}Q^{213}N^{214}P^{215}W^{216}R^{217}K^{218}N^{219}L^{220}C^{221}L^{222}L^{223}K^{224}K^{225}$
(SEQ ID NO: 363)

(244) $H^{186}L^{187}K^{188}V^{189}R^{190}L^{191}D^{192}V^{193}R^{194}G^{195}A^{196}K^{197}Q^{198}L^{199}P^{200}H^{201}L^{202}K^{203}V^{204}H^{205}L^{206}D^{207}V^{208}R^{209}G^{210}A^{211}K^{212}Q^{213}N^{214}P^{215}W^{216}R^{217}K^{218}N^{219}L^{220}C^{221}L^{222}L^{223}K^{224}K^{225}N^{226}V^{227}K^{228}$
(SEQ ID NO: 364)

(245) $H^{186}L^{187}K^{188}V^{189}R^{190}L^{191}D^{192}V^{193}R^{194}G^{195}A^{196}K^{197}Q^{198}L^{199}P^{200}H^{201}L^{202}K^{203}V^{204}H^{205}L^{206}D^{207}V^{208}R^{209}G^{210}A^{211}K^{212}Q^{213}N^{214}P^{215}W^{216}R^{217}K^{218}N^{219}L^{220}C^{221}L^{222}L^{223}K^{224}K^{225}N^{226}V^{227}K^{228}S^{229}A^{230}K^{231}$
(SEQ ID NO: 365)

(246) $K^{188}V^{189}R^{190}L^{191}D^{192}V^{193}R^{194}G^{195}A^{196}K^{197}Q^{198}L^{199}P^{200}H^{201}$
(SEQ ID NO: 366)

(247) $K^{188}V^{189}R^{190}L^{191}D^{192}V^{193}R^{194}G^{195}A^{196}K^{197}Q^{198}L^{199}P^{200}H^{201}L^{202}K^{203}V^{204}H^{205}$
(SEQ ID NO: 317)

(248) $K^{188}V^{189}R^{190}L^{191}D^{192}V^{193}R^{194}G^{195}A^{196}K^{197}Q^{198}L^{199}P^{200}H^{201}L^{202}K^{203}V^{204}H^{205}L^{206}D^{207}V^{208}R^{209}G^{210}A^{211}K^{212}Q^{213}N^{214}P^{215}W^{216}R^{217}K^{218}N^{219}L^{220}C^{221}L^{222}L^{223}K^{224}K^{225}N^{226}V^{227}K^{228}S^{229}A^{230}K^{231}Q^{232}L^{233}P^{234}H^{235}$
(SEQ ID NO: 275)

(249) $K^{197}Q^{198}L^{199}P^{200}H^{201}L^{202}K^{203}$
(SEQ ID NO: 84)

-continued (250) $K^{197}Q^{198}L^{199}P^{200}H^{201}L^{202}K^{203}V^{204}H^{205}$
(SEQ ID NO: 85)

(251) $K^{197}Q^{198}L^{199}P^{200}H^{201}L^{202}K^{203}V^{204}H^{205}L^{206}D^{207}V^{208}R^{209}G^{210}A^{211}K^{212}Q^{213}N^{214}P^{215}W^{216}R^{217}K^{218}N^{219}L^{220}C^{221}L^{222}L^{223}K^{224}K^{225}N^{226}V^{227}K^{228}S^{229}A^{230}K^{231}Q^{232}L^{233}P^{234}H^{235}$
(SEQ ID NO: 224)

(252) $H^{201}L^{202}K^{203}V^{204}H^{205}L^{206}D^{207}V^{208}R^{209}G^{210}A^{211}K^{212}$
(SEQ ID NO: 121)

(253) $H^{201}L^{202}K^{203}V^{204}H^{205}L^{206}D^{207}V^{208}R^{209}G^{210}A^{211}K^{212}Q^{213}N^{214}P^{215}W^{216}R^{217}K^{218}$
(SEQ ID NO: 225)

(254) $H^{201}L^{202}K^{203}V^{204}H^{205}L^{206}D^{207}V^{208}R^{209}G^{210}A^{211}K^{212}Q^{213}N^{214}P^{215}W^{216}R^{217}K^{218}N^{219}L^{220}C^{221}L^{222}L^{223}K^{224}$
(SEQ ID NO: 226)

(255) $H^{201}L^{202}K^{203}V^{204}H^{205}L^{206}D^{207}V^{208}R^{209}G^{210}A^{211}K^{212}Q^{213}N^{214}P^{215}W^{216}R^{217}K^{218}N^{219}L^{220}C^{221}L^{222}L^{223}K^{224}K^{225}$
(SEQ ID NO: 227)

(256) $H^{201}L^{202}K^{203}V^{204}H^{205}L^{206}D^{207}V^{208}R^{209}G^{210}A^{211}K^{212}Q^{213}N^{214}P^{215}W^{216}R^{217}K^{218}N^{219}L^{220}C^{221}L^{222}L^{223}K^{224}K^{225}N^{226}V^{227}K^{228}$
(SEQ ID NO: 228)

(257) $H^{201}L^{202}K^{203}V^{204}H^{205}L^{206}D^{207}V^{208}R^{209}G^{210}A^{211}K^{212}Q^{213}N^{214}P^{215}W^{216}R^{217}K^{218}N^{219}L^{220}C^{221}L^{222}L^{223}K^{224}K^{225}N^{226}V^{227}K^{228}S^{229}A^{230}K^{231}$
(SEQ ID NO: 229)

(258) $H^{201}L^{202}K^{203}V^{204}H^{205}L^{206}D^{207}V^{208}R^{209}G^{210}A^{211}K^{212}Q^{213}N^{214}P^{215}W^{216}R^{217}K^{218}N^{219}L^{220}C^{221}L^{222}L^{223}K^{224}K^{225}N^{226}V^{227}K^{228}S^{229}A^{230}K^{231}Q^{232}L^{233}P^{234}H^{235}L^{236}K^{237}$
(SEQ ID NO: 230)

(259) $H^{201}L^{202}K^{203}V^{204}H^{205}L^{206}D^{207}V^{208}R^{209}G^{210}A^{211}K^{212}Q^{213}N^{214}P^{215}W^{216}R^{217}K^{218}N^{219}L^{220}C^{221}L^{222}L^{223}K^{224}K^{225}N^{226}V^{227}K^{228}S^{229}A^{230}K^{231}Q^{232}L^{233}P^{234}H^{235}L^{236}K^{237}V^{238}L^{239}L^{240}D^{241}V^{242}R^{243}G^{244}A^{245}K^{246}$
(SEQ ID NO: 231)

(260) $K^{203}V^{204}H^{205}L^{206}D^{207}V^{208}R^{209}G^{210}A^{211}K^{212}$
(SEQ ID NO: 123)

(261) $K^{203}V^{204}H^{205}L^{206}D^{207}V^{208}R^{209}G^{210}A^{211}K^{212}Q^{213}N^{214}P^{215}W^{216}R^{217}K^{218}N^{219}L^{220}C^{221}L^{222}L^{223}K^{224}K^{225}N^{226}V^{227}K^{228}S^{229}A^{230}K^{231}Q^{232}L^{233}P^{234}H^{235}$
(SEQ ID NO: 232)

(262) $K^{203}V^{204}H^{205}L^{206}D^{207}V^{208}R^{209}G^{210}A^{211}K^{212}Q^{213}N^{214}P^{215}W^{216}R^{217}K^{218}N^{219}L^{220}C^{221}L^{222}L^{223}K^{224}K^{225}N^{226}V^{227}K^{228}S^{229}A^{230}K^{231}Q^{232}L^{233}P^{234}H^{235}L^{236}K^{237}V^{238}L^{239}L^{240}D^{241}V^{242}R^{243}G^{244}A^{245}K^{246}Q^{247}L^{248}P^{249}H^{250}$
(SEQ ID NO: 233)

(263) $H^{205}L^{206}D^{207}V^{208}R^{209}G^{210}A^{211}K^{212}Q^{213}N^{214}P^{215}W^{216}R^{217}K^{218}$
(SEQ ID NO: 234)

(264) $H^{205}L^{206}D^{207}V^{208}R^{209}G^{210}A^{211}K^{212}Q^{213}N^{214}P^{215}W^{216}R^{217}K^{218}N^{219}L^{220}C^{221}L^{222}L^{223}K^{224}$
(SEQ ID NO: 235)

(265) $H^{205}L^{206}D^{207}V^{208}R^{209}G^{210}A^{211}K^{212}Q^{213}N^{214}P^{215}W^{216}R^{217}K^{218}N^{219}L^{220}C^{221}L^{222}L^{223}K^{224}K^{225}$
(SEQ ID NO: 236)

(266) $H^{205}L^{206}D^{207}V^{208}R^{209}G^{210}A^{211}K^{212}Q^{213}N^{214}P^{215}W^{216}R^{217}K^{218}N^{219}L^{220}C^{221}L^{222}L^{223}K^{224}K^{225}N^{226}V^{227}K^{228}$
(SEQ ID NO: 237)

(267) $H^{205}L^{206}D^{207}V^{208}R^{209}G^{210}A^{211}K^{212}Q^{213}N^{214}P^{215}W^{216}R^{217}K^{218}N^{219}L^{220}C^{221}L^{222}L^{223}K^{224}K^{225}N^{226}V^{227}K^{228}S^{229}A^{230}K^{231}$
(SEQ ID NO: 238)

(268) $H^{205}L^{206}D^{207}V^{208}R^{209}G^{210}A^{211}K^{212}Q^{213}N^{214}P^{215}W^{216}R^{217}K^{218}N^{219}L^{220}C^{221}L^{222}L^{223}K^{224}K^{225}N^{226}V^{227}K^{228}S^{229}A^{230}K^{231}Q^{232}L^{233}P^{234}H^{235}L^{236}K^{237}$
(SEQ ID NO: 239)

(269) $H^{205}L^{206}D^{207}V^{208}R^{209}G^{210}A^{211}K^{212}Q^{213}N^{214}P^{215}W^{216}R^{217}K^{218}N^{219}L^{220}C^{221}L^{222}L^{223}K^{224}K^{225}N^{226}V^{227}K^{228}S^{229}A^{230}K^{231}Q^{232}L^{233}P^{234}H^{235}L^{236}K^{237}V^{238}L^{239}L^{240}D^{241}V^{242}R^{243}G^{244}A^{245}K^{246}$
(SEQ ID NO: 240)

(270) $H^{205}L^{206}D^{207}V^{208}R^{209}G^{210}A^{211}K^{212}Q^{213}N^{214}P^{215}W^{216}R^{217}K^{218}N^{219}L^{220}C^{221}L^{222}L^{223}K^{224}K^{225}N^{226}V^{227}K^{228}S^{229}A^{230}K^{231}Q^{232}L^{233}P^{234}H^{235}L^{236}K^{237}V^{238}L^{239}L^{240}D^{241}V^{242}R^{243}G^{244}A^{245}K^{246}Q^{247}L^{248}P^{249}H^{250}L^{251}K^{252}$
(SEQ ID NO: 241)

(271) $K^{212}Q^{213}N^{214}P^{215}W^{216}R^{217}K^{218}N^{219}L^{220}C^{221}L^{222}L^{223}K^{224}K^{225}N^{226}V^{227}K^{228}S^{229}A^{230}K^{231}Q^{232}L^{233}P^{234}H^{235}$
(SEQ ID NO: 63)

(272) $K^{212}Q^{213}N^{214}P^{215}W^{216}R^{217}K^{218}N^{219}L^{220}C^{221}L^{222}L^{223}K^{224}K^{225}N^{226}V^{227}K^{228}S^{229}A^{230}K^{231}Q^{232}L^{233}P^{234}H^{235}L^{236}K^{237}V^{238}L^{239}L^{240}D^{241}V^{242}R^{243}G^{244}A^{245}K^{246}Q^{247}L^{248}P^{249}H^{250}$
(SEQ ID NO: 242)

-continued (273) $K^{218}N^{219}L^{220}C^{221}L^{222}L^{223}K^{224}K^{225}N^{226}V^{227}K^{228}S^{229}A^{230}K^{231}Q^{232}L^{233}P^{234}H^{235}L^{236}K^{237}V^{238}L^{239}L^{240}D^{241}V^{242}R^{243}G^{244}A^{245}K^{246}Q^{247}L^{248}P^{249}H^{250}$
(SEQ ID NO: 243)

(274) $K^{218}N^{219}L^{220}C^{221}L^{222}L^{223}K^{224}K^{225}N^{226}V^{227}K^{228}S^{229}A^{230}K^{231}Q^{232}L^{233}P^{234}H^{235}L^{236}K^{237}V^{238}L^{239}L^{240}D^{241}V^{242}R^{243}G^{244}A^{245}K^{246}Q^{247}L^{248}P^{249}H^{250}L^{251}K^{252}V^{253}L^{254}L^{255}D^{256}V^{257}R^{258}G^{259}A^{260}K^{261}Q^{262}L^{263}P^{264}H^{265}$
(SEQ ID NO: 244)

(275) $K^{218}N^{219}L^{220}C^{221}L^{222}L^{223}K^{224}K^{225}N^{226}V^{227}K^{228}S^{229}A^{230}K^{231}Q^{232}L^{233}P^{234}H^{235}$
(SEQ ID NO: 68)

(276) $K^{224}K^{225}N^{226}V^{227}K^{228}S^{229}A^{230}K^{231}Q^{232}L^{233}P^{234}H^{235}$
(SEQ ID NO: 13)

(277) $K^{224}K^{225}N^{226}V^{227}K^{228}S^{229}A^{230}K^{231}Q^{232}L^{233}P^{234}H^{235}L^{236}K^{237}V^{238}L^{239}L^{240}D^{241}V^{242}R^{243}G^{244}A^{245}K^{246}Q^{247}L^{248}P^{249}H^{250}$
(SEQ ID NO: 275)

(278) $K^{224}K^{225}N^{226}V^{227}K^{228}S^{229}A^{230}K^{231}Q^{232}L^{233}P^{234}H^{235}L^{236}K^{237}V^{238}L^{239}L^{240}D^{241}V^{242}R^{243}G^{244}A^{245}K^{246}Q^{247}L^{248}P^{249}H^{250}L^{251}K^{252}V^{253}L^{254}L^{255}D^{256}V^{257}R^{258}G^{259}A^{260}K^{261}Q^{262}L^{263}P^{264}H^{265}$
(SEQ ID NO: 245)

(279) $K^{225}N^{226}V^{227}K^{228}S^{229}A^{230}K^{231}Q^{232}L^{233}P^{234}H^{235}$
(SEQ ID NO: 75)

(280) $K^{225}N^{226}V^{227}K^{228}S^{229}A^{230}K^{231}Q^{232}L^{233}P^{234}H^{235}L^{236}K^{237}V^{238}L^{239}L^{240}D^{241}V^{242}R^{243}G^{244}A^{245}K^{246}Q^{247}L^{248}P^{249}H^{250}$
(SEQ ID NO: 247)

(281) $K^{225}N^{226}V^{227}K^{228}S^{229}A^{230}K^{231}Q^{232}L^{233}P^{234}H^{235}L^{236}K^{237}V^{238}L^{239}L^{240}D^{241}V^{242}R^{243}G^{244}A^{245}K^{246}Q^{247}L^{248}P^{249}H^{250}L^{251}K^{252}V^{253}L^{254}L^{255}D^{256}V^{257}R^{258}G^{259}A^{260}K^{261}Q^{262}L^{263}P^{264}H^{265}$
(SEQ ID NO: 248)

(282) $K^{228}S^{229}A^{230}K^{231}Q^{232}L^{233}P^{234}H^{235}L^{236}K^{237}$
(SEQ ID NO: 14)

(283) $K^{228}S^{229}A^{230}K^{231}Q^{232}L^{233}P^{234}H^{235}L^{236}K^{237}V^{238}L^{239}L^{240}D^{241}V^{242}R^{243}G^{244}A^{245}K^{246}Q^{247}L^{248}P^{249}H^{250}$
(SEQ ID NO: 250)

(284) $K^{228}S^{229}A^{230}K^{231}Q^{232}L^{233}P^{234}H^{235}L^{236}K^{237}V^{238}L^{239}L^{240}D^{241}V^{242}R^{243}G^{244}A^{245}K^{246}Q^{247}L^{248}P^{249}H^{250}L^{251}K^{252}V^{253}L^{254}L^{255}D^{256}V^{257}R^{258}G^{259}A^{260}K^{261}Q^{262}L^{263}P^{264}H^{265}$
(SEQ ID NO: 251)

(285) $K^{231}Q^{232}L^{233}P^{234}H^{235}L^{236}K^{237}$
(SEQ ID NO: 84)

(286) $K^{231}Q^{232}L^{233}P^{234}H^{235}L^{236}K^{237}V^{238}L^{239}L^{240}D^{241}V^{242}R^{243}G^{244}A^{245}K^{246}Q^{247}L^{248}P^{249}H^{250}$
(SEQ ID NO: 253)

(287) $K^{231}Q^{232}L^{233}P^{234}H^{235}L^{236}K^{237}V^{238}L^{239}L^{240}D^{241}V^{242}R^{243}G^{244}A^{245}K^{246}Q^{247}L^{248}P^{249}H^{250}L^{251}K^{252}V^{253}L^{254}L^{255}D^{256}V^{257}R^{258}G^{259}A^{260}K^{261}Q^{262}L^{263}P^{264}H^{265}$
(SEQ ID NO: 254)

(288) $H^{235}L^{236}K^{237}V^{238}L^{239}L^{240}D^{241}V^{242}R^{243}G^{244}A^{245}K^{246}$
(SEQ ID NO: 256)

(289) $H^{235}L^{236}K^{237}V^{238}L^{239}L^{240}D^{241}V^{242}R^{243}G^{244}A^{245}K^{246}Q^{247}L^{248}P^{249}H^{250}L^{251}K^{252}$
(SEQ ID NO: 257)

(290) $H^{235}L^{236}K^{237}V^{238}L^{239}L^{240}D^{241}V^{242}R^{243}G^{244}A^{245}K^{246}Q^{247}L^{248}P^{249}H^{250}L^{251}K^{252}V^{253}L^{254}L^{255}D^{256}V^{257}R^{258}G^{259}A^{260}K^{261}$
(SEQ ID NO: 258)

(291) $H^{235}L^{236}K^{237}V^{238}L^{239}L^{240}D^{241}V^{242}R^{243}G^{244}A^{245}K^{246}Q^{247}L^{248}P^{249}H^{250}L^{251}K^{252}V^{253}L^{254}L^{255}D^{256}V^{257}R^{258}G^{259}A^{260}K^{261}Q^{262}L^{263}P^{264}H^{265}L^{266}K^{267}$
(SEQ ID NO: 259)

(292) $H^{235}L^{236}K^{237}V^{238}L^{239}L^{240}D^{241}V^{242}R^{243}G^{244}A^{245}K^{246}Q^{247}L^{248}P^{249}H^{250}L^{251}K^{252}V^{253}L^{254}L^{255}D^{256}V^{257}R^{258}G^{259}A^{260}K^{261}Q^{262}L^{263}P^{264}H^{265}L^{266}K^{267}V^{268}L^{269}L^{270}D^{271}V^{272}R^{273}G^{274}A^{275}K^{276}$
(SEQ ID NO: 274)

(293) $H^{235}L^{236}K^{237}V^{238}L^{239}L^{240}D^{241}V^{242}R^{243}G^{244}A^{245}K^{246}Q^{247}L^{248}P^{249}H^{250}L^{251}K^{252}V^{253}L^{254}L^{255}D^{256}V^{257}R^{258}G^{259}A^{260}K^{261}Q^{262}L^{263}P^{264}H^{265}L^{266}K^{267}V^{268}L^{269}L^{270}D^{271}V^{272}R^{273}G^{274}A^{275}K^{276}Q^{277}N^{278}P^{279}W^{280}R^{281}K^{282}$
(SEQ ID NO: 275)

(294) $K^{237}V^{238}L^{239}L^{240}D^{241}V^{242}R^{243}G^{244}A^{245}K^{246}Q^{247}L^{248}P^{249}H^{250}$
(SEQ ID NO: 262)

(295) $K^{237}V^{238}L^{239}L^{240}D^{241}V^{242}R^{243}G^{244}A^{245}K^{246}Q^{247}L^{248}P^{249}H^{250}L^{251}K^{252}V^{253}L^{254}L^{255}D^{256}V^{257}R^{258}G^{259}A^{260}K^{261}Q^{262}L^{263}P^{264}H^{265}$
(SEQ ID NO: 263)

-continued (296) $K^{246}Q^{247}L^{248}P^{249}H^{250}L^{251}K^{252}$
(SEQ ID NO: 84)

(297) $K^{246}Q^{247}L^{248}P^{249}H^{250}L^{251}K^{252}V^{253}L^{254}L^{255}D^{256}V^{257}R^{258}G^{259}A^{260}K^{261}Q^{262}L^{263}P^{264}H^{265}$
(SEQ ID NO: 253)

Replikin Sequences Located in Carboxy-Terminal Portion of Peptide (298) $H^{250}L^{251}K^{252}V^{253}L^{254}L^{255}D^{256}V^{257}R^{258}G^{259}A^{260}K^{261}$
(SEQ ID NO: 256)

(299) $H^{250}L^{251}K^{252}V^{253}L^{254}L^{255}D^{256}V^{257}R^{258}G^{259}A^{260}K^{261}Q^{262}L^{263}P^{264}H^{265}L^{266}K^{267}$
(SEQ ID NO: 257)

(300) $H^{250}L^{251}K^{252}V^{253}L^{254}L^{255}D^{256}V^{257}R^{258}G^{259}A^{260}K^{261}Q^{262}L^{263}P^{264}H^{265}L^{266}K^{267}V^{268}L^{269}L^{270}D^{271}V^{272}R^{273}$
$G^{274}A^{275}K^{276}$
(SEQ ID NO: 258)

(301) $H^{250}L^{251}K^{252}V^{253}L^{254}L^{255}D^{256}V^{257}R^{258}G^{259}A^{260}K^{261}Q^{262}L^{263}P^{264}H^{265}L^{266}K^{267}V^{268}L^{269}L^{270}D^{271}V^{272}R^{273}$
$G^{274}A^{275}K^{276}Q^{277}N^{278}P^{279}W^{280}R^{281}K^{282}$
(SEQ ID NO: 300)

(302) $H^{250}L^{251}K^{252}V^{253}L^{254}L^{255}D^{256}V^{257}R^{258}G^{259}A^{260}K^{261}Q^{262}L^{263}P^{264}H^{265}L^{266}K^{267}V^{268}L^{269}L^{270}D^{271}V^{272}R^{273}$
$G^{274}A^{275}K^{276}Q^{277}N^{278}P^{279}W^{280}R^{281}K^{282}N^{283}L^{284}C^{285}L^{286}L^{287}K^{288}$
(SEQ ID NO: 302)

(303) $H^{250}L^{251}K^{252}V^{253}L^{254}L^{255}D^{256}V^{257}R^{258}G^{259}A^{260}K^{261}Q^{262}L^{263}P^{264}H^{265}L^{266}K^{267}V^{268}L^{269}L^{270}D^{271}V^{272}R^{273}$
$G^{274}A^{275}K^{276}Q^{277}N^{278}P^{279}W^{280}R^{281}K^{282}N^{283}L^{284}C^{285}L^{286}L^{287}K^{288}K^{289}$
(SEQ ID NO: 303)

(304) $H^{250}L^{251}K^{252}V^{253}L^{254}L^{255}D^{256}V^{257}R^{258}G^{259}A^{260}K^{261}Q^{262}L^{263}P^{264}H^{265}L^{266}K^{267}V^{268}L^{269}L^{270}D^{271}V^{272}R^{273}$
$G^{274}A^{275}K^{276}Q^{277}N^{278}P^{279}W^{280}R^{281}K^{282}N^{283}L^{284}C^{285}L^{286}L^{287}K^{288}K^{289}N^{290}V^{291}K^{292}$
(SEQ ID NO: 299)

(305) $H^{250}L^{251}K^{252}V^{253}L^{254}L^{255}D^{256}V^{257}R^{258}G^{259}A^{260}K^{261}Q^{262}L^{263}P^{264}H^{265}L^{266}K^{267}V^{268}L^{269}L^{270}D^{271}V^{272}R^{273}$
$G^{274}A^{275}K^{276}Q^{277}N^{278}P^{279}W^{280}R^{281}K^{282}N^{283}L^{284}C^{285}L^{286}L^{287}K^{288}K^{289}N^{290}V^{291}K^{292}S^{293}A^{294}K^{295}$
(SEQ ID NO: 301)

(306) $K^{252}V^{253}L^{254}L^{255}D^{256}V^{257}R^{258}G^{259}A^{260}K^{261}Q^{262}L^{263}P^{264}H^{265}L^{266}K^{267}V^{268}L^{269}L^{270}D^{271}V^{272}R^{273}G^{274}A^{275}$
$K^{276}Q^{277}N^{278}P^{279}W^{280}R^{281}K^{282}N^{283}L^{284}C^{285}L^{286}L^{287}K^{288}K^{289}N^{290}V^{291}K^{292}S^{293}A^{294}K^{295}Q^{296}L^{297}P^{298}H^{299}$
(SEQ ID NO: 304)

(307) $K^{252}V^{253}L^{254}L^{255}D^{256}V^{257}R^{258}G^{259}A^{260}K^{261}Q^{262}L^{263}P^{264}H^{265}$
(SEQ ID NO: 262)

(308) $K^{261}Q^{262}L^{263}P^{264}H^{265}L^{266}K^{267}V^{268}L^{269}L^{270}D^{271}V^{272}R^{273}G^{274}A^{275}K^{276}Q^{277}N^{278}P^{279}W^{280}R^{281}K^{282}N^{283}L^{284}$
$C^{285}L^{286}L^{287}K^{288}K^{289}N^{290}V^{291}K^{292}S^{293}A^{294}K^{295}Q^{296}L^{297}P^{298}H^{299}$
(SEQ ID NO: 305)

(309) $K^{261}Q^{262}L^{263}P^{264}H^{265}L^{266}K^{267}$
(SEQ ID NO: 84)

(310) $H^{265}L^{266}K^{267}V^{268}L^{269}L^{270}D^{271}V^{272}R^{273}G^{274}A^{275}5K^{276}$
(SEQ ID NO: 256)

(311) $H^{265}L^{266}K^{267}V^{268}L^{269}L^{270}D^{271}V^{272}R^{273}G^{274}A^{275}K^{276}Q^{277}N^{278}P^{279}W^{280}R^{281}K^{282}$
(SEQ ID NO: 307)

(312) $H^{265}L^{266}K^{267}V^{268}L^{269}L^{270}D^{271}V^{272}R^{273}G^{274}A^{275}K^{276}Q^{277}N^{278}P^{279}W^{280}R^{281}K^{282}N^{283}L^{284}C^{285}L^{286}L^{287}K^{288}$
(SEQ ID NO: 309)

(313) $H^{265}L^{266}K^{267}V^{268}L^{269}L^{270}D^{271}V^{272}R^{273}G^{274}A^{275}K^{276}Q^{277}N^{278}P^{279}W^{280}R^{281}K^{282}N^{283}L^{284}C^{285}L^{286}L^{287}K^{288}$
$K^{289}$
(SEQ ID NO: 310)

(314) $H^{265}L^{266}K^{267}V^{268}L^{269}L^{270}D^{271}V^{272}R^{273}G^{274}A^{275}K^{276}Q^{277}N^{278}P^{279}W^{280}R^{281}K^{282}N^{283}L^{284}C^{285}L^{286}L^{287}K^{288}$
$K^{289}N^{290}V^{291}K^{292}S^{293}A^{294}K^{295}Q^{296}L^{297}P^{298}H^{299}L^{300}K^{301}$
(SEQ ID NO: 311)

(315) $H^{265}L^{266}K^{267}V^{268}L^{269}L^{270}D^{271}V^{272}R^{273}G^{274}A^{275}K^{276}Q^{277}N^{278}P^{279}W^{280}R^{281}K^{282}N^{283}L^{284}C^{285}L^{286}L^{287}K^{288}$
$K^{289}N^{290}V^{291}K^{292}$
(SEQ ID NO: 306)

(316) $H^{265}L^{266}K^{267}V^{268}L^{269}L^{270}D^{271}V^{272}R^{273}G^{274}A^{275}K^{276}Q^{277}N^{278}P^{279}W^{280}R^{281}K^{282}N^{283}L^{284}C^{285}L^{286}L^{287}K^{288}$
$K^{289}N^{290}V^{291}K^{292}S^{293}A^{294}K^{295}$
(SEQ ID NO: 308)

(317) $H^{265}L^{266}K^{267}V^{268}L^{269}L^{270}D^{271}V^{272}R^{273}G^{274}A^{275}K^{276}Q^{277}N^{278}P^{279}W^{280}R^{281}K^{282}N^{283}L^{284}C^{285}L^{286}L^{287}K^{288}$
$K^{289}N^{290}V^{291}K^{292}S^{293}A^{294}K^{295}Q^{296}L^{297}P^{298}H^{299}L^{300}K^{301}V^{302}L^{303}L^{304}D^{305}V^{306}R^{307}G^{308}A^{309}K^{310}$
(SEQ ID NO: 312)

-continued (318) $K^{267}V^{268}L^{269}L^{270}D^{271}V^{272}R^{273}G^{274}A^{275}K^{276}Q^{277}N^{278}P^{279}W^{280}R^{281}K^{282}N^{283}L^{284}C^{285}L^{286}L^{287}K^{288}K^{289}N^{290}$
$V^{291}K^{292}S^{293}A^{294}K^{295}Q^{296}L^{297}P^{298}H^{299}$
(SEQ ID NO: 313)

(319) $K^{267}V^{268}L^{269}L^{270}D^{271}V^{272}R^{273}G^{274}A^{275}K^{276}Q^{277}N^{278}P^{279}W^{280}R^{281}K^{282}N^{283}L^{284}C^{285}L^{286}L^{287}K^{288}K^{289}N^{290}$
$V^{291}K^{292}S^{293}A^{294}K^{295}Q^{296}L^{297}P^{298}H^{299}L^{300}K^{301}V^{302}L^{303}L^{304}D^{305}V^{306}R^{307}G^{308}A^{309}K^{310}Q^{311}L^{312}P^{313}H^{314}$
(SEQ ID NO: 314)

(320) $K^{276}Q^{277}N^{278}P^{279}W^{280}R^{281}K^{282}N^{283}L^{284}C^{285}L^{286}L^{287}K^{288}K^{289}N^{290}V^{291}K^{292}S^{293}A^{294}K^{295}Q^{296}L^{297}P^{298}H^{299}$
(SEQ ID NO: 63)

(321) $K^{276}Q^{277}N^{278}P^{279}W^{280}R^{281}K^{282}N^{283}L^{284}C^{285}L^{286}L^{287}K^{288}K^{289}N^{290}V^{291}K^{292}S^{293}A^{294}K^{295}Q^{296}L^{297}P^{298}H^{299}$
$L^{300}K^{301}V^{302}L^{303}L^{304}D^{305}V^{306}R^{307}G^{308}A^{309}K^{310}Q^{311}L^{312}P^{313}H^{314}$
(SEQ ID NO: 242)

(322) $K^{276}Q^{277}N^{278}P^{279}W^{280}R^{281}K^{282}N^{283}L^{284}C^{285}L^{286}L^{287}K^{288}K^{289}N^{290}V^{291}K^{292}S^{293}A^{294}K^{295}Q^{296}L^{297}P^{298}H^{299}$
$L^{300}K^{301}V^{302}L^{303}L^{304}D^{305}V^{306}R^{307}G^{308}A^{309}K^{310}Q^{311}L^{312}P^{313}H^{314}L^{315}K^{316}V^{317}H^{318}$
(SEQ ID NO: 315)

(323) $K^{282}N^{283}L^{284}C^{285}L^{286}L^{287}K^{288}K^{289}N^{290}V^{291}K^{292}S^{293}A^{294}K^{295}Q^{296}L^{297}P^{298}H^{299}$
(SEQ ID NO: 68)

(324) $K^{282}N^{283}L^{284}C^{285}L^{286}L^{287}K^{288}K^{289}N^{290}V^{291}K^{292}S^{293}A^{294}K^{295}Q^{296}L^{297}P^{298}H^{299}L^{300}K^{301}V^{302}L^{303}L^{304}D^{305}$
$V^{306}R^{307}G^{308}A^{309}K^{310}Q^{311}L^{312}P^{313}H^{314}$
(SEQ ID NO: 243)

(325) $K^{282}N^{283}L^{284}C^{285}L^{286}L^{287}K^{288}K^{289}N^{290}V^{291}K^{292}S^{293}A^{294}K^{295}Q^{296}L^{297}P^{298}H^{299}L^{300}K^{301}V^{302}L^{303}L^{304}D^{305}$
$V^{306}R^{307}G^{308}A^{309}K^{310}Q^{311}L^{312}P^{313}H^{314}L^{315}K^{316}V^{317}H^{318}$
(SEQ ID NO: 316)

(326) $K^{288}K^{289}N^{290}V^{291}K^{292}S^{293}A^{294}K^{295}Q^{296}L^{297}P^{298}H^{299}$
(SEQ ID NO: 13)

(327) $K^{288}K^{289}N^{290}V^{291}K^{292}S^{293}A^{294}K^{295}Q^{296}L^{297}P^{298}H^{299}L^{300}K^{301}V^{302}L^{303}L^{304}D^{305}V^{306}R^{307}G^{308}A^{309}K^{310}Q^{311}$
$L^{312}P^{313}H^{314}$
(SEQ ID NO: 3)

(328) $K^{288}K^{289}N^{290}V^{291}K^{292}S^{293}A^{294}K^{295}Q^{296}L^{297}P^{298}H^{299}L^{300}K^{301}V^{302}L^{303}L^{304}D^{305}V^{306}R^{307}G^{308}A^{309}K^{310}Q^{311}$
$L^{312}P^{313}H^{314}L^{315}K^{316}V^{317}H^{318}$
(SEQ ID NO: 4)

(329) $K^{289}N^{290}V^{291}K^{292}S^{293}A^{294}K^{295}Q^{296}L^{297}P^{298}H^{299}$
(SEQ ID NO: 75)

(330) $K^{289}N^{290}V^{291}K^{292}S^{293}A^{294}K^{295}Q^{296}L^{297}P^{298}H^{299}L^{300}K^{301}V^{302}L^{303}L^{304}D^{305}V^{306}R^{307}G^{308}A^{309}K^{310}Q^{311}L^{312}$
$P^{313}H^{314}$
(SEQ ID NO: 247)

(331) $K^{289}N^{290}V^{291}K^{292}S^{293}A^{294}K^{295}Q^{296}L^{297}P^{298}H^{299}L^{300}K^{301}V^{302}L^{303}L^{304}D^{305}V^{306}R^{307}G^{308}A^{309}K^{310}Q^{311}L^{312}$
$P^{313}H^{314}L^{315}K^{316}V^{317}H^{318}$
(SEQ ID NO: 318)

(332) $K^{292}S^{293}A^{294}K^{295}Q^{296}L^{297}P^{298}H^{299}L^{300}K^{301}$
(SEQ ID NO: 14)

(333) $K^{292}S^{293}A^{294}K^{295}Q^{296}L^{297}P^{298}H^{299}L^{300}K^{301}V^{302}L^{303}L^{304}D^{305}V^{306}R^{307}G^{308}A^{309}K^{310}Q^{311}L^{312}P^{313}H^{314}$
(SEQ ID NO: 250)

(334) $K^{292}S^{293}A^{294}K^{295}Q^{296}L^{297}P^{298}H^{299}L^{300}K^{301}V^{302}L^{303}L^{304}D^{305}V^{306}R^{307}G^{308}A^{309}K^{310}Q^{311}L^{312}P^{313}H^{314}L^{315}$
$K^{316}V^{317}H^{318}$
(SEQ ID NO: 319)

(335) $K^{295}Q^{296}L^{297}P^{298}H^{299}L^{300}K^{301}$
(SEQ ID NO: 84)

(336) $K^{295}Q^{296}L^{297}P^{298}H^{299}L^{300}K^{301}V^{302}L^{303}L^{304}D^{305}V^{306}R^{307}G^{308}A^{309}K^{310}Q^{311}L^{312}P^{313}H^{314}$
(SEQ ID NO: 253)

(337) $K^{295}Q^{296}L^{297}P^{298}H^{299}L^{300}K^{301}V^{302}L^{303}L^{304}D^{305}V^{306}R^{307}G^{308}A^{309}K^{310}Q^{311}L^{312}P^{313}H^{314}L^{315}K^{316}V^{317}H^{318}$
(SEQ ID NO: 265)

(338) $K^{295}Q^{296}L^{297}P^{298}H^{299}L^{300}K^{301}V^{302}L^{303}L^{304}D^{305}V^{306}R^{307}G^{308}A^{309}K^{310}Q^{311}L^{312}P^{313}H^{314}L^{315}K^{316}V^{317}H^{318}$
$L^{319}D^{320}V^{321}R^{322}G^{323}A^{324}K^{325}Q^{326}Q^{327}Q^{328}Q^{329}L^{330}C^{331}L^{332}P^{333}L^{334}K^{335}T^{336}I^{337}S^{338}T^{339}S^{340}F^{341}T^{342}H^{343}$
(SEQ ID NO: 320)

(339) $H^{299}L^{300}K^{301}V^{302}L^{303}L^{304}D^{305}V^{306}R^{307}G^{308}A^{309}K^{310}$
(SEQ ID NO: 256)

(340) $H^{299}L^{300}K^{301}V^{302}L^{303}L^{304}D^{305}V^{306}R^{307}G^{308}A^{309}K^{310}Q^{311}L^{312}P^{313}H^{314}L^{315}K^{316}$
(SEQ ID NO: 257)

-continued (341) $H^{299}L^{300}K^{301}V^{302}L^{303}L^{304}D^{305}V^{306}R^{307}G^{308}A^{309}K^{310}Q^{311}L^{312}P^{313}H^{314}L^{315}K^{316}V^{317}H^{318}L^{319}D^{320}V^{321}R^{322}G^{323}A^{324}K^{325}$
(SEQ ID NO: 266)

(342) $H^{299}L^{300}K^{301}V^{302}L^{303}L^{304}D^{305}V^{306}R^{307}G^{308}A^{309}K^{310}Q^{311}L^{312}P^{313}H^{314}L^{315}K^{316}V^{317}H^{318}L^{319}D^{320}V^{321}R^{322}G^{323}A^{324}K^{325}Q^{326}Q^{327}Q^{328}Q^{329}L^{330}C^{331}L^{332}P^{333}L^{334}K^{335}$
(SEQ ID NO: 321)

(343) $K^{301}V^{302}L^{303}L^{304}D^{305}V^{306}R^{307}G^{308}A^{309}K^{310}Q^{311}L^{312}P^{313}H^{314}$
(SEQ ID NO: 262)

(344) $K^{301}V^{302}L^{303}L^{304}D^{305}V^{306}R^{307}G^{308}A^{309}K^{310}Q^{311}L^{312}P^{313}H^{314}L^{315}K^{316}V^{317}H^{318}$
(SEQ ID NO: 272)

(345) $K^{301}V^{302}L^{303}L^{304}D^{305}V^{306}R^{307}G^{308}A^{309}K^{310}Q^{311}L^{312}P^{313}H^{314}L^{315}K^{316}V^{317}H^{318}L^{319}D^{320}V^{321}R^{322}G^{323}A^{324}K^{325}Q^{326}Q^{327}Q^{328}Q^{329}L^{330}C^{331}L^{332}P^{333}L^{334}K^{335}T^{336}I^{337}S^{338}T^{339}S^{340}F^{341}T^{342}H^{343}$
(SEQ ID NO: 322)

(346) $K^{310}Q^{311}L^{312}P^{313}H^{314}L^{315}K^{316}$
(SEQ ID NO: 84)

(347) $K^{310}Q^{311}L^{312}P^{313}H^{314}L^{315}K^{316}V^{317}H^{318}$
(SEQ ID NO: 85)

(348) $K^{310}Q^{311}L^{312}P^{313}H^{314}L^{315}K^{316}V^{317}H^{318}L^{319}D^{320}V^{321}R^{322}G^{323}A^{324}K^{325}Q^{326}Q^{327}Q^{328}Q^{329}L^{330}C^{331}L^{332}P^{333}L^{334}K^{335}T^{336}I^{337}S^{338}T^{339}S^{340}F^{341}T^{342}H^{343}$
(SEQ ID NO: 323)

(349) $K^{310}Q^{311}L^{312}P^{313}H^{314}L^{315}K^{316}V^{317}H^{318}L^{319}D^{320}V^{321}R^{322}G^{323}A^{324}K^{325}Q^{326}Q^{327}Q^{328}Q^{329}L^{330}C^{331}L^{332}P^{333}L^{334}K^{335}T^{336}I^{337}S^{338}T^{339}S^{340}F^{341}T^{342}H^{343}L^{344}L^{345}L^{346}C^{347}L^{348}Y^{349}M^{350}E^{351}Y^{352}G^{353}K^{354}H^{355}$
(SEQ ID NO: 324)

(350) $H^{314}L^{315}K^{316}V^{317}H^{318}L^{319}D^{320}V^{321}R^{322}G^{323}A^{324}K^{325}$
(SEQ ID NO: 121)

(351) $H^{314}L^{315}K^{316}V^{317}H^{318}L^{319}D^{320}V^{321}R^{322}G^{323}A^{324}K^{325}Q^{326}Q^{327}Q^{328}Q^{329}L^{330}C^{331}L^{332}P^{333}L^{334}K^{335}$
(SEQ ID NO: 325)

(352) $H^{314}L^{315}K^{316}V^{317}H^{318}L^{319}D^{320}V^{321}R^{322}G^{323}A^{324}K^{325}Q^{326}Q^{327}Q^{328}Q^{329}L^{330}C^{331}L^{332}P^{333}L^{334}K^{335}T^{336}I^{337}S^{338}T^{339}S^{340}F^{341}T^{342}H^{343}L^{344}L^{345}L^{346}C^{347}L^{348}Y^{349}M^{350}E^{351}Y^{352}G^{353}K^{354}H^{355}Q^{356}N^{357}L^{358}Q^{359}V^{360}K^{361}$
(SEQ ID NO: 326)

(353) $K^{316}V^{317}H^{318}L^{319}D^{320}V^{321}R^{322}G^{323}A^{324}K^{325}Q^{326}Q^{327}Q^{328}Q^{329}L^{330}C^{331}L^{332}P^{333}L^{334}K^{335}T^{336}I^{337}S^{338}T^{339}S^{340}F^{341}T^{342}H^{343}L^{344}L^{345}L^{346}C^{347}L^{348}Y^{349}M^{350}E^{351}Y^{352}G^{353}K^{354}H^{355}$
(SEQ ID NO: 328)

(354) $K^{316}V^{317}H^{318}L^{319}D^{320}V^{321}R^{322}G^{323}A^{324}K^{325}$
(SEQ ID NO: 123)

(355) $K^{316}V^{317}H^{318}L^{319}D^{320}V^{321}R^{322}G^{323}A^{324}K^{325}Q^{326}Q^{327}Q^{328}Q^{329}L^{330}C^{331}L^{332}P^{333}L^{334}K^{335}T^{336}I^{337}S^{338}T^{339}S^{340}F^{341}T^{342}H^{343}$
(SEQ ID NO: 327)

(356) $H^{318}L^{319}D^{320}V^{321}R^{322}G^{323}A^{324}K^{325}Q^{326}Q^{327}Q^{328}Q^{329}L^{330}C^{331}L^{332}P^{333}L^{334}K^{335}$
(SEQ ID NO: 329)

(357) $H^{318}L^{319}D^{320}V^{321}R^{322}G^{323}A^{324}K^{325}Q^{326}Q^{327}Q^{328}Q^{329}L^{330}C^{331}L^{332}P^{333}L^{334}K^{335}T^{336}I^{337}S^{338}T^{339}S^{340}F^{341}T^{342}H^{343}L^{344}L^{345}L^{346}C^{347}L^{348}Y^{349}M^{350}E^{351}Y^{352}G^{353}K^{354}H^{355}Q^{356}N^{357}L^{358}Q^{359}V^{360}K^{361}$
(SEQ ID NO: 330)

(358) $K^{325}Q^{326}Q^{327}Q^{328}Q^{329}L^{330}C^{331}L^{332}P^{333}L^{334}K^{335}T^{336}I^{337}S^{338}T^{339}S^{340}F^{341}T^{342}H^{343}$
(SEQ ID NO: 331)

(359) $K^{325}Q^{326}Q^{327}Q^{328}Q^{329}L^{330}C^{331}L^{332}P^{333}L^{334}K^{335}T^{336}I^{337}S^{338}T^{339}S^{340}F^{341}T^{342}H^{343}L^{344}L^{345}L^{346}C^{347}L^{348}Y^{349}M^{350}E^{351}Y^{352}G^{353}K^{354}H^{355}$
(SEQ ID NO: 332)

(360) $H^{343}L^{344}L^{345}L^{346}C^{347}L^{348}Y^{349}M^{350}E^{351}Y^{352}G^{353}K^{354}H^{355}Q^{356}N^{357}L^{358}Q^{359}V^{360}K^{361}$
(SEQ ID NO: 333)

(361) $K^{354}H^{355}Q^{356}N^{357}L^{358}Q^{359}V^{360}K^{361}$
(SEQ ID NO: 334)

Example 3

Determination of Low Replikin Concentrations in 2005 and 2007 Isolates of WSSV from Accession Nos. AAW88445 and ABS00973

In 2006 and 2007 White Spot Syndrome Virus (WSSV) has been observed to be dormant in shrimp. This continued decline of WSSV into "quiescent" or "dormant" levels in 2006-2007 is demonstrated in mean Replikin concentrations for viruses isolated during 2005-2007 that are very low as compared to years wherein the virus demonstrated greater virulence, such as 2001. See Table 4 in Example 4 below. The continued quiescence in WSSV in 2007 may be contrasted with an observed rising of Replikin concentration in Taura Syndrome Virus Replikin during this period.

As may be seen from the analysis below, Accession Nos. AAW88445 and ABS00973 have low observed Replikin concentrations. ABS00973 contains a single Replikin sequence in the entire disclosed amino acid sequence of 240 residues. The single Replikin sequence is underlined. The Replikin concentration of Accession No. ABS00973 is an inordinately low 0.5.

Replikin Analysis
PubMed Code: AAW88445
Description:
Isolated Year: 2005
Source: Shrimp White Spot Syndrome Virus $M^{1}S^{2}N^{3}G^{4}A^{5}T^{6}I^{7}S^{8}D^{9}E^{10}R^{11}L^{12}I^{13}L^{14}I^{15}L^{16}D^{17}K^{18}I^{19}V^{20}E^{21}R^{22}R^{23}G^{24}V^{25}S^{26}N^{27}L^{28}S^{29}E^{30}L^{31}L^{32}I^{33}H^{34}P^{35}I^{36}T^{37}$ $K^{38}H^{39}I^{40}N^{41}E^{42}L^{43}L^{44}K^{45}N^{46}T^{47}V^{48}R^{49}H^{50}G^{51}D^{52}R^{53}V^{54}Y^{55}M^{56}K^{57}D^{58}A^{59}E^{60}L^{61}D^{62}V^{63}R^{64}S^{65}R^{66}L^{67}E^{68}D^{69}I^{70}K^{71}$ $K^{72}D^{73}C^{74}V^{75}L^{76}K^{77}A^{78}I^{79}E^{80}K^{81}Q^{82}G^{83}I^{84}D^{85}V^{86}R^{87}Q^{88}I^{89}I^{90}T^{91}D^{92}Y^{93}L^{94}A^{95}K^{96}R^{97}K^{98}L^{99}T^{100}Q^{101}N^{102}L^{103}$ $V^{104}H^{105}W^{106}Y^{107}R^{108}P^{109}P^{110}I^{111}S^{112}C^{113}T^{114}D^{115}I^{116}D^{117}E^{118}K^{119}I^{120}Q^{121}Q^{122}E^{123}T^{124}G^{125}Q^{126}V^{127}G^{128}$ $R^{129}C^{130}S^{131}V^{132}A^{133}T^{134}Y^{135}N^{136}L^{137}R^{138}I^{139}G^{140}G^{141}D^{142}D^{143}G^{144}E^{145}F^{146}T^{147}R^{148}Y^{149}D^{150}F^{151}S^{152}I^{153}$ $P^{154}L^{155}G^{156}D^{157}F^{158}K^{159}I^{160}T^{161}A^{162}K^{163}L^{164}F^{165}R^{166}S^{167}I^{168}N^{169}D^{170}E^{171}D^{172}V^{173}D^{174}A^{175}V^{176}I^{177}L^{178}$ $V^{179}S^{180}R^{181}S^{182}D^{183}V^{184}V^{185}N^{186}D^{187}V^{188}L^{189}S^{190}F^{191}E^{192}A^{193}F^{194}N^{195}R^{196}T^{197}G^{198}E^{199}R^{200}V^{201}V^{202}I^{203}$ $F^{204}F^{205}N^{206}V^{207}I^{208}V^{209}E^{210}G^{211}K^{212}S^{213}K^{214}D^{215}I^{216}D^{217}I^{218}V^{219}C^{220}K^{221}S^{222}R^{223}Y^{224}K^{225}H^{226}T^{227}H^{228}$ $I^{229}L^{230}N^{231}G^{232}E^{233}S^{234}A^{235}T^{236}Y^{237}A^{238}V^{239}K^{240}R^{241}I^{242}K^{243}R^{244}G^{245}D^{246}T^{247}R^{248}D^{249}D^{250}I^{251}L^{252}F^{253}$ $A^{254}I^{255}T^{256}A^{257}F^{258}K^{259}E^{260}E^{261}$
(SEQ ID NO: 367)

Replikin Sequences in Amino-terminal Portion of Peptide (1) $H^{34}P^{35}I^{36}T^{37}K^{38}H^{39}I^{40}N^{41}E^{42}L^{43}L^{44}K^{45}N^{46}T^{47}V^{48}R^{49}H^{50}G^{51}D^{52}R^{53}V^{54}Y^{55}M^{56}K^{57}D^{58}A^{59}E^{60}L^{61}D^{62}V^{63}R^{64}S^{65}$
$R^{66}L^{67}E^{68}D^{69}I^{70}K^{71}K^{72}D^{73}C^{74}V^{75}L^{76}K^{77}$
(SEQ ID NO: 431)

(2) $H^{34}P^{35}I^{36}T^{37}K^{38}H^{39}I^{40}N^{41}E^{42}L^{43}L^{44}K^{45}$
(SEQ ID NO: 432)

(3) $H^{34}P^{35}I^{36}T^{37}K^{38}H^{39}I^{40}N^{41}E^{42}L^{43}L^{44}K^{45}N^{46}T^{47}V^{48}R^{49}H^{50}G^{51}D^{52}R^{53}V^{54}Y^{55}M^{56}K^{57}D^{58}A^{59}E^{60}L^{61}D^{62}V^{63}R^{64}S^{65}$
$R^{66}L^{67}E^{68}D^{69}I^{70}K^{71}K^{72}D^{73}C^{74}V^{75}L^{76}K^{77}A^{78}I^{79}E^{80}K^{81}$
(SEQ ID NO: 433)

(4) $K^{38}H^{39}I^{40}N^{41}E^{42}L^{43}L^{44}K^{45}$
(SEQ ID NO: 434)

(5) $K^{38}H^{39}I^{40}N^{41}E^{42}L^{43}L^{44}K^{45}N^{46}T^{47}V^{48}R^{49}H^{50}$
(SEQ ID NO: 435)

(6) $H^{39}I^{40}N^{41}E^{42}L^{43}L^{44}K^{45}N^{46}T^{47}V^{48}R^{49}H^{50}G^{51}D^{52}R^{53}V^{54}Y^{55}M^{56}K^{57}D^{58}A^{59}E^{60}L^{61}D^{62}V^{63}R^{64}S^{65}R^{66}L^{67}E^{68}D^{69}I^{70}$
$K^{71}K^{72}D^{73}C^{74}V^{75}L^{76}K^{77}$
(SEQ ID NO: 436)

(7) $H^{39}I^{40}N^{41}E^{42}L^{43}L^{44}K^{45}N^{46}T^{47}V^{48}R^{49}H^{50}G^{51}D^{52}R^{53}V^{54}Y^{55}M^{56}K^{57}D^{58}A^{59}E^{60}L^{61}D^{62}V^{63}R^{64}S^{65}R^{66}L^{67}E^{68}D^{69}I^{70}$
$K^{71}K^{72}D^{73}C^{74}V^{75}L^{76}K^{77}A^{78}I^{79}E^{80}K^{81}$
(SEQ ID NO: 437)

(8) $H^{50}G^{51}D^{52}R^{53}V^{54}Y^{55}M^{56}K^{57}D^{58}A^{59}E^{60}L^{61}D^{62}V^{63}R^{64}S^{65}R^{66}L^{67}E^{68}D^{69}I^{70}K^{71}K^{72}D^{73}C^{74}V^{75}L^{76}K^{77}$
(SEQ ID NO: 438)

(9) $H^{50}G^{51}D^{52}R^{53}V^{54}Y^{55}M^{56}K^{57}D^{58}A^{59}E^{60}L^{61}D^{62}V^{63}R^{64}S^{65}R^{66}L^{67}E^{68}D^{69}I^{70}K^{71}K^{72}D^{73}C^{74}V^{75}L^{76}K^{77}A^{78}I^{79}E^{80}K^{81}$
(SEQ ID NO: 439)

(10) $K^{71}K^{72}D^{73}C^{74}V^{75}L^{76}K^{77}A^{78}I^{79}E^{80}K^{81}Q^{82}G^{83}I^{84}D^{85}V^{86}R^{87}Q^{88}I^{89}I^{90}T^{91}D^{92}Y^{93}L^{94}A^{95}K^{96}R^{97}K^{98}L^{99}T^{100}Q^{101}$
$N^{102}L^{103}V^{104}H^{105}$
(SEQ ID NO: 440)

(11) $K^{72}D^{73}C^{74}V^{75}L^{76}K^{77}A^{78}I^{79}E^{80}K^{81}Q^{82}G^{83}I^{84}D^{85}V^{86}R^{87}Q^{88}I^{89}I^{90}T^{91}D^{92}Y^{93}L^{94}A^{95}K^{96}R^{97}K^{98}L^{99}T^{100}Q^{101}N^{102}$
$L^{103}V^{104}H^{105}$
(SEQ ID NO: 441)

-continued

Replikin Sequences in Mid-Molecule Portion of Peptide
Zero Replikins.
Replikin Sequences in Carboxy-Terminal Portion of Peptide

(12) $K^{212}S^{213}K^{214}D^{215}I^{216}D^{217}I^{218}V^{219}C^{220}K^{221}S^{222}R^{223}Y^{224}K^{225}H^{226}$
(SEQ ID NO: 442)

(13) $K^{212}S^{213}K^{214}D^{215}I^{216}D^{217}I^{218}V^{219}C^{220}K^{221}S^{222}R^{223}Y^{224}K^{225}H^{226}I^{227}H^{228}$
(SEQ ID NO: 443)

(14) $K^{214}D^{215}I^{216}D^{217}I^{218}V^{219}C^{220}K^{221}S^{222}R^{223}Y^{224}K^{225}H^{226}$
(SEQ ID NO: 444)

(15) $K^{214}D^{215}I^{216}D^{217}I^{218}V^{219}C^{220}K^{221}S^{222}R^{223}Y^{224}K^{225}H^{226}I^{227}H^{228}$
(SEQ ID NO: 445)

Replikin Count = Number of Replikins per 100 amino acids = 15/261 = 5.7

PubMed Code: ABS00973
Description:
Isolated: 2007
Source: Shrimp white spot syndrome virus $M^{1}D^{2}L^{3}S^{4}F^{5}T^{6}L^{7}S^{8}V^{9}V^{10}S^{11}A^{12}I^{13}L^{14}A^{15}I^{16}T^{17}A^{18}V^{19}I^{20}A^{21}V^{22}F^{23}I^{24}V^{25}I^{26}F^{27}R^{28}Y^{29}H^{30}N^{31}T^{32}V^{33}T^{34}K^{35}T^{36}I^{37}$ $E^{38}T^{39}H^{40}T^{41}G^{42}N^{43}I^{44}E^{45}T^{46}N^{47}M^{48}D^{49}E^{50}N^{51}L^{52}R^{53}I^{54}P^{55}V^{56}T^{57}A^{58}E^{59}V^{60}G^{61}S^{62}G^{63}Y^{64}F^{65}K^{66}M^{67}T^{68}D^{69}V^{70}S^{71}$ $F^{72}D^{73}S^{74}D^{75}T^{76}L^{77}G^{78}K^{79}I^{80}K^{81}I^{82}R^{83}N^{84}G^{85}K^{86}S^{87}D^{88}A^{89}Q^{90}M^{91}K^{92}E^{93}E^{94}D^{95}A^{96}D^{97}L^{98}V^{99}I^{100}T^{101}P^{102}V^{103}$ $E^{104}G^{105}R^{106}A^{107}L^{108}E^{109}V^{110}T^{111}V^{112}G^{113}Q^{114}N^{115}L^{116}T^{117}F^{118}E^{119}G^{120}T^{121}F^{122}K^{123}M^{124}W^{125}N^{126}N^{127}T^{128}$ $S^{129}R^{130}K^{131}I^{132}N^{133}I^{134}T^{135}G^{136}M^{137}Q^{138}M^{139}V^{140}P^{141}K^{142}I^{143}N^{144}P^{145}S^{146}K^{147}A^{148}F^{149}V^{150}G^{151}S^{152}S^{153}$ $N^{154}T^{155}S^{156}S^{157}F^{158}T^{159}P^{160}V^{161}S^{162}I^{163}D^{164}E^{165}D^{166}E^{167}V^{168}G^{169}T^{170}F^{171}V^{172}C^{173}G^{174}T^{175}T^{176}F^{177}G^{178}$ $A^{179}P^{180}I^{181}A^{182}A^{183}T^{184}A^{185}G^{186}G^{187}N^{188}L^{189}F^{190}D^{191}M^{192}Y^{193}V^{194}H^{195}V^{196}T^{197}Y^{198}S^{199}G^{200}T^{201}E^{202}T^{203}$ $E^{204}$
(SEQ ID NO: 446)

Replikin Sequences in Amino-Terminal Portion of Peptide (1) $H^{40}T^{41}G^{42}N^{43}I^{44}E^{45}T^{46}N^{47}M^{48}D^{49}E^{50}N^{51}L^{52}R^{53}I^{54}P^{55}V^{56}T^{57}A^{58}E^{59}V^{60}G^{61}S^{62}G^{63}Y^{64}F^{65}K^{66}M^{67}T^{68}D^{69}V^{70}$
$S^{71}F^{72}D^{73}S^{74}D^{75}T^{76}L^{77}G^{78}K^{79}I^{80}K^{81}I^{82}R^{83}N^{84}G^{85}K^{86}$
(SEQ ID NO: 447)

Mid-molecule: Zero Replikins.
Carboxy-terminal: Zero Replikins.
Replikin Count = Number of Replikins per 100 amino acids = 1/204 = 0.5

Example 4

Determination of Replikin Concentration in Publicly Available Accession Numbers for Isolates of WSSV from 1995 through 2007

Mean Replikin concentrations were determined for all amino acid sequences for WSSV with accession numbers publicly available at www.pubmed.com. The amino acid sequences were scanned for Replikin sequences of 7 to 50 amino acids comprising (1) at least one lysine residue located at a first terminus of the sequence and at least one lysine residue or at least one histidine residue located at a second terminus of the sequence; (2) a first lysine residue located six to ten residues from a second lysine residue; (3) at least one histidine residue; and (4) at least 6% lysine residues. The total number of Replikin sequences was determined for each available accession number. The total number of Replikin sequences in each accession number was then divided by the total number of amino acid residues disclosed in the accession number. The result was the Replikin concentration. The mean Replikin concentration was then determined for all viruses isolated and reported in a particular year. Table 4 provides the results of the Replikin concentration analysis.

TABLE 4

WSSV Replikin Concentration by Year

| Year | PubMed Accession Number-Replikin Count |
|---|---|
| 1995 | CAA88950 18 CAA91970 59 |
| | No. of isolates: 2 Mean Replikin Count: 4.4 Standard Deviation: 0.6 Significance: low $p < 0.10$ |
| 1996 | CAE17687 160 CAB03144 29 CAB03173 31 |
| | No. of isolates: 3 Mean Replikin Count: 6.0 Standard Deviation: 2.6 Significance: low $p > 0.50$, prev $p < 0.30$ |
| 1997 | |
| 1998 | ABA54417 48 |
| | No. of isolates: 1 Mean Replikin Count: 6.2 Standard Deviation: 0.0 Significance: prev $p > 0.50$ |
| 1999 | |

TABLE 4-continued

| WSSV Replikin Concentration by Year | |
|---|---|
| Year | PubMed Accession Number-Replikin Count |
| 2000 | NP_478030 361 NP_478019 361 NP_478001 361 NP_477774 361 NP_477756 361 NP_477753 361 NP_477809 361 NP_477768 361 NP_477523 361 NP_477959 361 NP_478053 361 NP_478052 361 NP_478051 361 NP_478050 361 NP_478049 361 NP_478048 361 NP_478047 361 NP_478046 361 NP_478045 361 NP_478044 361 NP_478043 361 NP_478042 361 NP_478041 361 NP_478039 361 NP_478038 361 NP_478037 361 NP_478036 361 NP_478035 361 NP_478034 361 NP_478033 361 NP_478032 361 NP_478031 361 NP_478029 361 NP_478028 361 NP_478027 361 NP_478026 361 NP_478025 361 NP_478024 361 NP_478023 361 NP_478022 361 NP_478021 361 NP_478020 361 NP_478018 361 NP_478017 361 NP_478016 361 NP_478015 361 NP_478014 361 NP_478013 361 NP_478012 361 NP_478011 361 NP_478010 361 NP_478009 361 NP_478008 361 NP_478007 361 NP_478006 361 NP_478005 361 NP_478004 361 NP_478003 361 NP_478002 361 NP_478000 361 NP_477999 361 NP_477998 361 NP_477997 361 NP_477996 361 NP_477995 361 NP_477994 361 NP_477993 361 NP_477992 361 NP_477991 361 NP_477990 361 NP_477989 361 NP_477988 361 NP_477987 361 NP_477986 361 NP_477985 361 NP_477984 361 NP_477983 361 NP_477982 361 NP_477981 361 NP_477980 361 NP_477979 361 NP_477978 361 NP_477977 361 NP_477976 361 NP_477975 361 NP_477974 361 NP_477973 361 NP_477972 361 NP_477971 361 NP_477970 361 NP_477969 361 NP_477968 361 NP_477967 361 NP_477966 361 NP_477965 361 NP_477964 361 NP_477963 361 NP_477962 361 NP_477961 361 NP_477960 361 NP_477958 361 NP_477957 361 NP_477956 361 NP_477955 361 NP_477954 361 NP_477953 361 NP_477952 361 NP_477951 361 NP_477950 361 NP_477949 361 NP_477948 361 NP_477947 361 NP_477946 361 NP_477945 361 NP_477944 361 NP_477943 361 NP_477942 361 NP_477941 361 NP_477940 361 NP_477939 361 NP_477938 361 NP_477937 361 NP_477936 361 NP_477935 361 NP_477934 361 NP_477933 361 NP_477932 361 NP_477931 361 NP_477930 361 NP_477929 361 NP_477928 361 NP_477927 361 NP_477926 361 NP_477925 361 NP_477924 361 NP_477923 361 NP_477922 361 NP_477921 361 NP_477920 361 NP_477919 361 NP_477918 361 NP_477917 361 NP_477916 361 NP_477915 361 NP_477914 361 NP_477913 361 NP_477912 361 NP_477911 361 NP_477910 361 NP_477909 361 NP_477908 361 NP_477907 361 NP_477906 361 NP_477905 361 NP_477904 361 NP_477903 361 NP_477902 361 NP_477901 361 NP_477900 361 NP_477899 361 NP_477898 361 NP_477897 361 NP_477896 361 NP_477895 361 NP_477894 361 NP_477893 361 NP_477892 361 NP_477891 361 NP_477890 361 NP_477889 361 NP_477888 361 NP_477887 361 NP_477886 361 NP_477885 361 NP_477884 361 NP_477883 361 NP_477882 361 NP_477881 361 NP_477880 361 NP_477879 361 NP_477878 361 NP_477877 361 NP_477876 361 NP_477875 361 NP_477874 361 NP_477873 361 NP_477872 361 NP_477871 361 NP_477870 361 NP_477869 361 NP_477868 361 NP_477867 361 NP_477866 361 NP_477865 361 NP_477864 361 NP_477863 361 NP_477862 361 NP_477861 361 NP_477860 361 NP_477859 361 NP_477858 361 NP_477857 361 NP_477856 361 NP_477855 361 NP_477854 361 NP_477853 361 NP_477852 361 NP_477851 361 NP_477850 361 NP_477849 361 NP_477848 361 NP_477847 361 NP_477846 361 NP_477845 361 NP_477844 361 NP_477843 361 NP_477842 361 NP_477841 361 NP_477840 361 NP_477839 361 NP_477838 361 NP_477837 361 NP_477836 361 NP_477835 361 NP_477834 361 NP_477833 361 NP_477832 361 NP_477831 361 NP_477830 361 NP_477829 361 NP_477828 361 NP_477827 361 NP_477826 361 NP_477825 361 NP_477824 361 NP_477823 361 NP_477822 361 NP_477821 361 NP_477820 361 NP_477819 361 NP_477818 361 NP_477817 361 NP_477816 361 NP_477815 361 NP_477814 361 NP_477813 361 NP_477812 361 NP_477811 361 NP_477810 361 NP_477808 361 NP_477807 361 NP_477806 361 NP_477805 361 NP_477804 361 NP_477803 361 NP_477802 361 NP_477801 361 NP_477800 361 NP_477799 361 NP_477798 361 NP_477797 361 NP_477796 361 NP_477795 361 NP_477794 361 NP_477793 361 NP_477792 361 NP_477791 361 NP_477790 361 NP_477789 361 NP_477788 361 NP_477787 361 NP_477786 361 NP_477785 361 NP_477784 361 NP_477783 361 NP_477782 361 NP_477781 361 NP_477780 361 NP_477779 361 NP_477778 361 NP_477777 361 NP_477776 361 NP_477775 361 NP_477773 361 NP_477772 361 NP_477771 361 NP_477770 361 NP_477769 361 NP_477767 361 NP_477766 361 NP_477765 361 NP_477764 361 NP_477763 361 NP_477762 361 NP_477761 361 NP_477760 361 NP_477759 361 NP_477758 361 NP_477757 361 NP_477755 361 NP_477754 361 NP_477752 361 NP_477751 361 NP_477750 361 NP_477749 361 NP_477748 361 NP_477747 361 NP_477746 361 NP_477745 361 NP_477744 361 NP_477743 361 NP_477742 361 NP_477741 361 NP_477740 361 NP_477739 361 NP_477738 361 NP_477737 361 NP_477736 361 NP_477735 361 NP_477734 361 NP_477733 361 NP_477732 361 NP_477731 361 NP_477730 361 NP_477729 361 NP_477728 361 NP_477727 361 NP_477726 361 NP_477725 361 NP_477724 361 NP_477723 361 NP_477722 361 NP_477721 361 NP_477720 361 NP_477719 361 NP_477718 361 NP_477717 361 NP_477716 361 NP_477715 361 NP_477714 361 NP_477713 361 NP_477712 361 NP_477711 361 NP_477710 361 NP_477709 361 NP_477708 361 NP_477707 361 NP_477706 361 NP_477705 361 NP_477704 361 NP_477703 361 NP_477702 361 NP_477701 361 NP_477700 361 NP_477699 361 NP_477698 361 NP_477697 361 NP_477696 361 NP_477695 361 NP_477694 361 NP_477693 361 NP_477692 361 NP_477691 361 NP_477690 361 NP_477689 361 NP_477688 361 NP_477687 361 NP_477686 361 NP_477685 361 NP_477684 361 NP_477683 361 NP_477682 361 NP_477681 361 NP_477680 361 NP_477679 361 NP_477678 361 NP_477677 361 NP_477676 361 NP_477675 361 NP_477674 361 NP_477673 361 NP_477672 361 NP_477671 361 NP_477670 361 NP_477669 361 NP_477668 361 NP_477667 361 NP_477666 361 NP_477665 361 NP_477664 361 NP_477663 361 NP_477662 361 NP_477661 361 NP_477660 361 NP_477659 361 NP_477658 361 NP_477657 361 NP_477656 361 NP_477655 361 NP_477654 361 NP_477653 361 NP_477652 361 NP_477651 361 NP_477650 361 NP_477649 361 NP_477648 361 NP_477647 361 NP_477646 361 NP_477645 361 NP_477644 361 NP_477643 361 NP_477642 361 NP_477641 361 NP_477640 361 NP_477639 361 NP_477638 361 NP_477637 361 NP_477636 361 |

TABLE 4-continued

| WSSV Replikin Concentration by Year | |
|---|---|
| Year | PubMed Accession Number-Replikin Count |
| | NP_477635 361 NP_477634 361 NP_477633 361 NP_477632 361 NP_477631 361 NP_477630 361 NP_477629 361 NP_477628 361 NP_477627 361 NP_477626 361 NP_477625 361 NP_477624 361 NP_477623 361 NP_477622 361 NP_477621 361 NP_477620 361 NP_477619 361 NP_477618 361 NP_477617 361 NP_477616 361 NP_477615 361 NP_477614 361 NP_477613 361 NP_477612 361 NP_477611 361 NP_477610 361 NP_477609 361 NP_477608 361 NP_477607 361 NP_477606 361 NP_477605 361 NP_477604 361 NP_477603 361 NP_477602 361 NP_477601 361 NP_477600 361 NP_477599 361 NP_477598 361 NP_477597 361 NP_477596 361 NP_477595 361 NP_477594 361 NP_477593 361 NP_477592 361 NP_477591 361 NP_477590 361 NP_477589 361 NP_477588 361 NP_477587 361 NP_477586 361 NP_477585 361 NP_477584 361 NP_477583 361 NP_477582 361 NP_477581 361 NP_477580 361 NP_477579 361 NP_477578 361 NP_477577 361 NP_477576 361 NP_477575 361 NP_477574 361 NP_477573 361 NP_477572 361 NP_477571 361 NP_477570 361 NP_477569 361 NP_477568 361 NP_477567 361 NP_477566 361 NP_477565 361 NP_477564 361 NP_477563 361 NP_477562 361 NP_477561 361 NP_477560 361 NP_477559 361 NP_477558 361 NP_477557 361 NP_477556 361 NP_477555 361 NP_477554 361 NP_477553 361 NP_477552 361 NP_477551 361 NP_477550 361 NP_477549 361 NP_477548 361 NP_477547 361 NP_477546 361 NP_477545 361 NP_477544 361 NP_477543 361 NP_477542 361 NP_477541 361 NP_477540 361 NP_477539 361 NP_477538 361 NP_477537 361 NP_477536 361 NP_477535 361 NP_477534 361 NP_477533 361 NP_477532 361 NP_477531 361 NP_477530 361 NP_477529 361 NP_477527 361 NP_477526 361 NP_477525 361 NP_477524 361 |
| | No. of isolates: 529 Mean Replikin Count: 97.6 Std. Deviation: 0.0 Significance: low $p < 0.001$ |
| 2002 | |
| 2003 | |
| 2004 | |
| 2005 | AAZ29239 9 XP_001681561 6 |
| | No. of isolates: 2 Mean Replikin Count: 2.6 Std. Deviation: 2.4 Significance: low $p > 0.20$, prev $p < 0.001$ |
| 2006 | ABM92267 14 ABP01348 1 ABM64218 6 ABI34434 6 ABI93178 4 ABI93177 3 ABI93176 6 ABI93174 12 ABQ12866 3 ABD65308 2 ABD65303 1 ABD65302 4 ABD65300 3 ABD65298 1 |
| | No. of isolates: 14 Mean Replikin Count: 2.7 Std. Deviation: 2.5 Significance: low $p < 0.001$, prev $p > 0.50$ |
| 2007 | 2ED6_L 1 2ED6_K 1 2ED6_J 1 2ED6_I 1 2ED6_H 1 2ED6_G 1 2ED6_F 1 2ED6_E 1 2ED6_D 1 2ED6_C 1 2ED6_B 1 2ED6_A 1 ABQ12772 15 ABQ12773 3 ABQ12771 6 ABQ12770 9 ABO69369 2 ABO69368 2 ABS00974 5 ABS00973 1 ABQ44211 3 ABQ44210 4 ABP52058 4 ABP52057 1 ABP52054 5 |
| | No. of isolates: 25 Mean Replikin Count: 1.3 Std. Deviation: 1.2 Significance: low $p < 0.001$, prev $p < 0.05$ |

Example 5

Determination of Replikin Concentrations in 2001 and 2005 Isolates of TSV Publicly Available at Accession Nos. AAM73766 and AAY89096

The Taura Syndrome Shrimp Virus is less virulent than WSSV and the structure of the TSV Replikin Scaffold is less closely related to influenza virus than are the structures of WSSV Replikin Scaffolds. In year 2000, TSV had a Replikin concentration of 3.3. Between 2001 and 2004, TSV had a lower mean Replikin concentration, as low as 0.7, and its Replikin Scaffold disappeared. In 2005 the Replikin Scaffold reappeared, with an increase in lysines and histidines, and a commensurate increase in Replikin concentration to 3.9, followed by an increase in TSV outbreaks in 2006-2007.

Below is a comparison of the Replikin Scaffold identified in AAK72220 in an isolate of TSV from 2000 and the Replikin Scaffold identified in AAY89096 in an isolate of TSV from 2005. The TSV Replikin Scaffolds are also compared to two Replikin Scaffolds in H1N1 influenza virus in the 1918 pandemic and shrimp WSSV in 2000.

| | | |
|---|---|---|
| kkgssypklsksyvnnkgkevlvlwgvhh | (SEQ ID NO: 384) | 1918 H1N1 Human Influenza Pandemic |
| -kgssypklsksyvnnkgkevlvlwgvhh | (SEQ ID NO: 448) | 1918 H1N1 Human Influenza Pandemic |
| -kyhldvkgvkqllhlkvrldvrgakqlh | (SEQ ID NO: 7) | 2000 Shrimp White Spot Syndrome Virus |
| kknvksakqlphlkvlkkldvrgakqlph | (SEQ ID NO: 6) | 2000 Shrimp White Spot Syndrome Virus |
| **kk**vqan**k**trvfaasnqglalalrryylsfld**h** | (SEQ ID NO: 8) | 2000 Taura Syndrome Virus AAK72220 |
| kk**acrnagykeacl**h**eldcksfllaqqgraga**h | (SEQ ID NO: 9) | 2005 Taura Syndrome Virus AAY89096 |

The following analysis of Accession Nos. AAM73766 and AAY89096 demonstrate Replikin concentration analysis of amino acid sequences of isolates of Taura Syndrome Virus having publicly available accession numbers at www.pubmed.com.

PubMed Code: AAM73766
Description:
Isolated: 2001
Source: Taura syndrome virus $M^{1}P^{2}A^{3}N^{4}P^{5}V^{6}E^{7}I^{8}D^{9}N^{10}F^{11}D^{12}T^{13}T^{14}T^{15}S^{16}G^{17}G^{18}L^{19}I^{20}P^{21}G^{22}G^{23}S^{24}V^{25}T^{26}N^{27}S^{28}E^{29}G^{30}S^{31}T^{32}I^{33}L^{34}M^{35}N^{36}D^{37}$ $I^{38}P^{39}I^{40}T^{41}N^{42}Q^{43}N^{44}V^{45}V^{46}L^{47}S^{48}K^{49}N^{50}V^{51}T^{52}D^{53}N^{54}L^{55}F^{56}E^{57}V^{58}Q^{59}D^{60}Q^{61}A^{62}L^{63}I^{64}E^{65}S^{66}L^{67}S^{68}R^{69}D^{70}V^{71}$ $L^{72}L^{73}H^{74}N^{75}D^{76}S^{77}W^{78}T^{79}S^{80}S^{81}D^{82}D^{83}E^{84}I^{85}G^{86}T^{87}T^{88}M^{89}T^{90}Q^{91}E^{92}Q^{93}L^{94}A^{95}T^{96}E^{97}F^{98}N^{99}Q^{100}P^{101}H^{102}L^{103}$ $Y^{104}E^{105}I^{106}S^{107}L^{108}P^{109}D^{110}D^{111}I^{112}V^{113}R^{114}K^{115}S^{116}L^{117}F^{118}M^{119}S^{120}N^{121}K^{122}L^{123}A^{124}N^{125}I^{126}A^{127}Y^{128}$ $M^{129}R^{130}C^{131}D^{132}Y^{133}E^{134}V^{135}T^{136}V^{137}R^{138}V^{139}Q^{140}A^{141}T^{142}P^{143}F^{144}L^{145}Q^{146}G^{147}A^{148}L^{149}W^{150}L^{151}W^{152}N^{153}$ $K^{154}M^{155}N^{156}A^{157}K^{158}Q^{159}T^{160}S^{161}I^{162}I^{163}R^{164}R^{165}T^{166}L^{167}T^{168}E^{169}H^{170}L^{171}R^{172}S^{173}I^{174}T^{175}S^{176}F^{177}P^{178}$ $G^{179}I^{180}E^{181}M^{182}N^{183}L^{184}Q^{185}S^{186}E^{187}A^{188}R^{189}A^{190}I^{191}T^{192}L^{193}S^{194}I^{195}P^{196}Y^{197}T^{198}S^{199}E^{200}F^{201}Q^{202}V^{203}$ $F^{204}N^{205}P^{206}R^{207}N^{208}V^{209}N^{210}N^{211}L^{212}N^{213}S^{214}I^{215}R^{216}L^{217}S^{218}V^{219}L^{220}S^{221}Q^{222}L^{223}Q^{224}G^{225}P^{226}E^{227}D^{228}$ $V^{229}E^{230}S^{231}A^{232}S^{233}Y^{234}S^{235}I^{236}Y^{237}G^{238}R^{239}L^{240}K^{241}N^{242}I^{243}K^{244}L^{245}Y^{246}G^{247}H^{248}A^{249}P^{250}S^{251}V^{252}T^{253}$ $S^{254}S^{255}V^{256}Y^{257}P^{258}S^{259}T^{260}Q^{261}S^{262}G^{263}Y^{264}D^{265}D^{266}D^{267}C^{268}P^{269}I^{270}V^{271}H^{272}A^{273}G^{274}T^{275}D^{276}E^{277}D^{278}$ $S^{279}S^{280}K^{281}Q^{282}G^{283}I^{284}V^{285}S^{286}R^{287}V^{288}A^{289}D^{290}T^{291}V^{292}G^{293}A^{294}V^{295}A^{296}N^{297}V^{298}V^{299}D^{300}G^{301}V^{302}G^{303}$ $V^{304}P^{305}I^{306}L^{307}S^{308}T^{309}I^{310}A^{311}K^{312}P^{313}V^{314}S^{315}W^{316}V^{317}S^{318}G^{319}V^{320}V^{321}S^{322}N^{323}V^{324}A^{325}S^{326}M^{327}F^{328}$ $G^{329}F^{330}S^{331}K^{332}D^{333}R^{334}D^{335}M^{336}T^{337}K^{338}V^{339}N^{340}A^{341}Y^{342}E^{343}N^{344}L^{345}P^{346}G^{347}K^{348}G^{349}F^{350}T^{351}H^{352}G^{353}$ $V^{354}G^{355}F^{356}D^{357}Y^{358}G^{359}V^{360}P^{361}L^{362}S^{363}L^{364}F^{365}P^{366}N^{367}N^{368}A^{369}I^{370}D^{371}P^{372}T^{373}I^{374}A^{375}V^{376}P^{377}E^{378}$ $G^{379}L^{389}D^{381}E^{382}M^{383}S^{384}I^{385}E^{386}Y^{387}L^{388}A^{389}Q^{390}R^{391}P^{392}Y^{393}M^{394}L^{395}N^{396}R^{397}Y^{398}T^{399}I^{400}R^{401}G^{402}G^{403}$ $D^{404}T^{405}P^{406}D^{407}V^{408}H^{409}G^{410}T^{411}I^{412}V^{413}A^{414}D^{415}I^{416}P^{417}V^{418}S^{419}P^{420}V^{421}N^{422}F^{423}S^{424}L^{425}Y^{426}G^{427}K^{428}$ $V^{429}I^{430}A^{431}K^{432}Y^{433}R^{434}T^{435}L^{436}F^{437}A^{438}A^{439}P^{440}V^{441}S^{442}L^{443}A^{444}V^{445}A^{446}M^{447}A^{448}N^{449}W^{450}W^{451}R^{452}G^{453}$ $N^{454}I^{455}N^{456}L^{457}N^{458}L^{459}R^{460}F^{461}A^{462}K^{463}T^{464}Q^{465}Y^{466}H^{467}Q^{468}C^{469}R^{470}L^{471}L^{472}V^{473}Q^{474}Y^{475}L^{476}P^{477}Y^{478}$ $G^{479}S^{480}G^{481}V^{482}Q^{483}P^{484}I^{485}E^{486}S^{487}I^{488}L^{489}S^{490}Q^{491}I^{492}I^{493}D^{494}I^{495}S^{496}Q^{497}V^{498}D^{499}D^{500}K^{501}G^{502}I^{503}$ $D^{504}I^{505}A^{506}F^{507}P^{508}S^{509}V^{510}Y^{511}P^{512}N^{513}K^{514}W^{515}M^{516}R^{517}V^{518}Y^{519}D^{520}P^{521}A^{522}K^{523}V^{524}G^{525}Y^{526}T^{527}A^{528}$ $D^{529}C^{530}A^{531}P^{532}G^{533}R^{534}I^{535}V^{536}I^{537}S^{538}V^{539}L^{540}N^{541}P^{542}L^{543}I^{544}S^{545}A^{546}S^{547}T^{548}V^{549}S^{550}P^{551}N^{552}I^{553}$ $V^{554}M^{555}Y^{556}P^{557}W^{558}V^{559}H^{560}W^{561}S^{562}N^{563}L^{564}E^{565}V^{566}A^{567}E^{568}P^{569}G^{570}T^{571}L^{572}A^{573}K^{574}A^{575}A^{576}I^{577}G^{578}$ $F^{579}N^{580}Y^{581}P^{582}A^{583}D^{584}V^{585}P^{586}E^{587}E^{588}P^{589}T^{590}F^{591}S^{592}V^{593}T^{594}R^{595}A^{596}P^{597}V^{598}S^{599}G^{600}T^{601}L^{602}F^{603}$ $T^{604}L^{605}L^{606}Q^{607}D^{608}T^{609}K^{610}V^{611}S^{612}L^{613}G^{614}E^{615}A^{616}D^{617}G^{618}V^{619}F^{620}S^{621}L^{622}Y^{623}F^{624}T^{625}N^{626}T^{627}T^{628}$ $T^{629}G^{630}R^{631}R^{632}H^{633}R^{634}L^{635}T^{636}Y^{637}A^{638}G^{639}L^{640}P^{641}G^{642}E^{643}L^{644}G^{645}S^{646}C^{647}E^{648}I^{649}V^{650}K^{651}L^{652}P^{653}$ $Q^{654}G^{655}Q^{656}Y^{657}S^{658}I^{659}E^{660}Y^{661}A^{662}A^{663}T^{664}S^{665}A^{666}P^{667}T^{668}L^{669}V^{670}L^{671}D^{672}R^{673}P^{674}I^{675}F^{676}S^{677}E^{678}$ $P^{679}I^{680}G^{681}P^{682}K^{683}Y^{684}V^{685}V^{686}T^{687}K^{688}V^{689}K^{690}N^{691}G^{692}D^{693}V^{694}V^{695}S^{696}I^{697}S^{698}E^{699}E^{700}T^{701}L^{702}V^{703}$ $T^{704}C^{705}G^{706}S^{707}M^{708}A^{709}A^{710}L^{711}G^{712}G^{713}A^{714}T^{715}V^{716}A^{717}L^{718}Q^{719}S^{720}V^{721}D^{722}E^{723}T^{724}I^{725}E^{726}I^{727}L^{728}$ $K^{729}L^{730}E^{731}S^{732}D^{733}F^{734}E^{735}S^{736}K^{737}A^{738}P^{739}V^{740}K^{741}F^{742}T^{743}P^{744}G^{745}N^{746}Y^{747}T^{748}V^{749}V^{750}T^{751}E^{752}A^{753}$ $S^{754}D^{755}V^{756}E^{757}L^{758}V^{759}T^{760}N^{761}Q^{762}D^{763}I^{764}T^{765}V^{766}N^{767}E^{768}H^{769}N^{770}P^{771}R^{772}T^{773}H^{774}A^{775}G^{776}I^{777}D^{778}$ $E^{779}E^{780}P^{781}P^{782}V^{783}K^{784}R^{785}S^{786}V^{787}I^{788}G^{789}R^{790}I^{791}V^{792}R^{793}R^{794}V^{795}A^{796}R^{797}Y^{798}V^{799}P^{800}N^{801}K^{802}L^{803}$ $I^{804}R^{805}R^{806}I^{807}L^{808}R^{809}D^{810}L^{811}S^{812}Q^{813}S^{814}P^{815}C^{816}I^{817}Y^{818}P^{819}S^{820}T^{821}H^{822}A^{823}G^{824}L^{825}D^{826}Y^{827}S^{828}$ $S^{829}S^{830}D^{831}T^{832}S^{833}T^{834}M^{835}L^{836}T^{837}T^{838}M^{839}G^{840}E^{841}Q^{842}F^{843}V^{844}S^{845}L^{846}R^{847}M^{848}L^{849}T^{850}R^{851}R^{852}S^{853}$ $S^{854}P^{855}V^{856}D^{857}I^{858}L^{859}R^{860}G^{861}D^{862}L^{863}V^{864}T^{865}L^{866}P^{867}G^{868}I^{869}S^{870}F^{871}G^{872}T^{873}D^{874}N^{875}S^{876}L^{877}R^{878}$ $Q^{879}S^{880}L^{881}V^{882}N^{883}I^{884}I^{885}S^{886}Y^{887}M^{888}Y^{889}R^{890}F^{891}T^{892}H^{893}G^{894}S^{895}I^{896}S^{897}Y^{898}K^{899}I^{900}I^{901}P^{902}K^{903}$ $N^{904}K^{905}G^{906}D^{907}L^{908}Y^{909}I^{910}T^{911}T^{912}T^{913}S^{914}P^{915}D^{916}S^{917}I^{918}E^{919}T^{920}S^{921}T^{922}S^{923}A^{924}Y^{925}Q^{926}F^{927}D^{928}$ $T^{929}N^{930}R^{931}A^{932}M^{933}H^{934}Y^{935}I^{936}N^{937}T^{938}S^{939}L^{940}N^{941}P^{942}M^{943}A^{944}Q^{945}I^{946}S^{947}L^{948}P^{949}Y^{950}Y^{951}S^{952}P^{953}$ $A^{954}E^{955}N^{956}L^{957}V^{958}I^{959}D^{960}S^{961}K^{962}S^{963}F^{964}P^{965}Q^{966}L^{967}S^{968}D^{969}L^{970}S^{971}I^{972}S^{973}N^{974}L^{975}E^{976}R^{977}T^{978}$ -continued $E^{979}N^{980}E^{981}Y^{982}F^{983}V^{984}L^{985}A^{986}S^{987}A^{988}G^{989}D^{990}D^{991}H^{992}T^{993}F^{994}S^{995}Q^{996}L^{997}A^{998}G^{999}C^{1000}P^{1001}A^{1002}$ $F^{1003}T^{1004}F^{1005}G^{1006}P^{1007}A^{1008}E^{1009}L^{1010}A^{1011}$
(SEQ ID NO: 449)

Replikin Sequences in Amino-Terminal Portion of Peptide (1) $H^{102}L^{103}Y^{104}E^{105}I^{106}S^{107}L^{108}P^{109}D^{110}D^{111}I^{112}V^{113}R^{114}K^{115}S^{116}L^{117}F^{118}M^{119}S^{120}N^{121}K^{122}$
(SEQ ID NO: 450)

(2) $K^{332}D^{333}R^{334}D^{335}M^{336}T^{337}K^{338}V^{339}N^{340}A^{341}Y^{342}E^{343}N^{344}L^{345}P^{346}G^{347}K^{348}G^{349}F^{350}T^{351}H^{352}$
(SEQ ID NO: 451)

(3) $K^{338}V^{339}N^{340}A^{341}Y^{342}E^{343}N^{344}L^{345}P^{346}G^{347}K^{348}G^{349}F^{350}T^{351}H^{352}$
(SEQ ID NO: 452)

Replikin Sequences in Mid-Molecule Portion of Peptide
Zero Replikins.

Replikin Sequences in Carboxy-Terminal Portion of Peptide (4) $K^{729}L^{730}E^{731}S^{732}D^{733}F^{734}E^{735}S^{736}K^{737}A^{738}P^{739}V^{740}K^{741}F^{742}T^{743}P^{744}G^{745}N^{746}Y^{747}T^{748}V^{749}V^{750}T^{751}E^{752}$
$A^{753}S^{754}D^{755}V^{756}E^{757}L^{758}V^{759}T^{760}N^{761}Q^{762}D^{763}I^{764}T^{765}V^{766}N^{767}E^{768}H^{769}N^{770}P^{771}R^{772}T^{773}H^{774}$
(SEQ ID NO: 453)

(5) $K^{729}L^{730}L^{731}S^{732}D^{733}F^{734}L^{735}S^{736}K^{737}A^{738}P^{739}V^{740}K^{741}F^{742}T^{743}P^{744}G^{745}N^{746}Y^{747}T^{748}V^{749}V^{750}T^{751}E^{752}$
$A^{753}S^{754}D^{755}V^{756}E^{757}L^{758}V^{759}T^{760}N^{761}Q^{762}D^{763}I^{764}T^{765}V^{766}N^{767}E^{768}H^{769}$
(SEQ ID NO: 454)

(6) $H^{893}G^{894}S^{895}I^{896}S^{897}Y^{898}K^{899}I^{900}I^{901}P^{902}K^{903}N^{904}K^{905}$
(SEQ ID NO: 455)

(7) $K^{899}I^{900}I^{901}P^{902}K^{903}N^{904}K^{905}G^{906}D^{907}L^{908}Y^{909}I^{910}T^{911}T^{912}T^{913}S^{914}P^{915}D^{916}S^{917}I^{918}E^{919}T^{920}S^{921}T^{922}$
$S^{923}A^{924}Y^{925}Q^{926}F^{927}D^{928}T^{929}N^{930}R^{931}A^{932}M^{933}H^{934}$
(SEQ ID NO: 456)

Replikin Count = Number of Replikins per 100 amino acids = 7/1011 = 0.7

PubMed Code: AAY89096
Description:
Isolated: 2005
Source: Taura syndrome virus $M^{1}A^{2}S^{3}Y^{4}Y^{5}L^{6}N^{7}I^{8}K^{9}T^{10}H^{11}N^{12}L^{13}R^{14}R^{15}T^{16}P^{17}G^{18}A^{19}H^{20}R^{21}A^{22}F^{23}Y^{24}V^{25}M^{26}N^{27}D^{28}D^{29}G^{30}E^{31}N^{32}R^{33}I^{34}Y^{35}S^{36}L^{37}$ $I^{38}G^{39}T^{40}L^{41}R^{42}R^{43}A^{44}P^{45}A^{46}F^{47}K^{48}V^{49}G^{50}S^{51}R^{52}R^{53}Y^{54}K^{55}S^{56}H^{57}I^{58}P^{59}Y^{60}R^{61}R^{62}K^{63}A^{64}T^{65}V^{66}A^{67}E^{68}L^{69}C^{70}$ $N^{71}Q^{72}L^{73}H^{74}D^{75}R^{76}V^{77}L^{78}P^{79}F^{80}A^{81}N^{82}P^{83}Q^{84}V^{85}W^{86}K^{87}E^{88}V^{89}I^{90}S^{91}E^{92}N^{93}K^{94}V^{95}Q^{96}P^{97}D^{98}S^{99}M^{100}L^{101}K^{102}$ $A^{103}A^{104}F^{105}G^{106}N^{107}W^{108}E^{109}E^{110}W^{111}P^{112}K^{113}D^{114}K^{115}V^{116}C^{117}E^{118}E^{119}L^{120}Y^{121}S^{122}E^{123}C^{124}E^{125}C^{126}G^{127}$ $Y^{128}V^{129}G^{130}T^{131}C^{132}Y^{133}V^{134}S^{135}V^{136}D^{137}W^{138}L^{139}R^{140}P^{141}Q^{142}A^{143}T^{144}K^{145}C^{146}N^{147}D^{148}C^{149}I^{150}L^{151}K^{152}$ $M^{153}N^{154}R^{155}N^{156}V^{157}E^{158}Y^{159}P^{160}Y^{161}H^{162}T^{163}I^{164}G^{165}V^{166}S^{167}G^{168}N^{169}V^{170}V^{171}T^{172}N^{173}T^{174}D^{175}I^{176}V^{177}$ $Y^{178}T^{179}G^{180}Y^{181}A^{182}D^{183}V^{184}F^{185}K^{186}C^{187}E^{188}K^{189}C^{190}D^{191}L^{192}L^{193}M^{194}G^{195}A^{196}W^{197}A^{198}P^{199}N^{200}D^{201}I^{202}$ $P^{203}A^{204}L^{205}T^{206}H^{207}N^{208}I^{209}R^{210}S^{211}S^{212}Q^{213}C^{214}V^{215}Q^{216}F^{217}K^{218}L^{219}P^{220}T^{221}E^{222}N^{223}L^{224}A^{225}A^{226}R^{227}$ $N^{228}Y^{229}V^{230}L^{231}L^{232}C^{233}E^{234}E^{235}I^{236}E^{237}R^{238}E^{239}N^{240}I^{241}P^{242}V^{243}I^{244}F^{245}Q^{246}D^{247}Y^{248}S^{249}E^{250}G^{251}N^{252}$ $V^{253}F^{254}T^{255}C^{256}R^{257}I^{258}V^{259}S^{260}G^{261}D^{262}L^{263}T^{264}A^{265}V^{266}G^{267}T^{268}A^{269}S^{270}N^{271}M^{272}Y^{273}T^{274}A^{275}R^{276}D^{277}$ $V^{278}A^{279}S^{280}K^{281}S^{282}L^{283}L^{284}D^{285}Q^{286}L^{287}H^{288}N^{289}T^{290}P^{291}N^{292}V^{293}H^{294}M^{295}H^{296}S^{297}L^{298}H^{299}S^{300}L^{301}P^{302}$ $Y^{303}E^{304}N^{305}F^{306}P^{307}C^{308}E^{309}A^{310}L^{311}E^{312}F^{313}A^{314}V^{315}E^{316}Q^{317}G^{318}I^{319}I^{320}P^{321}P^{322}V^{323}T^{324}F^{325}D^{326}E^{327}$ $V^{328}F^{329}A^{330}N^{331}D^{332}E^{333}Y^{334}V^{335}I^{336}T^{337}I^{338}S^{339}C^{340}S^{341}L^{342}L^{343}V^{344}V^{345}S^{346}D^{347}V^{348}G^{349}P^{350}T^{351}Q^{352}$ $A^{353}V^{354}A^{355}R^{356}E^{357}R^{358}A^{359}A^{360}K^{361}R^{362}F^{363}L^{364}K^{365}M^{366}Y^{367}D^{368}Y^{369}S^{370}A^{371}S^{372}Y^{373}P^{374}S^{375}T^{376}H^{377}$ $M^{378}F^{379}T^{380}L^{381}S^{382}T^{383}L^{384}P^{385}Q^{386}R^{387}S^{388}G^{389}E^{390}T^{391}L^{392}E^{393}L^{394}A^{395}N^{396}A^{397}T^{398}L^{399}N^{400}H^{401}V^{402}$ $N^{403}N^{404}V^{405}I^{406}D^{407}R^{408}H^{409}D^{410}E^{411}A^{412}I^{413}S^{414}N^{415}V^{416}R^{417}Q^{418}N^{419}V^{420}E^{421}V^{422}K^{423}L^{424}T^{425}D^{426}V^{427}$ $S^{428}R^{429}Q^{430}V^{431}G^{432}A^{433}M^{434}L^{435}P^{436}K^{437}V^{438}E^{439}T^{440}V^{441}I^{442}D^{443}D^{444}V^{445}S^{446}S^{447}T^{448}L^{449}S^{450}S^{451}F^{452}$ $R^{453}G^{454}V^{455}L^{456}D^{457}K^{458}I^{459}S^{460}A^{461}W^{462}M^{463}P^{464}S^{465}S^{466}N^{467}P^{468}K^{469}I^{470}I^{471}D^{472}L^{473}I^{474}K^{475}E^{476}T^{477}$ $F^{478}V^{479}S^{480}L^{481}F^{482}F^{483}A^{484}I^{485}L^{486}T^{487}K^{488}S^{489}L^{490}Y^{491}P^{492}I^{493}I^{494}Q^{495}G^{496}I^{497}S^{498}S^{499}Y^{500}A^{501}L^{502}$ $R^{503}N^{504}N^{505}L^{506}M^{507}A^{508}N^{509}H^{510}L^{511}T^{512}A^{513}L^{514}S^{515}E^{516}W^{517}L^{518}M^{519}T^{520}L^{521}E^{522}Y^{523}D^{524}S^{525}P^{526}D^{527}$ $E^{528}E^{529}E^{530}M^{531}P^{532}S^{533}T^{534}H^{535}G^{536}F^{537}M^{538}D^{539}D^{540}L^{541}T^{542}S^{543}R^{544}L^{545}P^{546}G^{547}L^{548}N^{549}G^{550}A^{551}K^{552}$ -continued $V^{553}Q^{554}A^{555}A^{556}T^{557}I^{558}Y^{559}E^{560}S^{561}I^{562}G^{563}T^{564}G^{565}L^{566}C^{567}V^{568}A^{569}L^{570}S^{571}G^{572}I^{573}L^{574}S^{575}F^{576}I^{577}$ $A^{578}V^{579}M^{580}C^{581}L^{582}G^{583}I^{584}T^{585}D^{586}L^{587}S^{588}A^{589}V^{590}T^{591}F^{592}N^{593}K^{594}L^{595}L^{596}T^{597}Q^{598}S^{599}S^{600}L^{601}V^{602}$ $G^{603}R^{604}A^{605}L^{606}V^{607}G^{608}V^{609}R^{610}S^{611}F^{612}K^{613}D^{614}V^{615}F^{616}F^{617}G^{618}I^{619}W^{620}D^{621}Y^{622}V^{623}D^{624}N^{625}Q^{626}V^{627}$ $C^{628}E^{629}I^{630}L^{631}Y^{632}G^{633}K^{634}S^{635}R^{636}K^{637}N^{638}L^{639}D^{640}L^{641}L^{642}K^{643}E^{644}Y^{645}P^{646}S^{647}L^{648}D^{649}S^{650}L^{651}L^{652}$ $S^{653}I^{654}F^{655}N^{656}Y^{657}F^{658}H^{659}D^{660}T^{661}V^{662}D^{663}A^{664}N^{665}V^{666}L^{667}I^{668}S^{669}C^{670}N^{671}R^{672}A^{673}A^{674}C^{675}E^{676}L^{677}$ $L^{678}V^{679}K^{680}A^{681}D^{682}N^{683}L^{684}Y^{685}Q^{686}G^{687}Y^{688}L^{689}D^{690}K^{691}S^{692}I^{693}T^{694}L^{695}M^{696}H^{697}R^{698}E^{699}I^{700}S^{701}S^{702}$ $R^{703}L^{704}K^{705}E^{706}A^{707}R^{708}N^{709}S^{710}V^{711}K^{712}D^{713}L^{714}I^{715}A^{716}K^{717}A^{718}Q^{719}V^{720}Y^{721}L^{722}T^{723}C^{724}G^{725}D^{726}G^{727}$ $S^{728}R^{729}V^{730}P^{731}P^{732}V^{733}V^{734}V^{735}Y^{736}M^{737}Y^{738}G^{739}D^{740}A^{741}G^{742}C^{743}G^{744}K^{745}T^{746}E^{747}L^{748}S^{749}M^{750}A^{751}L^{752}$ $Q^{753}D^{754}H^{755}F^{756}A^{757}T^{758}K^{759}Y^{760}F^{761}G^{762}E^{763}V^{764}P^{765}K^{766}K^{767}D^{768}V^{769}I^{770}Y^{771}S^{772}R^{773}K^{774}A^{775}E^{776}N^{777}$ $E^{778}F^{779}W^{780}D^{781}G^{782}V^{783}K^{784}Q^{785}S^{786}H^{787}K^{788}I^{789}I^{790}A^{791}Y^{792}D^{793}D^{794}V^{795}L^{796}Q^{797}I^{798}V^{799}D^{800}S^{801}A^{802}$ $Q^{803}K^{804}P^{805}N^{806}P^{807}E^{808}L^{809}F^{810}E^{811}F^{812}I^{813}R^{814}L^{815}N^{816}N^{817}S^{818}D^{819}P^{820}Y^{821}Q^{822}V^{823}H^{824}M^{825}S^{826}S^{827}$ $V^{828}S^{829}D^{830}K^{831}A^{832}N^{833}T^{834}F^{835}I^{836}A^{837}P^{838}S^{839}F^{840}V^{841}F^{842}A^{843}T^{844}S^{845}N^{846}V^{847}N^{848}P^{849}G^{850}T^{851}Y^{852}$ $V^{853}P^{854}K^{855}S^{856}I^{857}H^{858}S^{859}A^{860}D^{861}A^{862}F^{863}R^{864}R^{865}R^{866}L^{867}D^{868}L^{869}C^{870}V^{871}Y^{872}V^{873}D^{874}V^{875}K^{876}D^{877}$ $E^{878}F^{879}A^{880}R^{881}I^{882}V^{883}A^{884}G^{885}S^{886}K^{887}G^{888}H^{889}R^{890}K^{891}V^{892}P^{893}C^{894}E^{895}Q^{896}K^{897}I^{898}W^{899}L^{900}H^{901}Q^{902}$ $N^{903}P^{904}G^{905}K^{906}T^{907}Q^{908}H^{909}D^{910}M^{911}K^{912}H^{913}E^{914}I^{915}V^{916}A^{917}G^{918}T^{919}Y^{920}K^{921}I^{922}T^{923}P^{924}E^{925}T^{926}A^{927}$ $V^{928}Y^{929}E^{930}L^{931}H^{932}V^{933}D^{934}T^{935}T^{936}L^{937}A^{938}G^{939}D^{940}A^{941}Q^{942}S^{943}K^{944}V^{945}C^{946}A^{947}Y^{948}D^{949}G^{950}L^{951}V^{952}$ $S^{953}L^{954}I^{955}E^{956}Q^{957}V^{958}R^{959}R^{960}L^{961}R^{962}V^{963}A^{964}A^{965}H^{966}S^{967}D^{968}K^{969}V^{970}E^{971}T^{972}D^{973}V^{974}P^{975}V^{976}L^{977}$ $P^{978}T^{979}R^{980}L^{981}H^{982}E^{983}L^{984}S^{985}Q^{986}E^{987}T^{988}F^{989}P^{990}N^{991}T^{992}H^{993}A^{994}G^{995}V^{996}G^{997}F^{998}Q^{999}F^{1000}A^{1001}T^{1002}$ $D^{1003}W^{1004}L^{1005}G^{1006}D^{1007}F^{1008}D^{1009}R^{1010}P^{1011}V^{1012}E^{1013}A^{1014}L^{1015}S^{1016}Y^{1017}L^{1018}N^{1019}K^{1020}T^{1021}L^{1022}$ $E^{1023}A^{1024}H^{1025}F^{1026}V^{1027}S^{1028}R^{1029}S^{1030}A^{1031}N^{1032}D^{1033}G^{1034}S^{1035}M^{1036}F^{1037}I^{1038}P^{1039}A^{1040}S^{1041}E^{1042}$ $V^{1043}A^{1044}D^{1045}L^{1046}L^{1047}C^{1048}Q^{1049}R^{1050}H^{1051}N^{1052}N^{1053}T^{1054}N^{1055}L^{1056}N^{1057}E^{1058}E^{1059}L^{1060}V^{1061}Y^{1062}$ $L^{1063}T^{1064}W^{1065}M^{1066}T^{1067}Q^{1068}I^{1069}T^{1070}D^{1071}K^{1072}E^{1073}L^{1074}A^{1075}S^{1076}S^{1077}L^{1078}V^{1079}Y^{1080}F^{1081}T^{1082}$ $N^{1083}N^{1084}G^{1085}M^{1086}D^{1087}K^{1088}S^{1089}I^{1090}W^{1091}K^{1092}K^{1093}S^{1094}A^{1095}E^{1096}R^{1097}S^{1098}A^{1099}Q^{1100}A^{1101}I^{1102}$ $S^{1103}Q^{1104}C^{1105}K^{1106}N^{1107}A^{1108}W^{1109}T^{1110}R^{1111}I^{1112}N^{1113}D^{1114}F^{1115}L^{1116}K^{1117}N^{1118}H^{1119}W^{1120}I^{1121}S^{1122}$ $I^{1123}S^{1124}A^{1125}V^{1126}I^{1127}G^{1128}S^{1129}A^{1130}L^{1131}L^{1132}I^{1133}G^{1134}G^{1135}V^{1136}S^{1137}S^{1138}A^{1139}V^{1140}K^{1141}C^{1142}$ $A^{1143}T^{1144}K^{1145}C^{1146}R^{1147}V^{1148}R^{1149}K^{1150}I^{1151}L^{1152}Q^{1153}D^{1154}G^{1155}G^{1156}S^{1157}I^{1158}M^{1159}Q^{1160}L^{1161}V^{1162}$ $G^{1163}V^{1164}R^{1165}S^{1166}C^{1167}M^{1168}Y^{1169}A^{1170}C^{1171}Q^{1172}L^{1173}C^{1174}K^{1175}R^{1176}I^{1177}K^{1178}N^{1179}C^{1180}D^{1181}L^{1182}$ $R^{1183}L^{1184}R^{1185}V^{1186}R^{1187}N^{1188}R^{1189}S^{1190}E^{1191}G^{1192}V^{1193}T^{1194}T^{1195}F^{1196}V^{1197}P^{1198}G^{1199}D^{1200}V^{1201}R^{1202}$ $R^{1203}V^{1204}A^{1205}R^{1206}H^{1207}V^{1208}I^{1209}S^{1210}A^{1211}A^{1212}D^{1213}V^{1214}C^{1215}E^{1216}V^{1217}P^{1218}V^{1219}H^{1220}H^{1221}S^{1222}$ $F^{1223}I^{1224}Q^{1225}S^{1226}L^{1227}C^{1228}D^{1229}E^{1230}A^{1231}F^{1232}T^{1233}V^{1234}H^{1235}S^{1236}D^{1237}K^{1238}E^{1239}E^{1240}T^{1241}F^{1242}$ $S^{1243}I^{1244}L^{1245}D^{1246}F^{1247}T^{1248}P^{1249}E^{1250}A^{1251}K^{1252}G^{1253}R^{1254}N^{1255}P^{1256}P^{1257}E^{1258}S^{1259}A^{1260}V^{1261}V^{1262}$ $E^{1263}S^{1264}H^{1265}Q^{1266}D^{1267}Y^{1268}R^{1269}V^{1270}K^{1271}A^{1272}A^{1273}V^{1274}V^{1275}E^{1276}S^{1277}H^{1278}Q^{1279}D^{1280}F^{1281}K^{1282}$ $P^{1283}K^{1284}D^{1285}A^{1286}I^{1287}V^{1288}E^{1289}S^{1290}T^{1291}I^{1292}D^{1293}T^{1294}V^{1295}F^{1296}T^{1297}E^{1298}S^{1299}H^{1300}Q^{1301}D^{1302}$ $V^{1303}R^{1304}V^{1305}K^{1306}L^{1307}H^{1308}P^{1309}Q^{1310}I^{1311}E^{1312}S^{1313}H^{1314}Q^{1315}D^{1316}F^{1317}R^{1318}A^{1319}K^{1320}N^{1321}P^{1322}$ $I^{1323}V^{1324}E^{1325}S^{1326}R^{1327}K^{1328}P^{1329}D^{1330}Y^{1331}Q^{1332}V^{1333}E^{1334}W^{1335}T^{1336}D^{1337}L^{1338}R^{1339}T^{1340}E^{1341}S^{1342}$ $S^{1343}N^{1344}D^{1345}R^{1346}N^{1347}A^{1348}Q^{1349}D^{1350}I^{1351}S^{1352}N^{1353}R^{1354}I^{1355}L^{1356}S^{1357}R^{1358}N^{1359}F^{1360}V^{1361}R^{1362}$ $L^{1363}Y^{1364}V^{1365}P^{1366}G^{1367}S^{1368}S^{1369}L^{1370}Y^{1371}T^{1372}H^{1373}G^{1374}L^{1375}F^{1376}A^{1377}Y^{1378}G^{1379}R^{1380}M^{1381}L^{1382}$ $L^{1383}M^{1384}P^{1385}K^{1386}H^{1387}M^{1388}F^{1389}D^{1390}M^{1391}L^{1392}N^{1393}G^{1394}S^{1395}V^{1396}E^{1397}I^{1398}V^{1399}S^{1400}I^{1401}A^{1402}$ $D^{1403}K^{1404}G^{1405}N^{1406}T^{1407}R^{1408}V^{1409}H^{1410}V^{1411}K^{1412}I^{1413}Q^{1414}S^{1415}H^{1416}K^{1417}T^{1418}V^{1419}T^{1420}R^{1421}G^{1422}$ $G^{1423}Y^{1424}E^{1425}V^{1426}D^{1427}I^{1428}V^{1429}I^{1430}C^{1431}E^{1432}M^{1433}G^{1434}N^{1435}S^{1436}I^{1437}S^{1438}A^{1439}R^{1440}K^{1441}D^{1442}$ $I^{1443}T^{1444}S^{1445}Y^{1446}F^{1447}P^{1448}T^{1449}V^{1450}K^{1451}E^{1452}L^{1453}P^{1454}G^{1455}L^{1456}T^{1457}G^{1458}M^{1459}M^{1460}S^{1461}S^{1462}$ -continued $G^{1463}R^{1464}M^{1465}R^{1466}V^{1467}F^{1468}S^{1469}T^{1470}A^{1471}K^{1472}F^{1473}K^{1474}A^{1475}S^{1476}D^{1477}S^{1478}C^{1479}S^{1480}Y^{1481}L^{1482}$ $M^{1483}P^{1484}Q^{1485}D^{1486}F^{1487}V^{1488}A^{1489}K^{1490}Y^{1491}I^{1492}A^{1493}A^{1494}V^{1495}D^{1496}H^{1497}I^{1498}T^{1499}S^{1500}K^{1501}S^{1502}$ $P^{1503}E^{1504}K^{1505}K^{1506}S^{1507}Y^{1508}F^{1509}I^{1510}R^{1511}Q^{1512}G^{1513}F^{1514}E^{1515}A^{1516}E^{1517}S^{1518}D^{1519}S^{1520}M^{1521}Q^{1522}$ $G^{1523}D^{1524}C^{1525}C^{1526}S^{1527}P^{1528}Y^{1529}V^{1530}L^{1531}F^{1532}N^{1533}S^{1534}A^{1535}S^{1536}R^{1537}A^{1538}K^{1539}I^{1540}V^{1541}G^{1542}$ $L^{1543}H^{1544}C^{1545}A^{1546}G^{1547}F^{1548}D^{1549}G^{1550}T^{1551}A^{1552}R^{1553}V^{1554}F^{1555}A^{1556}Q^{1557}I^{1558}I^{1559}T^{1560}Q^{1561}E^{1562}$ $D^{1563}I^{1564}M^{1565}A^{1566}A^{1567}T^{1568}P^{1569}T^{1570}T^{1571}H^{1572}A^{1573}G^{1574}R^{1575}V^{1576}T^{1577}T^{1578}E^{1579}F^{1580}P^{1581}H^{1582}$ $T^{1583}S^{1584}L^{1585}R^{1586}D^{1587}S^{1588}P^{1589}L^{1590}P^{1591}N^{1592}S^{1593}M^{1594}A^{1595}I^{1596}G^{1597}S^{1598}V^{1599}K^{1600}T^{1601}A^{1602}$ $P^{1603}N^{1604}P^{1605}T^{1606}K^{1607}S^{1608}E^{1609}I^{1610}T^{1611}R^{1612}S^{1613}P^{1614}I^{1615}H^{1616}G^{1617}C^{1618}F^{1619}P^{1620}V^{1621}R^{1622}$ $T^{1623}A^{1624}P^{1625}A^{1626}T^{1627}L^{1628}Y^{1629}S^{1630}P^{1631}T^{1632}E^{1633}N^{1634}L^{1635}L^{1636}I^{1637}K^{1638}N^{1639}A^{1640}M^{1641}K^{1642}$ $V^{1643}T^{1644}K^{1645}N^{1646}V^{1647}E^{1648}L^{1649}L^{1650}E^{1651}E^{1652}D^{1653}L^{1654}I^{1655}D^{1656}A^{1657}C^{1658}V^{1659}H^{1660}D^{1661}V^{1662}$ $K^{1663}R^{1664}I^{1665}L^{1666}N^{1667}A^{1668}P^{1669}G^{1670}V^{1671}S^{1672}D^{1673}V^{1674}E^{1675}K^{1676}R^{1677}V^{1678}L^{1679}T^{1680}H^{1681}E^{1682}$ $E^{1683}S^{1684}I^{1685}T^{1686}G^{1687}I^{1688}E^{1689}N^{1690}R^{1691}Q^{1692}Y^{1693}M^{1694}N^{1695}A^{1696}L^{1697}N^{1698}R^{1699}S^{1700}T^{1701}S^{1702}$ $A^{1703}G^{1704}F^{1705}P^{1706}Y^{1707}S^{1708}S^{1709}R^{1710}K^{1711}A^{1712}K^{1713}G^{1714}K^{1715}S^{1716}G^{1717}K^{1718}Q^{1719}T^{1720}W^{1721}L^{1722}$ $G^{1723}S^{1724}E^{1725}E^{1726}F^{1727}I^{1728}V^{1729}D^{1730}N^{1731}P^{1732}D^{1733}L^{1734}K^{1735}E^{1736}H^{1737}V^{1738}E^{1739}K^{1740}I^{1741}V^{1742}$ $D^{1743}K^{1744}A^{1745}K^{1746}D^{1747}G^{1748}I^{1749}V^{1750}D^{1751}V^{1752}S^{1753}L^{1754}G^{1755}I^{1756}F^{1757}A^{1758}A^{1759}T^{1760}L^{1761}K^{1762}$ $D^{1763}E^{1764}R^{1765}R^{1766}P^{1767}L^{1768}E^{1769}K^{1770}V^{1171}Q^{1772}A^{1773}N^{1174}K^{1775}T^{1776}R^{1777}V^{1778}F^{1779}A^{1780}A^{1781}S^{1782}$ $N^{1783}Q^{1784}G^{1785}L^{1786}A^{1787}L^{1788}A^{1789}L^{1790}R^{1791}R^{1792}Y^{1793}Y^{1794}L^{1795}S^{1796}F^{1797}L^{1798}D^{1799}H^{1800}V^{1801}M^{1802}$ $T^{1803}N^{1804}R^{1805}I^{1806}D^{1807}N^{1808}E^{1809}I^{1810}G^{1811}L^{1812}G^{1813}V^{1814}N^{1815}V^{1816}Y^{1817}S^{1818}Y^{1819}D^{1820}W^{1821}T^{1822}$ $R^{1823}I^{1824}V^{1825}N^{1826}K^{1827}L^{1828}K^{1829}R^{1830}V^{1831}G^{1832}D^{1833}K^{1834}V^{1835}I^{1836}A^{1837}G^{1838}D^{1839}F^{1840}S^{1841}N^{1842}$ $F^{1843}D^{1844}G^{1845}S^{1846}L^{1847}N^{1848}S^{1849}Q^{1850}I^{1851}L^{1852}S^{1853}R^{1854}V^{1855}S^{1856}E^{1857}I^{1858}V^{1859}T^{1860}D^{1861}W^{1862}$ $Y^{1863}G^{1864}D^{1865}D^{1866}A^{1867}E^{1868}N^{1869}G^{1870}L^{1871}I^{1872}R^{1873}H^{1874}T^{1875}L^{1876}L^{1877}E^{1878}Y^{1879}L^{1880}F^{1881}N^{1882}$ $A^{1883}T^{1884}W^{1885}L^{1886}M^{1887}N^{1888}G^{1889}K^{1890}V^{1891}F^{1892}Q^{1893}L^{1894}N^{1895}H^{1896}S^{1897}Q^{1898}P^{1899}S^{1900}G^{1901}N^{1902}$ $P^{1903}L^{1904}T^{1905}T^{1906}L^{1907}I^{1908}N^{1909}C^{1910}V^{1911}Y^{1912}N^{1913}M^{1914}I^{1915}I^{1916}F^{1917}R^{1918}Y^{1919}V^{1920}Y^{1921}L^{1922}$ $L^{1923}A^{1924}Q^{1925}R^{1926}E^{1927}N^{1928}G^{1929}F^{1930}P^{1931}M^{1932}T^{1933}L^{1934}S^{1935}G^{1936}F^{1937}T^{1938}T^{1939}N^{1940}V^{1941}A^{1942}$ $C^{1943}I^{1944}F^{1945}Y^{1946}G^{1947}D^{1948}D^{1949}S^{1950}L^{1951}C^{1952}S^{1953}V^{1954}S^{1955}D^{1956}K^{1957}V^{1958}S^{1959}E^{1960}W^{1961}F^{1962}$ $N^{1963}Q^{1964}H^{1965}V^{1966}I^{1967}T^{1968}R^{1969}L^{1970}M^{1971}A^{1972}A^{1973}T^{1974}G^{1975}H^{1976}E^{1977}Y^{1978}T^{1979}D^{1980}E^{1981}T^{1982}$ $K^{1983}S^{1984}G^{1985}S^{1986}P^{1987}P^{1988}P^{1989}Y^{1990}R^{1991}S^{1992}L^{1993}N^{1994}E^{1995}V^{1996}T^{1997}F^{1998}L^{1999}K^{2000}R^{2001}E^{2002}$ $F^{2003}V^{2004}L^{2005}R^{2006}D^{2007}H^{2008}F^{2009}W^{2010}I^{2011}A^{2012}P^{2013}L^{2014}S^{2015}R^{2016}N^{2017}T^{2018}I^{2019}E^{2020}D^{2021}M^{2022}$ $C^{2023}M^{2024}W^{2025}S^{2026}R^{2027}K^{2028}N^{2029}I^{2030}D^{2031}A^{2032}Q^{2033}D^{2034}A^{2035}L^{2036}L^{2037}Q^{2038}T^{2039}T^{2040}R^{2041}I^{2042}$ $A^{2043}S^{2044}F^{2045}E^{2046}A^{2047}S^{2048}L^{2049}H^{2050}E^{2051}K^{2052}N^{2053}Y^{2054}F^{2055}L^{2056}M^{2057}F^{2058}C^{2059}D^{2060}V^{2061}I^{2062}$ $K^{2063}K^{2064}A^{2065}C^{2066}R^{2067}N^{2068}A^{2069}G^{2070}Y^{2071}K^{2072}E^{2073}A^{2074}C^{2075}L^{2076}H^{2077}E^{2078}L^{2079}D^{2080}C^{2081}K^{2082}$ $S^{2083}F^{2084}L^{2085}L^{2086}A^{2087}Q^{2088}Q^{2089}G^{2090}R^{2091}A^{2092}G^{2093}A^{2094}H^{2095}D^{2096}S^{2097}E^{2098}F^{2099}L^{2100}S^{2101}Q^{2102}$ $L^{2103}L^{2104}D^{2105}L^{2106}N^{2107}$
(SEQ ID NO: 457)

Replikin Sequences in Amino-Terminal Portion of Peptide (1) $H^{20}R^{21}A^{22}F^{23}Y^{24}V^{25}M^{26}N^{27}D^{28}D^{29}G^{30}E^{31}N^{32}R^{33}I^{34}Y^{35}S^{36}L^{37}I^{38}G^{39}T^{40}L^{41}R^{42}R^{43}A^{44}P^{45}A^{46}F^{47}K^{48}V^{49}G^{50}$
$S^{51}R^{52}R^{53}Y^{54}K^{55}S^{56}H^{57}I^{58}P^{59}Y^{60}R^{61}R^{62}K^{63}$
(SEQ ID NO: 458)

(2) $K^{48}V^{49}G^{50}S^{51}R^{52}R^{53}Y^{54}K^{55}S^{56}H^{57}$
(SEQ ID NO: 459)

(3) $K^{48}V^{49}G^{50}S^{51}R^{52}R^{53}Y^{54}K^{55}S^{56}H^{57}I^{58}P^{59}Y^{60}R^{61}R^{62}K^{63}A^{64}T^{65}V^{66}A^{67}E^{68}L^{69}C^{70}N^{71}Q^{72}L^{73}H^{74}$
(SEQ ID NO: 460)

(4) $K^{55}S^{56}H^{57}I^{58}P^{59}Y^{60}R^{61}R^{62}K^{63}$
(SEQ ID NO: 461)

-continued (5) $K^{55}S^{56}H^{57}I^{58}P^{59}Y^{60}R^{61}R^{62}K^{63}A^{64}T^{65}V^{66}A^{67}E^{68}L^{69}C^{70}N^{71}Q^{72}L^{73}H^{74}$
(SEQ ID NO: 462)

(6) $H^{57}I^{58}P^{59}Y^{60}R^{61}R^{62}K^{63}A^{64}T^{65}V^{66}A^{67}E^{68}L^{69}C^{70}N^{71}Q^{72}L^{73}H^{74}D^{75}R^{76}V^{77}L^{78}P^{79}F^{80}A^{81}N^{82}P^{83}Q^{84}V^{85}W^{86}K^{87}$
$E^{88}V^{89}I^{90}S^{91}E^{92}N^{93}K^{94}$
(SEQ ID NO: 463)

(7) $H^{57}I^{58}P^{59}Y^{60}R^{61}R^{62}K^{63}A^{64}T^{65}V^{66}A^{67}E^{68}L^{69}C^{70}N^{71}Q^{72}L^{73}H^{74}D^{75}R^{76}V^{77}L^{78}P^{79}F^{80}A^{81}N^{82}P^{83}Q^{84}V^{85}W^{86}K^{87}$
$E^{88}V^{89}I^{90}S^{91}E^{92}N^{93}K^{94}V^{95}Q^{96}P^{97}D^{98}S^{99}M^{100}L^{101}K^{102}$
(SEQ ID NO: 464)

(8) $H^{74}D^{75}R^{76}V^{77}L^{78}P^{79}F^{80}A^{81}N^{82}P^{83}Q^{84}V^{85}W^{86}K^{87}E^{88}V^{89}I^{90}S^{91}E^{92}N^{93}K^{94}V^{95}Q^{96}P^{97}D^{98}S^{99}M^{100}L^{101}K^{102}$
(SEQ ID NO: 465)

(9) $H^{74}D^{75}R^{76}V^{77}L^{78}P^{79}F^{80}A^{81}N^{82}P^{83}Q^{84}V^{85}W^{86}K^{87}E^{88}V^{89}I^{90}S^{91}E^{92}N^{93}K^{94}$
(SEQ ID NO: 466)

(10) $K^{145}C^{146}N^{147}D^{148}C^{149}I^{150}L^{151}K^{152}M^{153}N^{154}R^{155}N^{156}V^{157}E^{158}Y^{159}P^{160}Y^{161}H^{162}$
(SEQ ID NO: 467)

(11) $K^{469}I^{470}I^{471}D^{472}L^{473}I^{474}K^{475}E^{476}T^{477}F^{478}V^{479}S^{480}L^{481}F^{482}F^{483}A^{484}I^{485}L^{486}T^{487}K^{488}S^{489}L^{490}Y^{491}P^{492}$
$I^{493}I^{494}Q^{495}G^{496}I^{497}S^{498}S^{499}Y^{500}A^{501}L^{502}R^{503}N^{504}N^{505}L^{506}M^{507}A^{508}N^{509}H^{510}$
(SEQ ID NO: 468)

(12) $K^{634}S^{635}R^{636}K^{637}N^{638}L^{639}D^{640}L^{641}L^{642}K^{643}E^{644}Y^{645}P^{646}S^{647}L^{648}D^{649}S^{650}L^{651}L^{652}S^{653}I^{654}F^{655}N^{656}Y^{657}$
$F^{658}H^{659}$
(SEQ ID NO: 469)

(13) $K^{637}N^{638}L^{639}D^{640}L^{641}L^{642}K^{643}E^{644}Y^{645}P^{646}S^{647}L^{648}D^{649}S^{650}L^{651}L^{652}S^{653}I^{654}F^{655}N^{656}Y^{657}F^{658}H^{659}$
(SEQ ID NO: 470)

(14) $H^{697}R^{698}E^{699}I^{700}S^{701}S^{702}R^{703}L^{704}K^{705}E^{706}A^{707}R^{708}N^{709}S^{710}V^{711}K^{712}$
(SEQ ID NO: 471)

Replikin Sequences in Mid-Molecule Portion of Peptide

(15) $K^{705}E^{706}A^{707}R^{708}N^{709}S^{710}V^{711}K^{712}D^{713}L^{714}I^{715}A^{716}K^{717}A^{718}Q^{719}V^{720}Y^{721}L^{722}T^{723}C^{724}G^{725}D^{726}G^{727}S^{728}$
$R^{729}V^{730}P^{731}P^{732}V^{733}V^{734}V^{735}Y^{736}M^{737}Y^{738}G^{739}D^{740}A^{741}G^{742}C^{743}G^{744}K^{745}T^{746}E^{747}L^{748}S^{749}M^{750}A^{751}L^{752}$
$Q^{753}D^{754}H^{755}$
(SEQ ID NO: 472)

(16) $H^{755}F^{756}A^{757}T^{758}K^{759}Y^{760}F^{761}G^{762}E^{763}V^{764}P^{765}K^{766}$
(SEQ ID NO: 473)

(17) $H^{755}F^{756}A^{757}T^{758}K^{759}Y^{760}F^{761}G^{762}E^{763}V^{764}P^{765}K^{766}K^{767}$
(SEQ ID NO: 474)

(18) $H^{755}F^{756}A^{757}T^{758}K^{759}Y^{760}F^{761}G^{762}E^{763}V^{764}P^{765}K^{766}K^{767}D^{768}V^{769}I^{770}Y^{771}S^{772}R^{773}K^{774}$
(SEQ ID NO: 475)

(19) $H^{755}F^{756}A^{757}T^{758}K^{759}Y^{760}F^{761}G^{762}E^{763}V^{764}P^{765}K^{766}K^{767}D^{768}V^{769}I^{770}Y^{771}S^{772}R^{773}K^{774}A^{775}E^{776}N^{777}E^{778}$
$F^{779}W^{780}D^{781}G^{782}V^{783}K^{784}$
(SEQ ID NO: 476)

(20) $K^{759}Y^{760}F^{761}G^{762}E^{763}V^{764}P^{765}K^{766}K^{767}D^{768}V^{769}I^{770}Y^{771}S^{772}R^{773}K^{774}A^{775}E^{776}N^{777}E^{778}F^{779}W^{780}D^{781}G^{782}$
$V^{783}K^{784}Q^{785}S^{786}H^{787}$
(SEQ ID NO: 477)

(21) $K^{766}K^{767}D^{768}V^{769}I^{770}Y^{771}S^{772}R^{773}K^{774}A^{775}E^{776}N^{777}E^{778}F^{779}W^{780}D^{781}G^{782}V^{783}K^{784}Q^{785}S^{786}H^{787}$
(SEQ ID NO: 478)

(22) $K^{767}D^{768}V^{769}I^{770}Y^{771}S^{772}R^{773}K^{774}A^{775}E^{776}N^{777}E^{778}F^{779}W^{780}D^{781}G^{782}V^{783}K^{784}Q^{785}S^{786}H^{787}$
(SEQ ID NO: 479)

(23) $K^{774}A^{775}E^{776}N^{777}E^{778}F^{779}W^{780}D^{781}G^{782}V^{783}K^{784}Q^{785}S^{786}H^{787}$
(SEQ ID NO: 480)

(24) $K^{774}A^{775}E^{776}N^{777}E^{778}F^{779}W^{780}D^{781}G^{782}V^{783}K^{784}Q^{785}S^{786}H^{787}K^{788}I^{789}I^{790}A^{791}Y^{792}D^{793}D^{794}V^{795}L^{796}Q^{797}$
$I^{798}V^{799}D^{800}S^{801}A^{802}Q^{803}K^{804}P^{805}N^{806}P^{807}E^{808}L^{809}F^{810}E^{811}F^{812}I^{813}R^{814}L^{815}N^{816}N^{817}S^{818}D^{819}P^{820}Y^{821}$
$Q^{822}V^{823}H^{824}$
(SEQ ID NO: 481)

(25) $H^{858}S^{859}A^{860}D^{861}A^{862}F^{863}R^{864}R^{865}R^{866}L^{867}D^{868}L^{869}C^{870}V^{871}Y^{872}V^{873}D^{874}V^{875}K^{876}D^{877}E^{878}F^{879}A^{880}R^{881}$
$I^{882}V^{883}A^{884}G^{885}S^{886}K^{887}G^{888}H^{889}R^{890}K^{891}V^{892}P^{893}C^{894}E^{895}Q^{896}K^{897}I^{898}W^{899}L^{900}H^{901}Q^{902}N^{903}P^{904}G^{905}$
$K^{906}$
(SEQ ID NO: 482)

(26) $H^{858}S^{859}A^{860}D^{861}A^{862}F^{863}R^{864}R^{865}R^{866}L^{867}D^{868}L^{869}C^{870}V^{871}Y^{872}V^{873}D^{874}V^{875}K^{876}D^{877}E^{878}F^{879}A^{880}R^{881}$
$I^{882}V^{883}A^{884}G^{885}S^{886}K^{887}G^{888}H^{889}R^{890}K^{891}V^{892}P^{893}C^{894}E^{895}Q^{896}K^{897}$
(SEQ ID NO: 483)

-continued

(27) $K^{887}G^{888}H^{889}R^{890}K^{891}V^{892}P^{893}C^{894}E^{895}Q^{896}K^{897}I^{898}W^{899}L^{900}H^{901}Q^{902}N^{903}P^{904}G^{905}K^{906}T^{907}Q^{908}H^{909}D^{910}$
$M^{911}K^{912}H^{913}E^{914}I^{915}V^{916}A^{917}G^{918}T^{919}Y^{920}K^{921}I^{922}T^{923}P^{924}E^{925}T^{926}A^{927}V^{928}Y^{929}E^{930}L^{931}H^{932}$
(SEQ ID NO: 484)

(28) $K^{887}G^{888}H^{889}R^{890}K^{891}V^{892}P^{893}C^{894}E^{895}Q^{896}K^{897}I^{898}W^{899}L^{900}H^{901}$
(SEQ ID NO: 485)

(29) $K^{887}G^{888}H^{889}R^{890}K^{891}V^{892}P^{893}C^{894}E^{895}Q^{896}K^{897}$
(SEQ ID NO: 486)

(30) $K^{887}G^{888}H^{889}R^{890}K^{891}V^{892}P^{893}C^{894}E^{895}Q^{896}K^{897}I^{898}W^{899}L^{900}H^{901}Q^{902}N^{903}P^{904}G^{905}K^{906}T^{907}Q^{908}H^{909}$
(SEQ ID NO: 487)

(31) $K^{887}G^{888}H^{889}R^{890}K^{891}V^{892}P^{893}C^{894}E^{895}Q^{896}K^{897}I^{898}W^{899}L^{900}H^{901}Q^{902}N^{903}P^{904}G^{905}K^{906}T^{907}Q^{908}H^{909}D^{910}$
$M^{911}K^{912}H^{913}$
(SEQ ID NO: 488)

(32) $H^{889}R^{890}K^{891}V^{892}P^{893}C^{894}E^{895}Q^{896}K^{897}I^{898}W^{899}L^{900}H^{901}Q^{902}N^{903}P^{904}G^{905}K^{906}T^{907}Q^{908}H^{909}D^{910}M^{911}K^{912}$
$H^{913}E^{914}I^{915}V^{916}A^{917}G^{918}T^{919}Y^{920}K^{921}$
(SEQ ID NO: 489)

(33) $H^{889}R^{890}K^{891}V^{892}P^{893}C^{894}E^{895}Q^{896}K^{897}I^{898}W^{899}L^{900}H^{901}Q^{902}N^{903}P^{904}G^{905}K^{906}$
(SEQ ID NO: 490)

(34) $H^{889}R^{890}K^{891}V^{892}P^{893}C^{894}E^{895}Q^{896}K^{897}$
(SEQ ID NO: 491)

(35) $H^{889}R^{890}K^{891}V^{892}P^{893}C^{894}E^{895}Q^{896}K^{897}I^{898}W^{899}L^{900}H^{901}Q^{902}N^{903}P^{904}G^{905}K^{906}T^{907}Q^{908}H^{909}D^{910}M^{911}K^{912}$
(SEQ ID NO: 492)

(36) $K^{891}V^{892}P^{893}C^{894}E^{895}Q^{896}K^{897}I^{898}W^{899}L^{900}H^{901}$
(SEQ ID NO: 493)

(37) $K^{891}V^{892}P^{893}C^{894}E^{895}Q^{896}K^{897}I^{898}W^{899}L^{900}H^{901}Q^{902}N^{903}P^{904}G^{905}K^{906}T^{907}Q^{908}H^{909}$
(SEQ ID NO: 494)

(38) $K^{891}V^{892}P^{893}C^{894}E^{895}Q^{896}K^{897}I^{898}W^{899}L^{900}H^{901}Q^{902}N^{903}P^{904}G^{905}K^{906}T^{907}Q^{908}H^{909}D^{910}M^{911}K^{912}H^{913}$
(SEQ ID NO: 495)

(39) $K^{891}V^{892}P^{893}C^{894}E^{895}Q^{896}K^{897}I^{898}W^{899}L^{900}H^{901}Q^{902}N^{903}P^{904}G^{905}K^{906}T^{907}Q^{908}H^{909}D^{910}M^{911}K^{912}H^{913}E^{914}$
$I^{915}V^{916}A^{917}G^{918}T^{919}Y^{920}K^{921}I^{922}T^{923}P^{924}E^{925}T^{926}A^{927}V^{928}Y^{929}E^{930}L^{931}H^{932}$
(SEQ ID NO: 496)

(40) $K^{897}I^{898}W^{899}L^{900}H^{901}Q^{902}N^{903}P^{904}G^{905}K^{906}$
(SEQ ID NO: 497)

(41) $K^{897}I^{898}W^{899}L^{900}H^{901}Q^{902}N^{903}P^{904}G^{905}K^{906}T^{907}Q^{908}H^{909}$
(SEQ ID NO: 498)

(42) $K^{897}I^{898}W^{899}L^{900}H^{901}Q^{902}N^{903}P^{904}G^{905}K^{906}T^{907}Q^{908}H^{909}D^{910}M^{911}K^{912}H^{913}$
(SEQ ID NO: 499)

(43) $K^{897}I^{898}W^{899}L^{900}H^{901}Q^{902}N^{903}P^{904}G^{905}K^{906}T^{907}Q^{908}H^{909}D^{910}M^{911}K^{912}H^{913}E^{914}I^{915}V^{916}A^{917}G^{918}T^{919}Y^{920}$
$K^{921}I^{922}T^{923}P^{924}E^{925}T^{926}A^{927}V^{928}Y^{929}E^{930}L^{931}H^{932}$
(SEQ ID NO: 500)

(44) $H^{901}Q^{902}N^{903}P^{904}G^{905}K^{906}T^{907}Q^{908}H^{909}D^{910}M^{911}K^{912}$
(SEQ ID NO: 501)

(45) $H^{901}Q^{902}N^{903}P^{904}G^{905}K^{906}T^{907}Q^{908}H^{909}D^{910}M^{911}K^{912}H^{913}E^{914}I^{915}V^{916}A^{917}G^{918}T^{919}Y^{920}K^{921}$
(SEQ ID NO: 502)

(46) $K^{906}T^{907}Q^{908}H^{909}D^{910}M^{911}K^{912}$
(SEQ ID NO: 503)

(47) $K^{906}T^{907}Q^{908}H^{909}D^{910}M^{911}K^{912}H^{913}$
(SEQ ID NO: 504)

(48) $K^{906}T^{907}Q^{908}H^{909}D^{910}M^{911}K^{912}H^{913}E^{914}I^{915}V^{916}A^{917}G^{918}T^{919}Y^{920}K^{921}I^{922}T^{923}P^{924}E^{925}T^{926}A^{927}V^{928}Y^{929}$
$E^{930}L^{931}H^{932}$
(SEQ ID NO: 505)

(49) $H^{909}D^{910}M^{911}K^{912}H^{913}E^{914}I^{915}V^{916}A^{917}G^{918}T^{919}Y^{920}K^{921}$
(SEQ ID NO: 506)

(59) $K^{912}H^{913}E^{914}I^{915}V^{916}A^{917}G^{918}T^{919}Y^{920}K^{921}$
(SEQ ID NO: 507)

(51) $K^{912}H^{913}E^{914}I^{915}V^{916}A^{917}G^{918}T^{919}Y^{920}K^{921}I^{922}T^{923}P^{924}E^{925}T^{926}A^{927}V^{928}Y^{929}E^{930}L^{931}H^{932}$
(SEQ ID NO: 508)

-continued

(52) $H^{1119}W^{1120}I^{1121}S^{1122}I^{1123}S^{1124}A^{1125}V^{1126}I^{1127}G^{1128}S^{1129}A^{1130}L^{1131}L^{1132}I^{1133}G^{1134}G^{1135}V^{1136}S^{1137}S^{1138}A^{1139}V^{1140}K^{1141}C^{1142}A^{1143}T^{1144}K^{1145}C^{1146}R^{1147}V^{1148}R^{1149}K^{1150}$
(SEQ ID NO: 509)

(53) $H^{1278}Q^{1279}D^{1280}F^{1281}K^{1282}P^{1283}K^{1284}D^{1285}A^{1286}I^{1287}V^{1288}E^{1289}S^{1290}T^{1291}I^{1292}D^{1293}T^{1294}V^{1295}F^{1296}T^{1297}E^{1298}S^{1299}H^{1300}Q^{1301}D^{1302}V^{1303}R^{1304}V^{1305}K^{1306}L^{1307}H^{1308}P^{1309}Q^{1310}I^{1311}E^{1312}S^{1313}H^{1314}Q^{1315}D^{1316}F^{1317}R^{1318}A^{1319}K^{1320}N^{1321}P^{1322}I^{1323}V^{1324}E^{1325}S^{1326}R^{1327}K^{1328}$
(SEQ ID NO: 510)

(54) $H^{1300}Q^{1301}D^{1302}V^{1303}R^{1304}V^{1305}K^{1306}L^{1307}H^{1308}P^{1309}Q^{1310}I^{1311}E^{1312}S^{1313}H^{1314}Q^{1315}D^{1316}F^{1317}R^{1318}A^{1319}K^{1320}N^{1321}P^{1322}I^{1323}V^{1324}E^{1325}S^{1326}R^{1327}K^{1328}$
(SEQ ID NO: 511)

(55) $H^{1308}P^{1309}Q^{1310}I^{1311}E^{1312}S^{1313}H^{1314}Q^{1315}D^{1316}F^{1317}R^{1318}A^{1319}K^{1320}N^{1321}P^{1322}I^{1323}V^{1324}E^{1325}S^{1326}R^{1327}K^{1328}$
(SEQ ID NO: 512)

(56) $H^{1314}Q^{1315}D^{1316}F^{1317}R^{1318}A^{1319}K^{1320}N^{1321}P^{1322}I^{1323}V^{1324}E^{1325}S^{1326}R^{1327}K^{1328}$
(SEQ ID NO: 513)

(57) $H^{1373}G^{1374}L^{1375}F^{1376}A^{1377}Y^{1378}G^{1379}R^{1380}M^{1381}L^{1382}L^{1383}M^{1384}P^{1385}K^{1386}H^{1387}M^{1388}F^{1389}D^{1390}M^{1391}L^{1392}N^{1393}G^{1394}S^{1395}V^{1396}E^{1397}I^{1398}V^{1399}S^{1400}I^{1401}A^{1402}D^{1403}K^{1404}G^{1405}N^{1406}T^{1407}R^{1408}V^{1409}H^{1410}V^{1411}K^{1412}$
(SEQ ID NO: 514)

(58) $H^{1387}M^{1388}F^{1389}D^{1390}M^{1391}L^{1392}N^{1393}G^{1394}S^{1395}V^{1396}E^{1397}I^{1398}V^{1399}S^{1400}I^{1401}A^{1402}D^{1403}K^{1404}G^{1405}N^{1406}T^{1407}R^{1408}V^{1409}H^{1410}V^{1411}K^{1412}$
(SEQ ID NO: 515)

(59) $K^{1404}G^{1405}N^{1406}T^{1407}R^{1408}V^{1409}H^{1410}V^{1411}K^{1412}$
(SEQ ID NO: 516)

(60) $K^{1404}G^{1405}N^{1406}T^{1407}R^{1408}V^{1409}H^{1410}V^{1411}K^{1412}I^{1413}Q^{1414}S^{1415}H^{1416}$
(SEQ ID NO: 517)

Replikin Sequences in Carboxy-Terminal Portion of Peptide

(61) $H^{1410}V^{1411}K^{1412}I^{1413}Q^{1414}S^{1415}H^{1416}K^{1417}T^{1418}V^{1419}T^{1420}R^{1421}G^{1422}G^{1423}Y^{1424}E^{1425}V^{1426}D^{1427}I^{1428}V^{1429}I^{1430}C^{1431}E^{1432}M^{1433}G^{1434}N^{1435}S^{1436}I^{1437}S^{1438}A^{1439}R^{1440}K^{1441}D^{1442}I^{1443}T^{1444}S^{1445}Y^{1446}F^{1447}P^{1448}T^{1449}V^{1450}K^{1451}$
(SEQ ID NO: 518)

(62) $H^{1416}K^{1417}T^{1418}V^{1419}T^{1420}R^{1421}G^{1422}G^{1423}Y^{1424}E^{1425}V^{1426}D^{1427}I^{1428}V^{1429}I^{1430}C^{1431}E^{1432}M^{1433}G^{1434}N^{1435}S^{1436}I^{1437}S^{1438}A^{1439}R^{1440}K^{1441}D^{1442}I^{1443}T^{1444}S^{1445}Y^{1446}F^{1447}P^{1448}T^{1449}V^{1450}K^{1451}$
(SEQ ID NO: 519)

(63) $H^{1582}T^{1583}S^{1584}L^{1585}R^{1586}D^{1587}S^{1588}P^{1589}L^{1590}P^{1591}N^{1592}S^{1593}M^{1594}A^{1595}I^{1596}G^{1597}S^{1598}V^{1599}K^{1600}T^{1601}A^{1602}P^{1603}N^{1604}P^{1605}T^{1606}K^{1607}$
(SEQ ID NO: 520)

(64) $K^{1600}T^{1601}A^{1602}P^{1603}N^{1604}P^{1605}T^{1606}K^{1607}S^{1608}E^{1609}I^{1610}T^{1611}R^{1612}S^{1613}P^{1614}I^{1615}H^{1616}$
(SEQ ID NO: 521)

(65) $H^{1616}G^{1617}C^{1618}F^{1619}P^{1620}V^{1621}R^{1622}T^{1623}A^{1624}P^{1625}A^{1626}T^{1627}L^{1628}Y^{1629}S^{1630}P^{1631}T^{1632}E^{1633}N^{1634}L^{1635}L^{1636}I^{1637}K^{1638}N^{1639}A^{1640}M^{1641}K^{1642}V^{1643}T^{1644}K^{1645}$
(SEQ ID NO: 522)

(66) $K^{1638}N^{1639}A^{1640}M^{1641}K^{1642}V^{1643}T^{1644}K^{1645}N^{1646}V^{1647}E^{1648}L^{1649}L^{1650}E^{1651}E^{1652}D^{1653}L^{1654}I^{1655}D^{1656}A^{1657}C^{1658}V^{1659}H^{1660}$
(SEQ ID NO: 523)

(67) $K^{1638}N^{1639}A^{1640}M^{1641}K^{1642}V^{1643}T^{1644}K^{1645}N^{1646}V^{1647}E^{1648}L^{1649}L^{1650}E^{1651}E^{1652}D^{1653}L^{1654}I^{1655}D^{1656}A^{1657}C^{1658}V^{1659}H^{1660}D^{1661}V^{1662}K^{1663}R^{1664}I^{1665}L^{1666}N^{1667}A^{1668}P^{1669}G^{1670}V^{1671}S^{1672}D^{1673}V^{1674}E^{1675}K^{1676}R^{1677}V^{1678}L^{1679}T^{1680}H^{1681}$
(SEQ ID NO: 524)

(68) $H^{1681}E^{1682}E^{1683}S^{1684}I^{1685}T^{1686}G^{1687}I^{1688}E^{1689}N^{1690}R^{1691}Q^{1692}Y^{1693}M^{1694}N^{1695}A^{1696}L^{1697}N^{1698}R^{1699}S^{1700}T^{1701}S^{1702}A^{1703}G^{1704}F^{1705}P^{1706}Y^{1707}S^{1708}S^{1709}R^{1710}K^{1711}A^{1712}K^{1713}G^{1714}K^{1715}S^{1716}G^{1717}K^{1718}$
(SEQ ID NO: 525)

(69) $K^{1711}A^{1712}K^{1713}G^{1714}K^{1715}S^{1716}G^{1717}K^{1718}Q^{1719}T^{1720}W^{1721}L^{1722}G^{1723}S^{1724}E^{1725}E^{1726}F^{1727}I^{1728}V^{1729}D^{1730}N^{1731}P^{1732}D^{1733}L^{1734}K^{1735}E^{1736}H^{1737}$
(SEQ ID NO: 526)

(70) $K^{1735}E^{1736}H^{1737}V^{1738}E^{1739}K^{1740}I^{1741}V^{1742}D^{1743}K^{1744}$
(SEQ ID NO: 527)

(71) $H^{1737}V^{1738}E^{1739}K^{1740}I^{1741}V^{1742}D^{1743}K^{1744}A^{1745}K^{1746}D^{1747}G^{1748}I^{1749}V^{1750}D^{1751}V^{1752}S^{1753}L^{1754}G^{1755}I^{1756}F^{1757}A^{1758}A^{1759}T^{1760}L^{1761}K^{1762}D^{1763}E^{1764}R^{1765}R^{1766}P^{1767}L^{1768}E^{1769}K^{1770}$
(SEQ ID NO: 528)

-continued

(72) $H^{1737}V^{1738}E^{1739}K^{1740}I^{1741}V^{1742}D^{1743}K^{1744}A^{1745}K^{1746}$
(SEQ ID NO: 529)

(73) $K^{1762}D^{1763}E^{1764}R^{1765}R^{1766}P^{1767}L^{1768}E^{1769}K^{1770}V^{1771}Q^{1772}A^{1773}N^{1774}K^{1775}T^{1776}R^{1777}V^{1778}F^{1779}A^{1780}A^{1781}S^{1782}N^{1783}Q^{1784}G^{1785}L^{1786}A^{1787}L^{1788}A^{1789}L^{1790}R^{1791}R^{1792}Y^{1793}Y^{1794}L^{1795}S^{1796}F^{1797}L^{1798}D^{1799}H^{1800}$
(SEQ ID NO: 530)

(74) $H^{1800}V^{1801}M^{1802}T^{1803}N^{1804}R^{1805}I^{1806}D^{1807}N^{1808}E^{1809}I^{1810}G^{1811}L^{1812}G^{1813}V^{1814}N^{1815}V^{1816}Y^{1817}S^{1818}Y^{1819}D^{1820}W^{1821}T^{1822}R^{1823}I^{1824}V^{1825}N^{1826}K^{1827}L^{1828}K^{1829}R^{1830}V^{1831}G^{1832}D^{1833}K^{1834}$
(SEQ ID NO: 531)

(75) $K^{1827}L^{1828}K^{1829}R^{1830}V^{1831}G^{1832}D^{1833}K^{1834}V^{1835}I^{1836}A^{1837}G^{1838}D^{1839}F^{1840}S^{1841}N^{1842}F^{1843}D^{1844}G^{1845}S^{1846}L^{1847}N^{1848}S^{1849}Q^{1850}I^{1851}L^{1852}S^{1853}R^{1854}V^{1855}S^{1856}E^{1857}I^{1858}V^{1859}T^{1860}D^{1861}W^{1862}Y^{1863}G^{1864}D^{1865}D^{1866}A^{1867}E^{1868}N^{1869}G^{1870}L^{1871}I^{1872}R^{1873}H^{1874}$
(SEQ ID NO: 532)

(76) $H^{2050}E^{2051}K^{2052}N^{2053}Y^{2054}F^{2055}L^{2056}M^{2057}F^{2058}C^{2059}D^{2060}V^{2061}I^{2062}K^{2063}K^{2064}A^{2065}C^{2066}R^{2067}N^{2068}A^{2069}G^{2070}Y^{2071}K^{2072}$
(SEQ ID NO: 533)

(77) $H^{2050}E^{2051}K^{2052}N^{2053}Y^{2054}F^{2055}L^{2056}M^{2057}F^{2058}C^{2059}D^{2060}V^{2061}I^{2062}K^{2063}K^{2064}A^{2065}C^{2066}R^{2067}N^{2068}A^{2069}G^{2070}Y^{2071}K^{2072}E^{2073}A^{2074}C^{2075}L^{2076}H^{2077}E^{2078}L^{2079}D^{2080}C^{2081}K^{2082}$
(SEQ ID NO: 534)

(78) $K^{2063}K^{2064}A^{2065}C^{2066}R^{2067}N^{2068}A^{2069}G^{2070}Y^{2071}K^{2072}E^{2073}A^{2074}C^{2075}L^{2076}H^{2077}$
(SEQ ID NO: 535)

(79) $K^{2063}K^{2064}A^{2065}C^{2066}R^{2067}N^{2068}A^{2069}G^{2070}Y^{2071}K^{2072}E^{2073}A^{2074}C^{2075}L^{2076}H^{2077}E^{2078}L^{2079}D^{2080}C^{2081}K^{2082}S^{2083}F^{2084}L^{2085}L^{2086}A^{2087}Q^{2088}Q^{2089}G^{2090}R^{2091}A^{2092}G^{2093}A^{2094}H^{2095}$
(SEQ ID NO: 9)

(80) $K^{2064}A^{2065}C^{2066}R^{2067}N^{2068}A^{2069}G^{2070}Y^{2071}K^{2072}E^{2073}A^{2074}C^{2075}L^{2076}H^{2077}E^{2078}L^{2079}D^{2080}C^{2081}K^{2082}S^{2083}F^{2084}L^{2085}L^{2086}A^{2087}Q^{2088}Q^{2089}G^{2090}R^{2091}A^{2092}G^{2093}A^{2094}H^{2095}$
(SEQ ID NO: 536)

(81) $K^{2064}A^{2065}C^{2066}R^{2067}N^{2068}A^{2069}G^{2070}Y^{2071}K^{2072}E^{2073}A^{2074}C^{2075}L^{2076}H^{2077}$
(SEQ ID NO: 537)

(82) $K^{2072}E^{2073}A^{2074}C^{2075}L^{2076}H^{2077}E^{2078}L^{2079}D^{2080}C^{2081}K^{2082}$
(SEQ ID NO: 538)

(83) $K^{2072}E^{2073}A^{2074}C^{2075}L^{2076}H^{2077}E^{2078}L^{2079}D^{2080}C^{2081}K^{2082}S^{2083}F^{2084}L^{2085}L^{2086}A^{2087}Q^{2088}Q^{2089}G^{2090}R^{2091}A^{2092}G^{2093}A^{2094}H^{2095}$
(SEQ ID NO: 539)

Replikin Count = Number of Replikins per 100 amino acids = 83/2107 = 3.9

Example 6

Determination of Replikin Concentration in Publicly Available Accession Numbers for Isolates of TSV from 2000 Through 2005

Mean Replikin concentrations were determined for all amino acid sequences for Taura Syndrome Virus with accession numbers publicly available at www.pubmed.com. The amino acid sequences were scanned for Replikin sequences of 7 to 50 amino acids comprising (1) at least one lysine residue located at a first terminus of the sequence and at least one lysine residue or at least one histidine residue located at a second terminus of the sequence; (2) a first lysine residue located six to ten residues from a second lysine residue; (3) at least one histidine residue; and (4) at least 6% lysine residues. The total number of Replikin sequences was determined for each available accession number. The total number of Replikin sequences in each accession number was then divided by the total number of amino acid residues disclosed in the accession number. The result was the Replikin concentration. The mean Replikin concentration was then determined for all viruses isolated and reported in a particular year. Table 5 provides the results.

TABLE 5

TSV Replikin Concentration by Year

| Year | PubMed Accession Number-Replikin Count | No. of Isolates per year | Mean Replikin Concentration per year | S.D. | Significance |
|---|---|---|---|---|---|
| 2000 | NP_149058 70 NP_149057 70 AAK72221 70 AAK72220 70 AAG44834 4 | 5 | 2.7 | 1.3 | low $p < 0.02$ |
| 2001 | AAM73766 7 | 1 | 0.7 | 0.0 | prev $p < 0.02$ |
| 2002 | AAN77089 2 AAN77088 2 AAN77087 2 AAN77086 2 AAW32934 2 AAW32932 2 AAW32930 2 AAW32929 1 | 8 | 0.7 | 0.4 | low $p > 0.50$ |
| 2003 | AAR11292 6 AAR11291 6 AAR11290 6 | 3 | 0.6 | 0.0 | prev $p < 0.20$ |

TABLE 5-continued

TSV Replikin Concentration by Year

| Year | PubMed Accession Number-Replikin Count | No. of Isolates per year | Mean Replikin Concentration per year | S.D. | Significance |
|---|---|---|---|---|---|
| 2004 | AAX07125 2 AAX07117 2 AAT81157 75 AAT81158 75 AAX07127 2 AAX07126 2 AAX07124 2 AAX07123 2 AAX07122 2 AAX07121 2 AAX07120 2 AAX07119 2 AAX07118 2 AAX07116 2 AAX07115 2 AAX07114 2 AAX07113 2 AAX07112 2 AAX35819 2 AAX35818 1 AAX35817 2 AAX35816 1 AAX35815 2 | 23 | 0.8 | 0.9 | low $p < 0.40$, prev $p < 0.20$ |
| 2005 | AAY56364 71 AAY56363 71 AAY44822 1 AAY44821 1 AAY44820 1 AAY44819 1 AAY44818 1 AAY44817 1 AAY89097 83 AAY89096 83 ABB17263 63 ABB17264 63 | 12 | 1.8 | 1.7 | low $p < 0.02$, prev $p < 0.05$ |

Example 7

Comparison of the Replikin Concentration of Four Strains of Taura Syndrome Virus by an Independent Laboratory The Replikin concentrations of the protein sequences of four Taura Syndrome Virus (TSV) isolates from Hawaii, Belize, Thailand and Venezuela, respectively, were examined without any knowledge of the virulence of the four isolates, and the virulence was ranked quantitatively in the order of the Replikin concentrations. The virulence of the four TSV isolates was compared in an independent laboratory, without any knowledge of the Replikin concentrations. The virulence was compared through a per os laboratory infection in juvenile *Litopenaeus vannamei* (Kona stock, Oceanic Institute, Hawaii). The results showed that the Belize isolate is the most virulent, the Thailand isolate is the second most virulent, followed by the Hawaii isolate, and the Venezuela isolate, which is the least virulent. This is based on the analyses of cumulative survivals at the end of a bioassay and based on the time of 50% mortality. TSV infection as the cause of death was confirmed by positive reactions in RT-PCR detection and by the appearance of characteristic lesions observed in histological analysis. The correlation of Replikin concentrations with virulence as indicated by the Mortality Rate was quantitative and linear.

Challenge Methods:

Small juveniles of specific-pathogen-free *Litopenaeus vannamei* (20 shrimp per tank, mean weight: 1.8 g) were fed minced TSV-infected tissues (infected separately with each of the 4 isolates originating from Belize, Thailand, Venezuela and Hawaii) for 3 days at 5% of their body weight. These shrimp were maintained with pelleted ration (Rangen 35%) for the following 12 days. Each challenge bioassay of a specific isolate was triplicated. During the bioassay period, all tanks were checked daily for dead or moribund shrimp. All mortalities were removed from the tank and frozen. One to three moribund shrimp from each isolate were preserved in Davidson's AFA fixative and processed for routine histology to confirm viral infection. For each isolate, six moribund shrimp were collected during the acute phase infection and total RNA was extracted from their gill tissues with a High Pure RNA tissue kit (Roche). The extracted RNA was analyzed for the presence of TSV by real-time RT-PCR.

All tanks were outfitted with an acclimated biological filter and aeration, and were covered with plastic to contain aerosols. The average salinity of the water was 23 ppt and the water temperature was 28° C. The challenge study was terminated after 15 days with live animals counted as survivors.

Results

Comparison of Virulence: Mortality in Shrimp

Figure 7:
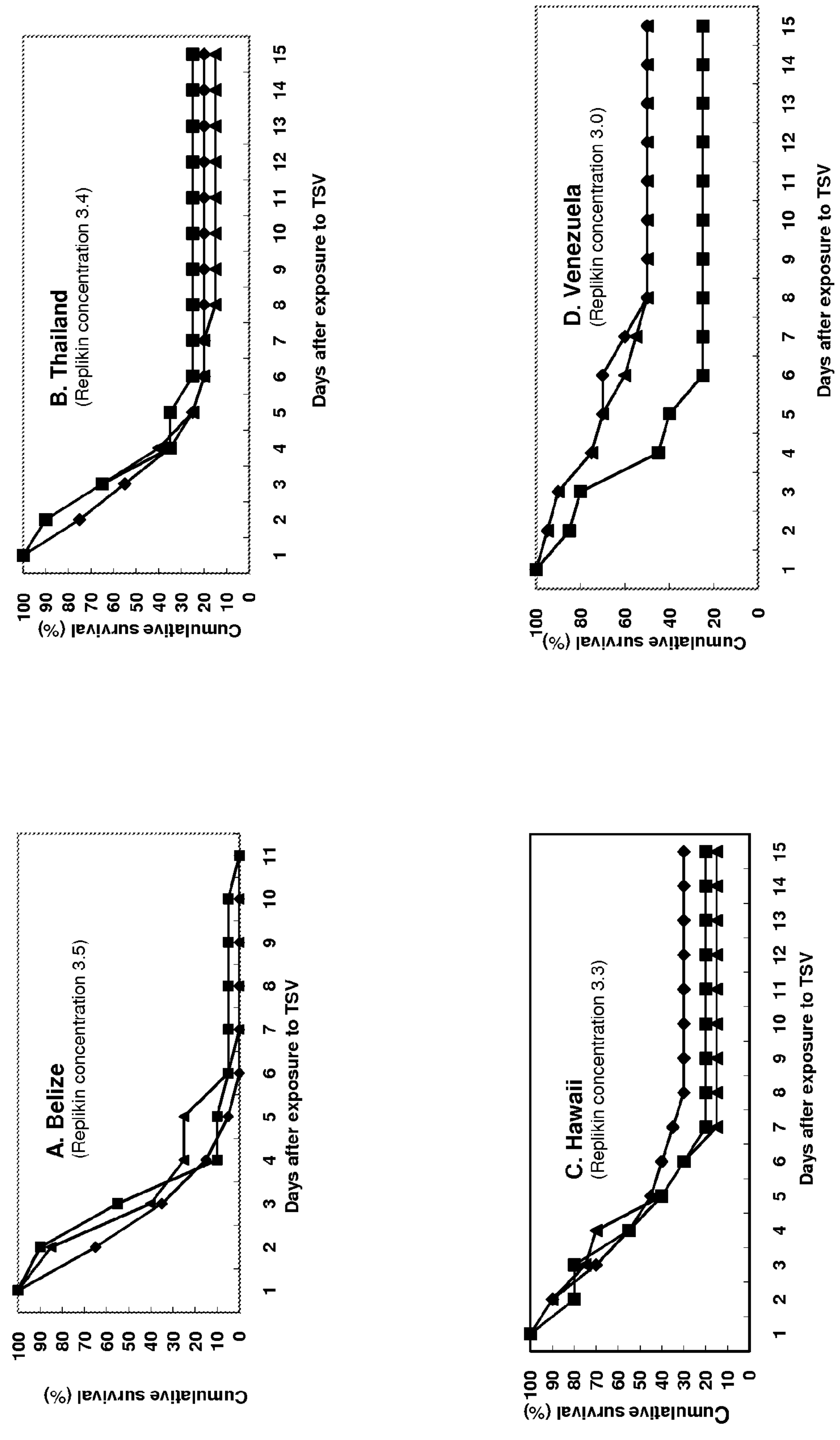
FIG. 7 illustrates that cumulative survival of *Litopenaeus vannamei* shrimp challenged with four different Taura Syndrome Virus isolates over 15 days (unless 100% mortality occurred prior to 15 days) correlates sequentially with the Replikin concentration of Open Reading Frame 1 (ORF1) of each isolate. Translated amino acid sequences of ORF1 of the genome of individual isolates of TSV from Belize, Thailand, Hawaii and Venezuela were analyzed for Replikin concentration. Replikin concentration was determined to be 3.5 for the Belize isolate, 3.4 for the Thailand isolate, 3.3 for the Hawaii isolate and 3.0 for the Venezuela isolate. Graph A illustrates observed percent survival in three trials of shrimp challenged with the Belize isolate of TSV. In one trial, total mortality was observed on day 6. In the other two trials, total mortality was observed on day 11. Graphs B, C and D illustrate observed percent survival of shrimp challenged with the Thailand isolate, the Hawaii isolate and the Venezuela isolate, respectively, each in three trials over 15 days. In the Thailand isolate, a mean of 80% percent mortality was observed on day 15. In the Hawaii isolate, a mean of 78.3% mortality was observed on day 15. In the Venezuela isolate, a mean of 58.3% mortality was observed on day 15.
Figure 8:
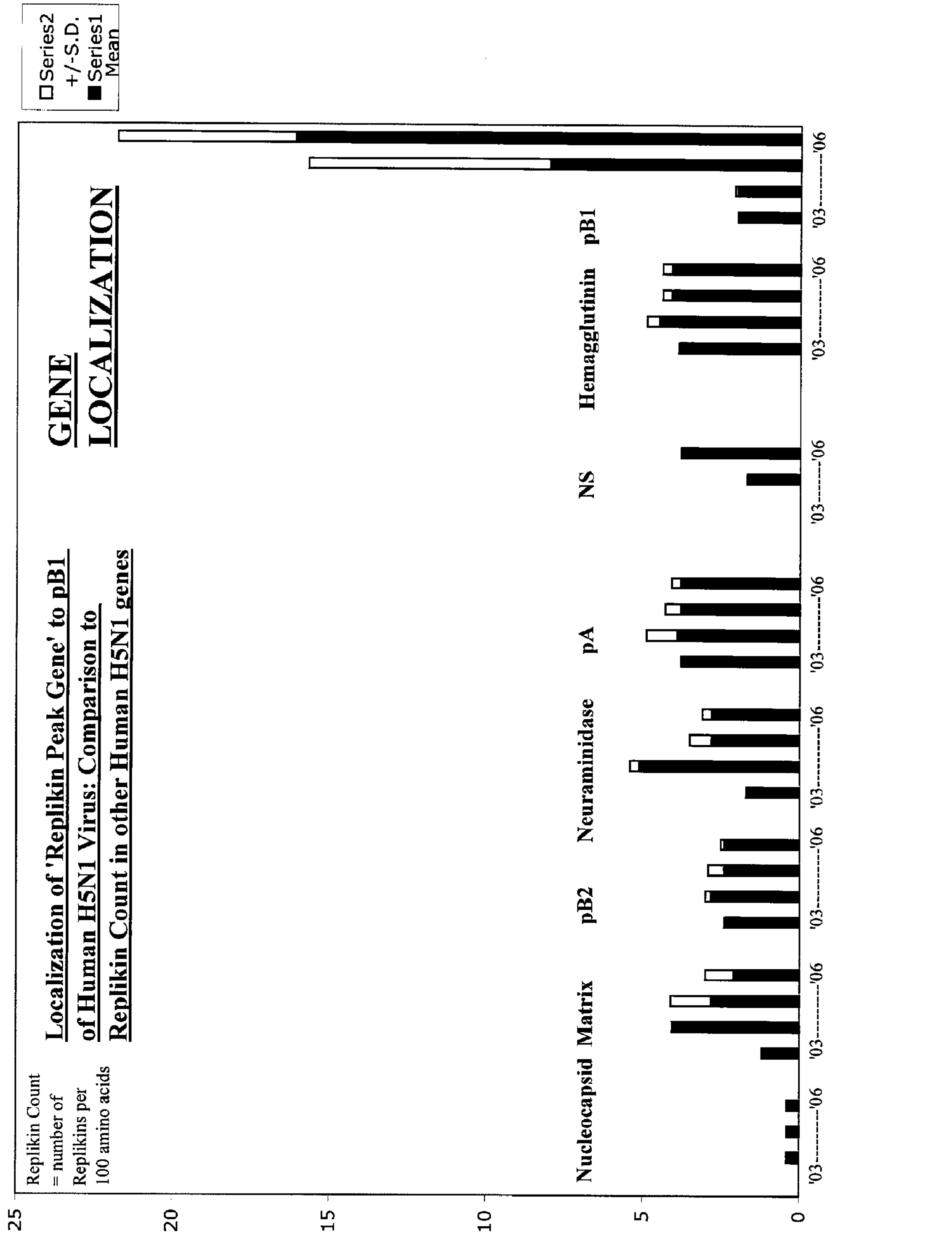
FIG. 8 illustrates the localization of the pB1 gene area as the Replikin Peak Gene in the genome of the H5N1 strain of influenza virus.
Figure 9:
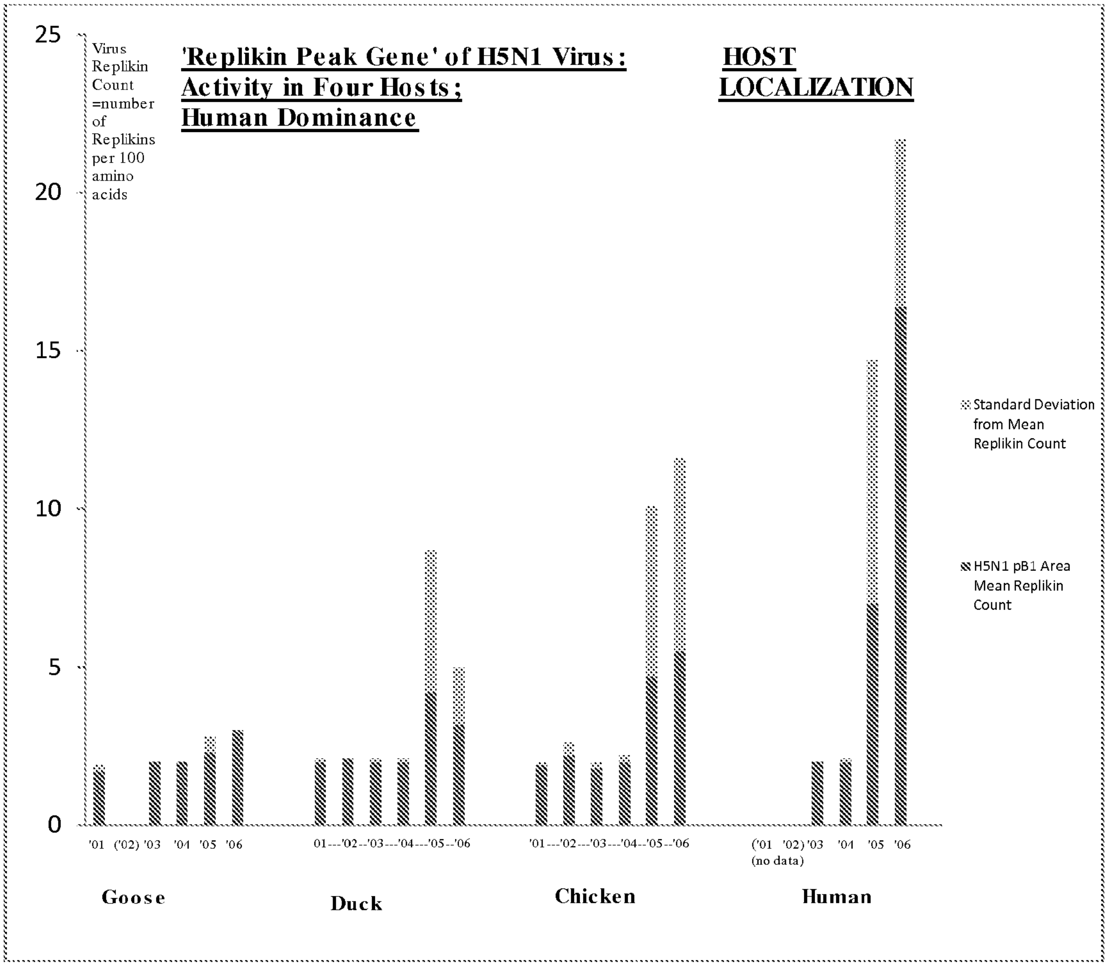
FIG. 9 illustrates a correlation between an increase in Replikin concentration in the pB1 gene area (Replikin Peak Gene) of the H5N1 strain of influenza virus in various bird species and humans over time with an increase in virulence of the H5N1 strain of influenza.
Figure 10:
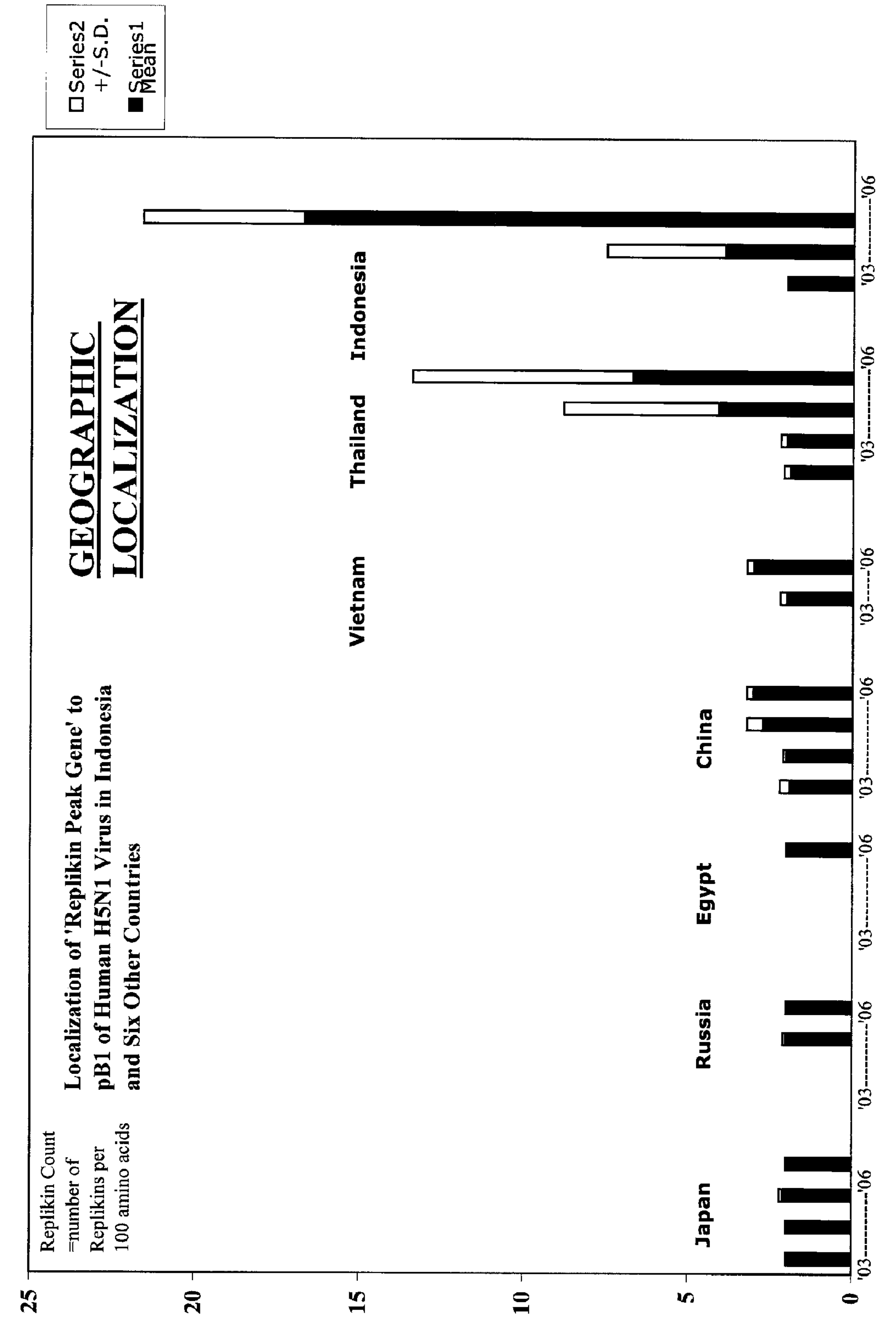
FIG. 10 is a bar graph depicting the number (with standard deviation) of Replikins per 100 amino acids in the pB1 gene area (Replikin Peak Gene) of H5N1 influenza virus strains identified annually in humans in Japan, Russia, Egypt, China, Vietnam, Thailand and Indonesia between 2003 and 2006. Incidence of human morbidity and mortality in the Indonesian outbreak were exceptionally high and evidence of possible human to human transmission was observed. Changes in Replikin concentration in the Replikin Peak Gene of the H5N1 isolates in FIG. 10 allows for identification of those geographic areas in which the influenza virus strain is more virulent than other geographic areas.

First mortality was seen on day 2 after exposure to TSV in all 4 isolates. For Belize isolate, most (83%) of shrimp died by day 4 and had a 0% survival at day 11 (FIG. 7, Table 6). For Thailand isolate, 63% mortalities occurred by day 4 and had a 20% survival at the end of 15-day bioassay (FIG. 7, Table 6). For Hawaii isolate, mortalities increased starting at day 2 and reached to a peak at day 5; the cumulative survival was 22% at the end (FIG. 7, Table 6). For Venezuela isolate, mortalities occurred slowly at days 2 and 3 with 22% of shrimp showed mortalities on day 4 and then mortalities slowed down; with 42% of shrimp surviving at the end (FIG. 7, Table 6). The time period for reaching 50% mortality caused by TSV infection for the isolate of Belize, Thailand, Hawaii and Venezuela were 2.8, 3.5, 4.5 and 7 days, respectively (Table 6).

TABLE 6

Results from per os TSV challenge in SPF *Litopenaeus vannamei* (Kona stock)

| TSV isolate | GenBank No. (ORF1) | Survival (%)(Mean) | Day of 50% mortality |
|---|---|---|---|
| Belize | AAT81157 | 0 | 2.8 |
| Thailand | AAY56363 | 20 | 3.5 |
| US-Hawaii | AAK72220 | 22 | 4.5 |
| Venezuela | ABB17263 | 42 | 7.0* |

*High variation was observed in Venezuela's triplicate tanks, thus the Day of 50% mortality was determined by Kaplan-Meier survival analysis with the Statistix 8 program.

Pathology

Histological analysis of the samples of *L. vannamei* juveniles is summarized in Table 7.

TABLE 7

Summary of histological findings

| UAZ ID# | TSV Isolate | Days after exposure | TSV lesions[1] | LOS[2] |
|---|---|---|---|---|
| O6-407J/1 | Belize | 3 | G4 | G4 |
| 06-407F/1 | Thailand | 3 | G4 | G2 |
| 06-407D/1 | Thailand | 4 | G4 | G3 |
| 06-407E/1 | Thailand | 4 | G3 | G2 |
| 06-407A/1 | Hawaii | 4 | G2 | G3 |

TABLE 7-continued

| Summary of histological findings | | | | |
|---|---|---|---|---|
| UAZ ID# | TSV Isolate | Days after exposure | TSV lesions[1] | LOS[2] |
| 06-407C/1 | Hawaii | 4 | G2 | G4 |
| 06-407H/1 | Venezuela | 4 | G4 | G2 |

Severity grade: G1: sign of infection; G2: moderate signs of infection; G3: moderate to high signs of infection; G4: severe infection.
[1]TSV lesions = Presence of TSV pathognomonic lesions in the gills, mouth, stomach, intecumental cuticular epithelium, and appendages.
[2]LOS = presence of lymphoid organ spheroids within the lymphoid organ.

Belize TSV. Acute lesions of diagnostic TSV infection were found in one representative shrimp sample at a severity grade of G4. Nuclear pyknosis and karyorrhexis were observed in the cuticular epithelium of the general body surface, appendages, gills, stomach and esophagus. Lymphoid organ spheroids were also found at severity grade G4.

Thailand TSV. Severe (G4) TSV infection was detected in 2 out of 3 shrimp, and another shrimp showed a moderate to high grade (G3) of infection. Lymphoid organ spheroids were found at severities of G2 and G3.

Hawaii TSV. Moderate level (G2) of TSV infection was detected in 2 shrimp collected at day 4. Lymphoid organ spheroids were found at severities of G3 and G4.

Venezuela TSV. Severe (G4) TSV infection was detected in one representative shrimp sampled at day 4. Lymphoid organ spheroids were found at severity of G2.

Real-Time TSV RT-PCR

All 24 samples (6 from each isolates) were all positive for TSV infection. This confirms that the mortalities observed from bioassays are from TSV infection.

TABLE 8

| Mean and range of TSV RNA in gills from shrimp challenge with TSV | |
|---|---|
| TSV isolate | Mean (Range) TSV copies/:l RNA |
| Belize | $2.7 \times 10^6$ ($4.8 \times 10^5$-$4.4 \times 10^6$) |
| Thailand | $2.7 \times 10^6$ ($4.3 \times 10^5$-$7.5 \times 10^6$) |
| Hawaii | $5.2 \times 10^7$ ($2.3 \times 10^7$-$7.5 \times 10^7$) |
| Venezuela | $6.5 \times 10^5$ ($6.5 \times 10^2$-$2.0 \times 10^5$) |

TABLE 9

| Percent Mortality and Blind Replikin Concentration The results of 4 TSV virulence (percent mortality) comparisons with blind Replikin Count are: | | |
|---|---|---|
| Isolate | Percent Mortality | Blind Replikin Concentration |
| Belize | 100 | 3.5 |
| Thailand | 80 | 3.4 |
| Hawaii | 78.3 | 3.3 |
| Venezuela | 58.3 | 3.0 |

Figure 5:
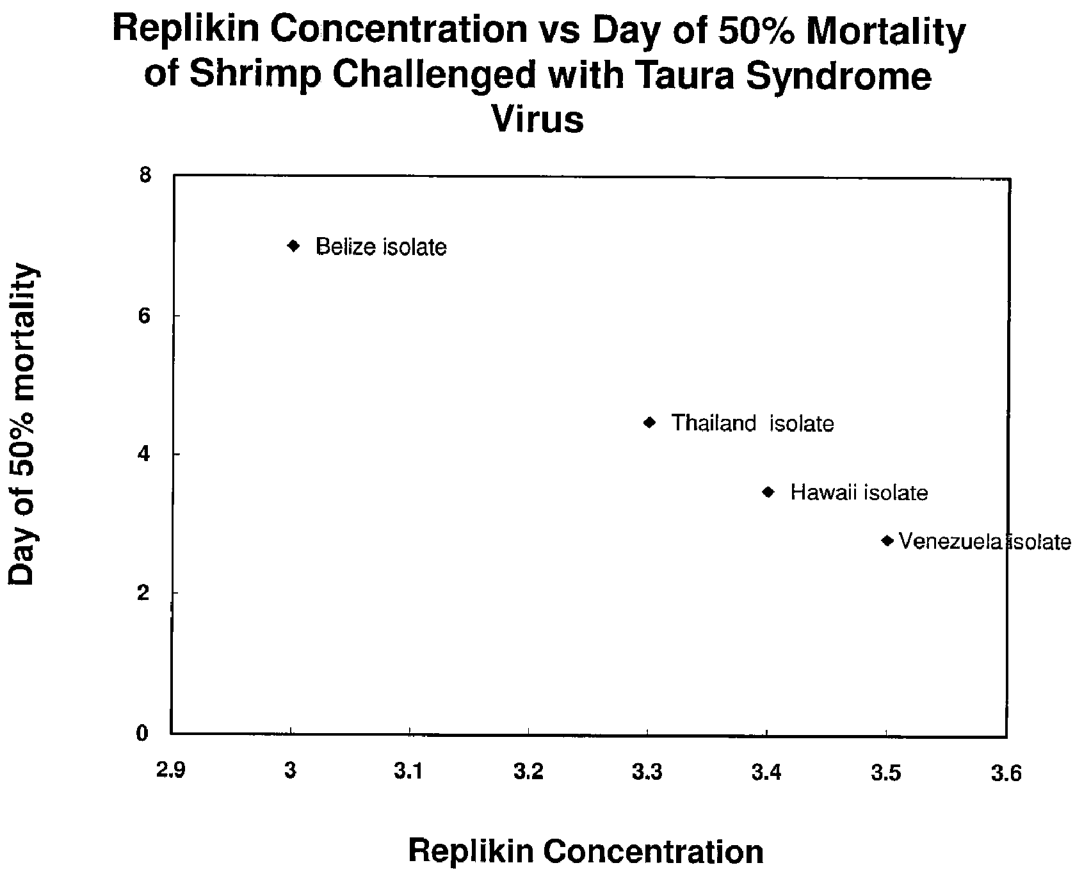
FIG. 5 illustrates a direct sequential correlation between Replikin concentration in isolates of Taura Syndrome Virus (TSV) collected from Belize, Thailand, Hawaii and Venezuela, respectively, and mean number of days until 50% mortality in *Litopenaeus vannamei* shrimp challenged with the respective TSV isolates on day zero. Statistical differences between the Replikin concentration for each isolate are significant at a level of $p<0.001$.
Figure 6:
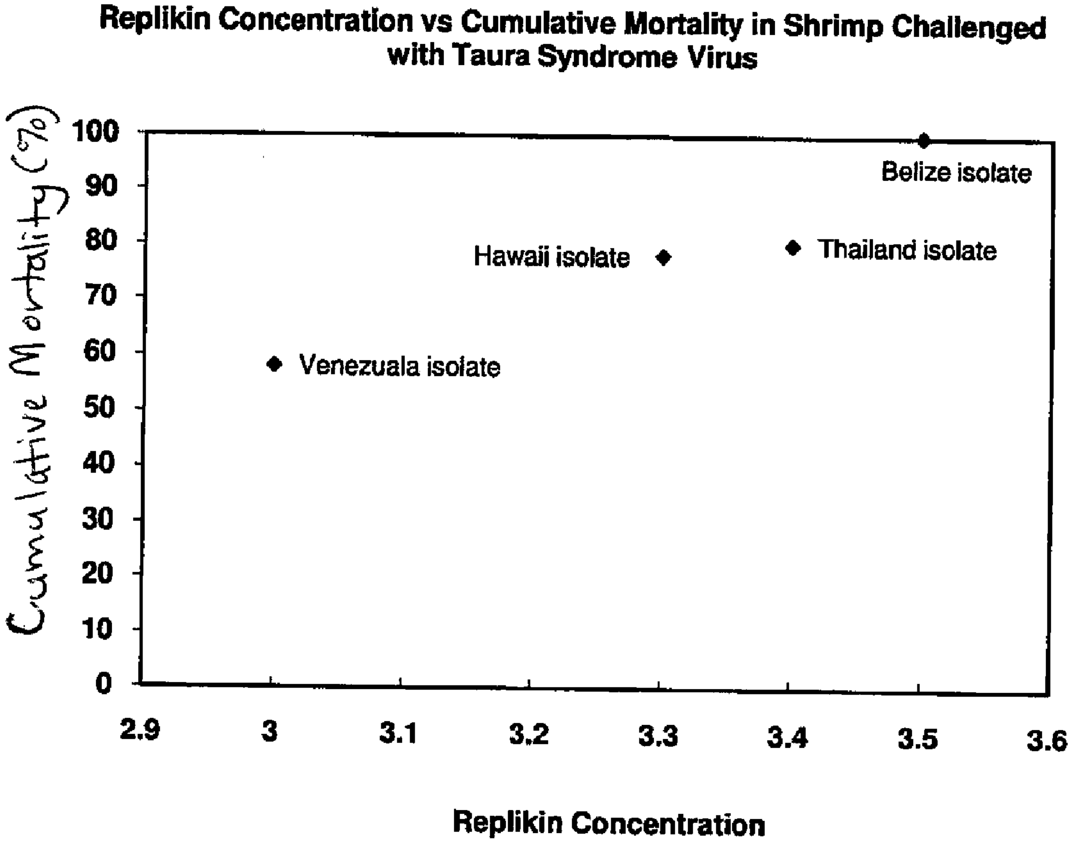
FIG. 6 illustrates a direct sequential correlation between Replikin concentration in isolates of Taura Syndrome Virus (TSV) collected from Belize, Thailand, Hawaii and Venezuela, respectively, and mean cumulative survival of *Litopenaeus vannamei* shrimp at 15 days after challenge with the respective TSV isolate. Statistical differences between the Replikin concentration for each isolate are significant at a level of $p<0.001$.

The order of virulence: Belize>Thailand> (or =) Hawaii>Venezuela, is in agreement with the Replikin concentration. The differences in the Replikin concentrations appear to be small but they are statistically significant at a level of $p<0.001$. See FIGS. 5 and 6.

Example 8

Increased Host Resistance to Taura Syndrome Virus by Administration of Synthetic Replikins Shrimp cultured using the Challenge Methods described in Example 7 above were exposed in a first experiment for two weeks to synthetic Replikins per os mixed in their feed. The Replikins were peptides specific to Replikin sequences present in the TSV Hawaii strain isolate with which the shrimp were challenged/

In the experiment, mortality was reduced by 50% compared to a control group. The control group was given feed not containing synthetic Replikin sequences. A second control group was fed Replikin sequences synthesized with the covalent binding of additional amino acids to the same synthetic Replikins fed to the shrimp. The covalently "blocked" Replikins did not increase shrimp resistance to the virus in the same experiment demonstrating that the increase in host resistance was specific to the Replikin peptide structure.

Because little is known about the details of the immune system of the shrimp (shrimp appear not to produce antibodies), the phenomenon of "resistance" to infection appears to be based in a "primitive immune system" perhaps similar to the "toll receptor" and related systems. Thus the term "increased resistance" is used for the observed phenomenon and Replikin feed is used rather than "vaccine" for the administered substance which increases resistance.

The surviving shrimp of the first challenge were then set up in a fresh culture, fed for an additional two weeks with feed containing Replikin sequences, then again challenged with the Hawaii strain of Taura syndrome virus. The Replikin sequence supplemented feed was maintained while the survivors were again challenged repeatedly by the same virus, in repeated cycles, until 100% of the shrimp survived the TSV challenge.

Example 9

H5N1 Replikin Concentration and Mortality Determinations

The inventors analyzed and compared percent human mortality from H5N1 infections in years 2005 through the first quarter of 2007 to mean concentration of Replikin sequences in (1) the whole genome (2) the polymerase gene, (3) the pB1 gene area, (4) the pB2 gene area, and (5) the pA gene area, respectively, of H5N1 influenza strains isolated in 2003 through the first quarter of 2007. The following data were observed:

TABLE 10

| H5N1 Replikin Concentration and Human Mortality | | | | | |
|---|---|---|---|---|---|
| | 2003 | 2004 | 2005 | 2006 | 2007 |
| H5N1 (Whole Virus) Replikin Concentration in Humans | 2.2 +/− 1.2 | 2.4 +/− 1.4 | 2.3 +/− 2.6 | 3.8 +/− 4.6 | 3.7 +/− 4.5 |

TABLE 10-continued

| H5N1 Replikin Concentration and Human Mortality | | | | | |
|---|---|---|---|---|---|
| | 2003 | 2004 | 2005 | 2006 | 2007 |
| H5N1 (Polymerase) Replikin Concentration In Humans | 2.6 +/− 0.8 | 2.9 +/− 0.9 | 4.8 +/− 5.0 | 7.4 +/− 7.0 | 7.3 +/− 6.7 |
| H5N1 Replikin Peak Gene (pB1 gene area) Replikin Concentration in Humans | 2.0 +/− 0 | 2.0 +/− 0.1 | 8.0 +/7.7 | 16.1 +/− 5.7 | 15.4 +/− 5.9 |
| H5N1 pB2 gene area Replikin Concentration In Humans | 2.4 +/− 0 | 2.8 +/− 0.3 | 2.4 +/0.4 | 2.4 +/− 0.1 | 2.4 +/− 0.3 |
| H5N1 pA gene area Replikin Concentration In Humans | 3.8 +/− 0 | 4.0 +/− 0.6 | 3.8 +/− 0.4 | 3.8 +/− 0.3 | 4.2 +/− 0.3 |
| H5N1 Human Mortality percent | | | 45 | 69 | 85 |

Table 10 provides mortality data for H5N1 infections from 2005 through 2007 and does not include earlier mortality data. Mortality data prior to 2005 has not been included in Table 10 (or in the data in FIGS. 1-3) because data prior to 2005 is inconsistent and understood by those of skill in the art to contain errors, including errors caused by under-reporting. The first generally agreed occasion when there were human deaths caused by proven H5N1 infection was in Hong Kong in 1997-1998. (This is probably incorrect, however, since there probably was mortality between 1959, when H5N1 was first reported, and 1997). The usual figures cited for 1997 are: 30 human cases, 8 deaths with mortality rate of about 27%. The number of cases (morbidity) and the number who died (mortality) that were not reported is unknown, but suspected to be significant. These errors are usually high in geographic areas where the medical care is less structured and scientific, and the reporting is incomplete. Press reports between 1998 and 2002 were few, scattered, and not in agreement. Mortality data between 2005 and 2007 appear to be more consistent and have a higher level of reliability. Table 10, therefore, contains data from these years.

In Table 10, a correlation was established between mean human mortality and (1) mean concentration of Replikin sequences in the whole genome (two-fold increase from 2003 to 2007), (2) mean concentration of Replikin sequences in the polymerase gene (four-fold increase from 2003 to 2007) and (3) mean concentration of Replikin sequences in the Replikin Peak Gene (pB1 gene area) (eight-fold increase from 2003 to 2007) of H5N1 influenza strains. As Replikin concentration increased by these three measures, human mortality was observed to increase. See FIG. 16.

Over the same period (2003-2007), however, no significant increase was observed in the pB2 and pA gene areas. See FIG. 17. The pB2 and pA gene areas are neighbors to the Replikin Peak Gene found in the pB1 gene area. The observation that no significant increase occurred in the pB2 and pA gene areas during a remarkable increase in Replikin concentration in the neighboring pB1 area and a correlated significant increase in human mortality, provides support both for the significant capacity of Replikin concentration in the Replikin Peak Gene to predict virulence and for the precision of the method of predicting virulence using Replikin concentration in the Replikin Peak Gene Area.

As may be seen from Table 10, while the three measures (whole genome Replikin concentration, polymerase gene Replikin concentration, and pB1 gene area Peak Gene Replikin concentration) provided a correlation with human mortality, changes in the Replikin concentration in the polymerase gene correlated more significantly with human mortality, and changes in the Replikin concentration in the Replikin Peak Gene (pB1 gene area) of the H5N1 genome correlated still more significantly with human mortality. Table 10 demonstrates, therefore, that identification of Replikin Peak Genes within viral genomes improves identifications and predictions of virulence and mechansisms of virulence using Replikin concentration data. As seen in Table 10, the increase in Replikin concentration is magnified in its correlation with human mortality when restricted to changes in Replikin concentration in the polymerase genes and magnified still when restricted solely to the Replikin Peak Gene identified using the methods described herein.

Test of Reliability of Method of Predicting Outbreaks with Replikin Concentration In addition to the correlative aspect of the increase in Replikin concentration being related to percent mortality, the data in Table 10 provides strong confirmation of the power and validity of the methodology of predicting changes in virulence and outbreaks of virus with changes in Replikin concentration. These data represent an objective test of the method of independently selecting and examining several thousand individual accession numbers within approximately 12 million total accession numbers in PubMed wherein each selection is independently submitted to the PubMed data base under a separate request using objective software. If there were not a reliable principle and a reliable method underlying each request, the potential for obtaining random results, or no results, or results which do not track each other at $p<0.001$ would markedly increase. Table 10 provides results wherein p was less than 0.001 between each group as compared one to another.

In Table 10 the structures that are correlated have, to the knowledge of the inventors, not been correlated before, that is, the inventors have examined the relationship of one internal virus structure to another internal virus structure or structures (e.g., three-way relationship between whole virus gene area, polymerase, and Replikin Peak Gene area) and have examined the external relation of these two or more internal structures to a host result of the virus infection, that is, percent mortality.

Table 10 represents consistent reproducible data, on repeated trials, which is the essence of the reliability of any method. For example, Table 10 provides independent data on (1) whole virus concentration of Replikins, (2) only the polymerase concentration of Replikins, and (3) only the Replikin Peak Gene concentration of Replikins. The data is then correlated with H5N1 mortality three times, namely in 2005, 2006 and 2007. The absence of significant changes in the pA and pB2 gene areas provides a control. In each case, the method measures Replikin concentration three ways, each of which correctly predict mortality, independently, thereby confirming the method, and further illustrating in the process, the magnifying function of the Replikin Peak Gene.

The sequence listing, saved as a filed named 47501-seqlisting.txt, created on Dec. 20, 2007, and totaling 241,027 bytes, is hereby incorporated by reference in its entirety.

What is claimed is:

1. A method of determining an increased probability of an outbreak of influenza virus within about one to about three years following an increase in Replikin concentration in an isolate of White Spot Syndrome Virus or an isolate of Taura Syndrome Virus comprising identifying said increase in the concentration of Replikin sequences in at least one first isolate of White Spot Syndrome Virus or Taura Syndrome Virus as compared to at least one other isolate of White Spot Syndrome Virus or Taura Syndrome Virus, wherein said at least one first isolate is isolated at least six months later than said at least one other isolate is isolated, and wherein when said at least one first isolate is a White Spot Syndrome Virus isolate said at least one other isolate is a White Spot Syndrome Virus isolate, and when said at least one first isolate is a Taura Syndrome Virus isolate said at least one other isolate is a Taura Syndrome Virus isolate, and wherein said increase in the concentration of Replikin sequences signifies the increased probability of the outbreak of influenza virus within about one to about three years following said increase in the concentration of Replikin sequences, wherein said method is performed on a processor.

2. The method of claim 1 wherein said identification of an increase in Replikin concentration in said at least one first isolate comprises: determining the concentration of Replikin sequences in (i) a plurality of isolates of White Spot Syndrome Virus, wherein said at least one first isolate has been isolated about six months to about three years later than said at least one other of said isolates of White Spot Syndrome Virus, or (ii) a plurality of isolates of Taura Syndrome Virus, wherein said at least one first isolate of Taura Syndrome Virus is isolated about six months to about three years later than at least one other isolate of Taura Syndrome Virus.

3. A computer readable medium having instructions stored thereon, wherein executing said instructions comprises using a processor to perform a method for predicting an outbreak of influenza virus comprising:

(1) determining a Replikin concentration of amino acid or nucleic acid sequences of a plurality of isolates of a virus wherein said virus is present in a reservoir of influenza virus and wherein at least one first isolate has been isolated about six months to about three years later than at least one other isolate; and (2) predicting an outbreak of influenza virus by identifying an increase in Replikin concentration in said at least one first isolate as compared to said at least one other isolate by comparing the Replikin concentrations of said at least one first isolate with said at least one other isolate wherein said outbreak of influenza virus is predicted to occur within about one to about three years from the time point at which said at least one first isolate was isolated.

4. The method of claim 1, wherein said increase in the concentration of Replikin sequences in said at least one first isolate as compared to said at least one other isolate is statistically significant.

5. The method of claim 1, wherein said increase in said concentration of Replikin sequences of said plurality of isolates is an increase in the mean concentration of at least two first isolates as compared to the mean concentration of at least two other isolates wherein said at least two first isolates are isolated about six months to about three years later than said at least two other isolates.

6. The method of claim 5, wherein said increase in said mean concentration of said at least two first isolates as compared to the mean concentration of said at least two other isolates is statistically significant.

7. The method of claim 1, wherein said increase in Replikin concentration is in an isolate of White Spot Syndrome Virus.

8. The method of claim 1, wherein said increase in Replikin concentration is in an isolate of Taura Syndrome Virus.

9. A method of predicting an outbreak of influenza virus comprising:

(1) obtaining a plurality of isolates of White Spot Syndrome Virus or a plurality of isolates of Taura Syndrome Virus wherein at least one of said isolates of White Spot Syndrome Virus is isolated about six months to about 3 years later than at least one other of said isolates of White Spot Syndrome Virus or wherein at least one of said isolates of Taura Syndrome Virus is isolated about six months to about 3 years later than at least one other of said isolates of Taura Syndrome Virus;

(2) analyzing the amino acid sequence of at least one encoded protein or protein fragment or a combination of encoded proteins and/or protein fragments in each isolate of the plurality of isolates of White Spot Syndrome Virus or the plurality of isolates of Taura Syndrome Virus for the presence and concentration of encoded Replikin sequences;

(3) comparing the concentrations of encoded Replikin sequences in the at least one protein or protein fragment or in the combination of proteins or protein fragments in each isolate of the plurality of isolates of White Spot Syndrome Virus or in each isolate of the plurality of isolates of Taura Syndrome Virus;

(4) identifying an increase in the concentration of encoded Replikin sequences in said plurality of isolates of White Spot Syndrome Virus or in said plurality of isolates of Taura Syndrome Virus over at least one time period of about six months or greater; and (5) predicting an outbreak of influenza within about one to about three years following said identified increase in the concentration of Replikin sequences in said isolates of White Spot Syndrome Virus or in the concentration of Replikin sequences in said isolates of Taura Syndrome Virus.

10. The method of claim 9, further comprising:

(1) identifying at least one Replikin Scaffold sequence present in at least one isolate of the plurality of isolates of White Spot Syndrome Virus identified as having an increase in the concentration of Replikin sequences as compared to at least one other isolate of the plurality of isolates of White Spot Syndrome Virus over a time period of about six months or greater or identifying at least one Replikin Scaffold sequence present in at least one isolate in the plurality of isolates of Taura Syndrome Virus identified as having an increase in the concentration of Replikin sequences as compared to at least one other isolate of the plurality of isolates of Taura Syndrome Virus over a time period of about six months or greater;

(2) identifying at least one Replikin Scaffold sequence present in at least one isolate of a strain of influenza virus; and (3) predicting the strain of influenza virus in which the at least one Replikin Scaffold sequence is identified as the strain of virus that will cause the predicted outbreak of influenza virus wherein a Replikin Scaffold is a peptide consisting of about 16 to about 34 amino acids comprising (1) a terminal lysine and optionally a lysine immediately adjacent to the terminal lysine; (2) a terminal histidine and optionally a histidine immediately adjacent to the terminal histidine, (3) a lysine within about 6 to about 10 amino acids of another lysine; and (4) at least 6% lysines.

11. The method of claim 10, wherein the Replikin Scaffold is a peptide having about 27 to about 33 amino acids.

12. The method of claim 9, wherein the increase in concentration of encoded Replikin sequences in said plurality of isolates of White Spot Syndrome Virus over at least one time period of about six months or more is ten or more Replikin sequences per 100 amino acids.

13. The method of claim 12, wherein the increase in concentration of encoded Replikin sequences in said plurality of isolates of White Spot Syndrome Virus over at least one time period of about six months or more is 90 or more Replikin sequences per 100 amino acids.

14. The method of claim 9, wherein the increase in concentration of encoded Replikin sequences in said plurality of isolates of Taura Syndrome Virus over at least one time period of about six months or more is one or more Replikin sequences per 100 amino acids.

15. The method of claim 14, wherein the increase in concentration of encoded Replikin sequences in said plurality of isolates of Taura Syndrome Virus over at least one time period of about six months or more is 2 or more Replikin sequences per 100 amino acids.

16. The method of claim 9, further comprising identifying an increase in the concentration of encoded Replikin sequences in said plurality of isolates of White Spot Syndrome Virus or said plurality of isolates of Taura Syndrome Virus over at least one to about three years.

17. The method of claim 1, wherein said outbreak of influenza is an outbreak of influenza A virus.

18. The method of claim 17 wherein said outbreak of influenza A virus is an outbreak of an H5N1 strain of influenza virus.

19. A method of predicting an outbreak of influenza virus comprising:

(1) obtaining a plurality of isolates of a first virus from at least one reservoir of Replikin sequences shared by influenza virus wherein the reservoir of Replikin sequences shared by influenza virus is any source of Replikin sequences that may be shared with an influenza virus including any host of influenza virus, any food source of a host of the influenza virus, any vector of influenza virus, or any substance wherein the genetic information of the influenza virus may be shared, mingled, mixed, exchanged or come into the proximity of the Replikin sequences of the reservoir;

(2) analyzing the amino acid sequence of at least one encoded protein or protein fragment or a combination of encoded proteins and/or protein fragments in each isolate of the plurality of isolates of said first virus for the presence and concentration of encoded Replikin sequences;

(3) comparing the concentrations of encoded Replikin sequences in the at least one protein or protein fragment or in the combination of proteins or protein fragments in each isolate of the plurality of isolates of said first virus;

(4) identifying an increase in the concentration of encoded Replikin sequences in said plurality of isolates of said virus over at least one time period of about six months or greater; and (5) predicting an outbreak of influenza within about one to about three years following said identified increase in the concentration of Replikin sequences in said isolates of said first virus.

20. The method of claim 19, further comprising:

(1) identifying at least one Replikin Scaffold sequence present in at least one isolate of the plurality of isolates of said first virus identified as having an increase in the concentration of Replikin sequences as compared to at least one other isolate of the plurality of isolates of said virus over a time period of about six month;

(2) identifying at least one Replikin Scaffold sequence present in at least one isolate of a strain of influenza virus; and (3) predicting the strain of influenza virus in which the at least one Replikin Scaffold sequence is identified as the strain of virus that will cause the predicted outbreak of influenza virus wherein a Replikin Scaffold is a peptide consisting of about 16 to about 34 amino acids comprising (1) a terminal lysine and optionally a lysine immediately adjacent to the terminal lysine; (2) a terminal histidine and optionally a histidine immediately adjacent to the terminal histidine, (3) a lysine within about 6 to about 10 amino acids of another lysine; and (4) at least 6% lysines.

21. The method of claim 19 or claim 20, wherein the reservoir is selected from the group consisting of shrimp, bird, migratory bird, chicken, duck, goose, and domestic bird.

* * * * *

```
                          SEQUENCE LISTING

<160> NUMBER OF SEQ ID NOS: 539

<210> SEQ ID NO 1
<211> LENGTH: 31
<212> TYPE: PRT
<213> ORGANISM: Shrimp white spot syndrome virus

<400> SEQUENCE: 1

Lys Lys Asn Val Lys Ser Ala Lys Gln Leu Pro His Leu Lys Val His
1               5                   10                  15

Leu Asp Val Lys Ser Ala Lys Gln Leu Pro His Leu Lys Val His
            20                  25                  30


<210> SEQ ID NO 2
<211> LENGTH: 27
<212> TYPE: PRT
<213> ORGANISM: Shrimp white spot syndrome virus

<400> SEQUENCE: 2

Lys Lys Asn Val Lys Ser Ala Lys Gln Leu Pro His Leu Lys Val His
1               5                   10                  15

Leu Asp Val Lys Gly Val Lys Gln Leu Leu His
            20                  25


<210> SEQ ID NO 3
<211> LENGTH: 27
<212> TYPE: PRT
<213> ORGANISM: Shrimp white spot syndrome virus

<400> SEQUENCE: 3

Lys Lys Asn Val Lys Ser Ala Lys Gln Leu Pro His Leu Lys Val Leu
1               5                   10                  15

Leu Asp Val Arg Gly Ala Lys Gln Leu Pro His
            20                  25


<210> SEQ ID NO 4
<211> LENGTH: 31
<212> TYPE: PRT
<213> ORGANISM: Shrimp white spot syndrome virus

<400> SEQUENCE: 4

Lys Lys Asn Val Lys Ser Ala Lys Gln Leu Pro His Leu Lys Val Leu
1               5                   10                  15

Leu Asp Val Arg Gly Ala Lys Gln Leu Pro His Leu Lys Val His
            20                  25                  30


<210> SEQ ID NO 5
<211> LENGTH: 5
<212> TYPE: PRT
<213> ORGANISM: Influenza A virus

<400> SEQUENCE: 5

Leu Val Leu Trp Gly
1               5
```

```
<210> SEQ ID NO 6
<211> LENGTH: 29
<212> TYPE: PRT
<213> ORGANISM: Shrimp white spot syndrome virus

<400> SEQUENCE: 6

Lys Lys Asn Val Lys Ser Ala Lys Gln Leu Pro His Leu Lys Val Leu
1               5                   10                  15

Lys Lys Leu Asp Val Arg Gly Ala Lys Gln Leu Pro His
            20                  25


<210> SEQ ID NO 7
<211> LENGTH: 28
<212> TYPE: PRT
<213> ORGANISM: Shrimp white spot syndrome virus

<400> SEQUENCE: 7

Lys Val His Leu Asp Val Lys Gly Val Lys Gln Leu Leu His Leu Lys
1               5                   10                  15

Val Arg Leu Asp Val Arg Gly Ala Lys Gln Leu His
            20                  25


<210> SEQ ID NO 8
<211> LENGTH: 32
<212> TYPE: PRT
<213> ORGANISM: Taura syndrome virus

<400> SEQUENCE: 8

Lys Lys Val Gln Ala Asn Lys Thr Arg Val Phe Ala Ala Ser Asn Gln
1               5                   10                  15

Gly Leu Ala Leu Ala Leu Arg Arg Tyr Tyr Leu Ser Phe Leu Asp His
            20                  25                  30


<210> SEQ ID NO 9
<211> LENGTH: 33
<212> TYPE: PRT
<213> ORGANISM: Taura syndrome virus

<400> SEQUENCE: 9

Lys Lys Ala Cys Arg Asn Ala Gly Tyr Lys Glu Ala Cys Leu His Glu
1               5                   10                  15

Leu Asp Cys Lys Ser Phe Leu Leu Ala Gln Gln Gly Arg Ala Gly Ala
            20                  25                  30

His


<210> SEQ ID NO 10
<211> LENGTH: 7
<212> TYPE: PRT
<213> ORGANISM: Shrimp white spot syndrome virus

<400> SEQUENCE: 10

Lys Gln Leu Leu His Leu Lys
1               5


<210> SEQ ID NO 11
<211> LENGTH: 7
<212> TYPE: PRT
<213> ORGANISM: Shrimp white spot syndrome virus

<400> SEQUENCE: 11

Lys Val His Leu Asp Val Lys
1               5
```

<210> SEQ ID NO 12
<211> LENGTH: 14
<212> TYPE: PRT
<213> ORGANISM: Shrimp white spot syndrome virus

<400> SEQUENCE: 12

Lys Val His Leu Asp Val Lys Gly Val Lys Gln Leu Leu His
1 5 10

<210> SEQ ID NO 13
<211> LENGTH: 12
<212> TYPE: PRT
<213> ORGANISM: Shrimp white spot syndrome virus

<400> SEQUENCE: 13

Lys Lys Asn Val Lys Ser Ala Lys Gln Leu Pro His
1 5 10

<210> SEQ ID NO 14
<211> LENGTH: 10
<212> TYPE: PRT
<213> ORGANISM: Shrimp white spot syndrome virus

<400> SEQUENCE: 14

Lys Ser Ala Lys Gln Leu Pro His Leu Lys
1 5 10

<210> SEQ ID NO 15
<211> LENGTH: 479
<212> TYPE: PRT
<213> ORGANISM: Shrimp white spot syndrome virus

<400> SEQUENCE: 15

Met Lys Ile Cys Gln Ile Ser Ser Pro Thr Leu Thr Leu Ser Ile Pro
1 5 10 15

Leu Glu Gly Val Tyr His Val Lys Gln Leu Leu His Leu Lys Val His
20 25 30

Leu Asp Val Lys Gly Val Lys Gln Leu Leu His Leu Lys Val Arg Leu
35 40 45

Asp Val Arg Gly Ala Lys Gln Asn Pro Trp Arg Lys Asn Leu Cys Leu
50 55 60

Leu Lys Lys Asn Val Lys Ser Ala Lys Gln Leu Pro His Leu Lys Val
65 70 75 80

His Leu Asp Val Lys Ser Ala Lys Gln Leu Pro His Leu Lys Val His
85 90 95

Leu Asp Val Arg Gly Ala Lys Gln Leu Pro His Leu Lys Val Arg Leu
100 105 110

Asp Val Lys Ser Ala Lys Gln Leu Pro His Leu Lys Val His Leu Asp
115 120 125

Val Arg Gly Ala Lys Gln Leu Pro His Leu Lys Val Arg Leu Asp Val
130 135 140

Arg Gly Ala Lys Gln Asn Pro Trp Arg Lys Asn Leu Cys Leu Leu Lys
145 150 155 160

Lys Asn Val Lys Ser Ala Lys Gln Leu Pro His Leu Lys Val His Leu
165 170 175

Asp Val Lys Gly Val Lys Gln Leu Leu His Leu Lys Val Arg Leu Asp
180 185 190

Val Arg Gly Ala Lys Gln Leu Leu His Leu Lys Val His Leu Asp Val
195 200 205

```
Arg Gly Ala Lys Gln Leu Pro His Leu Lys Val His Leu Asp Val Arg
    210                 215                 220

Gly Ala Lys Gln Asn Pro Trp Arg Lys Asn Leu Cys Leu Leu Lys Lys
225                 230                 235                 240

Asn Val Lys Ser Ala Lys Gln Leu Pro His Leu Lys Val Leu Leu Asp
                245                 250                 255

Val Arg Gly Ala Lys Gln Leu Pro His Leu Lys Val Leu Leu Asp Val
            260                 265                 270

Arg Gly Ala Lys Gln Leu Pro His Leu Lys Val His Leu Asp Val Arg
        275                 280                 285

Gly Ala Lys Gln Asn Pro Trp Arg Lys Asn Leu Cys Leu Leu Lys Lys
    290                 295                 300

Asn Val Lys Ser Ala Lys Gln Leu Pro His Leu Lys Val Leu Leu Asp
305                 310                 315                 320

Val Arg Gly Ala Lys Gln Leu Pro His Leu Lys Val Leu Leu Asp Val
                325                 330                 335

Arg Gly Ala Lys Gln Leu Pro His Leu Lys Val His Leu Asp Val Arg
            340                 345                 350

Gly Ala Lys Gln Leu Pro His Leu Lys Val Leu Leu Asp Val Arg Gly
        355                 360                 365

Ala Lys Gln Leu Pro His Leu Lys Val Leu Leu Asp Val Arg Gly Ala
    370                 375                 380

Lys Gln Asn Pro Trp Arg Lys Asn Leu Cys Leu Leu Lys Lys Asn Val
385                 390                 395                 400

Lys Ser Ala Lys Gln Leu Pro His Leu Lys Val Leu Leu Asp Val Arg
                405                 410                 415

Gly Ala Lys Gln Leu Pro His Leu Lys Val His Leu Asp Val Arg Gly
            420                 425                 430

Ala Lys Gln Gln Gln Gln Leu Cys Leu Pro Leu Lys Thr Ile Ser Thr
        435                 440                 445

Ser Phe Thr His Leu Leu Leu Cys Leu Tyr Met Glu Tyr Gly Lys His
    450                 455                 460

Gln Asn Leu Gln Val Lys Met Trp Leu Asn Ile Thr Tyr Thr Ser
465                 470                 475


<210> SEQ ID NO 16
<211> LENGTH: 9
<212> TYPE: PRT
<213> ORGANISM: Shrimp white spot syndrome virus

<400> SEQUENCE: 16

His Val Lys Gln Leu Leu His Leu Lys
1               5


<210> SEQ ID NO 17
<211> LENGTH: 15
<212> TYPE: PRT
<213> ORGANISM: Shrimp white spot syndrome virus

<400> SEQUENCE: 17

His Val Lys Gln Leu Leu His Leu Lys Val His Leu Asp Val Lys
1               5                   10                  15


<210> SEQ ID NO 18
<211> LENGTH: 18
<212> TYPE: PRT
<213> ORGANISM: Shrimp white spot syndrome virus
```

<400> SEQUENCE: 18

His Val Lys Gln Leu Leu His Leu Lys Val His Leu Asp Val Lys Gly
1 5 10 15

Val Lys

<210> SEQ ID NO 19
<211> LENGTH: 24
<212> TYPE: PRT
<213> ORGANISM: Shrimp white spot syndrome virus

<400> SEQUENCE: 19

His Val Lys Gln Leu Leu His Leu Lys Val His Leu Asp Val Lys Gly
1 5 10 15

Val Lys Gln Leu Leu His Leu Lys
20

<210> SEQ ID NO 20
<211> LENGTH: 33
<212> TYPE: PRT
<213> ORGANISM: Shrimp white spot syndrome virus

<400> SEQUENCE: 20

His Val Lys Gln Leu Leu His Leu Lys Val His Leu Asp Val Lys Gly
1 5 10 15

Val Lys Gln Leu Leu His Leu Lys Val Arg Leu Asp Val Arg Gly Ala
20 25 30

Lys

<210> SEQ ID NO 21
<211> LENGTH: 39
<212> TYPE: PRT
<213> ORGANISM: Shrimp white spot syndrome virus

<400> SEQUENCE: 21

His Val Lys Gln Leu Leu His Leu Lys Val His Leu Asp Val Lys Gly
1 5 10 15

Val Lys Gln Leu Leu His Leu Lys Val Arg Leu Asp Val Arg Gly Ala
20 25 30

Lys Gln Asn Pro Trp Arg Lys
35

<210> SEQ ID NO 22
<211> LENGTH: 45
<212> TYPE: PRT
<213> ORGANISM: Shrimp white spot syndrome virus

<400> SEQUENCE: 22

His Val Lys Gln Leu Leu His Leu Lys Val His Leu Asp Val Lys Gly
1 5 10 15

Val Lys Gln Leu Leu His Leu Lys Val Arg Leu Asp Val Arg Gly Ala
20 25 30

Lys Gln Asn Pro Trp Arg Lys Asn Leu Cys Leu Leu Lys
35 40 45

<210> SEQ ID NO 23
<211> LENGTH: 46
<212> TYPE: PRT
<213> ORGANISM: Shrimp white spot syndrome virus

<400> SEQUENCE: 23

His Val Lys Gln Leu Leu His Leu Lys Val His Leu Asp Val Lys Gly

-continued

```
1               5                   10                  15

Val Lys Gln Leu Leu His Leu Lys Val Arg Leu Asp Val Arg Gly Ala
            20                  25                  30

Lys Gln Asn Pro Trp Arg Lys Asn Leu Cys Leu Leu Lys Lys
        35                  40                  45


<210> SEQ ID NO 24
<211> LENGTH: 49
<212> TYPE: PRT
<213> ORGANISM: Shrimp white spot syndrome virus

<400> SEQUENCE: 24

His Val Lys Gln Leu Leu His Leu Lys Val His Leu Asp Val Lys Gly
1               5                   10                  15

Val Lys Gln Leu Leu His Leu Lys Val Arg Leu Asp Val Arg Gly Ala
            20                  25                  30

Lys Gln Asn Pro Trp Arg Lys Asn Leu Cys Leu Leu Lys Lys Asn Val
        35                  40                  45

Lys


<210> SEQ ID NO 25
<211> LENGTH: 9
<212> TYPE: PRT
<213> ORGANISM: Shrimp white spot syndrome virus

<400> SEQUENCE: 25

Lys Gln Leu Leu His Leu Lys Val His
1               5


<210> SEQ ID NO 26
<211> LENGTH: 20
<212> TYPE: PRT
<213> ORGANISM: Shrimp white spot syndrome virus

<400> SEQUENCE: 26

Lys Gln Leu Leu His Leu Lys Val His Leu Asp Val Lys Gly Val Lys
1               5                   10                  15

Gln Leu Leu His
            20


<210> SEQ ID NO 27
<211> LENGTH: 9
<212> TYPE: PRT
<213> ORGANISM: Shrimp white spot syndrome virus

<400> SEQUENCE: 27

His Leu Lys Val His Leu Asp Val Lys
1               5


<210> SEQ ID NO 28
<211> LENGTH: 12
<212> TYPE: PRT
<213> ORGANISM: Shrimp white spot syndrome virus

<400> SEQUENCE: 28

His Leu Lys Val His Leu Asp Val Lys Gly Val Lys
1               5                   10


<210> SEQ ID NO 29
<211> LENGTH: 18
<212> TYPE: PRT
<213> ORGANISM: Shrimp white spot syndrome virus
```

<400> SEQUENCE: 29

His Leu Lys Val His Leu Asp Val Lys Gly Val Lys Gln Leu Leu His
1 5 10 15

Leu Lys

<210> SEQ ID NO 30
<211> LENGTH: 27
<212> TYPE: PRT
<213> ORGANISM: Shrimp white spot syndrome virus

<400> SEQUENCE: 30

His Leu Lys Val His Leu Asp Val Lys Gly Val Lys Gln Leu Leu His
1 5 10 15

Leu Lys Val Arg Leu Asp Val Arg Gly Ala Lys
20 25

<210> SEQ ID NO 31
<211> LENGTH: 33
<212> TYPE: PRT
<213> ORGANISM: Shrimp white spot syndrome virus

<400> SEQUENCE: 31

His Leu Lys Val His Leu Asp Val Lys Gly Val Lys Gln Leu Leu His
1 5 10 15

Leu Lys Val Arg Leu Asp Val Arg Gly Ala Lys Gln Asn Pro Trp Arg
20 25 30

Lys

<210> SEQ ID NO 32
<211> LENGTH: 39
<212> TYPE: PRT
<213> ORGANISM: Shrimp white spot syndrome virus

<400> SEQUENCE: 32

His Leu Lys Val His Leu Asp Val Lys Gly Val Lys Gln Leu Leu His
1 5 10 15

Leu Lys Val Arg Leu Asp Val Arg Gly Ala Lys Gln Asn Pro Trp Arg
20 25 30

Lys Asn Leu Cys Leu Leu Lys
35

<210> SEQ ID NO 33
<211> LENGTH: 40
<212> TYPE: PRT
<213> ORGANISM: Shrimp white spot syndrome virus

<400> SEQUENCE: 33

His Leu Lys Val His Leu Asp Val Lys Gly Val Lys Gln Leu Leu His
1 5 10 15

Leu Lys Val Arg Leu Asp Val Arg Gly Ala Lys Gln Asn Pro Trp Arg
20 25 30

Lys Asn Leu Cys Leu Leu Lys Lys
35 40

<210> SEQ ID NO 34
<211> LENGTH: 43
<212> TYPE: PRT
<213> ORGANISM: Shrimp white spot syndrome virus

<400> SEQUENCE: 34

His Leu Lys Val His Leu Asp Val Lys Gly Val Lys Gln Leu Leu His

-continued

```
1               5                   10                  15

Leu Lys Val Arg Leu Asp Val Arg Gly Ala Lys Gln Asn Pro Trp Arg
            20                  25                  30

Lys Asn Leu Cys Leu Leu Lys Lys Asn Val Lys
        35                  40


<210> SEQ ID NO 35
<211> LENGTH: 46
<212> TYPE: PRT
<213> ORGANISM: Shrimp white spot syndrome virus

<400> SEQUENCE: 35

His Leu Lys Val His Leu Asp Val Lys Gly Val Lys Gln Leu Leu His
1               5                   10                  15

Leu Lys Val Arg Leu Asp Val Arg Gly Ala Lys Gln Asn Pro Trp Arg
            20                  25                  30

Lys Asn Leu Cys Leu Leu Lys Lys Asn Val Lys Ser Ala Lys
        35                  40                  45


<210> SEQ ID NO 36
<211> LENGTH: 48
<212> TYPE: PRT
<213> ORGANISM: Shrimp white spot syndrome virus

<400> SEQUENCE: 36

Lys Val His Leu Asp Val Lys Gly Val Lys Gln Leu Leu His Leu Lys
1               5                   10                  15

Val Arg Leu Asp Val Arg Gly Ala Lys Gln Asn Pro Trp Arg Lys Asn
            20                  25                  30

Leu Cys Leu Leu Lys Lys Asn Val Lys Ser Ala Lys Gln Leu Pro His
        35                  40                  45


<210> SEQ ID NO 37
<211> LENGTH: 10
<212> TYPE: PRT
<213> ORGANISM: Shrimp white spot syndrome virus

<400> SEQUENCE: 37

Lys Val His Leu Asp Val Lys Gly Val Lys
1               5                   10


<210> SEQ ID NO 38
<211> LENGTH: 14
<212> TYPE: PRT
<213> ORGANISM: Shrimp white spot syndrome virus

<400> SEQUENCE: 38

His Leu Asp Val Lys Gly Val Lys Gln Leu Leu His Leu Lys
1               5                   10


<210> SEQ ID NO 39
<211> LENGTH: 23
<212> TYPE: PRT
<213> ORGANISM: Shrimp white spot syndrome virus

<400> SEQUENCE: 39

His Leu Asp Val Lys Gly Val Lys Gln Leu Leu His Leu Lys Val Arg
1               5                   10                  15

Leu Asp Val Arg Gly Ala Lys
            20


<210> SEQ ID NO 40
```

-continued

<211> LENGTH: 29
<212> TYPE: PRT
<213> ORGANISM: Shrimp white spot syndrome virus

<400> SEQUENCE: 40

```
His Leu Asp Val Lys Gly Val Lys Gln Leu Leu His Leu Lys Val Arg
1               5                   10                  15

Leu Asp Val Arg Gly Ala Lys Gln Asn Pro Trp Arg Lys
            20                  25
```

<210> SEQ ID NO 41
<211> LENGTH: 35
<212> TYPE: PRT
<213> ORGANISM: Shrimp white spot syndrome virus

<400> SEQUENCE: 41

```
His Leu Asp Val Lys Gly Val Lys Gln Leu Leu His Leu Lys Val Arg
1               5                   10                  15

Leu Asp Val Arg Gly Ala Lys Gln Asn Pro Trp Arg Lys Asn Leu Cys
            20                  25                  30

Leu Leu Lys
        35
```

<210> SEQ ID NO 42
<211> LENGTH: 36
<212> TYPE: PRT
<213> ORGANISM: Shrimp white spot syndrome virus

<400> SEQUENCE: 42

```
His Leu Asp Val Lys Gly Val Lys Gln Leu Leu His Leu Lys Val Arg
1               5                   10                  15

Leu Asp Val Arg Gly Ala Lys Gln Asn Pro Trp Arg Lys Asn Leu Cys
            20                  25                  30

Leu Leu Lys Lys
        35
```

<210> SEQ ID NO 43
<211> LENGTH: 39
<212> TYPE: PRT
<213> ORGANISM: Shrimp white spot syndrome virus

<400> SEQUENCE: 43

```
His Leu Asp Val Lys Gly Val Lys Gln Leu Leu His Leu Lys Val Arg
1               5                   10                  15

Leu Asp Val Arg Gly Ala Lys Gln Asn Pro Trp Arg Lys Asn Leu Cys
            20                  25                  30

Leu Leu Lys Lys Asn Val Lys
        35
```

<210> SEQ ID NO 44
<211> LENGTH: 42
<212> TYPE: PRT
<213> ORGANISM: Shrimp white spot syndrome virus

<400> SEQUENCE: 44

```
His Leu Asp Val Lys Gly Val Lys Gln Leu Leu His Leu Lys Val Arg
1               5                   10                  15

Leu Asp Val Arg Gly Ala Lys Gln Asn Pro Trp Arg Lys Asn Leu Cys
            20                  25                  30

Leu Leu Lys Lys Asn Val Lys Ser Ala Lys
        35                  40
```

<210> SEQ ID NO 45
<211> LENGTH: 48
<212> TYPE: PRT
<213> ORGANISM: Shrimp white spot syndrome virus

<400> SEQUENCE: 45

His Leu Asp Val Lys Gly Val Lys Gln Leu Leu His Leu Lys Val Arg
1               5                   10                  15

Leu Asp Val Arg Gly Ala Lys Gln Asn Pro Trp Arg Lys Asn Leu Cys
            20                  25                  30

Leu Leu Lys Lys Asn Val Lys Ser Ala Lys Gln Leu Pro His Leu Lys
        35                  40                  45

<210> SEQ ID NO 46
<211> LENGTH: 10
<212> TYPE: PRT
<213> ORGANISM: Shrimp white spot syndrome virus

<400> SEQUENCE: 46

Lys Gly Val Lys Gln Leu Leu His Leu Lys
1               5                   10

<210> SEQ ID NO 47
<211> LENGTH: 42
<212> TYPE: PRT
<213> ORGANISM: Shrimp white spot syndrome virus

<400> SEQUENCE: 47

Lys Gly Val Lys Gln Leu Leu His Leu Lys Val Arg Leu Asp Val Arg
1               5                   10                  15

Gly Ala Lys Gln Asn Pro Trp Arg Lys Asn Leu Cys Leu Leu Lys Lys
            20                  25                  30

Asn Val Lys Ser Ala Lys Gln Leu Pro His
        35                  40

<210> SEQ ID NO 48
<211> LENGTH: 46
<212> TYPE: PRT
<213> ORGANISM: Shrimp white spot syndrome virus

<400> SEQUENCE: 48

Lys Gly Val Lys Gln Leu Leu His Leu Lys Val Arg Leu Asp Val Arg
1               5                   10                  15

Gly Ala Lys Gln Asn Pro Trp Arg Lys Asn Leu Cys Leu Leu Lys Lys
            20                  25                  30

Asn Val Lys Ser Ala Lys Gln Leu Pro His Leu Lys Val His
        35                  40                  45

<210> SEQ ID NO 49
<211> LENGTH: 39
<212> TYPE: PRT
<213> ORGANISM: Shrimp white spot syndrome virus

<400> SEQUENCE: 49

Lys Gln Leu Leu His Leu Lys Val Arg Leu Asp Val Arg Gly Ala Lys
1               5                   10                  15

Gln Asn Pro Trp Arg Lys Asn Leu Cys Leu Leu Lys Lys Asn Val Lys
            20                  25                  30

Ser Ala Lys Gln Leu Pro His
        35

<210> SEQ ID NO 50
<211> LENGTH: 43
<212> TYPE: PRT
<213> ORGANISM: Shrimp white spot syndrome virus

<400> SEQUENCE: 50

```
Lys Gln Leu Leu His Leu Lys Val Arg Leu Asp Val Arg Gly Ala Lys
1               5                   10                  15

Gln Asn Pro Trp Arg Lys Asn Leu Cys Leu Leu Lys Lys Asn Val Lys
            20                  25                  30

Ser Ala Lys Gln Leu Pro His Leu Lys Val His
        35                  40
```

<210> SEQ ID NO 51
<211> LENGTH: 12
<212> TYPE: PRT
<213> ORGANISM: Shrimp white spot syndrome virus

<400> SEQUENCE: 51

```
His Leu Lys Val Arg Leu Asp Val Arg Gly Ala Lys
1               5                   10
```

<210> SEQ ID NO 52
<211> LENGTH: 18
<212> TYPE: PRT
<213> ORGANISM: Shrimp white spot syndrome virus

<400> SEQUENCE: 52

```
His Leu Lys Val Arg Leu Asp Val Arg Gly Ala Lys Gln Asn Pro Trp
1               5                   10                  15

Arg Lys
```

<210> SEQ ID NO 53
<211> LENGTH: 24
<212> TYPE: PRT
<213> ORGANISM: Shrimp white spot syndrome virus

<400> SEQUENCE: 53

```
His Leu Lys Val Arg Leu Asp Val Arg Gly Ala Lys Gln Asn Pro Trp
1               5                   10                  15

Arg Lys Asn Leu Cys Leu Leu Lys
            20
```

<210> SEQ ID NO 54
<211> LENGTH: 25
<212> TYPE: PRT
<213> ORGANISM: Shrimp white spot syndrome virus

<400> SEQUENCE: 54

```
His Leu Lys Val Arg Leu Asp Val Arg Gly Ala Lys Gln Asn Pro Trp
1               5                   10                  15

Arg Lys Asn Leu Cys Leu Leu Lys Lys
            20                  25
```

<210> SEQ ID NO 55
<211> LENGTH: 28
<212> TYPE: PRT
<213> ORGANISM: Shrimp white spot syndrome virus

<400> SEQUENCE: 55

```
His Leu Lys Val Arg Leu Asp Val Arg Gly Ala Lys Gln Asn Pro Trp
1               5                   10                  15

Arg Lys Asn Leu Cys Leu Leu Lys Lys Asn Val Lys
```

20 25

<210> SEQ ID NO 56
<211> LENGTH: 31
<212> TYPE: PRT
<213> ORGANISM: Shrimp white spot syndrome virus

<400> SEQUENCE: 56

His Leu Lys Val Arg Leu Asp Val Arg Gly Ala Lys Gln Asn Pro Trp
1 5 10 15

Arg Lys Asn Leu Cys Leu Leu Lys Lys Asn Val Lys Ser Ala Lys
20 25 30

<210> SEQ ID NO 57
<211> LENGTH: 37
<212> TYPE: PRT
<213> ORGANISM: Shrimp white spot syndrome virus

<400> SEQUENCE: 57

His Leu Lys Val Arg Leu Asp Val Arg Gly Ala Lys Gln Asn Pro Trp
1 5 10 15

Arg Lys Asn Leu Cys Leu Leu Lys Lys Asn Val Lys Ser Ala Lys Gln
20 25 30

Leu Pro His Leu Lys
35

<210> SEQ ID NO 58
<211> LENGTH: 43
<212> TYPE: PRT
<213> ORGANISM: Shrimp white spot syndrome virus

<400> SEQUENCE: 58

His Leu Lys Val Arg Leu Asp Val Arg Gly Ala Lys Gln Asn Pro Trp
1 5 10 15

Arg Lys Asn Leu Cys Leu Leu Lys Lys Asn Val Lys Ser Ala Lys Gln
20 25 30

Leu Pro His Leu Lys Val His Leu Asp Val Lys
35 40

<210> SEQ ID NO 59
<211> LENGTH: 46
<212> TYPE: PRT
<213> ORGANISM: Shrimp white spot syndrome virus

<400> SEQUENCE: 59

His Leu Lys Val Arg Leu Asp Val Arg Gly Ala Lys Gln Asn Pro Trp
1 5 10 15

Arg Lys Asn Leu Cys Leu Leu Lys Lys Asn Val Lys Ser Ala Lys Gln
20 25 30

Leu Pro His Leu Lys Val His Leu Asp Val Lys Ser Ala Lys
35 40 45

<210> SEQ ID NO 60
<211> LENGTH: 33
<212> TYPE: PRT
<213> ORGANISM: Shrimp white spot syndrome virus

<400> SEQUENCE: 60

Lys Val Arg Leu Asp Val Arg Gly Ala Lys Gln Asn Pro Trp Arg Lys
1 5 10 15

Asn Leu Cys Leu Leu Lys Lys Asn Val Lys Ser Ala Lys Gln Leu Pro
20 25 30

-continued

His

<210> SEQ ID NO 61
<211> LENGTH: 37
<212> TYPE: PRT
<213> ORGANISM: Shrimp white spot syndrome virus

<400> SEQUENCE: 61

```
Lys Val Arg Leu Asp Val Arg Gly Ala Lys Gln Asn Pro Trp Arg Lys
1               5                   10                  15

Asn Leu Cys Leu Leu Lys Lys Asn Val Lys Ser Ala Lys Gln Leu Pro
            20                  25                  30

His Leu Lys Val His
        35
```

<210> SEQ ID NO 62
<211> LENGTH: 48
<212> TYPE: PRT
<213> ORGANISM: Shrimp white spot syndrome virus

<400> SEQUENCE: 62

```
Lys Val Arg Leu Asp Val Arg Gly Ala Lys Gln Asn Pro Trp Arg Lys
1               5                   10                  15

Asn Leu Cys Leu Leu Lys Lys Asn Val Lys Ser Ala Lys Gln Leu Pro
            20                  25                  30

His Leu Lys Val His Leu Asp Val Lys Ser Ala Lys Gln Leu Pro His
        35                  40                  45
```

<210> SEQ ID NO 63
<211> LENGTH: 24
<212> TYPE: PRT
<213> ORGANISM: Shrimp white spot syndrome virus

<400> SEQUENCE: 63

```
Lys Gln Asn Pro Trp Arg Lys Asn Leu Cys Leu Leu Lys Lys Asn Val
1               5                   10                  15

Lys Ser Ala Lys Gln Leu Pro His
            20
```

<210> SEQ ID NO 64
<211> LENGTH: 28
<212> TYPE: PRT
<213> ORGANISM: Shrimp white spot syndrome virus

<400> SEQUENCE: 64

```
Lys Gln Asn Pro Trp Arg Lys Asn Leu Cys Leu Leu Lys Lys Asn Val
1               5                   10                  15

Lys Ser Ala Lys Gln Leu Pro His Leu Lys Val His
            20                  25
```

<210> SEQ ID NO 65
<211> LENGTH: 39
<212> TYPE: PRT
<213> ORGANISM: Shrimp white spot syndrome virus

<400> SEQUENCE: 65

```
Lys Gln Asn Pro Trp Arg Lys Asn Leu Cys Leu Leu Lys Lys Asn Val
1               5                   10                  15

Lys Ser Ala Lys Gln Leu Pro His Leu Lys Val His Leu Asp Val Lys
            20                  25                  30

Ser Ala Lys Gln Leu Pro His
```

35

<210> SEQ ID NO 66
<211> LENGTH: 43
<212> TYPE: PRT
<213> ORGANISM: Shrimp white spot syndrome virus

<400> SEQUENCE: 66

```
Lys Gln Asn Pro Trp Arg Lys Asn Leu Cys Leu Leu Lys Lys Asn Val
1               5                   10                  15

Lys Ser Ala Lys Gln Leu Pro His Leu Lys Val His Leu Asp Val Lys
            20                  25                  30

Ser Ala Lys Gln Leu Pro His Leu Lys Val His
        35                  40
```

<210> SEQ ID NO 67
<211> LENGTH: 48
<212> TYPE: PRT
<213> ORGANISM: Shrimp white spot syndrome virus

<400> SEQUENCE: 67

```
Lys Asn Leu Cys Leu Leu Lys Lys Asn Val Lys Ser Ala Lys Gln Leu
1               5                   10                  15

Pro His Leu Lys Val His Leu Asp Val Lys Ser Ala Lys Gln Leu Pro
            20                  25                  30

His Leu Lys Val His Leu Asp Val Arg Gly Ala Lys Gln Leu Pro His
        35                  40                  45
```

<210> SEQ ID NO 68
<211> LENGTH: 18
<212> TYPE: PRT
<213> ORGANISM: Shrimp white spot syndrome virus

<400> SEQUENCE: 68

```
Lys Asn Leu Cys Leu Leu Lys Lys Asn Val Lys Ser Ala Lys Gln Leu
1               5                   10                  15

Pro His
```

<210> SEQ ID NO 69
<211> LENGTH: 22
<212> TYPE: PRT
<213> ORGANISM: Shrimp white spot syndrome virus

<400> SEQUENCE: 69

```
Lys Asn Leu Cys Leu Leu Lys Lys Asn Val Lys Ser Ala Lys Gln Leu
1               5                   10                  15

Pro His Leu Lys Val His
            20
```

<210> SEQ ID NO 70
<211> LENGTH: 33
<212> TYPE: PRT
<213> ORGANISM: Shrimp white spot syndrome virus

<400> SEQUENCE: 70

```
Lys Asn Leu Cys Leu Leu Lys Lys Asn Val Lys Ser Ala Lys Gln Leu
1               5                   10                  15

Pro His Leu Lys Val His Leu Asp Val Lys Ser Ala Lys Gln Leu Pro
            20                  25                  30

His
```

<210> SEQ ID NO 71
<211> LENGTH: 37
<212> TYPE: PRT
<213> ORGANISM: Shrimp white spot syndrome virus

<400> SEQUENCE: 71

Lys Asn Leu Cys Leu Leu Lys Lys Asn Val Lys Ser Ala Lys Gln Leu
1 5 10 15

Pro His Leu Lys Val His Leu Asp Val Lys Ser Ala Lys Gln Leu Pro
20 25 30

His Leu Lys Val His
35

<210> SEQ ID NO 72
<211> LENGTH: 16
<212> TYPE: PRT
<213> ORGANISM: Shrimp white spot syndrome virus

<400> SEQUENCE: 72

Lys Lys Asn Val Lys Ser Ala Lys Gln Leu Pro His Leu Lys Val His
1 5 10 15

<210> SEQ ID NO 73
<211> LENGTH: 27
<212> TYPE: PRT
<213> ORGANISM: Shrimp white spot syndrome virus

<400> SEQUENCE: 73

Lys Lys Asn Val Lys Ser Ala Lys Gln Leu Pro His Leu Lys Val His
1 5 10 15

Leu Asp Val Lys Ser Ala Lys Gln Leu Pro His
20 25

<210> SEQ ID NO 74
<211> LENGTH: 42
<212> TYPE: PRT
<213> ORGANISM: Shrimp white spot syndrome virus

<400> SEQUENCE: 74

Lys Lys Asn Val Lys Ser Ala Lys Gln Leu Pro His Leu Lys Val His
1 5 10 15

Leu Asp Val Lys Ser Ala Lys Gln Leu Pro His Leu Lys Val His Leu
20 25 30

Asp Val Arg Gly Ala Lys Gln Leu Pro His
35 40

<210> SEQ ID NO 75
<211> LENGTH: 11
<212> TYPE: PRT
<213> ORGANISM: Shrimp white spot syndrome virus

<400> SEQUENCE: 75

Lys Asn Val Lys Ser Ala Lys Gln Leu Pro His
1 5 10

<210> SEQ ID NO 76
<211> LENGTH: 15
<212> TYPE: PRT
<213> ORGANISM: Shrimp white spot syndrome virus

<400> SEQUENCE: 76

Lys Asn Val Lys Ser Ala Lys Gln Leu Pro His Leu Lys Val His
1 5 10 15

<210> SEQ ID NO 77
<211> LENGTH: 26
<212> TYPE: PRT
<213> ORGANISM: Shrimp white spot syndrome virus

<400> SEQUENCE: 77

```
Lys Asn Val Lys Ser Ala Lys Gln Leu Pro His Leu Lys Val His Leu
1               5                   10                  15

Asp Val Lys Ser Ala Lys Gln Leu Pro His
            20                  25
```

<210> SEQ ID NO 78
<211> LENGTH: 30
<212> TYPE: PRT
<213> ORGANISM: Shrimp white spot syndrome virus

<400> SEQUENCE: 78

```
Lys Asn Val Lys Ser Ala Lys Gln Leu Pro His Leu Lys Val His Leu
1               5                   10                  15

Asp Val Lys Ser Ala Lys Gln Leu Pro His Leu Lys Val His
            20                  25                  30
```

<210> SEQ ID NO 79
<211> LENGTH: 41
<212> TYPE: PRT
<213> ORGANISM: Shrimp white spot syndrome virus

<400> SEQUENCE: 79

```
Lys Asn Val Lys Ser Ala Lys Gln Leu Pro His Leu Lys Val His Leu
1               5                   10                  15

Asp Val Lys Ser Ala Lys Gln Leu Pro His Leu Lys Val His Leu Asp
            20                  25                  30

Val Arg Gly Ala Lys Gln Leu Pro His
        35                  40
```

<210> SEQ ID NO 80
<211> LENGTH: 38
<212> TYPE: PRT
<213> ORGANISM: Shrimp white spot syndrome virus

<400> SEQUENCE: 80

```
Lys Ser Ala Lys Gln Leu Pro His Leu Lys Val His Leu Asp Val Lys
1               5                   10                  15

Ser Ala Lys Gln Leu Pro His Leu Lys Val His Leu Asp Val Arg Gly
            20                  25                  30

Ala Lys Gln Leu Pro His
        35
```

<210> SEQ ID NO 81
<211> LENGTH: 12
<212> TYPE: PRT
<213> ORGANISM: Shrimp white spot syndrome virus

<400> SEQUENCE: 81

```
Lys Ser Ala Lys Gln Leu Pro His Leu Lys Val His
1               5                   10
```

<210> SEQ ID NO 82
<211> LENGTH: 23
<212> TYPE: PRT
<213> ORGANISM: Shrimp white spot syndrome virus

<400> SEQUENCE: 82

Lys Ser Ala Lys Gln Leu Pro His Leu Lys Val His Leu Asp Val Lys
1               5                   10                  15

Ser Ala Lys Gln Leu Pro His
            20

<210> SEQ ID NO 83
<211> LENGTH: 27
<212> TYPE: PRT
<213> ORGANISM: Shrimp white spot syndrome virus

<400> SEQUENCE: 83

Lys Ser Ala Lys Gln Leu Pro His Leu Lys Val His Leu Asp Val Lys
1               5                   10                  15

Ser Ala Lys Gln Leu Pro His Leu Lys Val His
            20                  25

<210> SEQ ID NO 84
<211> LENGTH: 7
<212> TYPE: PRT
<213> ORGANISM: Shrimp white spot syndrome virus

<400> SEQUENCE: 84

Lys Gln Leu Pro His Leu Lys
1               5

<210> SEQ ID NO 85
<211> LENGTH: 9
<212> TYPE: PRT
<213> ORGANISM: Shrimp white spot syndrome virus

<400> SEQUENCE: 85

Lys Gln Leu Pro His Leu Lys Val His
1               5

<210> SEQ ID NO 86
<211> LENGTH: 35
<212> TYPE: PRT
<213> ORGANISM: Shrimp white spot syndrome virus

<400> SEQUENCE: 86

Lys Gln Leu Pro His Leu Lys Val His Leu Asp Val Lys Ser Ala Lys
1               5                   10                  15

Gln Leu Pro His Leu Lys Val His Leu Asp Val Arg Gly Ala Lys Gln
            20                  25                  30

Leu Pro His
        35

<210> SEQ ID NO 87
<211> LENGTH: 20
<212> TYPE: PRT
<213> ORGANISM: Shrimp white spot syndrome virus

<400> SEQUENCE: 87

Lys Gln Leu Pro His Leu Lys Val His Leu Asp Val Lys Ser Ala Lys
1               5                   10                  15

Gln Leu Pro His
            20

<210> SEQ ID NO 88
<211> LENGTH: 24
<212> TYPE: PRT
<213> ORGANISM: Shrimp white spot syndrome virus -continued

<400> SEQUENCE: 88

Lys Gln Leu Pro His Leu Lys Val His Leu Asp Val Lys Ser Ala Lys
1 5 10 15

Gln Leu Pro His Leu Lys Val His
20

<210> SEQ ID NO 89
<211> LENGTH: 50
<212> TYPE: PRT
<213> ORGANISM: Shrimp white spot syndrome virus

<400> SEQUENCE: 89

Lys Gln Leu Pro His Leu Lys Val His Leu Asp Val Lys Ser Ala Lys
1 5 10 15

Gln Leu Pro His Leu Lys Val His Leu Asp Val Arg Gly Ala Lys Gln
20 25 30

Leu Pro His Leu Lys Val Arg Leu Asp Val Lys Ser Ala Lys Gln Leu
35 40 45

Pro His
50

<210> SEQ ID NO 90
<211> LENGTH: 12
<212> TYPE: PRT
<213> ORGANISM: Shrimp white spot syndrome virus

<400> SEQUENCE: 90

His Leu Lys Val His Leu Asp Val Lys Ser Ala Lys
1 5 10

<210> SEQ ID NO 91
<211> LENGTH: 18
<212> TYPE: PRT
<213> ORGANISM: Shrimp white spot syndrome virus

<400> SEQUENCE: 91

His Leu Lys Val His Leu Asp Val Lys Ser Ala Lys Gln Leu Pro His
1 5 10 15

Leu Lys

<210> SEQ ID NO 92
<211> LENGTH: 27
<212> TYPE: PRT
<213> ORGANISM: Shrimp white spot syndrome virus

<400> SEQUENCE: 92

His Leu Lys Val His Leu Asp Val Lys Ser Ala Lys Gln Leu Pro His
1 5 10 15

Leu Lys Val His Leu Asp Val Arg Gly Ala Lys
20 25

<210> SEQ ID NO 93
<211> LENGTH: 33
<212> TYPE: PRT
<213> ORGANISM: Shrimp white spot syndrome virus

<400> SEQUENCE: 93

His Leu Lys Val His Leu Asp Val Lys Ser Ala Lys Gln Leu Pro His
1 5 10 15

Leu Lys Val His Leu Asp Val Arg Gly Ala Lys Gln Leu Pro His Leu
20 25 30

Lys

<210> SEQ ID NO 94
<211> LENGTH: 39
<212> TYPE: PRT
<213> ORGANISM: Shrimp white spot syndrome virus

<400> SEQUENCE: 94

His Leu Lys Val His Leu Asp Val Lys Ser Ala Lys Gln Leu Pro His
1 5 10 15

Leu Lys Val His Leu Asp Val Arg Gly Ala Lys Gln Leu Pro His Leu
20 25 30

Lys Val Arg Leu Asp Val Lys
35

<210> SEQ ID NO 95
<211> LENGTH: 42
<212> TYPE: PRT
<213> ORGANISM: Shrimp white spot syndrome virus

<400> SEQUENCE: 95

His Leu Lys Val His Leu Asp Val Lys Ser Ala Lys Gln Leu Pro His
1 5 10 15

Leu Lys Val His Leu Asp Val Arg Gly Ala Lys Gln Leu Pro His Leu
20 25 30

Lys Val Arg Leu Asp Val Lys Ser Ala Lys
35 40

<210> SEQ ID NO 96
<211> LENGTH: 48
<212> TYPE: PRT
<213> ORGANISM: Shrimp white spot syndrome virus

<400> SEQUENCE: 96

His Leu Lys Val His Leu Asp Val Lys Ser Ala Lys Gln Leu Pro His
1 5 10 15

Leu Lys Val His Leu Asp Val Arg Gly Ala Lys Gln Leu Pro His Leu
20 25 30

Lys Val Arg Leu Asp Val Lys Ser Ala Lys Gln Leu Pro His Leu Lys
35 40 45

<210> SEQ ID NO 97
<211> LENGTH: 29
<212> TYPE: PRT
<213> ORGANISM: Shrimp white spot syndrome virus

<400> SEQUENCE: 97

Lys Val His Leu Asp Val Lys Ser Ala Lys Gln Leu Pro His Leu Lys
1 5 10 15

Val His Leu Asp Val Arg Gly Ala Lys Gln Leu Pro His
20 25

<210> SEQ ID NO 98
<211> LENGTH: 44
<212> TYPE: PRT
<213> ORGANISM: Shrimp white spot syndrome virus

<400> SEQUENCE: 98

Lys Val His Leu Asp Val Lys Ser Ala Lys Gln Leu Pro His Leu Lys
1 5 10 15

Val His Leu Asp Val Arg Gly Ala Lys Gln Leu Pro His Leu Lys Val
20 25 30

Arg Leu Asp Val Lys Ser Ala Lys Gln Leu Pro His
35 40

<210> SEQ ID NO 99
<211> LENGTH: 48
<212> TYPE: PRT
<213> ORGANISM: Shrimp white spot syndrome virus

<400> SEQUENCE: 99

Lys Val His Leu Asp Val Lys Ser Ala Lys Gln Leu Pro His Leu Lys
1 5 10 15

Val His Leu Asp Val Arg Gly Ala Lys Gln Leu Pro His Leu Lys Val
20 25 30

Arg Leu Asp Val Lys Ser Ala Lys Gln Leu Pro His Leu Lys Val His
35 40 45

<210> SEQ ID NO 100
<211> LENGTH: 10
<212> TYPE: PRT
<213> ORGANISM: Shrimp white spot syndrome virus

<400> SEQUENCE: 100

Lys Val His Leu Asp Val Lys Ser Ala Lys
1 5 10

<210> SEQ ID NO 101
<211> LENGTH: 14
<212> TYPE: PRT
<213> ORGANISM: Shrimp white spot syndrome virus

<400> SEQUENCE: 101

Lys Val His Leu Asp Val Lys Ser Ala Lys Gln Leu Pro His
1 5 10

<210> SEQ ID NO 102
<211> LENGTH: 18
<212> TYPE: PRT
<213> ORGANISM: Shrimp white spot syndrome virus

<400> SEQUENCE: 102

Lys Val His Leu Asp Val Lys Ser Ala Lys Gln Leu Pro His Leu Lys
1 5 10 15

Val His

<210> SEQ ID NO 103
<211> LENGTH: 14
<212> TYPE: PRT
<213> ORGANISM: Shrimp white spot syndrome virus

<400> SEQUENCE: 103

His Leu Asp Val Lys Ser Ala Lys Gln Leu Pro His Leu Lys
1 5 10

<210> SEQ ID NO 104
<211> LENGTH: 23
<212> TYPE: PRT
<213> ORGANISM: Shrimp white spot syndrome virus

<400> SEQUENCE: 104

His Leu Asp Val Lys Ser Ala Lys Gln Leu Pro His Leu Lys Val His
1 5 10 15

Leu Asp Val Arg Gly Ala Lys
20

<210> SEQ ID NO 105
<211> LENGTH: 29
<212> TYPE: PRT
<213> ORGANISM: Shrimp white spot syndrome virus

<400> SEQUENCE: 105

```
His Leu Asp Val Lys Ser Ala Lys Gln Leu Pro His Leu Lys Val His
1               5                   10                  15

Leu Asp Val Arg Gly Ala Lys Gln Leu Pro His Leu Lys
            20                  25
```

<210> SEQ ID NO 106
<211> LENGTH: 35
<212> TYPE: PRT
<213> ORGANISM: Shrimp white spot syndrome virus

<400> SEQUENCE: 106

```
His Leu Asp Val Lys Ser Ala Lys Gln Leu Pro His Leu Lys Val His
1               5                   10                  15

Leu Asp Val Arg Gly Ala Lys Gln Leu Pro His Leu Lys Val Arg Leu
            20                  25                  30

Asp Val Lys
        35
```

<210> SEQ ID NO 107
<211> LENGTH: 38
<212> TYPE: PRT
<213> ORGANISM: Shrimp white spot syndrome virus

<400> SEQUENCE: 107

```
His Leu Asp Val Lys Ser Ala Lys Gln Leu Pro His Leu Lys Val His
1               5                   10                  15

Leu Asp Val Arg Gly Ala Lys Gln Leu Pro His Leu Lys Val Arg Leu
            20                  25                  30

Asp Val Lys Ser Ala Lys
        35
```

<210> SEQ ID NO 108
<211> LENGTH: 44
<212> TYPE: PRT
<213> ORGANISM: Shrimp white spot syndrome virus

<400> SEQUENCE: 108

```
His Leu Asp Val Lys Ser Ala Lys Gln Leu Pro His Leu Lys Val His
1               5                   10                  15

Leu Asp Val Arg Gly Ala Lys Gln Leu Pro His Leu Lys Val Arg Leu
            20                  25                  30

Asp Val Lys Ser Ala Lys Gln Leu Pro His Leu Lys
        35                  40
```

<210> SEQ ID NO 109
<211> LENGTH: 23
<212> TYPE: PRT
<213> ORGANISM: Shrimp white spot syndrome virus

<400> SEQUENCE: 109

```
Lys Ser Ala Lys Gln Leu Pro His Leu Lys Val His Leu Asp Val Arg
1               5                   10                  15

Gly Ala Lys Gln Leu Pro His
            20
```

<210> SEQ ID NO 110
<211> LENGTH: 38
<212> TYPE: PRT
<213> ORGANISM: Shrimp white spot syndrome virus

<400> SEQUENCE: 110

Lys Ser Ala Lys Gln Leu Pro His Leu Lys Val His Leu Asp Val Arg
1 5 10 15

Gly Ala Lys Gln Leu Pro His Leu Lys Val Arg Leu Asp Val Lys Ser
20 25 30

Ala Lys Gln Leu Pro His
35

<210> SEQ ID NO 111
<211> LENGTH: 42
<212> TYPE: PRT
<213> ORGANISM: Shrimp white spot syndrome virus

<400> SEQUENCE: 111

Lys Ser Ala Lys Gln Leu Pro His Leu Lys Val His Leu Asp Val Arg
1 5 10 15

Gly Ala Lys Gln Leu Pro His Leu Lys Val Arg Leu Asp Val Lys Ser
20 25 30

Ala Lys Gln Leu Pro His Leu Lys Val His
35 40

<210> SEQ ID NO 112
<211> LENGTH: 20
<212> TYPE: PRT
<213> ORGANISM: Shrimp white spot syndrome virus

<400> SEQUENCE: 112

Lys Gln Leu Pro His Leu Lys Val His Leu Asp Val Arg Gly Ala Lys
1 5 10 15

Gln Leu Pro His
20

<210> SEQ ID NO 113
<211> LENGTH: 35
<212> TYPE: PRT
<213> ORGANISM: Shrimp white spot syndrome virus

<400> SEQUENCE: 113

Lys Gln Leu Pro His Leu Lys Val His Leu Asp Val Arg Gly Ala Lys
1 5 10 15

Gln Leu Pro His Leu Lys Val Arg Leu Asp Val Lys Ser Ala Lys Gln
20 25 30

Leu Pro His
35

<210> SEQ ID NO 114
<211> LENGTH: 39
<212> TYPE: PRT
<213> ORGANISM: Shrimp white spot syndrome virus

<400> SEQUENCE: 114

Lys Gln Leu Pro His Leu Lys Val His Leu Asp Val Arg Gly Ala Lys
1 5 10 15

Gln Leu Pro His Leu Lys Val Arg Leu Asp Val Lys Ser Ala Lys Gln
20 25 30

Leu Pro His Leu Lys Val His

-continued

```
        35


<210> SEQ ID NO 115
<211> LENGTH: 50
<212> TYPE: PRT
<213> ORGANISM: Shrimp white spot syndrome virus

<400> SEQUENCE: 115

Lys Gln Leu Pro His Leu Lys Val His Leu Asp Val Arg Gly Ala Lys
1               5                   10                  15

Gln Leu Pro His Leu Lys Val Arg Leu Asp Val Lys Ser Ala Lys Gln
            20                  25                  30

Leu Pro His Leu Lys Val His Leu Asp Val Arg Gly Ala Lys Gln Leu
        35                  40                  45

Pro His
    50


<210> SEQ ID NO 116
<211> LENGTH: 24
<212> TYPE: PRT
<213> ORGANISM: Shrimp white spot syndrome virus

<400> SEQUENCE: 116

His Leu Lys Val His Leu Asp Val Arg Gly Ala Lys Gln Leu Pro His
1               5                   10                  15

Leu Lys Val Arg Leu Asp Val Lys
            20


<210> SEQ ID NO 117
<211> LENGTH: 27
<212> TYPE: PRT
<213> ORGANISM: Shrimp white spot syndrome virus

<400> SEQUENCE: 117

His Leu Lys Val His Leu Asp Val Arg Gly Ala Lys Gln Leu Pro His
1               5                   10                  15

Leu Lys Val Arg Leu Asp Val Lys Ser Ala Lys
            20                  25


<210> SEQ ID NO 118
<211> LENGTH: 33
<212> TYPE: PRT
<213> ORGANISM: Shrimp white spot syndrome virus

<400> SEQUENCE: 118

His Leu Lys Val His Leu Asp Val Arg Gly Ala Lys Gln Leu Pro His
1               5                   10                  15

Leu Lys Val Arg Leu Asp Val Lys Ser Ala Lys Gln Leu Pro His Leu
            20                  25                  30

Lys


<210> SEQ ID NO 119
<211> LENGTH: 42
<212> TYPE: PRT
<213> ORGANISM: Shrimp white spot syndrome virus

<400> SEQUENCE: 119

His Leu Lys Val His Leu Asp Val Arg Gly Ala Lys Gln Leu Pro His
1               5                   10                  15

Leu Lys Val Arg Leu Asp Val Lys Ser Ala Lys Gln Leu Pro His Leu
            20                  25                  30
```

Lys Val His Leu Asp Val Arg Gly Ala Lys
35 40

<210> SEQ ID NO 120
<211> LENGTH: 48
<212> TYPE: PRT
<213> ORGANISM: Shrimp white spot syndrome virus

<400> SEQUENCE: 120

His Leu Lys Val His Leu Asp Val Arg Gly Ala Lys Gln Leu Pro His
1 5 10 15

Leu Lys Val Arg Leu Asp Val Lys Ser Ala Lys Gln Leu Pro His Leu
20 25 30

Lys Val His Leu Asp Val Arg Gly Ala Lys Gln Leu Pro His Leu Lys
35 40 45

<210> SEQ ID NO 121
<211> LENGTH: 12
<212> TYPE: PRT
<213> ORGANISM: Shrimp white spot syndrome virus

<400> SEQUENCE: 121

His Leu Lys Val His Leu Asp Val Arg Gly Ala Lys
1 5 10

<210> SEQ ID NO 122
<211> LENGTH: 18
<212> TYPE: PRT
<213> ORGANISM: Shrimp white spot syndrome virus

<400> SEQUENCE: 122

His Leu Lys Val His Leu Asp Val Arg Gly Ala Lys Gln Leu Pro His
1 5 10 15

Leu Lys

<210> SEQ ID NO 123
<211> LENGTH: 10
<212> TYPE: PRT
<213> ORGANISM: Shrimp white spot syndrome virus

<400> SEQUENCE: 123

Lys Val His Leu Asp Val Arg Gly Ala Lys
1 5 10

<210> SEQ ID NO 124
<211> LENGTH: 14
<212> TYPE: PRT
<213> ORGANISM: Shrimp white spot syndrome virus

<400> SEQUENCE: 124

Lys Val His Leu Asp Val Arg Gly Ala Lys Gln Leu Pro His
1 5 10

<210> SEQ ID NO 125
<211> LENGTH: 29
<212> TYPE: PRT
<213> ORGANISM: Shrimp white spot syndrome virus

<400> SEQUENCE: 125

Lys Val His Leu Asp Val Arg Gly Ala Lys Gln Leu Pro His Leu Lys
1 5 10 15

Val Arg Leu Asp Val Lys Ser Ala Lys Gln Leu Pro His
20 25

<210> SEQ ID NO 126
<211> LENGTH: 33
<212> TYPE: PRT
<213> ORGANISM: Shrimp white spot syndrome virus

<400> SEQUENCE: 126

Lys Val His Leu Asp Val Arg Gly Ala Lys Gln Leu Pro His Leu Lys
1 5 10 15

Val Arg Leu Asp Val Lys Ser Ala Lys Gln Leu Pro His Leu Lys Val
20 25 30

His

<210> SEQ ID NO 127
<211> LENGTH: 44
<212> TYPE: PRT
<213> ORGANISM: Shrimp white spot syndrome virus

<400> SEQUENCE: 127

Lys Val His Leu Asp Val Arg Gly Ala Lys Gln Leu Pro His Leu Lys
1 5 10 15

Val Arg Leu Asp Val Lys Ser Ala Lys Gln Leu Pro His Leu Lys Val
20 25 30

His Leu Asp Val Arg Gly Ala Lys Gln Leu Pro His
35 40

<210> SEQ ID NO 128
<211> LENGTH: 14
<212> TYPE: PRT
<213> ORGANISM: Shrimp white spot syndrome virus

<400> SEQUENCE: 128

His Leu Asp Val Arg Gly Ala Lys Gln Leu Pro His Leu Lys
1 5 10

<210> SEQ ID NO 129
<211> LENGTH: 20
<212> TYPE: PRT
<213> ORGANISM: Shrimp white spot syndrome virus

<400> SEQUENCE: 129

His Leu Asp Val Arg Gly Ala Lys Gln Leu Pro His Leu Lys Val Arg
1 5 10 15

Leu Asp Val Lys
20

<210> SEQ ID NO 130
<211> LENGTH: 23
<212> TYPE: PRT
<213> ORGANISM: Shrimp white spot syndrome virus

<400> SEQUENCE: 130

His Leu Asp Val Arg Gly Ala Lys Gln Leu Pro His Leu Lys Val Arg
1 5 10 15

Leu Asp Val Lys Ser Ala Lys
20

<210> SEQ ID NO 131
<211> LENGTH: 29
<212> TYPE: PRT
<213> ORGANISM: Shrimp white spot syndrome virus

<400> SEQUENCE: 131

```
His Leu Asp Val Arg Gly Ala Lys Gln Leu Pro His Leu Lys Val Arg
1               5                   10                  15

Leu Asp Val Lys Ser Ala Lys Gln Leu Pro His Leu Lys
            20                  25


<210> SEQ ID NO 132
<211> LENGTH: 38
<212> TYPE: PRT
<213> ORGANISM: Shrimp white spot syndrome virus

<400> SEQUENCE: 132

His Leu Asp Val Arg Gly Ala Lys Gln Leu Pro His Leu Lys Val Arg
1               5                   10                  15

Leu Asp Val Lys Ser Ala Lys Gln Leu Pro His Leu Lys Val His Leu
            20                  25                  30

Asp Val Arg Gly Ala Lys
        35


<210> SEQ ID NO 133
<211> LENGTH: 44
<212> TYPE: PRT
<213> ORGANISM: Shrimp white spot syndrome virus

<400> SEQUENCE: 133

His Leu Asp Val Arg Gly Ala Lys Gln Leu Pro His Leu Lys Val Arg
1               5                   10                  15

Leu Asp Val Lys Ser Ala Lys Gln Leu Pro His Leu Lys Val His Leu
            20                  25                  30

Asp Val Arg Gly Ala Lys Gln Leu Pro His Leu Lys
        35                  40


<210> SEQ ID NO 134
<211> LENGTH: 20
<212> TYPE: PRT
<213> ORGANISM: Shrimp white spot syndrome virus

<400> SEQUENCE: 134

Lys Gln Leu Pro His Leu Lys Val Arg Leu Asp Val Lys Ser Ala Lys
1               5                   10                  15

Gln Leu Pro His
            20


<210> SEQ ID NO 135
<211> LENGTH: 24
<212> TYPE: PRT
<213> ORGANISM: Shrimp white spot syndrome virus

<400> SEQUENCE: 135

Lys Gln Leu Pro His Leu Lys Val Arg Leu Asp Val Lys Ser Ala Lys
1               5                   10                  15

Gln Leu Pro His Leu Lys Val His
            20


<210> SEQ ID NO 136
<211> LENGTH: 35
<212> TYPE: PRT
<213> ORGANISM: Shrimp white spot syndrome virus

<400> SEQUENCE: 136

Lys Gln Leu Pro His Leu Lys Val Arg Leu Asp Val Lys Ser Ala Lys
1               5                   10                  15

Gln Leu Pro His Leu Lys Val His Leu Asp Val Arg Gly Ala Lys Gln
```

```
            20                  25                  30

Leu Pro His
        35


<210> SEQ ID NO 137
<211> LENGTH: 9
<212> TYPE: PRT
<213> ORGANISM: Shrimp white spot syndrome virus

<400> SEQUENCE: 137

His Leu Lys Val Arg Leu Asp Val Lys
1               5


<210> SEQ ID NO 138
<211> LENGTH: 12
<212> TYPE: PRT
<213> ORGANISM: Shrimp white spot syndrome virus

<400> SEQUENCE: 138

His Leu Lys Val Arg Leu Asp Val Lys Ser Ala Lys
1               5                   10


<210> SEQ ID NO 139
<211> LENGTH: 18
<212> TYPE: PRT
<213> ORGANISM: Shrimp white spot syndrome virus

<400> SEQUENCE: 139

His Leu Lys Val Arg Leu Asp Val Lys Ser Ala Lys Gln Leu Pro His
1               5                   10                  15

Leu Lys


<210> SEQ ID NO 140
<211> LENGTH: 27
<212> TYPE: PRT
<213> ORGANISM: Shrimp white spot syndrome virus

<400> SEQUENCE: 140

His Leu Lys Val Arg Leu Asp Val Lys Ser Ala Lys Gln Leu Pro His
1               5                   10                  15

Leu Lys Val His Leu Asp Val Arg Gly Ala Lys
            20                  25


<210> SEQ ID NO 141
<211> LENGTH: 33
<212> TYPE: PRT
<213> ORGANISM: Shrimp white spot syndrome virus

<400> SEQUENCE: 141

His Leu Lys Val Arg Leu Asp Val Lys Ser Ala Lys Gln Leu Pro His
1               5                   10                  15

Leu Lys Val His Leu Asp Val Arg Gly Ala Lys Gln Leu Pro His Leu
            20                  25                  30

Lys


<210> SEQ ID NO 142
<211> LENGTH: 42
<212> TYPE: PRT
<213> ORGANISM: Shrimp white spot syndrome virus

<400> SEQUENCE: 142

His Leu Lys Val Arg Leu Asp Val Lys Ser Ala Lys Gln Leu Pro His
1               5                   10                  15
```

```
Leu Lys Val His Leu Asp Val Arg Gly Ala Lys Gln Leu Pro His Leu
            20                  25                  30

Lys Val Arg Leu Asp Val Arg Gly Ala Lys
        35                  40


<210> SEQ ID NO 143
<211> LENGTH: 48
<212> TYPE: PRT
<213> ORGANISM: Shrimp white spot syndrome virus

<400> SEQUENCE: 143

His Leu Lys Val Arg Leu Asp Val Lys Ser Ala Lys Gln Leu Pro His
1               5                   10                  15

Leu Lys Val His Leu Asp Val Arg Gly Ala Lys Gln Leu Pro His Leu
            20                  25                  30

Lys Val Arg Leu Asp Val Arg Gly Ala Lys Gln Asn Pro Trp Arg Lys
        35                  40                  45


<210> SEQ ID NO 144
<211> LENGTH: 14
<212> TYPE: PRT
<213> ORGANISM: Shrimp white spot syndrome virus

<400> SEQUENCE: 144

Lys Val Arg Leu Asp Val Lys Ser Ala Lys Gln Leu Pro His
1               5                   10


<210> SEQ ID NO 145
<211> LENGTH: 18
<212> TYPE: PRT
<213> ORGANISM: Shrimp white spot syndrome virus

<400> SEQUENCE: 145

Lys Val Arg Leu Asp Val Lys Ser Ala Lys Gln Leu Pro His Leu Lys
1               5                   10                  15

Val His


<210> SEQ ID NO 146
<211> LENGTH: 29
<212> TYPE: PRT
<213> ORGANISM: Shrimp white spot syndrome virus

<400> SEQUENCE: 146

Lys Val Arg Leu Asp Val Lys Ser Ala Lys Gln Leu Pro His Leu Lys
1               5                   10                  15

Val His Leu Asp Val Arg Gly Ala Lys Gln Leu Pro His
            20                  25


<210> SEQ ID NO 147
<211> LENGTH: 27
<212> TYPE: PRT
<213> ORGANISM: Shrimp white spot syndrome virus

<400> SEQUENCE: 147

His Leu Lys Val His Leu Asp Val Arg Gly Ala Lys Gln Leu Pro His
1               5                   10                  15

Leu Lys Val Arg Leu Asp Val Arg Gly Ala Lys
            20                  25


<210> SEQ ID NO 148
<211> LENGTH: 33
<212> TYPE: PRT
```

-continued

<213> ORGANISM: Shrimp white spot syndrome virus

<400> SEQUENCE: 148

```
His Leu Lys Val His Leu Asp Val Arg Gly Ala Lys Gln Leu Pro His
1               5                   10                  15

Leu Lys Val Arg Leu Asp Val Arg Gly Ala Lys Gln Asn Pro Trp Arg
            20                  25                  30

Lys
```

<210> SEQ ID NO 149
<211> LENGTH: 39
<212> TYPE: PRT
<213> ORGANISM: Shrimp white spot syndrome virus

<400> SEQUENCE: 149

```
His Leu Lys Val His Leu Asp Val Arg Gly Ala Lys Gln Leu Pro His
1               5                   10                  15

Leu Lys Val Arg Leu Asp Val Arg Gly Ala Lys Gln Asn Pro Trp Arg
            20                  25                  30

Lys Asn Leu Cys Leu Leu Lys
        35
```

<210> SEQ ID NO 150
<211> LENGTH: 40
<212> TYPE: PRT
<213> ORGANISM: Shrimp white spot syndrome virus

<400> SEQUENCE: 150

```
His Leu Lys Val His Leu Asp Val Arg Gly Ala Lys Gln Leu Pro His
1               5                   10                  15

Leu Lys Val Arg Leu Asp Val Arg Gly Ala Lys Gln Asn Pro Trp Arg
            20                  25                  30

Lys Asn Leu Cys Leu Leu Lys Lys
        35                  40
```

<210> SEQ ID NO 151
<211> LENGTH: 43
<212> TYPE: PRT
<213> ORGANISM: Shrimp white spot syndrome virus

<400> SEQUENCE: 151

```
His Leu Lys Val His Leu Asp Val Arg Gly Ala Lys Gln Leu Pro His
1               5                   10                  15

Leu Lys Val Arg Leu Asp Val Arg Gly Ala Lys Gln Asn Pro Trp Arg
            20                  25                  30

Lys Asn Leu Cys Leu Leu Lys Lys Asn Val Lys
        35                  40
```

<210> SEQ ID NO 152
<211> LENGTH: 46
<212> TYPE: PRT
<213> ORGANISM: Shrimp white spot syndrome virus

<400> SEQUENCE: 152

```
His Leu Lys Val His Leu Asp Val Arg Gly Ala Lys Gln Leu Pro His
1               5                   10                  15

Leu Lys Val Arg Leu Asp Val Arg Gly Ala Lys Gln Asn Pro Trp Arg
            20                  25                  30

Lys Asn Leu Cys Leu Leu Lys Lys Asn Val Lys Ser Ala Lys
        35                  40                  45
```

<210> SEQ ID NO 153
<211> LENGTH: 48
<212> TYPE: PRT
<213> ORGANISM: Shrimp white spot syndrome virus

<400> SEQUENCE: 153

```
Lys Val His Leu Asp Val Arg Gly Ala Lys Gln Leu Pro His Leu Lys
1               5                   10                  15

Val Arg Leu Asp Val Arg Gly Ala Lys Gln Asn Pro Trp Arg Lys Asn
            20                  25                  30

Leu Cys Leu Leu Lys Lys Asn Val Lys Ser Ala Lys Gln Leu Pro His
        35                  40                  45
```

<210> SEQ ID NO 154
<211> LENGTH: 23
<212> TYPE: PRT
<213> ORGANISM: Shrimp white spot syndrome virus

<400> SEQUENCE: 154

```
His Leu Asp Val Arg Gly Ala Lys Gln Leu Pro His Leu Lys Val Arg
1               5                   10                  15

Leu Asp Val Arg Gly Ala Lys
            20
```

<210> SEQ ID NO 155
<211> LENGTH: 29
<212> TYPE: PRT
<213> ORGANISM: Shrimp white spot syndrome virus

<400> SEQUENCE: 155

```
His Leu Asp Val Arg Gly Ala Lys Gln Leu Pro His Leu Lys Val Arg
1               5                   10                  15

Leu Asp Val Arg Gly Ala Lys Gln Asn Pro Trp Arg Lys
            20                  25
```

<210> SEQ ID NO 156
<211> LENGTH: 35
<212> TYPE: PRT
<213> ORGANISM: Shrimp white spot syndrome virus

<400> SEQUENCE: 156

```
His Leu Asp Val Arg Gly Ala Lys Gln Leu Pro His Leu Lys Val Arg
1               5                   10                  15

Leu Asp Val Arg Gly Ala Lys Gln Asn Pro Trp Arg Lys Asn Leu Cys
            20                  25                  30

Leu Leu Lys
        35
```

<210> SEQ ID NO 157
<211> LENGTH: 36
<212> TYPE: PRT
<213> ORGANISM: Shrimp white spot syndrome virus

<400> SEQUENCE: 157

```
His Leu Asp Val Arg Gly Ala Lys Gln Leu Pro His Leu Lys Val Arg
1               5                   10                  15

Leu Asp Val Arg Gly Ala Lys Gln Asn Pro Trp Arg Lys Asn Leu Cys
            20                  25                  30

Leu Leu Lys Lys
        35
```

```
<210> SEQ ID NO 158
<211> LENGTH: 39
<212> TYPE: PRT
<213> ORGANISM: Shrimp white spot syndrome virus

<400> SEQUENCE: 158

His Leu Asp Val Arg Gly Ala Lys Gln Leu Pro His Leu Lys Val Arg
1               5                   10                  15

Leu Asp Val Arg Gly Ala Lys Gln Asn Pro Trp Arg Lys Asn Leu Cys
            20                  25                  30

Leu Leu Lys Lys Asn Val Lys
        35


<210> SEQ ID NO 159
<211> LENGTH: 42
<212> TYPE: PRT
<213> ORGANISM: Shrimp white spot syndrome virus

<400> SEQUENCE: 159

His Leu Asp Val Arg Gly Ala Lys Gln Leu Pro His Leu Lys Val Arg
1               5                   10                  15

Leu Asp Val Arg Gly Ala Lys Gln Asn Pro Trp Arg Lys Asn Leu Cys
            20                  25                  30

Leu Leu Lys Lys Asn Val Lys Ser Ala Lys
        35                  40


<210> SEQ ID NO 160
<211> LENGTH: 48
<212> TYPE: PRT
<213> ORGANISM: Shrimp white spot syndrome virus

<400> SEQUENCE: 160

His Leu Asp Val Arg Gly Ala Lys Gln Leu Pro His Leu Lys Val Arg
1               5                   10                  15

Leu Asp Val Arg Gly Ala Lys Gln Asn Pro Trp Arg Lys Asn Leu Cys
            20                  25                  30

Leu Leu Lys Lys Asn Val Lys Ser Ala Lys Gln Leu Pro His Leu Lys
        35                  40                  45


<210> SEQ ID NO 161
<211> LENGTH: 43
<212> TYPE: PRT
<213> ORGANISM: Shrimp white spot syndrome virus

<400> SEQUENCE: 161

Lys Gln Leu Pro His Leu Lys Val Arg Leu Asp Val Arg Gly Ala Lys
1               5                   10                  15

Gln Asn Pro Trp Arg Lys Asn Leu Cys Leu Leu Lys Lys Asn Val Lys
            20                  25                  30

Ser Ala Lys Gln Leu Pro His Leu Lys Val His
        35                  40


<210> SEQ ID NO 162
<211> LENGTH: 39
<212> TYPE: PRT
<213> ORGANISM: Shrimp white spot syndrome virus

<400> SEQUENCE: 162

Lys Gln Leu Pro His Leu Lys Val Arg Leu Asp Val Arg Gly Ala Lys
1               5                   10                  15

Gln Asn Pro Trp Arg Lys Asn Leu Cys Leu Leu Lys Lys Asn Val Lys
            20                  25                  30
```

```
Ser Ala Lys Gln Leu Pro His
        35


<210> SEQ ID NO 163
<211> LENGTH: 46
<212> TYPE: PRT
<213> ORGANISM: Shrimp white spot syndrome virus

<400> SEQUENCE: 163

His Leu Lys Val Arg Leu Asp Val Arg Gly Ala Lys Gln Asn Pro Trp
1               5                   10                  15

Arg Lys Asn Leu Cys Leu Leu Lys Lys Asn Val Lys Ser Ala Lys Gln
            20                  25                  30

Leu Pro His Leu Lys Val His Leu Asp Val Lys Gly Val Lys
        35                  40                  45


<210> SEQ ID NO 164
<211> LENGTH: 48
<212> TYPE: PRT
<213> ORGANISM: Shrimp white spot syndrome virus

<400> SEQUENCE: 164

Lys Val Arg Leu Asp Val Arg Gly Ala Lys Gln Asn Pro Trp Arg Lys
1               5                   10                  15

Asn Leu Cys Leu Leu Lys Lys Asn Val Lys Ser Ala Lys Gln Leu Pro
            20                  25                  30

His Leu Lys Val His Leu Asp Val Lys Gly Val Lys Gln Leu Leu His
        35                  40                  45


<210> SEQ ID NO 165
<211> LENGTH: 39
<212> TYPE: PRT
<213> ORGANISM: Shrimp white spot syndrome virus

<400> SEQUENCE: 165

Lys Gln Asn Pro Trp Arg Lys Asn Leu Cys Leu Leu Lys Lys Asn Val
1               5                   10                  15

Lys Ser Ala Lys Gln Leu Pro His Leu Lys Val His Leu Asp Val Lys
            20                  25                  30

Gly Val Lys Gln Leu Leu His
        35


<210> SEQ ID NO 166
<211> LENGTH: 48
<212> TYPE: PRT
<213> ORGANISM: Shrimp white spot syndrome virus

<400> SEQUENCE: 166

Lys Asn Leu Cys Leu Leu Lys Lys Asn Val Lys Ser Ala Lys Gln Leu
1               5                   10                  15

Pro His Leu Lys Val His Leu Asp Val Lys Gly Val Lys Gln Leu Leu
            20                  25                  30

His Leu Lys Val Arg Leu Asp Val Arg Gly Ala Lys Gln Leu Leu His
        35                  40                  45


<210> SEQ ID NO 167
<211> LENGTH: 33
<212> TYPE: PRT
<213> ORGANISM: Shrimp white spot syndrome virus

<400> SEQUENCE: 167
```

Lys Asn Leu Cys Leu Leu Lys Lys Asn Val Lys Ser Ala Lys Gln Leu
1 5 10 15

Pro His Leu Lys Val His Leu Asp Val Lys Gly Val Lys Gln Leu Leu
20 25 30

His

<210> SEQ ID NO 168
<211> LENGTH: 42
<212> TYPE: PRT
<213> ORGANISM: Shrimp white spot syndrome virus

<400> SEQUENCE: 168

Lys Lys Asn Val Lys Ser Ala Lys Gln Leu Pro His Leu Lys Val His
1 5 10 15

Leu Asp Val Lys Gly Val Lys Gln Leu Leu His Leu Lys Val Arg Leu
20 25 30

Asp Val Arg Gly Ala Lys Gln Leu Leu His
35 40

<210> SEQ ID NO 169
<211> LENGTH: 46
<212> TYPE: PRT
<213> ORGANISM: Shrimp white spot syndrome virus

<400> SEQUENCE: 169

Lys Lys Asn Val Lys Ser Ala Lys Gln Leu Pro His Leu Lys Val His
1 5 10 15

Leu Asp Val Lys Gly Val Lys Gln Leu Leu His Leu Lys Val Arg Leu
20 25 30

Asp Val Arg Gly Ala Lys Gln Leu Leu His Leu Lys Val His
35 40 45

<210> SEQ ID NO 170
<211> LENGTH: 26
<212> TYPE: PRT
<213> ORGANISM: Shrimp white spot syndrome virus

<400> SEQUENCE: 170

Lys Asn Val Lys Ser Ala Lys Gln Leu Pro His Leu Lys Val His Leu
1 5 10 15

Asp Val Lys Gly Val Lys Gln Leu Leu His
20 25

<210> SEQ ID NO 171
<211> LENGTH: 41
<212> TYPE: PRT
<213> ORGANISM: Shrimp white spot syndrome virus

<400> SEQUENCE: 171

Lys Asn Val Lys Ser Ala Lys Gln Leu Pro His Leu Lys Val His Leu
1 5 10 15

Asp Val Lys Gly Val Lys Gln Leu Leu His Leu Lys Val Arg Leu Asp
20 25 30

Val Arg Gly Ala Lys Gln Leu Leu His
35 40

<210> SEQ ID NO 172
<211> LENGTH: 45
<212> TYPE: PRT
<213> ORGANISM: Shrimp white spot syndrome virus

<400> SEQUENCE: 172

```
Lys Asn Val Lys Ser Ala Lys Gln Leu Pro His Leu Lys Val His Leu
1               5                   10                  15

Asp Val Lys Gly Val Lys Gln Leu Leu His Leu Lys Val Arg Leu Asp
            20                  25                  30

Val Arg Gly Ala Lys Gln Leu Leu His Leu Lys Val His
        35                  40                  45


<210> SEQ ID NO 173
<211> LENGTH: 23
<212> TYPE: PRT
<213> ORGANISM: Shrimp white spot syndrome virus

<400> SEQUENCE: 173

Lys Ser Ala Lys Gln Leu Pro His Leu Lys Val His Leu Asp Val Lys
1               5                   10                  15

Gly Val Lys Gln Leu Leu His
            20


<210> SEQ ID NO 174
<211> LENGTH: 38
<212> TYPE: PRT
<213> ORGANISM: Shrimp white spot syndrome virus

<400> SEQUENCE: 174

Lys Ser Ala Lys Gln Leu Pro His Leu Lys Val His Leu Asp Val Lys
1               5                   10                  15

Gly Val Lys Gln Leu Leu His Leu Lys Val Arg Leu Asp Val Arg Gly
            20                  25                  30

Ala Lys Gln Leu Leu His
        35


<210> SEQ ID NO 175
<211> LENGTH: 42
<212> TYPE: PRT
<213> ORGANISM: Shrimp white spot syndrome virus

<400> SEQUENCE: 175

Lys Ser Ala Lys Gln Leu Pro His Leu Lys Val His Leu Asp Val Lys
1               5                   10                  15

Gly Val Lys Gln Leu Leu His Leu Lys Val Arg Leu Asp Val Arg Gly
            20                  25                  30

Ala Lys Gln Leu Leu His Leu Lys Val His
        35                  40


<210> SEQ ID NO 176
<211> LENGTH: 20
<212> TYPE: PRT
<213> ORGANISM: Shrimp white spot syndrome virus

<400> SEQUENCE: 176

Lys Gln Leu Pro His Leu Lys Val His Leu Asp Val Lys Gly Val Lys
1               5                   10                  15

Gln Leu Leu His
            20


<210> SEQ ID NO 177
<211> LENGTH: 35
<212> TYPE: PRT
<213> ORGANISM: Shrimp white spot syndrome virus

<400> SEQUENCE: 177
```

```
Lys Gln Leu Pro His Leu Lys Val His Leu Asp Val Lys Gly Val Lys
1               5                   10                  15

Gln Leu Leu His Leu Lys Val Arg Leu Asp Val Arg Gly Ala Lys Gln
            20                  25                  30

Leu Leu His
        35


<210> SEQ ID NO 178
<211> LENGTH: 39
<212> TYPE: PRT
<213> ORGANISM: Shrimp white spot syndrome virus

<400> SEQUENCE: 178

Lys Gln Leu Pro His Leu Lys Val His Leu Asp Val Lys Gly Val Lys
1               5                   10                  15

Gln Leu Leu His Leu Lys Val Arg Leu Asp Val Arg Gly Ala Lys Gln
            20                  25                  30

Leu Leu His Leu Lys Val His
        35


<210> SEQ ID NO 179
<211> LENGTH: 50
<212> TYPE: PRT
<213> ORGANISM: Shrimp white spot syndrome virus

<400> SEQUENCE: 179

Lys Gln Leu Pro His Leu Lys Val His Leu Asp Val Lys Gly Val Lys
1               5                   10                  15

Gln Leu Leu His Leu Lys Val Arg Leu Asp Val Arg Gly Ala Lys Gln
            20                  25                  30

Leu Leu His Leu Lys Val His Leu Asp Val Arg Gly Ala Lys Gln Leu
        35                  40                  45

Pro His
    50


<210> SEQ ID NO 180
<211> LENGTH: 33
<212> TYPE: PRT
<213> ORGANISM: Shrimp white spot syndrome virus

<400> SEQUENCE: 180

His Leu Lys Val His Leu Asp Val Lys Gly Val Lys Gln Leu Leu His
1               5                   10                  15

Leu Lys Val Arg Leu Asp Val Arg Gly Ala Lys Gln Leu Leu His Leu
            20                  25                  30

Lys


<210> SEQ ID NO 181
<211> LENGTH: 42
<212> TYPE: PRT
<213> ORGANISM: Shrimp white spot syndrome virus

<400> SEQUENCE: 181

His Leu Lys Val His Leu Asp Val Lys Gly Val Lys Gln Leu Leu His
1               5                   10                  15

Leu Lys Val Arg Leu Asp Val Arg Gly Ala Lys Gln Leu Leu His Leu
            20                  25                  30

Lys Val His Leu Asp Val Arg Gly Ala Lys
        35                  40
```

```
<210> SEQ ID NO 182
<211> LENGTH: 48
<212> TYPE: PRT
<213> ORGANISM: Shrimp white spot syndrome virus

<400> SEQUENCE: 182

His Leu Lys Val His Leu Asp Val Lys Gly Val Lys Gln Leu Leu His
1               5                   10                  15

Leu Lys Val Arg Leu Asp Val Arg Gly Ala Lys Gln Leu Leu His Leu
            20                  25                  30

Lys Val His Leu Asp Val Arg Gly Ala Lys Gln Leu Pro His Leu Lys
        35                  40                  45


<210> SEQ ID NO 183
<211> LENGTH: 29
<212> TYPE: PRT
<213> ORGANISM: Shrimp white spot syndrome virus

<400> SEQUENCE: 183

Lys Val His Leu Asp Val Lys Gly Val Lys Gln Leu Leu His Leu Lys
1               5                   10                  15

Val Arg Leu Asp Val Arg Gly Ala Lys Gln Leu Leu His
            20                  25


<210> SEQ ID NO 184
<211> LENGTH: 33
<212> TYPE: PRT
<213> ORGANISM: Shrimp white spot syndrome virus

<400> SEQUENCE: 184

Lys Val His Leu Asp Val Lys Gly Val Lys Gln Leu Leu His Leu Lys
1               5                   10                  15

Val Arg Leu Asp Val Arg Gly Ala Lys Gln Leu Leu His Leu Lys Val
            20                  25                  30

His


<210> SEQ ID NO 185
<211> LENGTH: 44
<212> TYPE: PRT
<213> ORGANISM: Shrimp white spot syndrome virus

<400> SEQUENCE: 185

Lys Val His Leu Asp Val Lys Gly Val Lys Gln Leu Leu His Leu Lys
1               5                   10                  15

Val Arg Leu Asp Val Arg Gly Ala Lys Gln Leu Leu His Leu Lys Val
            20                  25                  30

His Leu Asp Val Arg Gly Ala Lys Gln Leu Pro His
        35                  40


<210> SEQ ID NO 186
<211> LENGTH: 48
<212> TYPE: PRT
<213> ORGANISM: Shrimp white spot syndrome virus

<400> SEQUENCE: 186

Lys Val His Leu Asp Val Lys Gly Val Lys Gln Leu Leu His Leu Lys
1               5                   10                  15

Val Arg Leu Asp Val Arg Gly Ala Lys Gln Leu Leu His Leu Lys Val
            20                  25                  30

His Leu Asp Val Arg Gly Ala Lys Gln Leu Pro His Leu Lys Val His
        35                  40                  45
```

<210> SEQ ID NO 187
<211> LENGTH: 38
<212> TYPE: PRT
<213> ORGANISM: Shrimp white spot syndrome virus

<400> SEQUENCE: 187

His Leu Asp Val Lys Gly Val Lys Gln Leu Leu His Leu Lys Val Arg
1 5 10 15

Leu Asp Val Arg Gly Ala Lys Gln Leu Leu His Leu Lys Val His Leu
20 25 30

Asp Val Arg Gly Ala Lys
35

<210> SEQ ID NO 188
<211> LENGTH: 44
<212> TYPE: PRT
<213> ORGANISM: Shrimp white spot syndrome virus

<400> SEQUENCE: 188

His Leu Asp Val Lys Gly Val Lys Gln Leu Leu His Leu Lys Val Arg
1 5 10 15

Leu Asp Val Arg Gly Ala Lys Gln Leu Leu His Leu Lys Val His Leu
20 25 30

Asp Val Arg Gly Ala Lys Gln Leu Pro His Leu Lys
35 40

<210> SEQ ID NO 189
<211> LENGTH: 29
<212> TYPE: PRT
<213> ORGANISM: Shrimp white spot syndrome virus

<400> SEQUENCE: 189

His Leu Asp Val Lys Gly Val Lys Gln Leu Leu His Leu Lys Val Arg
1 5 10 15

Leu Asp Val Arg Gly Ala Lys Gln Leu Leu His Leu Lys
20 25

<210> SEQ ID NO 190
<211> LENGTH: 23
<212> TYPE: PRT
<213> ORGANISM: Shrimp white spot syndrome virus

<400> SEQUENCE: 190

Lys Gly Val Lys Gln Leu Leu His Leu Lys Val Arg Leu Asp Val Arg
1 5 10 15

Gly Ala Lys Gln Leu Leu His
20

<210> SEQ ID NO 191
<211> LENGTH: 27
<212> TYPE: PRT
<213> ORGANISM: Shrimp white spot syndrome virus

<400> SEQUENCE: 191

Lys Gly Val Lys Gln Leu Leu His Leu Lys Val Arg Leu Asp Val Arg
1 5 10 15

Gly Ala Lys Gln Leu Leu His Leu Lys Val His
20 25

<210> SEQ ID NO 192
<211> LENGTH: 38
<212> TYPE: PRT

<213> ORGANISM: Shrimp white spot syndrome virus

<400> SEQUENCE: 192

Lys Gly Val Lys Gln Leu Leu His Leu Lys Val Arg Leu Asp Val Arg
1 5 10 15

Gly Ala Lys Gln Leu Leu His Leu Lys Val His Leu Asp Val Arg Gly
20 25 30

Ala Lys Gln Leu Pro His
35

<210> SEQ ID NO 193
<211> LENGTH: 42
<212> TYPE: PRT
<213> ORGANISM: Shrimp white spot syndrome virus

<400> SEQUENCE: 193

Lys Gly Val Lys Gln Leu Leu His Leu Lys Val Arg Leu Asp Val Arg
1 5 10 15

Gly Ala Lys Gln Leu Leu His Leu Lys Val His Leu Asp Val Arg Gly
20 25 30

Ala Lys Gln Leu Pro His Leu Lys Val His
35 40

<210> SEQ ID NO 194
<211> LENGTH: 20
<212> TYPE: PRT
<213> ORGANISM: Shrimp white spot syndrome virus

<400> SEQUENCE: 194

Lys Gln Leu Leu His Leu Lys Val Arg Leu Asp Val Arg Gly Ala Lys
1 5 10 15

Gln Leu Leu His
20

<210> SEQ ID NO 195
<211> LENGTH: 24
<212> TYPE: PRT
<213> ORGANISM: Shrimp white spot syndrome virus

<400> SEQUENCE: 195

Lys Gln Leu Leu His Leu Lys Val Arg Leu Asp Val Arg Gly Ala Lys
1 5 10 15

Gln Leu Leu His Leu Lys Val His
20

<210> SEQ ID NO 196
<211> LENGTH: 35
<212> TYPE: PRT
<213> ORGANISM: Shrimp white spot syndrome virus

<400> SEQUENCE: 196

Lys Gln Leu Leu His Leu Lys Val Arg Leu Asp Val Arg Gly Ala Lys
1 5 10 15

Gln Leu Leu His Leu Lys Val His Leu Asp Val Arg Gly Ala Lys Gln
20 25 30

Leu Pro His
35

<210> SEQ ID NO 197
<211> LENGTH: 39
<212> TYPE: PRT
<213> ORGANISM: Shrimp white spot syndrome virus

<400> SEQUENCE: 197

Lys Gln Leu Leu His Leu Lys Val Arg Leu Asp Val Arg Gly Ala Lys
1               5                   10                  15

Gln Leu Leu His Leu Lys Val His Leu Asp Val Arg Gly Ala Lys Gln
            20                  25                  30

Leu Pro His Leu Lys Val His
        35

<210> SEQ ID NO 198
<211> LENGTH: 18
<212> TYPE: PRT
<213> ORGANISM: Shrimp white spot syndrome virus

<400> SEQUENCE: 198

His Leu Lys Val Arg Leu Asp Val Arg Gly Ala Lys Gln Leu Leu His
1               5                   10                  15

Leu Lys

<210> SEQ ID NO 199
<211> LENGTH: 27
<212> TYPE: PRT
<213> ORGANISM: Shrimp white spot syndrome virus

<400> SEQUENCE: 199

His Leu Lys Val Arg Leu Asp Val Arg Gly Ala Lys Gln Leu Leu His
1               5                   10                  15

Leu Lys Val His Leu Asp Val Arg Gly Ala Lys
            20                  25

<210> SEQ ID NO 200
<211> LENGTH: 33
<212> TYPE: PRT
<213> ORGANISM: Shrimp white spot syndrome virus

<400> SEQUENCE: 200

His Leu Lys Val Arg Leu Asp Val Arg Gly Ala Lys Gln Leu Leu His
1               5                   10                  15

Leu Lys Val His Leu Asp Val Arg Gly Ala Lys Gln Leu Pro His Leu
            20                  25                  30

Lys

<210> SEQ ID NO 201
<211> LENGTH: 42
<212> TYPE: PRT
<213> ORGANISM: Shrimp white spot syndrome virus

<400> SEQUENCE: 201

His Leu Lys Val Arg Leu Asp Val Arg Gly Ala Lys Gln Leu Leu His
1               5                   10                  15

Leu Lys Val His Leu Asp Val Arg Gly Ala Lys Gln Leu Pro His Leu
            20                  25                  30

Lys Val His Leu Asp Val Arg Gly Ala Lys
        35                  40

<210> SEQ ID NO 202
<211> LENGTH: 48
<212> TYPE: PRT
<213> ORGANISM: Shrimp white spot syndrome virus

<400> SEQUENCE: 202

His Leu Lys Val Arg Leu Asp Val Arg Gly Ala Lys Gln Leu Leu His
1 5 10 15

Leu Lys Val His Leu Asp Val Arg Gly Ala Lys Gln Leu Pro His Leu
20 25 30

Lys Val His Leu Asp Val Arg Gly Ala Lys Gln Asn Pro Trp Arg Lys
35 40 45

<210> SEQ ID NO 203
<211> LENGTH: 14
<212> TYPE: PRT
<213> ORGANISM: Shrimp white spot syndrome virus

<400> SEQUENCE: 203

Lys Val Arg Leu Asp Val Arg Gly Ala Lys Gln Leu Leu His
1 5 10

<210> SEQ ID NO 204
<211> LENGTH: 18
<212> TYPE: PRT
<213> ORGANISM: Shrimp white spot syndrome virus

<400> SEQUENCE: 204

Lys Val Arg Leu Asp Val Arg Gly Ala Lys Gln Leu Leu His Leu Lys
1 5 10 15

Val His

<210> SEQ ID NO 205
<211> LENGTH: 29
<212> TYPE: PRT
<213> ORGANISM: Shrimp white spot syndrome virus

<400> SEQUENCE: 205

Lys Val Arg Leu Asp Val Arg Gly Ala Lys Gln Leu Leu His Leu Lys
1 5 10 15

Val His Leu Asp Val Arg Gly Ala Lys Gln Leu Pro His
20 25

<210> SEQ ID NO 206
<211> LENGTH: 33
<212> TYPE: PRT
<213> ORGANISM: Shrimp white spot syndrome virus

<400> SEQUENCE: 206

Lys Val Arg Leu Asp Val Arg Gly Ala Lys Gln Leu Leu His Leu Lys
1 5 10 15

Val His Leu Asp Val Arg Gly Ala Lys Gln Leu Pro His Leu Lys Val
20 25 30

His

<210> SEQ ID NO 207
<211> LENGTH: 20
<212> TYPE: PRT
<213> ORGANISM: Shrimp white spot syndrome virus

<400> SEQUENCE: 207

Lys Gln Leu Leu His Leu Lys Val His Leu Asp Val Arg Gly Ala Lys
1 5 10 15

Gln Leu Pro His
20

<210> SEQ ID NO 208
<211> LENGTH: 24

<212> TYPE: PRT
<213> ORGANISM: Shrimp white spot syndrome virus

<400> SEQUENCE: 208

```
Lys Gln Leu Leu His Leu Lys Val His Leu Asp Val Arg Gly Ala Lys
1               5                   10                  15

Gln Leu Pro His Leu Lys Val His
            20
```

<210> SEQ ID NO 209
<211> LENGTH: 27
<212> TYPE: PRT
<213> ORGANISM: Shrimp white spot syndrome virus

<400> SEQUENCE: 209

```
His Leu Lys Val His Leu Asp Val Arg Gly Ala Lys Gln Leu Pro His
1               5                   10                  15

Leu Lys Val His Leu Asp Val Arg Gly Ala Lys
            20                  25
```

<210> SEQ ID NO 210
<211> LENGTH: 33
<212> TYPE: PRT
<213> ORGANISM: Shrimp white spot syndrome virus

<400> SEQUENCE: 210

```
His Leu Lys Val His Leu Asp Val Arg Gly Ala Lys Gln Leu Pro His
1               5                   10                  15

Leu Lys Val His Leu Asp Val Arg Gly Ala Lys Gln Asn Pro Trp Arg
            20                  25                  30

Lys
```

<210> SEQ ID NO 211
<211> LENGTH: 39
<212> TYPE: PRT
<213> ORGANISM: Shrimp white spot syndrome virus

<400> SEQUENCE: 211

```
His Leu Lys Val His Leu Asp Val Arg Gly Ala Lys Gln Leu Pro His
1               5                   10                  15

Leu Lys Val His Leu Asp Val Arg Gly Ala Lys Gln Asn Pro Trp Arg
            20                  25                  30

Lys Asn Leu Cys Leu Leu Lys
        35
```

<210> SEQ ID NO 212
<211> LENGTH: 40
<212> TYPE: PRT
<213> ORGANISM: Shrimp white spot syndrome virus

<400> SEQUENCE: 212

```
His Leu Lys Val His Leu Asp Val Arg Gly Ala Lys Gln Leu Pro His
1               5                   10                  15

Leu Lys Val His Leu Asp Val Arg Gly Ala Lys Gln Asn Pro Trp Arg
            20                  25                  30

Lys Asn Leu Cys Leu Leu Lys Lys
        35                  40
```

<210> SEQ ID NO 213
<211> LENGTH: 43
<212> TYPE: PRT
<213> ORGANISM: Shrimp white spot syndrome virus

<400> SEQUENCE: 213

His Leu Lys Val His Leu Asp Val Arg Gly Ala Lys Gln Leu Pro His
1 5 10 15

Leu Lys Val His Leu Asp Val Arg Gly Ala Lys Gln Asn Pro Trp Arg
20 25 30

Lys Asn Leu Cys Leu Leu Lys Lys Asn Val Lys
35 40

<210> SEQ ID NO 214
<211> LENGTH: 46
<212> TYPE: PRT
<213> ORGANISM: Shrimp white spot syndrome virus

<400> SEQUENCE: 214

His Leu Lys Val His Leu Asp Val Arg Gly Ala Lys Gln Leu Pro His
1 5 10 15

Leu Lys Val His Leu Asp Val Arg Gly Ala Lys Gln Asn Pro Trp Arg
20 25 30

Lys Asn Leu Cys Leu Leu Lys Lys Asn Val Lys Ser Ala Lys
35 40 45

<210> SEQ ID NO 215
<211> LENGTH: 18
<212> TYPE: PRT
<213> ORGANISM: Shrimp white spot syndrome virus

<400> SEQUENCE: 215

Lys Val His Leu Asp Val Arg Gly Ala Lys Gln Leu Pro His Leu Lys
1 5 10 15

Val His

<210> SEQ ID NO 216
<211> LENGTH: 48
<212> TYPE: PRT
<213> ORGANISM: Shrimp white spot syndrome virus

<400> SEQUENCE: 216

Lys Val His Leu Asp Val Arg Gly Ala Lys Gln Leu Pro His Leu Lys
1 5 10 15

Val His Leu Asp Val Arg Gly Ala Lys Gln Asn Pro Trp Arg Lys Asn
20 25 30

Leu Cys Leu Leu Lys Lys Asn Val Lys Ser Ala Lys Gln Leu Pro His
35 40 45

<210> SEQ ID NO 217
<211> LENGTH: 23
<212> TYPE: PRT
<213> ORGANISM: Shrimp white spot syndrome virus

<400> SEQUENCE: 217

His Leu Asp Val Arg Gly Ala Lys Gln Leu Pro His Leu Lys Val His
1 5 10 15

Leu Asp Val Arg Gly Ala Lys
20

<210> SEQ ID NO 218
<211> LENGTH: 29
<212> TYPE: PRT
<213> ORGANISM: Shrimp white spot syndrome virus

<400> SEQUENCE: 218

His Leu Asp Val Arg Gly Ala Lys Gln Leu Pro His Leu Lys Val His
1 5 10 15

Leu Asp Val Arg Gly Ala Lys Gln Asn Pro Trp Arg Lys
20 25

<210> SEQ ID NO 219
<211> LENGTH: 35
<212> TYPE: PRT
<213> ORGANISM: Shrimp white spot syndrome virus

<400> SEQUENCE: 219

His Leu Asp Val Arg Gly Ala Lys Gln Leu Pro His Leu Lys Val His
1 5 10 15

Leu Asp Val Arg Gly Ala Lys Gln Asn Pro Trp Arg Lys Asn Leu Cys
20 25 30

Leu Leu Lys
35

<210> SEQ ID NO 220
<211> LENGTH: 36
<212> TYPE: PRT
<213> ORGANISM: Shrimp white spot syndrome virus

<400> SEQUENCE: 220

His Leu Asp Val Arg Gly Ala Lys Gln Leu Pro His Leu Lys Val His
1 5 10 15

Leu Asp Val Arg Gly Ala Lys Gln Asn Pro Trp Arg Lys Asn Leu Cys
20 25 30

Leu Leu Lys Lys
35

<210> SEQ ID NO 221
<211> LENGTH: 39
<212> TYPE: PRT
<213> ORGANISM: Shrimp white spot syndrome virus

<400> SEQUENCE: 221

His Leu Asp Val Arg Gly Ala Lys Gln Leu Pro His Leu Lys Val His
1 5 10 15

Leu Asp Val Arg Gly Ala Lys Gln Asn Pro Trp Arg Lys Asn Leu Cys
20 25 30

Leu Leu Lys Lys Asn Val Lys
35

<210> SEQ ID NO 222
<211> LENGTH: 42
<212> TYPE: PRT
<213> ORGANISM: Shrimp white spot syndrome virus

<400> SEQUENCE: 222

His Leu Asp Val Arg Gly Ala Lys Gln Leu Pro His Leu Lys Val His
1 5 10 15

Leu Asp Val Arg Gly Ala Lys Gln Asn Pro Trp Arg Lys Asn Leu Cys
20 25 30

Leu Leu Lys Lys Asn Val Lys Ser Ala Lys
35 40

<210> SEQ ID NO 223
<211> LENGTH: 48
<212> TYPE: PRT
<213> ORGANISM: Shrimp white spot syndrome virus

<400> SEQUENCE: 223

His Leu Asp Val Arg Gly Ala Lys Gln Leu Pro His Leu Lys Val His
1               5                   10                  15

Leu Asp Val Arg Gly Ala Lys Gln Asn Pro Trp Arg Lys Asn Leu Cys
            20                  25                  30

Leu Leu Lys Lys Asn Val Lys Ser Ala Lys Gln Leu Pro His Leu Lys
        35                  40                  45

<210> SEQ ID NO 224
<211> LENGTH: 39
<212> TYPE: PRT
<213> ORGANISM: Shrimp white spot syndrome virus

<400> SEQUENCE: 224

Lys Gln Leu Pro His Leu Lys Val His Leu Asp Val Arg Gly Ala Lys
1               5                   10                  15

Gln Asn Pro Trp Arg Lys Asn Leu Cys Leu Leu Lys Lys Asn Val Lys
            20                  25                  30

Ser Ala Lys Gln Leu Pro His
        35

<210> SEQ ID NO 225
<211> LENGTH: 18
<212> TYPE: PRT
<213> ORGANISM: Shrimp white spot syndrome virus

<400> SEQUENCE: 225

His Leu Lys Val His Leu Asp Val Arg Gly Ala Lys Gln Asn Pro Trp
1               5                   10                  15

Arg Lys

<210> SEQ ID NO 226
<211> LENGTH: 24
<212> TYPE: PRT
<213> ORGANISM: Shrimp white spot syndrome virus

<400> SEQUENCE: 226

His Leu Lys Val His Leu Asp Val Arg Gly Ala Lys Gln Asn Pro Trp
1               5                   10                  15

Arg Lys Asn Leu Cys Leu Leu Lys
            20

<210> SEQ ID NO 227
<211> LENGTH: 25
<212> TYPE: PRT
<213> ORGANISM: Shrimp white spot syndrome virus

<400> SEQUENCE: 227

His Leu Lys Val His Leu Asp Val Arg Gly Ala Lys Gln Asn Pro Trp
1               5                   10                  15

Arg Lys Asn Leu Cys Leu Leu Lys Lys
            20                  25

<210> SEQ ID NO 228
<211> LENGTH: 28
<212> TYPE: PRT
<213> ORGANISM: Shrimp white spot syndrome virus

<400> SEQUENCE: 228

His Leu Lys Val His Leu Asp Val Arg Gly Ala Lys Gln Asn Pro Trp
1               5                   10                  15

```
Arg Lys Asn Leu Cys Leu Leu Lys Lys Asn Val Lys
            20                  25
```

<210> SEQ ID NO 229
<211> LENGTH: 31
<212> TYPE: PRT
<213> ORGANISM: Shrimp white spot syndrome virus

<400> SEQUENCE: 229

```
His Leu Lys Val His Leu Asp Val Arg Gly Ala Lys Gln Asn Pro Trp
1               5                   10                  15

Arg Lys Asn Leu Cys Leu Leu Lys Lys Asn Val Lys Ser Ala Lys
            20                  25                  30
```

<210> SEQ ID NO 230
<211> LENGTH: 37
<212> TYPE: PRT
<213> ORGANISM: Shrimp white spot syndrome virus

<400> SEQUENCE: 230

```
His Leu Lys Val His Leu Asp Val Arg Gly Ala Lys Gln Asn Pro Trp
1               5                   10                  15

Arg Lys Asn Leu Cys Leu Leu Lys Lys Asn Val Lys Ser Ala Lys Gln
            20                  25                  30

Leu Pro His Leu Lys
        35
```

<210> SEQ ID NO 231
<211> LENGTH: 46
<212> TYPE: PRT
<213> ORGANISM: Shrimp white spot syndrome virus

<400> SEQUENCE: 231

```
His Leu Lys Val His Leu Asp Val Arg Gly Ala Lys Gln Asn Pro Trp
1               5                   10                  15

Arg Lys Asn Leu Cys Leu Leu Lys Lys Asn Val Lys Ser Ala Lys Gln
            20                  25                  30

Leu Pro His Leu Lys Val Leu Leu Asp Val Arg Gly Ala Lys
        35                  40                  45
```

<210> SEQ ID NO 232
<211> LENGTH: 33
<212> TYPE: PRT
<213> ORGANISM: Shrimp white spot syndrome virus

<400> SEQUENCE: 232

```
Lys Val His Leu Asp Val Arg Gly Ala Lys Gln Asn Pro Trp Arg Lys
1               5                   10                  15

Asn Leu Cys Leu Leu Lys Lys Asn Val Lys Ser Ala Lys Gln Leu Pro
            20                  25                  30

His
```

<210> SEQ ID NO 233
<211> LENGTH: 48
<212> TYPE: PRT
<213> ORGANISM: Shrimp white spot syndrome virus

<400> SEQUENCE: 233

```
Lys Val His Leu Asp Val Arg Gly Ala Lys Gln Asn Pro Trp Arg Lys
1               5                   10                  15

Asn Leu Cys Leu Leu Lys Lys Asn Val Lys Ser Ala Lys Gln Leu Pro
```

```
            20                  25                  30

His Leu Lys Val Leu Leu Asp Val Arg Gly Ala Lys Gln Leu Pro His
        35                  40                  45


<210> SEQ ID NO 234
<211> LENGTH: 14
<212> TYPE: PRT
<213> ORGANISM: Shrimp white spot syndrome virus

<400> SEQUENCE: 234

His Leu Asp Val Arg Gly Ala Lys Gln Asn Pro Trp Arg Lys
1               5                   10


<210> SEQ ID NO 235
<211> LENGTH: 20
<212> TYPE: PRT
<213> ORGANISM: Shrimp white spot syndrome virus

<400> SEQUENCE: 235

His Leu Asp Val Arg Gly Ala Lys Gln Asn Pro Trp Arg Lys Asn Leu
1               5                   10                  15

Cys Leu Leu Lys
            20


<210> SEQ ID NO 236
<211> LENGTH: 21
<212> TYPE: PRT
<213> ORGANISM: Shrimp white spot syndrome virus

<400> SEQUENCE: 236

His Leu Asp Val Arg Gly Ala Lys Gln Asn Pro Trp Arg Lys Asn Leu
1               5                   10                  15

Cys Leu Leu Lys Lys
            20


<210> SEQ ID NO 237
<211> LENGTH: 24
<212> TYPE: PRT
<213> ORGANISM: Shrimp white spot syndrome virus

<400> SEQUENCE: 237

His Leu Asp Val Arg Gly Ala Lys Gln Asn Pro Trp Arg Lys Asn Leu
1               5                   10                  15

Cys Leu Leu Lys Lys Asn Val Lys
            20


<210> SEQ ID NO 238
<211> LENGTH: 27
<212> TYPE: PRT
<213> ORGANISM: Shrimp white spot syndrome virus

<400> SEQUENCE: 238

His Leu Asp Val Arg Gly Ala Lys Gln Asn Pro Trp Arg Lys Asn Leu
1               5                   10                  15

Cys Leu Leu Lys Lys Asn Val Lys Ser Ala Lys
            20                  25


<210> SEQ ID NO 239
<211> LENGTH: 33
<212> TYPE: PRT
<213> ORGANISM: Shrimp white spot syndrome virus

<400> SEQUENCE: 239
```

His Leu Asp Val Arg Gly Ala Lys Gln Asn Pro Trp Arg Lys Asn Leu
1 5 10 15

Cys Leu Leu Lys Lys Asn Val Lys Ser Ala Lys Gln Leu Pro His Leu
20 25 30

Lys

<210> SEQ ID NO 240
<211> LENGTH: 42
<212> TYPE: PRT
<213> ORGANISM: Shrimp white spot syndrome virus

<400> SEQUENCE: 240

His Leu Asp Val Arg Gly Ala Lys Gln Asn Pro Trp Arg Lys Asn Leu
1 5 10 15

Cys Leu Leu Lys Lys Asn Val Lys Ser Ala Lys Gln Leu Pro His Leu
20 25 30

Lys Val Leu Leu Asp Val Arg Gly Ala Lys
35 40

<210> SEQ ID NO 241
<211> LENGTH: 48
<212> TYPE: PRT
<213> ORGANISM: Shrimp white spot syndrome virus

<400> SEQUENCE: 241

His Leu Asp Val Arg Gly Ala Lys Gln Asn Pro Trp Arg Lys Asn Leu
1 5 10 15

Cys Leu Leu Lys Lys Asn Val Lys Ser Ala Lys Gln Leu Pro His Leu
20 25 30

Lys Val Leu Leu Asp Val Arg Gly Ala Lys Gln Leu Pro His Leu Lys
35 40 45

<210> SEQ ID NO 242
<211> LENGTH: 39
<212> TYPE: PRT
<213> ORGANISM: Shrimp white spot syndrome virus

<400> SEQUENCE: 242

Lys Gln Asn Pro Trp Arg Lys Asn Leu Cys Leu Leu Lys Lys Asn Val
1 5 10 15

Lys Ser Ala Lys Gln Leu Pro His Leu Lys Val Leu Leu Asp Val Arg
20 25 30

Gly Ala Lys Gln Leu Pro His
35

<210> SEQ ID NO 243
<211> LENGTH: 33
<212> TYPE: PRT
<213> ORGANISM: Shrimp white spot syndrome virus

<400> SEQUENCE: 243

Lys Asn Leu Cys Leu Leu Lys Lys Asn Val Lys Ser Ala Lys Gln Leu
1 5 10 15

Pro His Leu Lys Val Leu Leu Asp Val Arg Gly Ala Lys Gln Leu Pro
20 25 30

His

<210> SEQ ID NO 244
<211> LENGTH: 48
<212> TYPE: PRT
<213> ORGANISM: Shrimp white spot syndrome virus

<400> SEQUENCE: 244

Lys Asn Leu Cys Leu Leu Lys Lys Asn Val Lys Ser Ala Lys Gln Leu
1 5 10 15

Pro His Leu Lys Val Leu Leu Asp Val Arg Gly Ala Lys Gln Leu Pro
20 25 30

His Leu Lys Val Leu Leu Asp Val Arg Gly Ala Lys Gln Leu Pro His
35 40 45

<210> SEQ ID NO 245
<211> LENGTH: 42
<212> TYPE: PRT
<213> ORGANISM: Shrimp white spot syndrome virus

<400> SEQUENCE: 245

Lys Lys Asn Val Lys Ser Ala Lys Gln Leu Pro His Leu Lys Val Leu
1 5 10 15

Leu Asp Val Arg Gly Ala Lys Gln Leu Pro His Leu Lys Val Leu Leu
20 25 30

Asp Val Arg Gly Ala Lys Gln Leu Pro His
35 40

<210> SEQ ID NO 246
<211> LENGTH: 46
<212> TYPE: PRT
<213> ORGANISM: Shrimp white spot syndrome virus

<400> SEQUENCE: 246

Lys Lys Asn Val Lys Ser Ala Lys Gln Leu Pro His Leu Lys Val Leu
1 5 10 15

Leu Asp Val Arg Gly Ala Lys Gln Leu Pro His Leu Lys Val Leu Leu
20 25 30

Asp Val Arg Gly Ala Lys Gln Leu Pro His Leu Lys Val His
35 40 45

<210> SEQ ID NO 247
<211> LENGTH: 26
<212> TYPE: PRT
<213> ORGANISM: Shrimp white spot syndrome virus

<400> SEQUENCE: 247

Lys Asn Val Lys Ser Ala Lys Gln Leu Pro His Leu Lys Val Leu Leu
1 5 10 15

Asp Val Arg Gly Ala Lys Gln Leu Pro His
20 25

<210> SEQ ID NO 248
<211> LENGTH: 41
<212> TYPE: PRT
<213> ORGANISM: Shrimp white spot syndrome virus

<400> SEQUENCE: 248

Lys Asn Val Lys Ser Ala Lys Gln Leu Pro His Leu Lys Val Leu Leu
1 5 10 15

Asp Val Arg Gly Ala Lys Gln Leu Pro His Leu Lys Val Leu Leu Asp
20 25 30

Val Arg Gly Ala Lys Gln Leu Pro His
35 40

<210> SEQ ID NO 249
<211> LENGTH: 45

<212> TYPE: PRT
<213> ORGANISM: Shrimp white spot syndrome virus

<400> SEQUENCE: 249

```
Lys Asn Val Lys Ser Ala Lys Gln Leu Pro His Leu Lys Val Leu Leu
1               5                   10                  15

Asp Val Arg Gly Ala Lys Gln Leu Pro His Leu Lys Val Leu Leu Asp
            20                  25                  30

Val Arg Gly Ala Lys Gln Leu Pro His Leu Lys Val His
        35                  40                  45
```

<210> SEQ ID NO 250
<211> LENGTH: 23
<212> TYPE: PRT
<213> ORGANISM: Shrimp white spot syndrome virus

<400> SEQUENCE: 250

```
Lys Ser Ala Lys Gln Leu Pro His Leu Lys Val Leu Leu Asp Val Arg
1               5                   10                  15

Gly Ala Lys Gln Leu Pro His
            20
```

<210> SEQ ID NO 251
<211> LENGTH: 38
<212> TYPE: PRT
<213> ORGANISM: Shrimp white spot syndrome virus

<400> SEQUENCE: 251

```
Lys Ser Ala Lys Gln Leu Pro His Leu Lys Val Leu Leu Asp Val Arg
1               5                   10                  15

Gly Ala Lys Gln Leu Pro His Leu Lys Val Leu Leu Asp Val Arg Gly
            20                  25                  30

Ala Lys Gln Leu Pro His
        35
```

<210> SEQ ID NO 252
<211> LENGTH: 42
<212> TYPE: PRT
<213> ORGANISM: Shrimp white spot syndrome virus

<400> SEQUENCE: 252

```
Lys Ser Ala Lys Gln Leu Pro His Leu Lys Val Leu Leu Asp Val Arg
1               5                   10                  15

Gly Ala Lys Gln Leu Pro His Leu Lys Val Leu Leu Asp Val Arg Gly
            20                  25                  30

Ala Lys Gln Leu Pro His Leu Lys Val His
        35                  40
```

<210> SEQ ID NO 253
<211> LENGTH: 20
<212> TYPE: PRT
<213> ORGANISM: Shrimp white spot syndrome virus

<400> SEQUENCE: 253

```
Lys Gln Leu Pro His Leu Lys Val Leu Leu Asp Val Arg Gly Ala Lys
1               5                   10                  15

Gln Leu Pro His
            20
```

<210> SEQ ID NO 254
<211> LENGTH: 35
<212> TYPE: PRT

<213> ORGANISM: Shrimp white spot syndrome virus

<400> SEQUENCE: 254

```
Lys Gln Leu Pro His Leu Lys Val Leu Leu Asp Val Arg Gly Ala Lys
1               5                   10                  15

Gln Leu Pro His Leu Lys Val Leu Leu Asp Val Arg Gly Ala Lys Gln
            20                  25                  30

Leu Pro His
        35
```

<210> SEQ ID NO 255
<211> LENGTH: 39
<212> TYPE: PRT
<213> ORGANISM: Shrimp white spot syndrome virus

<400> SEQUENCE: 255

```
Lys Gln Leu Pro His Leu Lys Val Leu Leu Asp Val Arg Gly Ala Lys
1               5                   10                  15

Gln Leu Pro His Leu Lys Val Leu Leu Asp Val Arg Gly Ala Lys Gln
            20                  25                  30

Leu Pro His Leu Lys Val His
        35
```

<210> SEQ ID NO 256
<211> LENGTH: 12
<212> TYPE: PRT
<213> ORGANISM: Shrimp white spot syndrome virus

<400> SEQUENCE: 256

```
His Leu Lys Val Leu Leu Asp Val Arg Gly Ala Lys
1               5                   10
```

<210> SEQ ID NO 257
<211> LENGTH: 18
<212> TYPE: PRT
<213> ORGANISM: Shrimp white spot syndrome virus

<400> SEQUENCE: 257

```
His Leu Lys Val Leu Leu Asp Val Arg Gly Ala Lys Gln Leu Pro His
1               5                   10                  15

Leu Lys
```

<210> SEQ ID NO 258
<211> LENGTH: 27
<212> TYPE: PRT
<213> ORGANISM: Shrimp white spot syndrome virus

<400> SEQUENCE: 258

```
His Leu Lys Val Leu Leu Asp Val Arg Gly Ala Lys Gln Leu Pro His
1               5                   10                  15

Leu Lys Val Leu Leu Asp Val Arg Gly Ala Lys
            20                  25
```

<210> SEQ ID NO 259
<211> LENGTH: 33
<212> TYPE: PRT
<213> ORGANISM: Shrimp white spot syndrome virus

<400> SEQUENCE: 259

```
His Leu Lys Val Leu Leu Asp Val Arg Gly Ala Lys Gln Leu Pro His
1               5                   10                  15

Leu Lys Val Leu Leu Asp Val Arg Gly Ala Lys Gln Leu Pro His Leu
```

20 25 30

Lys

<210> SEQ ID NO 260
<211> LENGTH: 42
<212> TYPE: PRT
<213> ORGANISM: Shrimp white spot syndrome virus

<400> SEQUENCE: 260

His Leu Lys Val Leu Leu Asp Val Arg Gly Ala Lys Gln Leu Pro His
1 5 10 15

Leu Lys Val Leu Leu Asp Val Arg Gly Ala Lys Gln Leu Pro His Leu
20 25 30

Lys Val His Leu Asp Val Arg Gly Ala Lys
35 40

<210> SEQ ID NO 261
<211> LENGTH: 48
<212> TYPE: PRT
<213> ORGANISM: Shrimp white spot syndrome virus

<400> SEQUENCE: 261

His Leu Lys Val Leu Leu Asp Val Arg Gly Ala Lys Gln Leu Pro His
1 5 10 15

Leu Lys Val Leu Leu Asp Val Arg Gly Ala Lys Gln Leu Pro His Leu
20 25 30

Lys Val His Leu Asp Val Arg Gly Ala Lys Gln Asn Pro Trp Arg Lys
35 40 45

<210> SEQ ID NO 262
<211> LENGTH: 14
<212> TYPE: PRT
<213> ORGANISM: Shrimp white spot syndrome virus

<400> SEQUENCE: 262

Lys Val Leu Leu Asp Val Arg Gly Ala Lys Gln Leu Pro His
1 5 10

<210> SEQ ID NO 263
<211> LENGTH: 29
<212> TYPE: PRT
<213> ORGANISM: Shrimp white spot syndrome virus

<400> SEQUENCE: 263

Lys Val Leu Leu Asp Val Arg Gly Ala Lys Gln Leu Pro His Leu Lys
1 5 10 15

Val Leu Leu Asp Val Arg Gly Ala Lys Gln Leu Pro His
20 25

<210> SEQ ID NO 264
<211> LENGTH: 33
<212> TYPE: PRT
<213> ORGANISM: Shrimp white spot syndrome virus

<400> SEQUENCE: 264

Lys Val Leu Leu Asp Val Arg Gly Ala Lys Gln Leu Pro His Leu Lys
1 5 10 15

Val Leu Leu Asp Val Arg Gly Ala Lys Gln Leu Pro His Leu Lys Val
20 25 30

His

-continued

<210> SEQ ID NO 265
<211> LENGTH: 24
<212> TYPE: PRT
<213> ORGANISM: Shrimp white spot syndrome virus

<400> SEQUENCE: 265

Lys Gln Leu Pro His Leu Lys Val Leu Leu Asp Val Arg Gly Ala Lys
1 5 10 15

Gln Leu Pro His Leu Lys Val His
20

<210> SEQ ID NO 266
<211> LENGTH: 27
<212> TYPE: PRT
<213> ORGANISM: Shrimp white spot syndrome virus

<400> SEQUENCE: 266

His Leu Lys Val Leu Leu Asp Val Arg Gly Ala Lys Gln Leu Pro His
1 5 10 15

Leu Lys Val His Leu Asp Val Arg Gly Ala Lys
20 25

<210> SEQ ID NO 267
<211> LENGTH: 39
<212> TYPE: PRT
<213> ORGANISM: Shrimp white spot syndrome virus

<400> SEQUENCE: 267

His Leu Lys Val Leu Leu Asp Val Arg Gly Ala Lys Gln Leu Pro His
1 5 10 15

Leu Lys Val His Leu Asp Val Arg Gly Ala Lys Gln Asn Pro Trp Arg
20 25 30

Lys Asn Leu Cys Leu Leu Lys
35

<210> SEQ ID NO 268
<211> LENGTH: 40
<212> TYPE: PRT
<213> ORGANISM: Shrimp white spot syndrome virus

<400> SEQUENCE: 268

His Leu Lys Val Leu Leu Asp Val Arg Gly Ala Lys Gln Leu Pro His
1 5 10 15

Leu Lys Val His Leu Asp Val Arg Gly Ala Lys Gln Asn Pro Trp Arg
20 25 30

Lys Asn Leu Cys Leu Leu Lys Lys
35 40

<210> SEQ ID NO 269
<211> LENGTH: 43
<212> TYPE: PRT
<213> ORGANISM: Shrimp white spot syndrome virus

<400> SEQUENCE: 269

His Leu Lys Val Leu Leu Asp Val Arg Gly Ala Lys Gln Leu Pro His
1 5 10 15

Leu Lys Val His Leu Asp Val Arg Gly Ala Lys Gln Asn Pro Trp Arg
20 25 30

Lys Asn Leu Cys Leu Leu Lys Lys Asn Val Lys
35 40

<210> SEQ ID NO 270

```
<211> LENGTH: 33
<212> TYPE: PRT
<213> ORGANISM: Shrimp white spot syndrome virus

<400> SEQUENCE: 270

His Leu Lys Val Leu Leu Asp Val Arg Gly Ala Lys Gln Leu Pro His
1               5                   10                  15

Leu Lys Val His Leu Asp Val Arg Gly Ala Lys Gln Asn Pro Trp Arg
            20                  25                  30

Lys


<210> SEQ ID NO 271
<211> LENGTH: 46
<212> TYPE: PRT
<213> ORGANISM: Shrimp white spot syndrome virus

<400> SEQUENCE: 271

His Leu Lys Val Leu Leu Asp Val Arg Gly Ala Lys Gln Leu Pro His
1               5                   10                  15

Leu Lys Val His Leu Asp Val Arg Gly Ala Lys Gln Asn Pro Trp Arg
            20                  25                  30

Lys Asn Leu Cys Leu Leu Lys Lys Asn Val Lys Ser Ala Lys
        35                  40                  45


<210> SEQ ID NO 272
<211> LENGTH: 18
<212> TYPE: PRT
<213> ORGANISM: Shrimp white spot syndrome virus

<400> SEQUENCE: 272

Lys Val Leu Leu Asp Val Arg Gly Ala Lys Gln Leu Pro His Leu Lys
1               5                   10                  15

Val His


<210> SEQ ID NO 273
<211> LENGTH: 48
<212> TYPE: PRT
<213> ORGANISM: Shrimp white spot syndrome virus

<400> SEQUENCE: 273

Lys Val Leu Leu Asp Val Arg Gly Ala Lys Gln Leu Pro His Leu Lys
1               5                   10                  15

Val His Leu Asp Val Arg Gly Ala Lys Gln Asn Pro Trp Arg Lys Asn
            20                  25                  30

Leu Cys Leu Leu Lys Lys Asn Val Lys Ser Ala Lys Gln Leu Pro His
        35                  40                  45


<210> SEQ ID NO 274
<211> LENGTH: 42
<212> TYPE: PRT
<213> ORGANISM: Shrimp white spot syndrome virus

<400> SEQUENCE: 274

His Leu Lys Val Leu Leu Asp Val Arg Gly Ala Lys Gln Leu Pro His
1               5                   10                  15

Leu Lys Val Leu Leu Asp Val Arg Gly Ala Lys Gln Leu Pro His Leu
            20                  25                  30

Lys Val Leu Leu Asp Val Arg Gly Ala Lys
        35                  40


<210> SEQ ID NO 275
```

<211> LENGTH: 48
<212> TYPE: PRT
<213> ORGANISM: Shrimp white spot syndrome virus

<400> SEQUENCE: 275

His Leu Lys Val Leu Leu Asp Val Arg Gly Ala Lys Gln Leu Pro His
1 5 10 15

Leu Lys Val Leu Leu Asp Val Arg Gly Ala Lys Gln Leu Pro His Leu
20 25 30

Lys Val Leu Leu Asp Val Arg Gly Ala Lys Gln Asn Pro Trp Arg Lys
35 40 45

<210> SEQ ID NO 276
<211> LENGTH: 46
<212> TYPE: PRT
<213> ORGANISM: Shrimp white spot syndrome virus

<400> SEQUENCE: 276

Lys Lys Asn Val Lys Ser Ala Lys Gln Leu Pro His Leu Lys Val Leu
1 5 10 15

Leu Asp Val Arg Gly Ala Lys Gln Leu Pro His Leu Lys Val Leu Leu
20 25 30

Asp Val Arg Gly Ala Lys Gln Leu Pro His Leu Lys Val His
35 40 45

<210> SEQ ID NO 277
<211> LENGTH: 50
<212> TYPE: PRT
<213> ORGANISM: Shrimp white spot syndrome virus

<400> SEQUENCE: 277

Lys Gln Leu Pro His Leu Lys Val Leu Leu Asp Val Arg Gly Ala Lys
1 5 10 15

Gln Leu Pro His Leu Lys Val Leu Leu Asp Val Arg Gly Ala Lys Gln
20 25 30

Leu Pro His Leu Lys Val His Leu Asp Val Arg Gly Ala Lys Gln Leu
35 40 45

Pro His
50

<210> SEQ ID NO 278
<211> LENGTH: 48
<212> TYPE: PRT
<213> ORGANISM: Shrimp white spot syndrome virus

<400> SEQUENCE: 278

His Leu Lys Val Leu Leu Asp Val Arg Gly Ala Lys Gln Leu Pro His
1 5 10 15

Leu Lys Val Leu Leu Asp Val Arg Gly Ala Lys Gln Leu Pro His Leu
20 25 30

Lys Val His Leu Asp Val Arg Gly Ala Lys Gln Leu Pro His Leu Lys
35 40 45

<210> SEQ ID NO 279
<211> LENGTH: 44
<212> TYPE: PRT
<213> ORGANISM: Shrimp white spot syndrome virus

<400> SEQUENCE: 279

Lys Val Leu Leu Asp Val Arg Gly Ala Lys Gln Leu Pro His Leu Lys
1 5 10 15

```
Val Leu Leu Asp Val Arg Gly Ala Lys Gln Leu Pro His Leu Lys Val
            20                  25                  30

His Leu Asp Val Arg Gly Ala Lys Gln Leu Pro His
        35                  40


<210> SEQ ID NO 280
<211> LENGTH: 35
<212> TYPE: PRT
<213> ORGANISM: Shrimp white spot syndrome virus

<400> SEQUENCE: 280

Lys Gln Leu Pro His Leu Lys Val Leu Leu Asp Val Arg Gly Ala Lys
1               5                   10                  15

Gln Leu Pro His Leu Lys Val His Leu Asp Val Arg Gly Ala Lys Gln
            20                  25                  30

Leu Pro His
        35


<210> SEQ ID NO 281
<211> LENGTH: 50
<212> TYPE: PRT
<213> ORGANISM: Shrimp white spot syndrome virus

<400> SEQUENCE: 281

Lys Gln Leu Pro His Leu Lys Val Leu Leu Asp Val Arg Gly Ala Lys
1               5                   10                  15

Gln Leu Pro His Leu Lys Val His Leu Asp Val Arg Gly Ala Lys Gln
            20                  25                  30

Leu Pro His Leu Lys Val Leu Leu Asp Val Arg Gly Ala Lys Gln Leu
        35                  40                  45

Pro His
    50


<210> SEQ ID NO 282
<211> LENGTH: 33
<212> TYPE: PRT
<213> ORGANISM: Shrimp white spot syndrome virus

<400> SEQUENCE: 282

His Leu Lys Val Leu Leu Asp Val Arg Gly Ala Lys Gln Leu Pro His
1               5                   10                  15

Leu Lys Val His Leu Asp Val Arg Gly Ala Lys Gln Leu Pro His Leu
            20                  25                  30

Lys


<210> SEQ ID NO 283
<211> LENGTH: 42
<212> TYPE: PRT
<213> ORGANISM: Shrimp white spot syndrome virus

<400> SEQUENCE: 283

His Leu Lys Val Leu Leu Asp Val Arg Gly Ala Lys Gln Leu Pro His
1               5                   10                  15

Leu Lys Val His Leu Asp Val Arg Gly Ala Lys Gln Leu Pro His Leu
            20                  25                  30

Lys Val Leu Leu Asp Val Arg Gly Ala Lys
        35                  40


<210> SEQ ID NO 284
<211> LENGTH: 48
<212> TYPE: PRT
```

<213> ORGANISM: Shrimp white spot syndrome virus

<400> SEQUENCE: 284

His Leu Lys Val Leu Leu Asp Val Arg Gly Ala Lys Gln Leu Pro His
1 5 10 15

Leu Lys Val His Leu Asp Val Arg Gly Ala Lys Gln Leu Pro His Leu
20 25 30

Lys Val Leu Leu Asp Val Arg Gly Ala Lys Gln Leu Pro His Leu Lys
35 40 45

<210> SEQ ID NO 285
<211> LENGTH: 29
<212> TYPE: PRT
<213> ORGANISM: Shrimp white spot syndrome virus

<400> SEQUENCE: 285

Lys Val Leu Leu Asp Val Arg Gly Ala Lys Gln Leu Pro His Leu Lys
1 5 10 15

Val His Leu Asp Val Arg Gly Ala Lys Gln Leu Pro His
20 25

<210> SEQ ID NO 286
<211> LENGTH: 44
<212> TYPE: PRT
<213> ORGANISM: Shrimp white spot syndrome virus

<400> SEQUENCE: 286

Lys Val Leu Leu Asp Val Arg Gly Ala Lys Gln Leu Pro His Leu Lys
1 5 10 15

Val His Leu Asp Val Arg Gly Ala Lys Gln Leu Pro His Leu Lys Val
20 25 30

Leu Leu Asp Val Arg Gly Ala Lys Gln Leu Pro His
35 40

<210> SEQ ID NO 287
<211> LENGTH: 35
<212> TYPE: PRT
<213> ORGANISM: Shrimp white spot syndrome virus

<400> SEQUENCE: 287

Lys Gln Leu Pro His Leu Lys Val His Leu Asp Val Arg Gly Ala Lys
1 5 10 15

Gln Leu Pro His Leu Lys Val Leu Leu Asp Val Arg Gly Ala Lys Gln
20 25 30

Leu Pro His
35

<210> SEQ ID NO 288
<211> LENGTH: 27
<212> TYPE: PRT
<213> ORGANISM: Shrimp white spot syndrome virus

<400> SEQUENCE: 288

His Leu Lys Val His Leu Asp Val Arg Gly Ala Lys Gln Leu Pro His
1 5 10 15

Leu Lys Val Leu Leu Asp Val Arg Gly Ala Lys
20 25

<210> SEQ ID NO 289
<211> LENGTH: 33
<212> TYPE: PRT
<213> ORGANISM: Shrimp white spot syndrome virus

<400> SEQUENCE: 289

His Leu Lys Val His Leu Asp Val Arg Gly Ala Lys Gln Leu Pro His
1               5                   10                  15

Leu Lys Val Leu Leu Asp Val Arg Gly Ala Lys Gln Leu Pro His Leu
            20                  25                  30

Lys

<210> SEQ ID NO 290
<211> LENGTH: 42
<212> TYPE: PRT
<213> ORGANISM: Shrimp white spot syndrome virus

<400> SEQUENCE: 290

His Leu Lys Val His Leu Asp Val Arg Gly Ala Lys Gln Leu Pro His
1               5                   10                  15

Leu Lys Val Leu Leu Asp Val Arg Gly Ala Lys Gln Leu Pro His Leu
            20                  25                  30

Lys Val Leu Leu Asp Val Arg Gly Ala Lys
        35                  40

<210> SEQ ID NO 291
<211> LENGTH: 48
<212> TYPE: PRT
<213> ORGANISM: Shrimp white spot syndrome virus

<400> SEQUENCE: 291

His Leu Lys Val His Leu Asp Val Arg Gly Ala Lys Gln Leu Pro His
1               5                   10                  15

Leu Lys Val Leu Leu Asp Val Arg Gly Ala Lys Gln Leu Pro His Leu
            20                  25                  30

Lys Val Leu Leu Asp Val Arg Gly Ala Lys Gln Asn Pro Trp Arg Lys
        35                  40                  45

<210> SEQ ID NO 292
<211> LENGTH: 29
<212> TYPE: PRT
<213> ORGANISM: Shrimp white spot syndrome virus

<400> SEQUENCE: 292

Lys Val His Leu Asp Val Arg Gly Ala Lys Gln Leu Pro His Leu Lys
1               5                   10                  15

Val Leu Leu Asp Val Arg Gly Ala Lys Gln Leu Pro His
            20                  25

<210> SEQ ID NO 293
<211> LENGTH: 23
<212> TYPE: PRT
<213> ORGANISM: Shrimp white spot syndrome virus

<400> SEQUENCE: 293

His Leu Asp Val Arg Gly Ala Lys Gln Leu Pro His Leu Lys Val Leu
1               5                   10                  15

Leu Asp Val Arg Gly Ala Lys
            20

<210> SEQ ID NO 294
<211> LENGTH: 29
<212> TYPE: PRT
<213> ORGANISM: Shrimp white spot syndrome virus

<400> SEQUENCE: 294

```
His Leu Asp Val Arg Gly Ala Lys Gln Leu Pro His Leu Lys Val Leu
1               5                   10                  15

Leu Asp Val Arg Gly Ala Lys Gln Leu Pro His Leu Lys
            20                  25


<210> SEQ ID NO 295
<211> LENGTH: 38
<212> TYPE: PRT
<213> ORGANISM: Shrimp white spot syndrome virus

<400> SEQUENCE: 295

His Leu Asp Val Arg Gly Ala Lys Gln Leu Pro His Leu Lys Val Leu
1               5                   10                  15

Leu Asp Val Arg Gly Ala Lys Gln Leu Pro His Leu Lys Val Leu Leu
            20                  25                  30

Asp Val Arg Gly Ala Lys
        35


<210> SEQ ID NO 296
<211> LENGTH: 44
<212> TYPE: PRT
<213> ORGANISM: Shrimp white spot syndrome virus

<400> SEQUENCE: 296

His Leu Asp Val Arg Gly Ala Lys Gln Leu Pro His Leu Lys Val Leu
1               5                   10                  15

Leu Asp Val Arg Gly Ala Lys Gln Leu Pro His Leu Lys Val Leu Leu
            20                  25                  30

Asp Val Arg Gly Ala Lys Gln Asn Pro Trp Arg Lys
        35                  40


<210> SEQ ID NO 297
<211> LENGTH: 50
<212> TYPE: PRT
<213> ORGANISM: Shrimp white spot syndrome virus

<400> SEQUENCE: 297

His Leu Asp Val Arg Gly Ala Lys Gln Leu Pro His Leu Lys Val Leu
1               5                   10                  15

Leu Asp Val Arg Gly Ala Lys Gln Leu Pro His Leu Lys Val Leu Leu
            20                  25                  30

Asp Val Arg Gly Ala Lys Gln Asn Pro Trp Arg Lys Asn Leu Cys Leu
        35                  40                  45

Leu Lys
    50


<210> SEQ ID NO 298
<211> LENGTH: 51
<212> TYPE: PRT
<213> ORGANISM: Shrimp white spot syndrome virus

<400> SEQUENCE: 298

His Leu Asp Val Arg Gly Ala Lys Gln Leu Pro His Leu Lys Val Leu
1               5                   10                  15

Leu Asp Val Arg Gly Ala Lys Gln Leu Pro His Leu Lys Val Leu Leu
            20                  25                  30

Asp Val Arg Gly Ala Lys Gln Asn Pro Trp Arg Lys Asn Leu Cys Leu
        35                  40                  45

Leu Lys Lys
    50
```

<210> SEQ ID NO 299
<211> LENGTH: 43
<212> TYPE: PRT
<213> ORGANISM: Shrimp white spot syndrome virus

<400> SEQUENCE: 299

His Leu Lys Val Leu Leu Asp Val Arg Gly Ala Lys Gln Leu Pro His
1 5 10 15

Leu Lys Val Leu Leu Asp Val Arg Gly Ala Lys Gln Asn Pro Trp Arg
20 25 30

Lys Asn Leu Cys Leu Leu Lys Lys Asn Val Lys
35 40

<210> SEQ ID NO 300
<211> LENGTH: 33
<212> TYPE: PRT
<213> ORGANISM: Shrimp white spot syndrome virus

<400> SEQUENCE: 300

His Leu Lys Val Leu Leu Asp Val Arg Gly Ala Lys Gln Leu Pro His
1 5 10 15

Leu Lys Val Leu Leu Asp Val Arg Gly Ala Lys Gln Asn Pro Trp Arg
20 25 30

Lys

<210> SEQ ID NO 301
<211> LENGTH: 46
<212> TYPE: PRT
<213> ORGANISM: Shrimp white spot syndrome virus

<400> SEQUENCE: 301

His Leu Lys Val Leu Leu Asp Val Arg Gly Ala Lys Gln Leu Pro His
1 5 10 15

Leu Lys Val Leu Leu Asp Val Arg Gly Ala Lys Gln Asn Pro Trp Arg
20 25 30

Lys Asn Leu Cys Leu Leu Lys Lys Asn Val Lys Ser Ala Lys
35 40 45

<210> SEQ ID NO 302
<211> LENGTH: 39
<212> TYPE: PRT
<213> ORGANISM: Shrimp white spot syndrome virus

<400> SEQUENCE: 302

His Leu Lys Val Leu Leu Asp Val Arg Gly Ala Lys Gln Leu Pro His
1 5 10 15

Leu Lys Val Leu Leu Asp Val Arg Gly Ala Lys Gln Asn Pro Trp Arg
20 25 30

Lys Asn Leu Cys Leu Leu Lys
35

<210> SEQ ID NO 303
<211> LENGTH: 40
<212> TYPE: PRT
<213> ORGANISM: Shrimp white spot syndrome virus

<400> SEQUENCE: 303

His Leu Lys Val Leu Leu Asp Val Arg Gly Ala Lys Gln Leu Pro His
1 5 10 15

Leu Lys Val Leu Leu Asp Val Arg Gly Ala Lys Gln Asn Pro Trp Arg

```
            20                  25                  30

Lys Asn Leu Cys Leu Leu Lys Lys
        35                  40


<210> SEQ ID NO 304
<211> LENGTH: 48
<212> TYPE: PRT
<213> ORGANISM: Shrimp white spot syndrome virus

<400> SEQUENCE: 304

Lys Val Leu Leu Asp Val Arg Gly Ala Lys Gln Leu Pro His Leu Lys
1               5                   10                  15

Val Leu Leu Asp Val Arg Gly Ala Lys Gln Asn Pro Trp Arg Lys Asn
            20                  25                  30

Leu Cys Leu Leu Lys Lys Asn Val Lys Ser Ala Lys Gln Leu Pro His
        35                  40                  45


<210> SEQ ID NO 305
<211> LENGTH: 39
<212> TYPE: PRT
<213> ORGANISM: Shrimp white spot syndrome virus

<400> SEQUENCE: 305

Lys Gln Leu Pro His Leu Lys Val Leu Leu Asp Val Arg Gly Ala Lys
1               5                   10                  15

Gln Asn Pro Trp Arg Lys Asn Leu Cys Leu Leu Lys Lys Asn Val Lys
            20                  25                  30

Ser Ala Lys Gln Leu Pro His
        35


<210> SEQ ID NO 306
<211> LENGTH: 28
<212> TYPE: PRT
<213> ORGANISM: Shrimp white spot syndrome virus

<400> SEQUENCE: 306

His Leu Lys Val Leu Leu Asp Val Arg Gly Ala Lys Gln Asn Pro Trp
1               5                   10                  15

Arg Lys Asn Leu Cys Leu Leu Lys Lys Asn Val Lys
            20                  25


<210> SEQ ID NO 307
<211> LENGTH: 18
<212> TYPE: PRT
<213> ORGANISM: Shrimp white spot syndrome virus

<400> SEQUENCE: 307

His Leu Lys Val Leu Leu Asp Val Arg Gly Ala Lys Gln Asn Pro Trp
1               5                   10                  15

Arg Lys


<210> SEQ ID NO 308
<211> LENGTH: 31
<212> TYPE: PRT
<213> ORGANISM: Shrimp white spot syndrome virus

<400> SEQUENCE: 308

His Leu Lys Val Leu Leu Asp Val Arg Gly Ala Lys Gln Asn Pro Trp
1               5                   10                  15

Arg Lys Asn Leu Cys Leu Leu Lys Lys Asn Val Lys Ser Ala Lys
            20                  25                  30
```

<210> SEQ ID NO 309
<211> LENGTH: 24
<212> TYPE: PRT
<213> ORGANISM: Shrimp white spot syndrome virus

<400> SEQUENCE: 309

His Leu Lys Val Leu Leu Asp Val Arg Gly Ala Lys Gln Asn Pro Trp
1 5 10 15

Arg Lys Asn Leu Cys Leu Leu Lys
20

<210> SEQ ID NO 310
<211> LENGTH: 25
<212> TYPE: PRT
<213> ORGANISM: Shrimp white spot syndrome virus

<400> SEQUENCE: 310

His Leu Lys Val Leu Leu Asp Val Arg Gly Ala Lys Gln Asn Pro Trp
1 5 10 15

Arg Lys Asn Leu Cys Leu Leu Lys Lys
20 25

<210> SEQ ID NO 311
<211> LENGTH: 37
<212> TYPE: PRT
<213> ORGANISM: Shrimp white spot syndrome virus

<400> SEQUENCE: 311

His Leu Lys Val Leu Leu Asp Val Arg Gly Ala Lys Gln Asn Pro Trp
1 5 10 15

Arg Lys Asn Leu Cys Leu Leu Lys Lys Asn Val Lys Ser Ala Lys Gln
20 25 30

Leu Pro His Leu Lys
35

<210> SEQ ID NO 312
<211> LENGTH: 46
<212> TYPE: PRT
<213> ORGANISM: Shrimp white spot syndrome virus

<400> SEQUENCE: 312

His Leu Lys Val Leu Leu Asp Val Arg Gly Ala Lys Gln Asn Pro Trp
1 5 10 15

Arg Lys Asn Leu Cys Leu Leu Lys Lys Asn Val Lys Ser Ala Lys Gln
20 25 30

Leu Pro His Leu Lys Val Leu Leu Asp Val Arg Gly Ala Lys
35 40 45

<210> SEQ ID NO 313
<211> LENGTH: 33
<212> TYPE: PRT
<213> ORGANISM: Shrimp white spot syndrome virus

<400> SEQUENCE: 313

Lys Val Leu Leu Asp Val Arg Gly Ala Lys Gln Asn Pro Trp Arg Lys
1 5 10 15

Asn Leu Cys Leu Leu Lys Lys Asn Val Lys Ser Ala Lys Gln Leu Pro
20 25 30

His

<210> SEQ ID NO 314

<211> LENGTH: 48
<212> TYPE: PRT
<213> ORGANISM: Shrimp white spot syndrome virus

<400> SEQUENCE: 314

Lys Val Leu Leu Asp Val Arg Gly Ala Lys Gln Asn Pro Trp Arg Lys
1 5 10 15

Asn Leu Cys Leu Leu Lys Lys Asn Val Lys Ser Ala Lys Gln Leu Pro
20 25 30

His Leu Lys Val Leu Leu Asp Val Arg Gly Ala Lys Gln Leu Pro His
35 40 45

<210> SEQ ID NO 315
<211> LENGTH: 43
<212> TYPE: PRT
<213> ORGANISM: Shrimp white spot syndrome virus

<400> SEQUENCE: 315

Lys Gln Asn Pro Trp Arg Lys Asn Leu Cys Leu Leu Lys Lys Asn Val
1 5 10 15

Lys Ser Ala Lys Gln Leu Pro His Leu Lys Val Leu Leu Asp Val Arg
20 25 30

Gly Ala Lys Gln Leu Pro His Leu Lys Val His
35 40

<210> SEQ ID NO 316
<211> LENGTH: 37
<212> TYPE: PRT
<213> ORGANISM: Shrimp white spot syndrome virus

<400> SEQUENCE: 316

Lys Asn Leu Cys Leu Leu Lys Lys Asn Val Lys Ser Ala Lys Gln Leu
1 5 10 15

Pro His Leu Lys Val Leu Leu Asp Val Arg Gly Ala Lys Gln Leu Pro
20 25 30

His Leu Lys Val His
35

<210> SEQ ID NO 317
<211> LENGTH: 18
<212> TYPE: PRT
<213> ORGANISM: Shrimp white spot syndrome virus

<400> SEQUENCE: 317

Lys Val Arg Leu Asp Val Arg Gly Ala Lys Gln Leu Pro His Leu Lys
1 5 10 15

Val His

<210> SEQ ID NO 318
<211> LENGTH: 30
<212> TYPE: PRT
<213> ORGANISM: Shrimp white spot syndrome virus

<400> SEQUENCE: 318

Lys Asn Val Lys Ser Ala Lys Gln Leu Pro His Leu Lys Val Leu Leu
1 5 10 15

Asp Val Arg Gly Ala Lys Gln Leu Pro His Leu Lys Val His
20 25 30

<210> SEQ ID NO 319
<211> LENGTH: 27
<212> TYPE: PRT

<213> ORGANISM: Shrimp white spot syndrome virus

<400> SEQUENCE: 319

Lys Ser Ala Lys Gln Leu Pro His Leu Lys Val Leu Leu Asp Val Arg
1 5 10 15

Gly Ala Lys Gln Leu Pro His Leu Lys Val His
20 25

<210> SEQ ID NO 320
<211> LENGTH: 49
<212> TYPE: PRT
<213> ORGANISM: Shrimp white spot syndrome virus

<400> SEQUENCE: 320

Lys Gln Leu Pro His Leu Lys Val Leu Leu Asp Val Arg Gly Ala Lys
1 5 10 15

Gln Leu Pro His Leu Lys Val His Leu Asp Val Arg Gly Ala Lys Gln
20 25 30

Gln Gln Gln Leu Cys Leu Pro Leu Lys Thr Ile Ser Thr Ser Phe Thr
35 40 45

His

<210> SEQ ID NO 321
<211> LENGTH: 37
<212> TYPE: PRT
<213> ORGANISM: Shrimp white spot syndrome virus

<400> SEQUENCE: 321

His Leu Lys Val Leu Leu Asp Val Arg Gly Ala Lys Gln Leu Pro His
1 5 10 15

Leu Lys Val His Leu Asp Val Arg Gly Ala Lys Gln Gln Gln Gln Leu
20 25 30

Cys Leu Pro Leu Lys
35

<210> SEQ ID NO 322
<211> LENGTH: 43
<212> TYPE: PRT
<213> ORGANISM: Shrimp white spot syndrome virus

<400> SEQUENCE: 322

Lys Val Leu Leu Asp Val Arg Gly Ala Lys Gln Leu Pro His Leu Lys
1 5 10 15

Val His Leu Asp Val Arg Gly Ala Lys Gln Gln Gln Gln Leu Cys Leu
20 25 30

Pro Leu Lys Thr Ile Ser Thr Ser Phe Thr His
35 40

<210> SEQ ID NO 323
<211> LENGTH: 34
<212> TYPE: PRT
<213> ORGANISM: Shrimp white spot syndrome virus

<400> SEQUENCE: 323

Lys Gln Leu Pro His Leu Lys Val His Leu Asp Val Arg Gly Ala Lys
1 5 10 15

Gln Gln Gln Gln Leu Cys Leu Pro Leu Lys Thr Ile Ser Thr Ser Phe
20 25 30

Thr His

<210> SEQ ID NO 324
<211> LENGTH: 46
<212> TYPE: PRT
<213> ORGANISM: Shrimp white spot syndrome virus

<400> SEQUENCE: 324

Lys Gln Leu Pro His Leu Lys Val His Leu Asp Val Arg Gly Ala Lys
1               5                   10                  15

Gln Gln Gln Gln Leu Cys Leu Pro Leu Lys Thr Ile Ser Thr Ser Phe
            20                  25                  30

Thr His Leu Leu Leu Cys Leu Tyr Met Glu Tyr Gly Lys His
        35                  40                  45

<210> SEQ ID NO 325
<211> LENGTH: 22
<212> TYPE: PRT
<213> ORGANISM: Shrimp white spot syndrome virus

<400> SEQUENCE: 325

His Leu Lys Val His Leu Asp Val Arg Gly Ala Lys Gln Gln Gln Gln
1               5                   10                  15

Leu Cys Leu Pro Leu Lys
            20

<210> SEQ ID NO 326
<211> LENGTH: 48
<212> TYPE: PRT
<213> ORGANISM: Shrimp white spot syndrome virus

<400> SEQUENCE: 326

His Leu Lys Val His Leu Asp Val Arg Gly Ala Lys Gln Gln Gln Gln
1               5                   10                  15

Leu Cys Leu Pro Leu Lys Thr Ile Ser Thr Ser Phe Thr His Leu Leu
            20                  25                  30

Leu Cys Leu Tyr Met Glu Tyr Gly Lys His Gln Asn Leu Gln Val Lys
        35                  40                  45

<210> SEQ ID NO 327
<211> LENGTH: 28
<212> TYPE: PRT
<213> ORGANISM: Shrimp white spot syndrome virus

<400> SEQUENCE: 327

Lys Val His Leu Asp Val Arg Gly Ala Lys Gln Gln Gln Gln Leu Cys
1               5                   10                  15

Leu Pro Leu Lys Thr Ile Ser Thr Ser Phe Thr His
            20                  25

<210> SEQ ID NO 328
<211> LENGTH: 40
<212> TYPE: PRT
<213> ORGANISM: Shrimp white spot syndrome virus

<400> SEQUENCE: 328

Lys Val His Leu Asp Val Arg Gly Ala Lys Gln Gln Gln Gln Leu Cys
1               5                   10                  15

Leu Pro Leu Lys Thr Ile Ser Thr Ser Phe Thr His Leu Leu Leu Cys
            20                  25                  30

Leu Tyr Met Glu Tyr Gly Lys His
        35                  40

<210> SEQ ID NO 329

<211> LENGTH: 18
<212> TYPE: PRT
<213> ORGANISM: Shrimp white spot syndrome virus

<400> SEQUENCE: 329

His Leu Asp Val Arg Gly Ala Lys Gln Gln Gln Gln Leu Cys Leu Pro
1 5 10 15

Leu Lys

<210> SEQ ID NO 330
<211> LENGTH: 44
<212> TYPE: PRT
<213> ORGANISM: Shrimp white spot syndrome virus

<400> SEQUENCE: 330

His Leu Asp Val Arg Gly Ala Lys Gln Gln Gln Gln Leu Cys Leu Pro
1 5 10 15

Leu Lys Thr Ile Ser Thr Ser Phe Thr His Leu Leu Leu Cys Leu Tyr
20 25 30

Met Glu Tyr Gly Lys His Gln Asn Leu Gln Val Lys
35 40

<210> SEQ ID NO 331
<211> LENGTH: 19
<212> TYPE: PRT
<213> ORGANISM: Shrimp white spot syndrome virus

<400> SEQUENCE: 331

Lys Gln Gln Gln Gln Leu Cys Leu Pro Leu Lys Thr Ile Ser Thr Ser
1 5 10 15

Phe Thr His

<210> SEQ ID NO 332
<211> LENGTH: 31
<212> TYPE: PRT
<213> ORGANISM: Shrimp white spot syndrome virus

<400> SEQUENCE: 332

Lys Gln Gln Gln Gln Leu Cys Leu Pro Leu Lys Thr Ile Ser Thr Ser
1 5 10 15

Phe Thr His Leu Leu Leu Cys Leu Tyr Met Glu Tyr Gly Lys His
20 25 30

<210> SEQ ID NO 333
<211> LENGTH: 19
<212> TYPE: PRT
<213> ORGANISM: Shrimp white spot syndrome virus

<400> SEQUENCE: 333

His Leu Leu Leu Cys Leu Tyr Met Glu Tyr Gly Lys His Gln Asn Leu
1 5 10 15

Gln Val Lys

<210> SEQ ID NO 334
<211> LENGTH: 8
<212> TYPE: PRT
<213> ORGANISM: Shrimp white spot syndrome virus

<400> SEQUENCE: 334

Lys His Gln Asn Leu Gln Val Lys
1 5

<210> SEQ ID NO 335
<211> LENGTH: 370
<212> TYPE: PRT
<213> ORGANISM: Shrimp white spot syndrome virus

<400> SEQUENCE: 335

Met Lys Ile Cys Gln Ile Ser Ser Pro Thr Leu Thr Leu Ser Ile Pro
1               5                   10                  15

Leu Glu Gly Val Tyr His Val Lys Gln Leu Leu His Leu Lys Val His
            20                  25                  30

Leu Asp Val Lys Gly Val Lys Gln Leu Leu His Leu Lys Val Arg Leu
        35                  40                  45

Asp Val Arg Gly Ala Lys Gln Asn Pro Trp Arg Lys Asn Leu Cys Leu
    50                  55                  60

Leu Lys Lys Asn Val Lys Ser Ala Lys Gln Leu Pro His Leu Lys Val
65                  70                  75                  80

His Leu Asp Val Lys Ser Ala Lys Gln Leu Pro His Leu Lys Val His
                85                  90                  95

Leu Asp Val Arg Gly Ala Lys Gln Leu Pro His Leu Lys Val Arg Leu
            100                 105                 110

Asp Val Lys Ser Ala Lys Gln Leu Pro His Leu Lys Val His Leu Asp
        115                 120                 125

Val Arg Gly Ala Lys Gln Leu Pro His Leu Lys Val Arg Leu Asp Val
    130                 135                 140

Arg Gly Ala Lys Gln Asn Pro Trp Arg Lys Asn Leu Cys Leu Leu Lys
145                 150                 155                 160

Lys Asn Val Lys Ser Ala Lys Gln Leu Pro His Leu Lys Val His Leu
                165                 170                 175

Asp Val Lys Gly Val Lys Gln Leu Leu His Leu Lys Val Arg Leu Asp
            180                 185                 190

Val Arg Gly Ala Lys Gln Leu Pro His Leu Lys Val His Leu Asp Val
        195                 200                 205

Arg Gly Ala Lys Gln Asn Pro Trp Arg Lys Asn Leu Cys Leu Leu Lys
    210                 215                 220

Lys Asn Val Lys Ser Ala Lys Gln Leu Pro His Leu Lys Val Leu Leu
225                 230                 235                 240

Asp Val Arg Gly Ala Lys Gln Leu Pro His Leu Lys Val Leu Leu Asp
                245                 250                 255

Val Arg Gly Ala Lys Gln Leu Pro His Leu Lys Val Leu Leu Asp Val
            260                 265                 270

Arg Gly Ala Lys Gln Asn Pro Trp Arg Lys Asn Leu Cys Leu Leu Lys
        275                 280                 285

Lys Asn Val Lys Ser Ala Lys Gln Leu Pro His Leu Lys Val Leu Leu
    290                 295                 300

Asp Val Arg Gly Ala Lys Gln Leu Pro His Leu Lys Val His Leu Asp
305                 310                 315                 320

Val Arg Gly Ala Lys Gln Gln Gln Gln Leu Cys Leu Pro Leu Lys Thr
                325                 330                 335

Ile Ser Thr Ser Phe Thr His Leu Leu Leu Cys Leu Tyr Met Glu Tyr
            340                 345                 350

Gly Lys His Gln Asn Leu Gln Val Lys Met Trp Leu Asn Ile Thr Tyr
        355                 360                 365

Thr Ser
    370

<210> SEQ ID NO 336
<211> LENGTH: 48
<212> TYPE: PRT
<213> ORGANISM: Shrimp white spot syndrome virus

<400> SEQUENCE: 336

```
Lys Asn Leu Cys Leu Leu Lys Lys Asn Val Lys Ser Ala Lys Gln Leu
1               5                   10                  15

Pro His Leu Lys Val His Leu Asp Val Lys Gly Val Lys Gln Leu Leu
            20                  25                  30

His Leu Lys Val Arg Leu Asp Val Arg Gly Ala Lys Gln Leu Pro His
        35                  40                  45
```

<210> SEQ ID NO 337
<211> LENGTH: 42
<212> TYPE: PRT
<213> ORGANISM: Shrimp white spot syndrome virus

<400> SEQUENCE: 337

```
Lys Lys Asn Val Lys Ser Ala Lys Gln Leu Pro His Leu Lys Val His
1               5                   10                  15

Leu Asp Val Lys Gly Val Lys Gln Leu Leu His Leu Lys Val Arg Leu
            20                  25                  30

Asp Val Arg Gly Ala Lys Gln Leu Pro His
        35                  40
```

<210> SEQ ID NO 338
<211> LENGTH: 46
<212> TYPE: PRT
<213> ORGANISM: Shrimp white spot syndrome virus

<400> SEQUENCE: 338

```
Lys Lys Asn Val Lys Ser Ala Lys Gln Leu Pro His Leu Lys Val His
1               5                   10                  15

Leu Asp Val Lys Gly Val Lys Gln Leu Leu His Leu Lys Val Arg Leu
            20                  25                  30

Asp Val Arg Gly Ala Lys Gln Leu Pro His Leu Lys Val His
        35                  40                  45
```

<210> SEQ ID NO 339
<211> LENGTH: 41
<212> TYPE: PRT
<213> ORGANISM: Shrimp white spot syndrome virus

<400> SEQUENCE: 339

```
Lys Asn Val Lys Ser Ala Lys Gln Leu Pro His Leu Lys Val His Leu
1               5                   10                  15

Asp Val Lys Gly Val Lys Gln Leu Leu His Leu Lys Val Arg Leu Asp
            20                  25                  30

Val Arg Gly Ala Lys Gln Leu Pro His
        35                  40
```

<210> SEQ ID NO 340
<211> LENGTH: 45
<212> TYPE: PRT
<213> ORGANISM: Shrimp white spot syndrome virus

<400> SEQUENCE: 340

```
Lys Asn Val Lys Ser Ala Lys Gln Leu Pro His Leu Lys Val His Leu
1               5                   10                  15

Asp Val Lys Gly Val Lys Gln Leu Leu His Leu Lys Val Arg Leu Asp
            20                  25                  30
```

Val Arg Gly Ala Lys Gln Leu Pro His Leu Lys Val His
35 40 45

<210> SEQ ID NO 341
<211> LENGTH: 38
<212> TYPE: PRT
<213> ORGANISM: Shrimp white spot syndrome virus

<400> SEQUENCE: 341

Lys Ser Ala Lys Gln Leu Pro His Leu Lys Val His Leu Asp Val Lys
1 5 10 15

Gly Val Lys Gln Leu Leu His Leu Lys Val Arg Leu Asp Val Arg Gly
20 25 30

Ala Lys Gln Leu Pro His
35

<210> SEQ ID NO 342
<211> LENGTH: 42
<212> TYPE: PRT
<213> ORGANISM: Shrimp white spot syndrome virus

<400> SEQUENCE: 342

Lys Ser Ala Lys Gln Leu Pro His Leu Lys Val His Leu Asp Val Lys
1 5 10 15

Gly Val Lys Gln Leu Leu His Leu Lys Val Arg Leu Asp Val Arg Gly
20 25 30

Ala Lys Gln Leu Pro His Leu Lys Val His
35 40

<210> SEQ ID NO 343
<211> LENGTH: 35
<212> TYPE: PRT
<213> ORGANISM: Shrimp white spot syndrome virus

<400> SEQUENCE: 343

Lys Gln Leu Pro His Leu Lys Val His Leu Asp Val Lys Gly Val Lys
1 5 10 15

Gln Leu Leu His Leu Lys Val Arg Leu Asp Val Arg Gly Ala Lys Gln
20 25 30

Leu Pro His
35

<210> SEQ ID NO 344
<211> LENGTH: 39
<212> TYPE: PRT
<213> ORGANISM: Shrimp white spot syndrome virus

<400> SEQUENCE: 344

Lys Gln Leu Pro His Leu Lys Val His Leu Asp Val Lys Gly Val Lys
1 5 10 15

Gln Leu Leu His Leu Lys Val Arg Leu Asp Val Arg Gly Ala Lys Gln
20 25 30

Leu Pro His Leu Lys Val His
35

<210> SEQ ID NO 345
<211> LENGTH: 33
<212> TYPE: PRT
<213> ORGANISM: Shrimp white spot syndrome virus

<400> SEQUENCE: 345

His Leu Lys Val His Leu Asp Val Lys Gly Val Lys Gln Leu Leu His
1 5 10 15

Leu Lys Val Arg Leu Asp Val Arg Gly Ala Lys Gln Leu Pro His Leu
20 25 30

Lys

<210> SEQ ID NO 346
<211> LENGTH: 42
<212> TYPE: PRT
<213> ORGANISM: Shrimp white spot syndrome virus

<400> SEQUENCE: 346

His Leu Lys Val His Leu Asp Val Lys Gly Val Lys Gln Leu Leu His
1 5 10 15

Leu Lys Val Arg Leu Asp Val Arg Gly Ala Lys Gln Leu Pro His Leu
20 25 30

Lys Val His Leu Asp Val Arg Gly Ala Lys
35 40

<210> SEQ ID NO 347
<211> LENGTH: 48
<212> TYPE: PRT
<213> ORGANISM: Shrimp white spot syndrome virus

<400> SEQUENCE: 347

His Leu Lys Val His Leu Asp Val Lys Gly Val Lys Gln Leu Leu His
1 5 10 15

Leu Lys Val Arg Leu Asp Val Arg Gly Ala Lys Gln Leu Pro His Leu
20 25 30

Lys Val His Leu Asp Val Arg Gly Ala Lys Gln Asn Pro Trp Arg Lys
35 40 45

<210> SEQ ID NO 348
<211> LENGTH: 29
<212> TYPE: PRT
<213> ORGANISM: Shrimp white spot syndrome virus

<400> SEQUENCE: 348

Lys Val His Leu Asp Val Lys Gly Val Lys Gln Leu Leu His Leu Lys
1 5 10 15

Val Arg Leu Asp Val Arg Gly Ala Lys Gln Leu Pro His
20 25

<210> SEQ ID NO 349
<211> LENGTH: 33
<212> TYPE: PRT
<213> ORGANISM: Shrimp white spot syndrome virus

<400> SEQUENCE: 349

Lys Val His Leu Asp Val Lys Gly Val Lys Gln Leu Leu His Leu Lys
1 5 10 15

Val Arg Leu Asp Val Arg Gly Ala Lys Gln Leu Pro His Leu Lys Val
20 25 30

His

<210> SEQ ID NO 350
<211> LENGTH: 38
<212> TYPE: PRT
<213> ORGANISM: Shrimp white spot syndrome virus

<400> SEQUENCE: 350

His Leu Asp Val Lys Gly Val Lys Gln Leu Leu His Leu Lys Val Arg
1 5 10 15

Leu Asp Val Arg Gly Ala Lys Gln Leu Pro His Leu Lys Val His Leu
20 25 30

Asp Val Arg Gly Ala Lys
35

<210> SEQ ID NO 351
<211> LENGTH: 44
<212> TYPE: PRT
<213> ORGANISM: Shrimp white spot syndrome virus

<400> SEQUENCE: 351

His Leu Asp Val Lys Gly Val Lys Gln Leu Leu His Leu Lys Val Arg
1 5 10 15

Leu Asp Val Arg Gly Ala Lys Gln Leu Pro His Leu Lys Val His Leu
20 25 30

Asp Val Arg Gly Ala Lys Gln Asn Pro Trp Arg Lys
35 40

<210> SEQ ID NO 352
<211> LENGTH: 50
<212> TYPE: PRT
<213> ORGANISM: Shrimp white spot syndrome virus

<400> SEQUENCE: 352

His Leu Asp Val Lys Gly Val Lys Gln Leu Leu His Leu Lys Val Arg
1 5 10 15

Leu Asp Val Arg Gly Ala Lys Gln Leu Pro His Leu Lys Val His Leu
20 25 30

Asp Val Arg Gly Ala Lys Gln Asn Pro Trp Arg Lys Asn Leu Cys Leu
35 40 45

Leu Lys
50

<210> SEQ ID NO 353
<211> LENGTH: 51
<212> TYPE: PRT
<213> ORGANISM: Shrimp white spot syndrome virus

<400> SEQUENCE: 353

His Leu Asp Val Lys Gly Val Lys Gln Leu Leu His Leu Lys Val Arg
1 5 10 15

Leu Asp Val Arg Gly Ala Lys Gln Leu Pro His Leu Lys Val His Leu
20 25 30

Asp Val Arg Gly Ala Lys Gln Asn Pro Trp Arg Lys Asn Leu Cys Leu
35 40 45

Leu Lys Lys
50

<210> SEQ ID NO 354
<211> LENGTH: 29
<212> TYPE: PRT
<213> ORGANISM: Shrimp white spot syndrome virus

<400> SEQUENCE: 354

His Leu Asp Val Lys Gly Val Lys Gln Leu Leu His Leu Lys Val Arg
1 5 10 15

Leu Asp Val Arg Gly Ala Lys Gln Leu Pro His Leu Lys
20 25

<210> SEQ ID NO 355
<211> LENGTH: 23
<212> TYPE: PRT
<213> ORGANISM: Shrimp white spot syndrome virus

<400> SEQUENCE: 355

Lys Gly Val Lys Gln Leu Leu His Leu Lys Val Arg Leu Asp Val Arg
1               5                   10                  15

Gly Ala Lys Gln Leu Pro His
            20

<210> SEQ ID NO 356
<211> LENGTH: 27
<212> TYPE: PRT
<213> ORGANISM: Shrimp white spot syndrome virus

<400> SEQUENCE: 356

Lys Gly Val Lys Gln Leu Leu His Leu Lys Val Arg Leu Asp Val Arg
1               5                   10                  15

Gly Ala Lys Gln Leu Pro His Leu Lys Val His
            20                  25

<210> SEQ ID NO 357
<211> LENGTH: 20
<212> TYPE: PRT
<213> ORGANISM: Shrimp white spot syndrome virus

<400> SEQUENCE: 357

Lys Gln Leu Leu His Leu Lys Val Arg Leu Asp Val Arg Gly Ala Lys
1               5                   10                  15

Gln Leu Pro His
            20

<210> SEQ ID NO 358
<211> LENGTH: 24
<212> TYPE: PRT
<213> ORGANISM: Shrimp white spot syndrome virus

<400> SEQUENCE: 358

Lys Gln Leu Leu His Leu Lys Val Arg Leu Asp Val Arg Gly Ala Lys
1               5                   10                  15

Gln Leu Pro His Leu Lys Val His
            20

<210> SEQ ID NO 359
<211> LENGTH: 18
<212> TYPE: PRT
<213> ORGANISM: Shrimp white spot syndrome virus

<400> SEQUENCE: 359

His Leu Lys Val Arg Leu Asp Val Arg Gly Ala Lys Gln Leu Pro His
1               5                   10                  15

Leu Lys

<210> SEQ ID NO 360
<211> LENGTH: 27
<212> TYPE: PRT
<213> ORGANISM: Shrimp white spot syndrome virus

<400> SEQUENCE: 360

His Leu Lys Val Arg Leu Asp Val Arg Gly Ala Lys Gln Leu Pro His
1               5                   10                  15

Leu Lys Val His Leu Asp Val Arg Gly Ala Lys
20 25

<210> SEQ ID NO 361
<211> LENGTH: 33
<212> TYPE: PRT
<213> ORGANISM: Shrimp white spot syndrome virus

<400> SEQUENCE: 361

His Leu Lys Val Arg Leu Asp Val Arg Gly Ala Lys Gln Leu Pro His
1 5 10 15

Leu Lys Val His Leu Asp Val Arg Gly Ala Lys Gln Asn Pro Trp Arg
20 25 30

Lys

<210> SEQ ID NO 362
<211> LENGTH: 39
<212> TYPE: PRT
<213> ORGANISM: Shrimp white spot syndrome virus

<400> SEQUENCE: 362

His Leu Lys Val Arg Leu Asp Val Arg Gly Ala Lys Gln Leu Pro His
1 5 10 15

Leu Lys Val His Leu Asp Val Arg Gly Ala Lys Gln Asn Pro Trp Arg
20 25 30

Lys Asn Leu Cys Leu Leu Lys
35

<210> SEQ ID NO 363
<211> LENGTH: 40
<212> TYPE: PRT
<213> ORGANISM: Shrimp white spot syndrome virus

<400> SEQUENCE: 363

His Leu Lys Val Arg Leu Asp Val Arg Gly Ala Lys Gln Leu Pro His
1 5 10 15

Leu Lys Val His Leu Asp Val Arg Gly Ala Lys Gln Asn Pro Trp Arg
20 25 30

Lys Asn Leu Cys Leu Leu Lys Lys
35 40

<210> SEQ ID NO 364
<211> LENGTH: 43
<212> TYPE: PRT
<213> ORGANISM: Shrimp white spot syndrome virus

<400> SEQUENCE: 364

His Leu Lys Val Arg Leu Asp Val Arg Gly Ala Lys Gln Leu Pro His
1 5 10 15

Leu Lys Val His Leu Asp Val Arg Gly Ala Lys Gln Asn Pro Trp Arg
20 25 30

Lys Asn Leu Cys Leu Leu Lys Lys Asn Val Lys
35 40

<210> SEQ ID NO 365
<211> LENGTH: 46
<212> TYPE: PRT
<213> ORGANISM: Shrimp white spot syndrome virus

<400> SEQUENCE: 365

His Leu Lys Val Arg Leu Asp Val Arg Gly Ala Lys Gln Leu Pro His
1 5 10 15

```
Leu Lys Val His Leu Asp Val Arg Gly Ala Lys Gln Asn Pro Trp Arg
            20                  25                  30

Lys Asn Leu Cys Leu Leu Lys Lys Asn Val Lys Ser Ala Lys
        35                  40                  45


<210> SEQ ID NO 366
<211> LENGTH: 14
<212> TYPE: PRT
<213> ORGANISM: Shrimp white spot syndrome virus

<400> SEQUENCE: 366

Lys Val Arg Leu Asp Val Arg Gly Ala Lys Gln Leu Pro His
1               5                   10


<210> SEQ ID NO 367
<211> LENGTH: 261
<212> TYPE: PRT
<213> ORGANISM: Shrimp white spot syndrome virus

<400> SEQUENCE: 367

Met Ser Asn Gly Ala Thr Ile Ser Asp Glu Arg Leu Ile Leu Ile Leu
1               5                   10                  15

Asp Lys Ile Val Glu Arg Arg Gly Val Ser Asn Leu Ser Glu Leu Leu
            20                  25                  30

Ile His Pro Ile Thr Lys His Ile Asn Glu Leu Leu Lys Asn Thr Val
        35                  40                  45

Arg His Gly Asp Arg Val Tyr Met Lys Asp Ala Glu Leu Asp Val Arg
    50                  55                  60

Ser Arg Leu Glu Asp Ile Lys Lys Asp Cys Val Leu Lys Ala Ile Glu
65                  70                  75                  80

Lys Gln Gly Ile Asp Val Arg Gln Ile Ile Thr Asp Tyr Leu Ala Lys
                85                  90                  95

Arg Lys Leu Thr Gln Asn Leu Val His Trp Tyr Arg Pro Pro Ile Ser
            100                 105                 110

Cys Thr Asp Ile Asp Glu Lys Ile Gln Gln Glu Thr Gly Gln Val Gly
        115                 120                 125

Arg Cys Ser Val Ala Thr Tyr Asn Leu Arg Ile Gly Gly Asp Asp Gly
    130                 135                 140

Glu Phe Thr Arg Tyr Asp Phe Ser Ile Pro Leu Gly Asp Phe Lys Ile
145                 150                 155                 160

Thr Ala Lys Leu Phe Arg Ser Ile Asn Asp Glu Asp Val Asp Ala Val
                165                 170                 175

Ile Leu Val Ser Arg Ser Asp Val Val Asn Asp Val Leu Ser Phe Glu
            180                 185                 190

Ala Phe Asn Arg Thr Gly Glu Arg Val Val Ile Phe Phe Asn Val Ile
        195                 200                 205

Val Glu Gly Lys Ser Lys Asp Ile Asp Ile Val Cys Lys Ser Arg Tyr
    210                 215                 220

Lys His Thr His Ile Leu Asn Gly Glu Ser Ala Thr Tyr Ala Val Lys
225                 230                 235                 240

Arg Ile Lys Arg Gly Asp Thr Arg Asp Asp Ile Leu Phe Ala Ile Thr
                245                 250                 255

Ala Phe Lys Glu Glu
            260


<210> SEQ ID NO 368
<211> LENGTH: 29
```

<212> TYPE: PRT
<213> ORGANISM: Influenza A virus

<400> SEQUENCE: 368

Lys Lys Gly Thr Ser Tyr Pro Lys Leu Ser Lys Ser Tyr Thr Asn Asn
1 5 10 15

Lys Gly Lys Glu Val Leu Val Leu Trp Gly Val His His
20 25

<210> SEQ ID NO 369
<211> LENGTH: 29
<212> TYPE: PRT
<213> ORGANISM: Influenza A virus

<400> SEQUENCE: 369

Lys Lys Gly Ser Ser Tyr Pro Lys Leu Ser Lys Ser Tyr Val Asn Asn
1 5 10 15

Lys Gly Lys Glu Val Leu Val Leu Trp Gly Val His His
20 25

<210> SEQ ID NO 370
<211> LENGTH: 29
<212> TYPE: PRT
<213> ORGANISM: Influenza A virus

<400> SEQUENCE: 370

Lys Lys Glu Asn Ser Tyr Pro Lys Leu Ser Lys Ser Tyr Val Asn Asn
1 5 10 15

Lys Gly Lys Glu Val Leu Val Leu Trp Gly Val His His
20 25

<210> SEQ ID NO 371
<211> LENGTH: 29
<212> TYPE: PRT
<213> ORGANISM: Influenza A virus

<400> SEQUENCE: 371

Lys Lys Gly Asp Ser Tyr Pro Lys Leu Thr Asn Ser Tyr Val Asn Asn
1 5 10 15

Lys Gly Lys Glu Val Leu Val Leu Trp Gly Val His His
20 25

<210> SEQ ID NO 372
<211> LENGTH: 29
<212> TYPE: PRT
<213> ORGANISM: Influenza A virus

<400> SEQUENCE: 372

Lys Lys Gly Thr Ser Tyr Pro Lys Leu Ser Lys Ser Tyr Thr Asn Asn
1 5 10 15

Lys Gly Lys Glu Val Leu Val Leu Trp Gly Val His His
20 25

<210> SEQ ID NO 373
<211> LENGTH: 29
<212> TYPE: PRT
<213> ORGANISM: Influenza A virus

<400> SEQUENCE: 373

Lys Lys Gly Thr Ser Tyr Pro Lys Leu Ser Lys Ser Tyr Thr Asn Asn
1 5 10 15

Lys Gly Lys Glu Val Leu Val Leu Trp Gly Val His His
20 25

<210> SEQ ID NO 374
<211> LENGTH: 29
<212> TYPE: PRT
<213> ORGANISM: Influenza A virus

<400> SEQUENCE: 374

```
Lys Lys Gly Asn Ser Tyr Pro Lys Leu Ser Lys Ser Tyr Thr Asn Asn
1               5                   10                  15

Lys Gly Lys Glu Val Leu Val Ile Trp Gly Val His His
            20                  25
```

<210> SEQ ID NO 375
<211> LENGTH: 29
<212> TYPE: PRT
<213> ORGANISM: Influenza A virus

<400> SEQUENCE: 375

```
Lys Lys Gly Asn Ser Tyr Pro Lys Leu Ser Lys Ser Tyr Thr Asn Asn
1               5                   10                  15

Lys Gly Lys Glu Val Leu Val Ile Trp Gly Val His His
            20                  25
```

<210> SEQ ID NO 376
<211> LENGTH: 29
<212> TYPE: PRT
<213> ORGANISM: Influenza A virus

<400> SEQUENCE: 376

```
Lys Lys Gly Thr Ser Tyr Pro Lys Leu Ser Lys Ser Tyr Thr Asn Asn
1               5                   10                  15

Lys Gly Lys Glu Val Leu Val Leu Trp Gly Val His His
            20                  25
```

<210> SEQ ID NO 377
<211> LENGTH: 29
<212> TYPE: PRT
<213> ORGANISM: Influenza A virus

<400> SEQUENCE: 377

```
Lys Lys Gly Asn Ser Tyr Pro Lys Leu Ser Lys Ser Tyr Thr Asn Asn
1               5                   10                  15

Lys Gly Lys Glu Val Leu Val Ile Trp Gly Val His His
            20                  25
```

<210> SEQ ID NO 378
<211> LENGTH: 29
<212> TYPE: PRT
<213> ORGANISM: Influenza A virus

<400> SEQUENCE: 378

```
Lys Lys Gly Thr Ser Tyr Pro Lys Leu Ser Lys Ser Tyr Thr Asn Asn
1               5                   10                  15

Lys Gly Lys Glu Val Leu Val Leu Trp Gly Val His His
            20                  25
```

<210> SEQ ID NO 379
<211> LENGTH: 29
<212> TYPE: PRT
<213> ORGANISM: Influenza A virus

<400> SEQUENCE: 379

```
Lys Lys Gly Thr Ser Tyr Pro Lys Leu Ser Lys Ser Tyr Thr Asn Asn
```

```
1               5                   10                  15

Lys Gly Lys Glu Val Leu Val Leu Trp Gly Val His His
            20                  25


<210> SEQ ID NO 380
<211> LENGTH: 29
<212> TYPE: PRT
<213> ORGANISM: Influenza A virus

<400> SEQUENCE: 380

Lys Lys Gly Asn Ser Tyr Pro Lys Leu Ser Lys Ser Tyr Thr Asn Asn
1               5                   10                  15

Lys Gly Lys Glu Val Leu Val Ile Trp Gly Val His His
            20                  25


<210> SEQ ID NO 381
<211> LENGTH: 29
<212> TYPE: PRT
<213> ORGANISM: Influenza A virus

<400> SEQUENCE: 381

Lys Lys Gly Asn Ser Tyr Pro Lys Leu Ser Lys Ser Tyr Thr Asn Asn
1               5                   10                  15

Lys Gly Lys Glu Val Leu Val Ile Trp Gly Val His His
            20                  25


<210> SEQ ID NO 382
<211> LENGTH: 29
<212> TYPE: PRT
<213> ORGANISM: Influenza A virus

<400> SEQUENCE: 382

Lys Lys Gly Asn Ser Tyr Pro Lys Leu Ser Lys Ser Tyr Thr Asn Asn
1               5                   10                  15

Lys Gly Lys Glu Val Leu Val Ile Trp Gly Val His His
            20                  25


<210> SEQ ID NO 383
<211> LENGTH: 29
<212> TYPE: PRT
<213> ORGANISM: Influenza A virus

<400> SEQUENCE: 383

Lys Lys Gly Asp Ser Tyr Pro Lys Leu Ser Lys Ser Tyr Thr Asn Asn
1               5                   10                  15

Lys Gly Lys Glu Val Leu Val Ile Trp Gly Val His His
            20                  25


<210> SEQ ID NO 384
<211> LENGTH: 29
<212> TYPE: PRT
<213> ORGANISM: Influenza A virus

<400> SEQUENCE: 384

Lys Lys Gly Ser Ser Tyr Pro Lys Leu Ser Lys Ser Tyr Val Asn Asn
1               5                   10                  15

Lys Gly Lys Glu Val Leu Val Leu Trp Gly Val His His
            20                  25


<210> SEQ ID NO 385
<211> LENGTH: 29
<212> TYPE: PRT
<213> ORGANISM: Influenza A virus
```

<400> SEQUENCE: 385

Lys Lys Gly Ser Ser Tyr Pro Lys Leu Ser Lys Ser Tyr Val Asn Asn
1 5 10 15

Lys Gly Lys Glu Val Leu Val Leu Trp Gly Val His His
20 25

<210> SEQ ID NO 386
<211> LENGTH: 29
<212> TYPE: PRT
<213> ORGANISM: Influenza A virus

<400> SEQUENCE: 386

Lys Lys Gly Asn Ser Tyr Pro Lys Leu Ser Lys Ser Tyr Thr Asn Asn
1 5 10 15

Lys Gly Lys Glu Val Leu Val Ile Trp Gly Val His His
20 25

<210> SEQ ID NO 387
<211> LENGTH: 29
<212> TYPE: PRT
<213> ORGANISM: Influenza A virus

<400> SEQUENCE: 387

Lys Lys Gly Asn Ser Tyr Pro Lys Leu Ser Lys Ser Tyr Thr Asn Asn
1 5 10 15

Lys Gly Lys Glu Val Leu Val Ile Trp Gly Val His His
20 25

<210> SEQ ID NO 388
<211> LENGTH: 29
<212> TYPE: PRT
<213> ORGANISM: Influenza A virus

<400> SEQUENCE: 388

Lys Lys Gly Asn Ser Tyr Pro Lys Leu Ser Lys Ser Tyr Thr Asn Asn
1 5 10 15

Lys Gly Lys Glu Val Leu Val Ile Trp Gly Val His His
20 25

<210> SEQ ID NO 389
<211> LENGTH: 29
<212> TYPE: PRT
<213> ORGANISM: Influenza A virus

<400> SEQUENCE: 389

Lys Lys Gly Asn Ser Tyr Pro Lys Leu Ser Lys Ser Tyr Thr Asn Asn
1 5 10 15

Lys Gly Lys Glu Val Leu Val Ile Trp Gly Val His His
20 25

<210> SEQ ID NO 390
<211> LENGTH: 29
<212> TYPE: PRT
<213> ORGANISM: Influenza A virus

<400> SEQUENCE: 390

Lys Lys Gly Asn Ser Tyr Pro Lys Ile Ser Lys Ser Tyr Ile Asn Asn
1 5 10 15

Lys Glu Lys Glu Val Leu Val Leu Trp Gly Ile His His
20 25

<210> SEQ ID NO 391
<211> LENGTH: 29
<212> TYPE: PRT
<213> ORGANISM: Influenza A virus

<400> SEQUENCE: 391

Lys Lys Gly Asn Ser Tyr Pro Lys Leu Ser Lys Ser Tyr Ile Asn Asn
1 5 10 15

Lys Lys Lys Glu Val Leu Val Ile Trp Gly Ile His His
20 25

<210> SEQ ID NO 392
<211> LENGTH: 29
<212> TYPE: PRT
<213> ORGANISM: Influenza A virus

<400> SEQUENCE: 392

Lys Lys Gly Asn Ser Tyr Pro Lys Leu Ser Lys Ser Tyr Ile Asn Asn
1 5 10 15

Lys Gly Lys Lys Val Leu Val Leu Trp Gly Ile His His
20 25

<210> SEQ ID NO 393
<211> LENGTH: 29
<212> TYPE: PRT
<213> ORGANISM: Influenza A virus

<400> SEQUENCE: 393

Lys Lys Gly Thr Ser Tyr Pro Lys Leu Ser Lys Ser Tyr Thr Asn Asn
1 5 10 15

Lys Lys Lys Glu Val Leu Val Leu Trp Gly Val His His
20 25

<210> SEQ ID NO 394
<211> LENGTH: 28
<212> TYPE: PRT
<213> ORGANISM: Influenza A virus

<400> SEQUENCE: 394

Lys Asn Gly Leu Tyr Pro Asn Leu Ser Lys Ser Tyr Ala Asn Asn Lys
1 5 10 15

Glu Lys Glu Val Leu Val Leu Trp Gly Val His His
20 25

<210> SEQ ID NO 395
<211> LENGTH: 28
<212> TYPE: PRT
<213> ORGANISM: Influenza A virus

<400> SEQUENCE: 395

Lys Asn Gly Leu Tyr Pro Asn Leu Ser Lys Ser Tyr Ala Asn Asn Lys
1 5 10 15

Glu Lys Glu Val Leu Ile Leu Trp Gly Val His His
20 25

<210> SEQ ID NO 396
<211> LENGTH: 29
<212> TYPE: PRT
<213> ORGANISM: Influenza A virus

<400> SEQUENCE: 396

Lys Lys Gly Pro Asn Tyr Pro Val Ala Lys Arg Ser Tyr Asn Asn Thr
1 5 10 15

Ser Gly Glu Gln Met Leu Ile Ile Trp Gly Val His His
20 25

<210> SEQ ID NO 397
<211> LENGTH: 29
<212> TYPE: PRT
<213> ORGANISM: Influenza A virus

<400> SEQUENCE: 397

Lys Lys Gly Pro Asn Tyr Pro Val Ala Lys Arg Ser Tyr Asn Asn Thr
1 5 10 15

Ser Gly Glu Gln Met Leu Ile Ile Trp Gly Ile His His
20 25

<210> SEQ ID NO 398
<211> LENGTH: 29
<212> TYPE: PRT
<213> ORGANISM: Influenza A virus

<400> SEQUENCE: 398

Lys Lys Glu Asn Ser Tyr Pro Lys Leu Arg Lys Ser Ile Ile Ile Asn
1 5 10 15

Lys Lys Glu Val Lys Leu Val Ile Trp Gly Ile His His
20 25

<210> SEQ ID NO 399
<211> LENGTH: 19
<212> TYPE: PRT
<213> ORGANISM: Influenza A virus

<400> SEQUENCE: 399

Lys Ser Tyr Lys Asn Thr Arg Lys Asp Pro Ala Leu Ile Ile Trp Gly
1 5 10 15

Ile His His

<210> SEQ ID NO 400
<211> LENGTH: 29
<212> TYPE: PRT
<213> ORGANISM: Influenza A virus

<400> SEQUENCE: 400

Lys Lys Asn Asn Ala Tyr Pro Thr Ile Lys Arg Thr Tyr Asn Asn Thr
1 5 10 15

Asn Val Glu Asp Leu Leu Ile Leu Trp Gly Ile His His
20 25

<210> SEQ ID NO 401
<211> LENGTH: 29
<212> TYPE: PRT
<213> ORGANISM: Influenza A virus

<400> SEQUENCE: 401

Lys Lys Asn Asn Ala Tyr Pro Thr Ile Lys Arg Ser Tyr Ser Asn Thr
1 5 10 15

Asn Gln Glu Asp Leu Leu Val Leu Trp Gly Ile His His
20 25

<210> SEQ ID NO 402
<211> LENGTH: 29
<212> TYPE: PRT
<213> ORGANISM: Influenza A virus

<400> SEQUENCE: 402

Lys Lys Asn Asn Ala Tyr Pro Thr Ile Lys Arg Thr Tyr Asn Asn Thr
1 5 10 15

Asn Ile Glu Asp Leu Leu Ile Leu Trp Gly Ile His His
20 25

<210> SEQ ID NO 403
<211> LENGTH: 29
<212> TYPE: PRT
<213> ORGANISM: Influenza A virus

<400> SEQUENCE: 403

Lys Lys Asn Asn Ala Tyr Pro Thr Ile Lys Arg Thr Tyr Asn Asn Thr
1 5 10 15

Asn Met Glu Asp Leu Leu Ile Leu Trp Gly Ile His His
20 25

<210> SEQ ID NO 404
<211> LENGTH: 29
<212> TYPE: PRT
<213> ORGANISM: Influenza A virus

<400> SEQUENCE: 404

Lys Lys Gly Asn Ala Tyr Pro Thr Ile Lys Arg Thr Tyr Asn Asn Thr
1 5 10 15

Asn Val Glu Asp Leu Leu Ile Leu Trp Gly Ile His His
20 25

<210> SEQ ID NO 405
<211> LENGTH: 29
<212> TYPE: PRT
<213> ORGANISM: Influenza A virus

<400> SEQUENCE: 405

Lys Lys Asn Asn Thr Tyr Pro Thr Ile Lys Arg Ser Tyr Asn Asn Thr
1 5 10 15

Asn Gln Glu Asp Leu Leu Ile Leu Trp Gly Ile His His
20 25

<210> SEQ ID NO 406
<211> LENGTH: 29
<212> TYPE: PRT
<213> ORGANISM: Influenza A virus

<400> SEQUENCE: 406

Lys Lys Asn Ser Ala Tyr Pro Thr Ile Lys Arg Ser Tyr Asn Asn Thr
1 5 10 15

Asn Gln Glu Asp Leu Leu Val Leu Trp Gly Ile His His
20 25

<210> SEQ ID NO 407
<211> LENGTH: 29
<212> TYPE: PRT
<213> ORGANISM: Influenza A virus

<400> SEQUENCE: 407

Lys Lys Asn Ser Ala Tyr Pro Thr Ile Lys Arg Ser Tyr Asn Asn Thr
1 5 10 15

Asn Gln Glu Asp Leu Leu Val Leu Trp Gly Ile His His
20 25

<210> SEQ ID NO 408
<211> LENGTH: 29
<212> TYPE: PRT

<213> ORGANISM: Influenza A virus

<400> SEQUENCE: 408

Lys Lys Asn Ser Ala Tyr Pro Thr Ile Lys Arg Ser Tyr Asn Asn Thr
1 5 10 15

Asn Gln Glu Asp Leu Leu Val Leu Trp Gly Ile His His
20 25

<210> SEQ ID NO 409
<211> LENGTH: 29
<212> TYPE: PRT
<213> ORGANISM: Influenza A virus

<400> SEQUENCE: 409

Lys Lys Asn Ser Ala Tyr Pro Thr Ile Lys Arg Ser Tyr Asn Asn Thr
1 5 10 15

Asn Gln Glu Asp Leu Leu Val Leu Trp Gly Ile His His
20 25

<210> SEQ ID NO 410
<211> LENGTH: 29
<212> TYPE: PRT
<213> ORGANISM: Influenza A virus

<400> SEQUENCE: 410

Lys Lys Asn Ser Ala Tyr Pro Thr Ile Lys Arg Ser Tyr Asn Asn Thr
1 5 10 15

Asn Gln Glu Asp Leu Leu Val Leu Trp Gly Ile His His
20 25

<210> SEQ ID NO 411
<211> LENGTH: 29
<212> TYPE: PRT
<213> ORGANISM: Influenza A virus

<400> SEQUENCE: 411

Lys Lys Asn Ser Ala Tyr Pro Thr Ile Lys Arg Ser Tyr Asn Asn Thr
1 5 10 15

Asn Gln Glu Asp Leu Leu Val Leu Trp Gly Ile His His
20 25

<210> SEQ ID NO 412
<211> LENGTH: 29
<212> TYPE: PRT
<213> ORGANISM: Influenza A virus

<400> SEQUENCE: 412

Lys Lys Asn Asn Ala Tyr Pro Thr Ile Lys Arg Ser Tyr Asn Asn Thr
1 5 10 15

Asn Gln Glu Asp Leu Leu Val Leu Trp Gly Ile His His
20 25

<210> SEQ ID NO 413
<211> LENGTH: 29
<212> TYPE: PRT
<213> ORGANISM: Influenza A virus

<400> SEQUENCE: 413

Lys Lys Asn Ser Ala Tyr Pro Thr Ile Lys Arg Ser Tyr Asn Asn Thr
1 5 10 15

Asn Gln Glu Asp Leu Leu Val Leu Trp Gly Ile His His
20 25

<210> SEQ ID NO 414
<211> LENGTH: 29
<212> TYPE: PRT
<213> ORGANISM: Influenza A virus

<400> SEQUENCE: 414

```
Lys Lys Asn Ser Thr Tyr Pro Thr Ile Lys Arg Ser Tyr Asn Asn Thr
1               5                   10                  15

Asn Gln Glu Asp Leu Leu Val Leu Trp Gly Ile His His
            20                  25
```

<210> SEQ ID NO 415
<211> LENGTH: 29
<212> TYPE: PRT
<213> ORGANISM: Influenza A virus

<400> SEQUENCE: 415

```
Lys Lys Asn Ser Thr Tyr Pro Thr Ile Lys Arg Ser Tyr Asn Asn Thr
1               5                   10                  15

Asn Gln Glu Asp Leu Leu Val Leu Trp Gly Ile His His
            20                  25
```

<210> SEQ ID NO 416
<211> LENGTH: 29
<212> TYPE: PRT
<213> ORGANISM: Influenza A virus

<400> SEQUENCE: 416

```
Lys Lys Asn Ser Thr Tyr Pro Thr Ile Lys Arg Ser Tyr Asn Asn Thr
1               5                   10                  15

Asn Gln Glu Asp Leu Leu Val Leu Trp Gly Ile His His
            20                  25
```

<210> SEQ ID NO 417
<211> LENGTH: 29
<212> TYPE: PRT
<213> ORGANISM: Influenza A virus

<400> SEQUENCE: 417

```
Lys Lys Asn Ser Thr Tyr Pro Thr Ile Lys Arg Ser Tyr Asn Asn Thr
1               5                   10                  15

Asn Gln Glu Asp Leu Leu Val Leu Trp Gly Ile His His
            20                  25
```

<210> SEQ ID NO 418
<211> LENGTH: 29
<212> TYPE: PRT
<213> ORGANISM: Influenza A virus

<400> SEQUENCE: 418

```
Lys Lys Asn Ser Thr Tyr Pro Thr Ile Lys Arg Ser Tyr Asn Asn Thr
1               5                   10                  15

Asn Gln Glu Asp Leu Leu Val Leu Trp Gly Ile His His
            20                  25
```

<210> SEQ ID NO 419
<211> LENGTH: 29
<212> TYPE: PRT
<213> ORGANISM: Influenza A virus

<400> SEQUENCE: 419

```
Lys Lys Asn Asn Ala Tyr Pro Thr Ile Lys Arg Ser Tyr Asn Asn Thr
1               5                   10                  15
```

Asn Gln Glu Asp Leu Leu Val Leu Trp Gly Ile His His
20 25

<210> SEQ ID NO 420
<211> LENGTH: 29
<212> TYPE: PRT
<213> ORGANISM: Influenza A virus

<400> SEQUENCE: 420

Lys Lys Asn Ser Thr Tyr Pro Thr Ile Lys Arg Ser Tyr Asn Asn Thr
1 5 10 15

Asn Gln Glu Asp Leu Leu Val Met Trp Gly Ile His His
20 25

<210> SEQ ID NO 421
<211> LENGTH: 29
<212> TYPE: PRT
<213> ORGANISM: Influenza A virus

<400> SEQUENCE: 421

Lys Lys Asn Ser Ala Tyr Pro Thr Ile Lys Arg Ser Tyr Asn Asn Thr
1 5 10 15

Asn Gln Glu Asp Leu Leu Val Leu Trp Gly Ile His His
20 25

<210> SEQ ID NO 422
<211> LENGTH: 29
<212> TYPE: PRT
<213> ORGANISM: Influenza A virus

<400> SEQUENCE: 422

Lys Lys Asn Ser Thr Tyr Pro Thr Ile Lys Arg Ser Tyr Asn Asn Thr
1 5 10 15

Asn Gln Glu Asp Leu Leu Val Leu Trp Gly Ile His His
20 25

<210> SEQ ID NO 423
<211> LENGTH: 29
<212> TYPE: PRT
<213> ORGANISM: Influenza A virus

<400> SEQUENCE: 423

Lys Lys Asn Ser Thr Tyr Pro Thr Ile Lys Arg Ser Tyr Asn Asn Thr
1 5 10 15

Asn Gln Glu Asp Leu Leu Val Leu Trp Gly Ile His His
20 25

<210> SEQ ID NO 424
<211> LENGTH: 29
<212> TYPE: PRT
<213> ORGANISM: Influenza A virus

<400> SEQUENCE: 424

Lys Lys Asn Ser Thr Tyr Pro Thr Ile Lys Arg Ser Tyr Asn Asn Thr
1 5 10 15

Asn Gln Glu Asp Leu Leu Val Leu Trp Gly Ile Gln His
20 25

<210> SEQ ID NO 425
<211> LENGTH: 29
<212> TYPE: PRT
<213> ORGANISM: Influenza A virus

<400> SEQUENCE: 425

Lys Lys Asn Ser Ala Tyr Pro Ile Ile Lys Arg Ser Tyr Asn Asn Thr
1 5 10 15

Asn Gln Glu Asp Leu Leu Val Leu Trp Gly Ile His His
20 25

<210> SEQ ID NO 426
<211> LENGTH: 29
<212> TYPE: PRT
<213> ORGANISM: Influenza A virus
<220> FEATURE:
<221> NAME/KEY: MOD_RES
<222> LOCATION: (13)..(13)
<223> OTHER INFORMATION: Variable amino acid

<400> SEQUENCE: 426

Lys Lys Asn Ser Ala Tyr Pro Thr Ile Lys Arg Ser Xaa Asn Asn Thr
1 5 10 15

Asn His Glu Asp Leu Leu Val Leu Trp Gly Ile His His
20 25

<210> SEQ ID NO 427
<211> LENGTH: 29
<212> TYPE: PRT
<213> ORGANISM: Influenza A virus

<400> SEQUENCE: 427

Lys Lys Asn Ser Ala Tyr Pro Thr Ile Lys Arg Ser Tyr Asn Asn Thr
1 5 10 15

Asn Gln Glu Asp Leu Leu Val Leu Trp Gly Ile His His
20 25

<210> SEQ ID NO 428
<211> LENGTH: 29
<212> TYPE: PRT
<213> ORGANISM: Influenza A virus

<400> SEQUENCE: 428

Lys Lys Asn Asn Ala Tyr Pro Thr Ile Lys Arg Ser Tyr Asn Asn Thr
1 5 10 15

Asn Gln Glu Asp Leu Leu Val Leu Trp Gly Ile His His
20 25

<210> SEQ ID NO 429
<211> LENGTH: 29
<212> TYPE: PRT
<213> ORGANISM: Influenza A virus

<400> SEQUENCE: 429

Lys Lys Asn Asn Thr Tyr Pro Thr Ile Lys Lys Ser Tyr Asn Asn Thr
1 5 10 15

Asn Gln Glu Asp Leu Leu Val Leu Trp Gly Ile His His
20 25

<210> SEQ ID NO 430
<211> LENGTH: 29
<212> TYPE: PRT
<213> ORGANISM: Influenza A virus

<400> SEQUENCE: 430

Lys Lys Asn Ser Thr Tyr Pro Thr Ile Lys Arg Ser Tyr Asn Asn Thr
1 5 10 15

Asn Gln Glu Asp Leu Leu Val Ile Trp Gly Ile His His 20 25

<210> SEQ ID NO 431
<211> LENGTH: 44
<212> TYPE: PRT
<213> ORGANISM: Shrimp white spot syndrome virus

<400> SEQUENCE: 431

His Pro Ile Thr Lys His Ile Asn Glu Leu Leu Lys Asn Thr Val Arg
1 5 10 15

His Gly Asp Arg Val Tyr Met Lys Asp Ala Glu Leu Asp Val Arg Ser
20 25 30

Arg Leu Glu Asp Ile Lys Lys Asp Cys Val Leu Lys
35 40

<210> SEQ ID NO 432
<211> LENGTH: 12
<212> TYPE: PRT
<213> ORGANISM: Shrimp white spot syndrome virus

<400> SEQUENCE: 432

His Pro Ile Thr Lys His Ile Asn Glu Leu Leu Lys
1 5 10

<210> SEQ ID NO 433
<211> LENGTH: 48
<212> TYPE: PRT
<213> ORGANISM: Shrimp white spot syndrome virus

<400> SEQUENCE: 433

His Pro Ile Thr Lys His Ile Asn Glu Leu Leu Lys Asn Thr Val Arg
1 5 10 15

His Gly Asp Arg Val Tyr Met Lys Asp Ala Glu Leu Asp Val Arg Ser
20 25 30

Arg Leu Glu Asp Ile Lys Lys Asp Cys Val Leu Lys Ala Ile Glu Lys
35 40 45

<210> SEQ ID NO 434
<211> LENGTH: 8
<212> TYPE: PRT
<213> ORGANISM: Shrimp white spot syndrome virus

<400> SEQUENCE: 434

Lys His Ile Asn Glu Leu Leu Lys
1 5

<210> SEQ ID NO 435
<211> LENGTH: 13
<212> TYPE: PRT
<213> ORGANISM: Shrimp white spot syndrome virus

<400> SEQUENCE: 435

Lys His Ile Asn Glu Leu Leu Lys Asn Thr Val Arg His
1 5 10

<210> SEQ ID NO 436
<211> LENGTH: 39
<212> TYPE: PRT
<213> ORGANISM: Shrimp white spot syndrome virus

<400> SEQUENCE: 436

His Ile Asn Glu Leu Leu Lys Asn Thr Val Arg His Gly Asp Arg Val
1 5 10 15

```
Tyr Met Lys Asp Ala Glu Leu Asp Val Arg Ser Arg Leu Glu Asp Ile
            20                  25                  30

Lys Lys Asp Cys Val Leu Lys
        35


<210> SEQ ID NO 437
<211> LENGTH: 43
<212> TYPE: PRT
<213> ORGANISM: Shrimp white spot syndrome virus

<400> SEQUENCE: 437

His Ile Asn Glu Leu Leu Lys Asn Thr Val Arg His Gly Asp Arg Val
1               5                   10                  15

Tyr Met Lys Asp Ala Glu Leu Asp Val Arg Ser Arg Leu Glu Asp Ile
            20                  25                  30

Lys Lys Asp Cys Val Leu Lys Ala Ile Glu Lys
        35                  40


<210> SEQ ID NO 438
<211> LENGTH: 28
<212> TYPE: PRT
<213> ORGANISM: Shrimp white spot syndrome virus

<400> SEQUENCE: 438

His Gly Asp Arg Val Tyr Met Lys Asp Ala Glu Leu Asp Val Arg Ser
1               5                   10                  15

Arg Leu Glu Asp Ile Lys Lys Asp Cys Val Leu Lys
            20                  25


<210> SEQ ID NO 439
<211> LENGTH: 32
<212> TYPE: PRT
<213> ORGANISM: Shrimp white spot syndrome virus

<400> SEQUENCE: 439

His Gly Asp Arg Val Tyr Met Lys Asp Ala Glu Leu Asp Val Arg Ser
1               5                   10                  15

Arg Leu Glu Asp Ile Lys Lys Asp Cys Val Leu Lys Ala Ile Glu Lys
            20                  25                  30


<210> SEQ ID NO 440
<211> LENGTH: 35
<212> TYPE: PRT
<213> ORGANISM: Shrimp white spot syndrome virus

<400> SEQUENCE: 440

Lys Lys Asp Cys Val Leu Lys Ala Ile Glu Lys Gln Gly Ile Asp Val
1               5                   10                  15

Arg Gln Ile Ile Thr Asp Tyr Leu Ala Lys Arg Lys Leu Thr Gln Asn
            20                  25                  30

Leu Val His
        35


<210> SEQ ID NO 441
<211> LENGTH: 34
<212> TYPE: PRT
<213> ORGANISM: Shrimp white spot syndrome virus

<400> SEQUENCE: 441

Lys Asp Cys Val Leu Lys Ala Ile Glu Lys Gln Gly Ile Asp Val Arg
1               5                   10                  15

Gln Ile Ile Thr Asp Tyr Leu Ala Lys Arg Lys Leu Thr Gln Asn Leu
```

```
            20                  25                  30

Val His


<210> SEQ ID NO 442
<211> LENGTH: 15
<212> TYPE: PRT
<213> ORGANISM: Shrimp white spot syndrome virus

<400> SEQUENCE: 442

Lys Ser Lys Asp Ile Asp Ile Val Cys Lys Ser Arg Tyr Lys His
1               5                   10                  15


<210> SEQ ID NO 443
<211> LENGTH: 17
<212> TYPE: PRT
<213> ORGANISM: Shrimp white spot syndrome virus

<400> SEQUENCE: 443

Lys Ser Lys Asp Ile Asp Ile Val Cys Lys Ser Arg Tyr Lys His Thr
1               5                   10                  15

His


<210> SEQ ID NO 444
<211> LENGTH: 13
<212> TYPE: PRT
<213> ORGANISM: Shrimp white spot syndrome virus

<400> SEQUENCE: 444

Lys Asp Ile Asp Ile Val Cys Lys Ser Arg Tyr Lys His
1               5                   10


<210> SEQ ID NO 445
<211> LENGTH: 15
<212> TYPE: PRT
<213> ORGANISM: Shrimp white spot syndrome virus

<400> SEQUENCE: 445

Lys Asp Ile Asp Ile Val Cys Lys Ser Arg Tyr Lys His Thr His
1               5                   10                  15


<210> SEQ ID NO 446
<211> LENGTH: 204
<212> TYPE: PRT
<213> ORGANISM: Shrimp white spot syndrome virus

<400> SEQUENCE: 446

Met Asp Leu Ser Phe Thr Leu Ser Val Val Ser Ala Ile Leu Ala Ile
1               5                   10                  15

Thr Ala Val Ile Ala Val Phe Ile Val Ile Phe Arg Tyr His Asn Thr
            20                  25                  30

Val Thr Lys Thr Ile Glu Thr His Thr Gly Asn Ile Glu Thr Asn Met
        35                  40                  45

Asp Glu Asn Leu Arg Ile Pro Val Thr Ala Glu Val Gly Ser Gly Tyr
    50                  55                  60

Phe Lys Met Thr Asp Val Ser Phe Asp Ser Asp Thr Leu Gly Lys Ile
65                  70                  75                  80

Lys Ile Arg Asn Gly Lys Ser Asp Ala Gln Met Lys Glu Glu Asp Ala
                85                  90                  95

Asp Leu Val Ile Thr Pro Val Glu Gly Arg Ala Leu Glu Val Thr Val
            100                 105                 110

Gly Gln Asn Leu Thr Phe Glu Gly Thr Phe Lys Met Trp Asn Asn Thr
```

```
        115                 120                 125

Ser Arg Lys Ile Asn Ile Thr Gly Met Gln Met Val Pro Lys Ile Asn
    130                 135                 140

Pro Ser Lys Ala Phe Val Gly Ser Ser Asn Thr Ser Ser Phe Thr Pro
145                 150                 155                 160

Val Ser Ile Asp Glu Asp Glu Val Gly Thr Phe Val Cys Gly Thr Thr
                165                 170                 175

Phe Gly Ala Pro Ile Ala Ala Thr Ala Gly Gly Asn Leu Phe Asp Met
            180                 185                 190

Tyr Val His Val Thr Tyr Ser Gly Thr Glu Thr Glu
        195                 200


<210> SEQ ID NO 447
<211> LENGTH: 47
<212> TYPE: PRT
<213> ORGANISM: Shrimp white spot syndrome virus

<400> SEQUENCE: 447

His Thr Gly Asn Ile Glu Thr Asn Met Asp Glu Asn Leu Arg Ile Pro
1               5                   10                  15

Val Thr Ala Glu Val Gly Ser Gly Tyr Phe Lys Met Thr Asp Val Ser
            20                  25                  30

Phe Asp Ser Asp Thr Leu Gly Lys Ile Lys Ile Arg Asn Gly Lys
        35                  40                  45


<210> SEQ ID NO 448
<211> LENGTH: 28
<212> TYPE: PRT
<213> ORGANISM: Shrimp white spot syndrome virus

<400> SEQUENCE: 448

Lys Gly Ser Ser Tyr Pro Lys Leu Ser Lys Ser Tyr Val Asn Asn Lys
1               5                   10                  15

Gly Lys Glu Val Leu Val Leu Trp Gly Val His His
            20                  25


<210> SEQ ID NO 449
<211> LENGTH: 1011
<212> TYPE: PRT
<213> ORGANISM: Taura syndrome virus

<400> SEQUENCE: 449

Met Pro Ala Asn Pro Val Glu Ile Asp Asn Phe Asp Thr Thr Thr Ser
1               5                   10                  15

Gly Gly Leu Ile Pro Gly Gly Ser Val Thr Asn Ser Glu Gly Ser Thr
            20                  25                  30

Ile Leu Met Asn Asp Ile Pro Ile Thr Asn Gln Asn Val Val Leu Ser
        35                  40                  45

Lys Asn Val Thr Asp Asn Leu Phe Glu Val Gln Asp Gln Ala Leu Ile
    50                  55                  60

Glu Ser Leu Ser Arg Asp Val Leu Leu His Asn Asp Ser Trp Thr Ser
65                  70                  75                  80

Ser Asp Asp Glu Ile Gly Thr Thr Met Thr Gln Glu Gln Leu Ala Thr
                85                  90                  95

Glu Phe Asn Gln Pro His Leu Tyr Glu Ile Ser Leu Pro Asp Asp Ile
            100                 105                 110

Val Arg Lys Ser Leu Phe Met Ser Asn Lys Leu Ala Asn Ile Ala Tyr
        115                 120                 125
```

```
Met Arg Cys Asp Tyr Glu Val Thr Val Arg Val Gln Ala Thr Pro Phe
    130                 135                 140

Leu Gln Gly Ala Leu Trp Leu Trp Asn Lys Met Asn Ala Lys Gln Thr
145                 150                 155                 160

Ser Ile Ile Arg Arg Thr Leu Thr Glu His Leu Arg Ser Ile Thr Ser
                165                 170                 175

Phe Pro Gly Ile Glu Met Asn Leu Gln Ser Glu Ala Arg Ala Ile Thr
            180                 185                 190

Leu Ser Ile Pro Tyr Thr Ser Glu Phe Gln Val Phe Asn Pro Arg Asn
        195                 200                 205

Val Asn Asn Leu Asn Ser Ile Arg Leu Ser Val Leu Ser Gln Leu Gln
    210                 215                 220

Gly Pro Glu Asp Val Glu Ser Ala Ser Tyr Ser Ile Tyr Gly Arg Leu
225                 230                 235                 240

Lys Asn Ile Lys Leu Tyr Gly His Ala Pro Ser Val Thr Ser Ser Val
                245                 250                 255

Tyr Pro Ser Thr Gln Ser Gly Tyr Asp Asp Asp Cys Pro Ile Val His
            260                 265                 270

Ala Gly Thr Asp Glu Asp Ser Ser Lys Gln Gly Ile Val Ser Arg Val
        275                 280                 285

Ala Asp Thr Val Gly Ala Val Ala Asn Val Val Asp Gly Val Gly Val
    290                 295                 300

Pro Ile Leu Ser Thr Ile Ala Lys Pro Val Ser Trp Val Ser Gly Val
305                 310                 315                 320

Val Ser Asn Val Ala Ser Met Phe Gly Phe Ser Lys Asp Arg Asp Met
                325                 330                 335

Thr Lys Val Asn Ala Tyr Glu Asn Leu Pro Gly Lys Gly Phe Thr His
            340                 345                 350

Gly Val Gly Phe Asp Tyr Gly Val Pro Leu Ser Leu Phe Pro Asn Asn
        355                 360                 365

Ala Ile Asp Pro Thr Ile Ala Val Pro Glu Gly Leu Asp Glu Met Ser
    370                 375                 380

Ile Glu Tyr Leu Ala Gln Arg Pro Tyr Met Leu Asn Arg Tyr Thr Ile
385                 390                 395                 400

Arg Gly Gly Asp Thr Pro Asp Val His Gly Thr Ile Val Ala Asp Ile
                405                 410                 415

Pro Val Ser Pro Val Asn Phe Ser Leu Tyr Gly Lys Val Ile Ala Lys
            420                 425                 430

Tyr Arg Thr Leu Phe Ala Ala Pro Val Ser Leu Ala Val Ala Met Ala
        435                 440                 445

Asn Trp Trp Arg Gly Asn Ile Asn Leu Asn Leu Arg Phe Ala Lys Thr
    450                 455                 460

Gln Tyr His Gln Cys Arg Leu Leu Val Gln Tyr Leu Pro Tyr Gly Ser
465                 470                 475                 480

Gly Val Gln Pro Ile Glu Ser Ile Leu Ser Gln Ile Ile Asp Ile Ser
                485                 490                 495

Gln Val Asp Asp Lys Gly Ile Asp Ile Ala Phe Pro Ser Val Tyr Pro
            500                 505                 510

Asn Lys Trp Met Arg Val Tyr Asp Pro Ala Lys Val Gly Tyr Thr Ala
        515                 520                 525

Asp Cys Ala Pro Gly Arg Ile Val Ile Ser Val Leu Asn Pro Leu Ile
    530                 535                 540

Ser Ala Ser Thr Val Ser Pro Asn Ile Val Met Tyr Pro Trp Val His
545                 550                 555                 560
```

```
Trp Ser Asn Leu Glu Val Ala Glu Pro Gly Thr Leu Ala Lys Ala Ala
                565                 570                 575

Ile Gly Phe Asn Tyr Pro Ala Asp Val Pro Glu Glu Pro Thr Phe Ser
            580                 585                 590

Val Thr Arg Ala Pro Val Ser Gly Thr Leu Phe Thr Leu Leu Gln Asp
        595                 600                 605

Thr Lys Val Ser Leu Gly Glu Ala Asp Gly Val Phe Ser Leu Tyr Phe
    610                 615                 620

Thr Asn Thr Thr Thr Gly Arg Arg His Arg Leu Thr Tyr Ala Gly Leu
625                 630                 635                 640

Pro Gly Glu Leu Gly Ser Cys Glu Ile Val Lys Leu Pro Gln Gly Gln
                645                 650                 655

Tyr Ser Ile Glu Tyr Ala Ala Thr Ser Ala Pro Thr Leu Val Leu Asp
            660                 665                 670

Arg Pro Ile Phe Ser Glu Pro Ile Gly Pro Lys Tyr Val Val Thr Lys
        675                 680                 685

Val Lys Asn Gly Asp Val Val Ser Ile Ser Glu Glu Thr Leu Val Thr
    690                 695                 700

Cys Gly Ser Met Ala Ala Leu Gly Gly Ala Thr Val Ala Leu Gln Ser
705                 710                 715                 720

Val Asp Glu Thr Ile Glu Ile Leu Lys Leu Glu Ser Asp Phe Glu Ser
                725                 730                 735

Lys Ala Pro Val Lys Phe Thr Pro Gly Asn Tyr Thr Val Val Thr Glu
            740                 745                 750

Ala Ser Asp Val Glu Leu Val Thr Asn Gln Asp Ile Thr Val Asn Glu
        755                 760                 765

His Asn Pro Arg Thr His Ala Gly Ile Asp Glu Glu Pro Pro Val Lys
    770                 775                 780

Arg Ser Val Ile Gly Arg Ile Val Arg Arg Val Ala Arg Tyr Val Pro
785                 790                 795                 800

Asn Lys Leu Ile Arg Arg Ile Leu Arg Asp Leu Ser Gln Ser Pro Cys
                805                 810                 815

Ile Tyr Pro Ser Thr His Ala Gly Leu Asp Tyr Ser Ser Ser Asp Thr
            820                 825                 830

Ser Thr Met Leu Thr Thr Met Gly Glu Gln Phe Val Ser Leu Arg Met
        835                 840                 845

Leu Thr Arg Arg Ser Ser Pro Val Asp Ile Leu Arg Gly Asp Leu Val
    850                 855                 860

Thr Leu Pro Gly Ile Ser Phe Gly Thr Asp Asn Ser Leu Arg Gln Ser
865                 870                 875                 880

Leu Val Asn Ile Ile Ser Tyr Met Tyr Arg Phe Thr His Gly Ser Ile
                885                 890                 895

Ser Tyr Lys Ile Ile Pro Lys Asn Lys Gly Asp Leu Tyr Ile Thr Thr
            900                 905                 910

Thr Ser Pro Asp Ser Ile Glu Thr Ser Thr Ser Ala Tyr Gln Phe Asp
        915                 920                 925

Thr Asn Arg Ala Met His Tyr Ile Asn Thr Ser Leu Asn Pro Met Ala
    930                 935                 940

Gln Ile Ser Leu Pro Tyr Tyr Ser Pro Ala Glu Asn Leu Val Ile Asp
945                 950                 955                 960

Ser Lys Ser Phe Pro Gln Leu Ser Asp Leu Ser Ile Ser Asn Leu Glu
                965                 970                 975

Arg Thr Glu Asn Glu Tyr Phe Val Leu Ala Ser Ala Gly Asp Asp His
```

```
            980                 985                 990

Thr Phe Ser Gln Leu Ala Gly Cys  Pro Ala Phe Thr Phe  Gly Pro Ala
        995                 1000                1005

Glu Leu  Ala
    1010


<210> SEQ ID NO 450
<211> LENGTH: 21
<212> TYPE: PRT
<213> ORGANISM: Taura syndrome virus

<400> SEQUENCE: 450

His Leu Tyr Glu Ile Ser Leu Pro Asp Asp Ile Val Arg Lys Ser Leu
1               5                   10                  15

Phe Met Ser Asn Lys
            20


<210> SEQ ID NO 451
<211> LENGTH: 21
<212> TYPE: PRT
<213> ORGANISM: Taura syndrome virus

<400> SEQUENCE: 451

Lys Asp Arg Asp Met Thr Lys Val Asn Ala Tyr Glu Asn Leu Pro Gly
1               5                   10                  15

Lys Gly Phe Thr His
            20


<210> SEQ ID NO 452
<211> LENGTH: 15
<212> TYPE: PRT
<213> ORGANISM: Taura syndrome virus

<400> SEQUENCE: 452

Lys Val Asn Ala Tyr Glu Asn Leu Pro Gly Lys Gly Phe Thr His
1               5                   10                  15


<210> SEQ ID NO 453
<211> LENGTH: 46
<212> TYPE: PRT
<213> ORGANISM: Taura syndrome virus

<400> SEQUENCE: 453

Lys Leu Glu Ser Asp Phe Glu Ser Lys Ala Pro Val Lys Phe Thr Pro
1               5                   10                  15

Gly Asn Tyr Thr Val Val Thr Glu Ala Ser Asp Val Glu Leu Val Thr
            20                  25                  30

Asn Gln Asp Ile Thr Val Asn Glu His Asn Pro Arg Thr His
        35                  40                  45


<210> SEQ ID NO 454
<211> LENGTH: 41
<212> TYPE: PRT
<213> ORGANISM: Taura syndrome virus

<400> SEQUENCE: 454

Lys Leu Glu Ser Asp Phe Glu Ser Lys Ala Pro Val Lys Phe Thr Pro
1               5                   10                  15

Gly Asn Tyr Thr Val Val Thr Glu Ala Ser Asp Val Glu Leu Val Thr
            20                  25                  30

Asn Gln Asp Ile Thr Val Asn Glu His
        35                  40
```

<210> SEQ ID NO 455
<211> LENGTH: 13
<212> TYPE: PRT
<213> ORGANISM: Taura syndrome virus

<400> SEQUENCE: 455

```
His Gly Ser Ile Ser Tyr Lys Ile Ile Pro Lys Asn Lys
1               5                   10
```

<210> SEQ ID NO 456
<211> LENGTH: 36
<212> TYPE: PRT
<213> ORGANISM: Taura syndrome virus

<400> SEQUENCE: 456

```
Lys Ile Ile Pro Lys Asn Lys Gly Asp Leu Tyr Ile Thr Thr Thr Ser
1               5                   10                  15

Pro Asp Ser Ile Glu Thr Ser Thr Ser Ala Tyr Gln Phe Asp Thr Asn
            20                  25                  30

Arg Ala Met His
        35
```

<210> SEQ ID NO 457
<211> LENGTH: 2107
<212> TYPE: PRT
<213> ORGANISM: Taura syndrome virus

<400> SEQUENCE: 457

```
Met Ala Ser Tyr Tyr Leu Asn Ile Lys Thr His Asn Leu Arg Arg Thr
1               5                   10                  15

Pro Gly Ala His Arg Ala Phe Tyr Val Met Asn Asp Asp Gly Glu Asn
            20                  25                  30

Arg Ile Tyr Ser Leu Ile Gly Thr Leu Arg Arg Ala Pro Ala Phe Lys
        35                  40                  45

Val Gly Ser Arg Arg Tyr Lys Ser His Ile Pro Tyr Arg Arg Lys Ala
    50                  55                  60

Thr Val Ala Glu Leu Cys Asn Gln Leu His Asp Arg Val Leu Pro Phe
65                  70                  75                  80

Ala Asn Pro Gln Val Trp Lys Glu Val Ile Ser Glu Asn Lys Val Gln
                85                  90                  95

Pro Asp Ser Met Leu Lys Ala Ala Phe Gly Asn Trp Glu Glu Trp Pro
            100                 105                 110

Lys Asp Lys Val Cys Glu Glu Leu Tyr Ser Glu Cys Glu Cys Gly Tyr
        115                 120                 125

Val Gly Thr Cys Tyr Val Ser Val Asp Trp Leu Arg Pro Gln Ala Thr
    130                 135                 140

Lys Cys Asn Asp Cys Ile Leu Lys Met Asn Arg Asn Val Glu Tyr Pro
145                 150                 155                 160

Tyr His Thr Ile Gly Val Ser Gly Asn Val Val Thr Asn Thr Asp Ile
                165                 170                 175

Val Tyr Thr Gly Tyr Ala Asp Val Phe Lys Cys Glu Lys Cys Asp Leu
            180                 185                 190

Leu Met Gly Ala Trp Ala Pro Asn Asp Ile Pro Ala Leu Thr His Asn
        195                 200                 205

Ile Arg Ser Ser Gln Cys Val Gln Phe Lys Leu Pro Thr Glu Asn Leu
    210                 215                 220

Ala Ala Arg Asn Tyr Val Leu Leu Cys Glu Glu Ile Glu Arg Glu Asn
```

```
225                 230                 235                 240

Ile Pro Val Ile Phe Gln Asp Tyr Ser Glu Gly Asn Val Phe Thr Cys
                245                 250                 255

Arg Ile Val Ser Gly Asp Leu Thr Ala Val Gly Thr Ala Ser Asn Met
            260                 265                 270

Tyr Thr Ala Arg Asp Val Ala Ser Lys Ser Leu Leu Asp Gln Leu His
        275                 280                 285

Asn Thr Pro Asn Val His Met His Ser Leu His Ser Leu Pro Tyr Glu
    290                 295                 300

Asn Phe Pro Cys Glu Ala Leu Glu Phe Ala Val Glu Gln Gly Ile Ile
305                 310                 315                 320

Pro Pro Val Thr Phe Asp Glu Val Phe Ala Asn Asp Glu Tyr Val Ile
                325                 330                 335

Thr Ile Ser Cys Ser Leu Leu Val Val Ser Asp Val Gly Pro Thr Gln
            340                 345                 350

Ala Val Ala Arg Glu Arg Ala Ala Lys Arg Phe Leu Lys Met Tyr Asp
        355                 360                 365

Tyr Ser Ala Ser Tyr Pro Ser Thr His Met Phe Thr Leu Ser Thr Leu
    370                 375                 380

Pro Gln Arg Ser Gly Glu Thr Leu Glu Leu Ala Asn Ala Thr Leu Asn
385                 390                 395                 400

His Val Asn Asn Val Ile Asp Arg His Asp Glu Ala Ile Ser Asn Val
                405                 410                 415

Arg Gln Asn Val Glu Val Lys Leu Thr Asp Val Ser Arg Gln Val Gly
            420                 425                 430

Ala Met Leu Pro Lys Val Glu Thr Val Ile Asp Asp Val Ser Ser Thr
        435                 440                 445

Leu Ser Ser Phe Arg Gly Val Leu Asp Lys Ile Ser Ala Trp Met Pro
    450                 455                 460

Ser Ser Asn Pro Lys Ile Ile Asp Leu Ile Lys Glu Thr Phe Val Ser
465                 470                 475                 480

Leu Phe Phe Ala Ile Leu Thr Lys Ser Leu Tyr Pro Ile Ile Gln Gly
                485                 490                 495

Ile Ser Ser Tyr Ala Leu Arg Asn Asn Leu Met Ala Asn His Leu Thr
            500                 505                 510

Ala Leu Ser Glu Trp Leu Met Thr Leu Glu Tyr Asp Ser Pro Asp Glu
        515                 520                 525

Glu Glu Met Pro Ser Thr His Gly Phe Met Asp Asp Leu Thr Ser Arg
    530                 535                 540

Leu Pro Gly Leu Asn Gly Ala Lys Val Gln Ala Ala Thr Ile Tyr Glu
545                 550                 555                 560

Ser Ile Gly Thr Gly Leu Cys Val Ala Leu Ser Gly Ile Leu Ser Phe
                565                 570                 575

Ile Ala Val Met Cys Leu Gly Ile Thr Asp Leu Ser Ala Val Thr Phe
            580                 585                 590

Asn Lys Leu Leu Thr Gln Ser Ser Leu Val Gly Arg Ala Leu Val Gly
        595                 600                 605

Val Arg Ser Phe Lys Asp Val Phe Phe Gly Ile Trp Asp Tyr Val Asp
    610                 615                 620

Asn Gln Val Cys Glu Ile Leu Tyr Gly Lys Ser Arg Lys Asn Leu Asp
625                 630                 635                 640

Leu Leu Lys Glu Tyr Pro Ser Leu Asp Ser Leu Leu Ser Ile Phe Asn
                645                 650                 655
```

-continued

```
Tyr Phe His Asp Thr Val Asp Ala Asn Val Leu Ile Ser Cys Asn Arg
            660                 665                 670

Ala Ala Cys Glu Leu Leu Val Lys Ala Asp Asn Leu Tyr Gln Gly Tyr
        675                 680                 685

Leu Asp Lys Ser Ile Thr Leu Met His Arg Glu Ile Ser Ser Arg Leu
    690                 695                 700

Lys Glu Ala Arg Asn Ser Val Lys Asp Leu Ile Ala Lys Ala Gln Val
705                 710                 715                 720

Tyr Leu Thr Cys Gly Asp Gly Ser Arg Val Pro Pro Val Val Val Tyr
                725                 730                 735

Met Tyr Gly Asp Ala Gly Cys Gly Lys Thr Glu Leu Ser Met Ala Leu
            740                 745                 750

Gln Asp His Phe Ala Thr Lys Tyr Phe Gly Glu Val Pro Lys Lys Asp
        755                 760                 765

Val Ile Tyr Ser Arg Lys Ala Glu Asn Glu Phe Trp Asp Gly Val Lys
    770                 775                 780

Gln Ser His Lys Ile Ile Ala Tyr Asp Asp Val Leu Gln Ile Val Asp
785                 790                 795                 800

Ser Ala Gln Lys Pro Asn Pro Glu Leu Phe Glu Phe Ile Arg Leu Asn
                805                 810                 815

Asn Ser Asp Pro Tyr Gln Val His Met Ser Ser Val Ser Asp Lys Ala
            820                 825                 830

Asn Thr Phe Ile Ala Pro Ser Phe Val Phe Ala Thr Ser Asn Val Asn
        835                 840                 845

Pro Gly Thr Tyr Val Pro Lys Ser Ile His Ser Ala Asp Ala Phe Arg
    850                 855                 860

Arg Arg Leu Asp Leu Cys Val Tyr Val Asp Val Lys Asp Glu Phe Ala
865                 870                 875                 880

Arg Ile Val Ala Gly Ser Lys Gly His Arg Lys Val Pro Cys Glu Gln
                885                 890                 895

Lys Ile Trp Leu His Gln Asn Pro Gly Lys Thr Gln His Asp Met Lys
            900                 905                 910

His Glu Ile Val Ala Gly Thr Tyr Lys Ile Thr Pro Glu Thr Ala Val
        915                 920                 925

Tyr Glu Leu His Val Asp Thr Thr Leu Ala Gly Asp Ala Gln Ser Lys
    930                 935                 940

Val Cys Ala Tyr Asp Gly Leu Val Ser Leu Ile Glu Gln Val Arg Arg
945                 950                 955                 960

Leu Arg Val Ala Ala His Ser Asp Lys Val Glu Thr Asp Val Pro Val
                965                 970                 975

Leu Pro Thr Arg Leu His Glu Leu Ser Gln Glu Thr Phe Pro Asn Thr
            980                 985                 990

His Ala Gly Val Gly Phe Gln Phe  Ala Thr Asp Trp Leu  Gly Asp Phe
        995                 1000                1005

Asp Arg  Pro Val Glu Ala Leu  Ser Tyr Leu Asn Lys  Thr Leu Glu
    1010                 1015                 1020

Ala His  Phe Val Ser Arg Ser  Ala Asn Asp Gly Ser  Met Phe Ile
    1025                 1030                 1035

Pro Ala  Ser Glu Val Ala Asp  Leu Leu Cys Gln Arg  His Asn Asn
    1040                 1045                 1050

Thr Asn  Leu Asn Glu Glu Leu  Val Tyr Leu Thr Trp  Met Thr Gln
    1055                 1060                 1065

Ile Thr  Asp Lys Glu Leu Ala  Ser Ser Leu Val Tyr  Phe Thr Asn
    1070                 1075                 1080
```

```
Asn Gly  Met Asp Lys Ser Ile  Trp Lys Lys Ser Ala  Glu Arg Ser
    1085                 1090                 1095

Ala Gln  Ala Ile Ser Gln Cys  Lys Asn Ala Trp Thr  Arg Ile Asn
    1100                 1105                 1110

Asp Phe  Leu Lys Asn His Trp  Ile Ser Ile Ser Ala  Val Ile Gly
    1115                 1120                 1125

Ser Ala  Leu Leu Ile Gly Gly  Val Ser Ser Ala Val  Lys Cys Ala
    1130                 1135                 1140

Thr Lys  Cys Arg Val Arg Lys  Ile Leu Gln Asp Gly  Gly Ser Ile
    1145                 1150                 1155

Met Gln  Leu Val Gly Val Arg  Ser Cys Met Tyr Ala  Cys Gln Leu
    1160                 1165                 1170

Cys Lys  Arg Ile Lys Asn Cys  Asp Leu Arg Leu Arg  Val Arg Asn
    1175                 1180                 1185

Arg Ser  Glu Gly Val Thr Thr  Phe Val Pro Gly Asp  Val Arg Arg
    1190                 1195                 1200

Val Ala  Arg His Val Ile Ser  Ala Ala Asp Val Cys  Glu Val Pro
    1205                 1210                 1215

Val His  His Ser Phe Ile Gln  Ser Leu Cys Asp Glu  Ala Phe Thr
    1220                 1225                 1230

Val His  Ser Asp Lys Glu Glu  Thr Phe Ser Ile Leu  Asp Phe Thr
    1235                 1240                 1245

Pro Glu  Ala Lys Gly Arg Asn  Pro Pro Glu Ser Ala  Val Val Glu
    1250                 1255                 1260

Ser His  Gln Asp Tyr Arg Val  Lys Ala Ala Val Val  Glu Ser His
    1265                 1270                 1275

Gln Asp  Phe Lys Pro Lys Asp  Ala Ile Val Glu Ser  Thr Ile Asp
    1280                 1285                 1290

Thr Val  Phe Thr Glu Ser His  Gln Asp Val Arg Val  Lys Leu His
    1295                 1300                 1305

Pro Gln  Ile Glu Ser His Gln  Asp Phe Arg Ala Lys  Asn Pro Ile
    1310                 1315                 1320

Val Glu  Ser Arg Lys Pro Asp  Tyr Gln Val Glu Trp  Thr Asp Leu
    1325                 1330                 1335

Arg Thr  Glu Ser Ser Asn Asp  Arg Asn Ala Gln Asp  Ile Ser Asn
    1340                 1345                 1350

Arg Ile  Leu Ser Arg Asn Phe  Val Arg Leu Tyr Val  Pro Gly Ser
    1355                 1360                 1365

Ser Leu  Tyr Thr His Gly Leu  Phe Ala Tyr Gly Arg  Met Leu Leu
    1370                 1375                 1380

Met Pro  Lys His Met Phe Asp  Met Leu Asn Gly Ser  Val Glu Ile
    1385                 1390                 1395

Val Ser  Ile Ala Asp Lys Gly  Asn Thr Arg Val His  Val Lys Ile
    1400                 1405                 1410

Gln Ser  His Lys Thr Val Thr  Arg Gly Gly Tyr Glu  Val Asp Ile
    1415                 1420                 1425

Val Ile  Cys Glu Met Gly Asn  Ser Ile Ser Ala Arg  Lys Asp Ile
    1430                 1435                 1440

Thr Ser  Tyr Phe Pro Thr Val  Lys Glu Leu Pro Gly  Leu Thr Gly
    1445                 1450                 1455

Met Met  Ser Ser Gly Arg Met  Arg Val Phe Ser Thr  Ala Lys Phe
    1460                 1465                 1470

Lys Ala  Ser Asp Ser Cys Ser  Tyr Leu Met Pro Gln  Asp Phe Val
```

-continued

```
    1475                1480                1485

Ala Lys  Tyr Ile Ala Ala Val  Asp His Ile Thr Ser  Lys Ser Pro
    1490                1495                1500

Glu Lys  Lys Ser Tyr Phe Ile  Arg Gln Gly Phe Glu  Ala Glu Ser
    1505                1510                1515

Asp Ser  Met Gln Gly Asp Cys  Cys Ser Pro Tyr Val  Leu Phe Asn
    1520                1525                1530

Ser Ala  Ser Arg Ala Lys Ile  Val Gly Leu His Cys  Ala Gly Phe
    1535                1540                1545

Asp Gly  Thr Ala Arg Val Phe  Ala Gln Ile Ile Thr  Gln Glu Asp
    1550                1555                1560

Ile Met  Ala Ala Thr Pro Thr  Thr His Ala Gly Arg  Val Thr Thr
    1565                1570                1575

Glu Phe  Pro His Thr Ser Leu  Arg Asp Ser Pro Leu  Pro Asn Ser
    1580                1585                1590

Met Ala  Ile Gly Ser Val Lys  Thr Ala Pro Asn Pro  Thr Lys Ser
    1595                1600                1605

Glu Ile  Thr Arg Ser Pro Ile  His Gly Cys Phe Pro  Val Arg Thr
    1610                1615                1620

Ala Pro  Ala Thr Leu Tyr Ser  Pro Thr Glu Asn Leu  Leu Ile Lys
    1625                1630                1635

Asn Ala  Met Lys Val Thr Lys  Asn Val Glu Leu Leu  Glu Glu Asp
    1640                1645                1650

Leu Ile  Asp Ala Cys Val His  Asp Val Lys Arg Ile  Leu Asn Ala
    1655                1660                1665

Pro Gly  Val Ser Asp Val Glu  Lys Arg Val Leu Thr  His Glu Glu
    1670                1675                1680

Ser Ile  Thr Gly Ile Glu Asn  Arg Gln Tyr Met Asn  Ala Leu Asn
    1685                1690                1695

Arg Ser  Thr Ser Ala Gly Phe  Pro Tyr Ser Ser Arg  Lys Ala Lys
    1700                1705                1710

Gly Lys  Ser Gly Lys Gln Thr  Trp Leu Gly Ser Glu  Glu Phe Ile
    1715                1720                1725

Val Asp  Asn Pro Asp Leu Lys  Glu His Val Glu Lys  Ile Val Asp
    1730                1735                1740

Lys Ala  Lys Asp Gly Ile Val  Asp Val Ser Leu Gly  Ile Phe Ala
    1745                1750                1755

Ala Thr  Leu Lys Asp Glu Arg  Arg Pro Leu Glu Lys  Val Gln Ala
    1760                1765                1770

Asn Lys  Thr Arg Val Phe Ala  Ala Ser Asn Gln Gly  Leu Ala Leu
    1775                1780                1785

Ala Leu  Arg Arg Tyr Tyr Leu  Ser Phe Leu Asp His  Val Met Thr
    1790                1795                1800

Asn Arg  Ile Asp Asn Glu Ile  Gly Leu Gly Val Asn  Val Tyr Ser
    1805                1810                1815

Tyr Asp  Trp Thr Arg Ile Val  Asn Lys Leu Lys Arg  Val Gly Asp
    1820                1825                1830

Lys Val  Ile Ala Gly Asp Phe  Ser Asn Phe Asp Gly  Ser Leu Asn
    1835                1840                1845

Ser Gln  Ile Leu Ser Arg Val  Ser Glu Ile Val Thr  Asp Trp Tyr
    1850                1855                1860

Gly Asp  Asp Ala Glu Asn Gly  Leu Ile Arg His Thr  Leu Leu Glu
    1865                1870                1875
```

```
Tyr Leu  Phe Asn Ala Thr Trp  Leu Met Asn Gly Lys  Val Phe Gln
    1880                 1885                 1890

Leu Asn  His Ser Gln Pro Ser  Gly Asn Pro Leu Thr  Thr Leu Ile
    1895                 1900                 1905

Asn Cys  Val Tyr Asn Met Ile  Ile Phe Arg Tyr Val  Tyr Leu Leu
    1910                 1915                 1920

Ala Gln  Arg Glu Asn Gly Phe  Pro Met Thr Leu Ser  Gly Phe Thr
    1925                 1930                 1935

Thr Asn  Val Ala Cys Ile Phe  Tyr Gly Asp Asp Ser  Leu Cys Ser
    1940                 1945                 1950

Val Ser  Asp Lys Val Ser Glu  Trp Phe Asn Gln His  Val Ile Thr
    1955                 1960                 1965

Arg Leu  Met Ala Ala Thr Gly  His Glu Tyr Thr Asp  Glu Thr Lys
    1970                 1975                 1980

Ser Gly  Ser Pro Pro Pro Tyr  Arg Ser Leu Asn Glu  Val Thr Phe
    1985                 1990                 1995

Leu Lys  Arg Glu Phe Val Leu  Arg Asp His Phe Trp  Ile Ala Pro
    2000                 2005                 2010

Leu Ser  Arg Asn Thr Ile Glu  Asp Met Cys Met Trp  Ser Arg Lys
    2015                 2020                 2025

Asn Ile  Asp Ala Gln Asp Ala  Leu Leu Gln Thr Thr  Arg Ile Ala
    2030                 2035                 2040

Ser Phe  Glu Ala Ser Leu His  Glu Lys Asn Tyr Phe  Leu Met Phe
    2045                 2050                 2055

Cys Asp  Val Ile Lys Lys Ala  Cys Arg Asn Ala Gly  Tyr Lys Glu
    2060                 2065                 2070

Ala Cys  Leu His Glu Leu Asp  Cys Lys Ser Phe Leu  Leu Ala Gln
    2075                 2080                 2085

Gln Gly  Arg Ala Gly Ala His  Asp Ser Glu Phe Leu  Ser Gln Leu
    2090                 2095                 2100

Leu Asp  Leu Asn
    2105


<210> SEQ ID NO 458
<211> LENGTH: 44
<212> TYPE: PRT
<213> ORGANISM: Taura syndrome virus

<400> SEQUENCE: 458

His Arg Ala Phe Tyr Val Met Asn Asp Asp Gly Glu Asn Arg Ile Tyr
1               5                   10                  15

Ser Leu Ile Gly Thr Leu Arg Arg Ala Pro Ala Phe Lys Val Gly Ser
            20                  25                  30

Arg Arg Tyr Lys Ser His Ile Pro Tyr Arg Arg Lys
        35                  40


<210> SEQ ID NO 459
<211> LENGTH: 10
<212> TYPE: PRT
<213> ORGANISM: Taura syndrome virus

<400> SEQUENCE: 459

Lys Val Gly Ser Arg Arg Tyr Lys Ser His
1               5                   10


<210> SEQ ID NO 460
<211> LENGTH: 27
<212> TYPE: PRT
```

<213> ORGANISM: Taura syndrome virus

<400> SEQUENCE: 460

Lys Val Gly Ser Arg Arg Tyr Lys Ser His Ile Pro Tyr Arg Arg Lys
1 5 10 15

Ala Thr Val Ala Glu Leu Cys Asn Gln Leu His
20 25

<210> SEQ ID NO 461
<211> LENGTH: 9
<212> TYPE: PRT
<213> ORGANISM: Taura syndrome virus

<400> SEQUENCE: 461

Lys Ser His Ile Pro Tyr Arg Arg Lys
1 5

<210> SEQ ID NO 462
<211> LENGTH: 20
<212> TYPE: PRT
<213> ORGANISM: Taura syndrome virus

<400> SEQUENCE: 462

Lys Ser His Ile Pro Tyr Arg Arg Lys Ala Thr Val Ala Glu Leu Cys
1 5 10 15

Asn Gln Leu His
20

<210> SEQ ID NO 463
<211> LENGTH: 38
<212> TYPE: PRT
<213> ORGANISM: Taura syndrome virus

<400> SEQUENCE: 463

His Ile Pro Tyr Arg Arg Lys Ala Thr Val Ala Glu Leu Cys Asn Gln
1 5 10 15

Leu His Asp Arg Val Leu Pro Phe Ala Asn Pro Gln Val Trp Lys Glu
20 25 30

Val Ile Ser Glu Asn Lys
35

<210> SEQ ID NO 464
<211> LENGTH: 46
<212> TYPE: PRT
<213> ORGANISM: Taura syndrome virus

<400> SEQUENCE: 464

His Ile Pro Tyr Arg Arg Lys Ala Thr Val Ala Glu Leu Cys Asn Gln
1 5 10 15

Leu His Asp Arg Val Leu Pro Phe Ala Asn Pro Gln Val Trp Lys Glu
20 25 30

Val Ile Ser Glu Asn Lys Val Gln Pro Asp Ser Met Leu Lys
35 40 45

<210> SEQ ID NO 465
<211> LENGTH: 29
<212> TYPE: PRT
<213> ORGANISM: Taura syndrome virus

<400> SEQUENCE: 465

His Asp Arg Val Leu Pro Phe Ala Asn Pro Gln Val Trp Lys Glu Val
1 5 10 15

```
Ile Ser Glu Asn Lys Val Gln Pro Asp Ser Met Leu Lys
            20                  25


<210> SEQ ID NO 466
<211> LENGTH: 21
<212> TYPE: PRT
<213> ORGANISM: Taura syndrome virus

<400> SEQUENCE: 466

His Asp Arg Val Leu Pro Phe Ala Asn Pro Gln Val Trp Lys Glu Val
1               5                   10                  15

Ile Ser Glu Asn Lys
            20


<210> SEQ ID NO 467
<211> LENGTH: 18
<212> TYPE: PRT
<213> ORGANISM: Taura syndrome virus

<400> SEQUENCE: 467

Lys Cys Asn Asp Cys Ile Leu Lys Met Asn Arg Asn Val Glu Tyr Pro
1               5                   10                  15

Tyr His


<210> SEQ ID NO 468
<211> LENGTH: 42
<212> TYPE: PRT
<213> ORGANISM: Taura syndrome virus

<400> SEQUENCE: 468

Lys Ile Ile Asp Leu Ile Lys Glu Thr Phe Val Ser Leu Phe Phe Ala
1               5                   10                  15

Ile Leu Thr Lys Ser Leu Tyr Pro Ile Ile Gln Gly Ile Ser Ser Tyr
            20                  25                  30

Ala Leu Arg Asn Asn Leu Met Ala Asn His
        35                  40


<210> SEQ ID NO 469
<211> LENGTH: 26
<212> TYPE: PRT
<213> ORGANISM: Taura syndrome virus

<400> SEQUENCE: 469

Lys Ser Arg Lys Asn Leu Asp Leu Leu Lys Glu Tyr Pro Ser Leu Asp
1               5                   10                  15

Ser Leu Leu Ser Ile Phe Asn Tyr Phe His
            20                  25


<210> SEQ ID NO 470
<211> LENGTH: 23
<212> TYPE: PRT
<213> ORGANISM: Taura syndrome virus

<400> SEQUENCE: 470

Lys Asn Leu Asp Leu Leu Lys Glu Tyr Pro Ser Leu Asp Ser Leu Leu
1               5                   10                  15

Ser Ile Phe Asn Tyr Phe His
            20


<210> SEQ ID NO 471
<211> LENGTH: 16
<212> TYPE: PRT
<213> ORGANISM: Taura syndrome virus
```

<400> SEQUENCE: 471

His Arg Glu Ile Ser Ser Arg Leu Lys Glu Ala Arg Asn Ser Val Lys
1 5 10 15

<210> SEQ ID NO 472
<211> LENGTH: 51
<212> TYPE: PRT
<213> ORGANISM: Taura syndrome virus

<400> SEQUENCE: 472

Lys Glu Ala Arg Asn Ser Val Lys Asp Leu Ile Ala Lys Ala Gln Val
1 5 10 15

Tyr Leu Thr Cys Gly Asp Gly Ser Arg Val Pro Pro Val Val Val Tyr
20 25 30

Met Tyr Gly Asp Ala Gly Cys Gly Lys Thr Glu Leu Ser Met Ala Leu
35 40 45

Gln Asp His
50

<210> SEQ ID NO 473
<211> LENGTH: 12
<212> TYPE: PRT
<213> ORGANISM: Taura syndrome virus

<400> SEQUENCE: 473

His Phe Ala Thr Lys Tyr Phe Gly Glu Val Pro Lys
1 5 10

<210> SEQ ID NO 474
<211> LENGTH: 13
<212> TYPE: PRT
<213> ORGANISM: Taura syndrome virus

<400> SEQUENCE: 474

His Phe Ala Thr Lys Tyr Phe Gly Glu Val Pro Lys Lys
1 5 10

<210> SEQ ID NO 475
<211> LENGTH: 20
<212> TYPE: PRT
<213> ORGANISM: Taura syndrome virus

<400> SEQUENCE: 475

His Phe Ala Thr Lys Tyr Phe Gly Glu Val Pro Lys Lys Asp Val Ile
1 5 10 15

Tyr Ser Arg Lys
20

<210> SEQ ID NO 476
<211> LENGTH: 30
<212> TYPE: PRT
<213> ORGANISM: Taura syndrome virus

<400> SEQUENCE: 476

His Phe Ala Thr Lys Tyr Phe Gly Glu Val Pro Lys Lys Asp Val Ile
1 5 10 15

Tyr Ser Arg Lys Ala Glu Asn Glu Phe Trp Asp Gly Val Lys
20 25 30

<210> SEQ ID NO 477
<211> LENGTH: 29
<212> TYPE: PRT

<213> ORGANISM: Taura syndrome virus

<400> SEQUENCE: 477

Lys Tyr Phe Gly Glu Val Pro Lys Lys Asp Val Ile Tyr Ser Arg Lys
1               5                   10                  15

Ala Glu Asn Glu Phe Trp Asp Gly Val Lys Gln Ser His
            20                  25

<210> SEQ ID NO 478
<211> LENGTH: 22
<212> TYPE: PRT
<213> ORGANISM: Taura syndrome virus

<400> SEQUENCE: 478

Lys Lys Asp Val Ile Tyr Ser Arg Lys Ala Glu Asn Glu Phe Trp Asp
1               5                   10                  15

Gly Val Lys Gln Ser His
            20

<210> SEQ ID NO 479
<211> LENGTH: 21
<212> TYPE: PRT
<213> ORGANISM: Taura syndrome virus

<400> SEQUENCE: 479

Lys Asp Val Ile Tyr Ser Arg Lys Ala Glu Asn Glu Phe Trp Asp Gly
1               5                   10                  15

Val Lys Gln Ser His
            20

<210> SEQ ID NO 480
<211> LENGTH: 14
<212> TYPE: PRT
<213> ORGANISM: Taura syndrome virus

<400> SEQUENCE: 480

Lys Ala Glu Asn Glu Phe Trp Asp Gly Val Lys Gln Ser His
1               5                   10

<210> SEQ ID NO 481
<211> LENGTH: 51
<212> TYPE: PRT
<213> ORGANISM: Taura syndrome virus

<400> SEQUENCE: 481

Lys Ala Glu Asn Glu Phe Trp Asp Gly Val Lys Gln Ser His Lys Ile
1               5                   10                  15

Ile Ala Tyr Asp Asp Val Leu Gln Ile Val Asp Ser Ala Gln Lys Pro
            20                  25                  30

Asn Pro Glu Leu Phe Glu Phe Ile Arg Leu Asn Asn Ser Asp Pro Tyr
        35                  40                  45

Gln Val His
    50

<210> SEQ ID NO 482
<211> LENGTH: 49
<212> TYPE: PRT
<213> ORGANISM: Taura syndrome virus

<400> SEQUENCE: 482

His Ser Ala Asp Ala Phe Arg Arg Arg Leu Asp Leu Cys Val Tyr Val
1               5                   10                  15

Asp Val Lys Asp Glu Phe Ala Arg Ile Val Ala Gly Ser Lys Gly His
20 25 30

Arg Lys Val Pro Cys Glu Gln Lys Ile Trp Leu His Gln Asn Pro Gly
35 40 45

Lys

<210> SEQ ID NO 483
<211> LENGTH: 40
<212> TYPE: PRT
<213> ORGANISM: Taura syndrome virus

<400> SEQUENCE: 483

His Ser Ala Asp Ala Phe Arg Arg Arg Leu Asp Leu Cys Val Tyr Val
1 5 10 15

Asp Val Lys Asp Glu Phe Ala Arg Ile Val Ala Gly Ser Lys Gly His
20 25 30

Arg Lys Val Pro Cys Glu Gln Lys
35 40

<210> SEQ ID NO 484
<211> LENGTH: 46
<212> TYPE: PRT
<213> ORGANISM: Taura syndrome virus

<400> SEQUENCE: 484

Lys Gly His Arg Lys Val Pro Cys Glu Gln Lys Ile Trp Leu His Gln
1 5 10 15

Asn Pro Gly Lys Thr Gln His Asp Met Lys His Glu Ile Val Ala Gly
20 25 30

Thr Tyr Lys Ile Thr Pro Glu Thr Ala Val Tyr Glu Leu His
35 40 45

<210> SEQ ID NO 485
<211> LENGTH: 15
<212> TYPE: PRT
<213> ORGANISM: Taura syndrome virus

<400> SEQUENCE: 485

Lys Gly His Arg Lys Val Pro Cys Glu Gln Lys Ile Trp Leu His
1 5 10 15

<210> SEQ ID NO 486
<211> LENGTH: 11
<212> TYPE: PRT
<213> ORGANISM: Taura syndrome virus

<400> SEQUENCE: 486

Lys Gly His Arg Lys Val Pro Cys Glu Gln Lys
1 5 10

<210> SEQ ID NO 487
<211> LENGTH: 23
<212> TYPE: PRT
<213> ORGANISM: Taura syndrome virus

<400> SEQUENCE: 487

Lys Gly His Arg Lys Val Pro Cys Glu Gln Lys Ile Trp Leu His Gln
1 5 10 15

Asn Pro Gly Lys Thr Gln His
20

<210> SEQ ID NO 488

```
<211> LENGTH: 27
<212> TYPE: PRT
<213> ORGANISM: Taura syndrome virus

<400> SEQUENCE: 488

Lys Gly His Arg Lys Val Pro Cys Glu Gln Lys Ile Trp Leu His Gln
1               5                   10                  15

Asn Pro Gly Lys Thr Gln His Asp Met Lys His
            20                  25


<210> SEQ ID NO 489
<211> LENGTH: 33
<212> TYPE: PRT
<213> ORGANISM: Taura syndrome virus

<400> SEQUENCE: 489

His Arg Lys Val Pro Cys Glu Gln Lys Ile Trp Leu His Gln Asn Pro
1               5                   10                  15

Gly Lys Thr Gln His Asp Met Lys His Glu Ile Val Ala Gly Thr Tyr
            20                  25                  30

Lys


<210> SEQ ID NO 490
<211> LENGTH: 18
<212> TYPE: PRT
<213> ORGANISM: Taura syndrome virus

<400> SEQUENCE: 490

His Arg Lys Val Pro Cys Glu Gln Lys Ile Trp Leu His Gln Asn Pro
1               5                   10                  15

Gly Lys


<210> SEQ ID NO 491
<211> LENGTH: 9
<212> TYPE: PRT
<213> ORGANISM: Taura syndrome virus

<400> SEQUENCE: 491

His Arg Lys Val Pro Cys Glu Gln Lys
1               5


<210> SEQ ID NO 492
<211> LENGTH: 24
<212> TYPE: PRT
<213> ORGANISM: Taura syndrome virus

<400> SEQUENCE: 492

His Arg Lys Val Pro Cys Glu Gln Lys Ile Trp Leu His Gln Asn Pro
1               5                   10                  15

Gly Lys Thr Gln His Asp Met Lys
            20


<210> SEQ ID NO 493
<211> LENGTH: 11
<212> TYPE: PRT
<213> ORGANISM: Taura syndrome virus

<400> SEQUENCE: 493

Lys Val Pro Cys Glu Gln Lys Ile Trp Leu His
1               5                   10


<210> SEQ ID NO 494
<211> LENGTH: 19
```

<212> TYPE: PRT
<213> ORGANISM: Taura syndrome virus

<400> SEQUENCE: 494

Lys Val Pro Cys Glu Gln Lys Ile Trp Leu His Gln Asn Pro Gly Lys
1 5 10 15

Thr Gln His

<210> SEQ ID NO 495
<211> LENGTH: 23
<212> TYPE: PRT
<213> ORGANISM: Taura syndrome virus

<400> SEQUENCE: 495

Lys Val Pro Cys Glu Gln Lys Ile Trp Leu His Gln Asn Pro Gly Lys
1 5 10 15

Thr Gln His Asp Met Lys His
20

<210> SEQ ID NO 496
<211> LENGTH: 42
<212> TYPE: PRT
<213> ORGANISM: Taura syndrome virus

<400> SEQUENCE: 496

Lys Val Pro Cys Glu Gln Lys Ile Trp Leu His Gln Asn Pro Gly Lys
1 5 10 15

Thr Gln His Asp Met Lys His Glu Ile Val Ala Gly Thr Tyr Lys Ile
20 25 30

Thr Pro Glu Thr Ala Val Tyr Glu Leu His
35 40

<210> SEQ ID NO 497
<211> LENGTH: 10
<212> TYPE: PRT
<213> ORGANISM: Taura syndrome virus

<400> SEQUENCE: 497

Lys Ile Trp Leu His Gln Asn Pro Gly Lys
1 5 10

<210> SEQ ID NO 498
<211> LENGTH: 13
<212> TYPE: PRT
<213> ORGANISM: Taura syndrome virus

<400> SEQUENCE: 498

Lys Ile Trp Leu His Gln Asn Pro Gly Lys Thr Gln His
1 5 10

<210> SEQ ID NO 499
<211> LENGTH: 17
<212> TYPE: PRT
<213> ORGANISM: Taura syndrome virus

<400> SEQUENCE: 499

Lys Ile Trp Leu His Gln Asn Pro Gly Lys Thr Gln His Asp Met Lys
1 5 10 15

His

<210> SEQ ID NO 500
<211> LENGTH: 36
<212> TYPE: PRT

<213> ORGANISM: Taura syndrome virus

<400> SEQUENCE: 500

```
Lys Ile Trp Leu His Gln Asn Pro Gly Lys Thr Gln His Asp Met Lys
1               5                   10                  15

His Glu Ile Val Ala Gly Thr Tyr Lys Ile Thr Pro Glu Thr Ala Val
            20                  25                  30

Tyr Glu Leu His
        35
```

<210> SEQ ID NO 501
<211> LENGTH: 12
<212> TYPE: PRT
<213> ORGANISM: Taura syndrome virus

<400> SEQUENCE: 501

```
His Gln Asn Pro Gly Lys Thr Gln His Asp Met Lys
1               5                   10
```

<210> SEQ ID NO 502
<211> LENGTH: 21
<212> TYPE: PRT
<213> ORGANISM: Taura syndrome virus

<400> SEQUENCE: 502

```
His Gln Asn Pro Gly Lys Thr Gln His Asp Met Lys His Glu Ile Val
1               5                   10                  15

Ala Gly Thr Tyr Lys
            20
```

<210> SEQ ID NO 503
<211> LENGTH: 7
<212> TYPE: PRT
<213> ORGANISM: Taura syndrome virus

<400> SEQUENCE: 503

```
Lys Thr Gln His Asp Met Lys
1               5
```

<210> SEQ ID NO 504
<211> LENGTH: 8
<212> TYPE: PRT
<213> ORGANISM: Taura syndrome virus

<400> SEQUENCE: 504

```
Lys Thr Gln His Asp Met Lys His
1               5
```

<210> SEQ ID NO 505
<211> LENGTH: 27
<212> TYPE: PRT
<213> ORGANISM: Taura syndrome virus

<400> SEQUENCE: 505

```
Lys Thr Gln His Asp Met Lys His Glu Ile Val Ala Gly Thr Tyr Lys
1               5                   10                  15

Ile Thr Pro Glu Thr Ala Val Tyr Glu Leu His
            20                  25
```

<210> SEQ ID NO 506
<211> LENGTH: 13
<212> TYPE: PRT
<213> ORGANISM: Taura syndrome virus

```
<400> SEQUENCE: 506

His Asp Met Lys His Glu Ile Val Ala Gly Thr Tyr Lys
1               5                   10


<210> SEQ ID NO 507
<211> LENGTH: 10
<212> TYPE: PRT
<213> ORGANISM: Taura syndrome virus

<400> SEQUENCE: 507

Lys His Glu Ile Val Ala Gly Thr Tyr Lys
1               5                   10


<210> SEQ ID NO 508
<211> LENGTH: 21
<212> TYPE: PRT
<213> ORGANISM: Taura syndrome virus

<400> SEQUENCE: 508

Lys His Glu Ile Val Ala Gly Thr Tyr Lys Ile Thr Pro Glu Thr Ala
1               5                   10                  15

Val Tyr Glu Leu His
            20


<210> SEQ ID NO 509
<211> LENGTH: 32
<212> TYPE: PRT
<213> ORGANISM: Taura syndrome virus

<400> SEQUENCE: 509

His Trp Ile Ser Ile Ser Ala Val Ile Gly Ser Ala Leu Leu Ile Gly
1               5                   10                  15

Gly Val Ser Ser Ala Val Lys Cys Ala Thr Lys Cys Arg Val Arg Lys
            20                  25                  30


<210> SEQ ID NO 510
<211> LENGTH: 51
<212> TYPE: PRT
<213> ORGANISM: Taura syndrome virus

<400> SEQUENCE: 510

His Gln Asp Phe Lys Pro Lys Asp Ala Ile Val Glu Ser Thr Ile Asp
1               5                   10                  15

Thr Val Phe Thr Glu Ser His Gln Asp Val Arg Val Lys Leu His Pro
            20                  25                  30

Gln Ile Glu Ser His Gln Asp Phe Arg Ala Lys Asn Pro Ile Val Glu
        35                  40                  45

Ser Arg Lys
    50


<210> SEQ ID NO 511
<211> LENGTH: 29
<212> TYPE: PRT
<213> ORGANISM: Taura syndrome virus

<400> SEQUENCE: 511

His Gln Asp Val Arg Val Lys Leu His Pro Gln Ile Glu Ser His Gln
1               5                   10                  15

Asp Phe Arg Ala Lys Asn Pro Ile Val Glu Ser Arg Lys
            20                  25
```

<210> SEQ ID NO 512
<211> LENGTH: 21
<212> TYPE: PRT
<213> ORGANISM: Taura syndrome virus

<400> SEQUENCE: 512

```
His Pro Gln Ile Glu Ser His Gln Asp Phe Arg Ala Lys Asn Pro Ile
1               5                   10                  15

Val Glu Ser Arg Lys
            20
```

<210> SEQ ID NO 513
<211> LENGTH: 15
<212> TYPE: PRT
<213> ORGANISM: Taura syndrome virus

<400> SEQUENCE: 513

```
His Gln Asp Phe Arg Ala Lys Asn Pro Ile Val Glu Ser Arg Lys
1               5                   10                  15
```

<210> SEQ ID NO 514
<211> LENGTH: 40
<212> TYPE: PRT
<213> ORGANISM: Taura syndrome virus

<400> SEQUENCE: 514

```
His Gly Leu Phe Ala Tyr Gly Arg Met Leu Leu Met Pro Lys His Met
1               5                   10                  15

Phe Asp Met Leu Asn Gly Ser Val Glu Ile Val Ser Ile Ala Asp Lys
            20                  25                  30

Gly Asn Thr Arg Val His Val Lys
        35                  40
```

<210> SEQ ID NO 515
<211> LENGTH: 26
<212> TYPE: PRT
<213> ORGANISM: Taura syndrome virus

<400> SEQUENCE: 515

```
His Met Phe Asp Met Leu Asn Gly Ser Val Glu Ile Val Ser Ile Ala
1               5                   10                  15

Asp Lys Gly Asn Thr Arg Val His Val Lys
            20                  25
```

<210> SEQ ID NO 516
<211> LENGTH: 9
<212> TYPE: PRT
<213> ORGANISM: Taura syndrome virus

<400> SEQUENCE: 516

```
Lys Gly Asn Thr Arg Val His Val Lys
1               5
```

<210> SEQ ID NO 517
<211> LENGTH: 13
<212> TYPE: PRT
<213> ORGANISM: Taura syndrome virus

<400> SEQUENCE: 517

```
Lys Gly Asn Thr Arg Val His Val Lys Ile Gln Ser His
1               5                   10
```

<210> SEQ ID NO 518
<211> LENGTH: 42
<212> TYPE: PRT
<213> ORGANISM: Taura syndrome virus

<400> SEQUENCE: 518

His Val Lys Ile Gln Ser His Lys Thr Val Thr Arg Gly Gly Tyr Glu
1 5 10 15

Val Asp Ile Val Ile Cys Glu Met Gly Asn Ser Ile Ser Ala Arg Lys
20 25 30

Asp Ile Thr Ser Tyr Phe Pro Thr Val Lys
35 40

<210> SEQ ID NO 519
<211> LENGTH: 36
<212> TYPE: PRT
<213> ORGANISM: Taura syndrome virus

<400> SEQUENCE: 519

His Lys Thr Val Thr Arg Gly Gly Tyr Glu Val Asp Ile Val Ile Cys
1 5 10 15

Glu Met Gly Asn Ser Ile Ser Ala Arg Lys Asp Ile Thr Ser Tyr Phe
20 25 30

Pro Thr Val Lys
35

<210> SEQ ID NO 520
<211> LENGTH: 26
<212> TYPE: PRT
<213> ORGANISM: Taura syndrome virus

<400> SEQUENCE: 520

His Thr Ser Leu Arg Asp Ser Pro Leu Pro Asn Ser Met Ala Ile Gly
1 5 10 15

Ser Val Lys Thr Ala Pro Asn Pro Thr Lys
20 25

<210> SEQ ID NO 521
<211> LENGTH: 17
<212> TYPE: PRT
<213> ORGANISM: Taura syndrome virus

<400> SEQUENCE: 521

Lys Thr Ala Pro Asn Pro Thr Lys Ser Glu Ile Thr Arg Ser Pro Ile
1 5 10 15

His

<210> SEQ ID NO 522
<211> LENGTH: 30
<212> TYPE: PRT
<213> ORGANISM: Taura syndrome virus

<400> SEQUENCE: 522

His Gly Cys Phe Pro Val Arg Thr Ala Pro Ala Thr Leu Tyr Ser Pro
1 5 10 15

Thr Glu Asn Leu Leu Ile Lys Asn Ala Met Lys Val Thr Lys
20 25 30

<210> SEQ ID NO 523
<211> LENGTH: 23
<212> TYPE: PRT
<213> ORGANISM: Taura syndrome virus

<400> SEQUENCE: 523

```
Lys Asn Ala Met Lys Val Thr Lys Asn Val Glu Leu Leu Glu Glu Asp
1               5                   10                  15

Leu Ile Asp Ala Cys Val His
            20
```

<210> SEQ ID NO 524
<211> LENGTH: 44
<212> TYPE: PRT
<213> ORGANISM: Taura syndrome virus

<400> SEQUENCE: 524

```
Lys Asn Ala Met Lys Val Thr Lys Asn Val Glu Leu Leu Glu Glu Asp
1               5                   10                  15

Leu Ile Asp Ala Cys Val His Asp Val Lys Arg Ile Leu Asn Ala Pro
            20                  25                  30

Gly Val Ser Asp Val Glu Lys Arg Val Leu Thr His
        35                  40
```

<210> SEQ ID NO 525
<211> LENGTH: 38
<212> TYPE: PRT
<213> ORGANISM: Taura syndrome virus

<400> SEQUENCE: 525

```
His Glu Glu Ser Ile Thr Gly Ile Glu Asn Arg Gln Tyr Met Asn Ala
1               5                   10                  15

Leu Asn Arg Ser Thr Ser Ala Gly Phe Pro Tyr Ser Ser Arg Lys Ala
            20                  25                  30

Lys Gly Lys Ser Gly Lys
        35
```

<210> SEQ ID NO 526
<211> LENGTH: 27
<212> TYPE: PRT
<213> ORGANISM: Taura syndrome virus

<400> SEQUENCE: 526

```
Lys Ala Lys Gly Lys Ser Gly Lys Gln Thr Trp Leu Gly Ser Glu Glu
1               5                   10                  15

Phe Ile Val Asp Asn Pro Asp Leu Lys Glu His
            20                  25
```

<210> SEQ ID NO 527
<211> LENGTH: 10
<212> TYPE: PRT
<213> ORGANISM: Taura syndrome virus

<400> SEQUENCE: 527

```
Lys Glu His Val Glu Lys Ile Val Asp Lys
1               5                   10
```

<210> SEQ ID NO 528
<211> LENGTH: 34
<212> TYPE: PRT
<213> ORGANISM: Taura syndrome virus

<400> SEQUENCE: 528

His Val Glu Lys Ile Val Asp Lys Ala Lys Asp Gly Ile Val Asp Val
1               5                   10                  15

Ser Leu Gly Ile Phe Ala Ala Thr Leu Lys Asp Glu Arg Arg Pro Leu
            20                  25                  30

Glu Lys

<210> SEQ ID NO 529
<211> LENGTH: 10
<212> TYPE: PRT
<213> ORGANISM: Taura syndrome virus

<400> SEQUENCE: 529

His Val Glu Lys Ile Val Asp Lys Ala Lys
1               5                   10

<210> SEQ ID NO 530
<211> LENGTH: 39
<212> TYPE: PRT
<213> ORGANISM: Taura syndrome virus

<400> SEQUENCE: 530

Lys Asp Glu Arg Arg Pro Leu Glu Lys Val Gln Ala Asn Lys Thr Arg
1               5                   10                  15

Val Phe Ala Ala Ser Asn Gln Gly Leu Ala Leu Ala Leu Arg Arg Tyr
            20                  25                  30

Tyr Leu Ser Phe Leu Asp His
        35

<210> SEQ ID NO 531
<211> LENGTH: 35
<212> TYPE: PRT
<213> ORGANISM: Taura syndrome virus

<400> SEQUENCE: 531

His Val Met Thr Asn Arg Ile Asp Asn Glu Ile Gly Leu Gly Val Asn
1               5                   10                  15

Val Tyr Ser Tyr Asp Trp Thr Arg Ile Val Asn Lys Leu Lys Arg Val
            20                  25                  30

Gly Asp Lys
        35

<210> SEQ ID NO 532
<211> LENGTH: 48
<212> TYPE: PRT
<213> ORGANISM: Taura syndrome virus

<400> SEQUENCE: 532

Lys Leu Lys Arg Val Gly Asp Lys Val Ile Ala Gly Asp Phe Ser Asn
1               5                   10                  15

Phe Asp Gly Ser Leu Asn Ser Gln Ile Leu Ser Arg Val Ser Glu Ile
            20                  25                  30

Val Thr Asp Trp Tyr Gly Asp Asp Ala Glu Asn Gly Leu Ile Arg His
        35                  40                  45

<210> SEQ ID NO 533
<211> LENGTH: 23
<212> TYPE: PRT
<213> ORGANISM: Taura syndrome virus

<400> SEQUENCE: 533

His Glu Lys Asn Tyr Phe Leu Met Phe Cys Asp Val Ile Lys Lys Ala
1               5                   10                  15

Cys Arg Asn Ala Gly Tyr Lys
            20

<210> SEQ ID NO 534
<211> LENGTH: 33
<212> TYPE: PRT
<213> ORGANISM: Taura syndrome virus

<400> SEQUENCE: 534

His Glu Lys Asn Tyr Phe Leu Met Phe Cys Asp Val Ile Lys Lys Ala
1               5                   10                  15

Cys Arg Asn Ala Gly Tyr Lys Glu Ala Cys Leu His Glu Leu Asp Cys
            20                  25                  30

Lys

<210> SEQ ID NO 535
<211> LENGTH: 15
<212> TYPE: PRT
<213> ORGANISM: Taura syndrome virus

<400> SEQUENCE: 535

Lys Lys Ala Cys Arg Asn Ala Gly Tyr Lys Glu Ala Cys Leu His
1               5                   10                  15

<210> SEQ ID NO 536
<211> LENGTH: 32
<212> TYPE: PRT
<213> ORGANISM: Taura syndrome virus

<400> SEQUENCE: 536

Lys Ala Cys Arg Asn Ala Gly Tyr Lys Glu Ala Cys Leu His Glu Leu
1               5                   10                  15

Asp Cys Lys Ser Phe Leu Leu Ala Gln Gln Gly Arg Ala Gly Ala His
            20                  25                  30

<210> SEQ ID NO 537
<211> LENGTH: 14
<212> TYPE: PRT
<213> ORGANISM: Taura syndrome virus

<400> SEQUENCE: 537

Lys Ala Cys Arg Asn Ala Gly Tyr Lys Glu Ala Cys Leu His
1               5                   10

<210> SEQ ID NO 538
<211> LENGTH: 11
<212> TYPE: PRT
<213> ORGANISM: Taura syndrome virus

<400> SEQUENCE: 538

Lys Glu Ala Cys Leu His Glu Leu Asp Cys Lys
1               5                   10

<210> SEQ ID NO 539
<211> LENGTH: 24
<212> TYPE: PRT
<213> ORGANISM: Taura syndrome virus -continued

```
<400> SEQUENCE: 539

Lys Glu Ala Cys Leu His Glu Leu Asp Cys Lys Ser Phe Leu Leu Ala
1               5                   10                  15

Gln Gln Gly Arg Ala Gly Ala His
            20
```